(12) United States Patent
Ready et al.

(10) Patent No.: US 9,789,096 B2
(45) Date of Patent: Oct. 17, 2017

(54) METHODS AND COMPOSITIONS FOR SELECTIVE AND TARGETED CANCER THERAPY

(71) Applicant: Board of Regents of the University of Texas System, Austin, TX (US)

(72) Inventors: Joseph M. Ready, Carrollton, TX (US); Deepak Nijhawan, Dallas, TX (US); Stephen S. Gonzales, Frisco, TX (US); Pano Theodoropoulos, Dallas, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/916,644

(22) PCT Filed: Sep. 4, 2014

(86) PCT No.: PCT/US2014/054099
§ 371 (c)(1),
(2) Date: Mar. 4, 2016

(87) PCT Pub. No.: WO2015/035051
PCT Pub. Date: Mar. 12, 2015

(65) Prior Publication Data
US 2016/0200695 A1 Jul. 14, 2016

Related U.S. Application Data

(60) Provisional application No. 61/873,781, filed on Sep. 4, 2013, provisional application No. 61/938,603, filed on Feb. 11, 2014.

(51) Int. Cl.
| | |
|---|---|
| A61K 31/428 | (2006.01) |
| A61K 31/426 | (2006.01) |
| C07C 235/88 | (2006.01) |
| C07D 333/70 | (2006.01) |
| C07D 409/12 | (2006.01) |
| C07D 417/12 | (2006.01) |
| C07D 513/04 | (2006.01) |
| C12N 9/99 | (2006.01) |
| A61K 31/381 | (2006.01) |
| C07D 405/14 | (2006.01) |
| C07D 213/75 | (2006.01) |
| C07D 215/48 | (2006.01) |
| C07D 217/02 | (2006.01) |
| C07D 405/12 | (2006.01) |
| C07D 409/14 | (2006.01) |
| C07D 239/90 | (2006.01) |
| C07D 417/14 | (2006.01) |
| C07D 209/08 | (2006.01) |
| C07D 277/82 | (2006.01) |
| C07D 209/44 | (2006.01) |
| C07C 271/44 | (2006.01) |
| C07C 271/46 | (2006.01) |

(Continued)

(52) U.S. Cl.
CPC .......... *A61K 31/426* (2013.01); *A61K 31/381* (2013.01); *A61K 31/428* (2013.01); *C07C 233/56* (2013.01); *C07C 233/73* (2013.01); *C07C 235/38* (2013.01); *C07C 235/56* (2013.01); *C07C 235/66* (2013.01); *C07C 235/70* (2013.01); *C07C 235/88* (2013.01); *C07C 237/08* (2013.01); *C07C 271/44* (2013.01); *C07C 271/46* (2013.01); *C07C 271/48* (2013.01); *C07C 275/24* (2013.01); *C07C 275/30* (2013.01); *C07C 275/54* (2013.01); *C07D 209/08* (2013.01); *C07D 209/44* (2013.01); *C07D 213/75* (2013.01); *C07D 215/48* (2013.01); *C07D 217/02* (2013.01); *C07D 239/90* (2013.01); *C07D 277/82* (2013.01); *C07D 333/70* (2013.01); *C07D 405/12* (2013.01); *C07D 405/14* (2013.01); *C07D 409/12* (2013.01); *C07D 409/14* (2013.01); *C07D 417/12* (2013.01); *C07D 417/14* (2013.01); *C07D 513/04* (2013.01); *C12N 9/99* (2013.01); *C07C 2101/02* (2013.01); *C07C 2101/04* (2013.01); *C07C 2101/08* (2013.01); *C07C 2101/14* (2013.01); *C07C 2101/18* (2013.01); *C07C 2103/26* (2013.01)

(58) Field of Classification Search
None
See application file for complete search history.

(56) References Cited

U.S. PATENT DOCUMENTS

2008/0039629 A1  2/2008  Ramesh et al.
2009/0137420 A1  5/2009  Von Hoff et al.
(Continued)

OTHER PUBLICATIONS

Bradshaw et al., The Development of the Antitumour Benzothiazole Prodrug, Phortress, as a Clinical Candidate, Current Medicinal Chemistry 11, pp. 1-13 (pp. 1241-1253) 2004; (retrieved from the Internet) http://www.pharminox.com/pdf/Phortess_rev.pdf.
(Continued)

*Primary Examiner* — Samantha Shterengarts
(74) *Attorney, Agent, or Firm* — Greenberg Traurig, LLP; David J. Dykeman; Fang Xie

(57) ABSTRACT

Provided herein are methods and compositions for selective and targeted cancer therapy, in particular certain benzothiophenes, benzothiazoles, oxalamides, N-acyl ureas and chromones, and their use in selectively treating certain adenocarcinomas. In some embodiments, the selective toxicity of the compounds may be mediated through SCD1 and/or CYP450 such as CYP4F11.

6 Claims, 24 Drawing Sheets

(51) Int. Cl.
*C07C 271/48* (2006.01)
*C07C 275/24* (2006.01)
*C07C 275/30* (2006.01)
*C07C 275/54* (2006.01)
*C07C 233/56* (2006.01)
*C07C 233/73* (2006.01)
*C07C 235/38* (2006.01)
*C07C 235/56* (2006.01)
*C07C 235/66* (2006.01)
*C07C 235/70* (2006.01)
*C07C 237/08* (2006.01)

(56) References Cited

U.S. PATENT DOCUMENTS

2009/0143376 A1  6/2009  Milburn et al.
2013/0096181 A1  4/2013  Ashkenazi et al.

OTHER PUBLICATIONS

PCT International Search Report based on PCT/US14/54099 dated Jan. 29, 2015.
Bruno et al., "Targeting Cytochrome P450 Enzymes: A New Approach in Anti-Cancer Drug Development", Bioorganic & Medicinal Chemistry, vol. 15, Issue 15, Aug. 1, 2007, pp. 5047-5060.
Patterson et al., "Tumour Cytochrome P450 and Drug Activation", Current Pharmaceutical Design, vol. 8, No. 15, Jul. 1, 2002, pp. 1335-1347.

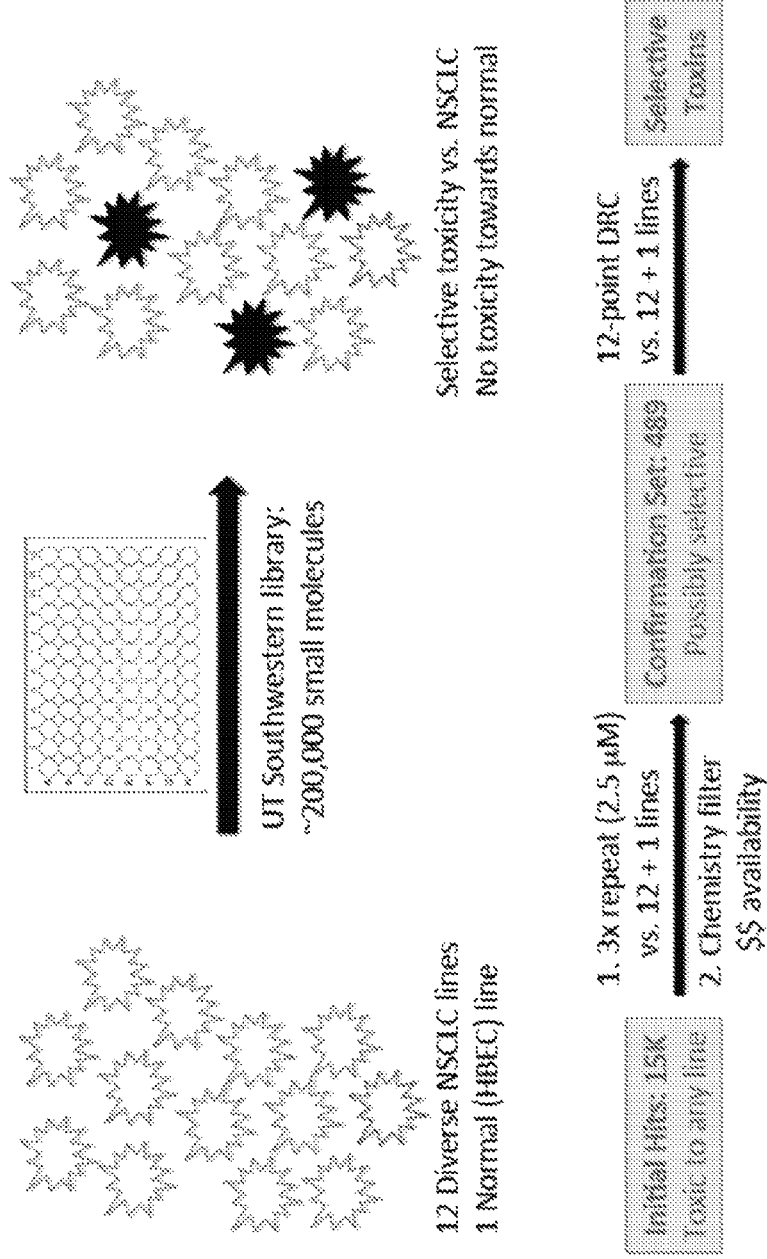
Fig 1, cont.

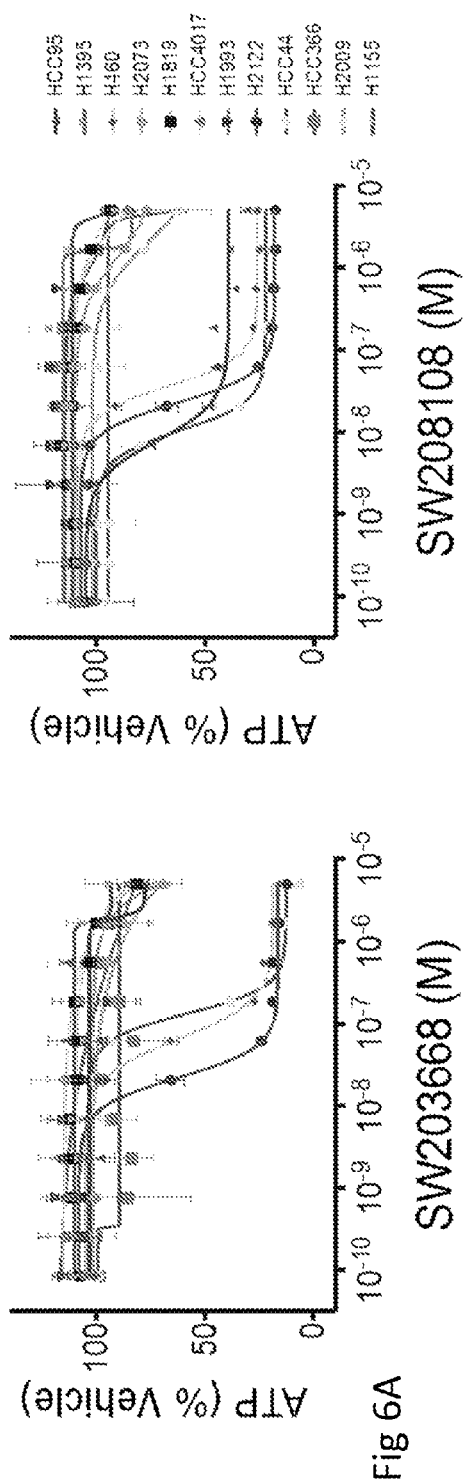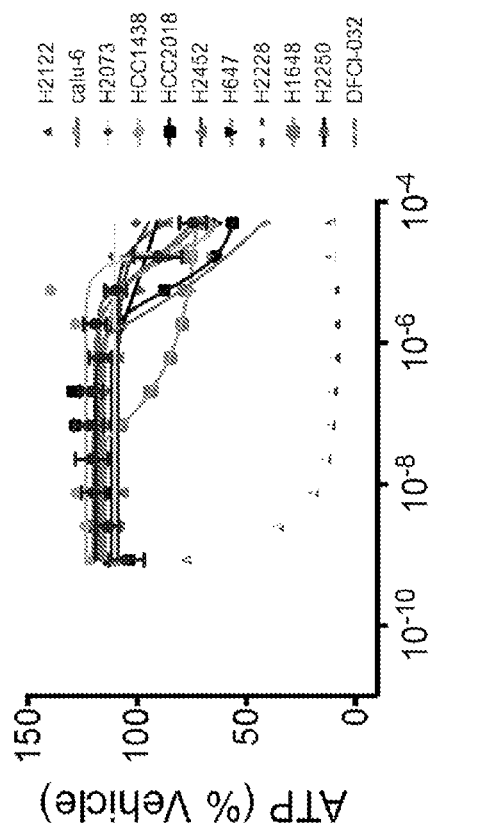
Fig 6A
Fig 6B

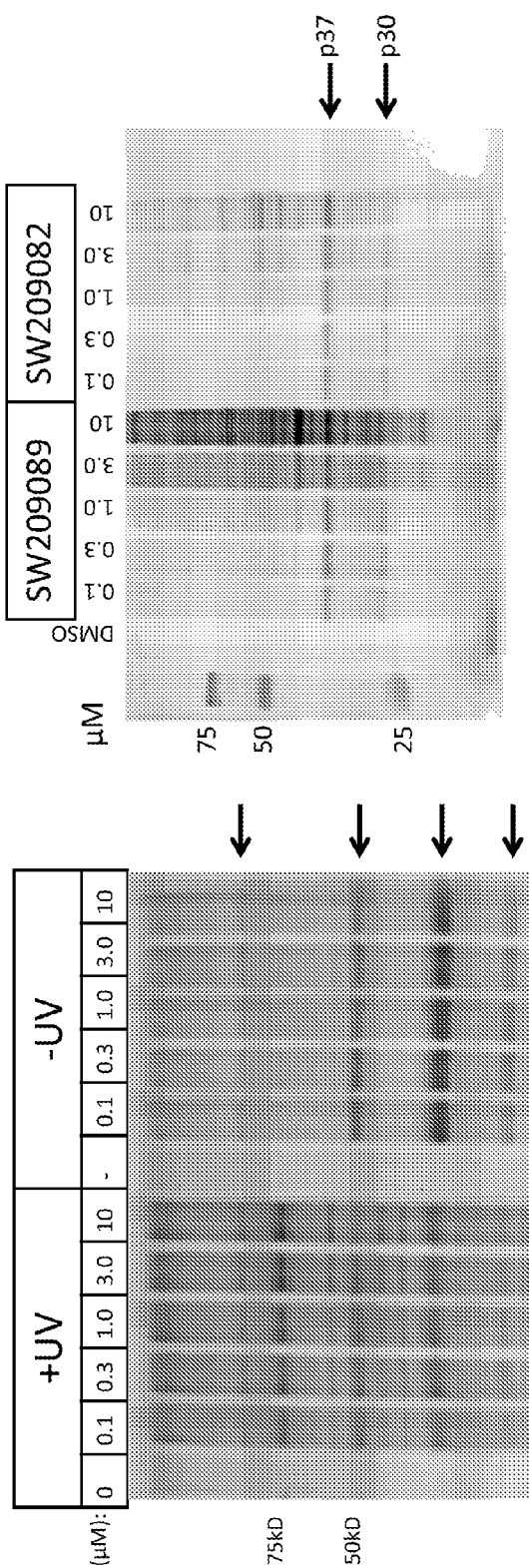
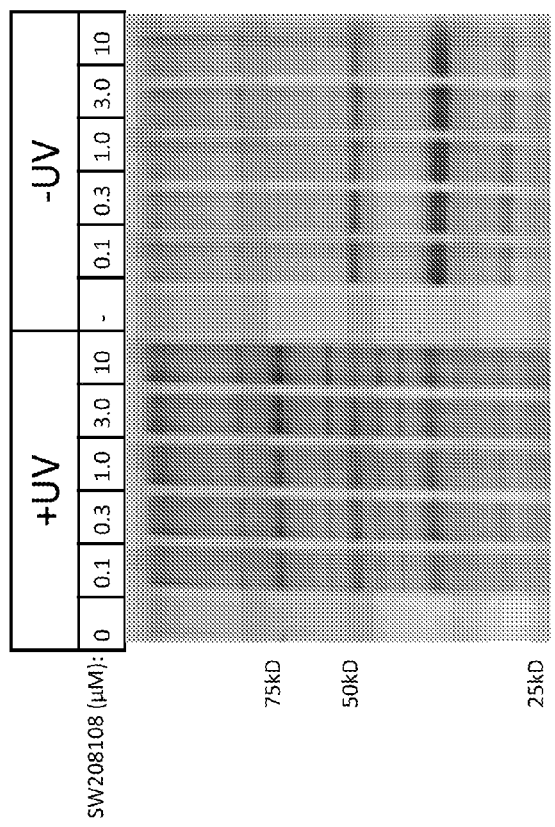
Fig 7A
Fig 7B

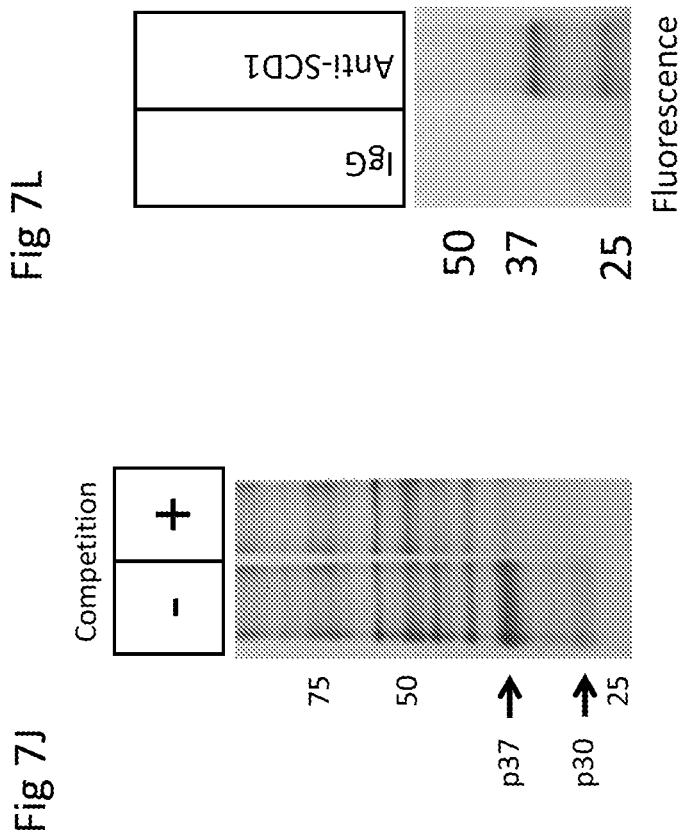

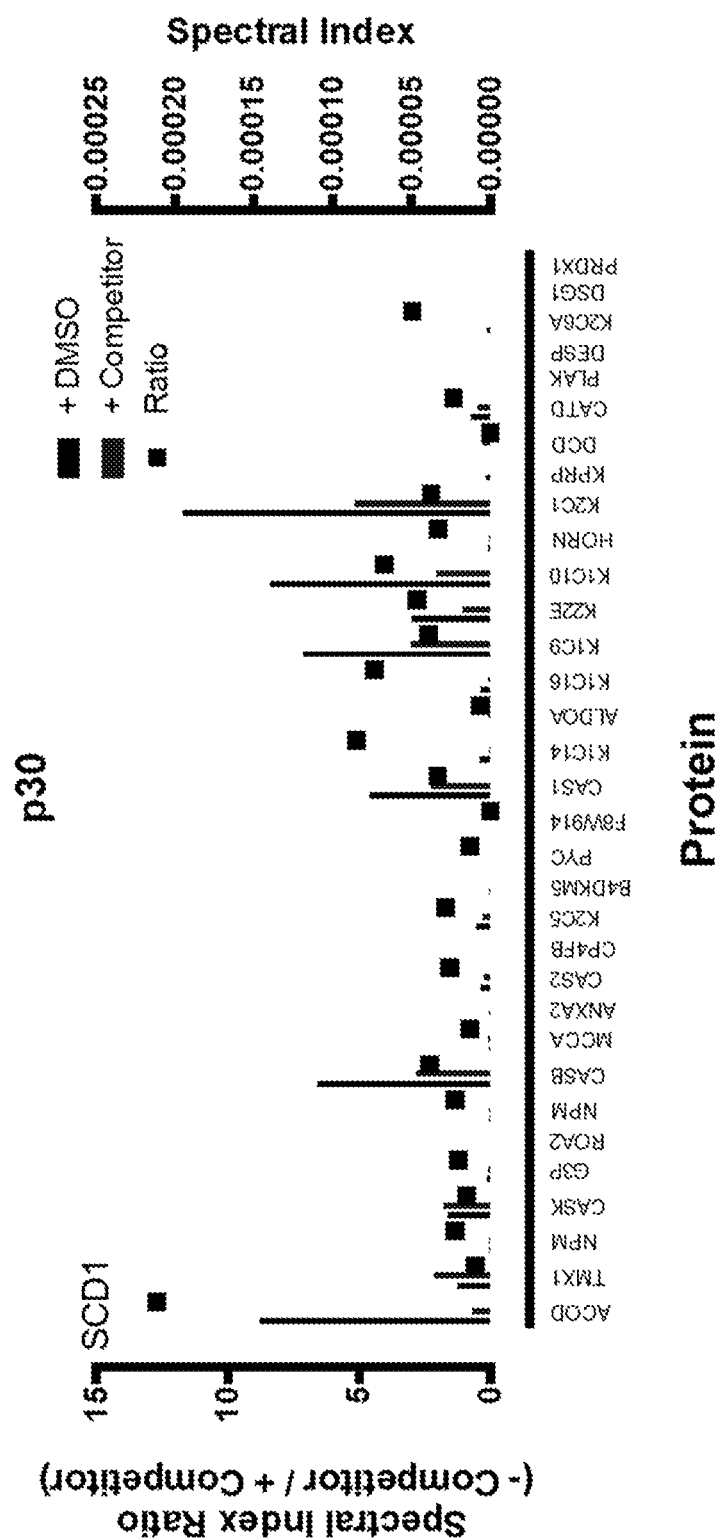

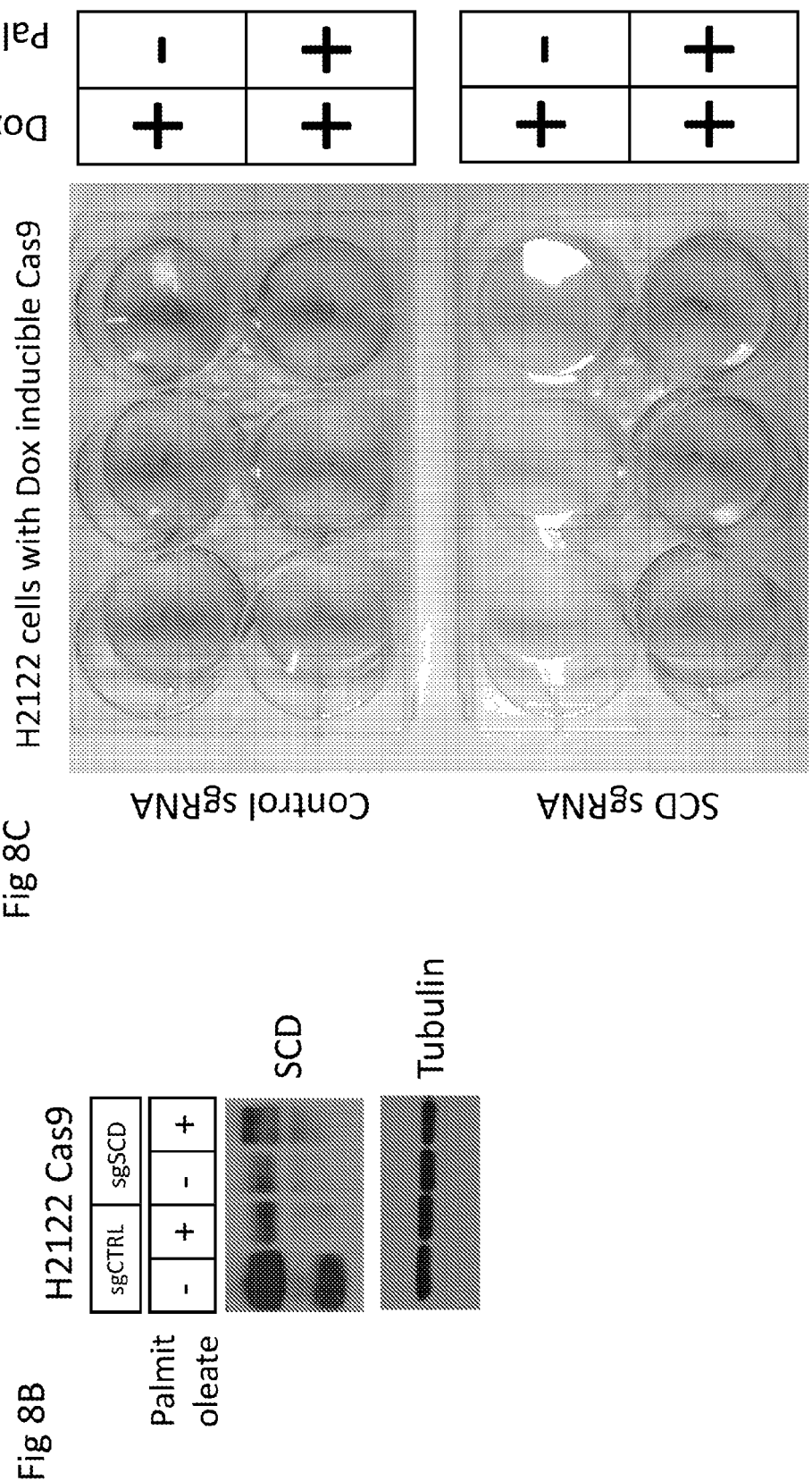

METHODS AND COMPOSITIONS FOR SELECTIVE AND TARGETED CANCER THERAPY

CROSS REFERENCE TO RELATED APPLICATIONS

This application is a U.S. National Phase application of International Application No. PCT/US2014/054099 filed Sep. 4, 2014, which claims priority to and the benefit of U.S. Provisional Application Nos. 61/873,781 filed Sep. 4, 2013 and 61/938,603 filed Feb. 11, 2014, the disclosures of which are incorporated herein by reference in their entirety.

FIELD

Presented herein are methods and compositions for selective and targeted cancer therapy, in particular N-acylated amino heterocycles, heterocyclic carboxamides, oxalamides, N-acyl ureas, and chromones and their use in selectively treating certain cancers.

BACKGROUND

Cancer therapies aim to exploit differences between cancer cells and normal cells to obtain a therapeutic window wherein the treatment is toxic to the cancer but not the organism. Since cancers are the consequence of somatic genetic alterations that collectively lead to tumor formation and growth, a dominant therapeutic paradigm is to target these altered genes and their pathways.[1] These underlying principles fueled the cancer genomic revolution leading to the discovery of many of the genes (and genotypes) that initiate and drive cancer growth. Unfortunately, these genes seldom affect proteins that can readily be chemically manipulated, leaving a long list of putative targets but little guidance as to which to "drug". In order to fulfill the promise of targeted therapy, we now need to match these cancer genotypes with new chemical sensitivities.

Lung cancer remains the leading cause of cancer related death in the United States and there is an urgent need for new and effective therapy. Lung adenocarcinomas, the most common histologic type, originate from somatic alterations in different genes that drive tumor growth including the tyrosine kinases, EGFR and ALK. Mutations in EGFR or structural rearrangements of ALK lead to constitutive tyrosine kinase activity that these cancers depend on to grow. As such, patients whose tumors harbor these alterations exhibit dramatic clinical responses to their respective inhibitors, erlotinib and crizotinib.[2,3] Unfortunately, EGFR mutations and ALK alterations occur in the minority of patients, and most patients still lack a comparably efficacious targeted therapy. Hence, a first step toward new therapies has been to characterize cancer genomes in order to identify genetic alterations that can be similarly targeted.

Large-scale efforts to characterize the cancer genome in lung adenocarcinoma, however, have not revealed common alterations that can be readily "drugged". The most frequent alterations discovered in whole genome sequence analysis of 200 lung adenocarcinomas were in already known driver genes including TP53, KRAS, EGFR, and ALK.[4,5] Newly discovered alterations were the exception and, unlike EGFR or ALK, offer no clear path for developing small molecule modulators. Likewise, genome-wide copy number analyses across hundreds of lung adenocarcinomas have identified putative targets, but again without any known corresponding chemical dependency.[6]

Thus, a need exists for new chemical identities that selectively target specific anomalies (e.g., genetic, epigenetic and/or metabolic) in select cancer patient sub-population, thereby permitting the development of personalized medicine in cancer therapy. An important consideration in the development of such therapeutic agents is their relative toxicity towards normal human tissue and the cancerous tissue or cells. This therapeutic index defines the dose at which treatments can be administered and their effectiveness. In this context, identification of novel approaches to target cancerous tissue while sparing normal tissue remains an important objective.

SUMMARY

Presented herein are methods and compositions for selective and targeted cancer therapy, in particular N-acylated amino heterocycles, heterocyclic carboxamides, oxalamides N-acyl ureas and chromones, and their use in selectively treating certain cancers. Most existing therapies are non-selectively toxic towards all cancer lines. The compounds (or pharmaceutically acceptable salts or prodrugs thereof) described herein are toxic to sub-sets of cancer cells, while other cancer cells and normal cells appear insensitive to these agents. The large difference in selectivity (>1000-fold in some cases) between sensitive and insensitive cancer cell lines and between sensitive and non-cancerous cell lines offers the chance for high therapeutic indices. Additionally, in some embodiments, these compounds are selectively converted from an inactive, or pro-drug, form to an active toxin by the enzymes within the affected cancer cell. Thus, selective toxicity can be achieved by generating the toxin locally within the tumor by the action of the cancer cells themselves. Moreover, the selective toxins are found to irreversibly react with certain enzymes, thereby inhibiting their enzymatic function.

In some embodiments, a method for selectively treating cancer is provided, comprising administering, to a patient having a first predetermined cancer genotype, an effective amount of a compound of formula (A) or a pharmaceutically acceptable salt thereof, wherein said compound or salt thereof is ineffective against a second predetermined cancer genotype:

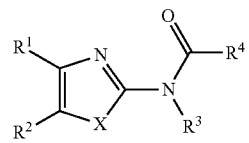

(A)

wherein:
X is selected from S, $NR^A$, $NR^B$, O and C=O;
$R^1$ and $R^2$ are each independently selected from: hydrogen; halo; hydroxyl; $C_{1-6}$ (e.g., $C_{1-3}$) alkoxyl optionally substituted with 1 or more hydroxyl, cyano and/or halo; $C_{1-6}$ (e.g., $C_{1-3}$) carbonyl; $C_{1-6}$ (e.g., $C_{1-3}$) alkoxycarbonyl; cyano; nitro; amine; —$(O(CH_2)_{1-3})_n$—CCH wherein n is an integral selected from 1-5; $R^A$; and $R^B$; or $R^1$ and $R^2$ together with the carbons they are attached to form a 5-7 membered saturated, unsaturated or aryl ring, wherein each position in the ring is selected from nitrogen or optionally substituted carbon;
$R^3$ and $R^A$ are each independently selected from $C_{1-6}$ (e.g., $C_{1-3}$) alkyl, $C_{2-6}$ (e.g., $C_{2-3}$) alkenyl and $C_{2-6}$ (e.g., $C_{2-3}$)

alkynyl, each optionally substituted with 1 or more halo, hydroxyl, $C_{1-6}$ (e.g., $C_{1-3}$) alkoxyl, $C_{1-6}$ (e.g., $C_{1-3}$) carbonyl, $C_{1-6}$ (e.g., $C_{1-3}$) alkoxycarbonyl, cyano, nitro, and/or amine; and $R^4$ and $R^B$ are each independently selected from $C_{3-12}$ cycloalkyl, $C_{2-6}$ heterocyclyl, $C_{6-12}$ aryl and $C_{4-12}$ heteroaryl, each optionally substituted with 1 or more halo; hydroxyl; $C_{1-6}$ alkyl optionally substituted with 1 or more $C_{3-12}$ cycloalkyl, $C_{2-6}$ heterocyclyl, $C_{6-12}$ aryl, $C_{4-12}$ heteroaryl, amine, oxo, halo and/or hydroxyl; $C_{1-6}$ alkoxyl optionally substituted with 1 or more $C_{3-12}$ cycloalkyl, $C_{2-6}$ heterocyclyl, $C_{6-12}$ aryl, $C_{4-12}$ heteroaryl, amine, oxo, halo and/or hydroxyl; $C_{1-6}$ (e.g., $C_{1-3}$) carbonyl optionally substituted with 1 or more $C_{3-12}$ cycloalkyl, $C_{2-6}$ heterocyclyl, $C_{6-12}$ aryl, $C_{4-12}$ heteroaryl, and/or amine; $C_{2-6}$ (e.g., $C_{2-3}$) alkoxycarbonyl; cyano; nitro; azide; amine; $C_{3-12}$ cycloalkyl; $C_{2-6}$ heterocyclyl; $C_{6-12}$ aryl; and/or $C_{4-12}$ heteroaryl; wherein each of the substituents $C_{3-12}$ cycloalkyl, $C_{2-6}$ heterocyclyl, $C_{6-12}$ aryl and $C_{4-12}$ heteroaryl is additionally optionally substituted with 1 or more halo, hydroxyl, $C_{1-6}$ alkyl, $C_{1-6}$ (e.g., $C_{1-3}$) alkoxyl, $C_{1-6}$ (e.g., $C_{1-3}$) alkoxycarbonyl, cyano, nitro and/or amine.

In some embodiments, the compound or salt has formula (I):

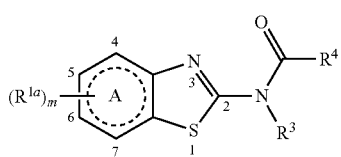

(I)

wherein:

A is a saturated, unsaturated or aryl ring such as cyclohexane, cyclohexene or phenyl, wherein any position (e.g., any one or more of C4, C5, C6 and C7) in said ring is optionally substituted with nitrogen;

$R^{1a}$ is attached to any one or more of C4, C5, C6 and C7 position, and at each occurrence selected from: hydrogen; halo; hydroxyl; $C_{1-6}$ (e.g., $C_{1-3}$) alkoxyl optionally substituted with 1 or more hydroxyl, cyano and/or halo; $C_{1-6}$ (e.g., $C_{1-3}$) carbonyl; $C_{1-6}$ (e.g., $C_{1-3}$) alkoxycarbonyl; cyano; nitro; amine; —(O($CH_2$)$_{1-3}$)$_n$—CCH wherein n is an integral selected from 1-5; and $R^A$; and m is an integral selected from 0-4.

In some embodiments, the compound or salt has formula (II):

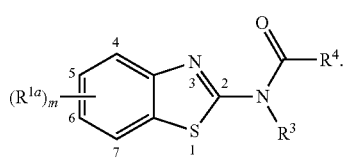

(II)

In one aspect, a compound of formula (III) or a pharmaceutically acceptable salt thereof is provided:

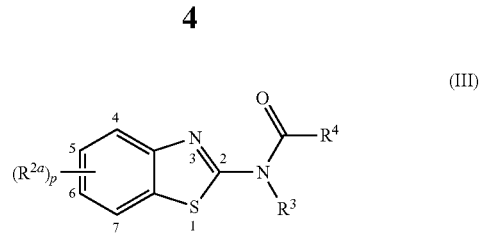

(III)

wherein:

$R^{2a}$ is attached to any one or more of C4, C5, C6 and C7 position, and at each occurrence is hydrogen, hydroxyl, $C_{1-12}$ alkoxyl, $C_{6-12}$ aryloxyl, $C_{4-12}$ heteroaryloxyl or —(O($CH_2$)$_{1-3}$)$_n$—CCH wherein n is an integral selected from 1-5;

p is an integral selected from 1-4;

$R^3$ is selected from $C_{1-6}$ (e.g., $C_{1-3}$) alkyl, $C_{2-6}$ (e.g., $C_{2-3}$) alkenyl and $C_{2-6}$ (e.g., $C_{2-3}$) alkynyl, each optionally substituted with 1 or more halo, hydroxyl, $C_{1-6}$ (e.g., $C_{1-3}$) alkoxyl, $C_{1-6}$ (e.g., $C_{1-3}$) carbonyl, $C_{1-6}$ (e.g., $C_{1-3}$) alkoxycarbonyl, cyano, nitro, and/or amine; and $R^4$ is selected from $C_{3-12}$ cycloalkyl, $C_{2-6}$ heterocyclyl, $C_{6-12}$ aryl and $C_{4-12}$ heteroaryl, each optionally substituted with 1 or more halo; hydroxyl; $C_{1-6}$ alkyl optionally substituted with 1 or more $C_{3-12}$ cycloalkyl, $C_{2-6}$ heterocyclyl, $C_{6-12}$ aryl, $C_{4-12}$ heteroaryl, amine, oxo, halo and/or hydroxyl; $C_{1-6}$ alkoxyl optionally substituted with 1 or more $C_{3-12}$ cycloalkyl, $C_{2-6}$ heterocyclyl, $C_{6-12}$ aryl, $C_{4-12}$ heteroaryl, amine, oxo, halo and/or hydroxyl; $C_{1-6}$ (e.g., $C_{1-3}$) carbonyl optionally substituted with 1 or more $C_{3-12}$ cycloalkyl, $C_{2-6}$ heterocyclyl, $C_{6-12}$ aryl, $C_{4-12}$ heteroaryl, and/or amine; $C_{2-6}$ (e.g., $C_{2-3}$) alkoxycarbonyl; cyano; nitro; azide; amine; $C_{3-12}$ cycloalkyl; $C_{2-6}$ heterocyclyl; $C_{6-12}$ aryl; and/or $C_{4-12}$ heteroaryl; wherein each of the substituents $C_{3-12}$ cycloalkyl, $C_{2-6}$ heterocyclyl, $C_{6-12}$ aryl and $C_{4-12}$ heteroaryl is additionally optionally substituted with 1 or more halo, hydroxyl, $C_{1-6}$ alkyl, $C_{1-6}$ (e.g., $C_{1-3}$) alkoxyl, $C_{1-6}$ (e.g., $C_{1-3}$) alkoxycarbonyl, cyano, nitro and/or amine.

In certain embodiments, a compound of formula (IV) or a pharmaceutically acceptable salt thereof is provided:

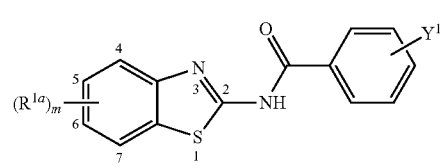

(IV)

wherein:

$R^{1a}$ is attached to any one or more of C4, C5, C6 and C7 position, and at each occurrence is selected from: hydrogen; halo; hydroxyl; $C_{1-6}$ (e.g., $C_{1-3}$) alkoxyl optionally substituted with 1 or more hydroxyl, cyano and/or halo; $C_{1-6}$ (e.g., $C_{1-3}$) carbonyl; $C_{1-6}$ (e.g., $C_{1-3}$) alkoxycarbonyl; cyano; nitro; amine; —(O($CH_2$)$_{1-3}$)$_n$—CCH wherein n is an integral selected from 1-5; and $R^A$;

m is an integral selected from 0-4; and $Y^1$ is selected from: azide; —C(O)$R^a$, —CH(OH)$R^a$, —CH($NH_2$)$R^a$, —NH$R^a$, —C(O)NH($CH_2$)$_{0-6}R^a$ and —C(O)N($R^b$)($R^c$), each optionally substituted with 1 or more $R^A$;

wherein $R^A$ is selected from $C_{1-6}$ (e.g., $C_{1-3}$) alkyl, $C_{2-6}$ (e.g., $C_{2-3}$) alkenyl and $C_{2-6}$ (e.g., $C_{2-3}$) alkynyl, each optionally substituted with 1 or more halo, hydroxyl, $C_{1-6}$ (e.g., $C_{1-3}$)

alkoxyl, $C_{1-6}$ (e.g., $C_{1-3}$) carbonyl, $C_{1-6}$ (e.g., $C_{1-3}$) alkoxycarbonyl, cyano, nitro, and/or amine;

wherein $R^a$ is, at each occurrence, independently selected from $C_{3-12}$ cycloalkyl, $C_{2-6}$ heterocyclyl, $C_{6-12}$ aryl and $C_{4-12}$ heteroaryl, each optionally substituted with 1 or more halo, hydroxyl, $C_{1-6}$ alkyl, $C_{1-6}$ (e.g., $C_{1-3}$) alkoxyl, $C_{1-6}$ (e.g., $C_{1-3}$) alkoxycarbonyl, cyano, nitro and/or amine;

wherein $R^b$ and $R^c$ are each independently selected from $R^a$ and $R^A$; or $R^b$ and $R^c$ together with the nitrogen they are attached to form a $C_{2-6}$ heterocyclyl or $C_{4-12}$ heteroaryl ring.

In an embodiment, in the compound or salt of formula (IV), $Y^1$ is at the para position.

Another aspect of the present invention relates to a method for selectively treating cancer, comprising administering, to a patient having a first predetermined cancer genotype, an effective amount of a compound of formula (V) or a pharmaceutically acceptable salt thereof, wherein said compound or salt thereof is ineffective against a second predetermined cancer genotype:

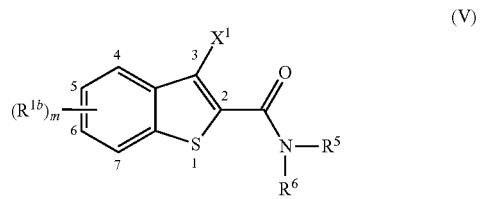

wherein:
$X^1$ is halo;
$R^{1b}$ is attached to any one or more of the C4, C5, C6 and C7 position, and at each occurrence is selected from: hydrogen; halo; hydroxyl; $C_{1-6}$ (e.g., $C_{1-3}$) alkoxyl optionally substituted with 1 or more hydroxyl, cyano and/or halo; $C_{1-6}$ (e.g., $C_{1-3}$) carbonyl; $C_{1-6}$ (e.g., $C_{1-3}$) alkoxycarbonyl; cyano; nitro; amine; —$(O(CH_2)_{1-3})_n$—CCH wherein n is an integral selected from 1-5; and $R^A$;
m is an integral selected from 0-4;
one of $R^5$ and $R^6$ is selected from hydrogen and $C_{1-6}$ alkyl; and
the other of $R^5$ and $R^6$ is selected from $C_{3-12}$ cycloalkyl, $C_{2-6}$ heterocyclyl, $C_{6-12}$ aryl and $C_{4-12}$ heteroaryl, each optionally substituted with 1 or more halo; hydroxyl; $C_{1-6}$ alkyl optionally substituted with 1 or more $C_{3-12}$ cycloalkyl, $C_{2-6}$ heterocyclyl, $C_{6-12}$ aryl, $C_{4-12}$ heteroaryl, amine, oxo, halo and/or hydroxyl; $C_{1-6}$ alkoxyl optionally substituted with 1 or more $C_{3-12}$ cycloalkyl, $C_{2-6}$ heterocyclyl, $C_{6-12}$ aryl, $C_{4-12}$ heteroaryl, amine, oxo, halo and/or hydroxyl; $C_{1-6}$ (e.g., $C_{1-3}$) carbonyl optionally substituted with 1 or more $C_{3-12}$ cycloalkyl, $C_{2-6}$ heterocyclyl, $C_{6-12}$ aryl, $C_{4-12}$ heteroaryl, and/or amine; $C_{2-6}$ (e.g., $C_{2-3}$) alkoxycarbonyl; cyano; nitro; azide; amine; $C_{3-12}$ cycloalkyl; $C_{2-6}$ heterocyclyl; $C_{6-12}$ aryl; and/or $C_{4-12}$ heteroaryl; wherein each of the substituents $C_{3-12}$ cycloalkyl, $C_{2-6}$ heterocyclyl, $C_{6-12}$ aryl and $C_{4-12}$ heteroaryl is additionally optionally substituted with 1 or more halo, hydroxyl, $C_{1-6}$ alkyl, $C_{1-6}$ (e.g., $C_{1-3}$)alkoxyl, $C_{1-6}$ (e.g., $C_{1-3}$) alkoxycarbonyl, cyano, nitro and/or amine;
wherein $R^A$ is selected from $C_{1-6}$ (e.g., $C_{1-3}$) alkyl, $C_{2-6}$ (e.g., $C_{2-3}$) alkenyl and $C_{2-6}$ (e.g., $C_{2-3}$) alkynyl, each optionally substituted with 1 or more halo, hydroxyl, $C_{1-6}$ (e.g., $C_{1-3}$) alkoxyl, $C_{1-6}$ (e.g., $C_{1-3}$) carbonyl, $C_{1-6}$ (e.g., $C_{1-3}$) alkoxycarbonyl, cyano, nitro, and/or amine.

Also included in the present invention is a compound of formula (VI) or a pharmaceutically acceptable salt thereof:

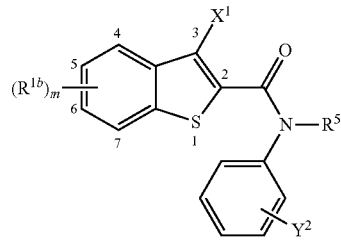

wherein:
$X^1$ is halo;
$R^{1b}$ is attached to any one or more of the C4, C5, C6 and C7 position, and at each occurrence is selected from: hydrogen; halo; hydroxyl; $C_{1-6}$ (e.g., $C_{1-3}$) alkoxyl optionally substituted with 1 or more hydroxyl, cyano and/or halo; $C_{1-6}$ (e.g., $C_{1-3}$) carbonyl; $C_{1-6}$ (e.g., $C_{1-3}$) alkoxycarbonyl; cyano; nitro; amine; —$(O(CH_2)_{1-3})_n$—CCH wherein n is an integral selected from 1-5; and $R^A$;
m is an integral selected from 0-4;
$R^5$ is selected from hydrogen and $C_{1-6}$ alkyl; and
$Y^2$ is selected from: halo; hydroxyl; $C_{1-6}$ alkyl optionally substituted with 1 or more $C_{3-12}$ cycloalkyl, $C_{2-6}$ heterocyclyl, $C_{6-12}$ aryl, $C_{4-12}$ heteroaryl, amine, oxo, halo and/or hydroxyl; $C_{1-6}$ alkoxyl optionally substituted with 1 or more $C_{3-12}$ cycloalkyl, $C_{2-6}$ heterocyclyl, $C_{6-12}$ aryl, $C_{4-12}$ heteroaryl, amine, oxo, halo and/or hydroxyl; $C_{1-6}$ (e.g., $C_{1-3}$) carbonyl optionally substituted with 1 or more $C_{3-12}$ cycloalkyl, $C_{2-6}$ heterocyclyl, $C_{6-12}$ aryl, $C_{4-12}$ heteroaryl, and/or amine; $C_{2-6}$ (e.g., $C_{2-3}$) alkoxycarbonyl; nitro; azide; amine; $C_{3-12}$ cycloalkyl; $C_{2-6}$ heterocyclyl; $C_{6-12}$ aryl; and/or $C_{4-12}$ heteroaryl; wherein each of the substituents $C_{3-12}$ cycloalkyl, $C_{2-6}$ heterocyclyl, $C_{6-12}$ aryl and $C_{4-12}$ heteroaryl is additionally optionally substituted with 1 or more halo, hydroxyl, $C_{1-6}$ alkyl, $C_{1-6}$ (e.g., $C_{1-3}$) alkoxyl, $C_{1-6}$ (e.g., $C_{1-3}$) alkoxycarbonyl, cyano, nitro and/or amine;
wherein $R^A$ is selected from $C_{1-6}$ (e.g., $C_{1-3}$) alkyl, $C_{2-6}$ (e.g., $C_{2-3}$) alkenyl and $C_{2-6}$ (e.g., $C_{2-3}$) alkynyl, each optionally substituted with 1 or more halo, hydroxyl, $C_{1-6}$ (e.g., $C_{1-3}$) alkoxyl, $C_{1-6}$ (e.g., $C_{1-3}$) carbonyl, $C_{1-6}$ (e.g., $C_{1-3}$) alkoxycarbonyl, cyano, nitro, and/or amine.

In some embodiments, $Y^2$ is not methoxycarbonyl.

A further aspect relates to a method for selectively treating cancer, comprising administering, to a patient having a first predetermined cancer genotype, an effective amount of a compound of formula (VII) or a pharmaceutically acceptable salt thereof, wherein said compound or salt thereof is ineffective against a second predetermined cancer genotype:

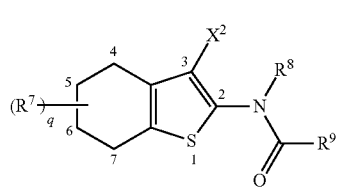

wherein:
$X^2$ is —$C(O)R^d$ wherein $R^d$ is hydroxyl, $C_{1-6}$ (e.g., $C_{1-3}$) alkoxyl, or amine;
$R^7$ is attached to any one or more of the C4, C5, C6 and C7 position, and at each occurrence is selected from: hydrogen; halo; hydroxyl; $C_{1-6}$ (e.g., $C_{1-3}$) alkoxyl optionally substituted with 1 or more hydroxyl, cyano and/or halo; $C_{1-6}$ (e.g., $C_{1-3}$) carbonyl; $C_{1-6}$ (e.g., $C_{1-3}$) alkoxycarbonyl; cyano; nitro; amine; $-(O(CH_2)_{1-3})_n-CCH$ wherein n is an integral selected from 1-5; and $R^A$;

q is an integral selected from 0-4;

$R^8$ is selected from hydrogen and $C_{1-6}$ alkyl; and $R^9$ is selected from $C_{3-12}$ cycloalkyl, $C_{2-6}$ heterocyclyl, $C_{6-12}$ aryl and $C_{4-12}$ heteroaryl, each substituted with 1 or more halo; hydroxyl; $C_{1-6}$ alkyl optionally substituted with 1 or more $C_{3-12}$ cycloalkyl, $C_{2-6}$ heterocyclyl, $C_{6-12}$ aryl, $C_{4-12}$ heteroaryl, amine, oxo, halo, hydroxyl, $C_{1-6}$ alkoxyl and/or phenol; $C_{3-12}$ cycloalkyl; $C_{2-6}$ heterocyclyl; $C_{6-12}$ aryl; and/or $C_{4-12}$ heteroaryl; wherein each of the substituents $C_{3-12}$ cycloalkyl, $C_{2-6}$ heterocyclyl, $C_{6-12}$ aryl and $C_{4-12}$ heteroaryl is additionally optionally substituted with 1 or more halo, hydroxyl, $C_{1-6}$ alkyl, $C_{1-6}$ (e.g., $C_{1-3}$) alkoxyl, $C_{1-6}$ (e.g., $C_{1-3}$) alkoxycarbonyl, cyano, nitro and/or amine;

wherein $R^A$ is selected from $C_{1-6}$ (e.g., $C_{1-3}$) alkyl, $C_{2-6}$ (e.g., $C_{2-3}$) alkenyl and $C_{2-6}$ (e.g., $C_{2-3}$) alkynyl, each optionally substituted with 1 or more halo, hydroxyl, $C_{1-6}$ (e.g., $C_{1-3}$) alkoxyl, $C_{1-6}$ (e.g., $C_{1-3}$) carbonyl, $C_{1-6}$ (e.g., $C_{1-3}$) alkoxycarbonyl, cyano, nitro, and/or amine.

A still further aspect relates to compound of formula (VII) or a pharmaceutically acceptable salt thereof:

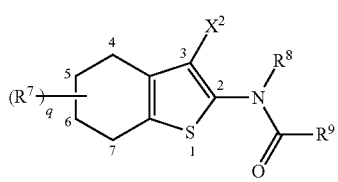

(VII)

wherein:

$X^2$ is $-C(O)R^d$ wherein $R^d$ is hydroxyl, $C_{1-6}$ (e.g., $C_{1-3}$) alkoxyl, or amine;

$R^7$ is attached to any one or more of the C4, C5, C6 and C7 position, and at each occurrence is selected from: hydrogen; halo; hydroxyl; $C_{1-6}$ (e.g., $C_{1-3}$) alkoxyl optionally substituted with 1 or more hydroxyl, cyano and/or halo; $C_{1-6}$ (e.g., $C_{1-3}$) carbonyl; $C_{1-6}$ (e.g., $C_{1-3}$) alkoxycarbonyl; cyano; nitro; amine; $-(O(CH_2)_{1-3})_n-CCH$ wherein n is an integral selected from 1-5; and $R^A$;

q is an integral selected from 0-4;

$R^8$ is selected from hydrogen and $C_{1-6}$ alkyl; and $R^9$ is selected from $C_{3-12}$ cycloalkyl, $C_{2-6}$ heterocyclyl, $C_{6-12}$ aryl and $C_{4-12}$ heteroaryl, each substituted with 1 or more halo; hydroxyl; $C_{1-6}$ alkyl optionally substituted with 1 or more $C_{3-12}$ cycloalkyl, $C_{2-6}$ heterocyclyl, $C_{6-12}$ aryl, $C_{4-12}$ heteroaryl, amine, oxo, halo, hydroxyl, $C_{1-6}$ alkoxyl and/or phenol; $C_{3-12}$ cycloalkyl; $C_{2-6}$ heterocyclyl; $C_{6-12}$ aryl; and/or $C_{4-12}$ heteroaryl; wherein each of the substituents $C_{3-12}$ cycloalkyl, $C_{2-6}$ heterocyclyl, $C_{6-12}$ aryl and $C_{4-12}$ heteroaryl is additionally optionally substituted with 1 or more halo, hydroxyl, $C_{1-6}$ alkyl, $C_{1-6}$ (e.g., $C_{1-3}$) alkoxyl, $C_{1-6}$ (e.g., $C_{1-3}$) alkoxycarbonyl, cyano, nitro and/or amine;

wherein $R^A$ is selected from $C_{1-6}$ (e.g., $C_{1-3}$) alkyl, $C_{2-6}$ (e.g., $C_{2-3}$) alkenyl and $C_{2-6}$ (e.g., $C_{2-3}$) alkynyl, each optionally substituted with 1 or more halo, hydroxyl, $C_{1-6}$ (e.g., $C_{1-3}$) alkoxyl, $C_{1-6}$ (e.g., $C_{1-3}$) carbonyl, $C_{1-6}$ (e.g., $C_{1-3}$) alkoxycarbonyl, cyano, nitro, and/or amine.

In another aspect, compounds of formula (B) are provided:

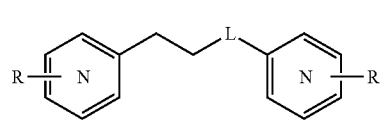

(B)

In the above formula (B), R is optional and at each occurrence is attached to the aromatic ring at one or more positions (e.g., 1, 2, 3, 4 or 5). Rat each occurrence is independently selected from: hydrogen; halo; hydroxyl; $C_{1-6}$ (e.g., $C_{1-3}$) alkoxyl, $C_{6-12}$ aryloxyl and $C_{4-12}$ heteroaryloxyl, each optionally substituted with 1 or more hydroxyl, cyano and/or halo; $C_{1-6}$ (e.g., $C_{1-3}$) carbonyl; $C_{1-6}$ (e.g., $C_{1-3}$) alkoxycarbonyl; cyano; nitro; amine; $-(O(CH_2)_{1-3})_n-CCH$ wherein n is an integral selected from 1-5; and $C_{1-6}$ (e.g., $C_{1-3}$) alkyl, $C_{2-6}$ (e.g., $C_{2-3}$) alkenyl and $C_{2-6}$ (e.g., $C_{2-3}$) alkynyl, each optionally substituted with 1 or more halo, hydroxyl, $C_{1-6}$ (e.g., $C_{1-3}$) alkoxyl, $C_{6-12}$ aryloxyl, $C_{4-12}$ heteroaryloxyl, $C_{1-6}$ (e.g., $C_{1-3}$) carbonyl, $C_{1-6}$ (e.g., $C_{1-3}$) alkoxycarbonyl, cyano, nitro, and/or amine. L can be an amide containing linker, such as:

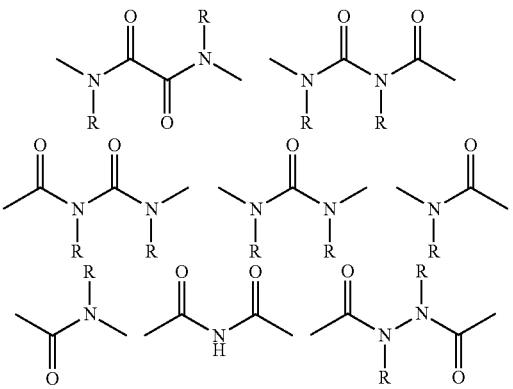

where each R is independently hydrogen, $C_{1-6}$ (e.g., $C_{1-3}$) alkyl, $C_{2-6}$ (e.g., $C_{2-3}$) alkenyl and $C_{2-6}$ (e.g., $C_{2-3}$) alkynyl, each optionally substituted with 1 or more halo, hydroxyl, $C_{1-6}$ (e.g., $C_{1-3}$) alkoxyl, $C_{1-6}$ (e.g., $C_{1-3}$) carbonyl, $C_{1-6}$ (e.g., $C_{1-3}$) alkoxycarbonyl, cyano, nitro, and/or amine.

represents an aromatic ring optionally substituted with 1 or more N (e.g., $C_{6-12}$ aryl or $C_{4-12}$ heteroaryl, such as phenyl and pyridyl).

In a further aspect, compounds of formula (C) are provided:

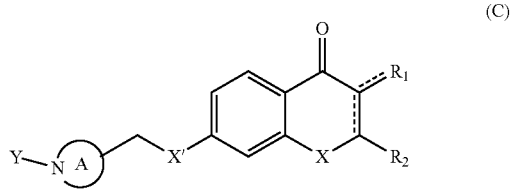

(C)

wherein:
X and X' are independently selected from O and NR, wherein R is selected from hydrogen and R', wherein R' is selected from C1-12 alkyl, C2-12 alkenyl, C2-12 alkynyl, C3-12 cycloalkyl, C2-6 heterocyclyl, C6-12 aryl and C4-12 heteroaryl, each optionally substituted with 1 or more R", wherein R" is selected from halo; hydroxyl; C1-6 alkyl optionally substituted with 1 or more C3-12 cycloalkyl, C2-6 heterocyclyl, C6-12 aryl, C4-12 heteroaryl, amine, oxo, halo, hydroxyl, C1-6 alkoxyl and/or phenol; C1-6 (e.g., C1-3) alkoxyl; C1-6 (e.g., C1-3) alkoxycarbonyl; cyano; nitro; amine; C3-12 cycloalkyl; C2-6 heterocyclyl; C6-12 aryl; and/or C4-12 heteroaryl; wherein each of the substituents C3-12 cycloalkyl, C2-6 heterocyclyl, C6-12 aryl and C4-12 heteroaryl is additionally optionally substituted with 1 or more halo, hydroxyl, C1-6 alkyl, C1-6 (e.g., C1-3) alkoxyl, C1-6 (e.g., C1-3) alkoxycarbonyl, cyano, nitro and/or amine;
Y is selected from C6-12 aryl and C4-12 heteroaryl, each optionally substituted with 1 or more R";

represents heteroaryl ring containing 1 or more N wherein at least 1 nitrogen is linked to Y, such as pyrazole, triazole, pyrrole, indazole, indole, and imidazole;
and R1 and R2 are independently selected from hydrogen, halo, R' and C1-12 alkoxyl optionally substituted with 1 or more R".

A compound of formula (VIII), or a pharmaceutically acceptable sale thereof is also provided:

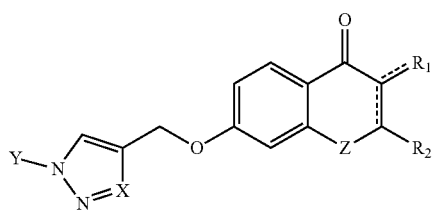

wherein:
X is CH, CR' or N; wherein R' is selected from C1-12 alkyl, C2-12 alkenyl, C2-12 alkynyl, C3-12 cycloalkyl, C2-6 heterocyclyl, C6-12 aryl and C4-12 heteroaryl, each optionally substituted with 1 or more R"; wherein R" is selected from halo; hydroxyl; C1-6 alkyl optionally substituted with 1 or more C3-12 cycloalkyl, C2-6 heterocyclyl, C6-12 aryl, C4-12 heteroaryl, amine, oxo, halo, hydroxyl, C1-6 alkoxyl and/or phenol; C1-6 (e.g., C1-3) alkoxyl; C1-6 (e.g., C1-3) alkoxycarbonyl; cyano; nitro; amine; C3-12 cycloalkyl; C2-6 heterocyclyl; C6-12 aryl; and/or C4-12 heteroaryl; wherein each of the substituents C3-12 cycloalkyl, C2-6 heterocyclyl, C6-12 aryl and C4-12 heteroaryl is additionally optionally substituted with 1 or more halo, hydroxyl, C1-6 alkyl, C1-6 (e.g., C1-3) alkoxyl, C1-6 (e.g., C1-3) alkoxycarbonyl, cyano, nitro and/or amine;
Y is selected from C6-12 aryl and C4-12 heteroaryl, each optionally substituted with 1 or more R";
Z is O or N(CH$_3$);
and R1 and R2 are independently selected from hydrogen, halo, R' and C1-12 alkoxyl optionally substituted with 1 or more R".

Additionally provided is a compound of formula (IX), or a pharmaceutically acceptable sale thereof:

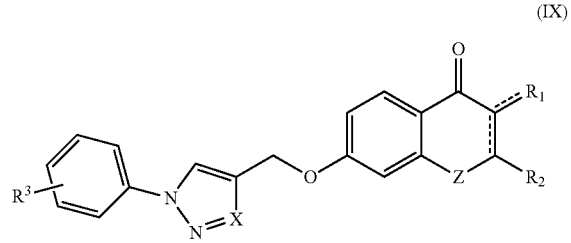

wherein:
X is CH, CR' or N; wherein R' is selected from C1-12 alkyl, C2-12 alkenyl, C2-12 alkynyl, C3-12 cycloalkyl, C2-6 heterocyclyl, C6-12 aryl and C4-12 heteroaryl, each optionally substituted with 1 or more R"; wherein R" is selected from halo; hydroxyl; C1-6 alkyl optionally substituted with 1 or more C3-12 cycloalkyl, C2-6 heterocyclyl, C6-12 aryl, C4-12 heteroaryl, amine, oxo, halo, hydroxyl, C1-6 alkoxyl and/or phenol; C1-6 (e.g., C1-3) alkoxyl; C1-6 (e.g., C1-3) alkoxycarbonyl; cyano; nitro; amine; C3-12 cycloalkyl; C2-6 heterocyclyl; C6-12 aryl; and/or C4-12 heteroaryl; wherein each of the substituents C3-12 cycloalkyl, C2-6 heterocyclyl, C6-12 aryl and C4-12 heteroaryl is additionally optionally substituted with 1 or more halo, hydroxyl, C1-6 alkyl, C1-6 (e.g., C1-3) alkoxyl, C1-6 (e.g., C1-3) alkoxycarbonyl, cyano, nitro and/or amine;
Z is O or N(CH$_3$);
R2 is selected from hydrogen and C1-12 alkyl optionally substituted with 1 or more R";
and R1 and R3 are independently selected from hydrogen, halo, R' and C1-12 alkoxyl optionally substituted with 1 or more R".

In a further aspect, compounds of formula (A), (B), (C) or (I)-(IX), or pharmaceutically acceptable salts thereof, can be used to selectively treat cancer or kill a cancer cell, such as certain non-small cell lung cancer. These compounds or salts thereof can be particularly useful in developing personalized medicine and therapy.

Certain compounds can act as prodrugs that are activated once administered to the patient. Such prodrugs can be activated by cytochrome P450 enzymes expressed by a cancer cell, thereby offering selective targeting. After activation, the activated form or drug may inhibit SCD1 (Stearoyl-CoA desaturase).

Accordingly, a method for selectively treating cancer or killing a cancer cell is provided, comprising administering a prodrug of formula (A), (B), (C) or (I)-(IX), or a pharmaceutically acceptable salt thereof, to a patient in need thereof, wherein said prodrug is activated by a cytochrome P450 enzyme, and the activated drug inhibits SCD1. Also provided is a method for selectively treating cancer or killing a cancer cell, comprising activating a prodrug by a cytochrome P450 enzyme, and inhibiting SCD1 with the activated drug. In some embodiments, the cytochrome P450 enzyme is CYP4F11. The CYP4F11 can be overexpressed in the cancer cell in the patient. In certain embodiments, the cancer is non-small cell lung cancer.

Another aspect of the present invention includes a method of inhibiting an enzyme with a hydroxyarene, wherein the enzyme contains iron that converts the hydroxyarene to a reactive species capable of forming an irreversible adduct with the enzyme. The enzyme can be a cytochrome P450, hemeoxygenase 1 or 2 or SCD1.

BRIEF DESCRIPTION OF THE DRAWINGS

FIG. 6A. Representative dose-response curves for 2 toxins against 12 non-small cell lung cancer lines demonstrating selective toxicity to a subset of human cancer cell lines. Cell viability is plotted vs. compound concentration. Compound was added to cells plated at 15% confluence in 96-well plates in RPMI-1640 media supplemented with 5% Fetal Bovine Serum and 2 mM L-Glutamine. After 4 days of incubation, ATP levels were measured using Cell Titer Glo (Promega). Data are presented as the average of 2 replicates ±SEM.

FIG. 6B. Dose response curves assaying the toxicity of a representative chromone, SW208833, to a panel of lung cancer cell lines. H2122 cells are sensitive to benzothiazoles, oxalamides, N-acyl ureas and chromones.

FIG. 7A. SW208108 covalently cross links proteins in H2122 cells in the absence of UV irradiation. H2122 cells were treated with the indicated concentrations of SW208108 for 4 h followed by irradiation with a UV light or no irradiation. Cells were then lysed, protein was precipitated, resuspended in buffer and conjugated to an azide-containing dye using Cu catalysis following standard protocols. Samples were resolved under denaturing conditions on an SDS-PAGE gel and visualized using a fluorescent imager at the indicated wavelengths. Arrows highlight prominent bands that demonstrate UV-independent covalent bond formation between SW208108 and several proteins.

FIG. 7B. Chromone and Benzothiazole alkynes, like the oxalamide, covalently bind proteins of similar molecular weight. The arrows indicate a 37 kD and 30 kD band common to all three scaffolds.

FIG. 7F. Two enantiomers of an N-aryl aminothiazole. FIG. 7G. Dose-response curves showing the toxicity of the two enantiomers to H2122 non-small cell lung cancer cells indicating that the S enantiomer is 4.4-fold more active. FIG. 7H. Using the competition assay described in FIG. 7B, SW208109 and SW208110 were found to compete for binding to p30 and p37, with the latter showing higher potency. FIG. 7I. Quantification of the intensity of the p37 band in FIG. 7H. The S enantiomer competes with SW208108 5.4-times more effectively than the R enantiomer.

FIG. 7J. Purification of proteins that bind to SW208108. Lysate was collected from H2122 cells that were incubated with 100 nM of SW208108 with either DMSO or 3 µM 208110 for 2 hours. These lysates were "clicked" to diazo-biotin (Click Chemistry Tools) in order to "tag" drug bound proteins. Following "click", protein was precipitated by the addition of acetone and resuspended in a binding buffer. Biotinylated proteins were affinity-purified by using an agarose-strepavidin conjugate beads. Following washing of the beads, bound proteins were eluted by cleaving the diazo linker using sodium dithionite. Eluent was resolved on a denaturing gel. Silver staining reveals two bands, p37 and p30 that are specifically competed by a 30-fold excess of an active compound lacking an alkyne.

FIG. 7L. Antibodies against SCD1 (Pierce) immunoprecipitate SW208108-bound protein. Samples were prepared as in FIG. 7A, and immunoprecipitated with either anti-SCD1 or IgG. The fluorescent bands confirm that p30 and p37 represent isoforms of SCD1.

FIGS. 8B-8C. Genetic ablation of SCD1 recapitulates toxicity observed with covalent binders of SCD1. FIG. 8B. Using a doxycycline-inducible Cas9 Crisper system, SCD1 was depleted from H2122 cells. FIG. 8B shows a western blot of cells treated with doxycycline for 2 days in the presence or absence of palmitoleate. Control cells express SCD1 in the absence but not presence of an unsaturated fatty acid, palmitoleate, while sgSCD cells express little if any SCD1 under either condition. FIG. 8C. SCD1 knockout is toxic to H2122 cells, and toxicity can be rescued with palmitoleate. Shown are three replicate wells of cells cultured in the presence of doxycycline and with or without palmitoleate. After 4 days, cells were stained with cresyl violet. Purple staining indicates viable cells. The results suggest that inhibition of SCD1 is toxic due to loss of unsaturated fatty acids.

FIG. 8D shows dose-response curves against 4 sensitive lines in the presence or absence of 100 μM sodium oleate. FIG. 8E shows that a known inhibitor of SCD1 is selectively toxic to the same 4 NSCLC lines. The data indicate that toxicity of SW208108 and related compounds is due to depletion of unsaturated fatty acids and is phenocopied by known SCD1 inhibitors.

FIG. 9A. 12 NSCLC cell lines were incubated with SW208108 and processed as described in FIG. 7. Fluorescence imaging reveals pronounced bands and p37 and p30 in the sensitive (underlined) lines but not in the majority of the insensitive lines. FIG. 9B. SCD1 expression was quantified by western blot across the same 12 NSCLC lines as in panel A and revealed little correlation between sensitivity and SCD1 expression. FIG. 9C. A representative oxalamide was found to be metabolized by a sensitive (H2122, IC50=350 nM) but not by an insensitive cell line (HCC4017, IC50>10 uM). Demethylation is the anticipated mode of metabolism. FIG. 9D. A representative benzothiazole is demethylated by sensitive cell lines. The chart shows the decrease in the parent compound, SW202857, and the increase in the demethylated metabolite, SW202864, in the presence of H2122 cells. Values in FIGS. 9C and 9D were obtained by tandem HPLC/MS/MS.

FIG. 10A. relative expression levels of mRNA for a panel of cytochrome P450 enzymes from the cancer cell line encyclopedia (CCLE, http://www.broadinstitute.org/ccle) showing CYP4F11 in particular is highly expressed in 4 NSCLC lines that are sensitive to SCD1 inhibition. FIG. 10B. Western blot showing that CYP4F11 protein is expressed in all sensitive cell lines but not in the majority of insensitive cell lines. FIG. 10C. H2122 cells were incubated with SW208108 in the presence of increasing quantities of a selective cytochrome P450 4F inhibitor, HET0016, and then conjugated with a fluorescent dye as described in FIG. 7. Inhibition of CYP4F blocks the formation of a covalent adduct between SW208108 and SCD1, indicating that metabolism of the former is required for covalent adduct formation and inhibition of SCD1. The approximated EC50 for inhibiting crosslinking (ca. 100 nM) compares favorably to the IC50 of HET0016 vs. CYP4 family members. FIG. 10D. Cells were incubated with either a methoxy-containing oxalamide, which represents the pro-drug form, or the hydroxy containing oxalamide, which represents the active form of the drug. Toxicity of the pro-drug was blocked by inhibition of CYP4 family members with HET0016. In contrast, the demethylated version of the same compound was fully active in the presence or absence of HET0016 indicating that it represents the active form of the drug. FIG. 10E. 293t cells were transfected with mammalian expression plasmids containing SCD1 or CYP4F11 as indicated. Cells were treated with either SW208108 or its demethylated congener, SW211666, and conjugated with a fluorescent dye as described in FIG. 7. Cells containing CYP4F11 form covalent adducts with both the pro-drug (methoxy) and drug form (demethylated, i.e. OH). The methylated, pro-drug form, SW208108, requires CYP4F11 as shown by the absence of cross-linked SCD1 in the absence of CYP4F11 or the presence of the CYP4 inhibitor HET0016. FIG. 10F. Shown are the results of a tritium release assay in which tritiated water is produced from tritiated stearoyl CoA by the action of SCD1. Thus, SCD1 is potently inhibited in the mouse liver, which expresses CYP4F11, by both SW208108 and SW211666 (top). By contrast, SW211666 but not SW208108 inhibits SCD1 in mouse preputial gland, which lacks CYP4F11 (bottom). The data indicate that metabolism of SW208108 into SW211666 is required for enzyme inhibition.

DETAILED DESCRIPTION

Figure 1:
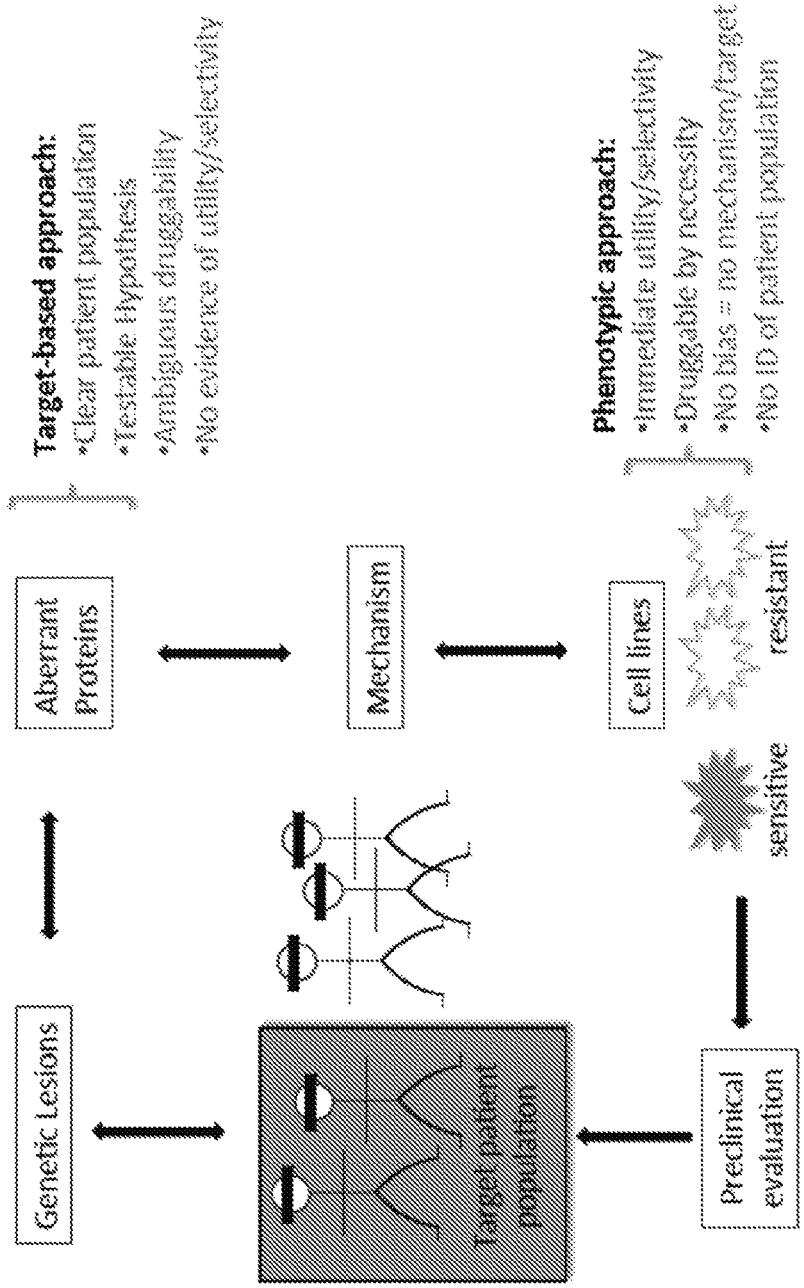
FIG. 1 compares traditional target-based approaches to phenotypic approaches and shows a representative phenotypic screen to identify selective cancer treatments.

Many anticancer agents are toxic to almost all cells. In contrast, we identified a class of small molecules that are selectively toxic towards some, but not all, cancer cell lines and are nontoxic towards normal cell lines. Moreover, for full toxicity, certain of these small molecules require enzymatic activation by cytochrome P450 enzymes, including dealkylation and hydroxylation. In this way, certain small molecules are selectively converted from a pro-drug state to an active drug by the cancerous cells or tissues, and therefore offer the possibility of localized delivery of an active cytotoxin. Additionally, they appear well tolerated in animal tests. Thus, the selective agents of the present invention are generally less toxic, have fewer side effects, and are better suited for identification of a suitable patient sub-population. For example, certain N-benzoyl aminobenzothiazoles are found to kill several cultured non-small cell lung cancer lines with potencies in the 1-100 nM range. In contrast, other non-small cell lung cancer lines and normal cell lines are not affected at concentrations up to 10 micromolar. Thus, these compounds could potentially be used to treat cancers with a high selectivity towards certain patient sub-populations.

In various embodiments, compounds having any one of formula (A), (B), (C) or (I)-(IX), or a pharmaceutically acceptable salt thereof, as described above and further described with exemplary embodiments hereunder can be used to selectively treat cancer.

Definitions

As used herein, "selective" or "selectivity" generally means that a compound is selectively toxic towards some, but not all, cancer cell lines and/or cell types. As such, the compounds (or pharmaceutically acceptable salts or prod-rugs thereof) described herein can be used to target specific anomalies (e.g., genetic, epigenetic and/or metabolic) of the sensitive cells (which have a corresponding "first predetermined cancer genotype"), while other cells appear insensitive to these agents (and have a corresponding "second predetermined cancer genotype"). Additionally, the term 'pro-drug' or 'prodrug' refers to a compound that requires chemical conversion in tissue, plasma or tumor to be converted into an active drug. This process can be mediated by an enzyme, for example a cytochrome P450 enzyme, and could involve addition of oxygen atoms or the cleavage of certain groups. In an embodiment, such selectivity might be mediated through inhibition of SCD1 or SCD (Stearoyl-CoA desaturase or delta-9-desaturase) and might require the activity of cytochrome P450 4F isoforms.

Selectivity may be measured by the half maximal inhibitory concentration ($IC_{50}$), which, as used herein, is a measure of the effectiveness of a compound in killing cells. This quantitative measure indicates how much of a particular compound is needed to kill a particular cell population by half (e.g., as indicated by the amount of ATP). In other words, it is the half maximal (50%) inhibitory concentration (IC) of a substance (50% IC, or $IC_{50}$). The $IC_{50}$ can be determined by constructing a dose-response curve. The lower the $IC_{50}$, the higher the potency, and the greater the difference between IC50 values for different cell lines (e.g., sensitive lines vs. insensitive lines, and sensitive lines vs. normal lines) the greater the selectivity. Generally, $IC_{50}$ lower than 5 μM (e.g., in the range of 1-100 nM) indicates high selectivity.

"Click" or "clicking" or related terms refer to Cu-promoted reactions between an organic azide and a terminal alkyne to form a disubstituted triazole. This process joins two molecules, such as a protein-bound small molecule and a dye.

"An effective amount" refers to an amount of a compound that confers a therapeutic effect (e.g., treats, e.g., controls, relieves, ameliorates, alleviates, or slows the progression of; or prevents, e.g., delays the onset of or reduces the risk of developing, a disease, disorder, or condition or symptoms thereof) on the treated subject. The therapeutic effect may be objective (i.e., measurable by some test or marker) or subjective (i.e., subject gives an indication of or feels an effect). An effective amount of the compound described above may range from about 0.01 mg/kg to about 1000 mg/kg, (e.g., from about 0.1 mg/kg to about 100 mg/kg, from about 1 mg/kg to about 100 mg/kg). Effective doses will also vary depending on route of administration, as well as the possibility of co-usage with other agents.

The following definitions are used, unless otherwise described. Specific and general values listed below for radicals, substituents, and ranges, are for illustration only; they do not exclude other defined values or other values within defined ranges for the radicals and substituents. Unless otherwise indicated, alkyl, alkoxy, alkenyl, and the like denote both straight and branched groups.

The term "halo" or "halogen" refers to any radical of fluorine, chlorine, bromine or iodine.

In general, and unless otherwise indicated, substituent (radical) prefix names are derived from the parent hydride by either (i) replacing the "ane" in the parent hydride with the suffixes "yl," "diyl," "triyl," "tetrayl," etc.; or (ii) replacing the "e" in the parent hydride with the suffixes "yl," "diyl," "triyl," "tetrayl," etc. (here the atom(s) with the free valence, when specified, is (are) given numbers as low as is consistent with any established numbering of the parent hydride). Accepted contracted names, e.g., adamantyl, naphthyl, anthryl, phenanthryl, furyl, pyridyl, quinolyl, and piperidyl, and trivial names, e.g., vinyl, allyl, phenyl, and thienyl are also used herein throughout. Conventional numbering/lettering systems are also adhered to for substituent numbering and the nomenclature of fused, bicyclic, tricyclic, polycyclic rings.

The term "alkyl" refers to a saturated hydrocarbon chain that may be a straight chain or branched chain, containing the indicated number of carbon atoms. For example, $C_{1-6}$ alkyl indicates that the group may have 1 to 6 (inclusive) carbon atoms in it. Any atom can be optionally substituted, e.g., by one or more substituents. Examples of alkyl groups include without limitation methyl, ethyl, n-propyl, isopropyl, and tert-butyl.

As referred to herein, the term "alkoxy" refers to a group of formula —O(alkyl). Alkoxy can be, for example, methoxy (—$OCH_3$), ethoxy, propoxy, isopropoxy, butoxy, iso-butoxy, sec-butoxy, pentoxy, 2-pentoxy, 3-pentoxy, or hexyloxy. As used herein, the term "hydroxyl," employed alone or in combination with other terms, refers to a group of formula —OH.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl. One of the double bond carbons can optionally be the point of attachment of the alkenyl substituent.

The term "alkynyl" refers to a straight or branched hydrocarbon chain containing the indicated number of carbon atoms and having one or more carbon-carbon triple bonds. Alkynyl groups can be optionally substituted, e.g., by one or more substituents. Alkynyl groups can include, e.g., ethynyl, propargyl, and 3-hexynyl. One of the triple bond carbons can optionally be the point of attachment of the alkynyl substituent.

The term "heterocyclyl" refers to a fully saturated monocyclic, bicyclic, tricyclic or other polycyclic ring system having one or more constituent heteroatom ring atoms independently selected from O, N (it is understood that one or two additional groups may be present to complete the nitrogen valence and/or form a salt), or S. The heteroatom or ring carbon can be the point of attachment of the heterocyclyl substituent to another moiety. Any atom can be optionally substituted, e.g., by one or more substituents. Heterocyclyl groups can include, e.g., tetrahydrofuryl, tetrahydropyranyl, piperidyl (piperidino), piperazinyl, morpholinyl (morpholino), pyrrolinyl, and pyrrolidinyl. By way of example, the phrase "heterocyclic ring containing from 5-6 ring atoms, wherein 1-2 of the ring atoms is independently selected from N, NH, N($C_1$-$C_6$ alkyl), NC(O)($C_1$-$C_6$ alkyl), O, and S; and wherein said heterocyclic ring is optionally substituted with 1-3 independently selected $R^{a\prime\prime}$" would include (but not be limited to) tetrahydrofuryl, tetrahydropyranyl, piperidyl (piperidino), piperazinyl, morpholinyl (morpholino), pyrrolinyl, and pyrrolidinyl.

The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "aryl" refers to an aromatic monocyclic, bicyclic (2 fused rings), or tricyclic (3 fused rings), or polycyclic (>3 fused rings) hydrocarbon ring system. One or more ring atoms can be optionally substituted, e.g., by one or more substituents. Aryl moieties include, e.g., phenyl and naphthyl.

The term "heteroaryl" refers to an aromatic monocyclic, bicyclic (2 fused rings), tricyclic (3 fused rings), or polycyclic (>3 fused rings) hydrocarbon groups having one or more heteroatom ring atoms independently selected from O, N (it is understood that one or two additional groups may be present to complete the nitrogen valence and/or form a salt), or S. One or more ring atoms can be optionally substituted, e.g., by one or more substituents. Examples of heteroaryl groups include, but are not limited to, 2H-pyrrolyl, 3H-indolyl, 4H-quinolizinyl, acridinyl, benzo[b]thienyl, benzothiazolyl, P-carbolinyl, carbazolyl, coumarinyl, chromenyl, cinnolinyl, dibenzo[b,d]furanyl, furazanyl, furyl, imidazolyl, imidizolyl, indazolyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, and xanthenyl.

The descriptors "C=O" or "C(O)" or "oxo" are used interchangeably and refer to a carbon atom that is doubly bonded to an oxygen atom.

The term "carboxyl" refers to a group of formula —C(O)OH. The term "alkoxycarbonyl" refers to a group of formula —C(O)O-(alkyl). The term "carboxyalkyl" refers to a group of formula -(alkyl)—C(O)OH wherein the carboxyl group may be attached to any carbon atom in the alkyl group.

As used herein, the term "cyano," employed alone or in combination with other terms, refers to a group of formula —CN, wherein the carbon and nitrogen atoms are bound together by a triple bond. The term "azide" refers to a group of formula —$N_3$. The term "nitro" refers to a group of formula —$NO_2$.

The term "amine" includes primary (—$NH_2$), secondary (—NHR), tertiary (—NRR'), and quaternary (—$N^+$RR'R") amine having one, two or three independently selected substituents such as straight chain or branched chain alkyl, alkenyl, alkynyl, cycloalkyl, aryl, heteroaryl, heterocycle, and the like. In general, when a definition for a particular variable includes both hydrogen and non-hydrogen (halo, alkyl, aryl, etc.) possibilities, the term "substituent(s) other than hydrogen" refers collectively to the non-hydrogen possibilities for that particular variable.

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group, replacing one or more hydrogen atom therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted. It is understood that substitution at a given atom is limited by valency. Common substituents include halo, straight chain or branched chain alkyl, alkenyl, alkynyl, cycloalkyl, aryl, heteroaryl, heterocycle, alkylsulfonyl, nitro, cyano, —COOR, —C(O)NRR', —OR, —SR, —NRR', and oxo, such as mono- or di- or tri-substitutions with moieties such as trifluoromethoxy, methoxy, chlorine, bromine, fluorine, methyl, methoxy, pyridyl, furyl, triazyl, piperazinyl, pyrazoyl, imidazoyl, and the like. Unless otherwise noted, all groups described herein optionally contain one or more common substituents, to the extent permitted by valency.

Compounds

In certain embodiments, some of the compounds can be represented by the following formula:

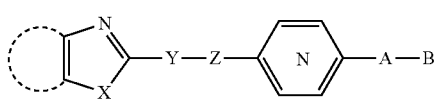

In the above formula, X can be S or N. Y can be NR and Z can be C(O), or Y can be C(O) or Z can be NR, where R is hydrogen, $C_{1-6}$ (e.g., $C_{1-3}$) alkyl, $C_{2-6}$ (e.g., $C_{2-3}$) alkenyl and $C_{2-6}$ (e.g., $C_{2-3}$) alkynyl, each optionally substituted with 1 or more halo, hydroxyl, $C_{1-6}$ (e.g., $C_{1-3}$) alkoxyl, $C_{1-6}$ (e.g., $C_{1-3}$) carbonyl, $C_{1-6}$ (e.g., $C_{1-3}$) alkoxycarbonyl, cyano, nitro, and/or amine.

represents an aromatic ring optionally substituted with 1 or more N. A can be a hydrophilic group such as CHOH, $CHNR_2$, C(O)NR, C(O), O, NR, S(O)n (n=0-2) wherein each R is independently hydrogen, $C_{1-6}$ (e.g., $C_{1-3}$) alkyl, $C_{2-6}$ (e.g., $C_{2-3}$) alkenyl and $C_{2-6}$ (e.g., $C_{2-3}$) alkynyl, each optionally substituted with 1 or more halo, hydroxyl, $C_{1-6}$ (e.g., $C_{1-3}$) alkoxyl, $C_{1-6}$ (e.g., $C_{1-3}$) carbonyl, $C_{1-6}$ (e.g., $C_{1-3}$) alkoxycarbonyl, cyano, nitro, and/or amine. B can be a hydrophobic group such as an aryl or heteroaryl group (e.g., optionally substituted phenyl or pyridyl).

In additional embodiments, certain compounds can be represented by the following formula:

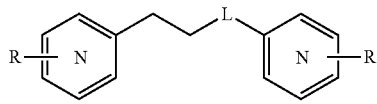

In the above formula, R is optional and at each occurrence is attached to the aromatic ring at one or more positions (e.g., 1, 2, 3, 4 or 5). Rat each occurrence is independently selected from: hydrogen; halo; hydroxyl; $C_{1-6}$ (e.g., $C_{1-3}$) alkoxyl, $C_{6-12}$ aryloxyl, and $C_{4-12}$ heteroaryloxyl, each optionally substituted with 1 or more hydroxyl, cyano and/or halo; $C_{1-6}$ (e.g., $C_{1-3}$) carbonyl; $C_{1-6}$ (e.g., $C_{1-3}$) alkoxycarbonyl; cyano; nitro; amine; —$(O(CH_2)_{1-3})_n$—CCH wherein n is an integral selected from 1-5; and $C_{1-6}$ (e.g., $C_{1-3}$) alkyl, $C_{2-6}$ (e.g., $C_{2-3}$) alkenyl and $C_{2-6}$ (e.g., $C_{2-3}$) alkynyl, each optionally substituted with 1 or more halo, hydroxyl, $C_{1-6}$ (e.g., $C_{1-3}$) alkoxyl, $C_{6-12}$ aryloxyl, $C_{4-12}$ heteroaryloxyl, $C_{1-6}$ (e.g., $C_{1-3}$) carbonyl, $C_{1-6}$ (e.g., $C_{1-3}$) alkoxycarbonyl, cyano, nitro, and/or amine. L can be an amide containing linker, such as:

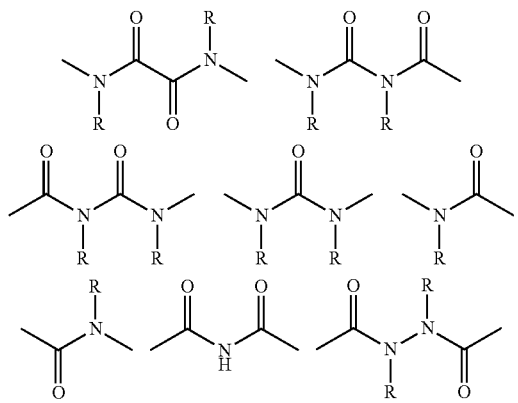

where each R is independently hydrogen, $C_{1-6}$ (e.g., $C_{1-3}$) alkyl, $C_{2-6}$ (e.g., $C_{2-3}$) alkenyl and $C_{2-6}$ (e.g., $C_{2-3}$) alkynyl, each optionally substituted with 1 or more halo, hydroxyl, $C_{1-6}$ (e.g., $C_{1-3}$) alkoxyl, $C_{1-6}$ (e.g., $C_{1-3}$) carbonyl, $C_{1-6}$ (e.g., $C_{1-3}$) alkoxycarbonyl, cyano, nitro, and/or amine.

represents an aromatic ring optionally substituted with 1 or more N.

Compound Identification

There are three approaches underway to link cancer genotypes with chemical vulnerabilities. The first is to correlate a genotype with chemical sensitivity by assaying the toxicity of well-characterized chemicals (<1000) to gene alterations in hundreds of cancer cell lines.[7,8] To its credit, this approach assays the critical phenotype—potency and selective toxicity, however, it is limited to just a small group of hand picked chemicals. A second approach uses large and diverse chemical libraries (>100,000) to screen for probes that effect gene products whose role in tumor growth have been validated in genetic models of cancer. This approach is powered by evaluation of far more compounds and chemical diversity. Unlike the first approach, however, it fails to necessarily assay the desired phenotype. Moreover, even large chemical libraries have failed to identify probes for some of the most common validated targets (e.g., Myc, KRAS). A third method combines the strengths of the first two by using a large chemical library to perform phenotypic screens (FIG. 1). In an unprecedented effort, the University of Texas Southwestern Medical Center investigators used a phenotypic screen, allowing identification of potent and selectively toxic chemicals that we can now use to guides target discovery, as described herein.

A major challenge in cancer research is to identify chemicals that target specific cancer genotypes. To address this challenge, we analyzed the results of an unprecedented screen assaying the impact of 230,000 small molecules on the proliferation of 12 lung adenocarcinoma cell lines. We identified compounds that have the hallmark of targeted therapy—potent and selective toxicity to a subset of cancer cell lines and no effect on non-cancerous epithelial cells.

To discover selective agents, twelve cell lines of diverse genotype were selected for analysis. 108 lung cancer cell lines were initially clustered into six groups based on mRNA expression of genes that underwent frequent copy number variation. Two cell lines were chosen from each group for high throughput chemical screening. All 12 of the chosen cell lines were derived from lung adenocarcinomas, eliminating both lineage and histology as confounders. None of the cell lines chosen for screening harbored EGFR mutations or ALK rearrangements, so that the final set represented a collection of diverse lung adenocarcinoma genotypes for which there are no targeted therapy.

The proliferative impact of each compound in the library was assayed by analyzing total ATP four days after administration of 2.5 μM in a single well. This first pass yielded 15,843 toxins defined as a compound where ATP levels were less than three standard deviations below the mean for at least one cell line. For each of these putative toxins, the average effect on proliferation was retested on each cancer cell line and a non-cancerous immortalized HBEC line (control), yielding a confirmation dataset.

Amongst confirmed toxins, we identified several compounds that were non-toxic to the HBEC and at least 40% more toxic to at least two of the adenocarcinoma cell lines than others. Among these compounds, benzothiophene carboxamides appeared particularly promising, such as SW118753 and SW025780:

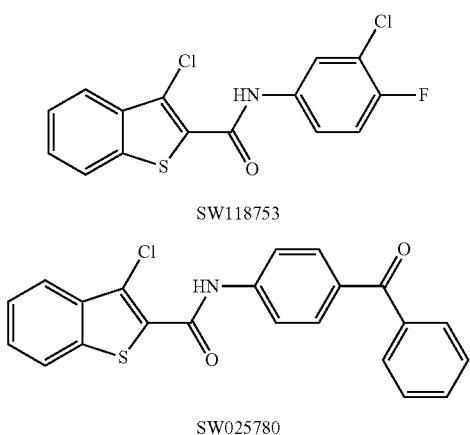

SW118753

SW025780

In addition, N-acyl benzothiazoles was also discovered, such as 4-amino-N-(6-methoxybenzo[d]thiazol-2-yl)benzamide (ATB). We compared the proliferation of 12 lung adenocarcinoma cell lines and three HBEC lines after the addition of ATB. The ATB $IC_{50}$ was 48 nM against the most sensitive cell line (H2122) but greater than 1 μM against 10 other cell lines, including the normal line.

We subsequently synthesized various derivatives that are both selective and potent (Tables 1 and 2). The $IC_{50}$ of each derivative for at least one of the 12 lung adenocarcinoma cell lines is shown in Tables 3 and 4. One leading candidate is a benzothiazole, SW202857, that inhibits proliferation in three of 12 adenocarcinoma cell lines at concentrations less than 10 nM. This chemical shows no toxic effect on the other 9 adenocarcinoma cell lines up to 10 μM, nor does it affect the vitality of 3 human bronchial epithelial (HBEC) cell lines at 10 μM.

TABLE 1

| Compound ID | Compound Structure |
|---|---|
| SW155113 | $C_{19}H_{17}ClN_2O_2S_2$ |
| SW023441 | $C_{22}H_{14}Cl_2N_2O_2S$ |

TABLE 1-continued

| Compound ID | Compound Structure |
|---|---|
| SW004989 | $C_{16}H_{12}ClNO_2S$ |
| SW006505 | $C_{15}H_9ClFNOS$ |
| SW023008-2 | $C_{20}H_{13}ClN_2O_3S$ |
| SW023441-2 | $C_{22}H_{14}Cl_2N_2O_2S$ |
| SW118094 | $C_{15}H_9ClFNOS$ |

TABLE 1-continued

| Compound ID | Compound Structure |
|---|---|
| SW119800 | C₁₆H₁₁ClN₂O₂S |
| SW163400 | C₂₀H₁₃ClN₂O₃S |
| SW174698 | C₁₉H₁₇ClN₂OS |
| SW202550 | C₁₅H₉ClFNOS |
| SW202551 | C₁₆H₁₁ClFNOS |
| SW202552 | C₁₅H₈ClFN₂O₃S |
| SW025780 | C₂₂H₁₄ClNO₂S |
| SW118753 | C₁₅H₈Cl₂FNOS |
| SW202855-1 | C₂₃H₁₆ClNO₃S |
| SW202856-1 | C₂₂H₁₄ClNO₃S |
| SW202858-1 | C₁₈H₁₉NO₃S |
| SW202859-1 | C₁₈H₁₈FNO₃S |

TABLE 1-continued
| Compound ID | Compound Structure |
|---|---|
| SW108364-2 | 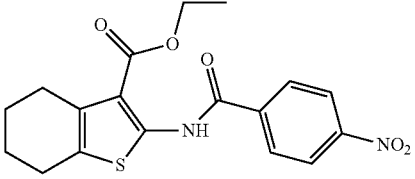<br>$C_{18}H_{18}N_2O_5S$ |
| SW004989 | 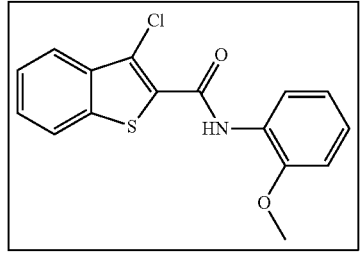<br>$C_{16}H_{12}ClNO_2S$ |
| SW119324 | 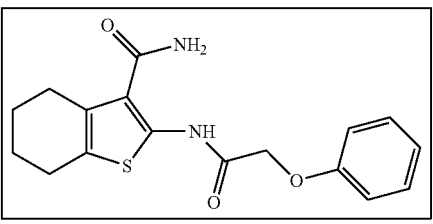 [SMILES: NC(=O)c1c(NC(=O)COc2ccccc2)sc2c1CCCC2] |
| SW172864 | 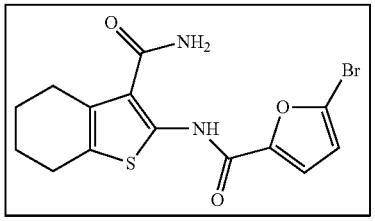 [SMILES: NC(=O)c1c(NC(=O)c2ccc(Br)o2)sc2c1CCCC2] |
| SW173997 | 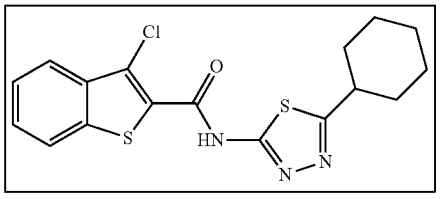 [SMILES: O=C(Nc1nnc(C2CCCCC2)s1)c1sc2ccccc2c1Cl] |
TABLE 2
| Compound ID | Compound Structure |
|---|---|
| SW003992 | 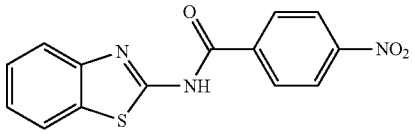<br>$C_{14}H_9N_3O_3S$ |
| SW001286 | 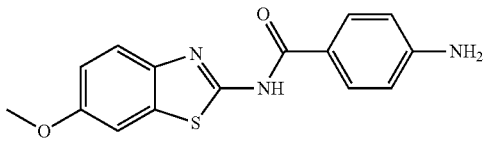 [SMILES: COc1ccc2nc(NC(=O)c3ccc(N)cc3)sc2c1]<br>$C_{15}H_{13}N_3O_2S$ |
| SW001811 | 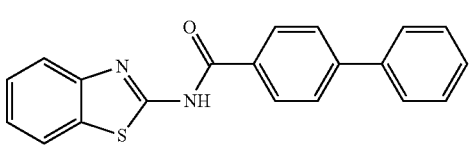 [SMILES: O=C(Nc1nc2ccccc2s1)c1ccc(-c2ccccc2)cc1]<br>$C_{20}H_{14}N_2OS$ |

TABLE 2-continued
| Compound ID | Compound Structure |
|---|---|
| SW045964 | 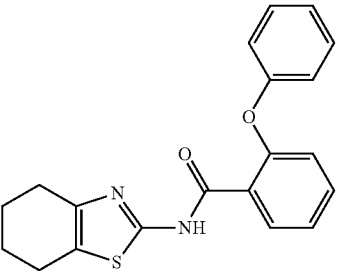 [SMILES: O=C(Nc1nc2c(s1)CCCC2)c1ccccc1Oc1ccccc1]<br>$C_{20}H_{18}N_2O_2S$ |
| SW006981 | 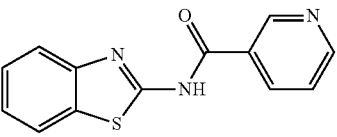 [SMILES: O=C(Nc1nc2ccccc2s1)c1cccnc1]<br>$C_{13}H_9N_3OS$ |
| SW053831 | 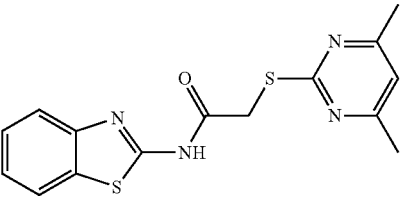 [SMILES: Cc1cc(C)nc(SCC(=O)Nc2nc3ccccc3s2)n1]<br>$C_{15}H_{14}N_4OS_2$ |
| SW003087 | 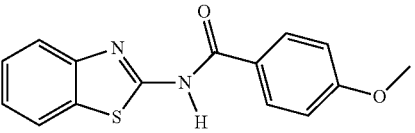 [SMILES: COc1ccc(C(=O)Nc2nc3ccccc3s2)cc1]<br>$C_{15}H_{12}N_2O_2S$ |
| SW202754 | 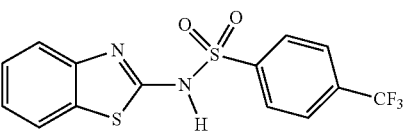 [SMILES: O=S(=O)(Nc1nc2ccccc2s1)c1ccc(C(F)(F)F)cc1]<br>$C_{14}H_9F_3N_2O_2S_2$ |
| SW202755 | 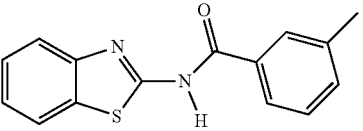 [SMILES: Cc1cccc(C(=O)Nc2nc3ccccc3s2)c1]<br>$C_{15}H_{12}N_2OS$ |
| SW202743 | 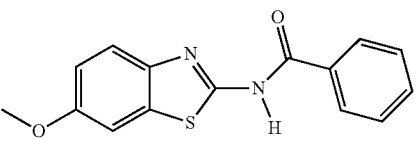 [SMILES: COc1ccc2nc(NC(=O)c3ccccc3)sc2c1]<br>$C_{15}H_{12}N_2O_2S$ |

TABLE 2-continued
| Compound ID | Compound Structure |
| --- | --- |
| SW202744 | 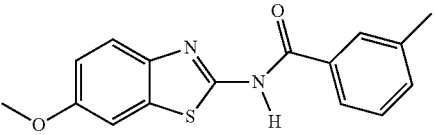<br>C₁₆H₁₄N₂O₂S |
| SW202745 | 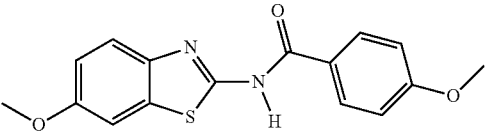<br>C₁₆H₁₄N₂O₃S |
| SW202746 | 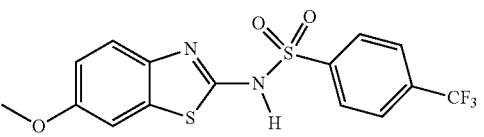 [SMILES: COc1ccc2nc(NS(=O)(=O)c3ccc(C(F)(F)F)cc3)sc2c1]<br>C₁₅H₁₁F₃N₂O₃S₂ |
| SW202749 | 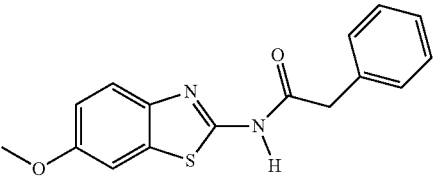 [SMILES: COc1ccc2nc(NC(=O)Cc3ccccc3)sc2c1]<br>C₁₆H₁₄N₂O₂S |
| SW008027 | 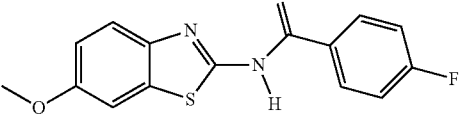<br>C₁₅H₁₁FN₂O₂S |
| SW202750 | 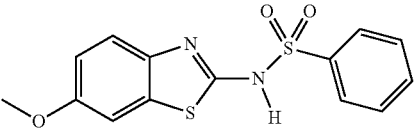 [SMILES: COc1ccc2nc(NS(=O)(=O)c3ccccc3)sc2c1]<br>C₁₄H₁₂N₂O₃S₂ |
| SW202752 | 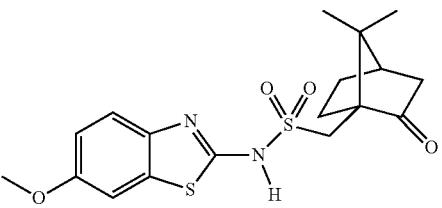 [SMILES: COc1ccc2nc(NS(=O)(=O)CC34CCC(CC3=O)C4(C)C)sc2c1]<br>C₁₈H₂₂N₂O₄S₂ |

TABLE 2-continued
| Compound ID | Compound Structure |
|---|---|
| SW166942 | 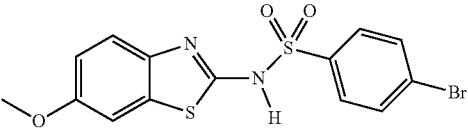 [SMILES: COc1ccc2nc(NS(=O)(=O)c3ccc(Br)cc3)sc2c1]<br>$C_{14}H_{11}BrN_2O_3S_2$ |
| SW166933 | 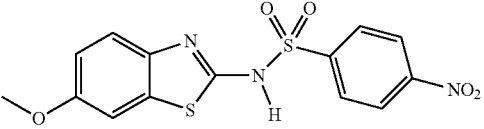 [SMILES: COc1ccc2nc(NS(=O)(=O)c3ccc([N+](=O)[O-])cc3)sc2c1]<br>$C_{14}H_{11}N_3O_5S_2$ |
| SW202747 | 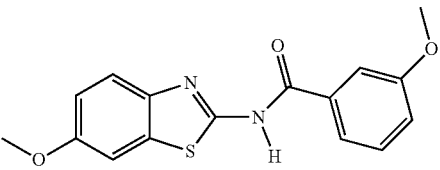 [SMILES: COc1cccc(C(=O)Nc2nc3ccc(OC)cc3s2)c1]<br>$C_{16}H_{14}N_2O_3S$ |
| SW202753 | 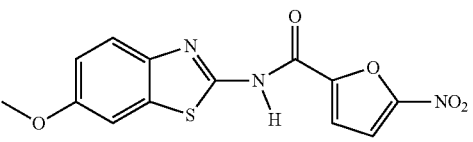 [SMILES: COc1ccc2nc(NC(=O)c3ccc([N+](=O)[O-])o3)sc2c1]<br>$C_{13}H_9N_3O_5S$ |
| SW000931 | 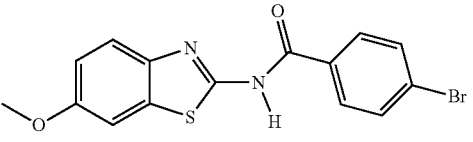 [SMILES: COc1ccc2nc(NC(=O)c3ccc(Br)cc3)sc2c1]<br>$C_{15}H_{11}BrN_2O_2S$ |
| SW202751 | 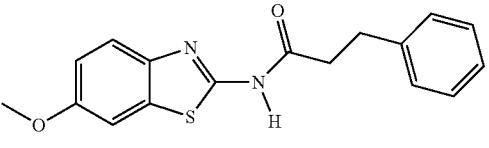 [SMILES: COc1ccc2nc(NC(=O)CCc3ccccc3)sc2c1]<br>$C_{17}H_{16}N_2O_2S$ |
| SW202748 | 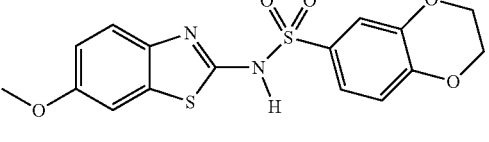<br>$C_{16}H_{14}N_2O_5S_2$ |
| SW004400 | 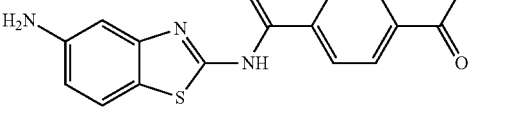<br>$C_{16}H_{13}N_3O_3S$ |

TABLE 2-continued
| Compound ID | Compound Structure |
|---|---|
| SW053525 | 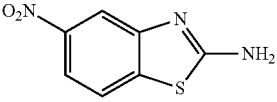 [SMILES: Nc1nc2cc([N+](=O)[O-])ccc2s1]<br>C$_7$H$_5$N$_3$O$_2$S |
| SW138238 | 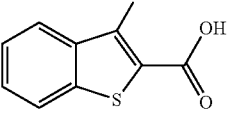<br>C$_9$H$_5$ClO$_2$S |
| SW202739 | 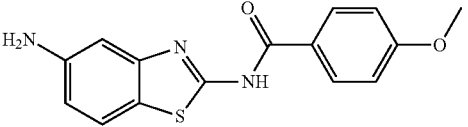 [SMILES: COc1ccc(C(=O)Nc2nc3cc(N)ccc3s2)cc1]<br>C$_{15}$H$_{13}$N$_3$O$_2$S |
| SW202740 | 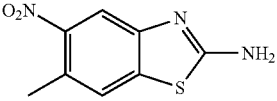<br>C$_8$H$_7$N$_3$O$_2$S |
| SW202741 | 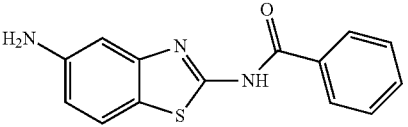 [SMILES: Nc1ccc2sc(NC(=O)c3ccccc3)nc2c1]<br>C$_{14}$H$_{11}$N$_3$OS |
| SW202857-1 | 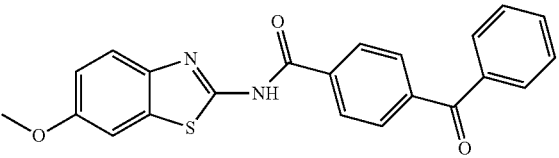 [SMILES: COc1ccc2nc(NC(=O)c3ccc(C(=O)c4ccccc4)cc3)sc2c1]<br>C$_{22}$H$_{16}$N$_2$O$_3$S |
| SW202860-1 | 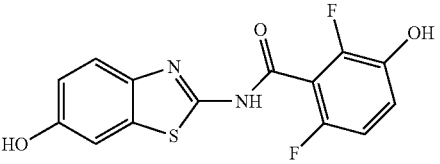 [SMILES: O=C(Nc1nc2ccc(O)cc2s1)c1c(F)ccc(O)c1F]<br>C$_{14}$H$_8$F$_2$N$_2$O$_3$S |
| SW001282-2 | 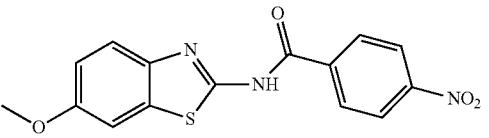 [SMILES: COc1ccc2nc(NC(=O)c3ccc([N+](=O)[O-])cc3)sc2c1]<br>C$_{15}$H$_{11}$N$_3$O$_4$S |

TABLE 2-continued
| Compound ID | Compound Structure |
|---|---|
| SW202773-1 | 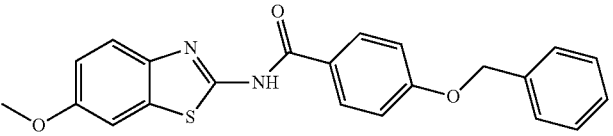 [SMILES: COc1ccc2nc(NC(=O)c3ccc(OCc4ccccc4)cc3)sc2c1]<br>C$_{22}$H$_{18}$N$_2$O$_3$S |
| SW202774-1 | 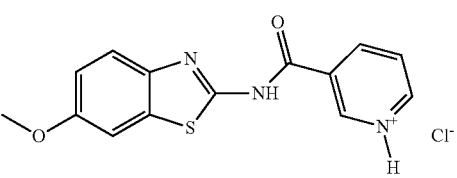 [SMILES: COc1ccc2nc(NC(=O)c3ccc[nH+]c3)sc2c1 ; [Cl-]]<br>C$_{14}$H$_{12}$ClN$_3$O$_2$S |
| SW202775-1 | 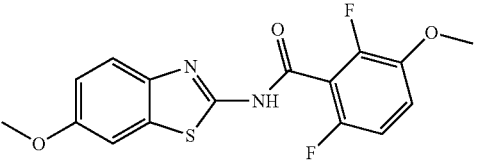<br>C$_{16}$H$_{12}$F$_2$N$_2$O$_3$S |
| SW202776-1 | 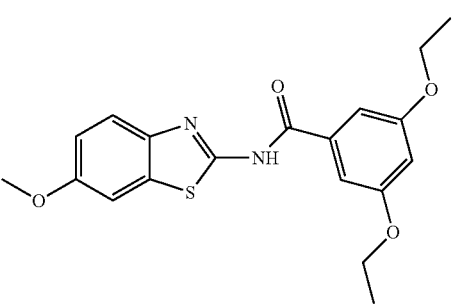 [SMILES: CCOc1cc(OCC)cc(C(=O)Nc2nc3ccc(OC)cc3s2)c1]<br>C$_{19}$H$_{20}$N$_2$O$_4$S |
| SW202864-1 | 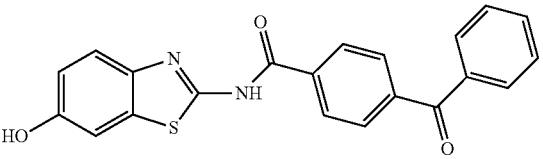 [SMILES: O=C(Nc1nc2ccc(O)cc2s1)c1ccc(C(=O)c2ccccc2)cc1]<br>C$_{21}$H$_{14}$N$_2$O$_3$S |
| SW202868 | 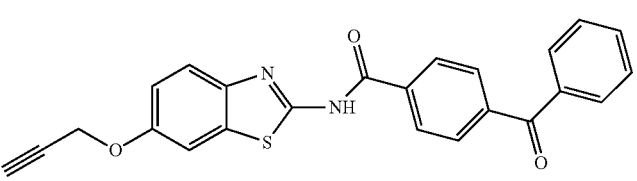 [SMILES: C#CCOc1ccc2nc(NC(=O)c3ccc(C(=O)c4ccccc4)cc3)sc2c1]<br>C$_{24}$H$_{16}$N$_2$O$_3$S |
| SW001296 | 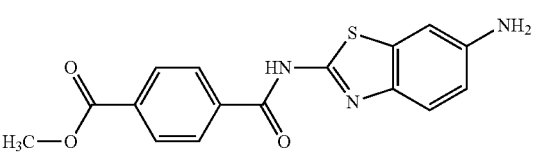 |

TABLE 2-continued

| Compound ID | Compound Structure |
|---|---|
| SW004969 | 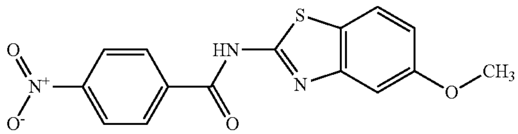 [SMILES: COc1ccc2sc(NC(=O)c3ccc([N+](=O)[O-])cc3)nc2c1] |
| SW008283 | 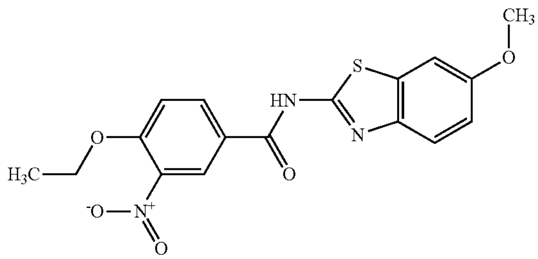 |
| SW011940 | 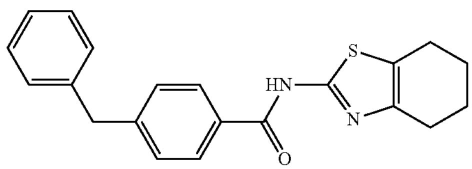 [SMILES: O=C(Nc1nc2c(s1)CCCC2)c1ccc(Cc2ccccc2)cc1] |
| SW018825 | 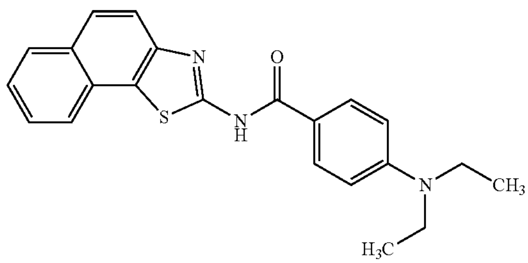 [SMILES: CCN(CC)c1ccc(C(=O)Nc2nc3ccc4ccccc4c3s2)cc1] |
| SW147703 | 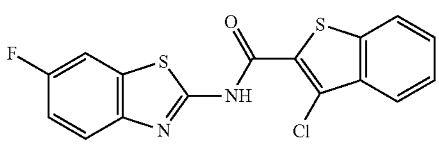 [SMILES: O=C(Nc1nc2ccc(F)cc2s1)c1sc2ccccc2c1Cl] |
| SW203668 | 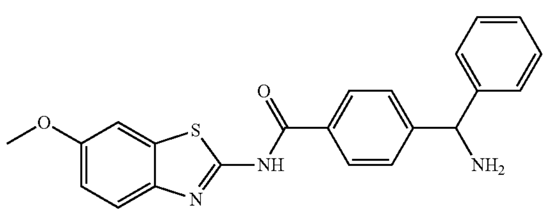 |
| | O=C(C1=CC=C(C(N)C2=CC=CC=C2)C=C1)NC3=NC4=CC=C(OC)C=C4S3 |
| SW203669 | 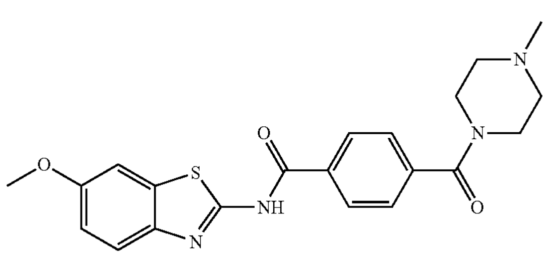 |
| | O=C(C1=CC=C(C(N2CCN(C)CC2)=O)C=C1)NC3=NC4=CC=C(OC)C=C4S3 |

TABLE 2-continued

| Compound ID | Compound Structure |
|---|---|
| SW203670 | O=C(C1=CC=C(NC2=CC=CC=C2)C=C1)NC3=NC4=CC=C(OC)C=C4S3 |
| SW203671 | O=C(C1=CC=C(NC2=CC=C(OC)C=C2)C=C1)NC3=NC4=CC=C(OC)C=C4S3 |
| SW203726 | COC1=CC=C2C(SC(NC(C3=CC=C(C(O)C4=CC=CC=N4)C=C3)=O)=N2)=C1 |
| SW203727 | COC1=CC=C2C(SC(NC(C3=CC=C(C(C4=CC=CC=N4)=O)C=C3)=O)=N2)=C1 |
| SW203728 | COC1=CC=C2C(SC(NC(C3=CC=C(N=[N+]=[N-])C=C3)=O)=N2)=C1 |
| SW203729 | COC1=CC=C2C(SC(NC(C3=CC=CC=C3N=[N+]=[N-])=O)=N2)=C1 |

TABLE 2-continued

| Compound ID | Compound Structure |
|---|---|
| SW203730 | 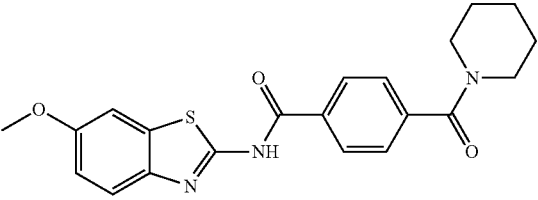 [SMILES: COc1ccc2nc(NC(=O)c3ccc(C(=O)N4CCCCC4)cc3)sc2c1]<br>COC1=CC=C2C(SC(NC(C3=CC=C(C(N4CCCCC4)=O)C=C3)=O)=N2)=C1 |
| SW203731 | 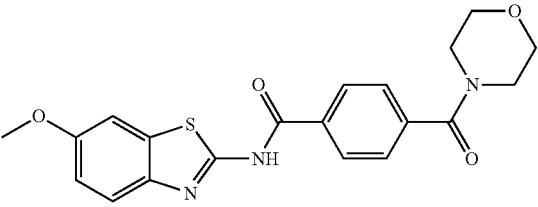 [SMILES: COc1ccc2nc(NC(=O)c3ccc(C(=O)N4CCOCC4)cc3)sc2c1]<br>COC1=CC=C2C(SC(NC(C3=CC=C(C(N4CCOCC4)=O)C=C3)=O)=N2)=C1 |
| SW203732 | 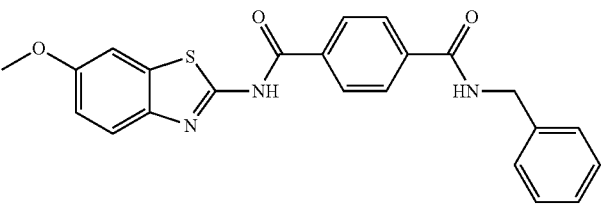 [SMILES: COc1ccc2nc(NC(=O)c3ccc(C(=O)NCc4ccccc4)cc3)sc2c1]<br>COC1=CC=C2C(SC(NC(C3=CC=C(C(NCC4=CC=CC=C4)=O)C=C3)=O)=N2)=C1 |
| SW203733 | 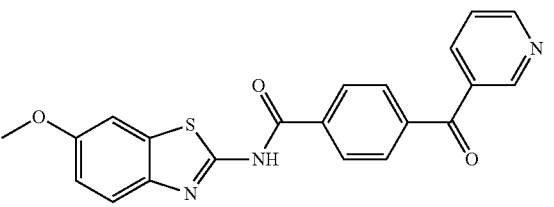 [SMILES: COc1ccc2nc(NC(=O)c3ccc(C(=O)c4cccnc4)cc3)sc2c1]<br>COC1=CC=C2C(SC(NC(C3=CC=C(C(C4=CC=CN=C4)=O)C=C3)=O)=N2)=C1 |
| SW203734 | 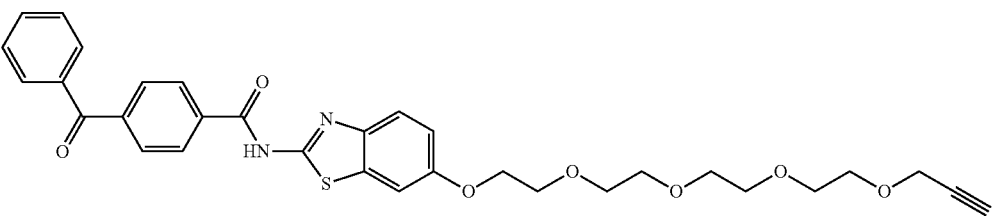 [SMILES: C#CCOCCOCCOCCOCCOc1ccc2nc(NC(=O)c3ccc(C(=O)c4ccccc4)cc3)sc2c1]<br>O=C(C1=CC=C(C(C2=CC=CC=C2)=O)C=C1)NC3=NC4=CC=C(OCCOCCOCCOCCOCC#C)C=C4S3 |
| SW203735 | 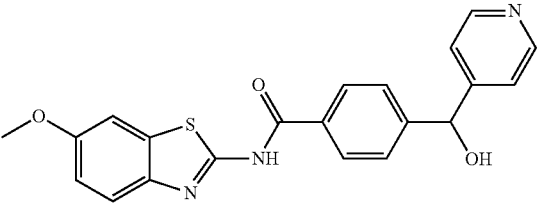 [SMILES: COc1ccc2nc(NC(=O)c3ccc(C(O)c4ccncc4)cc3)sc2c1]<br>COC1=CC=C2C(SC(NC(C3=CC=C(C(O)C4=CC=NC=C4)C=C3)=O)=N2)=C1 |

TABLE 2-continued

| Compound ID | Compound Structure |
| --- | --- |
| SW207003 | $C_{22}H_{18}N_2O_3S$ |
| SW208186 | O=C(C1=CC=C(C(C2=CC=CC=C2)=O)C=C1)NC3=NC4=CC=C(OCCC)C=C4S3 |
| SW208187 | O=C(C1=CC=C(C(C2=CC=C(OC)C=C2)=O)C=C1)NC3=NC4=CC=C(OCC#C)C=C4S3 |
| SW208110 | COC1=CC=C2C(SC(NC(C3=CC=C([C@H](N)C4=CC=CC=C4)C=C3)=O)=N2)=C1 |
| SW208109 | COC1=CC=C2C(SC(NC(C3=CC=C([C@@H](N)C4=CC=CC=C4)C=C3)=O)=N2)=C1 |
| SW208235 | O=C(C1=CC=C(C(C2=CC=CC=C2)=O)C=C1)NC3=NC4=CC=C(OCCCBr)C=C4S3 |

TABLE 2-continued

| Compound ID | Compound Structure |
| --- | --- |
| SW208236 | 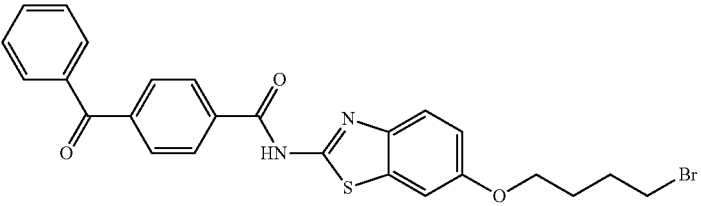 [SMILES: O=C(Nc1nc2ccc(OCCCCBr)cc2s1)c1ccc(C(=O)c2ccccc2)cc1]<br>O=C(C1=CC=C(C(C2=CC=CC=C2)=O)C=C1)NC3=NC4=CC=C(OCCCCBr)C=C4S3 |
| SW208237 | 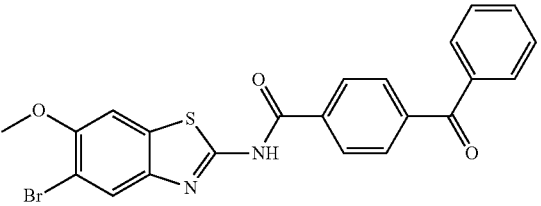 [SMILES: COc1cc2sc(NC(=O)c3ccc(C(=O)c4ccccc4)cc3)nc2cc1Br]<br>O=C(C1=CC=C(C(C2=CC=CC=C2)=O)C=C1)NC3=NC4=CC(Br)=C(OC)C=C4S3 |
| SW208233-1 | 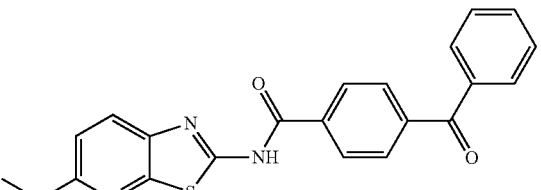<br>O=C(C1=CC=C(C(C2=CC=CC=C2)=O)C=C1)NC3=NC4=CC=C(OC)N=C4S3 |
| SW208652-1 | 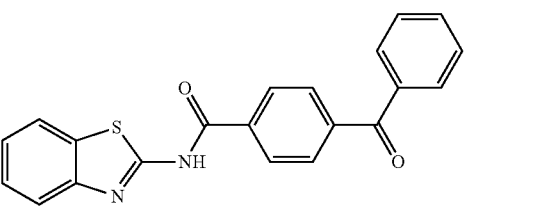<br>O=C(C1=CC=C(C(C2=CC=CC=C2)=O)C=C1)NC3=NC4=CC=CC=C4S3 |
| SW208653-1 | 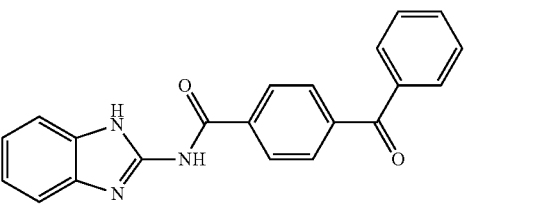 [SMILES: O=C(Nc1nc2ccccc2[nH]1)c1ccc(C(=O)c2ccccc2)cc1]<br>O=C(C1=CC=C(C(C2=CC=CC=C2)=O)C=C1)NC3=NC4=CC=CC=C4N3 |
| SW208665-1 | 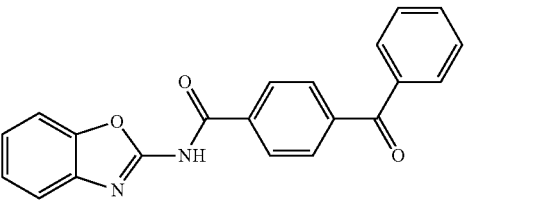 [SMILES: O=C(Nc1nc2ccccc2o1)c1ccc(C(=O)c2ccccc2)cc1]<br>O=C(C1=CC=C(C(C2=CC=CC=C2)=O)C=C1)NC3=NC4=CC=CC=C4O3 |

TABLE 2-continued
| Compound ID | Compound Structure |
|---|---|
| SW208666-1 | 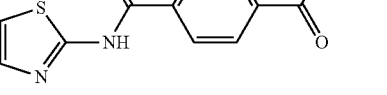<br>O=C(C1=CC=C(C(C2=CC=CC=C2)=O)C=C1)NC3=NC4=C(S3)CCC4 |
| SW208700-1 | 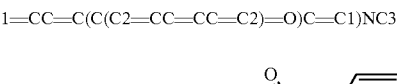<br>FC(F)(F)C1(N=N1)C1=CC=C(C=C1)C(=O)NC1=NC2=CC=C(OCC#C)C=C2S1 |
| SW208741-1 | 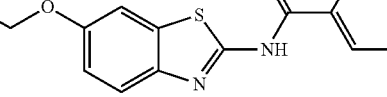<br>O=C(NC1=NC2=C(CCCC2)S1)C1=CC=C(C=C1)C(=O)C1=CC=CC=C1 |
| SW208770-1 | 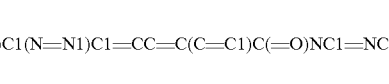<br>CN1C(NC(=O)C2=CC=C(C=C2)C(=O)C2=CC=CC=C2)=NC2=CC=CC=C12 |
| SW208771-1 | <br>O=C(NC1=NC=CS1)C1=CC=C(C=C1)C(=O)C1=CC=CC=C1 |
| SW209017 | 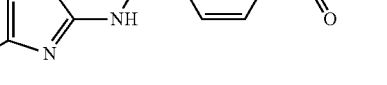<br>O=C(C1=CC=C(C(C2=CC=CC=C2)=O)C=C1)NC3=NC=C(C4=CC=CC=C4)S3 |

TABLE 2-continued
| Compound ID | Compound Structure |
| --- | --- |
| SW208834 | 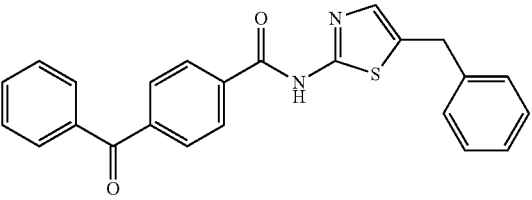 [SMILES: O=C(Nc1ncc(Cc2ccccc2)s1)c1ccc(C(=O)c2ccccc2)cc1]
O=C(C1=CC=C(C(C2=CC=CC=C2)=O)C=C1)NC3=NC=C(CC4=CC=CC=C4)S3 |
| SW209018 | 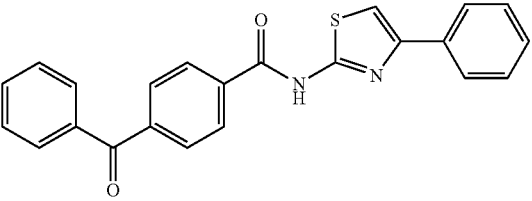 [SMILES: O=C(Nc1nc(-c2ccccc2)cs1)c1ccc(C(=O)c2ccccc2)cc1]
O=C(C1=CC=C(C(C2=CC=CC=C2)=O)C=C1)NC3=NC(C4=CC=CC=C4)=CS3 |
| SW209049-1 | 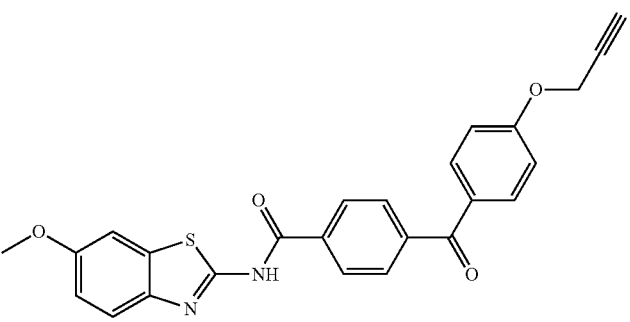 [SMILES: C#CCOc1ccc(C(=O)c2ccc(C(=O)Nc3nc4ccc(OC)cc4s3)cc2)cc1]
COC1=CC=C2C(SC(NC(C3=CC=C(C(C4=CC=C(OCC#C)C=C4)=O)C=C3)=O)=N2)=C1 |
| SW209091-1 | 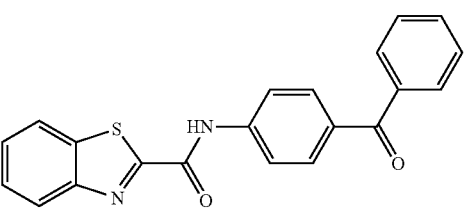 [SMILES: O=C(c1ccccc1)c1ccc(NC(=O)c2nc3ccccc3s2)cc1]
O=C(C1=CC=CC=C1)C2=CC=C(NC(C3=NC4=CC=CC=C4S3)=O)C=C2 |
| SW209082-1 | 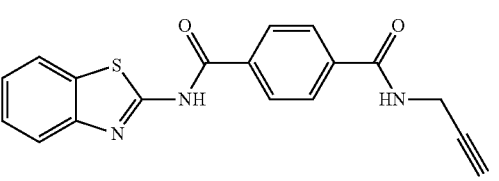 [SMILES: C#CCNC(=O)c1ccc(C(=O)Nc2nc3ccccc3s2)cc1]
O=C(NCC#C)C1=CC=C(C(NC2=NC3=CC=CC=C3S2)=O)C=C1 |

TABLE 2-continued

| Compound ID | Compound Structure |
|---|---|
| SW209047-1 | [N−]=[N+]=NC1=C(CNC(=O)C2=CC=C(C=C2)C(=O)NC2=NC3=CC=C(OCC#C)C=C3S2)C=CC=C1 |
| SW001296-3 | COC(=O)C1=CC=C(C=C1)C(=O)NC1=NC2=C(S1)C=C(N)C=C2 |
| SW209049-2 | COC1=CC=C2N=C(NC(=O)C3=CC=C(C=C3)C(=O)C3=CC=C(OCC#C)C=C3)SC2=C1 |
| SW209168-1 | O=C(NC1=CC=C(C=C1)C(=O)NC1=NC2=CC=CC=C2S1)OCC#C |
| SW209205-1 | [O−][N+](=O)C1=CC(=CC=C1)C(=O)NC1=NC2=CC=CC=C2S1 |
| SW209206-1 | [O−][N+](=O)C1=CC=C(C=C1)C(=O)NC1=NC2=CC=CC=C2N1 |

TABLE 2-continued

| Compound ID | Compound Structure |
|---|---|
| SW209322-1 | 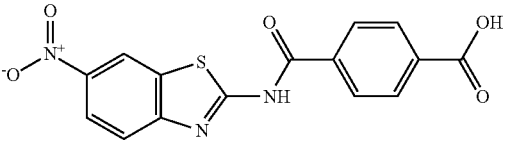<br>OC(=O)C1=CC=C(C=C1)C(=O)NC1=NC2=C(S1)C=C(C=C2)[N+]([O−])=O |
| SW209323-1 | 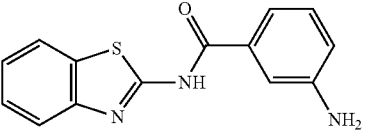 [SMILES: Nc1cccc(C(=O)Nc2nc3ccccc3s2)c1]<br>NC1=CC(=CC=C1)C(=O)NC1=NC2=C(S1)C=CC=C2 |
| SW209411-1 | 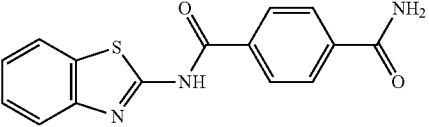 [SMILES: NC(=O)c1ccc(C(=O)Nc2nc3ccccc3s2)cc1]<br>NC(=O)C1=CC=C(C=C1)C(=O)NC1=NC2=C(S1)C=CC=C2 |
| SW209413-1 | 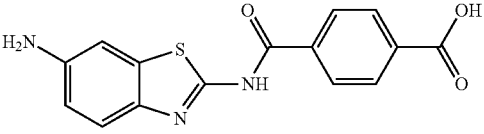 [SMILES: Nc1ccc2nc(NC(=O)c3ccc(C(=O)O)cc3)sc2c1]<br>NC1=CC=C2N=C(NC(=O)C3=CC=C(C=C3)C(O)=O)SC2=C1 |
| SW209414-1 | 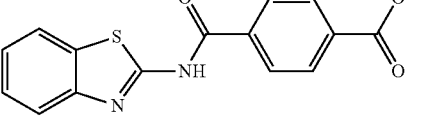<br>COC(=O)C1=CC=C(C=C1)C(=O)NC1=NC2=CC=CC=C2S1 |
| SW209412-1 | 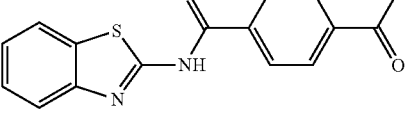<br>OC(=O)C1=CC=C(C=C1)C(=O)NC1=NC2=CC=CC=C2S1 |
| SW209562-1 | 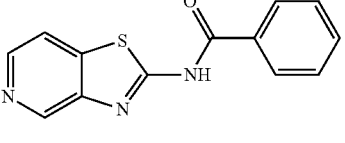<br>O=C(NC1=NC2=CN=CC=C2S1)C1=CC=CC=C1 |
| SW209563-1 | 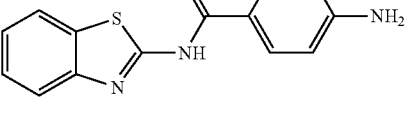<br>NC1=CC=C(C=C1)C(=O)NC1=NC2=CC=CC=C2S1 |

TABLE 2-continued

| Compound ID | Compound Structure |
|---|---|
| SW211559-1 | 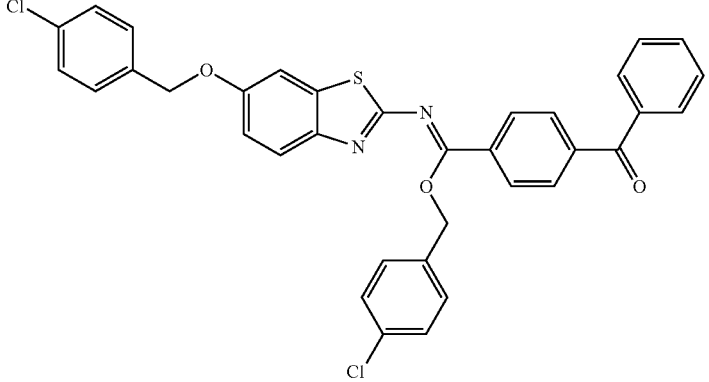 [SMILES: O=C(c1ccccc1)c1ccc(/C(=N/c2nc3ccc(OCc4ccc(Cl)cc4)cc3s2)OCc2ccc(Cl)cc2)cc1]<br>O=C(C1=CC=CC=C1)C(C=C2)=CC=C2/C(OCC3=CC=C(Cl)C=C3)=N/C4=NC5=CC=C(OCC6=CC=C(Cl)C=C6)C=C5S4 |
| SW211561-1 | 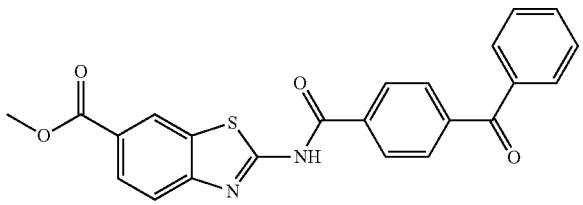 [SMILES: COC(=O)c1ccc2nc(NC(=O)c3ccc(C(=O)c4ccccc4)cc3)sc2c1]<br>O=C(C1=CC=C(C(C2=CC=CC=C2)=O)C=C1)NC3=NC4=CC=C(C(OC)=O)C=C4S3 |
| SW211566 | 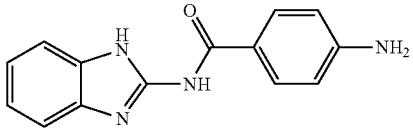 [SMILES: Nc1ccc(C(=O)Nc2nc3ccccc3[nH]2)cc1]<br>NC1=CC=C(C=C1)C(=O)NC1=NC2=CC=CC=C2N1 |

TABLE 3

| Compound ID | HBEC30KT IC50 | IC50 (uM) vs indicated non-small cell lung cancer cell line | | | | | |
|---|---|---|---|---|---|---|---|
| | | H1155 | H1395 | H1819 | H1993 | H2009 | H2073 |
| SW155113 | 33 | 14.5 | 13.4 | 14 | 8.1 | 32 | 6 |
| SW023441 | 30 | 29 | 10.5 | 16.4 | 11 | 9.4 | 6.2 |
| SW004989 | 64.8 | | | | | | |
| SW006505 | 63.9 | | | | | | |
| SW023008-2 | 82.5 | | | | | | |
| SW023441-2 | 31.8 | | | | | | |
| SW118094 | 34.1 | | | 1.21 | | | |
| SW119800 | 85.4 | | | | | | |
| SW163400 | 69.3 | | | | | | |
| SW174698 | 4950 | | | | | | |
| SW202550 | 105.1 | | | | | | |
| SW202551 | 4950 | | | | | | |
| SW202552 | 4950 | | | | | | |
| SW025780 | 51 | 33 | 99 | 27 | 31 | 60 | 0.08 |
| SW118753 | 108 | 105 | 600 | 38 | 73 | 65 | 0.9 |
| SW202855-1 | 24.3 | 46.1 | 28.4 | 32 | 17.8 | 13.9 | 36.2 |
| SW202856-1 | 6.08 | 20.4 | | 40.2 | 13.6 | 4.76 | 48.4 |
| SW202858-1 | 48.8 | | | | | 38.6 | |
| SW202859-1 | 38.2 | | | | 47.1 | | |
| SW108364-2 | 35.2 | | | | 23.4 | 15.8 | 24.3 |
| SW004989 | 31.989 | | | 43.652 | >5 | >8 | 0.052 |
| SW119324 | 10.447 | 44.463 | | | >8 | 0.881 | |
| SW172864 | 12.589 | | 44.463 | | 0.871 | 3.2 | 0.129 |
| SW173997 | | 23.768 | 41.305 | 48.529 | 16.904 | 21.528 | 11.402 |

TABLE 3-continued

| Compound ID | IC50 (uM) vs indicated non-small cell lung cancer cell line | | | | | |
|---|---|---|---|---|---|---|
|  | H2122 | H460 | HCC366 | HCC4017 | HCC44 | HCC95 |
| SW155113 | 0.36 | 29 | 22.5 | 23 | 27 | 100 |
| SW023441 | 0.39 | 48 | 23 | 18 | 32 | 14 |
| SW004989 | 0.801 |  |  | 249.1 | 56.8 |  |
| SW006505 | 1.7 |  |  | 261.8 | 0.657 |  |
| SW023008-2 | 1.27 |  |  | 809.2 | 105.3 |  |
| SW023441-2 | 0.473 |  |  | 46 | 27.7 |  |
| SW118094 | 1.05 | 0.606 | 123.8 | 0.322 | 0.09 |  |
| SW119800 | 2.66 |  |  | 466.7 | 205.8 |  |
| SW163400 | 0.897 |  |  | 4950 | 723.4 |  |
| SW174698 | 5.12 |  |  | 402.9 | 3.06 |  |
| SW202550 | 1.91 |  |  | 17.3 | 0.566 |  |
| SW202551 | 1.36 |  |  | 390.4 | 1.42 |  |
| SW202552 | 121.8 |  |  | 4950 | 4950 |  |
| SW025780 | 0.007 | 46 | 248 | 56 | 64 | 7.7 |
| SW118753 | 0.8 | 5000 | 375 | 700 | 265 | 300 |
| SW202855-1 | 18.3 | 28.8 | 49 | 15.7 | 25.4 | 9.84 |
| SW202856-1 | 33.8 | 44.5 | 40.6 | 13.3 | 1.06 | 12.8 |
| SW202858-1 | 2.69 |  |  |  |  |  |
| SW202859-1 |  |  |  |  |  | 31.4 |
| SW108364-2 | 5.92 |  |  | 35.2 | 35.2 |  |
| SW004989 | 1.023 |  |  |  | 38.726 |  |
| SW119324 |  |  |  |  | 34.356 | 28.51 |
| SW172864 |  | 35.075 |  | 1.71 | 2.518 | 43.551 |
| SW173997 | 0.27 | 44.463 | 40.926 | 24.044 | 23.121 | 23.768 |

TABLE 4

| Compound ID | HBEC30KT IC50 | IC50 (uM) vs indicated non-small cell lung cancer cell line | | | | | |
|---|---|---|---|---|---|---|---|
|  |  | H1155 | H1395 | H1819 | H1993 | H2009 | H2073 |
| SW003992 | 1626 | 2871 | 1576 | 358 | 524 | 5000 | 0.65 |
| SW001286 | 130 | 25 | 35 | 24 | 27 | 22 | 0.3 |
| SW001811 | 348 | 125 | 185 | 59 | 85 | 125 |  |
| SW045964 | 321 | 389 | 620 | 143 | 55.9 | 55 | 3.2 |
| SW006981 | 272 | 95 | 51 | 50 | 21.5 | 325 | 12.5 |
| SW053831 | 60 | 43 | 65 | 63 | 29 | 104 | 0.85 |
| SW003087 | 100.3 |  |  | 37.4 |  | 31.3 | 11.7 |
| SW202754 | 198 |  |  | 30.2 |  | 32.7 | 24.8 |
| SW202755 | 105.6 |  |  | 47.8 |  | 53.9 | 25.1 |
| SW202743 | 22.3 |  |  | 19.8 |  | 20.6 | 7.04 |
| SW202744 | 36.2 |  |  | 53.5 |  | 24.8 | 25.6 |
| SW202745 | 335.9 |  |  | 64.3 |  | 148.9 | 2.12 |
| SW202746 | 4950 |  |  | 36 |  | 42.7 | 38 |
| SW202749 | 234.3 |  |  | 57.6 |  | 75.2 | 70.4 |
| SW008027 | 32.2 |  |  | 67.3 |  | 24.6 | 5.1 |
| SW202750 | 126.6 |  |  | 143.8 |  | 4950 | 97.6 |
| SW202752 | 4950 |  |  | 166.2 |  | 4950 | 109.8 |
| SW166942 | 4950 |  |  | 46.7 |  | 78.6 | 47.6 |
| SW166933 | 4950 |  |  | 55.2 |  | 4950 | 55.4 |
| SW202747 | 29.5 |  |  | 20.5 |  | 21.2 | 10.3 |
| SW202753 | 20 |  |  | 18.2 |  | 13.4 | 6.25 |
| SW000931 | 360 |  |  | 307.9 |  | 4950 | 2.33 |
| SW202751 | 376.4 |  |  | 995.2 |  | 4950 | 4950 |
| SW202748 | 4950 |  |  | 69 |  | 4950 | 4950 |
| SW004400 | 74.3 |  |  | 54.6 |  | 77.5 | 182.5 |
| SW053525 | 4950 |  |  | 181.7 |  | 1527 | 4950 |
| SW138238 | 4950 |  |  | 1168 |  | 179.1 | 3242 |
| SW202739 | 250.3 |  |  | 132.4 |  | 137.4 | 126.4 |
| SW202740 | 129.1 |  |  | 82.5 |  | 110.6 | 114.3 |
| SW202741 | 13 |  |  | 11.9 |  | 8.42 | 9.79 |
| SW202857-1 | 22.8 | 22.3 | 31.8 | 42.7 | 21.3 | 3.16 | 0.0185 |
| SW202860-1 |  | 49.2 |  |  | 35.6 | 41.7 | 18.1 |
| SW001282-2 | 49.2 |  |  |  |  | 2.81 | 0.752 |
| SW202773-1 | 24.9 | 23.6 | 25.9 | 42.9 | 21.7 | 16.6 | 0.268 |
| SW202774-1 | 46.7 | 35.2 |  | 25.5 |  | 36.6 | 1.34 |
| SW202775-1 |  | 35.5 |  |  | 8.87 |  | 5.96 |
| SW202776-1 |  | 46.2 |  |  |  | 15.3 | 4.56 |
| SW202364-1 |  |  |  |  |  |  |  |
| SW202868 |  |  |  |  |  |  |  |
| SW001296 |  |  |  |  |  |  | 3.72 |
| SW004969 |  |  |  |  |  | 5.495 | 0.658 |
| SW008283 |  |  |  |  |  | 18.88 | 1.178 |

TABLE 4-continued

| | | | | | | | |
|---|---|---|---|---|---|---|---|
| SW011940 | | 21.727 | 35.645 | 46.345 | 12.706 | 7 | 2.63 |
| SW018825 | 0 | | | | 47.534 | | 0.424 |
| SW147703 | 33.266 | 13.274 | | | 13.521 | 34.514 | 1.122 |
| SW203668 | | | | | | | |
| SW203669 | | | | | | | |
| SW203670 | | | | | | | |
| SW203671 | | | | | | | |
| SW203726 | | | | | | | |
| SW203727 | | | | | | | |
| SW203728 | | | | | | | |
| SW203729 | | | | | | | |
| SW203730 | | | | | | | |
| SW203731 | | | | | | | |
| SW203732 | | | | | | | |
| SW203733 | | | | | | | |
| SW203734 | | | | | | | |
| SW203735 | | | | | | | |
| SW207003 | 3.5E+07 | | | 7950000 | | | |
| SW208186 | | | | 12.99 | | | |
| SW208187 | | | | 0.6968 | | | |
| SW208110 | | | | 5.969 | | | |
| SW208109 | | | | 7.748 | | | |
| SW 208235 | | | | | | 49.5 | |
| SW 208236 | | | | | | 49.5 | |
| SW 208237 | | | | | | 6.90144 | |
| SW208233-1 | | | | | | 49.5 | |
| SW208652-1 | | | | | | 2.42 | |
| SW208653-1 | | | | | | 1.80 | |
| SW208665-1 | | | | | | | |
| SW208666-1 | | | | | | | |
| SW208700-1 | | | | | | | |
| SW208741-1 | | | | | | | |
| SW208770-1 | | | | | | 3.06 | |
| SW208771-1 | | | | | | 49.50 | |
| SW209017 | | | | | | 4.950 | |
| SW208834 | | | | | | 16.500 | |
| SW209018 | | | | | | 14.787 | |
| SW209049-1 | | | | 21.000 | | | 81 |
| SW209091-1 | | | | 9.03 | | | 24 |
| SW209082-1 | | | | 45.5 | | | 45.5 |
| SW209047-1 | | | | | | 1.20 | |
| SW001296-3 | | | | 28.600 | | | 49.500 |
| SW209049-2 | | | | 21.000 | | | 18.000 |
| SW209168-1 | | | | 40.100 | | | 39.200 |
| SW209205-1 | | | | 0.468 | | | 49.500 |
| SW209206-1 | | | | 49.500 | | | 49.500 |
| SW209322-1 | | | | 39.907 | | | 36.008 |
| SW209323-1 | | | | 40.316 | | | 0.816 |
| SW209411-1 | | | | 3.102 | | | 27.830 |
| SW209413-1 | | | | 49.500 | | | 49.500 |
| SW209414-1 | | | | 49.500 | | | 49.500 |
| SW209412-1 | | | | 49.50002 | | | 49.50002 |
| SW209562-1 | | | | 49.50002 | | | 49.50002 |
| SW209563-1 | | | | 19.66451 | | | 0.183745 |
| SW211559-1 | | | | 0.900 | | | 0.165 |
| SW211561-1 | | | | 16.500 | | | 29.119 |
| SW211566 | | | | 49.5 | | | 49.5 |

| | IC50 (uM) vs indicated non-small cell lung cancer cell line | | | | | | |
|---|---|---|---|---|---|---|---|
| Compound ID | H2122 | H460 | HCC366 | HCC4017 | HCC44 | HCC95 | HopS62 |
| SW003992 | 0.14 | 5000 | 1042 | 1439 | 3500 | 2272 | |
| SW001286 | 0.048 | 0.4 | 35 | 35 | 3 | 2 | |
| SW001811 | 0.7 | 450 | 220 | 120 | 165 | 58 | |
| SW045964 | 1 | 5000 | 149 | 407 | 489 | 140 | |
| SW006981 | 0.26 | 180 | 85 | 76 | 63.7 | 109.5 | |
| SW053831 | 47 | 5000 | 80 | 98 | 33 | 85 | |
| SW003087 | 2.62 | | | | | | |
| SW202754 | 35.4 | | | | | | |
| SW202755 | 0.734 | | | | | | |
| SW202743 | 0.538 | | | | | | |
| SW202744 | 1.16 | | | | | | |
| SW202745 | 1.09 | | | | | | |
| SW202746 | 46.1 | | | | | | |
| SW202749 | 60.4 | | | | | | |
| SW008027 | 0.899 | | | | | | |
| SW202750 | 4950 | | | | | | |
| SW202752 | 4950 | | | | | | |
| SW166942 | 59.6 | | | | | | |

TABLE 4-continued

| | | | | | | | |
|---|---|---|---|---|---|---|---|
| SW166933 | 489.7 | | | | | | |
| SW202747 | 0.306 | | | | | | |
| SW202753 | 4.36 | | | | | | |
| SW000931 | 2.62 | | | | | | |
| SW202751 | 4950 | | | | | | |
| SW202748 | 4950 | | | | | | |
| SW004400 | 297.3 | | | | | | |
| SW053525 | 4950 | | | | | | |
| SW138238 | 4950 | | | | | | |
| SW202739 | 114 | | | | | | |
| SW202740 | 4950 | | | | | | |
| SW202741 | 8.13 | | | | | | |
| SW202857-1 | 0.00839 | 0.046 | | 32.6 | 0.0236 | 10.8 | |
| SW202860-1 | 4.05 | 47.8 | 42.6 | 47.5 | 15.1 | 44.9 | |
| SW001282-2 | 0.159 | 0.512 | | | 30.1 | 19.6 | |
| SW202773-1 | 0.0431 | 0.157 | 41.8 | 21.1 | 0.122 | 0.163 | |
| SW202774-1 | 1.08 | 1.31 | | | 1.01 | 0.336 | |
| SW202775-1 | 6.53 | 48 | | | 16.9 | 3.19 | |
| SW202776-1 | | | | | | 8.15 | |
| SW202364-1 | 30.8 | | | | 38.6 | | |
| SW202868 | 0.005 | | | | | | |
| SW001296 | 35.075 | 4.46 | | | 0.34 | | |
| SW004969 | 0.21 | 0.521 | | | | 0.2 | |
| SW008283 | 0.481 | | | | | 0.511 | |
| SW011940 | 0.037 | 2.128 | | 4.256 | 50559 | 5.861 | |
| SW018825 | 0.129 | | | | | 2.228 | |
| SW147703 | 3.296 | | | | 37.497 | 32.434 | |
| SW203668 | 0.035 | | | | | | |
| SW203669 | 49.5 | | | | | | |
| SW203670 | 0.108 | | | | | | |
| SW203671 | 0.314 | | | | | | |
| SW203726 | 0.029 | | | | | | |
| SW203727 | 0.016 | | | | | | |
| SW203728 | 0.12 | | | | | | |
| SW203729 | 3.22 | | | | | | |
| SW203730 | 0.845 | | | | | | |
| SW203731 | 2.28 | | | | | | |
| SW203732 | 0.013 | | | | | | |
| SW203733 | 0.017 | | | | | | |
| SW203734 | 0.939 | | | | | | |
| SW203735 | 0.036 | | | | | | |
| SW207003 | 0.006 | | | | | | |
| SW208186 | 0.107 | | | | | | |
| SW208187 | 0.2881 | | | | | | |
| SW208110 | 0.01198 | | | | | | |
| SW208109 | 0.06698 | | | | | | |
| SW 208235 | 49.5 | | | | 49.5 | | |
| SW 208236 | 49.5 | | | | 49.5 | | |
| SW 208237 | 0.61 | | | | 6.5 | | |
| SW208233-1 | 49.5 | | | | 49.5 | | |
| SW208652-1 | 0.009 | | | | 0.025 | | |
| SW208653-1 | 0.042 | | | | 3.626 | | |
| SW208665-1 | 42.67 | | | | 2.14 | | 1.93 |
| SW208666-1 | 0.26 | | | | 3.52 | | 0.09 |
| SW208700-1 | 7.92 | | | | 49.50 | | |
| SW208741-1 | 0.22 | | | | 3.64 | | |
| SW208770-1 | 31.41 | | | | 12.71 | | |
| SW208771-1 | 32.94 | | | | 8.43 | | |
| SW209017 | 5.761 | | | | 49.500 | | |
| SW208834 | 3.549 | | | | 49.500 | | |
| SW209018 | 4.730 | | | | 49.500 | | |
| SW209049-1 | 0.131 | | | | | | |
| SW209091-1 | 0.010 | | | | | | |
| SW209082-1 | 0.100 | | | | | | |
| SW209047-1 | 0.09 | | | | | | |
| SW001296-3 | 18.500 | | | | | | |
| SW209049-2 | 0.131 | | | | | | |
| SW209168-1 | 0.029 | | | | | | |
| SW209205-1 | 0.397 | | | | | | |
| SW209206-1 | 49.500 | | | | | | |
| SW209322-1 | 49.500 | | | | | | |
| SW209323-1 | 0.099 | | | | | | |
| SW209411-1 | 49.50002 | | | | | | |
| SW209413-1 | 49.50002 | | | | | | |
| SW209414-1 | 49.50002 | | | | | | |
| SW209412-1 | 49.500 | | | | | | |
| SW209562-1 | 49.500 | | | | | | |
| SW209563-1 | 0.027 | | | | | | |

TABLE 4-continued

| | |
|---|---|
| SW211559-1 | 0.086 |
| SW211561-1 | 7.751 |
| SW211566 | 49.5 |

Figure 2:
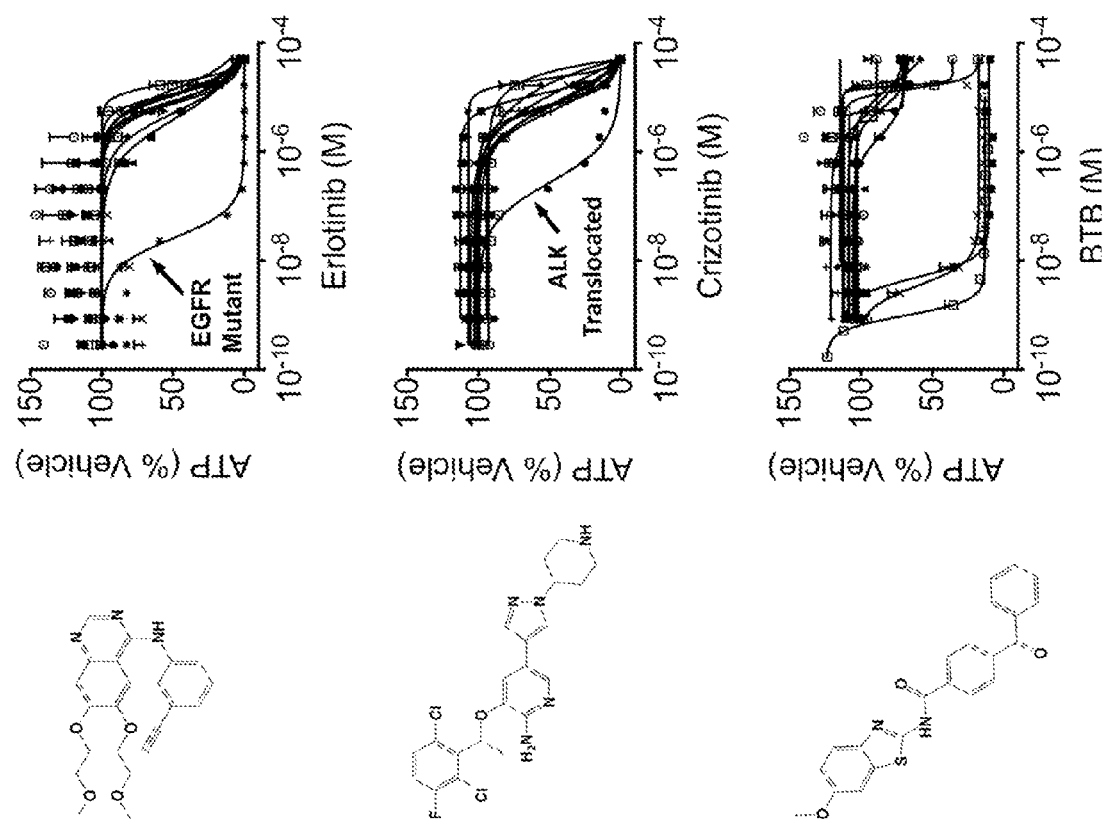
FIG. 2 shows the degree of selective toxicity of an exemplary compound, BTB (SW202857) which has similar or superior potency and selectivity compared to clinically used agents erlotinib and crizotinib.

Specifically, 4-benzoyl-N-(6-methoxybenzo[d]thiazol-2-yl)benzamide (BTB, also known as SW202857) is now toxic at less than 50 nM against four sensitive cell lines, which is a 10- to >100-fold lower concentration than that required to inhibit the growth of other lines analyzed. Notably, the degree of selective toxicity of BTB is superior to both erlotinib and crizotinib (FIG. 2). One possible explanation for BTB's effect could be that sensitive cells concentrate intracellular BTB either through selective uptake or lack of efflux. However, we have found that the intracellular concentration of BTB was not markedly lower in insensitive cell lines compared to sensitive cell lines ruling out this possibility (data not shown).

Although there is no published activity for BTB, other benzothiazole derivatives have been reported to inhibit kinases[9] yet we have surprisingly found that 0.10 μM BTB failed to inhibit any of about 300 protein kinase enzymes in vitro (Millipore) (Table 5). Specifically, kinase inhibition assays were performed at EMD Millipore at 1, 10 and 100 nM SW202857 and individually optimized concentrations of ATP. GSK3beta showed 21% inhibition at 100 nM. No other kinase showed greater than 15% inhibition at the highest concentration. Listed kinases are the human enzyme unless indicated: mouse (m), rat (r), yeast (y). Thus, BTB likely does not act to kill cells by inhibiting kinase activities.

TABLE 5

| | | | |
|---|---|---|---|
| Abl | cdk5/p35 | EphA8 | Insulin Receptor |
| Abl | cdk6/cyclin D3 | EphB1 | IRAK1 |
| Abl (H396P) | cdk7/cyclin H/MAT1 | EphB2 | IRAK4 |
| Abl (M351T) | cdk9/cyclin T1 | EphB3 | IRR |
| Abl (Q252H) | CHK1 | EphB4 | Itk |
| Abl (T315I) | CHK2 | erbB-4/HER-4 | JAK2 |
| Abl (Y253F) | CHK2 (I157T) | FAK | JAK3 |
| ACK1 | CHK2 (R145W) | Fer | JNK1α1/SAPK1c |
| ALK | CK1gamma 1 | FES/FPS | JNK2α2/SAPK1a |
| ALK4 | CK1gamma 2 | FGFR1 | JNK2α2/SAPK1a |
| AMPK (α1, β1, γ1), | CK1delta | FGFR1 (V561M) | JNK3/SAPK1b |
| AMPK (α2, β1, γ1), | CK1 (y) | FGFR2 | KDR |
| Arg | CK2 | FGFR2 (N549H) | Lck, activated |
| Arg (m) | CK3 | FGFR3 | Lck |
| ARK5 | c-Kit (D816H) | FGFR4 | LIM Kinase 1 |
| ASK1 | c-Kit (D816V) | Fgr | LKB1/STRADα/MO25α |
| Aurora A | c-Kit (V560G) | Flt-1 | LOK |
| Aurora B | c-Kit (V654A) | Flt-3 (D835Y) | Lyn |
| Aurora C | c-Kit | Flt-3 | Lyn (m) |
| Axl | CSK | Flt-4 | MAP Kinase 1/Erk1 |
| Blk | c-RAF | Fms | MAP Kinase 2/Erk2 |
| Blk (m) | cSRC | Fms (Y969C) | MAP Kinase 2/Erk2 (m) |
| Bmx | DAPK1 | Fyn | MAPKAP Kinase 2 |
| Brk | DAPK2 | GCK | MAPKAP Kinase 3 |
| BrSK1 | DCAMKL2 | GRK5 | MARK1 |
| BrSK2 | DDR2 | GRK6 | MEK1 |
| BTK | DMPK | GRK7 | MELK |
| BTK (R28H) | DRAK1 | GSK3α | Mer |
| CaM Kinase I | DYRK2 | GSK3β | Met |
| CaM Kinase IIβ | eEF-2K | Haspin | Met (D1246H) |
| CaM Kinase IIγ | EGFR | Hck, activated | Met (D1246N) |
| CaM Kinase IIδ | EGFR (L858R) | Hck | Met (M1268T) |
| CaM Kinase IV | EGFR (L861Q) | HIPK1 | Met (Y1248C) |
| CaM Kinase Iδ, active 14-731 3 | EGFR (T790M) | HIPK2 | Met (Y1248D) |
| cdk1/cyclin B, active 14-450 3 | EGFR (T790M, L858R) | HIPK3 | Met (Y1248H) |
| cdk2/cyclin A | EphA1 | IGF-1R, activated | MINK |
| cdk2/cyclin E | EphA2 | IGF-IR | MKK4/SKK1 (m) |
| cdk3/cyclin E | EphA3 | IKKα | MKK6/SKK3 |
| cdk5/p25 | EphA4 | IKKβ | MKK7β1 |
| | EphA5 | IKKε | MLCK |
| | EphA7 | Insulin Receptor, activated | MLK1 |
| Mnk2 | PI3 Kinase (p110β/p85a) (m) | ROKα/ROCK-II | Txk |
| MRCKα | PI3 kinase delta p85a (m) | ROKα/ROCK-II (r) | ULK2 |
| MRCKβ | PI3 kinase alpha, p65alpha | ROKβ/ROCK-I | ULK3 |
| MSK1 | PI3 Kinase (p110δ/p85a) | Ron | VRK2 |
| MSK2 | PI3 Kinase (p120γ) | Ros | WNK2 |
| MSSK1 | PI3 Kinase C2α | Rse | WNK3 |
| MST1 | PI3 Kinase C2γ | Rsk1/MAPKAP Kinase | Yes |
| MST2 | Pim-1 | Rsk1/MAPKAP Kinase 1a (r) | ZAP-70 |
| MST3 | Pim-2 | Rsk2/MAPKAP Kinase | ZIPK |
| mTOR | Pim-3 | Rsk3 | |
| mTOR/FKBP12 | PIP4K2α | Rsk4 | |
| MuSK | PIP5K1α | SAPK2a | |
| NEK2 | PIP5K1γ | SAPK2a(t106M) | |
| NEK3 | PKA, catalytic subunit | SAPK2b | |

TABLE 5-continued

| | | |
|---|---|---|
| NEK6 | PKBalpha | SAPK3 |
| NEK7 | PKBbeta | SAPK4 |
| NEK11 | PKBgamma | SGK1 |
| NLK | PKCα | SGK2 |
| p70 S6 Kinase (T412E) | PKCβI | SGK3 |
| PAK2 | PKCβII | SIK |
| PAK4 | PKCγ | Snk |
| PAK5 | PKCδ | Src (1-530) |
| PAK6 | PKCε | Src (T341M) |
| PAR-1Ba | PKCzeta | SRPK1 |
| PASK | PKCη | SRPK2 |
| PDGFRα | PKCthehta | STK33 |
| PDGFRα (550-end, V561D) | PKCiota | Syk |
| PDGFRα (D842V) | PKCμ | TAK1-TAB1 fusion |
| PDGFRβ | PKD2 | TAO1 |
| PDK1 | PKG1α | TAO2 |
| PEK | PKG1β | TAO3 |
| PhKγ2 | Plk1 | TBK1 |
| PI3 Kinase (p110α, (E542K)/p85α) | Plk3 | Tec |
| PI3 Kinase (p110α, (E542K)/p85α) (m) | PRAK | TGFBR1 |
| PI3 Kinase (p110α, (E545K)/p85α) | PRK2 | Tie2 |
| PI3 Kinase (p110α), (E545K)/p85α) (m) | PRKX | Tie2 (R849W) |
| PI3 Kinase (p110α), (H1047R)/p85α) (m) | PTK5 | Tie2 (Y897S) |
| PI3 Kinase (p110α, (H1047R)/p85α) | Pyk2 | TLK2 |
| PI3 Kinase (p110α/p65α) | Ret (V804L) | TrkA |
| PI3 Kinase (p110α/p65α) (m) | Ret (V804M) | TrkB |
| PI3 Kinase (p110α/p85α) (m) | Ret | TSSK1 |
| PI3 Kinase (p110β/p85a) | RIPK2 | TSSK2 |

Figure 3:
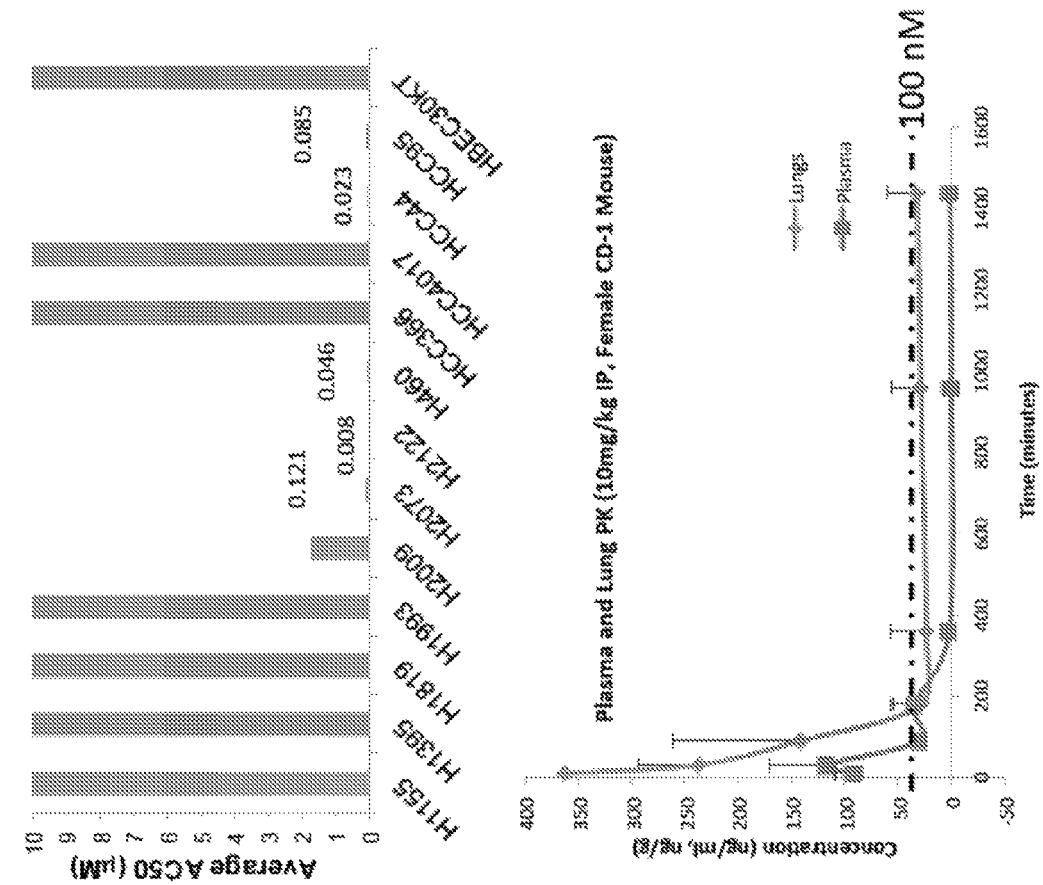
FIG. 3 shows that an exemplary compound, BTB (SW202857) has high chemical stability, high potency and high selectivity.
Figure 3:
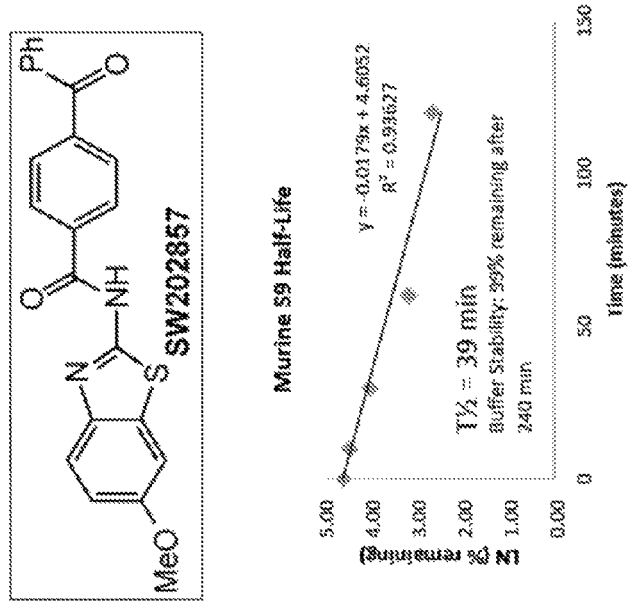

We found that SW202857 was chemically stable in the presence of mouse liver S9 fractions, in addition to its high potency and selectivity (FIG. 3).

Figure 4:
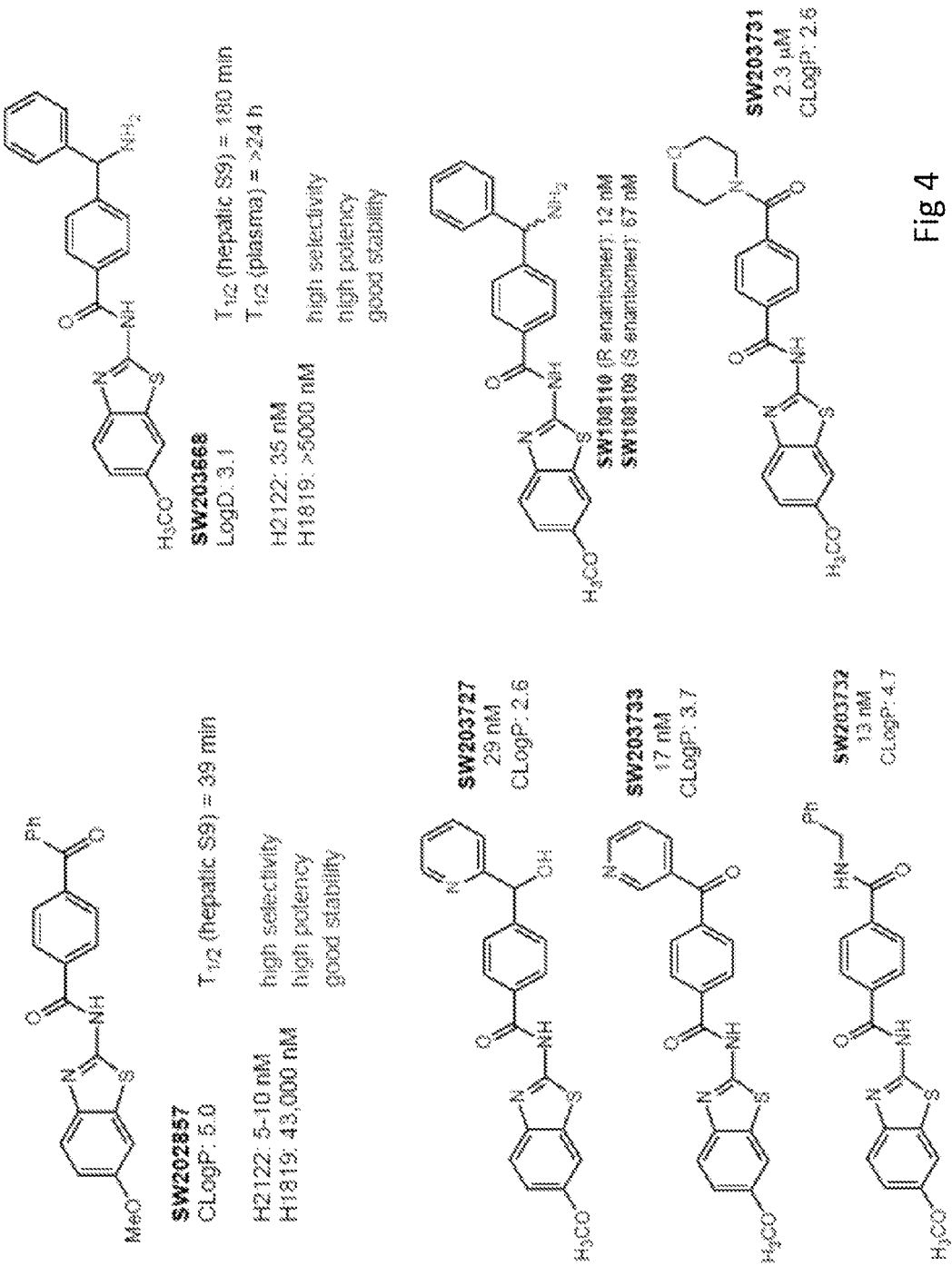
FIG. 4 shows several exemplary compounds having high selectivity.
Figure 5:
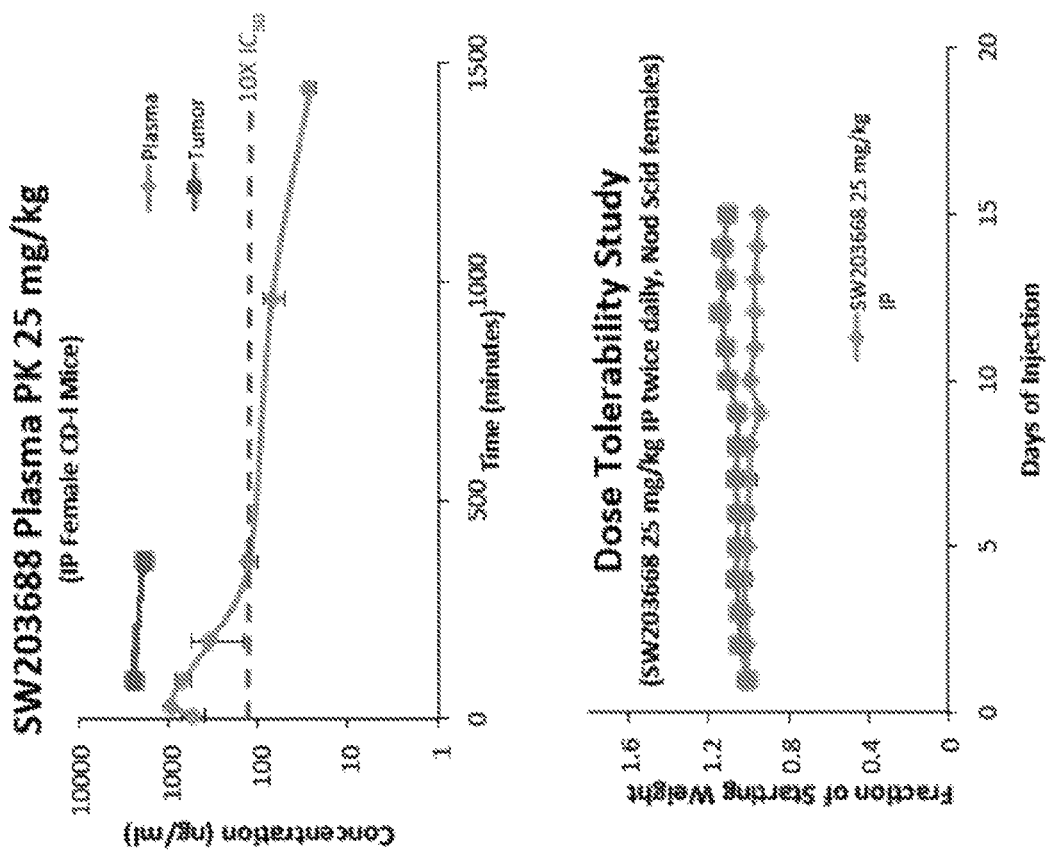
FIG. 5 shows that an exemplary compound, SW203668 has appropriate absorption, distribution, metabolism, and excretion ("ADME") for xenograft studies.
Figure 5:
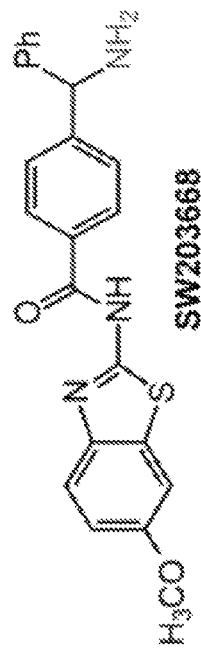

Other derivative including SW203668 (see, e.g., FIG. 4 and Table 4) also displayed high selectivity. Upon further investigation, SW203668 shows appropriate absorption, distribution, metabolism, and excretion ("ADME") in xenograft studies (FIG. 5).

Similarly, we found that an oxalamide, SW208108, shows potent toxicity to a similar subset of non-small cell lung cancer cell lines as both SW202857 and SW203668 (FIG. 6A). Indeed, a broad class of compounds is also found to be selectively toxic to certain non-small cell lung cancer cell lines, as well as to display high potency (e.g., low nM concentrations). These include certain oxalamides and N-acyl ureas as well as some amides and ureas represented by formula (B). Examples and their toxicity data are shown in Tables 6 and 7 below.

Figure 6C:
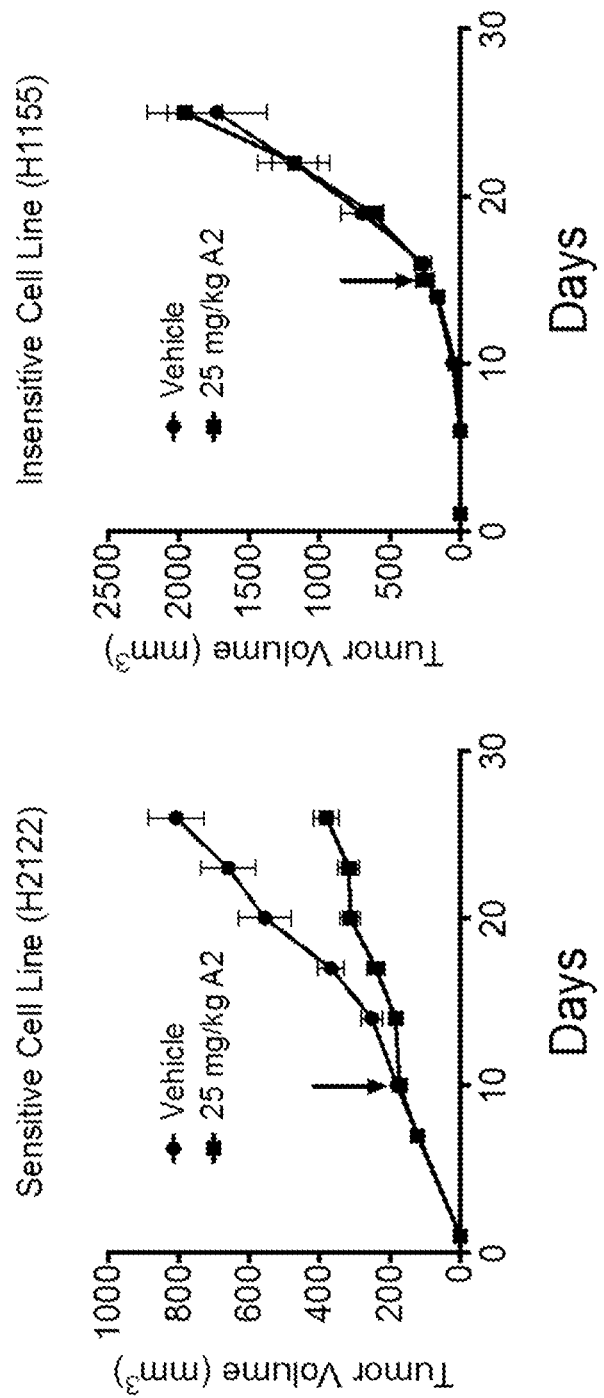
FIG. 6C. An in vivo efficacy study demonstrating selective tumor growth inhibition with selective toxins. NOD/SCID mice were injected with either H2122 (sensitive) or H1155 (insensitive) cells subcutaneously on day 0. When tumors reached 200 cubic mm, treatment with SW203668 (listed as A2) or vehicle was initiated (as indicated by the arrow) with twice daily doses of 25 mg/kg, IP. Tumor size was measured every 3 days for the duration of the study. Data are plotted as mean±SEM; n=12 for each group.

Likewise, a chromone-containing small molecule was found to target H2122 and other cell lines that are sensitive to the oxalamides and benzothiazoles (FIG. 6B). In addition, in preclinical mouse models, SW203668 shows selective toxicity in H2122 xenografts, but not H1155 xenografts with twice daily dosing 25 mg/kg intraperitoneal injection (IP) (FIG. 6C).

With this information, we synthesized and tested a series of small molecules derived in conception from the oxalamide and chromone scaffold including N-acyl ureas, as shown in Tables 6-8. Each compound was tested in a 12-point dose-response study starting at 50 micromolar and decreasing in 3-fold increments to sub-nanomolar concentrations, in duplicate. Additionally, one or more additional cell line was tested in the same way.

TABLE 6

| Compound ID | Structure |
|---|---|
| SW027949 | COC1=CC=C(CCNC(=O)C(=O)NC2=CC=C(C)C(C)=C2)C=C1 |
| SW027951 | COC1=CC=C(CCNC(=O)C(=O)NC2=CC=C(Cl)C=C2)C=C1 |

TABLE 6-continued
| Compound ID | Structure |
|---|---|
| SW027952 | 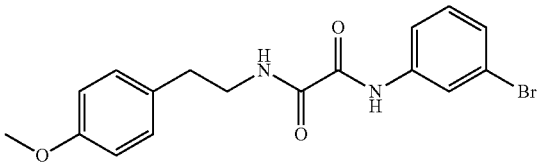 [SMILES: COc1ccc(CCNC(=O)C(=O)Nc2cccc(Br)c2)cc1]<br>COC1=CC=C(CCNC(=O)C(=O)NC2=CC=CC(Br)=C2)C=C1 |
| SW027950 | 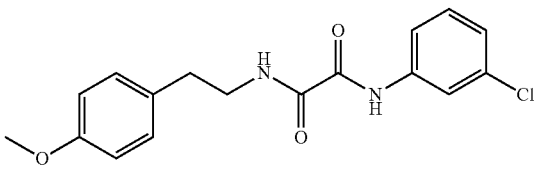 [SMILES: COc1ccc(CCNC(=O)C(=O)Nc2cccc(Cl)c2)cc1]<br>COC1=CC=C(CCNC(=O)C(=O)NC2=CC=CC(Cl)=C2)C=C1 |
| SW027951-2-A | 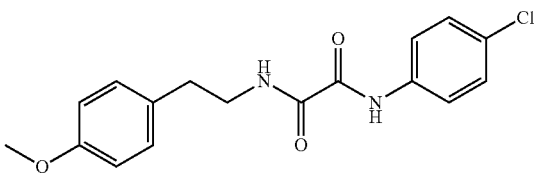 [SMILES: COc1ccc(CCNC(=O)C(=O)Nc2ccc(Cl)cc2)cc1]<br>O=C(C(NC1=CC=C(Cl)C=C1)=O)NCCC2=CC=C(OC)C=C2 |
| SW027954-2-A | 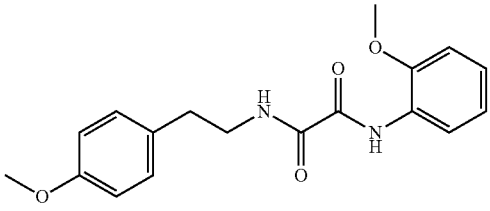 [SMILES: COc1ccc(CCNC(=O)C(=O)Nc2ccccc2OC)cc1]<br>O=C(C(NC1=CC=CC=C1OC)=O)NCCC2=CC=C(OC)C=C2 |
| SW027962-2-A | 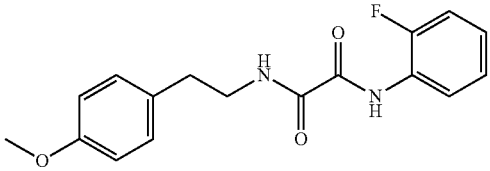 [SMILES: COc1ccc(CCNC(=O)C(=O)Nc2ccccc2F)cc1]<br>O=C(C(NC1=CC=CC=C1F)=O)NCCC2=CC=C(OC)C=C2 |
| SW027952-2-A | 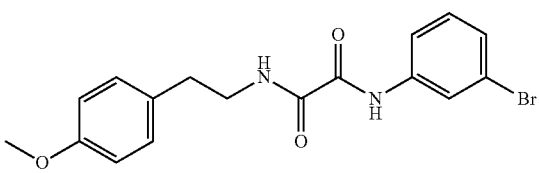 [SMILES: COc1ccc(CCNC(=O)C(=O)Nc2cccc(Br)c2)cc1]<br>O=C(C(NC1=CC(Br)=CC=C1)=O)NCCC2=CC=C(OC)C=C2 |
| SW206859-1-A | 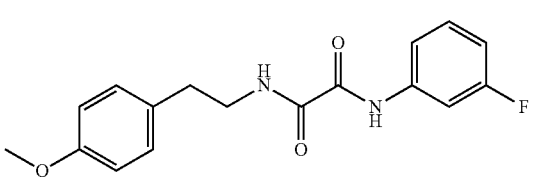 [SMILES: COc1ccc(CCNC(=O)C(=O)Nc2cccc(F)c2)cc1]<br>O=C(C(NC1=CC=CC(F)=C1)=O)NCCC2=CC=C(OC)C=C2 |

TABLE 6-continued

| Compound ID | Structure |
| --- | --- |
| SW206860-1-A | 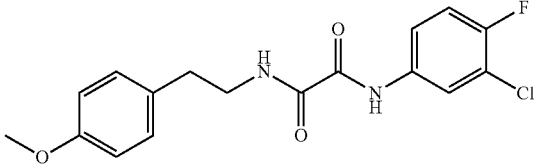 [SMILES: COc1ccc(CCNC(=O)C(=O)Nc2ccc(F)c(Cl)c2)cc1]<br>O=C(C(NC1=CC=C(F)C(Cl)=C1)=O)NCCC2=CC=C(OC)C=C2 |
| SW206861-1-A | 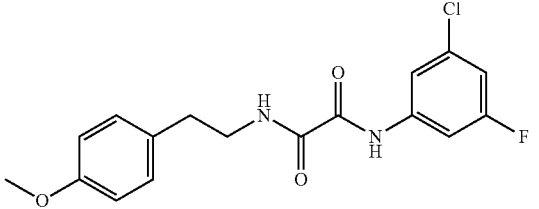 [SMILES: COc1ccc(CCNC(=O)C(=O)Nc2cc(F)cc(Cl)c2)cc1]<br>O=C(C(NC1=CC(F)=CC(Cl)=C1)=O)NCCC2=CC=C(OC)C=C2 |
| SW206862-1-A | 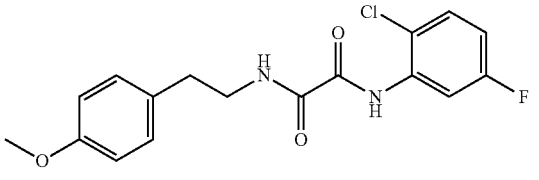 [SMILES: COc1ccc(CCNC(=O)C(=O)Nc2cc(F)ccc2Cl)cc1]<br>O=C(C(NC1=CC(F)=CC=C1Cl)=O)NCCC2=CC=C(OC)C=C2 |
| SW206863-1-a | 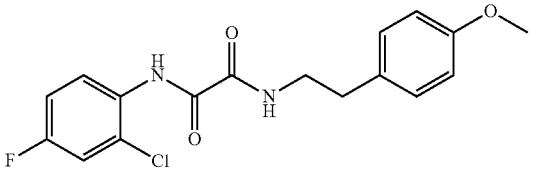 [SMILES: COc1ccc(CCNC(=O)C(=O)Nc2ccc(F)cc2Cl)cc1]<br>O=C(C(NC1=CC=C(F)C=C1Cl)=O)NCCC2=CC=C(OC)C=C2 |
| SW206864-1-A | 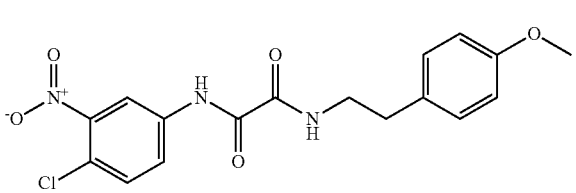<br>O=C(C(NC1=CC=C(Cl)C([N+]([O-])=O)=C1)=O)NCCC2=CC=C(OC)C=C2 |
| SW206866-1-A | 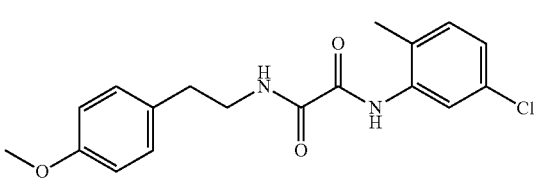 [SMILES: COc1ccc(CCNC(=O)C(=O)Nc2cc(Cl)ccc2C)cc1]<br>O=C(C(NC1=CC(Cl)=CC=C1C)=O)NCCC2=CC=C(OC)C=C2 |
| SW206867-1-A | 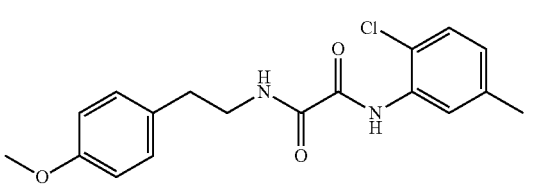<br>O=C(C(NC1=CC(C)=CC=C1Cl)=O)NCCC2=CC=C(OC)C=C2 |

TABLE 6-continued
| Compound ID | Structure |
| --- | --- |
| SW206868-1-A | 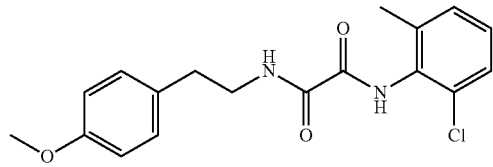 [SMILES: COc1ccc(CCNC(=O)C(=O)Nc2c(C)cccc2Cl)cc1] |
|  | O=C(C(NC1=C(C)C=CC=C1Cl)=O)NCCC2=CC=C(OC)C=C2 |
| SW206869-1-A | 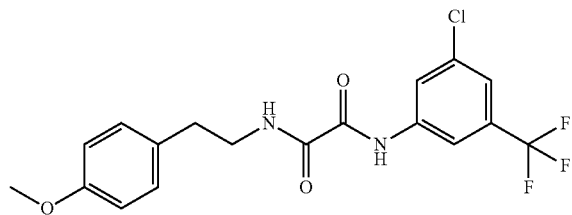 [SMILES: COc1ccc(CCNC(=O)C(=O)Nc2cc(Cl)cc(C(F)(F)F)c2)cc1] |
|  | O=C(C(NC1=CC(C(F)(F)F)=CC(Cl)=C1)=O)NCCC2=CC=C(OC)C=C2 |
| SW206870-1-A | 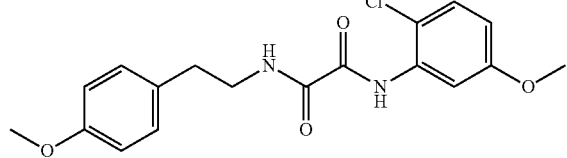 |
|  | O=C(C(NC1=CC(OC)=CC=C1Cl)=O)NCCC2=CC=C(OC)C=C2 |
| SW206871-1-A | 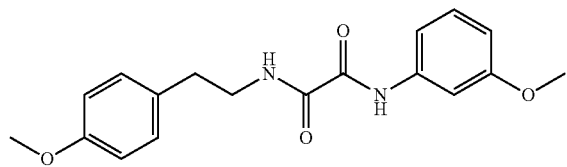 |
|  | O=C(C(NC1=CC=CC(OC)=C1)=O)NCCC2=CC=C(OC)C=C2 |
| SW206872-1-A | 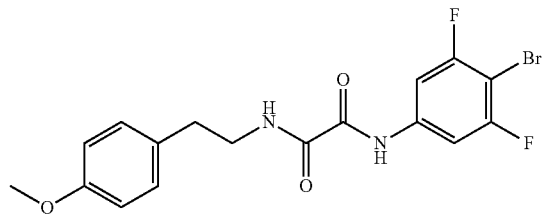 [SMILES: COc1ccc(CCNC(=O)C(=O)Nc2cc(F)c(Br)c(F)c2)cc1] |
|  | O=C(C(NC1=CC(F)=C(Br)C(F)=C1)=O)NCCC2=CC=C(OC)C=C2 |
| SW206874-A | 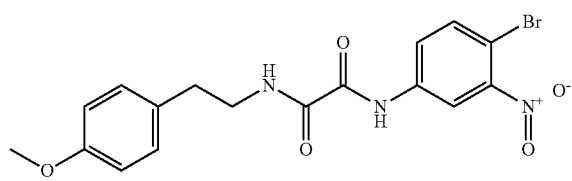 |
|  | O=C(C(NC1=CC=C(Br)C([N+]([O-])=O)=C1)=O)NCCC2=CC=C(OC)C=C2 |

TABLE 6-continued
| Compound ID | Structure |
|---|---|
| SW206875-1-A | 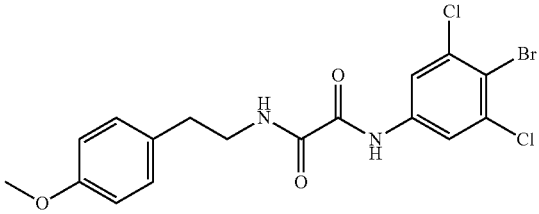
O=C(C(NC1=CC(Cl)=C(Br)C(Cl)=C1)=O)NCCC2=CC=C(OC)C=C2 |
| SW206876-1-A | 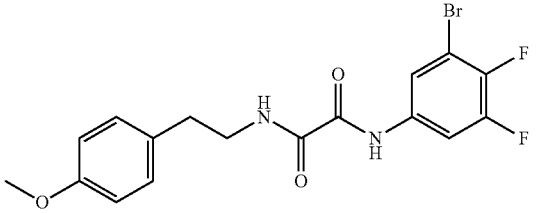 [SMILES: COc1ccc(CCNC(=O)C(=O)Nc2cc(F)c(F)c(Br)c2)cc1]
O=C(C(NC1=CC(F)=C(F)C(Br)=C1)=O)NCCC2=CC=C(OC)C=C2 |
| SW206877-1-A | 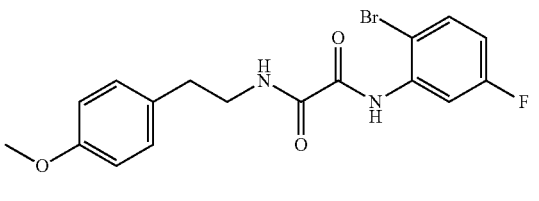 [SMILES: COc1ccc(CCNC(=O)C(=O)Nc2cc(F)ccc2Br)cc1]
O=C(C(NC1=CC(F)=CC=C1Br)=O)NCCC2=CC=C(OC)C=C2 |
| SW206878-1-A | 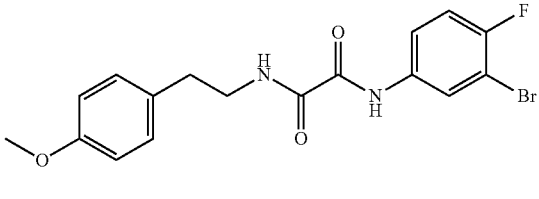 [SMILES: COc1ccc(CCNC(=O)C(=O)Nc2ccc(F)c(Br)c2)cc1]
O=C(C(NC1=CC=C(F)C(Br)=C1)=O)NCCC2=CC=C(OC)C=C2 |
| SW206879-1-A | 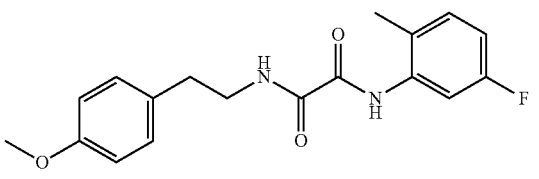 [SMILES: COc1ccc(CCNC(=O)C(=O)Nc2cc(F)ccc2C)cc1]
O=C(C(NC1=CC(F)=CC=C1C)=O)NCCC2=CC=C(OC)C=C2 |
| SW206880-1-A | 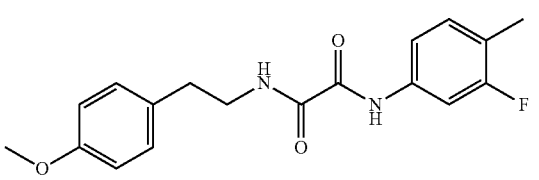 [SMILES: COc1ccc(CCNC(=O)C(=O)Nc2ccc(C)c(F)c2)cc1]
O=C(C(NC1=CC=C(C)C(F)=C1)=O)NCCC2=CC=C(OC)C=C2 |

TABLE 6-continued

| Compound ID | Structure |
| --- | --- |
| SW206881-1-A | O=C(C(NC1=CC(C)=CC(F)=C1)=O)NCCC2=CC=C(OC)C=C2 |
| SW206882-1-A | O=C(C(NC1=CC=CC(F)=C1C)=O)NCCC2=CC=C(OC)C=C2 |
| SW206883-1-A | O=C(C(NC1=CC=C(C)C=C1F)=O)NCCC2=CC=C(OC)C=C2 |
| SW206884-1-A | O=C(C(NC1=CC(F)=CC=C1F)=O)NCCC2=CC=C(OC)C=C2 |
| SW206885-1-A | O=C(C(NC1=CC([N+]([O-])=O)=CC=C1F)=O)NCCC2=CC=C(OC)C=C2 |
| SW206887-1-A | O=C(C(NC1=C(Br)C=CC=C1Br)=O)NCCC2=CC=C(OC)C=C2 |
| SW206888-1-A | O=C(C(NC1=CC=C(Br)C=C1Br)=O)NCCC2=CC=C(OC)C=C2 |

TABLE 6-continued
| Compound ID | Structure |
|---|---|
| SW206889-1-A | 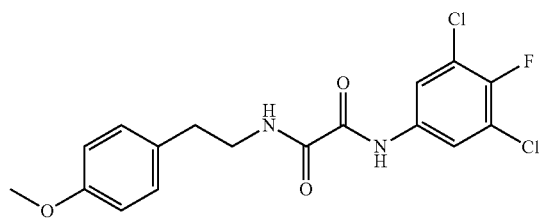 |
| | 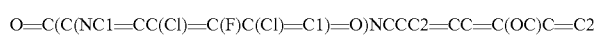 |
| | O=C(C(NC1=CC(Cl)=C(F)C(Cl)=C1)=O)NCCC2=CC=C(OC)C=C2 |
| SW206890-1-A | 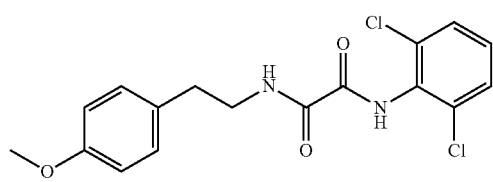 [SMILES: COc1ccc(CCNC(=O)C(=O)Nc2c(Br)cccc2Br)cc1] |
| | 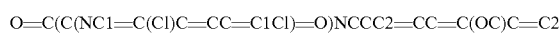 |
| | O=C(C(NC1=C(Cl)C=CC=C1Cl)=O)NCCC2=CC=C(OC)C=C2 |
| SW206891-1-A | 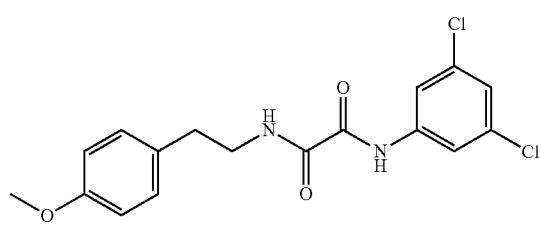 [SMILES: COc1ccc(CCNC(=O)C(=O)Nc2cc(Cl)cc(Cl)c2)cc1] |
| | 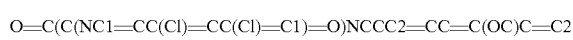 |
| | O=C(C(NC1=CC(Cl)=CC(Cl)=C1)=O)NCCC2=CC=C(OC)C=C2 |
| SW206891-2 | 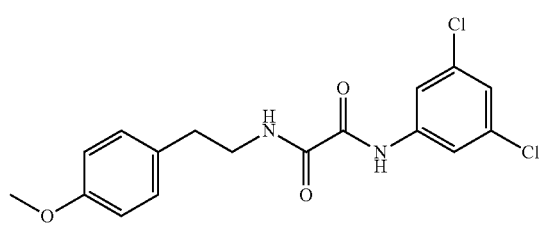 [SMILES: COc1ccc(CCNC(=O)C(=O)Nc2cc(Cl)cc(Cl)c2)cc1] |
| | 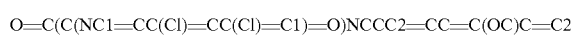 |
| | O=C(C(NC1=CC(Cl)=CC(Cl)=C1)=O)NCCC2=CC=C(OC)C=C2 |
| SW206926-1 | 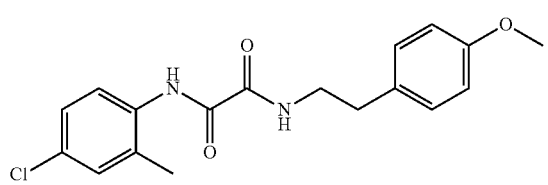 [SMILES: COc1ccc(CCNC(=O)C(=O)Nc2ccc(Cl)cc2C)cc1] |
| | 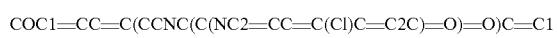 |
| | COC1=CC=C(CCNC(C(NC2=CC=C(Cl)C=C2C)=O)=O)C=C1 |
| SW206951-1 | 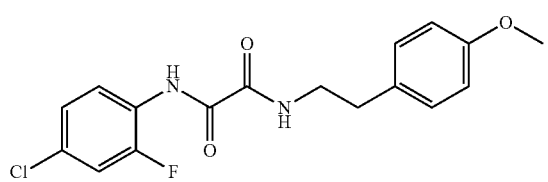 [SMILES: COc1ccc(CCNC(=O)C(=O)Nc2ccc(Cl)cc2F)cc1] |
| | 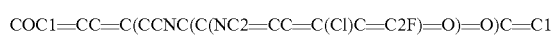 |
| | COC1=CC=C(CCNC(C(NC2=CC=C(Cl)C=C2F)=O)=O)C=C1 |

TABLE 6-continued

| Compound ID | Structure |
|---|---|
| SW206952-1 | 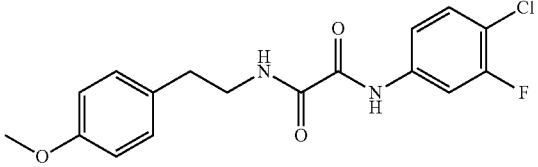 [SMILES: COc1ccc(CCNC(=O)C(=O)Nc2ccc(Cl)c(F)c2)cc1]<br>COC1=CC=C(CCNC(C(NC2=CC(F)=C(Cl)C=C2)=O)=O)C=C1 |
| SW206953-1 | 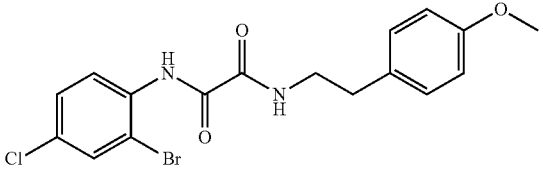 [SMILES: COc1ccc(CCNC(=O)C(=O)Nc2ccc(Cl)cc2Br)cc1]<br>COC1=CC=C(CCNC(C(NC2=CC=C(Cl)C=C2Br)=O)=O)C=C1 |
| SW206954-1 | 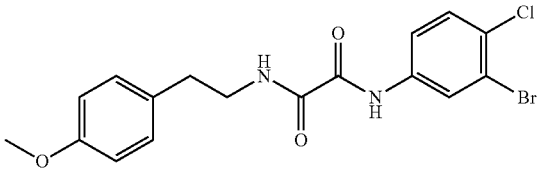 [SMILES: COc1ccc(CCNC(=O)C(=O)Nc2ccc(Cl)c(Br)c2)cc1]<br>COC1=CC=C(CCNC(C(NC2=CC(Br)=C(Cl)C=C2)=O)=O)C=C1 |
| SW206955-1 | 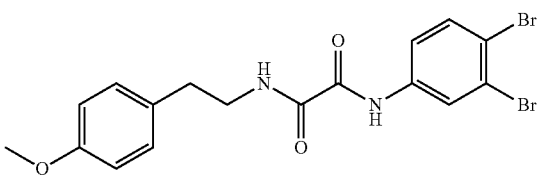 [SMILES: COc1ccc(CCNC(=O)C(=O)Nc2ccc(Br)c(Br)c2)cc1]<br>COC1=CC=C(CCNC(C(NC2=CC(Br)=C(Br)C=C2)=O)=O)C=C1 |
| SW206959-1 | 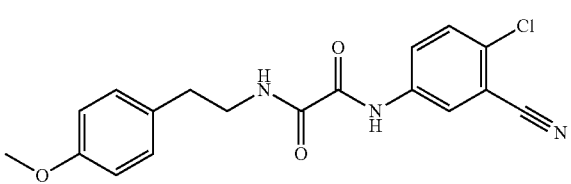 [SMILES: COc1ccc(CCNC(=O)C(=O)Nc2ccc(Cl)c(C#N)c2)cc1]<br>COC1=CC=C(CCNC(C(NC2=CC(C#N)=C(Cl)C=C2)=O)=O)C=C1 |
| SW206960-1 | 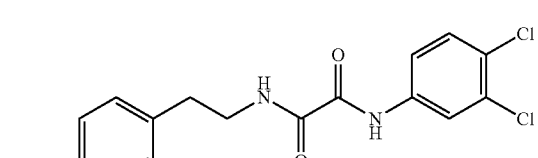<br>COC1=CC=C(CCNC(C(NC2=CC(Cl)=C(Cl)C=C2)=O)=O)C=C1 |
| SW206961-1 | 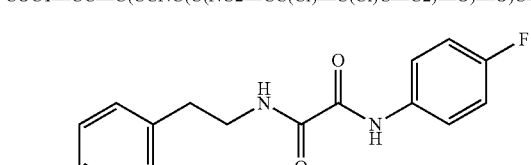<br>O=C(C(NC1=CC=C(F)C=C1)=O)NCCC2=CC=C(OC)C=C2 |

TABLE 6-continued

| Compound ID | Structure |
|---|---|
| SW206962-1 | 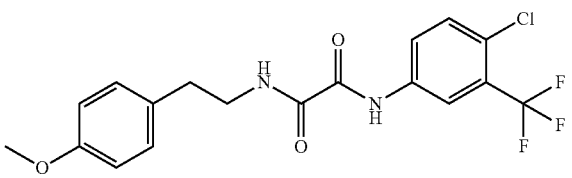 [SMILES: COc1ccc(CCNC(=O)C(=O)Nc2ccc(Cl)c(C(F)(F)F)c2)cc1]<br>O=C(C(NC1=CC=C(Cl)C(C(F)(F)F)=C1)=O)NCCC2=CC=C(OC)C=C2 |
| SW206963-1 | 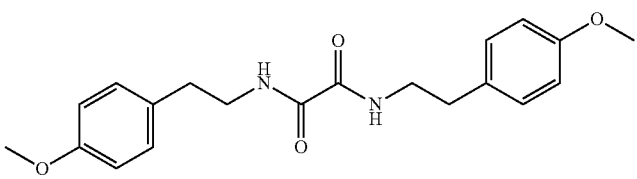<br>O=C(C(NCCC1=CC=C(OC)C=C1)=O)NCCC2=CC=C(OC)C=C2 |
| SW206964-1 | 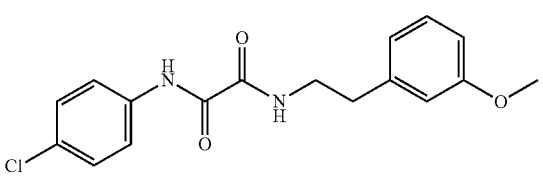 [SMILES: COc1cccc(CCNC(=O)C(=O)Nc2ccc(Cl)cc2)c1]<br>O=C(C(NC1=CC=C(Cl)C=C1)=O)NCCC2=CC(OC)=CC=C2 |
| SW206965-1 | 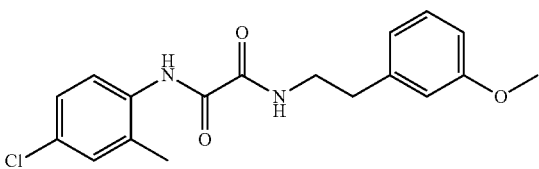 [SMILES: COc1cccc(CCNC(=O)C(=O)Nc2ccc(Cl)cc2C)c1]<br>O=C(C(NC1=CC=C(Cl)C=C1C)=O)NCCC2=CC(OC)=CC=C2 |
| SW206966-1 | 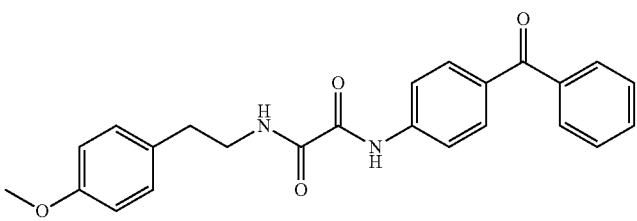 [SMILES: COc1ccc(CCNC(=O)C(=O)Nc2ccc(C(=O)c3ccccc3)cc2)cc1]<br>COC1=CC=C(CCNC(C(NC2=CC=C(C(C3=CC=CC=C3)=O)C=C2)=O)=O)C=C1 |
| SW206967-1 | 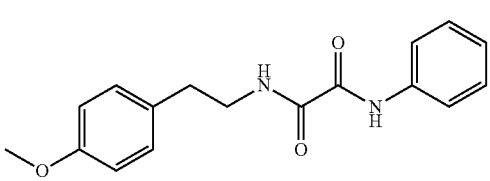 [SMILES: COc1ccc(CCNC(=O)C(=O)Nc2ccccc2)cc1]<br>COC1=CC=C(CCNC(C(NC2=CC=CC=C2)=O)=O)C=C1 |
| SW206968-1 | 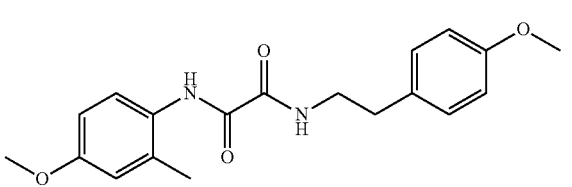<br>O=C(C(NC1=CC=C(OC)C=C1C)=O)NCCC2=CC=C(OC)C=C2 |

TABLE 6-continued
| Compound ID | Structure |
| --- | --- |
| SW206969-1 | 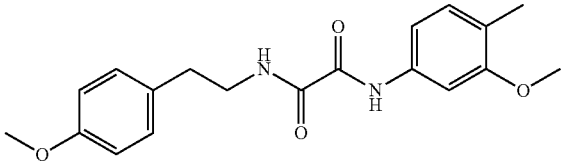<br>O=C(C(NC1=CC=C(C)C(OC)=C1)=O)NCCC2=CC=C(OC)C=C2 |
| SW206970-1 | 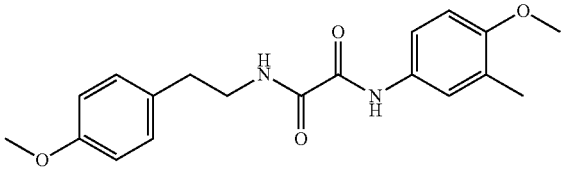<br>O=C(C(NC1=CC=C(OC)C(C)=C1)=O)NCCC2=CC=C(OC)C=C2 |
| SW206971-1 | 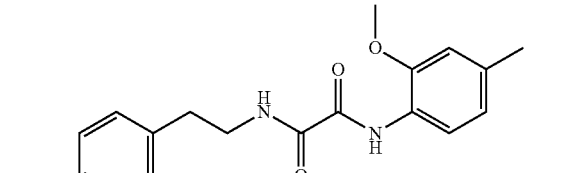<br>O=C(C(NC1=CC=C(C)C=C1OC)=O)NCCC2=CC=C(OC)C=C2 |
| SW206972-1 | 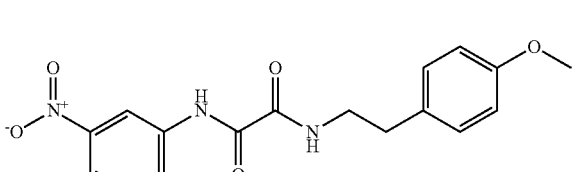<br>O=C(C(NC1=CC=C(OC)C([N+]([O-])=O)=C1)=O)NCCC2=CC=C(OC)C=C2 |
| SW206973-1 | 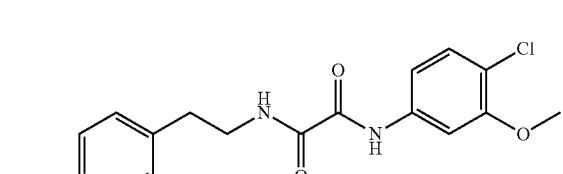<br>COC1=CC=C(CCNC(C(NC2=CC(OC)=C(Cl)C=C2)=O)=O)C=C1 |
| SW206974-1 | 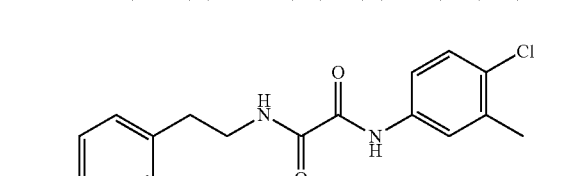<br>COC1=CC=C(CCNC(C(NC2=CC(C)=C(Cl)C=C2)=O)=O)C=C1 |

TABLE 6-continued
| Compound ID | Structure |
|---|---|
| SW207004-1 | 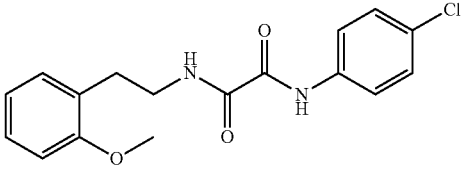 [SMILES: COc1ccccc1CCNC(=O)C(=O)Nc1ccc(Cl)cc1]<br>COC1=CC=CC=C1CCNC(C(NC2=CC=C(Cl)C=C2)=O)=O |
| SW207005-1 | 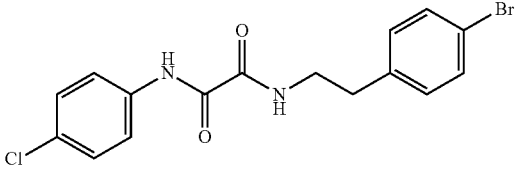 [SMILES: O=C(NCCc1ccc(Br)cc1)C(=O)Nc1ccc(Cl)cc1]<br>BrC1=CC=C(CCNC(C(NC2=CC=C(Cl)C=C2)=O)=O)C=C1 |
| SW207006-1 | 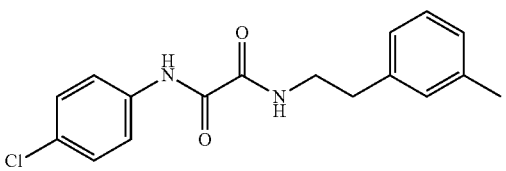 [SMILES: Cc1cccc(CCNC(=O)C(=O)Nc2ccc(Cl)cc2)c1]<br>O=C(C(NC1=CC=C(Cl)C=C1)=O)NCCC2=CC=CC(C)=C2 |
| SW027902-2-A | 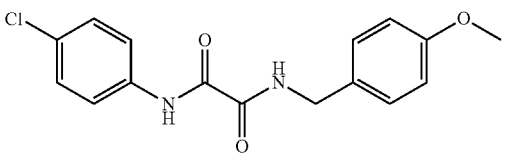 [SMILES: COc1ccc(CNC(=O)C(=O)Nc2ccc(Cl)cc2)cc1]<br>COC1=CC=C(CNC(C(NC2=CC=C(Cl)C=C2)=O)=O)C=C1 |
| SW207007-1 | 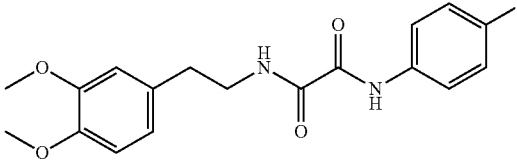<br>O=C(C(NC1=CC=C(Cl)C=C1)=O)NCCC2=CC=C(OC)C(OC)=C2 |
| SW207008-1 | 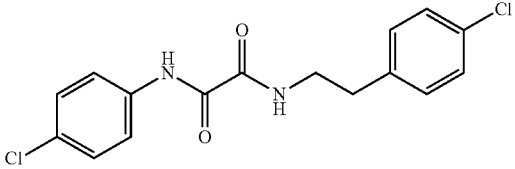 [SMILES: O=C(NCCc1ccc(Cl)cc1)C(=O)Nc1ccc(Cl)cc1]<br>O=C(C(NC1=CC=C(Cl)C=C1)=O)NCCC2=CC=C(Cl)C=C2 |
| SW207009-1 | 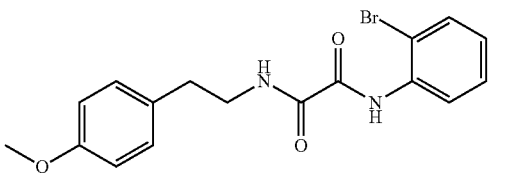 [SMILES: COc1ccc(CCNC(=O)C(=O)Nc2ccccc2Br)cc1]<br>COC1=CC=C(CCNC(C(NC2=CC=CC=C2Br)=O)=O)C=C1 |

TABLE 6-continued

| Compound ID | Structure |
|---|---|
| SW207010-1 | COC1=CC=C(CCNC(C(NC2=CC([N+]([O-])=O)=C(OC(F)(F)F)C=C2)=O)=O)C=C1 |
| SW207011-1 | COC1=CC=C(CCNC(C(NC2=CC(Cl)=CC=C2OC)=O)=O)C=C1 |
| SW207012-1 | COC1=CC=C(CCNC(C(NC2=CC(C(F)(F)F)=C(Br)C(C(F)(F)F)=C2)=O)=O)C=C1 |
| SW207013-1 | COC1=CC=C(CCNC(C(NC2=CC=C(Cl)C=C2C(F)(F)F)=O)=O)C=C1 |
| SW207014-1 | COC1=CC=C(CCNC(C(NC2=CC(Br)=C(C)C=C2)=O)=O)C=C1 |
| SW207015-1 | COC1=CC=C(CCNC(C(NC2=CC(Br)=C(C(F)(F)F)C=C2)=O)=O)C=C1 |

TABLE 6-continued
| Compound ID | Structure |
|---|---|
| SW207016-1 | 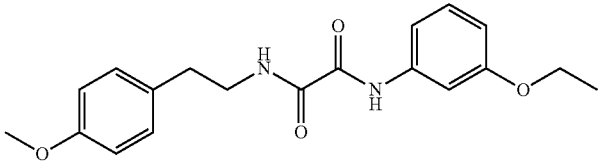 [SMILES: CCOc1cccc(NC(=O)C(=O)NCCc2ccc(OC)cc2)c1]
COC1=CC=C(CCNC(C(NC2=CC=CC(OCC)=C2)=O)=O)C=C1 |
| SW207017-1 | 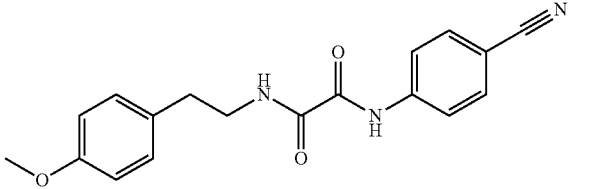 [SMILES: COc1ccc(CCNC(=O)C(=O)Nc2ccc(C#N)cc2)cc1]
COC1=CC=C(CCNC(C(NC2=CC=C(C#N)C=C2)=O)=O)C=C1 |
| SW207018-1 | 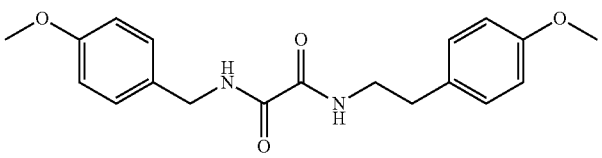
COC1=CC=C(CCNC(C(NCC2=CC=C(OC)C=C2)=O)=O)C=C1 |
| SW207019-1 | 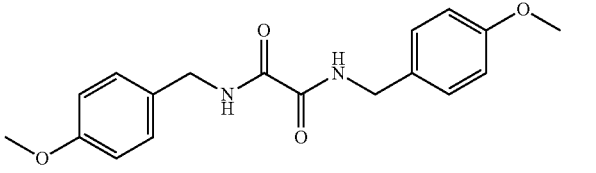
O=C(C(NCC1=CC=C(OC)C=C1)=O)NCC2=CC=C(OC)C=C2 |
| SW207020-1 | 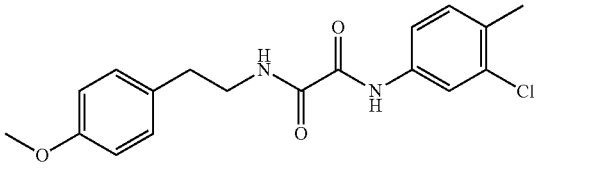
COC1=CC=C(CCNC(C(NC2=CC(Cl)=C(C)C=C2)=O)=O)C=C1 |
| SW207021-1 | 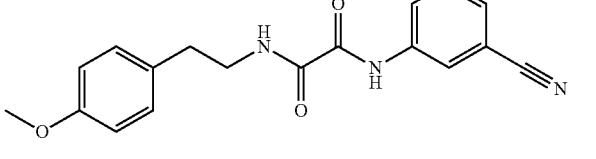
COC1=CC=C(CCNC(C(NC2=CC=CC(C#N)=C2)=O)=O)C=C1 |

TABLE 6-continued
| Compound ID | Structure |
|---|---|
| SW207038 | 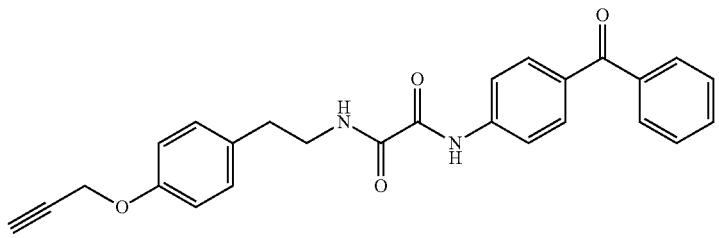 [SMILES: C#CCOc1ccc(CCNC(=O)C(=O)Nc2ccc(C(=O)c3ccccc3)cc2)cc1]<br>O=C(NCCC1=CC=C(OCC#C)C=C1)C(=O)NC1=CC=C(C=C1)C(=O)C1=CC=CC=C1 |
| SW113361-2-A | 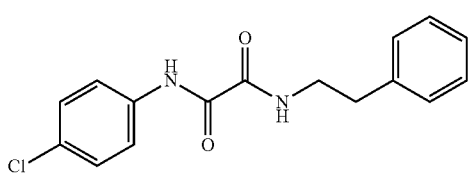 [SMILES: O=C(NCCc1ccccc1)C(=O)Nc1ccc(Cl)cc1]<br>O=C(C(NC1=CC=C(Cl)C=C1)=O)NCCC2=CC=CC=C2 |
| SW113878-2-A | 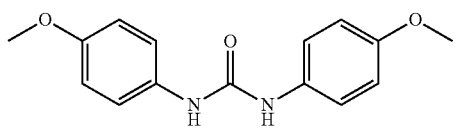<br>O=C(NC1=CC=C(OC)C=C1)NC2=CC=C(OC)C=C2 |
| SW207038-2-A | 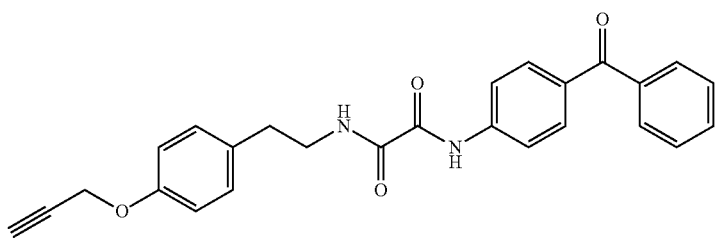 [SMILES: C#CCOc1ccc(CCNC(=O)C(=O)Nc2ccc(C(=O)c3ccccc3)cc2)cc1]<br>O=C(C(NC1=CC=C(C(C2=CC=CC=C2)=O)C=C1)=O)NCCC3=CC=C(OCC#C)C=C3 |
| SW208009-1-A | 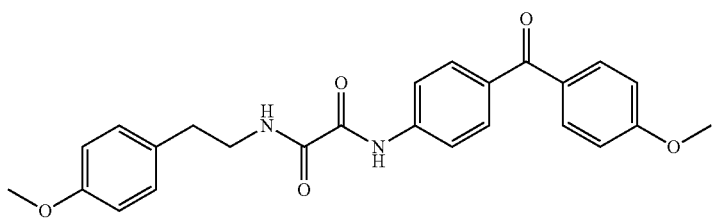<br>COC1=CC=C(CCNC(C(NC2=CC=C(C(C3=CC=C(OC)C=C3)=O)C=C2)=O)=O)C=C1 |
| SW208023-1-A | 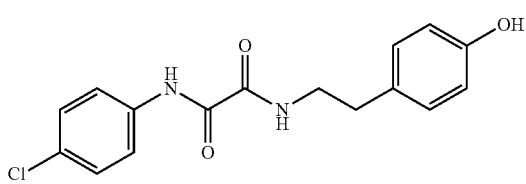 [SMILES: O=C(NCCc1ccc(O)cc1)C(=O)Nc1ccc(Cl)cc1]<br>O=C(C(NC1=CC=C(Cl)C=C1)=O)NCCC2=CC=C(O)C=C2 |

TABLE 6-continued
| Compound ID | Structure |
|---|---|
| SW208024-1-A | 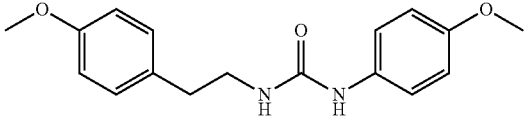<br>O=C(NC1=CC=C(OC)C=C1)NCCC2=CC=C(OC)C=C2 |
| SW208025-1-A | 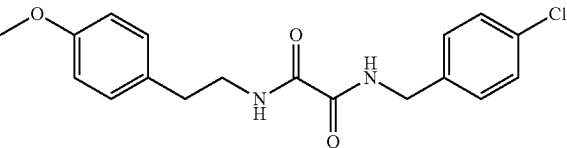 [SMILES: COc1ccc(CCNC(=O)C(=O)NCc2ccc(Cl)cc2)cc1]<br>O=C(C(NCC1=CC=C(Cl)C=C1)=O)NCCC2=CC=C(OC)C=C2 |
| SW208026-1-A | 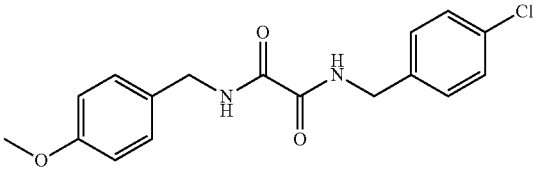 [SMILES: COc1ccc(CNC(=O)C(=O)NCc2ccc(Cl)cc2)cc1]<br>COC1=CC=C(CNC(C(NCC2=CC=C(Cl)C=C2)=O)=O)C=C1 |
| SW208027-1-A | 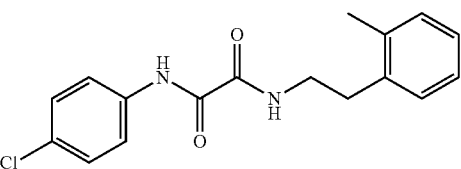 [SMILES: Cc1ccccc1CCNC(=O)C(=O)Nc1ccc(Cl)cc1]<br>CC1=C(CCNC(C(NC2=CC=C(Cl)C=C2)=O)=O)C=CC=C1 |
| SW208028-1-A | 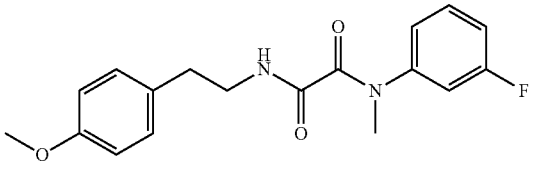 [SMILES: COc1ccc(CCNC(=O)C(=O)N(C)c2cccc(F)c2)cc1]<br>O=C(C(N(C)C1=CC=CC(F)=C1)=O)NCCC2=CC=C(OC)C=C2 |
| SW208029-1-A | 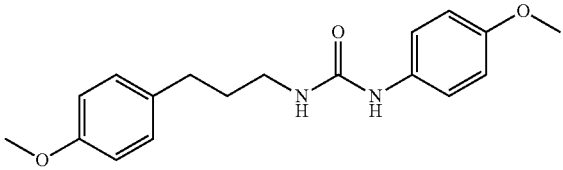<br>COC1=CC=C(CCCNC(NC2=CC=C(OC)C=C2)=O)C=C1 |
| SW208030-1-A | 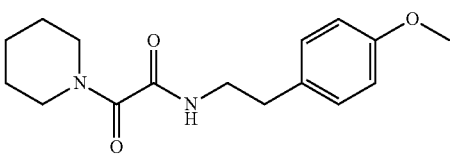 [SMILES: COc1ccc(CCNC(=O)C(=O)N2CCCCC2)cc1]<br>COC1=CC=C(CCNC(C(N2CCCCC2)=O)=O)C=C1 |

TABLE 6-continued
| Compound ID | Structure |
|---|---|
| SW208031-1-A | 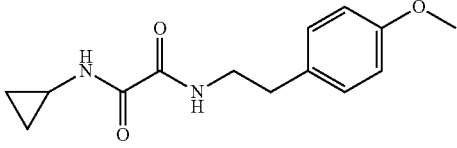 [SMILES: COc1ccc(CCNC(=O)C(=O)NC2CC2)cc1]<br>COC1=CC=C(CCNC(C(NC2CC2)=O)=O)C=C1 |
| SW208032-1-A | 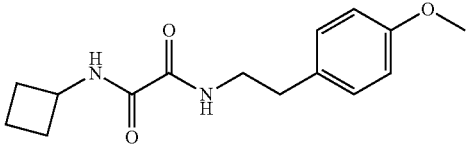 [SMILES: COc1ccc(CCNC(=O)C(=O)NC2CCC2)cc1]<br>COC1=CC=C(CCNC(C(NC2CCC2)=O)=O)C=C1 |
| SW208033-1-A | 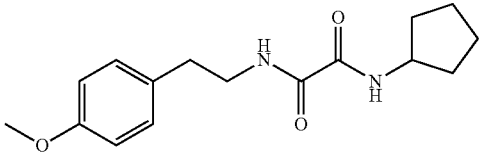 [SMILES: COc1ccc(CCNC(=O)C(=O)NC2CCCC2)cc1]<br>COC1=CC=C(CCNC(C(NC2CCCC2)=O)=O)C=C1 |
| SW208034-1-A | 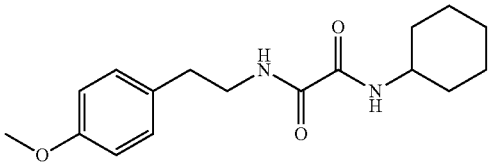<br>COC1=CC=C(CCNC(C(NC2CCCCC2)=O)=O)C=C1 |
| SW208035-1-A | 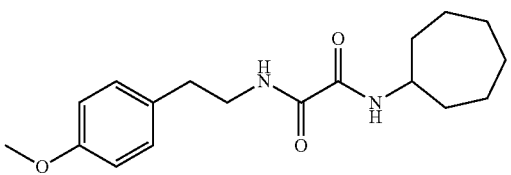 [SMILES: COc1ccc(CCNC(=O)C(=O)NC2CCCCCC2)cc1]<br>COC1=CC=C(CCNC(C(NC2CCCCCC2)=O)=O)C=C1 |
| SW208036-1-A | 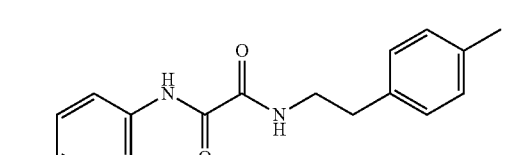<br>CC1=CC=C(CCNC(C(NC2=CC=C(Cl)C=C2)=O)=O)C=C1 |
| SW208037-1-A | 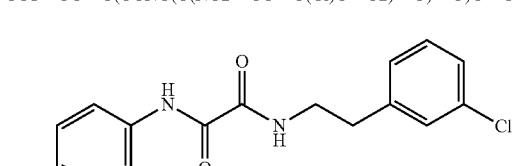<br>O=C(C(NC1=CC=C(Cl)C=C1)=O)NCCC2=CC(Cl)=CC=C2 |

TABLE 6-continued

| Compound ID | Structure |
| --- | --- |
| SW208038-1-A | COC1=CC=C(CCNC(COC2=CC=C(Cl)C=C2)=O)C=C1 |
| SW208039-1-A | O=C(C(NC1=CC=C(Cl)C=C1)=O)NCCC2=CC=C(F)C=C2 |
| SW208040-1-A | COC1=CC=C(CNC(COC2=CC=C(Cl)C=C2)=O)C=C1 |
| SW208041-1-A | O=C(CNC1=CC=C(Cl)C=C1)NCCC2=CC=C(OC)C=C2 |
| SW208042-1-A | O=C(CNC1=CC=C(Cl)C=C1)NCC2=CC=C(OC)C=C2 |
| SW208043-2-A | COC1=CC=C(CCNC(NCC2=CC=CC=C2)=O)C=C1 |
| SW208044-1-A | COC1=CC=C(CCNC(C(N2CCOCC2)=O)=O)C=C1 |

TABLE 6-continued
| Compound ID | Structure |
|---|---|
| SW208045-1-A | 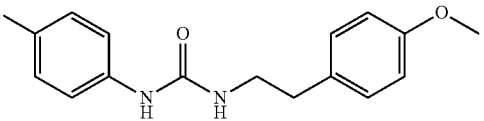<br>COC1=CC=C(CCNC(NC2=CC=C(Cl)C=C2)=O)C=C1 |
| SW208046-1-A | 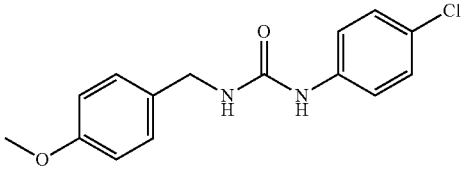 [SMILES: COc1ccc(CNC(=O)Nc2ccc(Cl)cc2)cc1]<br>O=C(NC1=CC=C(Cl)C=C1)NCC2=CC=C(OC)C=C2 |
| SW208047-1-A | 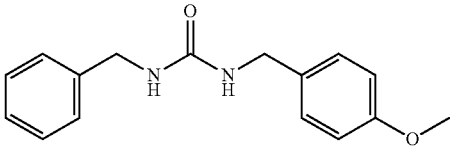 [SMILES: COc1ccc(CNC(=O)NCc2ccccc2)cc1]<br>O=C(NCC1=CC=CC=C1)NCC2=CC=C(OC)C=C2 |
| SW208048-1-A | 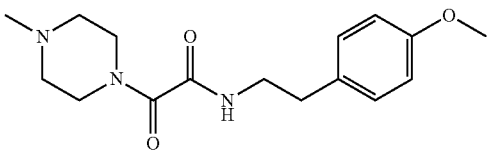<br>COC1=CC=C(CCNC(C(N2CCN(C)CC2)=O)=O)C=C1 |
| SW208049-1-A | 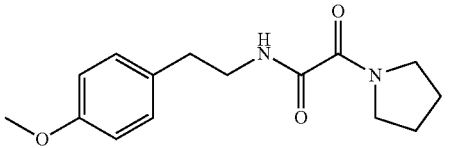 [SMILES: COc1ccc(CCNC(=O)C(=O)N2CCCC2)cc1]<br>COC1=CC=C(CCNC(C(N2CCCC2)=O)=O)C=C1 |
| SW208050-1-A | 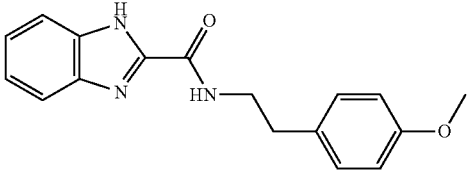 [SMILES: COc1ccc(CCNC(=O)c2nc3ccccc3[nH]2)cc1]<br>COC1=CC=C(CCNC(C2=NC3=C(C=CC=C3)N2)=O)C=C1 |
| SW208051-1-A | 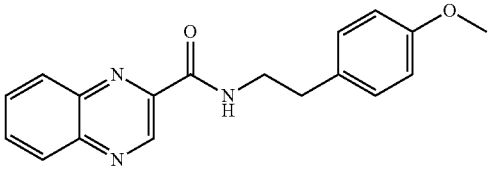 [SMILES: COc1ccc(CCNC(=O)c2cnc3ccccc3n2)cc1]<br>COC1=CC=C(CCNC(C2=CN=C(C=CC=C3)C3=N2)=O)C=C1 |

TABLE 6-continued
| Compound ID | Structure |
|---|---|
| SW208052-1-A | 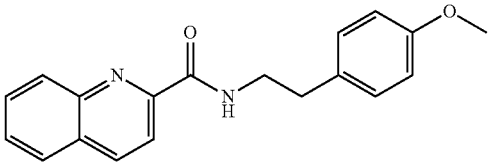 [SMILES: COc1ccc(CCNC(=O)c2ccc3ccccc3n2)cc1] |
COC1=CC=C(CCNC(C2=CC=C(C=CC=C3)C3=N2)=O)C=C1
| SW208053-1-A | 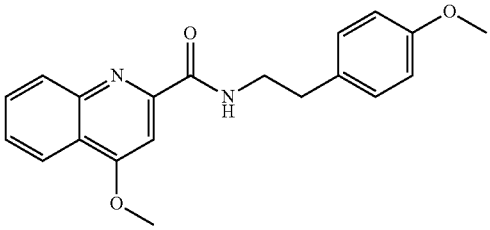 [SMILES: COc1ccc(CCNC(=O)c2cc(OC)c3ccccc3n2)cc1] |
COC1=CC=C(CCNC(C2=CC(OC)=C(C=CC=C3)C3=N2)=O)C=C1
| SW208054-1-A | 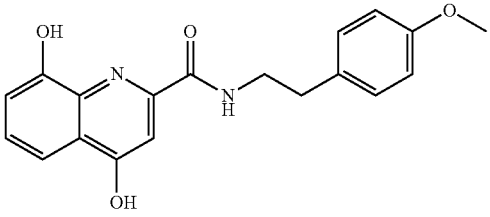 [SMILES: COc1ccc(CCNC(=O)c2cc(O)c3cccc(O)c3n2)cc1] |
COC1=CC=C(CCNC(C2=CC(O)=C(C=CC=C3O)C3=N2)=O)C=C1
| SW208055-1-A | 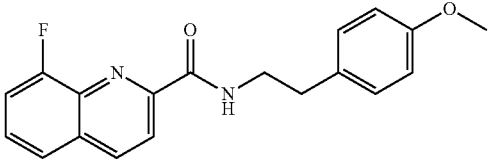 [SMILES: COc1ccc(CCNC(=O)c2ccc3cccc(F)c3n2)cc1] |
COC1=CC=C(CCNC(C2=CC=C(C=CC=C3F)C3=N2)=O)C=C1
| SW208056-1-A | 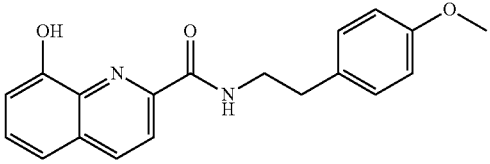 [SMILES: COc1ccc(CCNC(=O)c2ccc3cccc(O)c3n2)cc1] |
COC1=CC=C(CCNC(C2=CC=C(C=CC=C3O)C3=N2)=O)C=C1
| SW208057-1-A | 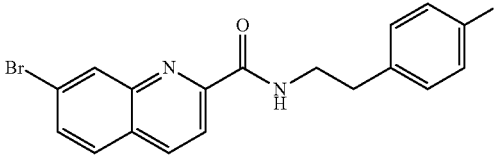 |
COC1=CC=C(CCNC(C2=CC=C(C=CC(Br)=C3)C3=N2)=O)C=C1

TABLE 6-continued

| Compound ID | Structure |
|---|---|
| SW208058-1-A | COC1=CC=C(CCNC(C(N2CC(C=CC=C3)=C3C2)=O)=O)C=C1 |
| SW208059-1-A | COC1=CC=C(CCNC(C(N2C(C=CC=C3)=C3CC2)=O)=O)C=C1 |
| SW208060-1-A | COC1=CC=C(CCNC(C(N2CC(C=CC=C3)=C3CC2)=O)=O)C=C1 |
| SW208061-1-A | O=C(C(NC1=CC=C(Cl)C=C1)=O)NCCC2=CC=C(OCC)C=C2 |
| SW208062-1-A | O=C(NCC1=CC=CC=C1)NCC2=CC=CC=C2 |
| SW208063-1-A | COC1=CC=C(CCNC(C(N2)=NC3=C(C=CC=C3)C2=O)=O)C=C1 |
| SW208108-1-A | O=C(C(NC1=CC=C(C(C2=CC=C(OCC#C)C=C2)=O)C=C1)=O)NCCC3=CC=C(OC)C=C3 |

TABLE 6-continued

| Compound ID | Structure |
|---|---|
| SW208117-1-A | 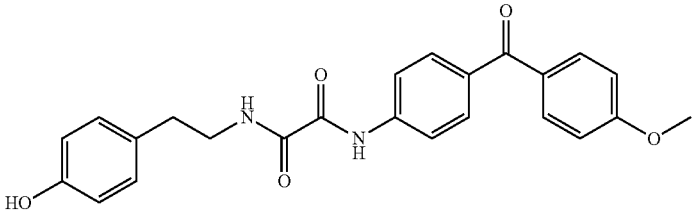 [SMILES: COc1ccc(C(=O)c2ccc(NC(=O)C(=O)NCCc3ccc(O)cc3)cc2)cc1]<br>OC1=CC=C(CCNC(C(NC2=CC=C(C(C3=CC=C(OC)C=C3)=O)C=C2)=O)=O)C=C1 |
| SW208119-1-A | 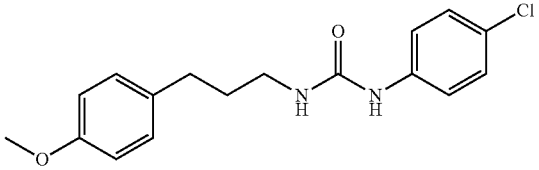 [SMILES: COc1ccc(CCCNC(=O)Nc2ccc(Cl)cc2)cc1]<br>COC1=CC=C(CCCNC(NC2=CC=C(Cl)C=C2)=O)C=C1 |
| SW208120-1-A | 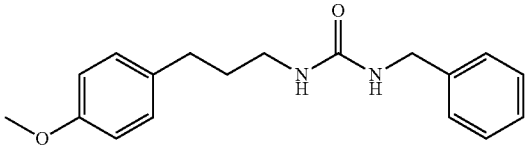 [SMILES: COc1ccc(CCCNC(=O)NCc2ccccc2)cc1]<br>COC1=CC=C(CCCNC(NCC2=CC=CC=C2)=O)C=C1 |
| SW208121-1-A | 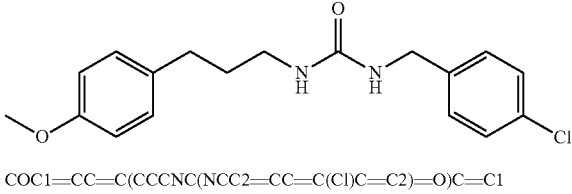<br>COC1=CC=C(CCCNC(NCC2=CC=C(Cl)C=C2)=O)C=C1 |
| SW208122-1-A | 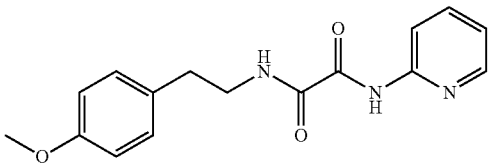 [SMILES: COc1ccc(CCNC(=O)C(=O)Nc2ccccn2)cc1]<br>COC1=CC=C(CCNC(C(NC2=CC=CC=N2)=O)=O)C=C1 |
| SW208123-1-A | 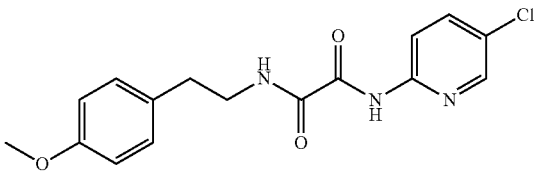<br>COC1=CC=C(CCNC(C(NC2=CC=C(Cl)C=N2)=O)=O)C=C1 |
| SW208124-1-A | 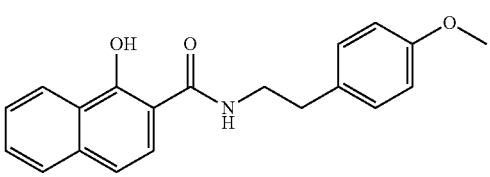 [SMILES: COc1ccc(CCNC(=O)c2ccc3ccccc3c2O)cc1]<br>COC1=CC=C(CCNC(C2=CC=C(C=CC=C3)C3=C2O)=O)C=C1 |

TABLE 6-continued
| Compound ID | Structure |
|---|---|
| SW208125-1-A | 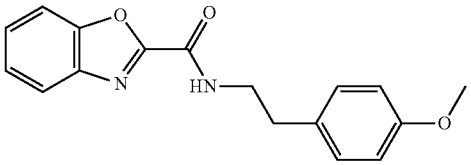 [SMILES: COc1ccc(CCNC(=O)c2nc3ccccc3o2)cc1]<br>COC1=CC=C(CCNC(C2=NC3=C(C=CC=C3)O2)=O)C=C1 |
| SW208126-1-A | 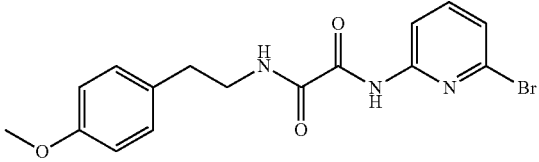 [SMILES: COc1ccc(CCNC(=O)C(=O)Nc2cccc(Br)n2)cc1]<br>COC1=CC=C(CCNC(C(NC2=CC=CC(Br)=N2)=O)=O)C=C1 |
| SW208127-1-A | 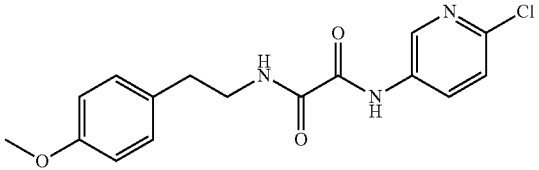 [SMILES: COc1ccc(CCNC(=O)C(=O)Nc2ccc(Cl)nc2)cc1]<br>COC1=CC=C(CCNC(C(NC2=CN=C(Cl)C=C2)=O)=O)C=C1 |
| SW208128-1-A | 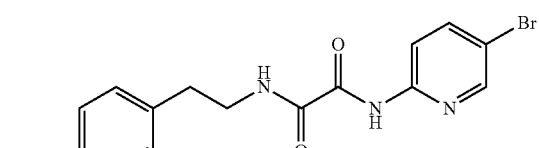<br>COC1=CC=C(CCNC(C(NC2=CC=C(Br)C=N2)=O)=O)C=C1 |
| SW208129-1-A | 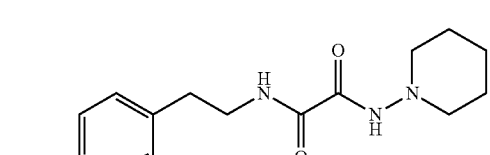<br>COC1=CC=C(CCNC(C(NN2CCCCC2)=O)=O)C=C1 |
| SW208130-1-A | 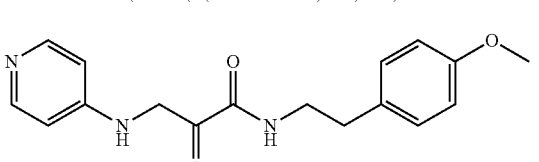<br>COC1=CC=C(CCNC(C(CNC2=CC=NC=C2)=O)=O)C=C1 |
| SW208131-1-A | 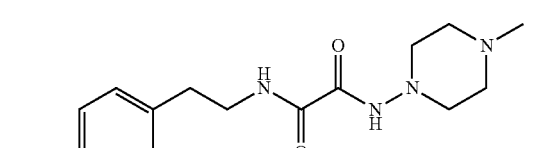<br>COC1=CC=C(CCNC(C(NN2CCN(C)CC2)=O)=O)C=C1 |

TABLE 6-continued

| Compound ID | Structure |
|---|---|
| SW208132-1-A | OC(C(NCCC1=CC=C(OC)C=C1)=O)=O |
| SW208133-1-A | COC1=CC=C(CCNC(C(NC2=CC=CN=C2F)=O)=O)C=C1 |
| SW208134-1-A | COC1=CC=C(CCNC(C(NC2=C(C)C=CN=C2)=O)=O)C=C1 |
| SW208135-1-A | COC1=CC=C(CCNC(C(NC2=CC=NC=C2)=O)=O)C=C1 |
| SW209136-1-A | COC1=CC=C(CCNC(C(NC2=CC=CC(F)=N2)=O)=O)C=C1 |
| SW208137-1-A | COC1=CC=C(CCNC(C(NC2=CN=CC=N2)=O)=O)C=C1 |
| SW208138-1-A | COC1=CC=C(CCNC(C(NC2=CC(C)=NC=C2)=O)=O)C=C1 |

TABLE 6-continued

| Compound ID | Structure |
|---|---|
| SW208139-1-A | 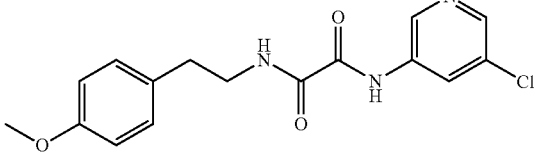<br>COC1=CC=C(CCNC(C(NC2=CN=CC(Cl)=C2)=O)=O)C=C1 |
| SW208140-1-A | 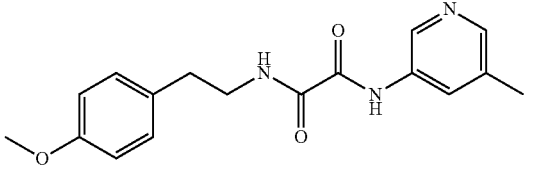<br>COC1=CC=C(CCNC(C(NC2=CC(C)=CN=C2)=O)=O)C=C1 |
| SW208141-1-A | 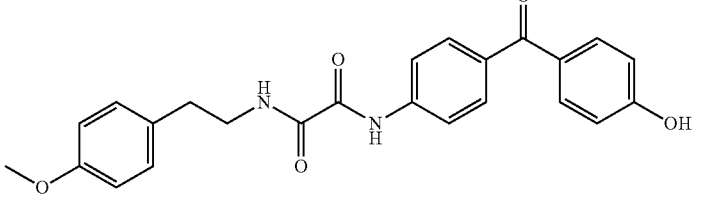<br>O=C(C(NC1=CC=C(C(C2=CC=C(O)C=C2)=O)C=C1)=O)NCCC3=CC=C(OC)C=C3 |
| SW208142-1-A | 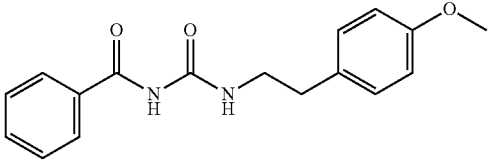 [SMILES: COc1ccc(CCNC(=O)NC(=O)c2ccccc2)cc1]<br>COC1=CC=C(CCNC(NC(C2=CC=CC=C2)=O)=O)C=C1 |
| SW208143-1-A | 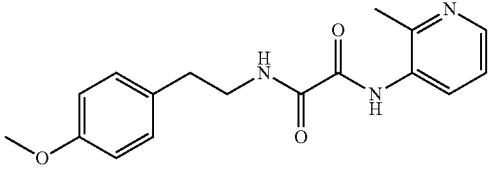<br>COC1=CC=C(CCNC(C(NC2=CC=CN=C2C)=O)=O)C=C1 |
| SW208144-1-A | 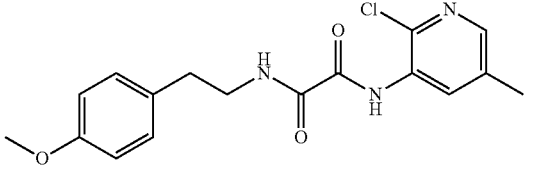<br>COC1=CC=C(CCNC(C(NC2=CC(C)=CN=C2Cl)=O)=O)C=C1 |
| SW208145-1-A | 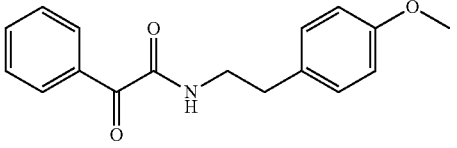 [SMILES: COc1ccc(CCNC(=O)C(=O)c2ccccc2)cc1]<br>COC1=CC=C(CCNC(C(C2=CC=CC=C2)=O)=O)C=C1 |

TABLE 6-continued
| Compound ID | Structure |
|---|---|
| SW208146-1-A | 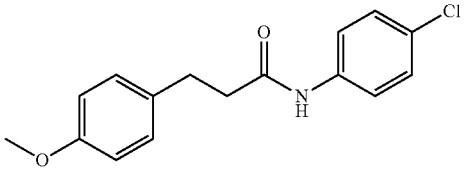 [SMILES: COc1ccc(CCC(=O)Nc2ccc(Cl)cc2)cc1]<br>COC1=CC=C(CCC(NC2=CC=C(Cl)C=C2)=O)C=C1 |
| SW208147-1-A | 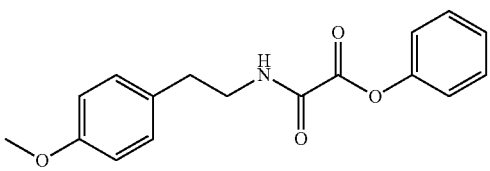 [SMILES: COc1ccc(CCNC(=O)C(=O)Oc2ccccc2)cc1]<br>COC1=CC=C(CCNC(C(OC2=CC=CC=C2)=O)=O)C=C1 |
| SW208148-1-A | 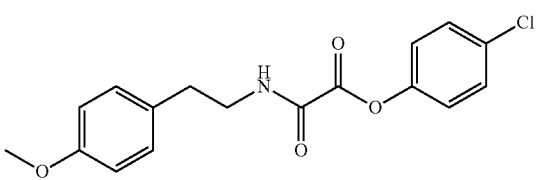 [SMILES: COc1ccc(CCNC(=O)C(=O)Oc2ccc(Cl)cc2)cc1]<br>COC1=CC=C(CCNC(C(OC2=CC=C(Cl)C=C2)=O)=O)C=C1 |
| SW208149-1-A | 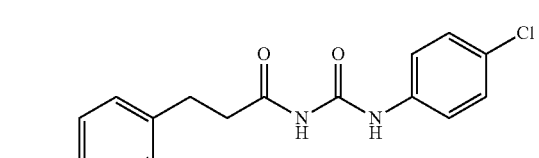<br>COC1=CC=C(CCC(NC(NC2=CC=C(Cl)C=C2)=O)=O)C=C1 |
| SW208151-1-A | 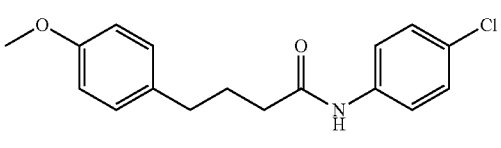 [SMILES: COc1ccc(CCCC(=O)Nc2ccc(Cl)cc2)cc1]<br>O=C(NC1=CC=C(Cl)C=C1)CCCC2=CC=C(OC)C=C2 |
| SW208152-1-A | 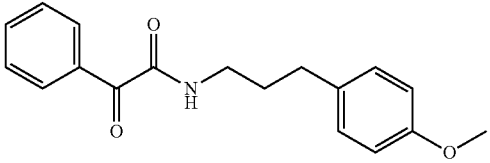 [SMILES: COc1ccc(CCCNC(=O)C(=O)c2ccccc2)cc1]<br>O=C(C(C1=CC=CC=C1)=O)NCCCC2=CC=C(OC)C=C2 |
| SW208153-1-A | 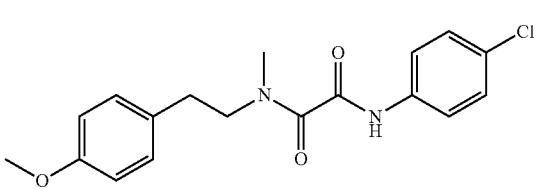 [SMILES: COc1ccc(CCN(C)C(=O)C(=O)Nc2ccc(Cl)cc2)cc1]<br>COC1=CC=C(CCN(C)C(C(NC2=CC=C(Cl)C=C2)=O)=O)C=C1 |

TABLE 6-continued

| Compound ID | Structure |
|---|---|
| SW208189-1-A | 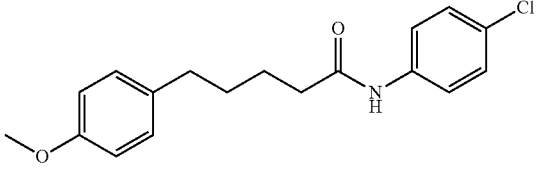 [SMILES: COc1ccc(CCCCC(=O)Nc2ccc(Cl)cc2)cc1]<br>COC1=CC=C(CCCCC(NC2=CC=C(Cl)C=C2)=O)C=C1 |
| SW208217-1-A | 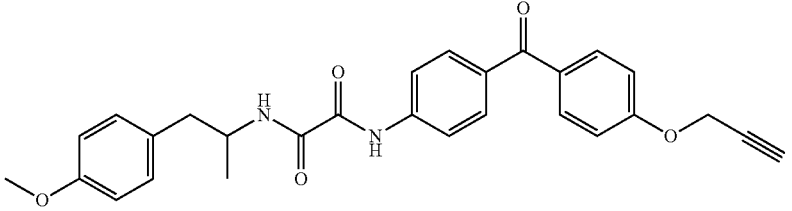 [SMILES: C#CCOc1ccc(C(=O)c2ccc(NC(=O)C(=O)NC(C)Cc3ccc(OC)cc3)cc2)cc1]<br>O=C(C(NC1=CC=C(C(C2=CC=C(OCC#C)C=C2)=O)C=C1)=O)NC(C)CC3=CC=C(OC)C=C3 |
| SW208219-1-A | 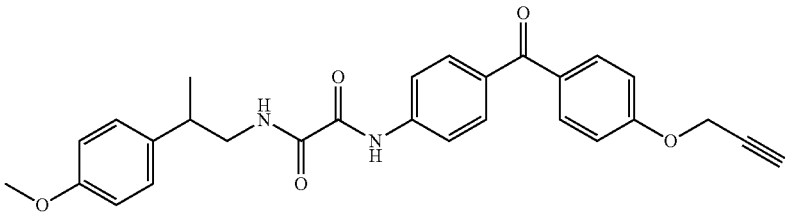 [SMILES: C#CCOc1ccc(C(=O)c2ccc(NC(=O)C(=O)NCC(C)c3ccc(OC)cc3)cc2)cc1]<br>O=C(C(NC1=CC=C(C(C2=CC=C(OCC#C)C=C2)=O)C=C1)=O)NCC(C)C3=CC=C(OC)C=C3 |
| SW208220-1-A | 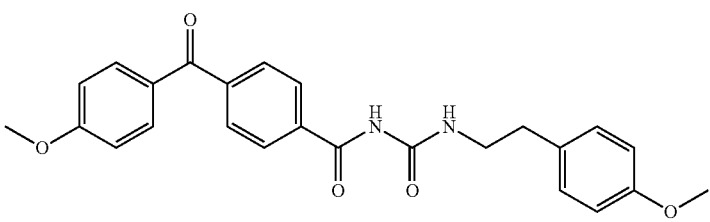<br>O=C(NC(NCCC1=CC=C(OC)C=C1)=O)C2=CC=C(C(C3=CC=C(OC)C=C3)=O)C=C2 |
| SW208222-1-A | 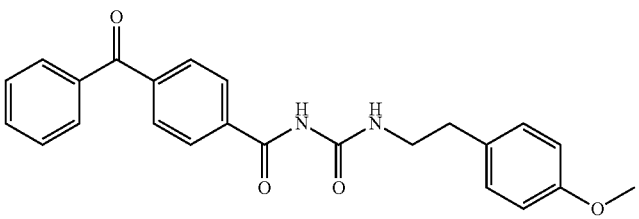<br>O=C(NC(NCCC1=CC=C(OC)C=C1)=O)C2=CC=C(C(C3=CC=CC=C3)=O)C=C2 |
| SW208386-1-A | 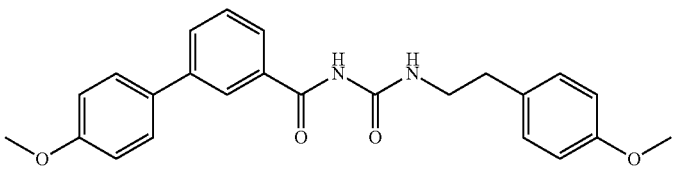<br>O=C(NC(NCCC1=CC=C(OC)C=C1)=O)C2=CC(C3=CC=C(OC)C=C3)=CC=C2 |

TABLE 6-continued

| Compound ID | Structure |
|---|---|
| SW208387-1-A | 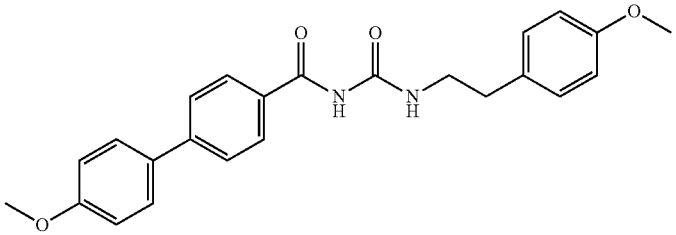<br>O=C(NC(NCCC1=CC=C(OC)C=C1)=O)C2=CC=C(C3=CC=C(OC)C=C3)C=C2 |
| SW208388-1-A | 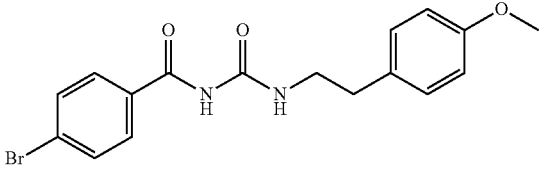<br>O=C(NC(NCCC1=CC=C(OC)C=C1)=O)C2=CC=C(Br)C=C2 |
| SW208389-1-A | 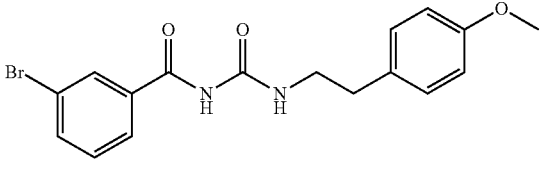<br>O=C(NC(NCCC1=CC=C(OC)C=C1)=O)C2=CC(Br)=CC=C2 |
| SW208390-1-A | 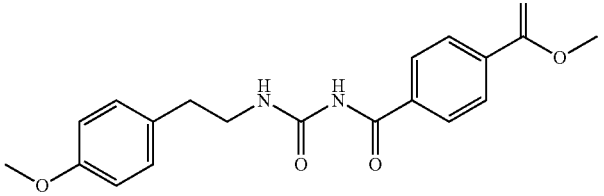<br>O=C(NC(NCCC1=CC=C(OC)C=C1)=O)C2=CC=C(C(OC)=O)C=C2 |
| SW208391-1-A | 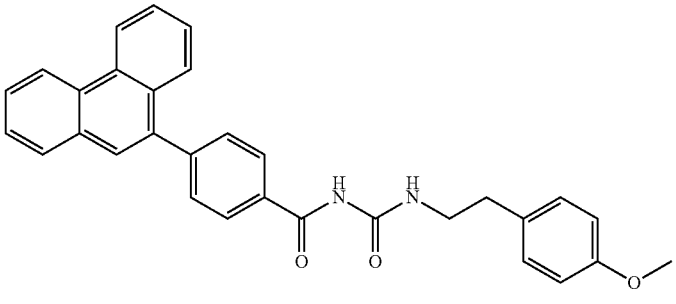 [SMILES: COc1ccc(CCNC(=O)NC(=O)c2ccc(-c3cc4ccccc4c4ccccc34)cc2)cc1]<br>O=C(NC(NCCC1=CC=C(OC)C=C1)=O)C2=CC=C(C3=C(C=CC=C4)C4=C(C=CC=C5)C5=C3)C=C2 |
| SW208392-1-A | 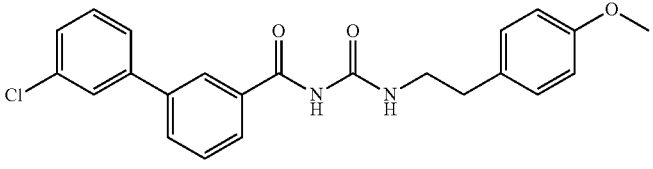 [SMILES: COc1ccc(CCNC(=O)NC(=O)c2cccc(-c3cccc(Cl)c3)c2)cc1]<br>O=C(NC(NCCC1=CC=C(OC)C=C1)=O)C2=CC(C3=CC(Cl)=CC=C3)=CC=C2 |

TABLE 6-continued

| Compound ID | Structure |
|---|---|
| SW208393-1-A | 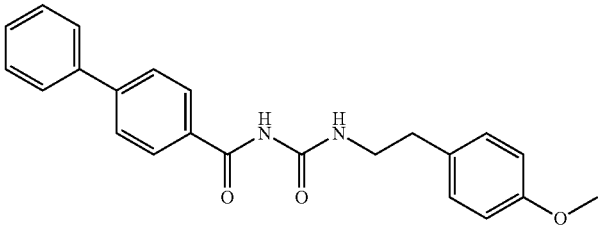 [SMILES: COc1ccc(CCNC(=O)NC(=O)c2ccc(-c3ccccc3)cc2)cc1]<br>O=C(NC(NCCC1=CC=C(OC)C=C1)=O)C2=CC=C(C3=CC=CC=C3)C=C2 |
| SW208394-1-A | 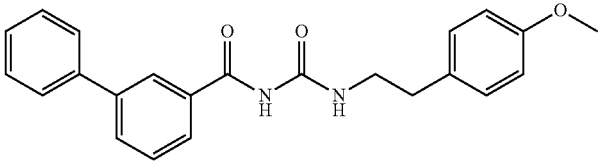 [SMILES: COc1ccc(CCNC(=O)NC(=O)c2cccc(-c3ccccc3)c2)cc1]<br>O=C(NC(NCCC1=CC=C(OC)C=C1)=O)C2=CC(C3=CC=CC=C3)=CC=C2 |
| SW208395-1-A | 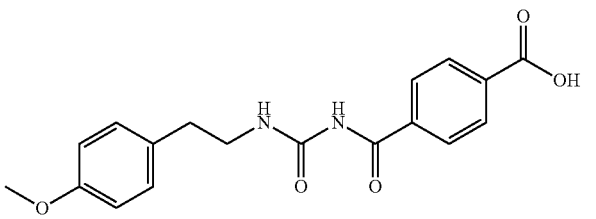 [SMILES: COc1ccc(CCNC(=O)NC(=O)c2ccc(C(=O)O)cc2)cc1]<br>O=C(NC(NCCC1=CC=C(OC)C=C1)=O)C2=CC=C(C(O)=O)C=C2 |
| SW208396-1-A | 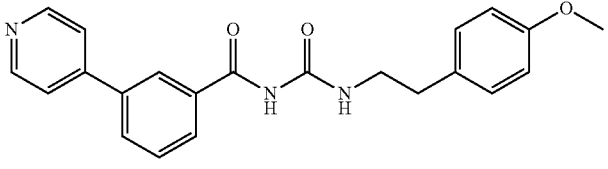 [SMILES: COc1ccc(CCNC(=O)NC(=O)c2cccc(-c3ccncc3)c2)cc1]<br>O=C(NC(NCCC1=CC=C(OC)C=C1)=O)C2=CC(C3=CC=NC=C3)=CC=C2 |
| SW208397-1-A | 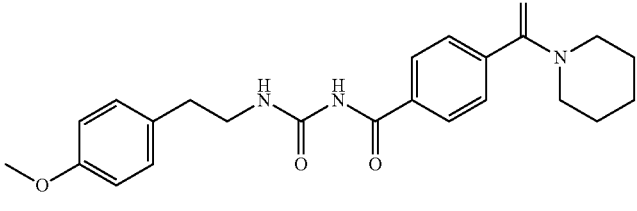<br>O=C(NC(NCCC1=CC=C(OC)C=C1)=O)C2=CC=C(C(N3CCCCC3)=O)C=C2 |
| SW208398-1-A | 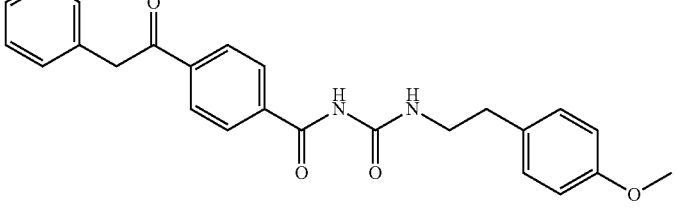<br>O=C(NC(NCCC1=CC=C(OC)C=C1)=O)C2=CC=C(C(CC3=CC=CC=C3)=O)C=C2 |

TABLE 6-continued
| Compound ID | Structure |
|---|---|
| SW208399-1-A | 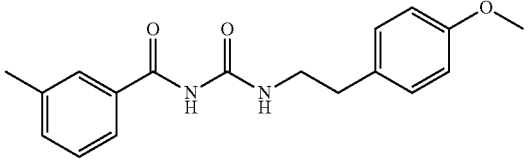<br>O=C(NC(NCCC1=CC=C(OC)C=C1)=O)C2=CC(C)=CC=C2 |
| SW208400-1-A | 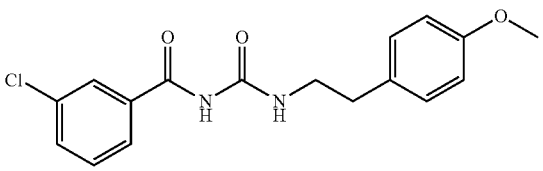<br>O=C(NC(NCCC1=CC=C(OC)C=C1)=O)C2=CC(Cl)=CC=C2 |
| SW208401-1-A | 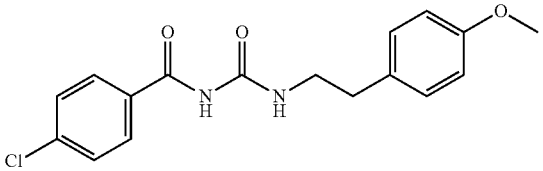 [SMILES: COc1ccc(CCNC(=O)NC(=O)c2ccc(Cl)cc2)cc1]<br>O=C(NC(NCCC1=CC=C(OC)C=C1)=O)C2=CC=C(Cl)C=C2 |
| SW208402-1-A | 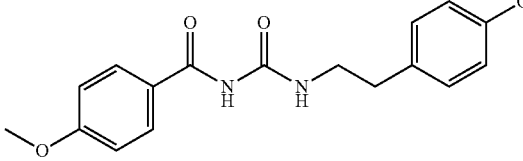<br>O=C(NC(NCCC1=CC=C(OC)C=C1)=O)C2=CC=C(OC)C=C2 |
| SW208403-1-A | 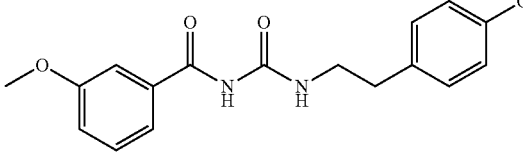<br>O=C(NC(NCCC1=CC=C(OC)C=C1)=O)C2=CC(OC)=CC=C2 |
| SW208404-1-A | 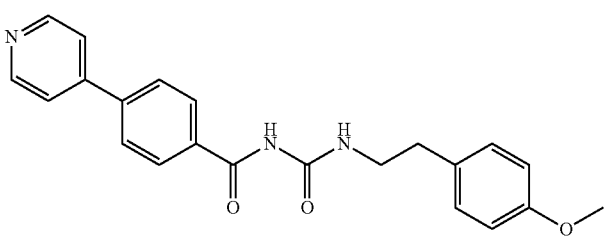 [SMILES: COc1ccc(CCNC(=O)NC(=O)c2ccc(-c3ccncc3)cc2)cc1]<br>O=C(NC(NCCC1=CC=C(OC)C=C1)=O)C2=CC=C(C3=CC=NC=C3)C=C2 |

TABLE 6-continued
| Compound ID | Structure |
| --- | --- |
SW208408-1-A
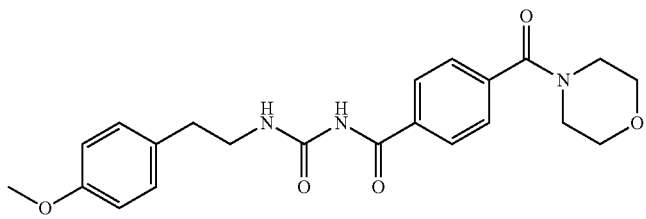 [SMILES: COc1ccc(CCNC(=O)NC(=O)c2ccc(C(=O)N3CCOCC3)cc2)cc1]
O=C(NC(NCCC1=CC=C(OC)C=C1)=O)C2=CC=C(C(N3CCOCC3)=O)C=C2
SW208410-1-A
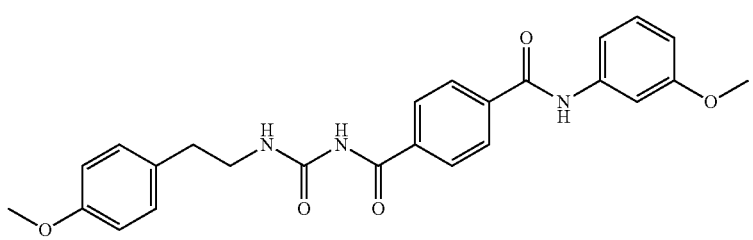
O=C(NC(NCCC1=CC=C(OC)C=C1)=O)C2=CC=C(C(NC3=CC=CC(OC)=C3)=O)C=C2
SW208409-1-A
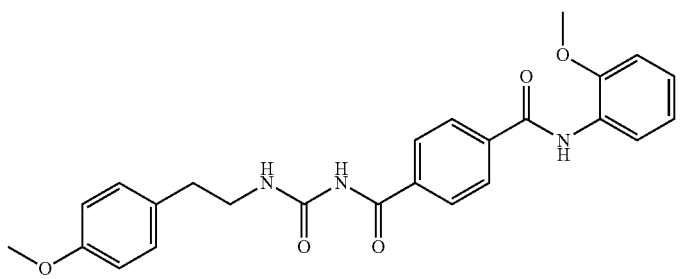 [SMILES: COc1ccc(CCNC(=O)NC(=O)c2ccc(C(=O)Nc3ccccc3OC)cc2)cc1]
O=C(NC(NCCC1=CC=C(OC)C=C1)=O)C2=CC=C(C(NC3=CC=CC=C3OC)=O)C=C2
SW208411-1-A
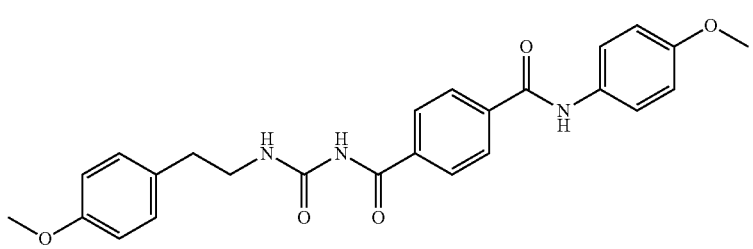
O=C(NC(NCCC1=CC=C(OC)C=C1)=O)C2=CC=C(C(NC3=CC=C(OC)C=C3)=O)C=C2
SW208412-1-A
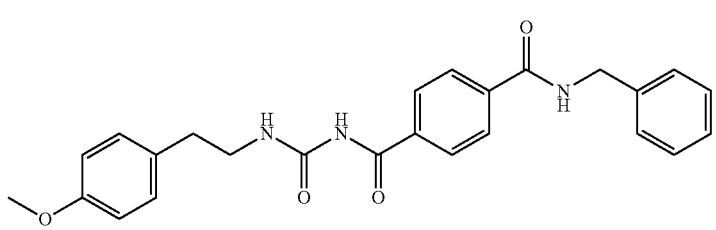 [SMILES: COc1ccc(CCNC(=O)NC(=O)c2ccc(C(=O)NCc3ccccc3)cc2)cc1]
O=C(NC(NCCC1=CC=C(OC)C=C1)=O)C2=CC=C(C(NCC3=CC=CC=C3)=O)C=C2

TABLE 6-continued
| Compound ID | Structure |
|---|---|
| SW208413-1-A | 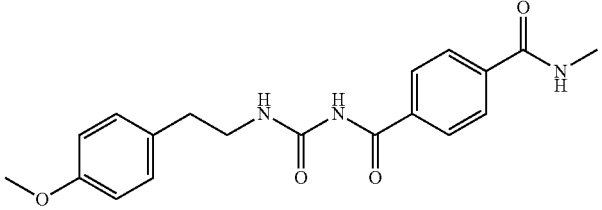<br>O=C(NC(NCCC1=CC=C(OC)C=C1)=O)C2=CC=C(C(NC)=O)C=C2 |
| SW208414-1-A | 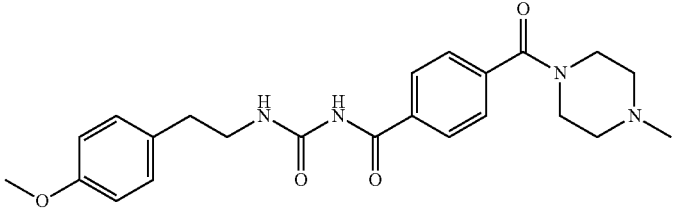<br>O=C(NC(NCCC1=CC=C(OC)C=C1)=O)C2=CC=C(C(N3CCN(C)CC3)=O)C=C2 |
| SW208452-1-A | 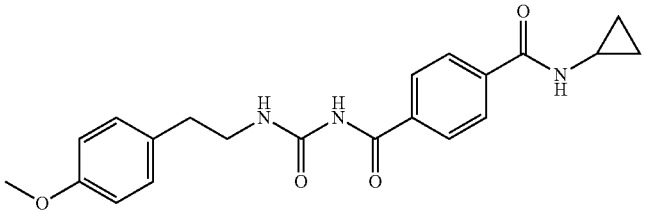 [SMILES: COc1ccc(CCNC(=O)NC(=O)c2ccc(C(=O)NC3CC3)cc2)cc1]<br>O=C(NC(NCCC1=CC=C(OC)C=C1)=O)C2=CC=C(C(NC3CC3)=O)C=C2 |
| SW208453-1-A | 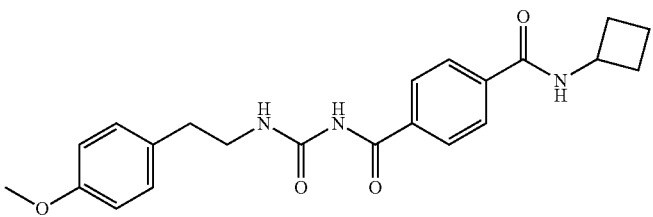 [SMILES: COc1ccc(CCNC(=O)NC(=O)c2ccc(C(=O)NC3CCC3)cc2)cc1]<br>O=C(NC(NCCC1=CC=C(OC)C=C1)=O)C2=CC=C(C(NC3CCC3)=O)C=C2 |
| SW208454-1-A | 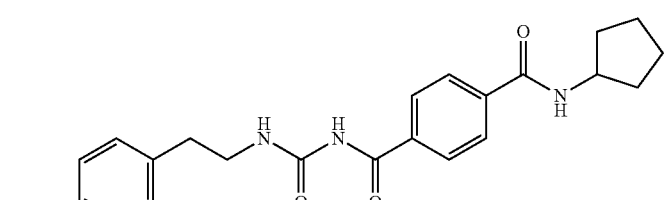<br>O=C(NC(NCCC1=CC=C(OC)C=C1)=O)C2=CC=C(C(NC3CCCC3)=O)C=C2 |
| SW208455-1-A | 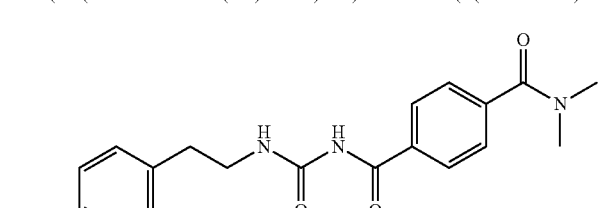<br>O=C(NC(NCCC1=CC=C(OC)C=C1)=O)C2=CC=C(C(N(C)C)=O)C=C2 |

TABLE 6-continued

| Compound ID | Structure |
|---|---|
| SW208456-1-A | 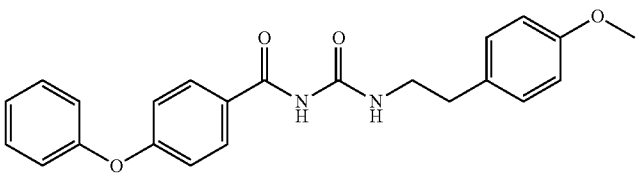 [SMILES: COc1ccc(CCNC(=O)NC(=O)c2ccc(Oc3ccccc3)cc2)cc1]<br>O=C(NC(NCCC1=CC=C(OC)C=C1)=O)C2=CC=C(OC3=CC=CC=C3)C=C2 |
| SW208457-1-A | 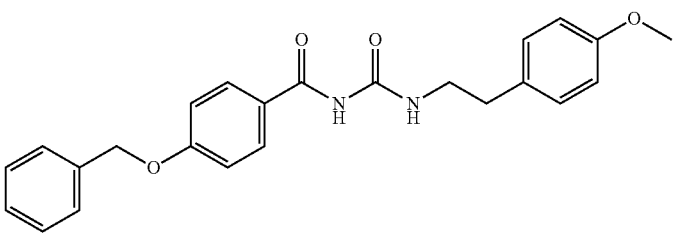 [SMILES: COc1ccc(CCNC(=O)NC(=O)c2ccc(OCc3ccccc3)cc2)cc1]<br>O=C(NC(NCCC1=CC=C(OC)C=C1)=O)C2=CC=C(OCC3=CC=CC=C3)C=C2 |
| SW208458-1-A | 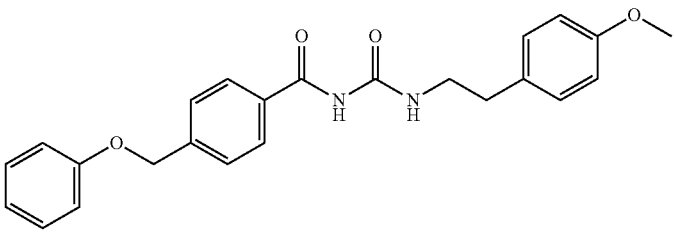 [SMILES: COc1ccc(CCNC(=O)NC(=O)c2ccc(COc3ccccc3)cc2)cc1]<br>O=C(NC(NCCC1=CC=C(OC)C=C1)=O)C2=CC=C(COC3=CC=CC=C3)C=C2 |
| SW208459-1-A | 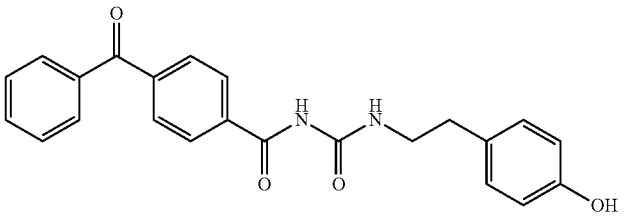 [SMILES: O=C(NCCc1ccc(O)cc1)NC(=O)c1ccc(C(=O)c2ccccc2)cc1]<br>O=C(NC(NCCC1=CC=C(O)C=C1)=O)C2=CC=C(C(C3=CC=CC=C3)=O)C=C2 |
| SW208460-1-A | 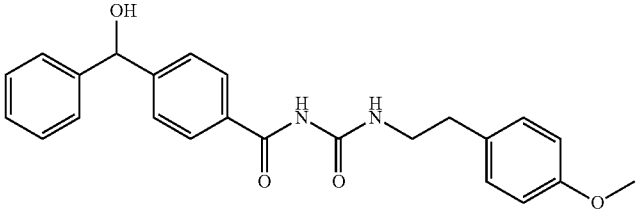<br>O=C(NC(NCCC1=CC=C(OC)C=C1)=O)C2=CC=C(C(O)C3=CC=CC=C3)C=C2 |
| SW208461-1-A | 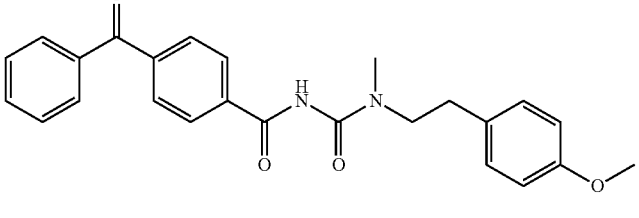<br>O=C(NC(N(C)CCC1=CC=C(OC)C=C1)=O)C2=CC=C(C(C3=CC=CC=C3)=O)C=C2 |

TABLE 6-continued
| Compound ID | Structure |
| --- | --- |
SW208462-1-A
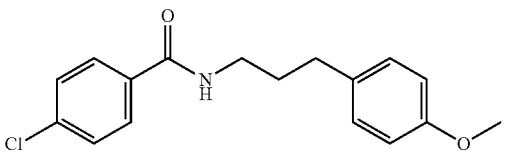 [SMILES: COc1ccc(CCCNC(=O)c2ccc(Cl)cc2)cc1]
O=C(NCCCC1=CC=C(OC)C=C1)C2=CC=C(C1)C=C2
SW208463-1-A
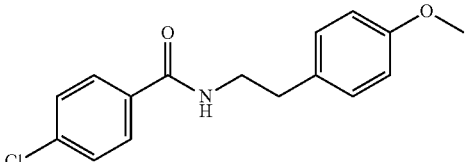
O=C(NCCC1=CC=C(OC)C=C1)C2=CC=C(Cl)C=C2
SW208464-1-A
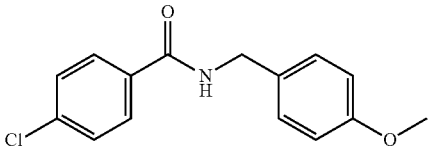 [SMILES: COc1ccc(CNC(=O)c2ccc(Cl)cc2)cc1]
O=C(NCC1=CC=C(OC)C=C1)C2=CC=C(Cl)C=C2
SW208465-1-A
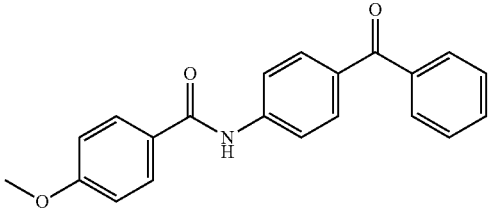 [SMILES: COc1ccc(C(=O)Nc2ccc(C(=O)c3ccccc3)cc2)cc1]
O=C(C1=CC=CC=C1)C2=CC=C(NC(C3=CC=C(OC)C=C3)=O)C=C2
SW208466-1-A
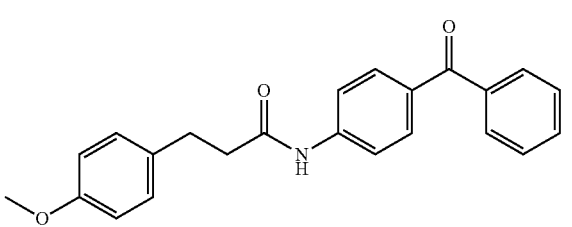 [SMILES: COc1ccc(CCC(=O)Nc2ccc(C(=O)c3ccccc3)cc2)cc1]
O=C(C1=CC=CC=C1)C2=CC=C(NC(CCC3=CC=C(OC)C=C3)=O)C=C2
SW208470-1-A
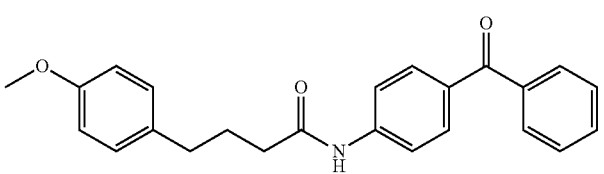 [SMILES: COc1ccc(CCCC(=O)Nc2ccc(C(=O)c3ccccc3)cc2)cc1]
O=C(C1=CC=CC=C1)C2=CC=C(NC(CCCC3=CC=C(OC)C=C3)=O)C=C2

TABLE 6-continued

| Compound ID | Structure |
|---|---|
| SW208480-1-A | 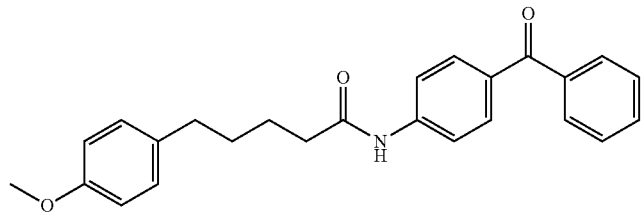 [SMILES: COc1ccc(CCCCC(=O)Nc2ccc(C(=O)c3ccccc3)cc2)cc1]<br>O=C(C1=CC=CC=C1)C2=CC=C(NC(CCCCC3=CC=C(OC)C=C3)=O)C=C2 |
| SW208522-1-A | 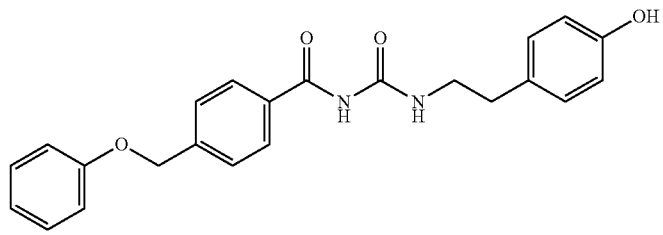 [SMILES: O=C(NCCc1ccc(O)cc1)NC(=O)c1ccc(COc2ccccc2)cc1]<br>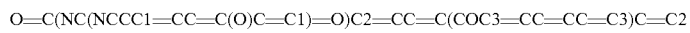O=C(NC(NCCC1=CC=C(O)C=C1)=O)C2=CC=C(COC3=CC=CC=C3)C=C2 |
| SW208523-1-A | 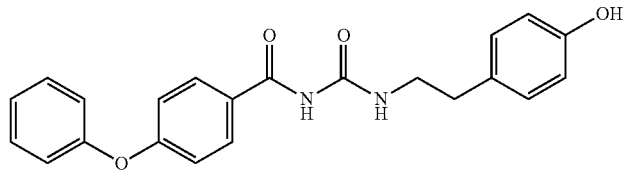 [SMILES: O=C(NCCc1ccc(O)cc1)NC(=O)c1ccc(Oc2ccccc2)cc1]<br>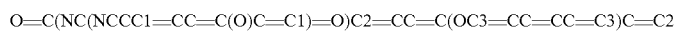O=C(NC(NCCC1=CC=C(O)C=C1)=O)C2=CC=C(OC3=CC=CC=C3)C=C2 |
| SW208524-1-A | 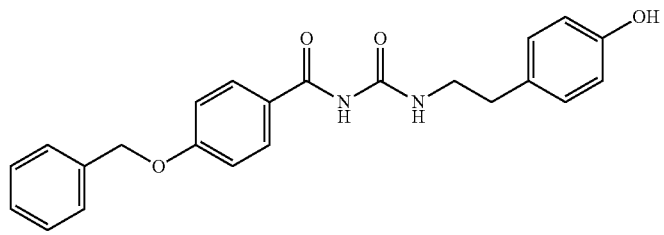 [SMILES: O=C(NCCc1ccc(O)cc1)NC(=O)c1ccc(OCc2ccccc2)cc1]<br>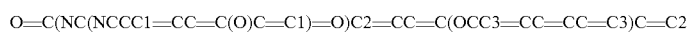O=C(NC(NCCC1=CC=C(O)C=C1)=O)C2=CC=C(OCC3=CC=CC=C3)C=C2 |
| SW208561-1-A | 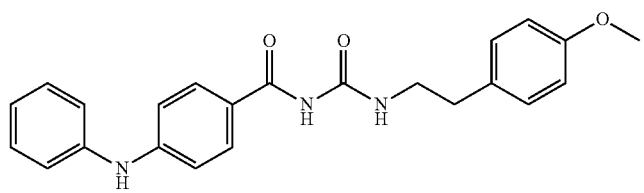 [SMILES: COc1ccc(CCNC(=O)NC(=O)c2ccc(Nc3ccccc3)cc2)cc1]<br>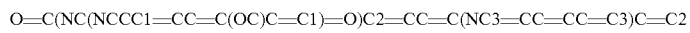O=C(NC(NCCC1=CC=C(OC)C=C1)=O)C2=CC=C(NC3=CC=CC=C3)C=C2 |
| SW208563-1-A | 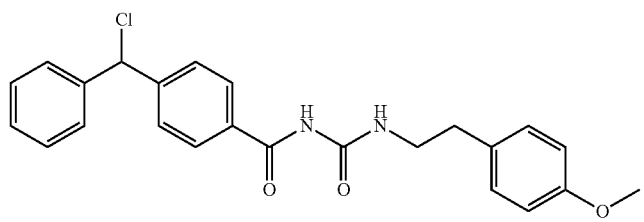 [SMILES: COc1ccc(CCNC(=O)NC(=O)c2ccc(C(Cl)c3ccccc3)cc2)cc1]<br>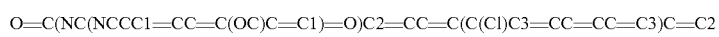O=C(NC(NCCC1=CC=C(OC)C=C1)=O)C2=CC=C(C(Cl)C3=CC=CC=C3)C=C2 |

TABLE 6-continued

| Compound ID | Structure |
|---|---|
| SW208564-1-A | 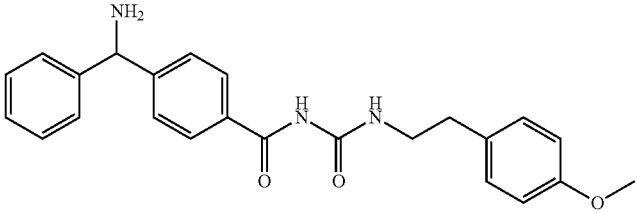<br>O=C(NC(NCCC1=CC=C(OC)C=C1)=O)C2=CC=C(C(N)C3=CC=CC=C3)C=C2 |
| SW208565-1-A | 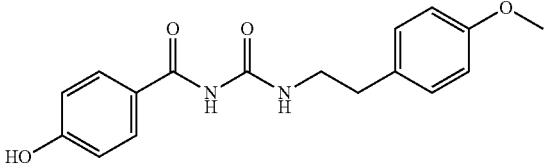 [SMILES: COc1ccc(CCNC(=O)NC(=O)c2ccc(O)cc2)cc1]<br>O=C(NC(NCCC1=CC=C(OC)C=C1)=O)C2=CC=C(O)C=C2 |
| SW208562-1-A | 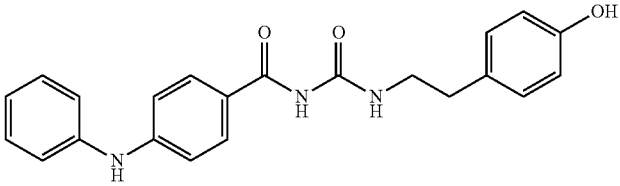 [SMILES: O=C(NCCc1ccc(O)cc1)NC(=O)c1ccc(Nc2ccccc2)cc1]<br>O=C(NC(NCCC1=CC=C(O)C=C1)=O)C2=CC=C(NC3=CC=CC=C3)C=C2 |
| SW208566-1-A | 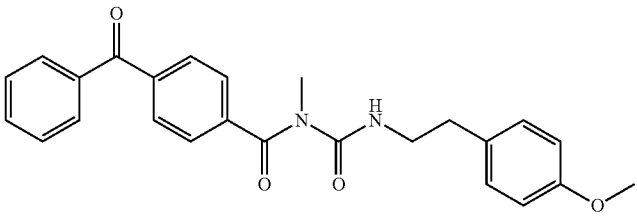 [SMILES: COc1ccc(CCNC(=O)N(C)C(=O)c2ccc(C(=O)c3ccccc3)cc2)cc1]<br>O=C(N(C)C(NCCC1=CC=C(OC)C=C1)=O)C2=CC=C(C(C3=CC=CC=C3)=O)C=C2 |
| SW208567-1-A | 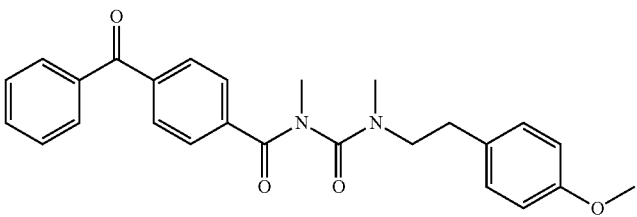 [SMILES: COc1ccc(CCN(C)C(=O)N(C)C(=O)c2ccc(C(=O)c3ccccc3)cc2)cc1]<br>O=C(N(C)C(N(C)CCC1=CC=C(OC)C=C1)=O)C2=CC=C(C(C3=CC=CC=C3)=O)C=C2 |
| SW208579-1-A | 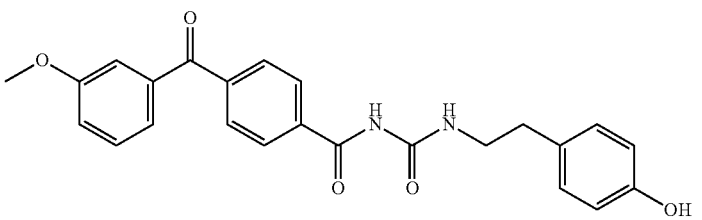 [SMILES: COc1cccc(C(=O)c2ccc(C(=O)NC(=O)NCCc3ccc(O)cc3)cc2)c1]<br>O=C(NC(NCCC1=CC=C(O)C=C1)=O)C2=CC=C(C(C3=CC=CC(OC)=C3)=O)C=C2 |

TABLE 6-continued

| Compound ID | Structure |
| --- | --- |
| SW208580-1-A | 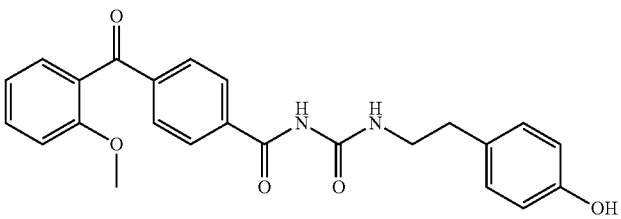 [SMILES: COc1ccccc1C(=O)c1ccc(C(=O)NC(=O)NCCc2ccc(O)cc2)cc1]<br>O=C(NC(NCCC1=CC=C(O)C=C1)=O)C2=CC=C(C(C3=CC=CC=C3OC)=O)C=C2 |
| SW208581-1-A | 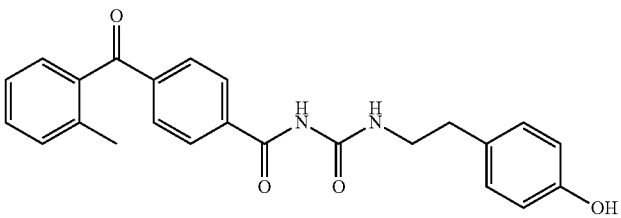 [SMILES: Cc1ccccc1C(=O)c1ccc(C(=O)NC(=O)NCCc2ccc(O)cc2)cc1]<br>O=C(NC(NCCC1=CC=C(O)C=C1)=O)C2=CC=C(C(C3=CC=CC=C3C)=O)C=C2 |
| SW208582-1-A | 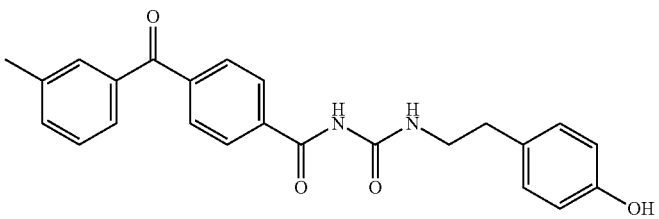 [SMILES: Cc1cccc(C(=O)c2ccc(C(=O)NC(=O)NCCc3ccc(O)cc3)cc2)c1]<br>O=C(NC(NCCC1=CC=C(O)C=C1)=O)C2=CC=C(C(C3=CC=CC(C)=C3)=O)C=C2 |
| SW208583-1-A | 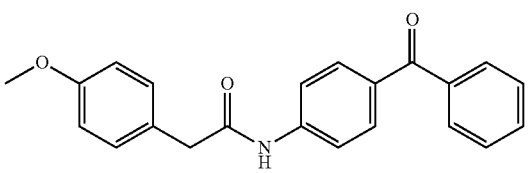 [SMILES: COc1ccc(CC(=O)Nc2ccc(C(=O)c3ccccc3)cc2)cc1]<br>O=C(C(C1=CC=CC=C1)C2=CC=C(NC(CC3=CC=C(OC)C=C3)=O)C=C2 |
| SW208584-1-A | 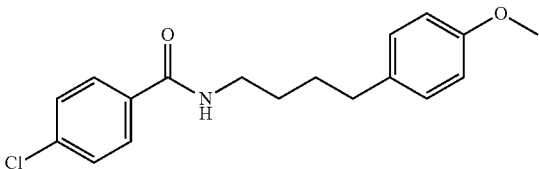 [SMILES: COc1ccc(CCCCNC(=O)c2ccc(Cl)cc2)cc1]<br>O=C(NCCCCC1=CC=C(OC)C=C1)C2=CC=C(C1)C=C2 |
| SW209033-1 | 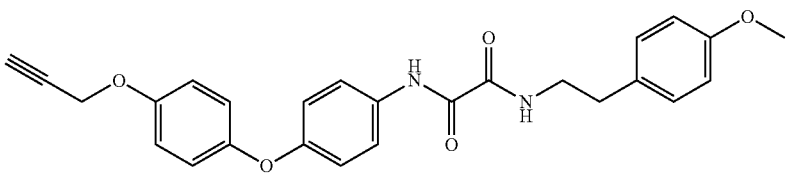 [SMILES: C#CCOc1ccc(Oc2ccc(NC(=O)C(=O)NCCc3ccc(OC)cc3)cc2)cc1]<br>COC1=CC=C(CCNC(=O)C(=O)NC2=CC=C(OC3=CC=C(OCC#C)C=C3)C=C2)C=C1 |

TABLE 6-continued

| Compound ID | Structure |
|---|---|
| SW209048-1 | COC1=CC=C(CCNC(=O)C(=O)NC2=CC=C(OCC3=CC=C(Br)C=C3)C=C2)C=C1 |
| SW209050-1 | COC1=CC=C(CCNC(=O)C(=O)NC2=CC=C(COC3=CC=C(Br)C=C3)C=C2)C=C1 |
| SW209075-1 | COC1=CC=C(CCNC(=O)C(=O)NC2=CC=C(OC3=CC=C(Br)C=C3)C=C2)C=C1 |
| SW211560-1 | O=C(NCCC1=CC=CC=C1)C(=O)NC1=CC=C(C=C1)C(=O)C1=CC=C(OCC#C)C=C1 |

TABLE 7

| Compound ID | H1155 | H1395 | H1819 | H1993 | H2009 | H2073 | H2122 | H460 | HCC366 | HCC4017 | HCC44 | HCC95 | HBEC30KT |
|---|---|---|---|---|---|---|---|---|---|---|---|---|---|
| SW027949 | 50 | 50 | 50 | 50 | 50 | 50 | 0.70 | 1.31 | 50 | 50 | 50 | 0.17 | 41.4868718 |
| SW027951 | 50 | 50 | 50 | 50 | 50 | 50 | 0.15 | 1.345 | 50 | 50 | 50 | 0.09 | 50 |
| SW027952 | 50 | 50 | 50 | 50 | 11.27 | 17.53 | 1.04 | 50 | 50 | 50 | 50 | 0.24 | 19.7708808 |
| SW027950 | 50 | 50 | 50 | 50 | 20.3 | 1.4 | 0.35 | 3.9 | 50 | 50 | 34 | 0.35 | 34 |
| SW027951-2-A | | | 49.5 | | | | 0.28 | | | | | | |
| SW027954-2-A | | | 49.5 | | | | 49.5 | | | | | | |
| SW027962-2-A | | | 49.5 | | | | 49.5 | | | | | | |
| SW027952-2-A | | | 49.5 | | | | 3.1 | | | | | | |
| SW206889-1-A | | | 49.5 | | | | 2.26 | | | | | | |
| SW206860-1-A | | | 49.5 | | | | 0.738 | | | | | | |
| SW206861-1-A | | | 44.2 | | | | 49.5 | | | | | | |

TABLE 7-continued

| Compound ID | H1155 | H1395 | H1819 | H1993 | H2009 | H2073 | H2122 | H460 | HCC366 | HCC4017 | HCC44 | HCC95 | HBEC30KT |
|---|---|---|---|---|---|---|---|---|---|---|---|---|---|
| SW206862-1-A | | | 49.5 | | | | 49.5 | | | | | | |
| SW206863-1-a | | | 49.5 | | | | 49.5 | | | | | | |
| SW206864-1-A | | | 49.5 | | | | 1.3 | | | | | | |
| SW206866-1-A | | | 49.5 | | | | 49.5 | | | | | | |
| SW206867-1-A | | | 49.5 | | | | 49.5 | | | | | | |
| SW206868-1-A | | | 49.5 | | | | 49.5 | | | | | | |
| SW206869-1-A | | | 49.5 | | | | 49.5 | | | | | | |
| SW206870-1-A | | | 49.5 | | | | 49.5 | | | | | | |
| SW206871-1-A | | | 49.5 | | | | 0.932 | | | | | | |
| SW206872-1-A | | | 49.5 | | | | 49.5 | | | | | | |
| SW206874-A | | | 49.5 | | | | 1.06 | | | | | | |
| SW206875-1-A | | | 17.8 | | | | 25.3 | | | | | | |
| SW206876-1-A | | | 49.5 | | | | 49.5 | | | | | | |
| SW206877-1-A | | | 49.5 | | | | 49.5 | | | | | | |
| SW206878-1-A | | | 49.5 | | | | 0.384 | | | | | | |
| SW206879-1-A | | | 49.5 | | | | 49.5 | | | | | | |
| SW206880-1-A | | | 49.5 | | | | 0.306 | | | | | | |
| SW206881-1-A | | | 49.5 | | | | 9.9 | | | | | | |
| SW206882-1-A | | | 49.5 | | | | 49.5 | | | | | | |
| SW206883-1-A | | | 49.5 | | | | 0.727 | | | | | | |
| SW206884-1-A | | | 49.5 | | | | 49.5 | | | | | | |
| SW206885-1-A | | | 46 | | | | 49.5 | | | | | | |
| SW206887-1-A | | | 49.5 | | | | 49.5 | | | | | | |
| SW206888-1-A | | | 49.5 | | | | 49.5 | | | | | | |
| SW206889-1-A | | | 49.5 | | | | 49.5 | | | | | | |
| SW206890-1-A | | | 49.5 | | | | 49.5 | | | | | | |
| SW206891-1-A | | | 43.8 | | | | 49.5 | | | | | | |
| SW206891-2 | | | 49.5 | | | | 49.5 | | | | | | |
| SW206926-1 | | | 49.5 | | | | 49.5 | | | | | | |
| SW206951-1 | | | 49.5 | | | | 49.5 | | | | | | |
| SW206952-1 | | | 49.5 | | | | 0.294 | | | | | | |
| SW206953-1 | | | 41.7 | | | | 49.5 | | | | | | |
| SW206954-1 | | | 49.5 | | | | 0.871 | | | | | | |
| SW206955-1 | | | 49.5 | | | | 0.421 | | | | | | |
| SW206959-1 | | | 49.5 | | | | 0.398 | | | | | | |
| SW206960-1 | | | 49.5 | | | | 0.491 | | | | | | |
| SW206961-1 | | | 49.5 | | | | 0.286 | | | | | | |
| SW206962-1 | | | 49.5 | | | | 1.4 | | | | | | |

TABLE 7-continued

| Compound ID | H1155 | H1395 | H1819 | H1993 | H2009 | H2073 | H2122 | H460 | HCC366 | HCC4017 | HCC44 | HCC95 | HBEC30KT |
|---|---|---|---|---|---|---|---|---|---|---|---|---|---|
| SW206963-1 | | | 49.5 | | | | 49.5 | | | | | | |
| SW206964-1 | | | 49.5 | | | | 49.5 | | | | | | |
| SW206965-1 | | | 49.5 | | | | 49.5 | | | | | | |
| SW206966-1 | | | 49.5 | | | | 0.085 | | | | | | |
| SW206967-1 | | | 49.5 | | | | 0.456 | | | | | | |
| SW206968-1 | | | 49.5 | | | | 49.5 | | | | | | |
| SW206969-1 | | | 49.S | | | | 49.5 | | | | | | |
| SW206970-1 | | | 49.5 | | | | 0.809 | | | | | | |
| SW206971-1 | | | 49.5 | | | | 49.5 | | | | | | |
| SW206972-1 | | | 49.5 | | | | 0.267 | | | | | | |
| SW206973-1 | | | 49.S | | | | 49.5 | | | | | | |
| SW206974-1 | | | 49.5 | | | | 0.697 | | | | | | |
| SW207004-1 | | | 49.5 | | | | 49.5 | | | | | | 49.5 |
| SW207005-1 | | | 49.5 | | | | 49.5 | | | | | | 49.5 |
| SW207006-1 | | | 49.5 | | | | 49.5 | | | | | | 49.5 |
| SW027902-2-A | | | 49.5 | | | | 49.5 | | | | | | 49.5 |
| SW207007-1 | | | 49.5 | | | | 49.5 | | | | | | 49.5 |
| SW207008-1 | | | 49.5 | | | | 49.5 | | | | | | 49.5 |
| SW207009-1 | | | 49.5 | | | | 49.5 | | | | | | 49.5 |
| SW207010-1 | | | 49.5 | | | | 0.331 | | | | | | 49.5 |
| SW207011-1 | | | 49.5 | | | | 49.5 | | | | | | 49.5 |
| SW207012-1 | | | 49.5 | | | | 11.8 | | | | | | 18 |
| SW207013-1 | | | 49.5 | | | | 49.5 | | | | | | 49.5 |
| SW207014-1 | | | 49.5 | | | | 0.89 | | | | | | 49.5 |
| SW207015-1 | | | 49.5 | | | | 0.456 | | | | | | 44.1 |
| SW207016-1 | | | 49.5 | | | | 23.8 | | | | | | 49.5 |
| SW207017-1 | | | 49.5 | | | | 0.712 | | | | | | 49.5 |
| SW207018-1 | | | 49.5 | | | | 49.5 | | | | | | 49.5 |
| SW207019-1 | | | 49.5 | | | | 49.5 | | | | | | 49.5 |
| SW207020-1 | | | 49.5 | | | | 0.602 | | | | | | 49.5 |
| SW207021-1 | | | 49.5 | | | | 0.407 | | | | | | 49.5 |
| SW207038 | | | | | | | >1 uM | | | | | | |
| SW113361-2-A | | | 49.5 | | | | 49.5 | | | | | | |
| SW113878-2-A | | | 49.5 | | | | 49.5 | | | | | | |
| SW207038-2-A | | | 49.5 | | | | 3.17 | | | | | | |
| SW208009-1-A | | | 49.5 | | | | 0.081 | | | | | | |
| SW208023-1-A | | | 7.74 | | | | 0.257 | | | | | | |
| SW208024-1-A | | | 49.5 | | | | 49.5 | | | | | | |
| SW208025-1-A | | | 49.5 | | | | 49.5 | | | | | | |

TABLE 7-continued

| Compound ID | H1155 | H1395 | H1819 | H1993 | H2009 | H2073 | H2122 | H460 | HCC366 | HCC4017 | HCC44 | HCC95 | HBEC30KT |
|---|---|---|---|---|---|---|---|---|---|---|---|---|---|
| SW208026-1-A | | | 49.5 | | | | 49.5 | | | | | | |
| SW208027-1-A | | | 49.5 | | | | 49.5 | | | | | | |
| SW208028-1-A | | | 49.5 | | | | 49.5 | | | | | | |
| SW208029-1-A | | | 49.5 | | | | 49.5 | | | | | | |
| SW208030-1-A | | | 49.5 | | | | 49.5 | | | | | | |
| SW208031-1-A | | | 49.5 | | | | 49.5 | | | | | | |
| SW208032-1-A | | | 49.5 | | | | 49.5 | | | | | | |
| SW208033-1-A | | | 49.5 | | | | 49.5 | | | | | | |
| SW208034-1-A | | | 49.5 | | | | 49.5 | | | | | | |
| SW208035-1-A | | | 49.5 | | | | 49.5 | | | | | | |
| SW208036-1-A | | | 49.5 | | | | 49.5 | | | | | | |
| SW208037-1-A | | | 49.5 | | | | 49.5 | | | | | | |
| SW208038-1-A | | | 49.5 | | | | 49.5 | | | | | | |
| SW208039-1-A | | | 49.5 | | | | 47.5 | | | | | | |
| SW208040-1-A | | | 49.5 | | | | 49.5 | | | | | | |
| SW208041-1-A | | | 49.5 | | | | 48.4 | | | | | | |
| SW208042-1-A | | | 49.5 | | | | 49.5 | | | | | | |
| SW208043-2-A | | | 49.5 | | | | 49.5 | | | | | | |
| SW208044-1-A | | | 49.5 | | | | 49.5 | | | | | | |
| SW208045-1-A | | | 49.5 | | | | 49.5 | | | | | | |
| SW208046-1-A | | | 49.5 | | | | 49.5 | | | | | | |
| SW208047-1-A | | | 49.5 | | | | 49.5 | | | | | | |
| SW208048-1-A | | | 49.5 | | | | 49.5 | | | | | | |
| SW208049-1-A | | | 49.5 | | | | 49.5 | | | | | | |
| SW208050-1-A | | | 49.5 | | | | 49.5 | | | | | | |
| SW208051-1-A | | | 49.5 | | | | 49.5 | | | | | | |
| SW208052-1-A | | | 49.5 | | | | 49.5 | | | | | | |
| SW208053-1-A | | | 32 | | | | 45.9 | | | | | | |
| SW208054-1-A | | | 49.5 | | | | 46.3 | | | | | | |
| SW208055-1-A | | | 49.5 | | | | 49.5 | | | | | | |
| SW208056-1-A | | | 29.8 | | | | 30.2 | | | | | | |
| SW208057-1-A | | | 34.9 | | | | 49.5 | | | | | | |
| SW208058-1-A | | | 49.5 | | | | 49.5 | | | | | | |
| SW208059-1-A | | | 49.5 | | | | 49.5 | | | | | | |
| SW208060-1-A | | | 49.5 | | | | 49.5 | | | | | | |
| SW208061-1-A | | | 49.5 | | | | 49.5 | | | | | | |
| SW208062-1-A | | | 49.5 | | | | 49.5 | | | | | | |
| SW208063-1-A | | | 49.5 | | | | 49.5 | | | | | | |

TABLE 7-continued

| Compound ID | H1155 | H1395 | H1819 | H1993 | H2009 | H2073 | H2122 | H460 | HCC366 | HCC4017 | HCC44 | HCC95 | HBEC30KT |
|---|---|---|---|---|---|---|---|---|---|---|---|---|---|
| SW208108-1-A | | | 49.50 | | | | 0.028 | | | | | | |
| SW208117-1-A | | | 15.60 | | | | 0.031 | | | | | | |
| SW208119-1-A | | | 35.60 | | | | 2.650 | | | | | | |
| SW208120-1-A | | | 49.50 | | | | 38.900 | | | | | | |
| SW208121-1-A | | | 5.75 | | | | 3.670 | | | | | | |
| SW208122-1-A | | | 49.50 | | | | 45.000 | | | | | | |
| SW208123-1-A | | | 46.30 | | | | 0.348 | | | | | | |
| SW208124-1-A | | | 34.10 | | | | 36.200 | | | | | | |
| SW208125-1-A | | | 49.50 | | | | 30.400 | | | | | | |
| SW208126-1-A | | | 49.50 | | | | 49.500 | | | | | | |
| SW208127-1-A | | | 49.50 | | | | 0.438 | | | | | | |
| SW208128-1-A | | | 49.50 | | | | 0.289 | | | | | | |
| SW208129-1-A | | | 49.50 | | | | 49.500 | | | | | | |
| SW208130-1-A | | | 49.50 | | | | 49.500 | | | | | | |
| SW208131-1-A | | | 49.50 | | | | 49.500 | | | | | | |
| SW208132-1-A | | | 49.50 | | | | 49.500 | | | | | | |
| SW208133-1-A | | | 49.50 | | | | 49.500 | | | | | | |
| SW208134-1-A | | | 49.50 | | | | 49.500 | | | | | | |
| SW208135-1-A | | | 49.50 | | | | 49.500 | | | | | | |
| SW209136-1-A | | | 49.50 | | | | 49.500 | | | | | | |
| SW208137-1-A | | | 49.50 | | | | 49.500 | | | | | | |
| SW208138-1-A | | | 49.50 | | | | 49.500 | | | | | | |
| SW208139-1-A | | | 49.50 | | | | 5.880 | | | | | | |
| SW208140-1-A | | | 16.50 | | | | 2.620 | | | | | | |
| SW208141-1-A | | | 49.50 | | | | 49.500 | | | | | | |
| SW208142-1-A | | | 49.50 | | | | 1.090 | | | | | | |
| SW208143-1-A | | | 49.50 | | | | 49.500 | | | | | | |
| SW208144-1-A | | | 49.50 | | | | 49.500 | | | | | | |
| SW208145-1-A | | | 49.50 | | | | 49.500 | | | | | | |
| SW208146-1-A | | | 49.50 | | | | 0.756 | | | | | | |
| SW208147-1-A | | | 49.50 | | | | 2.070 | | | | | | |
| SW208148-1-A | | | 49.50 | | | | 7.170 | | | | | | |
| SW208149-1-A | | | 49.50 | | | | 6.440 | | | | | | |
| SW208151-1-A | | | 46.40 | | | | 2.080 | | | | | | |
| SW208152-1-A | | | 49.50 | | | | 15.200 | | | | | | |
| SW208153-1-A | | | 49.50 | | | | 10.500 | | | | | | |
| SW208189-1-A | | | 49.50 | | | | 1.030 | | | | | | |
| SW208217-1-A | | | | | 12.3 | | 49.5 | | | | 49.5 | | |

TABLE 7-continued

| Compound ID | H1155 | H1395 | H1819 | H1993 | H2009 | H2073 | H2122 | H460 | HCC366 | HCC4017 | HCC44 | HCC95 | HBEC30KT |
|---|---|---|---|---|---|---|---|---|---|---|---|---|---|
| SW208219-1-A | | | | | 49.5 | | 49.5 | | | | 49.5 | | |
| SW208220-1-A | | | | | 49.5 | | 49.5 | | | | 49.5 | | |
| SW208222-1-A | | | | | 48.0 | | 0.105 | | | | 0.241 | | |
| SW208386-1-A | | | | | 13.14 | | 49.50 | | | | 49.50 | | |
| SW208387-1-A | | | | | 49.50 | | 0.18 | | | | 0.25 | | |
| SW208388-1-A | | | | | 49.50 | | 0.16 | | | | 0.42 | | |
| SW208389-1-A | | | | | 35.64 | | 49.50 | | | | 49.50 | | |
| SW208390-1-A | | | | | 49.50 | | 49.50 | | | | 49.50 | | |
| SW208391-1-A | | | | | 7.16 | | 49.50 | | | | 49.50 | | |
| SW208392-1-A | | | | | 49.50 | | 6.71 | | | | 49.50 | | |
| SW208393-1-A | | | | | 49.50 | | 0.17 | | | | 49.50 | | |
| SW208394-1-A | | | | | 49.50 | | 49.50 | | | | 49.50 | | |
| SW208395-1-A | | | | | 49.50 | | 49.50 | | | | 49.50 | | |
| SW208396-1-A | | | | | 4.95 | | 2.23 | | | | 49.50 | | |
| SW208397-1-A | | | | | 16.50 | | 2.28 | | | | 49.50 | | |
| SW208398-1-A | | | | | 16.50 | | 0.36 | | | | 49.50 | | |
| SW208399-1-A | | | | | 16.50 | | 49.50 | | | | 49.50 | | |
| SW208400-1-A | | | | | 49.50 | | 49.50 | | | | 49.50 | | |
| SW208401-1-A | | | | | 49.50 | | 0.15 | | | | 0.54 | | |
| SW208402-1-A | | | | | 49.50 | | 1.03 | | | | 49.50 | | |
| SW208403-1-A | | | | | 42.73 | | 1.09 | | | | 49.50 | | |
| SW208404-1-A | | | | | 49.50 | | 21.76 | | | | 49.50 | | |
| SW208408-1-A | | | | | 46.85 | | 49.50 | | | | 49.50 | | |
| SW208410-1-A | | | | | 1.37 | | 49.50 | | | | 49.50 | | |
| SW208409-1-A | | | | | 49.50 | | 0.14 | | | | 49.50 | | |
| SW208411-1-A | | | | | 49.50 | | 49.50 | | | | 49.50 | | |
| SW208412-1-A | | | | | 2.14 | | 0.27 | | | | 49.50 | | |
| SW208413-1-A | | | | | 16.32 | | 49.50 | | | | 49.50 | | |
| SW208414-1-A | | | | | 5.05 | | 49.50 | | | | 49.50 | | |
| SW208452-1-A | | | | | 13.126 | | 49.500 | | | | 49.500 | | |
| SW208453-1-A | | | | | 1.630 | | 0.864 | | | | 49.500 | | |
| SW208454-1-A | | | | | 49.500 | | 0.939 | | | | 49.500 | | |
| SW208455-1-A | | | | | 16.500 | | 49.500 | | | | 49.500 | | |
| SW208456-1-A | | | | | 49.500 | | 0.031 | | | | 0.022 | | |
| SW208457-1-A | | | | | 49.500 | | 0.031 | | | | 0.023 | | |
| SW208458-1-A | | | | | 0.099 | | 0.010 | | | | 0.008 | | |
| SW208459-1-A | | | | | 0.299 | | 0.097 | | | | 0.073 | | |
| SW208460-1-A | | | | | 49.500 | | 0.097 | | | | 0.084 | | |

TABLE 7-continued

| Compound ID | H1155 | H1395 | H1819 | H1993 | H2009 | H2073 | H2122 | H460 | HCC366 | HCC4017 | HCC44 | HCC95 | HBEC30KT |
|---|---|---|---|---|---|---|---|---|---|---|---|---|---|
| SW208461-1-A | | | | | 49.500 | | 8.669 | | | | 49.500 | | |
| SW208462-1-A | | | | | 49.500 | | 49.500 | | | | 49.500 | | |
| SW208463-1-A | | | | | 49.500 | | 49.500 | | | | 49.500 | | |
| SW208464-1-A | | | | | 49.500 | | 49.500 | | | | 49.500 | | |
| SW208465-1-A | | | | | 49.500 | | 49.500 | | | | 49.500 | | |
| SW208466-1-A | | | | | 49.500 | | 49.500 | | | | 49.500 | | |
| SW208470-1-A | | | | | 34.404 | | 49.500 | | | | 34.833 | | |
| SW208480-1-A | | | | | 49.500 | | 2.513 | | | | 1.406 | | |
| SW208522-1-A | | | | | 0.01 | | 0.01 | | | | 0.01 | | |
| SW208523-1-A | | | | | 0.02 | | 0.02 | | | | 0.02 | | |
| SW208524-1-A | | | | | 0.01 | | 0.02 | | | | 0.01 | | |
| SW208561-1-A | | | | | 0.88 | | 0.08 | | | | 0.03 | | |
| SW208563-1-A | | | | | 0.99 | | 0.06 | | | | 0.03 | | |
| SW208564-1-A | | | | | 5.62 | | 0.32 | | | | 0.06 | | |
| SW208565-1-A | | | | | 5.90 | | 18.03 | | | | 2.75 | | |
| SW208562-1-A | | | | | 0.01 | | 0.09 | | | | 12.19 | | |
| SW208566-1-A | | | | | 10.26 | | 6.15 | | | | 7.76 | | |
| SW208567-1-A | | | | | 16.50 | | 15.65 | | | | 8.00 | | |
| SW208579-1-A | | | | | 0.42 | | 0.82 | | | | 0.46 | | |
| SW208580-1-A | | | | | 2.14 | | 9.46 | | | | 8.08 | | |
| SW208581-1-A | | | | | 0.51 | | 1.52 | | | | 0.87 | | |
| SW208582-1-A | | | | | 0.50 | | 2.73 | | | | 1.53 | | |
| SW208583-1-A | | | | | 49.50 | | 3.40 | | | | 4.30 | | |
| SW208S84-1-A | | | | | 5.57 | | 3.27 | | | | 37.85 | | |
| SW209048-1 | | | | | | 49.50 | 0.157 | | | | | | |
| SW209050-1 | | | | | | 25.85 | 0.031 | | | | | | |
| SW209075-1 | | | | | | 8.07 | 0.029 | | | | | | |
| SW211560-1 | | | 49.500 | | | 22.730 | 49.500 | | | | | | |

TABLE 8

| Compound ID | Structure | H1819 AC50 | H2009 AC50 | H2073 AC50 | H2122 AC50 | HCC44 AC50 |
|---|---|---|---|---|---|---|
| SW043139 | (structure) | 50.000 | 50.000 | 50.000 | 0.166 | 50.000 |
| SW208232 | C$_{25}$H$_{17}$FN$_2$O$_4$ (structure) | | 49.5 | | 49.5 | 49.5 |
| SW043139-2-A | (structure) FC1=C(OC2=COC(C=C(OCC3=CN(C4=CC=CC=C4)N=N3)C=C5)=C5C2=O)C=CC=C1 | | 15.864 | | 0.292 | 49.500 |
| | FC1=C(OC2=COC(C=C(OCC3=CN(C4=CC=CC=C4)N=C3)C=C5)=C5C2=O)C=CC=C1 | | | | | |

TABLE 8-continued

| Compound ID | Structure | H1819 AC50 | H2009 AC50 | H2073 AC50 | H2122 AC50 | HCC44 AC50 |
|---|---|---|---|---|---|---|
| SW208467 | FC1=C(OC2=COC(C=C(OC3=CN(C4=CC(F)=CC=C4)N=C3)C=C5)=C5C2=O)C=CC=C1 | | 12.644 | | 49.500 | 49.500 |
| SW208468 | FC1=C(OC2=COC(C=C(OC3=CN(C4=CC(F)C=C4)N=C3)C=C5)=C5C2=O)C=CC=C1 | | 22.274 | | 49.500 | 49.500 |
| SW208469 | FC1=C(OC2=COC(C=C(OC3=CN(C4=CC=C(Cl)C=C4)N=C3)C=C5)=C5C2=O)C=CC=C1 | | 16.461 | | 49.500 | 49.500 |

TABLE 8-continued

| Compound ID | Structure | H1819 AC50 | H2009 AC50 | H2073 AC50 | H2122 AC50 | HCC44 AC50 |
|---|---|---|---|---|---|---|
| SW 208585-1 | O=C1C(OC2=CC=CC=C2Br)=COC3=C1C=CC(OCC4=CN(C5=CC=CC=C5)N=C4)=C3 | | 35.00 | | 0.10 | |
| SW 208586-1 | O=C1C(OC2=CC=CC=C2)=COC3=C1C=CC(OCC4=CN(C5=CC=CC=C5)N=C4)=C3 | | 49.50 | | 0.11 | 0.15 |
| SW 208587-1 | O=C1C(OC2=CC=CC=C2F)=C(C)OC3=C1C=CC(OCC4=CN(C5=CC=CC=C5)N=C4)=C3 | | 16.50 | | 0.39 | 49.50 |
| SW 208589-1 | O=C1C(OC2=CC=CC=C2Cl)=COC3=C1C=CC(OCC4=CN(C5=CC=CC=C5)N=C4)=C3 | | 4.76 | | 0.12 | 49.50 |

TABLE 8-continued
| Compound ID | Structure | H1819 AC50 | H2009 AC50 | H2073 AC50 | H2122 AC50 | HCC44 AC50 |
|---|---|---|---|---|---|---|
| SW 208591-1 | 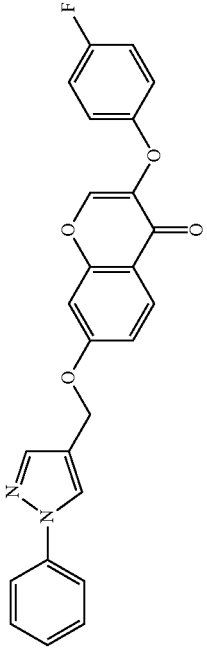 O=C1C(OC2=CC=CC=CC(F)C2)=COC3=C1C=CC(OCC4=CN(C5=CC=CC=CC=C5)N=C4)=C3 | | 15.97 | | 0.15 | 0.07 |
| SW208592-1 | 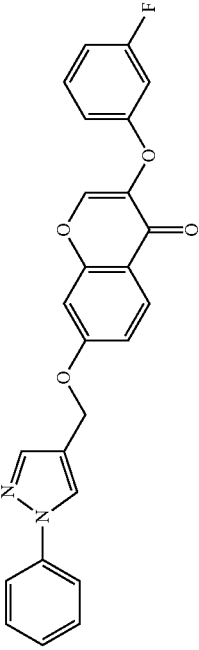 O=C1C(OC2=CC=CC=CC(F)=C2)=COC3=C1C=CC(OCC4=CN(C5=CC=CC=CC=C5)N=C4)=C3 | | 16.50 | | 0.15 | 0.08 |
| SW 208593-1 | 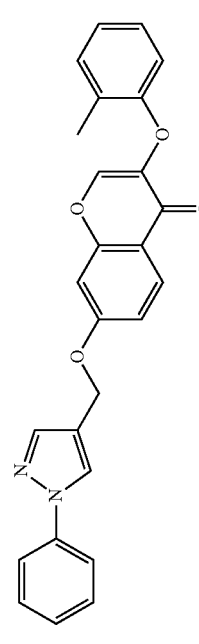 O=C1C(OC2=CC=CC=CC(F)=C2C)=COC3=C1C=CC(OCC4=CN(C5=CC=CC=CC=C5)N=C4)=C3 | | >15 | | 0.11 | >15 |
| SW 208594-1 | 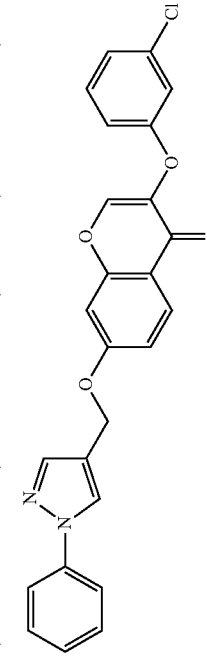 O=C1C(OC2=CC=CC=CC(Cl)=C2)=COC3=C1C=CC(OCC4=CN(C5=CC=CC=CC=C5)N=C4)=C3 | | 16.5 | | 0.22 | 0.08 |

TABLE 8-continued
| Compound ID | Structure | H1819 AC50 | H2009 AC50 | H2073 AC50 | H2122 AC50 | HCC44 AC50 |
|---|---|---|---|---|---|---|
| SW 208595-1 | 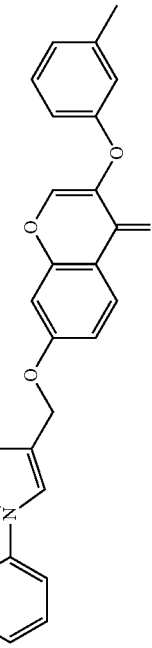 O=C1C(OC2=CC=CC(C)=C2)=COC3=C1C=CC(OCC4=CN(C5=CC=CC=CC=C5)N=C4)=C3 | | 16.5 | | 0.20 | 0.10 |
| SW 208596-1 | 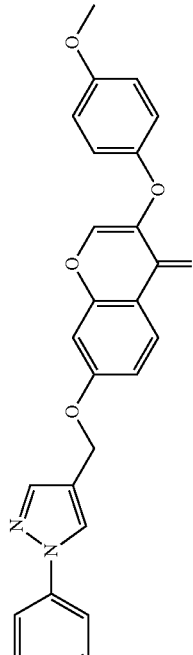 O=C1C(OC2=CC=C(OC)C=C2)=COC3=C1C=CC(OCC4=CN(C5=CC=CC=CC=C5)N=C4)=C3 | | 16.5 | | 0.22 | 16.50 |
| SW 208629-1 | 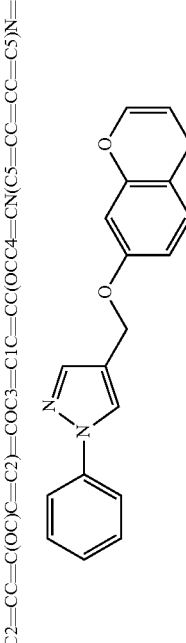 O=C1C=COC2=C1C=CC(OCC3=CN(C4=CC=CC=CC=C4)N=C3)=C2 | | 49.50 | | 49.5000 | 49.50 |
| SW 208630-1 | 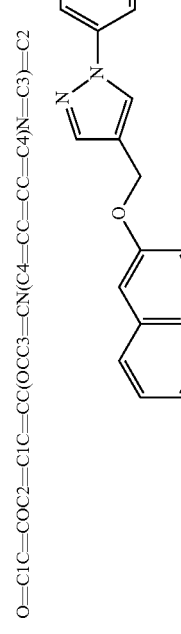 C1(OCC2=CN(C3=CC=CC=CC=C3)N=C2)=CC4=C(C=C1)C=C(OCC5=CN(C6=CC=CC=CC=C6)N=C5)C=C4 | | 49.50 | | 49.5000 | 49.50 |

TABLE 8-continued

| Compound ID | Structure | H1819 AC50 | H2009 AC50 | H2073 AC50 | H2122 AC50 | HCC44 AC50 |
|---|---|---|---|---|---|---|
| SW 208631-1 | O=C1C(C2=CC=CC=C2)COC3=C1C=CC(OCC4=CN(C5=CC=CC=C5)N=C4)=C3 | | 49.50 | | 0.2802 | 49.50 |
| SW208670-1 | O=C1C(O)=COC2=C1C=CC(OCC3=CN(C4=CC=CC=C4)N=C3)=C2 | | | | 3.24 | 3.22 |
| SW208731 | O=C1C(I)=COC2=C1C=CC(OCC3=CN(C4=CC=CC=C4)N=C3)=C2 | | | | 49.50 | 49.50 |

TABLE 8-continued

| Compound ID | Structure | H1819 AC50 | H2009 AC50 | H2073 AC50 | H2122 AC50 | HCC44 AC50 |
|---|---|---|---|---|---|---|
| SW208670-1 | O=C1C(C2=CN=CC=C2)=COC3=C1C=CC(OCC4=CN(C5=CC=CC=C5)N=C4)=C3 | | | | 49.50 | 49.50 |
| SW208731 | O=C1C(C2=CC=NC=C2)=COC3=C1C=CC(OCC4=CN(C5=CC=CC=C5)N=C4)=C3 | | | | 9.49 | 7.41 |
| SW208732 | O=C1C(C2=CC=CC=N2)=COC3=C1C=CC(OCC4=CN(C5=CC=CC=C5)N=C4)=C3 | | | | 49.50 | |

TABLE 8-continued
| Compound ID | Structure | H1819 AC50 | H2009 AC50 | H2073 AC50 | H2122 AC50 | HCC44 AC50 |
|---|---|---|---|---|---|---|
| SW208733 | 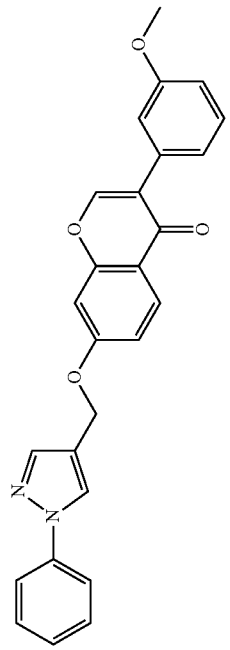 O=C1C(C2=CC=CC(OC)=C2)=COC3=C1C=CC(OCC4=CN(C5=CC=CC=C5)N=C4)=C3 | | | | 0.74 | 49.50 |
| SW208734 | 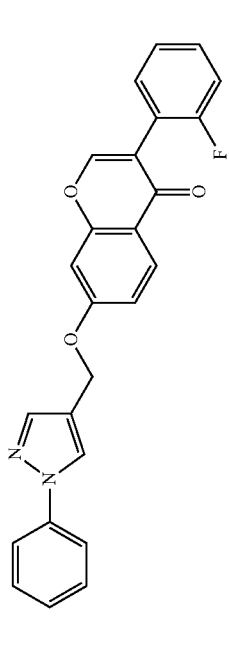 O=C1C(C2=CC=CC=CC=C2F)=COC3=C1C=CC(OCC4=CN(C5=CC=CC=C5)N=C4)=C3 | | | | 49.50 | |
| SW208735 | 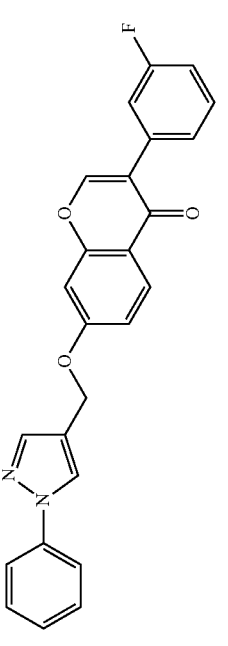 O=C1C(C2=CC=CC(F)=C2)=COC3=C1C=CC(OCC4=CN(C5=CC=CC=C5)N=C4)=C3 | | | | 0.55 | 49.50 |

TABLE 8-continued

| Compound ID | Structure | H1819 AC50 | H2009 AC50 | H2073 AC50 | H2122 AC50 | HCC44 AC50 |
|---|---|---|---|---|---|---|
| SW208737 | (4-fluorophenyl chromone with phenylpyrazolylmethoxy substituent) O=C1C(C2=CC=CC(F)C2)=COC3=C1C=CC(OCC4=CN(C5=CC=CC=C5)N=C4)=C3 | | | | 0.27 | 49.50 |
| SW208738 | (4-chlorophenyl chromone with phenylpyrazolylmethoxy substituent) O=C1C(C2=CC=C(Cl)C2)=COC3=C1C=CC(OCC4=CN(C5=CC=CC=C5)N=C4)=C3 | | 49.50 | | 49.50 | |
| SW208740 | (3-hydroxyphenyl chromone with phenylpyrazolylmethoxy substituent) O=C1C(C2=CC=CC(O)=C2)=COC3=C1C=CC(OCC4=CN(C5=CC=CC=C5)N=C4)=C3 | | 39.02 | | 21.04 | |

TABLE 8-continued
| Compound ID | Structure | H1819 AC50 | H2009 AC50 | H2073 AC50 | H2122 AC50 | HCC44 AC50 |
|---|---|---|---|---|---|---|
| SW208757-1 | 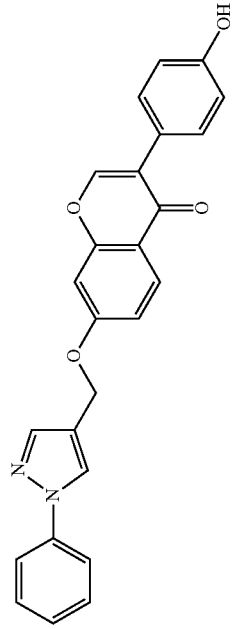<br>O=C1C(C2=CC=C(O)C=C2)=COC3=C1C=CC(OCC4=CN(C5=CC=CC=C5)N=C4)=C3 | | 5.63 | | 49.50 | 49.50 |
| SW208758-1 | 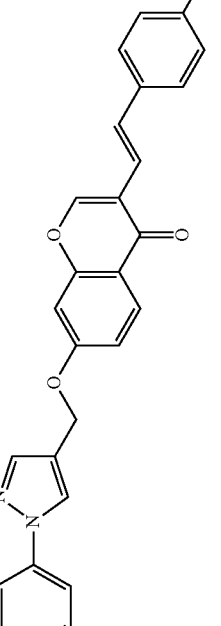<br>O=C1C(/C=C/C2=CC=C(C)C=C2)=COC3=C1C=CC(OCC4=CN(C5=CC=CC=C5)N=C4)=C3 | | 16.50 | | 49.50 | 49.50 |
| SW208759-1 | 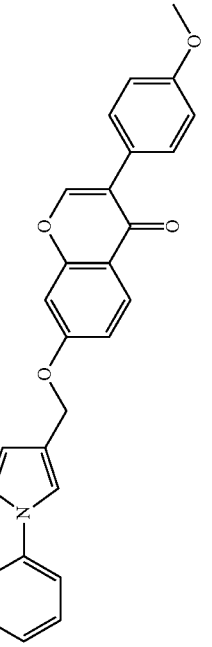<br>O=C1C(C2=CC=C(OC)C=C2)=COC3=C1C=CC(OCC4=CN(C5=CC=CC=C5)N=C4)=C3 | | 49.50 | | 49.50 | 49.50 |

TABLE 8-continued

| Compound ID | Structure | H1819 AC50 | H2009 AC50 | H2073 AC50 | H2122 AC50 | HCC44 AC50 |
|---|---|---|---|---|---|---|
| SW208760-1 | O=C1C(C2=CC=C(F)C=C2F)=COC3=C1C=CC(OCC4=CN(C5=CC=CC=C5)N=C4)=C3 | | 20.72 | | 0.11 | 49.50 |
| SW208761-1 | O=C1C(C2=CC=C(C=CC=C3)C3=C2)COC4=C1C=CC(OCC5=CN(C6=CC=CC=C6)N=C5)=C4 | | 32.40 | | 49.50 | 49.50 |
| SW208762-1 | O=C1C(C2=CC=C(F)C(F)=C2)=COC3=C1C=CC(OCC4=CN(C5=CC=CC=C5)N=C4)=C3 | | 43.17 | | 0.18 | 49.50 |

TABLE 8-continued
| Compound ID | Structure | H1819 AC50 | H2009 AC50 | H2073 AC50 | H2122 AC50 | HCC44 AC50 |
|---|---|---|---|---|---|---|
| SW208763-1 | <br>O=C1C(C2=CC(C(F)(F)F)=CC(C(F)(F)F)=C2)=COC3=C1C=CC(OCC4=CN(C5=CC=CC=C5)N=C4)=C3 | | 3.26 | | 0.08 | 1.36 |
| SW208764-1 | 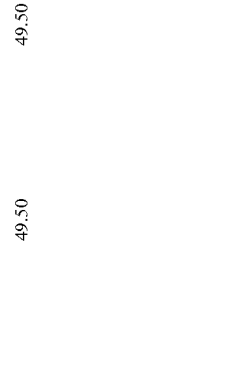<br>O=C1C(C2=CCCCC2)=COC3=C1C=CC(OCC4=CN(C5=CC=CC=C5)N=C4)=C3 | | 49.50 | | 49.50 | 49.50 |
| SW208765-1 | <br>O=C1C(C2=CC=C(OCC)C=C2)=COC3=C1C=CC(OCC4=CN(C5=CC=CC=C5)N=C4)=C3 | | 16.50 | | 49.50 | 49.50 |

TABLE 8-continued

| Compound ID | Structure | H1819 AC50 | H2009 AC50 | H2073 AC50 | H2122 AC50 | HCC44 AC50 |
|---|---|---|---|---|---|---|
| SW208766-1 | (structure) | | 49.50 | | 16.50 | 49.50 |
| | O=C1C(C2CC2)=COC3=C1C=CC(OCC4=CN(C5=CC=CC=C5)N=C4)=C3 | | | | | |
| SW208767-1 | (structure) | | 49.50 | | 2.07 | 4.06 |
| | O=C1C(C2=CC=C(OC)C=C2C)COC3=C1C=CC(OCC4=CN(C5=CC=CC=C5)N=C4)=C3 | | | | | |
| SW208768-1 | (structure) | | 19.950 | | 24.761 | 16.500 |
| | O=C1C(C#CC2=CC=CC=C2)=COC3=C1C=CC(OCC4=CN(N=C4)C5=CC=CC=C5)=C3 | | | | | |

TABLE 8-continued

| Compound ID | Structure | H1819 AC50 | H2009 AC50 | H2073 AC50 | H2122 AC50 | HCC44 AC50 |
|---|---|---|---|---|---|---|
| SW208769-1 | O=C1C(CC2=CC=CC=C2)=COC3=C1C=CC(OCC4=CN(C5=CC=CC=C5)N=C4)=C3 | | 49.500 | | 0.027 | 3.183 |
| SW208832-1 | O=C1C=CN(C)C2=C1C=CC=CC=C2=COC3=CN(C4=CC=CC=C4)N=C3)=C2 | | 7.511 | | 7.559 | 49.500 |
| SW208833-1 | O=C1C(C(O)C2=CC=CC=C2)=COC3=C1C=CC(OCC4=CN(C5=CC=CC=C5)N=C4)=C3 | | 8.298 | | 0.216 | 9.861 |
| SW208844-1 | O=C1C(C(C2=CC=CC=C2)=O)=COC3=C1C=CC(OCC4=CN(C5=CC=CC=C5)N=C4)=C3 | | 29.954 | | 0.864 | 23.699 |

TABLE 8-continued

| Compound ID | Structure | H1819 AC50 | H2009 AC50 | H2073 AC50 | H2122 AC50 | HCC44 AC50 |
|---|---|---|---|---|---|---|
| SW209021-1 | O=C1C(CC#C)=COC2=C1C=CC(OCC3=CN(C4=CC=CC=C4)N=C3)=C2 | 49.500 | | 49.500 | 0.846 | |
| SW209022-1 | O=C1C(CC=C)=COC2=C1C=CC(OCC3=CN(C4=CC=CC=C4)N=C3)=C2 | 47.104 | | 49.500 | 0.323 | |
| SW 209087-1 | O=C1C(C2=CC=CC(OC#C)=C2)=COC3=C1C=CC(OCC4=CN(C5=CC=CC=C5)N=C4)=C3 | 49.500 | | 49.500 | 0.106 | |
| SW 209088-1 | OC1=CC=CC(/C=C2\COC3=C(C=CC(OCC4=CN(N=C4)C4=CC=CC=C4)=C3)C2=O)=C1 | 9.540 | | 14.907 | 21.053 | |

TABLE 8-continued

| Compound ID | Structure | H1819 AC50 | H2009 AC50 | H2073 AC50 | H2122 AC50 | HCC44 AC50 |
|---|---|---|---|---|---|---|
| SW 209089-1 | OC(CCC1=CC=C(Br)C=C1)CN1C=CN=C1 | 49.500 | | 49.500 | 49.500 | |
| SW209185-1 | FC(F)(F)C1=CC=C(CC2=COC3=C(C=CC(OCC4=CN(N=C4)C4=CC=CC=C4)=C3)C2=O)C=C1 | 28.626 | | | 0.085 | |
| SW209186-1 | FC(F)(F)C1=CC=CC(CC2=COC3=C(C=CC(OCC4=CN(N=C4)C4=CC=CC=C4)=C3)C2=O)=C1 | 49.500 | | | 0.047 | |
| SW209187-1 | O=C1C(CC2=NC=CC=C2)=COC2=C1C=CC(OCC1=CN(N=C1)C1=CC=CC=C1)=C2 | 49.500 | | 49.500 | 0.280 | |

TABLE 8-continued

| Compound ID | Structure | H1819 AC50 | H2009 AC50 | H2073 AC50 | H2122 AC50 | HCC44 AC50 |
|---|---|---|---|---|---|---|
| SW209188-1 | FC1=CC=C(CC2=COC3=C(C=CC(OCC4=CN(N=C4)C4=CC=CC=CC4)=C3)C2=O)C=C1 | 49.500 | | | 0.086 | |
| SW209189-1 | FC1=C(CC2=COC3=C(C=CC(OCC4=CN(N=C4)C4=CC=CC=CC4)=C3)C2=O)C=CC=C1 | 49.50 | | | 0.080 | |
| SW209190-1 | CC1=CC=C(CC2=COC3=C(C=CC(OCC4=CN(N=C4)C4=CC=CC=CC4)=C3)C2=O)C=C1 | 49.500 | | | 0.092 | |
| SW209191-1 | BrC1=CC=C(CC2=COC3=C(C=CC(OCC4=CN(N=C4)C4=CC=CC=CC4)=C3)C2=O)C=C1 | 49.500 | | | 0.087 | |

TABLE 8-continued

| Compound ID | Structure | H1819 AC50 | H2009 AC50 | H2073 AC50 | H2122 AC50 | HCC44 AC50 |
|---|---|---|---|---|---|---|
| SW209192-1 | FC(F)(F)C1=CC(CC2=COC3=C(C=CC(OCC4=CN(N=C4)C4=CC=CC=C4)C3C2=O)C=CC=C1 | 49.500 | | | 0.028 | |
| SW209193-1 | FC(F)(F)C1=CC(CC2=COC3=C(C=CC(OCC4=CN(N=C4)C4=CC=CC=C4)C3C2=O)C=CC=C1 (O=C1C(CC2=CC=NC=C2)=COC2=C1C=CC(OCC1=CN(N=C1)C1=CC=CC=C1)C2) | 49.500 | | 49.500 | 0.549 | |
| SW209194-1 | FC1=CC=C(C=C1)/C=C2/COC3=C(C=CC(OCC4=CN(N=C4)C4=CC=CC=C4)C3)C2=O | 49.500 | | 49.500 | 0.876 | |

TABLE 8-continued

| Compound ID | Structure | H1819 AC50 | H2009 AC50 | H2073 AC50 | H2122 AC50 | HCC44 AC50 |
|---|---|---|---|---|---|---|
| SW209195-1 | FC(F)(F)C1=C(/C=C2/COC3=C(C=CC=C23)OCC4=CN(N=C4)C4=CC=CC=C1 | 49.500 | | 0.390 | 0.085 | |
| SW209196-1 | FC1=C(/C=C2/COC3=C(C=CC=C23)OCC4=CN(N=C4)C4=CC=CC=C1 | 41.042 | | 49.500 | 0.827 | |
| SW209197-1 | FC(F)(F)C1=CC=CC(/C=C2/COC3=C(C=CC=C23)OCC4=CN(N=C4)C4=CC=CC=C1 | 21.816 | | 25.996 | 0.042 | |

TABLE 8-continued

| Compound ID | Structure | H1819 AC50 | H2009 AC50 | H2073 AC50 | H2122 AC50 | HCC44 AC50 |
|---|---|---|---|---|---|---|
| SW209198-1 | FC(F)(F)C1=CC=C(C=C1)/C=C2/COC3=C(C=CC(OCC4=CN(N=C4)C4=CC=CC=C4)=C3)C2=O)C=C1 | 49.500 | | 49.500 | 1.438 | |
| SW209199-1 | CC1=CC=C(C=C1)/C=C2/COC3=C(C=CC(OCC4=CN(N=C4)C4=CC=CC=C4)=C3)C2=O)C=C1 | 39.513 | | 36.113 | 43.711 | |
| SW209200-1 | CC1=CC=CC=C1/C=C2/COC3=C(C=CC(OCC4=CN(N=C4)C4=CC=CC=C4)=C3)C2=O)C=C1 | 49.500 | | 49.500 | 0.874 | |
| SW209201-1 | BrC1=CC=C(CCC(=O)CN2C=CN=C2)C=C1 | 49.500 | | 49.500 | 49.500 | |

TABLE 8-continued

| Compound ID | Structure | H1819 AC50 | H2009 AC50 | H2073 AC50 | H2122 AC50 | HCC44 AC50 |
|---|---|---|---|---|---|---|
| SW209202-1 | 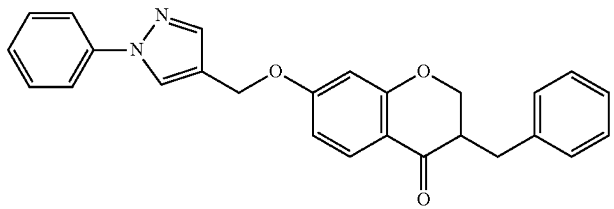 [SMILES: O=C1c2ccc(OCc3cnn(-c4ccccc4)c3)cc2OCC1Cc1ccccc1] | 49.500 | | 49.500 | 0.307 | |
| SW209203-1 | O=C1C(CC2=CC=CC=C2)COC2=C1C=CC(OCC1=CN(N=C1)C1=CC=CC=C1)=C2 | 49.50002 | | | 3.168 | |
| SW209207-1 | O=C1C(CC2=CN=CC=CN=C2)COC2=C1C=CC(OCC1=CN(N=C1)C1=CC=CC=C1)=C2 | 49.50002 | | 44.028 | 26.631 | |
| SW209377-1 | O=C1C(CC2=NC=CN=C2)COC2=C1C=CC(OCC1=CN(N=C1)C1=CC=CC=C1)=C2 | 49.50002 | | 49.500 | 0.232 | |
| | COC1=C(CC2=COC3=C(C=C(OCC4=CN(N=C4)C4=CC=CC=C4)C=C3)C2=O)C=CC=N1 | | | 0.204 | | |

TABLE 8-continued

| Compound ID | Structure | H1819 AC50 | H2009 AC50 | H2073 AC50 | H2122 AC50 | HCC44 AC50 |
|---|---|---|---|---|---|---|
| SW209378-1 | O=C1C(CC2=CC=CS2)COC2=C1C=CC(OCC1=CN(N=C1)C1=CC=CC=C1)=C2 | 49.50002 | | 0.068 | 0.081 | |
| SW209379-1 | O=C1C(CC2=CSC=C2)COC2=C1C=CC(OCC1=CN(N=C1)C1=CC=CC=C1)=C2 | 49.50002 | | 0.087 | 0.082 | |
| SW209380-1 | O=C1C(CC2=NC=CS2)COC2=C1C=CC(OCC1=CN(N=C1)C1=CC=CC=C1)=C2 | 21.16284 | | 17.698 | 0.352 | |
| SW209381-1 | OC1=CC=CC(CC2=COC3=C(C=CC(OCC4=CN(N=C4)C4=CC=CC=C4)=C3)C2=O)=C1 | 49.50002 | | 49.500 | 7.026 | |

TABLE 8-continued

| Compound ID | Structure | H1819 AC50 | H2009 AC50 | H2073 AC50 | H2122 AC50 | HCC44 AC50 |
|---|---|---|---|---|---|---|
| SW209382-1 | ClC1=NC=C(CC2=COC3=C(C=CC(OCC4=CN(N=C4)C4=CC=CC=C4)=C3)C2=O)C=C1 | 49.50002 | | 0.244 | 0.325 | |
| SW209383-1 | NCCCCCOC1=CC=C(CC2=COC3=C(C=CC(OCC4=CN(N=C4)C4=CC=CC=C4)=C3)C2=O)C=C1 | 49.50002 | | 49.500 | 2.371 | |
| SW209384-1 | O=C1C(COC2=C1C=CC(OCC1=CN(N=C1)C1=CC=CC=C1)=C2)=CC1=NC=CN1 | 15.49422 | | 9.677 | 13.953 | |
| SW209385-1 | O=C1C(COC2=C1C=CC(OCC1=CN(N=C1)C1=CC=CC=C1)=C2)=CC1=CNC=N1 | 17.96611 | | 12.219 | 49.500 | |

Target Identification

To identify the target of the benzothiazoles, oxalamides, N-acyl ureas and chromones, we generated a potent oxalamide, SW208108, that features both a "crosslinker" and a "tag". Upon exposure to UV light, the benzophenone group becomes reactive and was anticipated to crosslink to a nearby amino acid, and the alkyne serves as a "tag" by its capacity to react with an azide through "click chemistry". Combining these features, we treated H2122 cells with various concentrations of SW208108 and either cultured them normally ("−UV") or irradiated them briefly with UV light ("+UV"). Subsequently, we "clicked" the resulting lysate to a fluorescent azide, and detected multiple fluorescently labeled proteins on SDS-PAGE (FIG. 7A). Surprisingly, several prominent bands were evident in the −UV samples. Critically, this data demonstrates that these selective toxins covalently modify one or more proteins in the absence of UV irradiation. Using the same assay conditions, we discovered that a chromone alkyne and benzothiazole alkyne both covalently modified proteins of similar molecular weight including 37 kD (p37) and 30 kD (p30) (FIG. 7B).

Figure 7D:
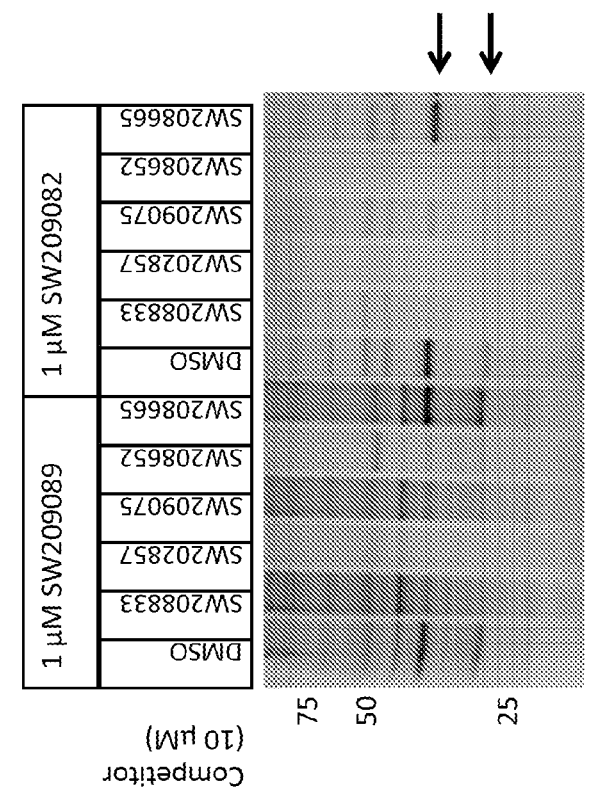
FIG. 7D. Chromone, benzothiazole, and oxalamides covalently modify the same two proteins, p37 and p30. In a similar assay as described in 7C, either a chromone or benzothiazole alkyne was incubated in the presence of excess competitor. Active derivatives of any of the three scaffolds were able to compete the alkynes.
Figure 7C:
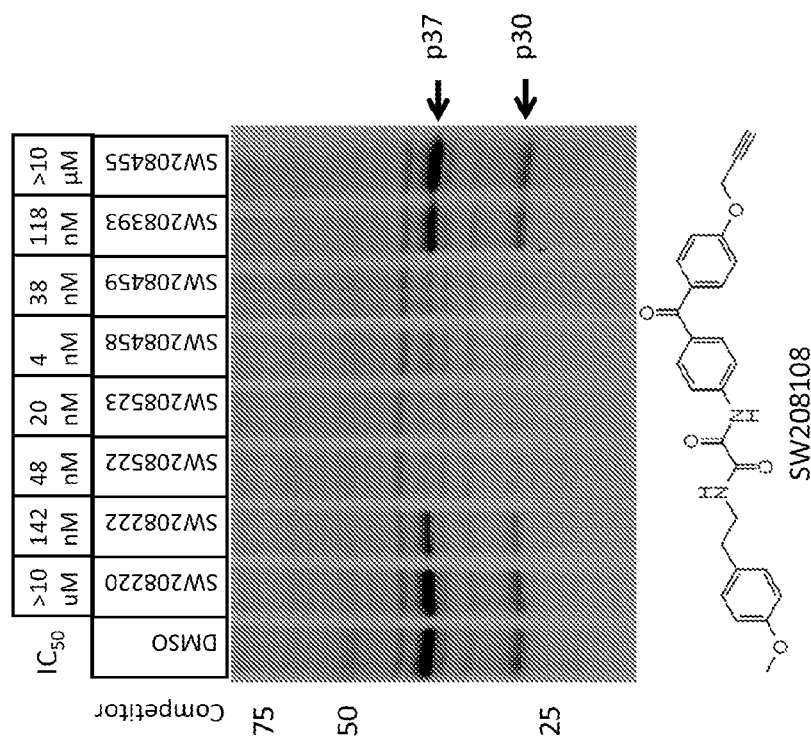
FIG. 7C. The ability of chemicals to covalently bind proteins with apparent molecular weight of 37 (p37) and 30 KDa (p30) correlates with their cytotoxicity. H2122 cells were incubated with 1 µM SW208108 in the absence ('DMSO') or presence of 10 µM of a competitor molecule lacking an alkyne. The toxicity of the competitor molecule is indicated in the figure (IC50 against H2122 cells). Samples were processed, resolved and visualized as described in FIG. 7A. The intensity of the bands associated with p37 and p30 is reduced in the presence of active competitors but largely unaffected by the presence of inactive competitors. The correlation between activity and binding to p37/p30 suggested the biological relevance of these two bands.

To differentiate between non-specific and functional targets, we took advantage of the extensive collection of analogs of the benzothiazoles, oxalamides and chromones that we had prepared and tested and which displayed varying levels of toxicity towards H2122 cells. Thus, SW208108 was incubated with H2122 cells in the presence of an excess of several derivatives featuring a range of IC50 values vs. H2122 cells (FIG. 7C). The resulting cell pellets were then conjugated to an azide-tagged dye using 'click' chemistry (100 µM TBTA (dissolved in 3:1 DMSO, t-butanol), 2 mM CuSO4, 1 mM TCEP, 25 µM Azide). The samples were resolved on a SDS-PAGE gel and visualized with a fluorescent imager. The resulting banding pattern shows that active derivatives of SW208108 can decrease the intensity of two previously noted bands, p37 and p30. In contrast, inactive derivatives of SW208108 had little effect on the intensity of the p30 or p37 bands. The ability of active, but not inactive, derivatives of SW208108 to compete with SW208108 for binding suggests that the p37 and p30 bands are biologically relevant. Moreover, the data indicated that they could be the biological targets of our selective toxins. We note that several weaker bands were not affected by the presence or absence of competitors, and we therefore conclude that these are likely not biologically relevant.

To explore whether the chromone and benzothiazole alkyne also covalently bind to the same 37 kD and 30 kD proteins as the oxalamide, we co-incubated excess non-alkyne containing chromones, benzothiazoles, and oxalamides with either an alkyne-chromone or alkyne-benzothiazole. The intensity of the 37 kD and 30 kD proteins that covalently modify the chromone alkyne, SW209089, and the benzothiazole alkyne, SW209082, decreased in the presence of excess active chromones, benzothiazoles, and oxalamides (FIG. 7D). In contrast, inactive molecules of any scaffold did not affect binding. We concluded that the chromone, benzothiazole, and oxalamide series covalently modify the same two proteins.

Figure 7E:
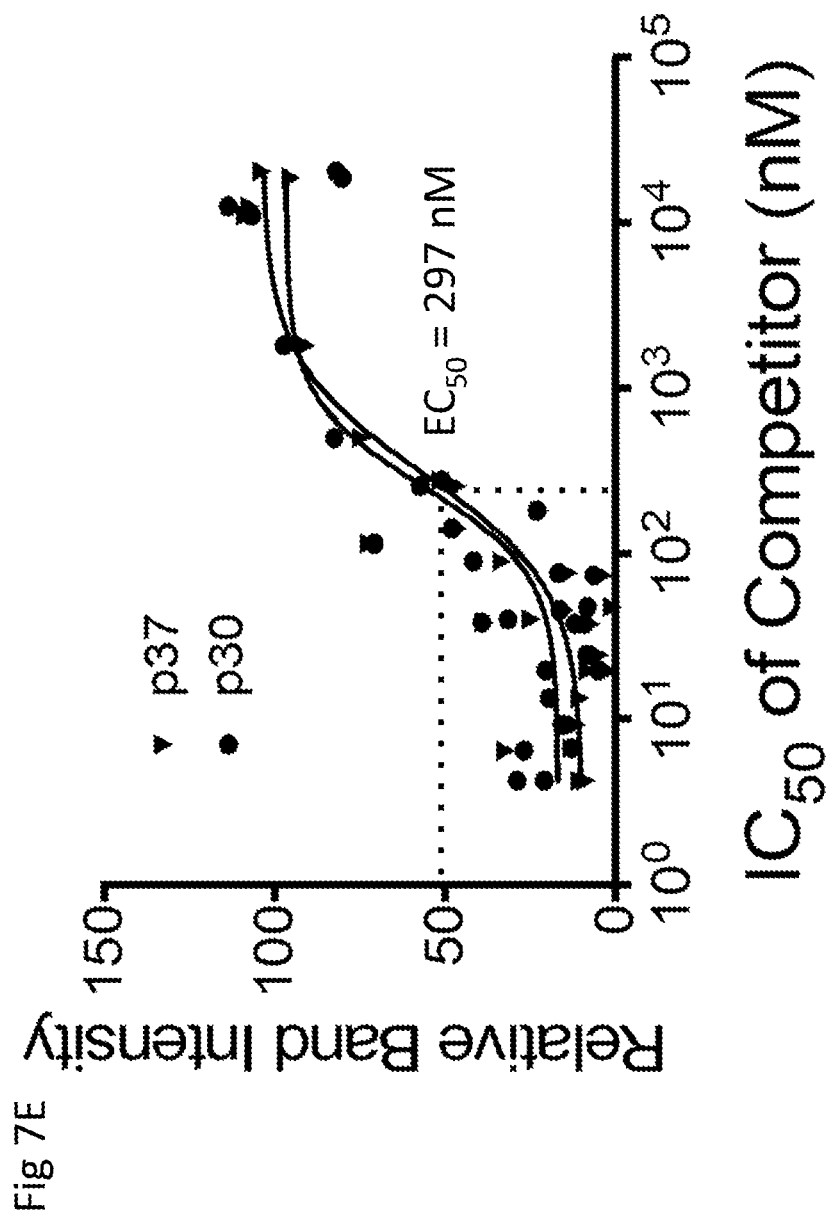
FIG. 7E. Using the experimental design described in FIG. 7B, multiple analogs were evaluated for their ability to compete for binding to p37 and p30 with SW208108. Plotted are intensity of the bands corresponding to p30 and p37 relative to DMSO-treated controls vs. the IC50 of the corresponding competitors. Competitors include representative oxalamides and benzothiazoles. Fitting the data reveals an EC50 of 300 nM, which is 10-fold the IC50 of SW208108. This value is consistent with the fact that the competitors are used in a 10-fold excess in this experiment.
Figure 7F:
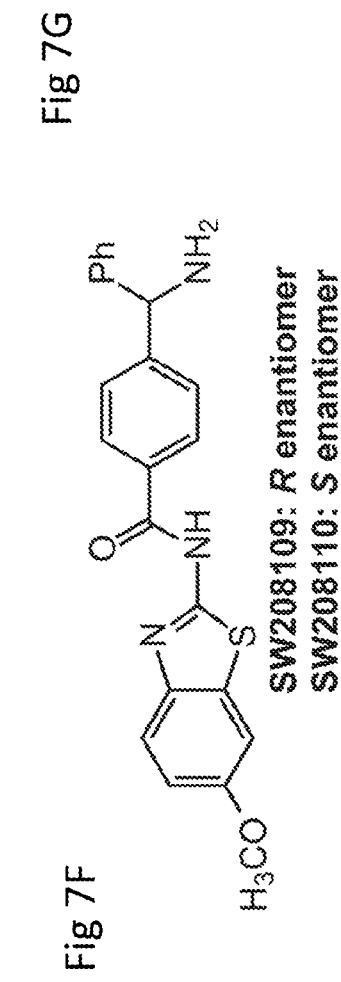
FIGS. 7F-7I. Benzothiazoles covalently bind p30 and p37.
Figure 7G:
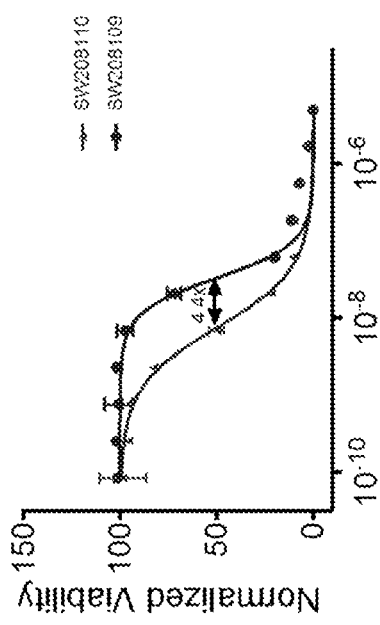
Figure 7H:
Figure 7I:
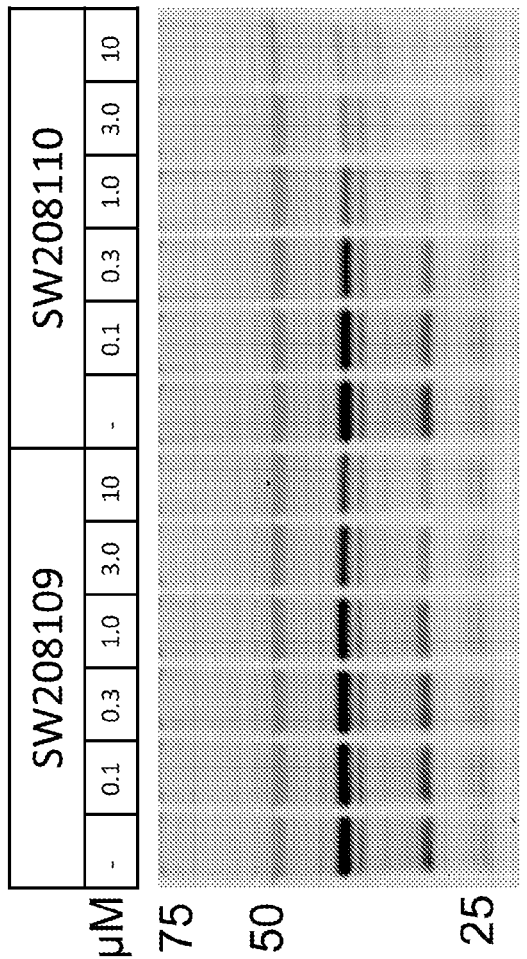

Having shown that active toxins could compete with SW208108 for binding to p37 and p30, we proceeded to test a broader variety of compounds, including benzothiazoles, N-acyl ureas and chromones. These experiments were performed as described above for the initial competition experiments featured in FIG. 7B. In particular, we quantified the intensity of the band formed by SW208108 in the presence of a 10-fold excess of a test compound relative to the band intensity in the presence of SW208108 alone (Table 9). This relative intensity is plotted vs. the IC50 of the competitor in FIG. 7E. The chart provides further evidence that active, but not inactive, compounds can compete with SW208108 for binding to p30 and p37. Of note, the calculated EC50 for competition is approximately 300 nM. This value is consistent with the observation that the IC50 of SW208108 towards H2122 cells is 30 nM, and the competitors were used in a 10-fold excess. In other words, a hypothetical analog that was $\frac{1}{10}^{th}$ as potent as SW208108 would reduce by half the intensity of the p30 and p37 bands when used in a 10-fold excess.

TABLE 9

| Competitor | IC50 to H2122 cells (nM) | Band Intensity Relative to DMSO |
|---|---|---|
| SW206959 | 182 | 22.4% |
| SW202857 | 9.23 | 11.7% |
| SW202864 | 256 | 46.5% |
| SW208652 | 6.44 | 32.4% |
| SW208653 | 38.3 | 38.8% |
| SW208665 | 800 | 107.5% |
| SW001286 | 40 | 24.8% |
| SW208401 | 90 | 33.4% |
| SW205823 | 19.7 | 8.1% |
| SW208458 | 4.25 | 8.8% |
| SW208562 | 73.7 | 3.7% |
| SW208117 | 24.4 | 4.7% |
| SW208456 | 13.4 | 10.5% |
| SW208459 | 37.7 | 9.5% |
| SW208561 | 76.3 | 13.8% |
| SW208110 | 6.66 | 12.8% |
| SW206883 | 500 | 74.7% |
| SW208460 | 45.6 | 15.1% |
| SW208580 | 800 | 108.7% |
| SW208582 | 800 | 90.9% |
| SW208412 | 277 | 51.2% |
| SW208220 | 800 | 95.3% |
| SW208222 | 142 | 46.4% |
| SW208522 | 47.7 | 1.1% |
| SW208523 | 19.7 | 2.1% |
| SW208458 | 4.25 | 10.6% |
| SW208459 | 37.7 | 7.3% |
| SW208393 | 115 | 72.4% |
| SW208455 | 800 | 103.8% |

Further evidence for the relevance of the p30 and p37 bands and for the similarity in mechanism of action among the classes of selective toxins is provided in FIG. 7F-I. Specifically, the panels show the ability of the competition assay to distinguish subtle chemical changes. The two enantiomers of SW203668 are named SW208109 an SW208110. These enantiomers display an approximately 5-fold difference in toxicity towards H2122 cells, with the S enantiomer showing higher activity. Remarkably, the S enantiomer also competes with SW208108 for binding to p30 and p37 approximately 5-fold more effectively than the R enantiomer.

Figure 7K:
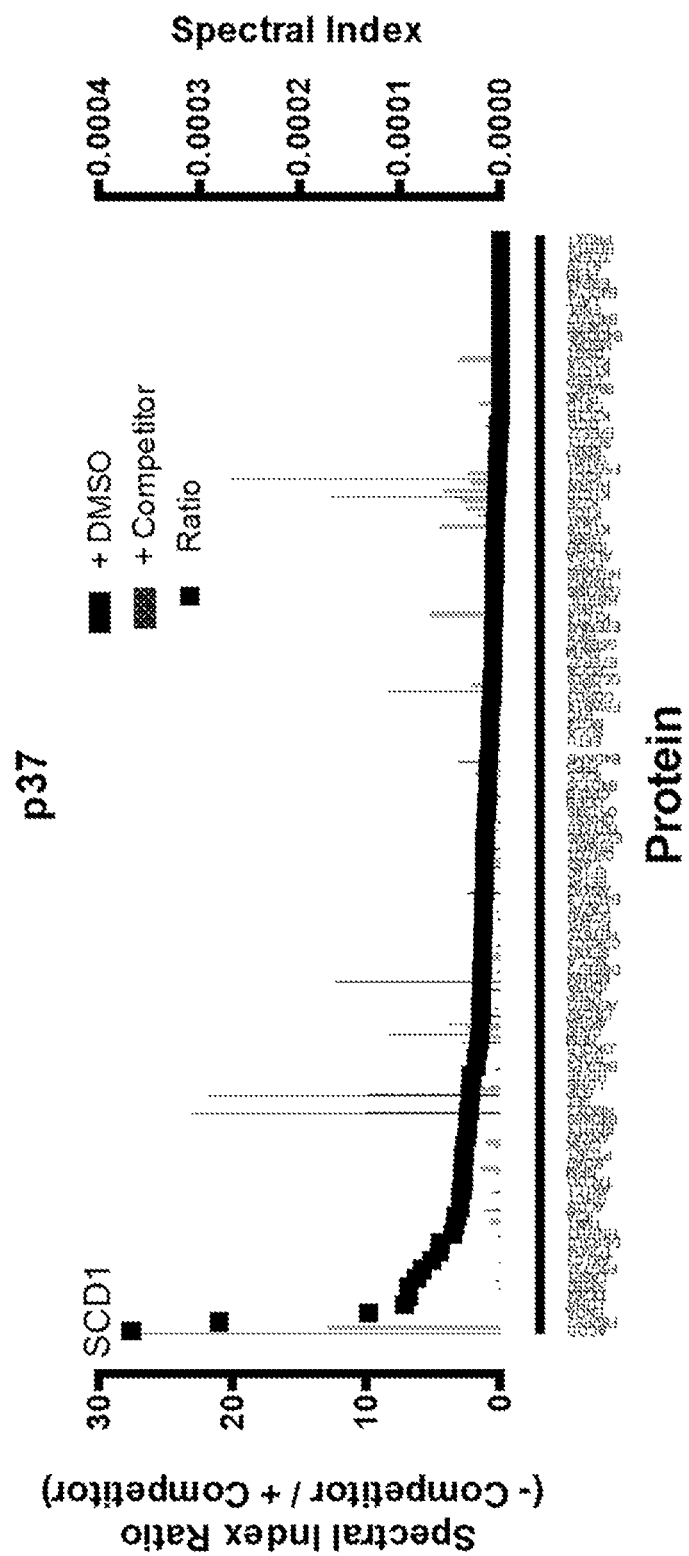
FIG. 7K. The p30 and p37 bands identified in FIG. 7J were excised, digested with trypsin, and analyzed by HPLC/MS/MS. Peptide mass fingerprinting revealed the protein components of p37 and p30. Protein amounts in each sample were quantified based on spectral index. The highest ratio of spectral index between samples treated with DMSO or the competitor (SW208110) revealed SCD1 as a leading candidate for both p37 and p30.

Having compelling evidence of the biological relevance of p30 and p37, we set out to identify the proteins within these spots and the functional target of the benzothiazoles, oxalamides, N-acyl ureas and chromones. To this end, we used click chemistry to conjugate cross-linked samples from H2122 cells to an azide-containing biotin. Critically, as described Yang et al (Chemistry & Biology 17 (2010) 1212-1222) a cleavable linker was used between the azide and biotin moieties. The biotintylated proteins were isolated by exposure to streptavidin-coated beads and washed extensively. The proteins covalently bound to SW208108 were eluted from the streptavidin beads by cleavage of the linker under reducing conditions. Concurrently, an identical sample, save for the inclusion of an excess of an active competitor, was prepared. The protein mixtures were then resolved on an SDS-PAGE gel and proteins were visualized with silver stain (FIG. 7J). Prominent bands were observed at approximately 30 and 37 KDa, and the intensity of these bands markedly decreased in the presence of the active competitor. The bands were excised, and the proteins within were digested with trypsin. The resulting peptides were resolved and identified using tandem HPLC/MS/MS (Table 10). The results in FIG. 7K show that p37 included SCD1 (also known as ACOD) and HO2 as major components;

SCD1 was additionally a major component of p30 (FIG. 7K). The quantitative ratio of SCD1 in the sample without competitor to the sample with competitor was the highest of all identified proteins. Of note, HMOX2 (also known as HO2) had amongst the highest spectral index in both samples. However, the competitor only resulted in a 2.3 fold decrease in HMOX2. Based on this result, HMOX2 binds SW208108 but is less likely to be responsible for cytotoxicity.

TABLE 10

| Protein | − Competitor p37 | + Competitor p37 | Ratio - p37 | − Competitor p30 | + Competitor p30 | Ratio - p30 |
| --- | --- | --- | --- | --- | --- | --- |
| ACOD | 0.000377 | 0.0000137 | 27.6 | 0.000147 | 0.0000116 | 12.7 |
| F8VR82 | 0.0000032 | 0.000000152 | 21 | | | |
| ENOA | 0.000000871 | 8.88E−08 | 9.81 | | | |
| LDHA | 0.0000211 | 0.00000296 | 7.14 | | | |
| TX264 | 0.00000117 | 0.000000172 | 6.82 | | | |
| S35B2 | 0.00000215 | 0.000000315 | 6.81 | | | |
| LASP1 | 0.00000477 | 0.000000764 | 6.24 | | | |
| F5GY37 | 0.00000205 | 0.00000035 | 5.84 | | | |
| AK1C3 | 0.000000922 | 0.00000018 | 5.12 | | | |
| TOM34 | 0.00000189 | 0.000000416 | 4.55 | | | |
| D6R9L0 | 0.00000139 | 0.00000031 | 4.47 | | | |
| HNRH3 | 0.00000355 | 0.00000101 | 3.54 | | | |
| TMX1 | 0.0000014 | 0.000000416 | 3.38 | 0.0000211 | 0.0000356 | 0.592 |
| IF2A | 0.00000464 | 0.00000142 | 3.28 | | | |
| ALDR | 0.0000162 | 0.00000538 | 3 | | | |
| GHC1 | 0.00000391 | 0.00000131 | 2.99 | | | |
| AK1C1 | 0.00000786 | 0.00000274 | 2.87 | | | |
| TALDO | 0.000031 | 0.0000112 | 2.78 | | | |
| NPM | 0.0000149 | 0.00000537 | 2.78 | 0.00000135 | 0.00000101 | 1.35 |
| ROAO | 0.00000106 | 0.000000387 | 2.74 | | | |
| PTGR1 | 0.00000114 | 0.00000042 | 2.71 | | | |
| CASK | 0.0000182 | 0.00000689 | 2.64 | 0.0000273 | 0.0000303 | 0.899 |
| ANXA3 | 0.000000671 | 0.000000267 | 2.51 | | | |
| RDH13 | 0.000000895 | 0.000000364 | 2.46 | | | |
| B4 DK69 | 0.000000761 | 0.00000031 | 2.45 | | | |
| HMOX2 | 0.000307 | 0.000134 | 2.3 | | | |
| SET | 0.00000102 | 0.000000451 | 2.26 | | | |
| G3P | 0.000293 | 0.000132 | 2.23 | 0.00000205 | 0.0000017 | 1.21 |
| LDHB | 0.0000196 | 0.00000895 | 2.19 | | | |
| HDGF | 0.00000385 | 0.00000178 | 2.17 | | | |
| B4DXP5 | 0.00000524 | 0.00000287 | 1.83 | | | |
| ROA2 | 0.000138 | 0.0000756 | 1.83 | 0.000000651 | 0 | |
| J3KQL8 | 0.00000044 | 0.000000267 | 1.65 | | | |
| NPM | 0.0000384 | 0.0000249 | 1.54 | 0.00000122 | 0.000000906 | 1.35 |
| CASB | 0.00011 | 0.0000737 | 1.5 | 0.00011 | 0.0000473 | 2.33 |
| AK1BA | 0.0000752 | 0.0000505 | 1.49 | | | |
| LRC59 | 0.0000162 | 0.0000112 | 1.44 | | | |
| A6NE09 | 0.00000725 | 0.00000503 | 1.44 | | | |
| HYEP | 0.000000733 | 0.000000513 | 1.43 | | | |
| IDH3A | 0.0000249 | 0.0000175 | 1.42 | | | |
| MDHM | 0.000164 | 0.000116 | 1.41 | | | |
| D6RE79 | 0.00000271 | 0.00000198 | 1.37 | | | |
| MCCA | 0.000000456 | 0.000000337 | 1.35 | 0.00000123 | 0.00000153 | 0.802 |
| SFXN1 | 0.00000614 | 0.00000458 | 1.34 | | | |
| C9KOC3 | 0.00000386 | 0.00000289 | 1.34 | | | |
| HOY6Y5 | 0.00000246 | 0.00000185 | 1.33 | | | |
| PCBP1 | 0.000000387 | 0.000000309 | 1.26 | | | |
| SCAM3 | 0.00000298 | 0.00000241 | 1.24 | | | |
| CAZA1 | 0.00000326 | 0.00000264 | 1.24 | | | |
| B4DTC3 | 0.000000695 | 0.000000564 | 1.23 | | | |
| ANXA2 | 0.0000357 | 0.0000302 | 1.18 | 0.000000833 | 0 | |
| EF1A1 | 0.000000436 | 0.000000371 | 1.18 | | | |
| EF1A2 | 0.000000435 | 0.00000037 | 1.18 | | | |
| CAS2 | 0.0000226 | 0.0000193 | 1.17 | 0.0000067 | 0.00000435 | 1.54 |
| C9IZQ1 | 0.00000425 | 0.00000369 | 1.15 | | | |
| F8W617 | 0.0000103 | 0.00000907 | 1.14 | | | |
| E2QRM6 | 0.000000725 | 0.000000638 | 1.14 | | | |
| H0YKF0 | 0.0000101 | 0.00000912 | 1.11 | | | |
| DHRS7 | 0.00000268 | 0.00000253 | 1.06 | | | |
| Q5T946 | 0.00000151 | 0.00000145 | 1.04 | | | |
| ODPB | 0.0000225 | 0.0000224 | 1.01 | | | |
| CP4FB | 0.00000328 | 0.00000337 | 0.975 | 0.000000648 | 0 | |
| B4 DY35 | 0.00000253 | 0.0000026 | 0.972 | | | |
| K2C5 | 0.00000403 | 0.00000424 | 0.951 | 0.00000902 | 0.00000529 | 1.7 |

TABLE 10-continued

| Protein | − Competitor p37 | + Competitor p37 | Ratio - p37 | − Competitor p30 | + Competitor p30 | Ratio - p30 |
|---|---|---|---|---|---|---|
| FPPS | 0.00000138 | 0.00000145 | 0.948 | | | |
| B4DKM5 | 0.0000419 | 0.0000497 | 0.844 | 0.000000929 | 0 | |
| TRYP* | 0.000942* | 0.001140* | 0.8300* | 0.001450* | 0.002730* | 0.531* |
| EFTU | 0.00000154 | 0.00000191 | 0.805 | | | |
| SUCA | 0.00000307 | 0.00000397 | 0.774 | | | |
| MOT4 | 0.00000142 | 0.00000189 | 0.751 | | | |
| PYC | 0.00000151 | 0.00000201 | 0.749 | 0.000000196 | 0.000000248 | 0.793 |
| F8W914 | 0.00000502 | 0.00000722 | 0.695 | 0 | 0.000000284 | 0 |
| GDPD3 | 0.0000046 | 0.00000721 | 0.638 | | | |
| CAS1 | 0.000111 | 0.000179 | 0.62 | 0.0000768 | 0.000038 | 2.02 |
| Q5QPL9 | 0.00000271 | 0.00000465 | 0.582 | | | |
| PCCA | 0.000000374 | 0.000000653 | 0.573 | | | |
| E7ER27 | 0.000000834 | 0.00000147 | 0.566 | | | |
| AATM | 0.000000221 | 0.000000405 | 0.545 | | | |
| G5E9V5 | 0.0000016 | 0.00000307 | 0.522 | | | |
| EIF3I | 0.00000103 | 0.00000202 | 0.51 | | | |
| E7EMM4 | 0.000000602 | 0.00000119 | 0.505 | | | |
| K1C14 | 0.00000176 | 0.00000354 | 0.497 | 0.00000685 | 0.00000135 | 5.08 |
| CH60 | 0.000000575 | 0.00000116 | 0.495 | | | |
| HNRDL | 0.000000964 | 0.000002 | 0.483 | | | |
| G3V3M6 | 9.95E−07 | 0.00000208 | 0.478 | | | |
| LMAN2 | 0.00000125 | 0.00000277 | 0.45 | | | |
| HOYKH6 | 0.00000151 | 0.00000352 | 0.43 | | | |
| PDI P2 | 0.000000514 | 0.0000012 | 0.429 | | | |
| ALDOA | 0.000000281 | 0.000000676 | 0.415 | 0.0000007 | 0.00000181 | 0.388 |
| IDH3B | 0.000000157 | 0.000000383 | 0.41 | | | |
| GBB1 | 0.000000954 | 0.00000237 | 0.402 | | | |
| K1C16 | 0.000000232 | 0.00000062 | 0.375 | 0.00000635 | 0.00000144 | 4.4 |
| JAM1 | 0.00000302 | 0.00000836 | 0.362 | | | |
| K1C9 | 0.000022 | 0.0000785 | 0.28 | 0.000119 | 0.0000506 | 2.35 |
| K22E | 0.0000191 | 0.0000694 | 0.275 | 0.0000498 | 0.0000179 | 2.79 |
| K1C10 | 0.0000461 | 0.000169 | 0.272 | 0.00014 | 0.0000344 | 4.05 |
| HORN | 0.000000355 | 0.0000014 | 0.254 | 0.00000169 | 0.000000843 | 2.01 |
| K2C1 | 0.000053 | 0.000268 | 0.198 | 0.000196 | 0.0000864 | 2.26 |
| F5GYQ1 | 0.000000166 | 0.000000849 | 0.196 | | | |
| GNAI3 | 0.00000029 | 0.00000151 | 0.192 | | | |
| KPRP | 9.06E−08 | 0.000000493 | 0.184 | 0.00000318 | 0 | |
| SCOT1 | 0.000000461 | 0.00000262 | 0.176 | | | |
| E7ESZ7 | 0.000000361 | 0.00000344 | 0.105 | | | |
| DCD | 0.00000166 | 0.0000168 | 0.0988 | 0 | 0.00000489 | 0 |
| K2C1B | 0 | 0.00000527 | 0 | | | |
| CATD | 0 | 0.000000258 | 0 | 0.0000124 | 0.00000874 | 1.42 |
| PLAK | 0 | 0.000000711 | 0 | 0.000000617 | 0 | |
| B9A067 | 0 | 0.000000066 | 0 | | | |
| DESP | 0 | 0.000000186 | 0 | 0.000000304 | 0 | |
| K1C19 | 0 | 0.00000313 | 0 | | | |
| K2C6A | 0 | 0.000000203 | 0 | 0.00000217 | 0.000000727 | 2.99 |
| DSG1 | 0 | 8.15E−08 | 0 | 0.000000511 | 0 | |
| MBOA7 | 0 | 0.000000767 | 0 | | | |
| B4DDM6 | 0 | 0.000000476 | 0 | | | |
| CASPE | 0 | 0.000000841 | 0 | | | |
| B4DV12 | 0 | 0.00000203 | 0 | | | |
| ENPL | 0 | 6.39E−08 | 0 | | | |
| LAT1 | 0 | 0.00000172 | 0 | | | |
| B4DLV4 | 0 | 0.000000472 | 0 | | | |
| ERP44 | 0 | 0.000000696 | 0 | | | |
| PP1B | 0 | 0.000000367 | 0 | | | |
| RT29 | 0 | 0.000000339 | 0 | | | |
| TCEA1 | 0 | 0.000000292 | 0 | | | |
| RDH14 | 0 | 0.000000338 | 0 | | | |
| PRDX1 | 0 | 0.000000467 | 0 | 0.000000746 | 0 | |
| RM44 | 0 | 0.000000507 | 0 | | | |
| DECOY Group 1 Number 43043 | 0 | 0.000000595 | 0 | | | |
| SFXN3 | 0 | 0.00000029 | 0 | | | |

SCD1 is the functional target of the oxalamides, benzothiazoles, chromones, and related derivatives. Covalent binding of SW208108 to SCD1 was confirmed by incubating cells in the presence of SW208108, lysing them, immunoprecipitating with antibodies to SCD1, and then clicking drug-bound proteins to a dye. Shown in FIG. 7L, antibodies to SCD1 uniquely yield bands corresponding to p30 and p37, which are interpreted as isoforms of SCD1.

Figure 7M:
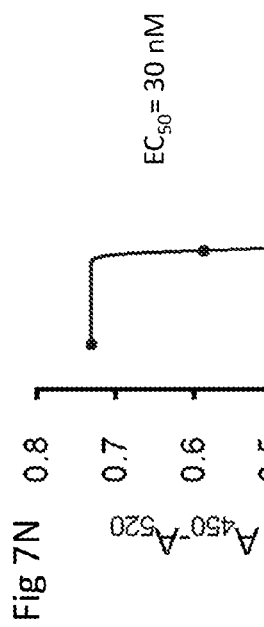
FIG. 7M. HMOX2 binds to SW208108 and is partially competed by an active competitor. Lysates collected from H2122 cells treated with SW208108 with or without competitor were immunoprecipitated with either IgG or anti-HMOX2 and then "clicked" to a dye-azide (as described in FIG. 7A). HMOX2 binds to SW208108 and binding is partially diminished in the presence of a competitor.
Figure 7N:
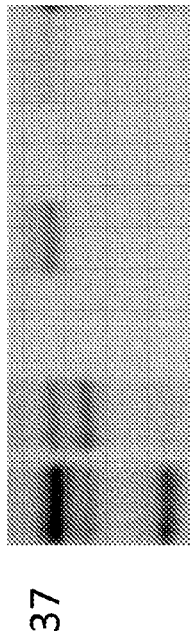
FIG. 7N. Oxalamide inhibits the activity of HMOX2 in vitro. H2122 cell homogenate was incubated with varying concentrations of SW208108 in the presence of excess NADPH, NADPH cytochrome reductase, and biliverdin reductase. The samples were extracted with chloroform and absorbance was measured at 450 nm refecting bilirubin production.
Figure 7O:
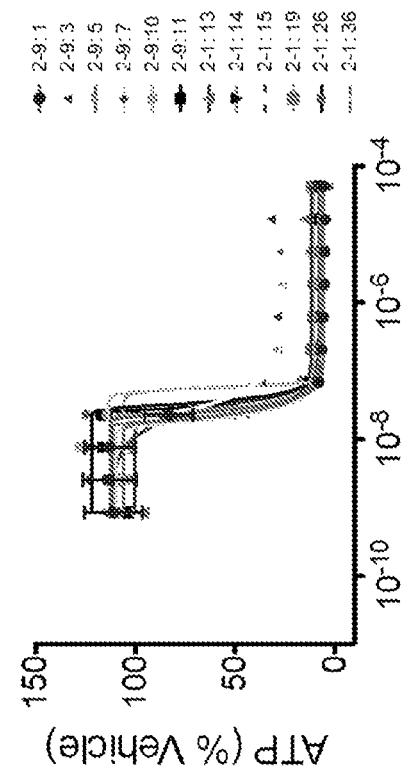
FIG. 7O. H2122 cells were engineered to have homozygous or heterozygous loss of HMOX2. hCas9 and guide RNA's targeting HMOX2 were co-expressed in H2122 cells and then cells were individually cloned. Individual clones were raised and analyzed for HMOX2 expression. Clones either exhibit normal, approximately 50%, or no HMOX2 protein.
Figure 7P:
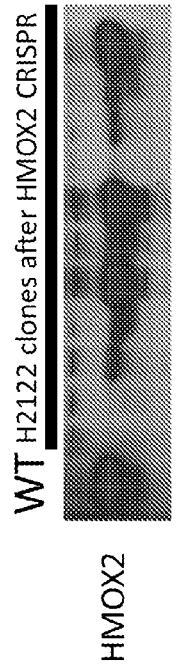
FIG. 7P. HMOX2 loss has no impact on the sensitivity of cells to SW208108. A dose response curve assaying the toxicity of SW208108 to H2122 clones identified in FIG. 7O was determined. There is no correlation between HMOX2 expression and SW208108 potency.

We have confirmed that HO2 is covalently bound by SW208108 (FIG. 7M), and inhibited by active toxins in vitro (FIG. 7N). However, when HO2 was knocked out from H2122 cells using Crisper technology (FIG. 7O), no toxicity was observed, and SW208108 and related compounds retained toxicity towards H2122 cells (FIG. 7P). We conclude that HO2 is not required for cell survival or for the cytotoxicity of the selective toxins.

Figure 8A:
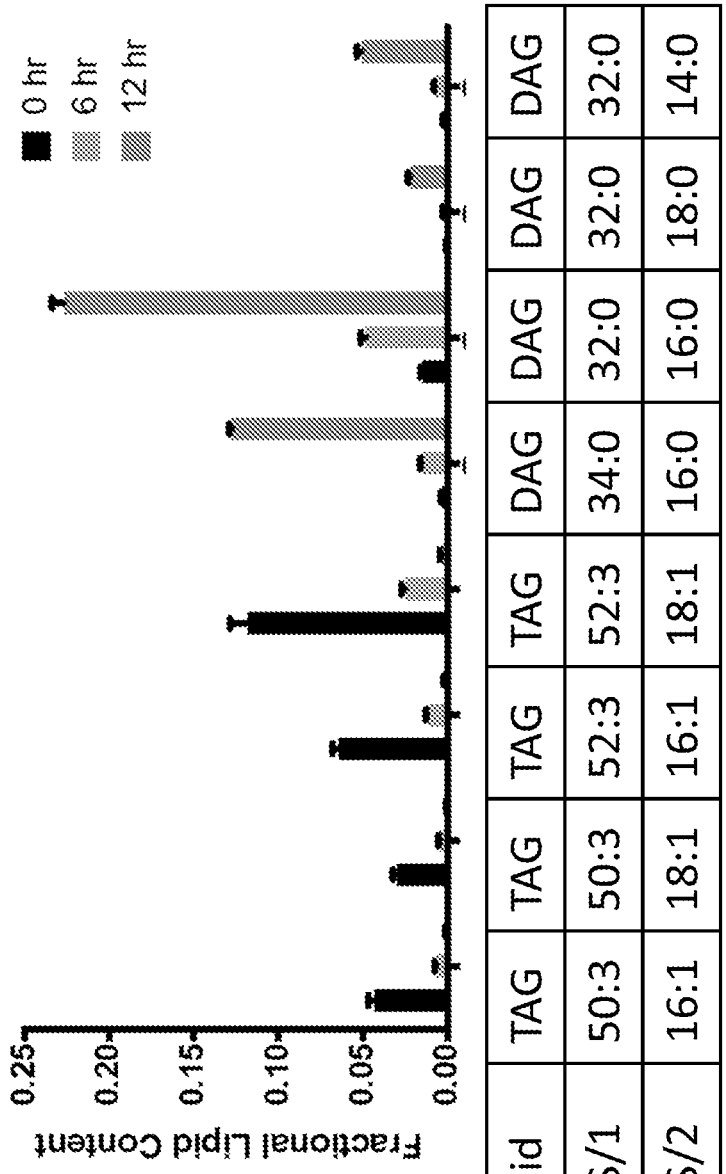
FIG. 8A. Covalent binders of SCD1 affect lipid ratios in human cancer cells. H2122 cells were treated with 100 nM SW208108 for the indicated times before a lipid extraction was performed. Lipid extracts were analyzed by MS/MS in order to determine the fractional content of 8 different lipid species including triacylglycerols (TAG) and diacylglycerols (DAG). In MS/1, the total number of carbons and number of unsaturated bonds was determined for all of the fatty acid chains. For example, TAG (50:3) is a triacylglycerol with 3 fatty acid chains that all together have 50 carbons and 3 unsaturated bonds. The mass for one of these fatty acids was determined in MS/2 and is listed as noted by its carbon length and unsaturated bond number using the same notation. The data show a time-dependent decrease in unsaturated fatty acids and a corresponding increase in saturated fatty acids. The data indicate that covalent binding of SCD1 by SW208108 and other compounds inhibits enzymatic activity.

SCD1 catalyzes the dehydrogenation of saturated fatty acid-CoA's to form unsaturated fatty acid-CoA's. For example, the enzyme gets its name from the conversion of stearic acid-CoA to oleic acid-CoA. For this reason, inhibition SCD1 was expected to alter the ratio of saturated: unsaturated fatty acids. Indeed, as shown in FIG. 8A, SW208108 increased the percentage of neutral lipids containing saturated fatty acids and decreased the percentage of neutral lipids containing unsaturated fatty acids in H2122 cells within as little as 6 hours. The data suggest that SW208108 and other selective toxins described herein inhibit SCD1 and thereby prevent the synthesis of unsaturated fatty acids.

Furthermore, we hypothesized that cells require SCD1 activity and the unsaturated fatty acids SCD1 generates for growth and survival. To test this hypothesis, H2122 cells were depleted of SCD1 using a doxycycline-inducible Crisper system. As shown in FIG. 8B, levels of SCD1 were decreased by upward of 90% in dox-treated cells. Moreover, depletion of SCD1 proved toxic to H2122 cells (FIG. 8C). In particular, doxycycline-induced knockout of SCD1 but not expression of a control guide RNA caused cell death of H2122 cells. Critically, addition of an unsaturated fatty acid, sodium palmitoleic acid, rescued cells from knockout of SCD1. The data are consistent with a model in which certain lung cancer cell lines, such as H2122, require SCD1 for survival, and that the necessary role of SCD1 is the generation of unsaturated fatty acids.

Figure 8D:
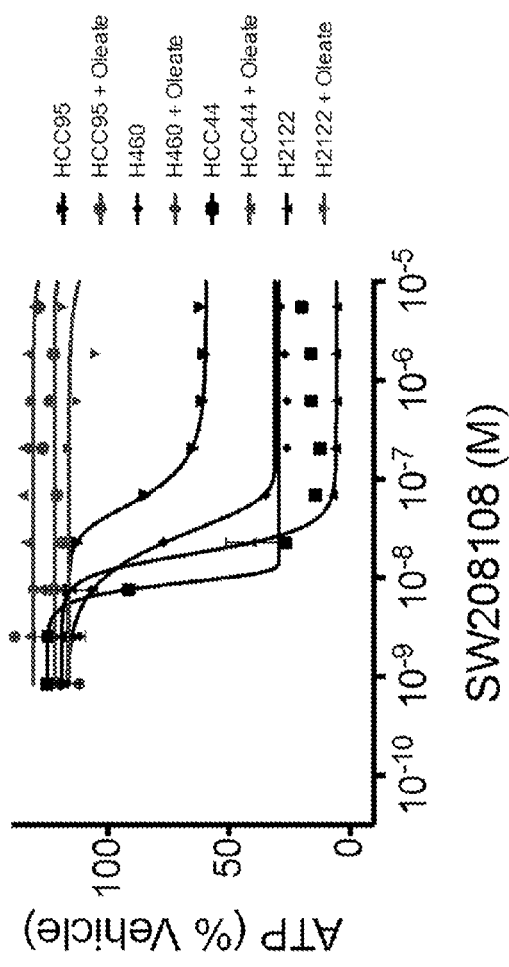
FIGS. 8D-8E. Sodium oleate rescues the toxicity of SCD1 inhibitors.
Figure 8E:
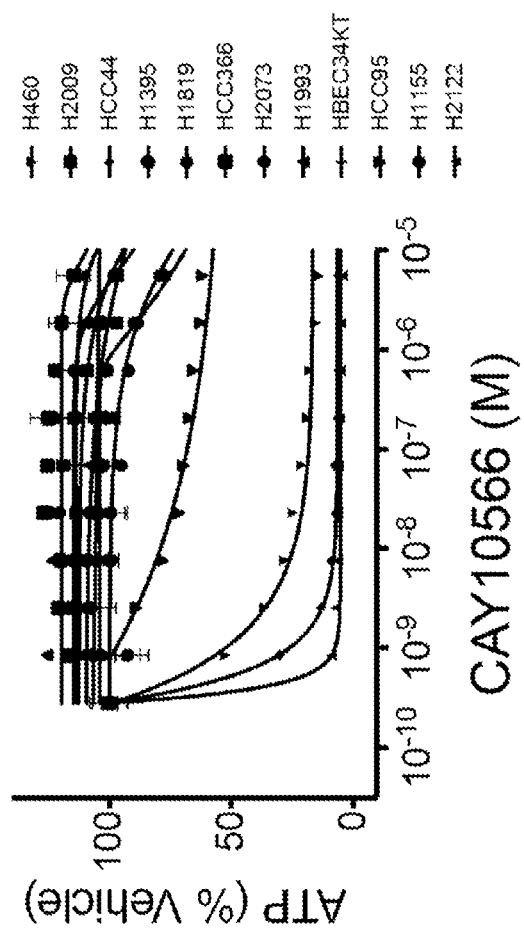

The fact that certain cancer cell lines require the enzymatic activity of SCD1 for survival combined with the observation that the selective toxins described herein block the synthesis of unsaturated fatty acids indicated that these selective toxins exert their effects through inhibition of SCD1 and corresponding depletion of unsaturated fatty acids. Consistent with this interpretation, the toxicity of SW208108 against 4 sensitive cell lines was fully rescued by adding sodium oleic acid to the culture media (FIG. 8D). Moreover, a commercially available SCD1 inhibitor (Cayman chemicals), originally described by Liu et al (compound 28c in the Journal of Medicinal Chemistry, 2007, 50, 3086-3100) was likewise toxic to the same 4 non-small cell lung cancer cell lines (FIG. 8E).

Figure 9C:
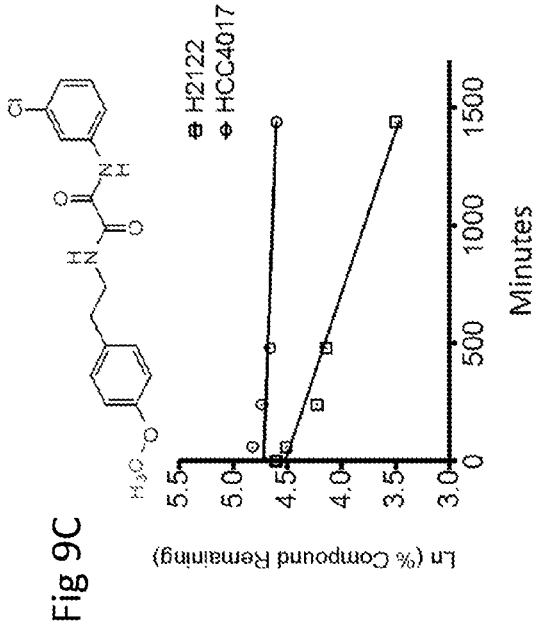
FIGS. 9A-9D. Selective toxins selectively cross-link to SCD1 in sensitive cells and are selectively metabolized in sensitive cells.
Figure 9D:
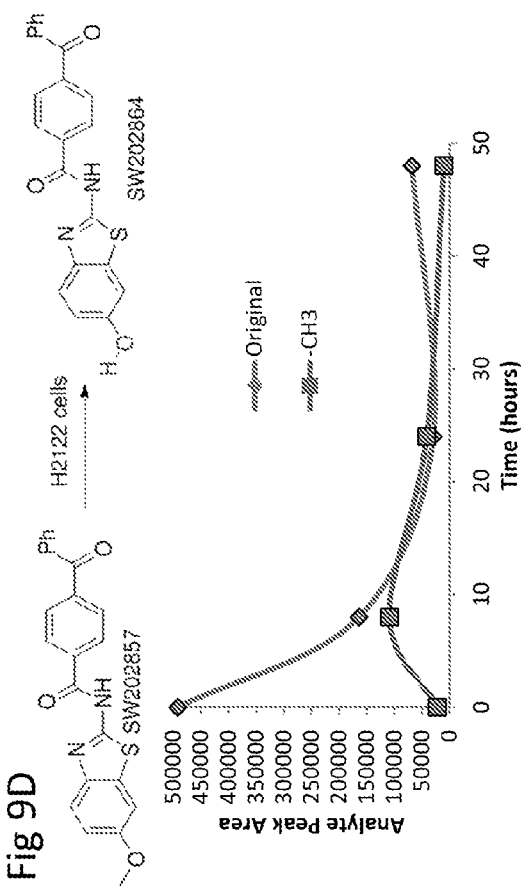
Figure 9A:
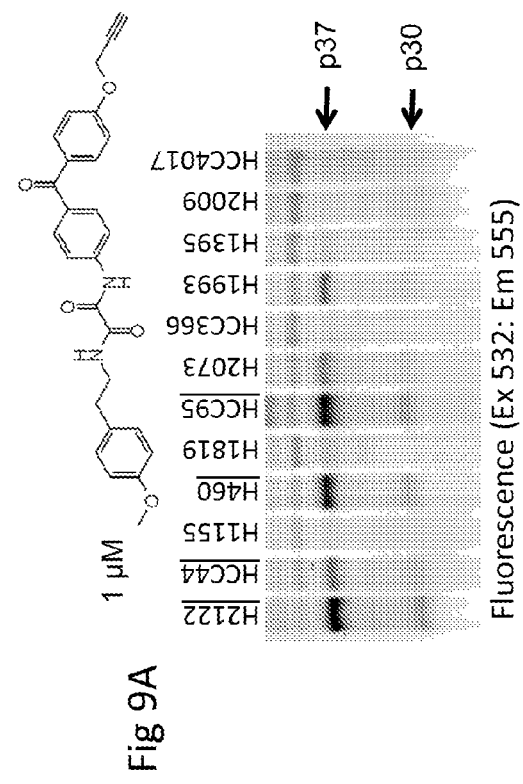
Figure 9B:
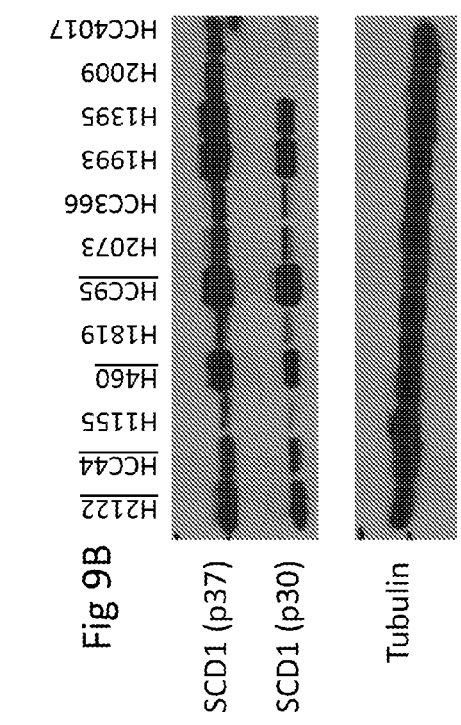

The selective toxicity of these small molecules to a subset of cancer lines suggested that they might be selectively inhibiting SCD1 within the sensitive cell lines. In this context, 12 different NSCLC cell lines were treated with SW208108, lysed and clicked to a dye as previously described. Prominent cross linked bands attributed to SCD1 were observed in all of the sensitive cell lines, but not the majority of insensitive cell lines (FIG. 9A). However, western blots of lysates from the same samples showed that the levels of SCD1 did not solely predict SW208108 binding or SW208108 sensitivity: all of the sensitive lines robustly express SCD1, but several of the insensitive cell lines also express the enzyme at equivalent levels (FIG. 9B). To understand how SW208108 could selectively cross-link to SCD1 within some cell lines that expressed the enzyme but not other cell lines that expressed the same enzyme, we investigated the stability of a representative oxalamide in the presence of a sensitive and insensitive cell line. This experiment was designed to test the hypothesis that insensitive cell lines might selectively metabolize the toxins to an inactive form, for example by hydrolysis of the amide bond. Surprisingly, the experiment revealed the opposite result: SW027950 was completely stable in the presence of an insensitive cell line but was metabolized, likely through oxidative demethylation, by sensitive H2122 cells (FIG. 9C). Similarly, a representative benzothiazole was metabolized by H2122 cells through, at least in part, the loss of the O-methyl group (FIG. 9D). These results suggested that certain selective toxins might represent pro-drugs that required conversion to an active form to exert their toxicity.

Figure 10A:
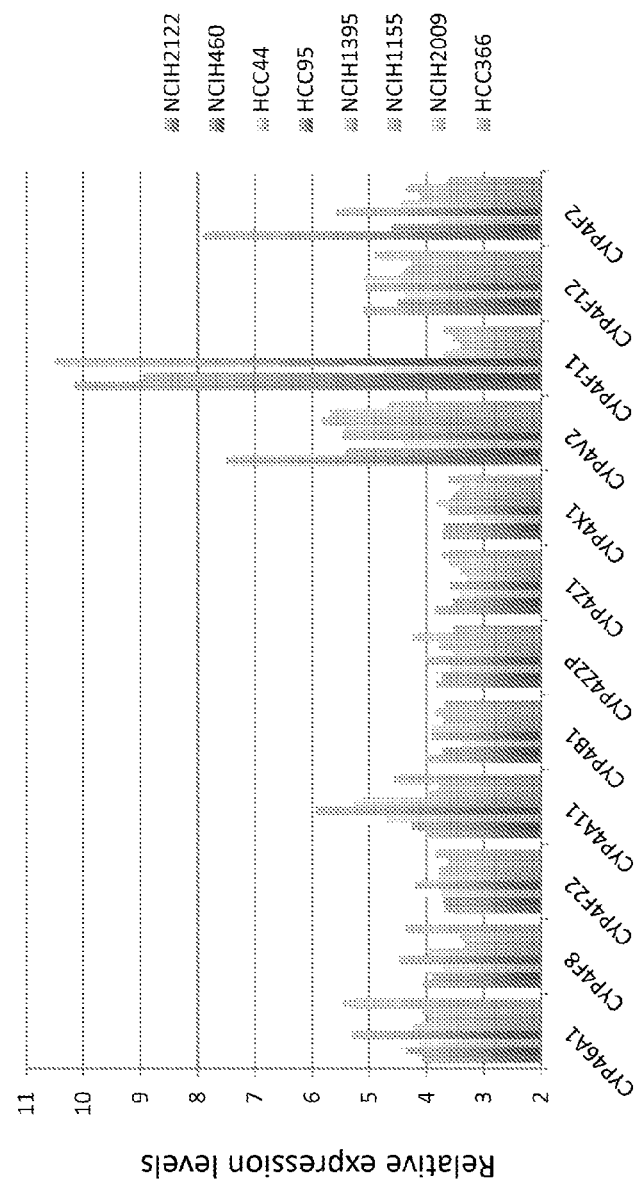
FIGS. 10A-10F. Sensitive cells express high levels of CYP4 family members.
Figure 10B:
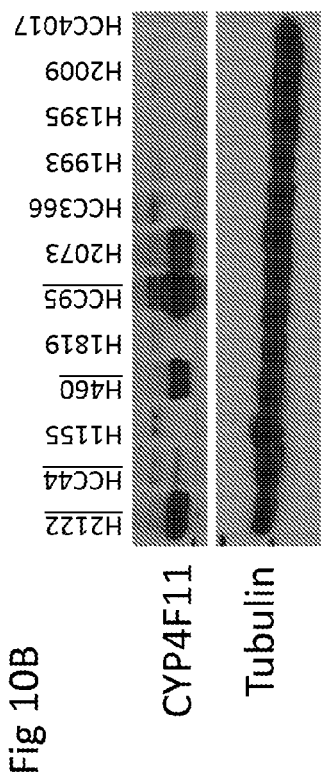

The selective metabolism of certain toxins by sensitive cell lines in general, and the observation of demethylation in specific, pointed to the action of cytochrome P450 enzymes on these compounds. In this connection, we examined the relative expression levels of CYP450 enzymes across a panel of lung cancer cell lines using publically available data sets. As shown in FIG. 10A, several CYP450 isoforms are more highly expressed by sensitive cell lines than by insensitive cell lines. Particularly noteworthy is the high expression of CYP4F11. While these values represent relative mRNA levels, they are also reflected in the relative protein levels (FIG. 10B). Western blotting revealed that all the sensitive and few of the insensitive cell lines express CYP4F11.

Figure 10C:
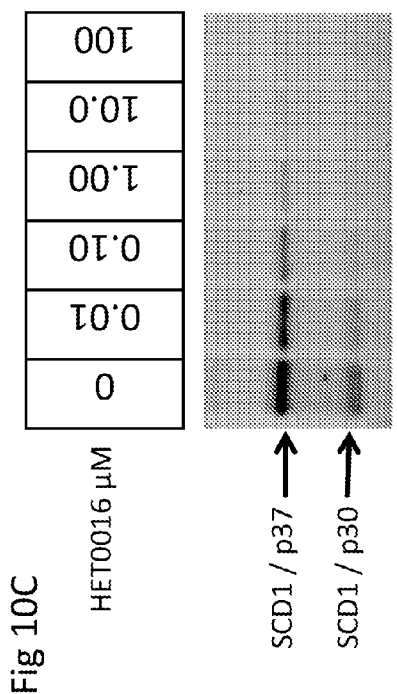
Figure 10D:
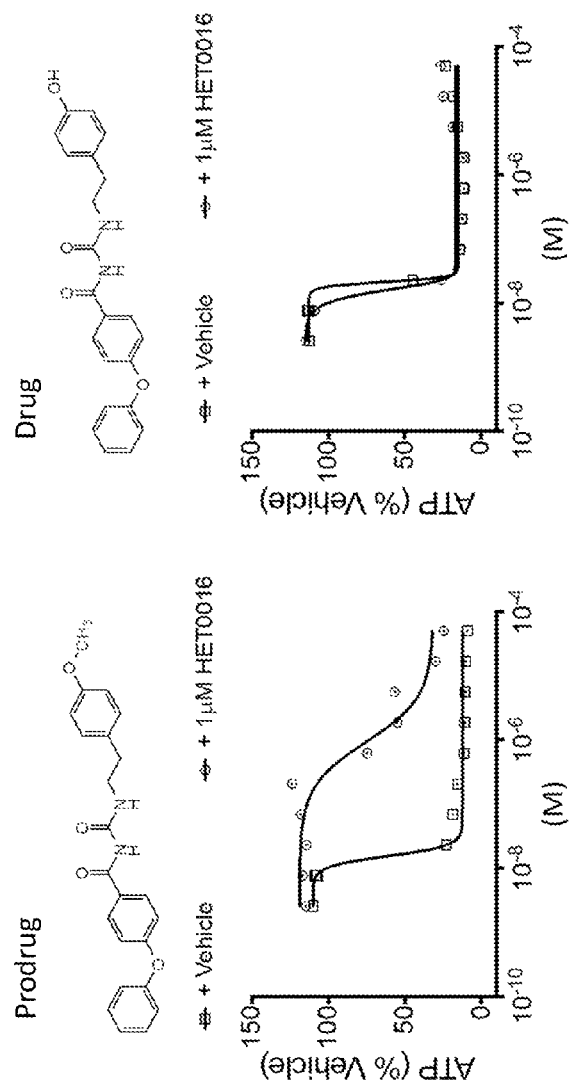

To test the biological relevance of CYP4F11 activity on the ability of the selective toxins to inhibit SCD1, we incubated H2122 cells with SW208108 and various concentrations of a known inhibitor of the CYP450 4F family members, HET0016. Samples were prepared and clicked to a dye as described above. Remarkably, HET0016 blocked covalent binding of SW208108 to both isoforms of SCD1 in a dose responsive manner (FIG. 10C) with an IC50 around 100 nM. Moreover, the CYP450 inhibitor rescued H2122 cells from a representative N-acyl urea, SW208456 (FIG. 10D, left). In a critical experiment, we discovered that the demethylated form of SW208456, also known as SW208523, was toxic to H2122 cells in the presence or absence of the CYP450 inhibitor (FIG. 10D, right). These observations suggest that CYP4F11 demethylates the pro-drug SW208456 to form SW208523 which covalently binds to and inhibits SCD1.

Figure 10F:
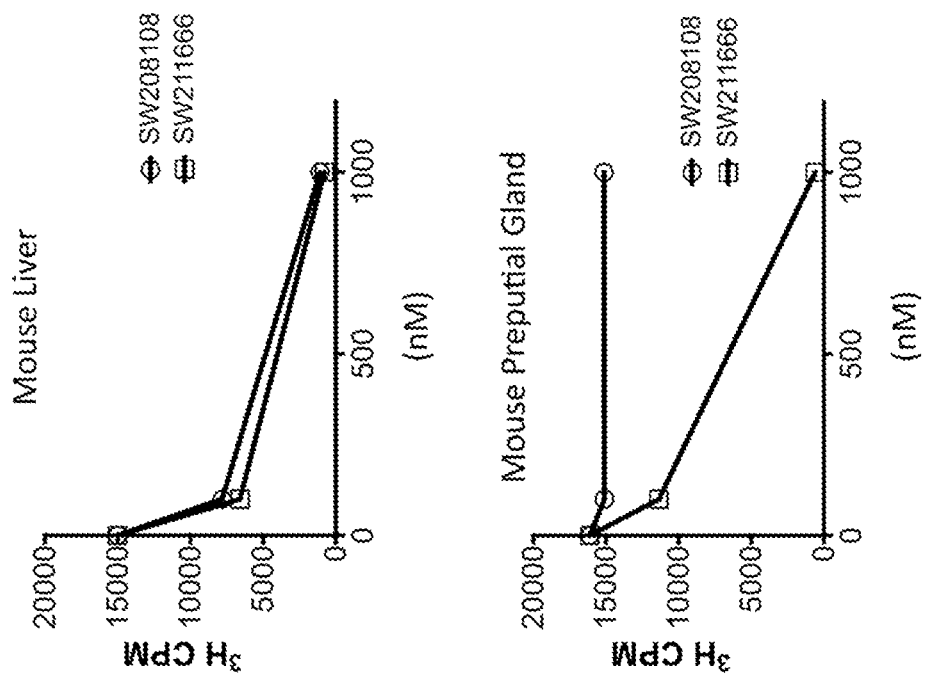
Figure 10E:
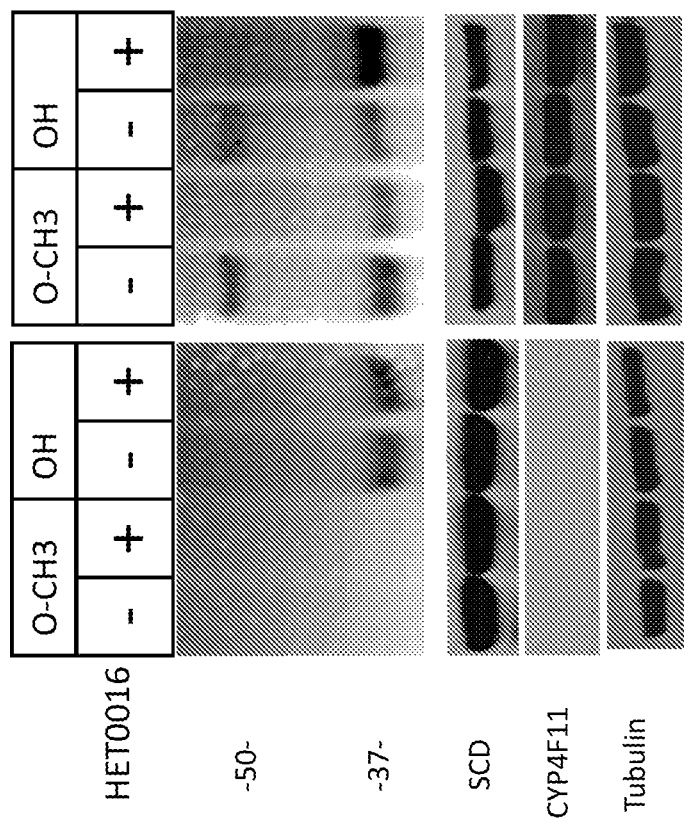
Figure 11:
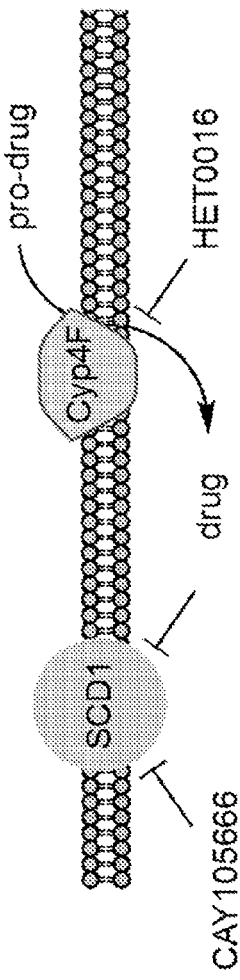
FIG. 11. Model for CYP450-mediated activation of SCD1 inhibitors. Pro-drugs can be metabolized by selectively expressed CYP450 enzymes, for example CYP4F11, by either dealkylation or hydroxylation to yield an active enzyme inhibitor in CYP-expressing cells. The toxicity of these pro-drugs is blocked by HET0016, an inhibitor of CYP4 P450s, and this mode of inhibition differs from known SCD1 inhibitors such as CAY105666 (Cayman chemicals).

To confirm that CYP450 activation of certain selective toxins was required for covalent binding to SCD1, this enzyme was expressed in 293t cells with or without concurrent expression of CYP4F11. In the absence of the required CYP450, the methyl-containing pro-drug, SW208108, was unable to covalently modify SCD1 (FIG. 10E, left). However, the demethylated, drug form, SW211666, did not require the CYP450 for covalent adduct formation. Similarly, expression of both SCD1 and CYP4F11 enabled SW208108 to covalently modify SCD1, an activity that was blocked by the CYP450 inhibitor HET0016 (FIG. 10E, right). Finally, the drug form, SW211666, was able to cross-link to SCD1 in the presence or absence of the CYP450 inhibitor. We additionally note in passing that both the drug and pro-drug forms of the selective toxin covalently bind CYP4F11, and that this activity is inhibited by HET0016. The band at approximately 52 KDa corresponds to the drug-bound form of CYP4F11. Having demonstrated the existence of a prodrug and drug form of the selective toxins, and having shown that conversion from prodrug to drug involved CYP450 enzymes, we sought evidence that the ability to covalently modify SCD1 correlated with the ability to inhibit enzymatic activity. To probe this question, tissues with varying levels of CYP4F11 were tested for SCD1 activity in the presence or absence of representative selective toxins. Thus, tissue derived from mouse liver and preputial gland was independently exposed vehicle, the pro-drug (SW208108) or the drug form (SW211666). The drug form potently inhibited SCD1 in tissue derived from both the liver and the preputial gland (FIG. 10F). By contrast, the pro-drug, SW208108, only inhibited SCD1 activity in the liver, which highly expresses CYP4F11, but not in the preputial gland, which expresses no detectable level of CYP4F11. Taken together, the results described support a model of CYP450-mediated activation of certain SCD1 inhibitors, and that SCD1 inhibition leads to cell death through depletion of unsaturated fatty acids (FIG. 11). This mechanism differentiates the selective toxins described herein from other known SCD1 inhibitors, which inhibit SCD1 independently of CYP450 expression (Zhang et al., J. Med Chem, 2014 (57) 5039). For clarity, we emphasize that CYP450 expression is necessary to activate these inhibitors, but is not necessarily related to a cell's dependence on SCD1. Thus, as shown in FIG. 8E, a known CYP450-independent inhibitor of SCD1 is toxic to the same cell lines as are killed by the oxalamides, benzothiazoles, N-acyl ureas and chromones. Fortuitously, sensitive cell lines additionally express CYP4F11 for reasons that are not presently clear.

Thus, the compounds described herein can be useful in selectively treating, or in making a medicament for selectively treating a cancer, such that the compound is effective in a patient having a first predetermined cancer genotype, and is ineffective against a second predetermined cancer genotype. Such selectivity may be mediated through one or more of SCD1, and/or selected CYP450 enzymes, for example CYP4F11. The cancer that the compound of the present invention can treat is not particularly limited, and examples thereof include lung cancer (small cell and non-small cell), colon cancer, prostate cancer, breast cancer, pancreatic cancer, esophageal cancer, gastric cancer, liver cancer, biliary tract cancer, spleen cancer, renal cancer, bladder cancer, uterine cancer, ovarian cancer, testicular cancer, thyroid cancer, brain cancer, hematological malignancies (lymphoma, leukemia), sarcoma, neuroendocrine derived cancers, germ cell tumors, melanoma, squamous cell cancers (cervical, laryngeal, oropharynx, nasopharyngeal, skin), and gastrointestinal stromal tumors.

Figure 12:
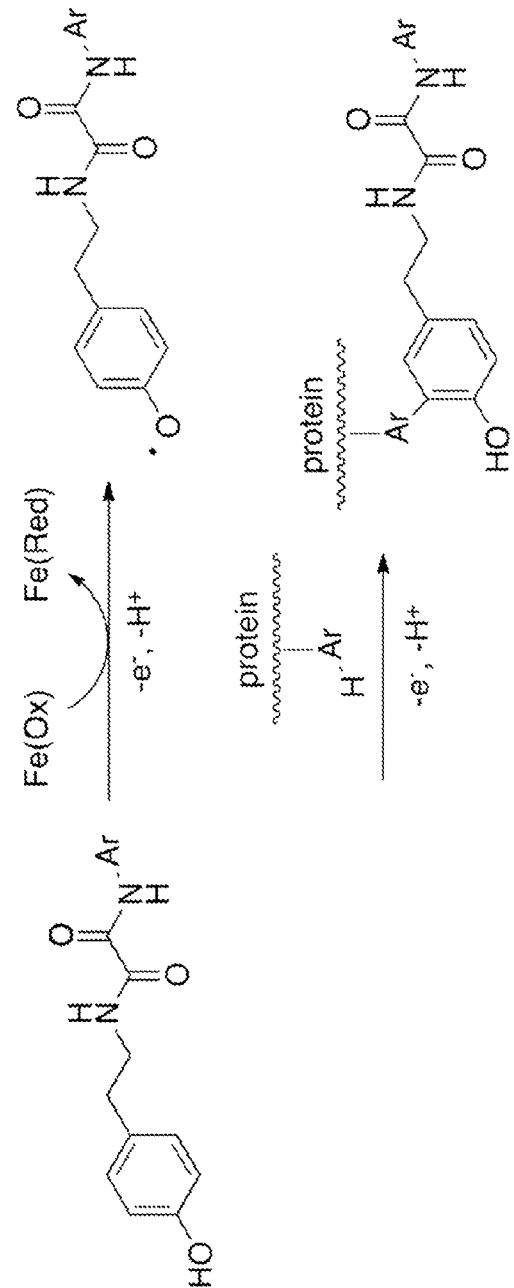
FIG. 12. Mechanism of Fe-mediated covalent adduct formation between hydroxy arenes and proteins. Oxidation of a phenol by Fe-containing enzymes can yield a phenolic radical. Subsequent coupling to an aromatic side chain (tyrosine, tryptophan, phenylalanine, histidine) or a sulfhydryl (cysteine, not shown) gives a covalent adduct between an active compound and the Fe-containing protein. Coupling to the protein could alternatively result in an O-linked adduct: Ar—O-(amino acid) (not shown).

In addition to revealing new classes of SCD1 inhibitors and a new mechanism for selectively targeting cancer cells, the reactivity of certain hydroxyarenes, for example SW211666, represents a new method to covalently modify proteins and inhibit their function. The oxalamides, N-acyl ureas, benzothiazoles, and chromones have been shown to bind three enzymes, SCD1, HO2, CYP4F11. In the two cases that have been tested, SCD1 and HO2, covalent binding leads to inhibition of the enzyme. All three of these enzymes contain iron cofactors, pointing to the role of the catalytic activity of these enzymes for the formation of a covalent adduct. In fact, an inhibitor of CYP4F11, HET0016, blocked the formation of a covalent adduct between CYP4F11 and SW211666 (FIG. 10E). These results can be understood by a model involving Fe-mediated oxidation of hydroxy arenes to yield a phenol radical (FIG. 12). Phenols are well known to undergo single electron oxidation, a fact that undergirds BHT's (butylated hydroxy toluene) and ascorbic acid's use as antioxidants and preservatives. Furthermore, it is known that phenolic radicals can couple with arenes. In the context of a protein active site, an enzyme-generated phenolic radical can be expected to react with aromatic residues including tryptophan, phenylalanine, tyrosine, or histidine. Similarly, the phenolic radical could couple with the —SH moiety of cysteine. Such a coupling reaction would result in a covalent adduct between the small molecule, for example SW211666, and the Fe-containing protein. Inasmuch as the covalent modification is likely to occur near the active site of the enzyme, such a conjugation is expected to inhibit the enzyme. In this way, certain hydroxyarenes are anticipated to act as suicide inhibitors, meaning they leverage the enzymatic activity of their target to generate a reactive species capable of modifying the same enzyme.

Compound Forms and Salts

The compounds described herein may contain one or more asymmetric centers and thus occur as racemates and racemic mixtures, enantiomerically enriched mixtures, single enantiomers, individual diastereomers and diastereomeric mixtures. All such isomeric forms of these compounds are expressly included in the presently disclosed embodiments. The compounds of the presently disclosed embodiments may also contain linkages (e.g., carbon-carbon bonds, carbon-nitrogen bonds such as amide bonds) wherein bond rotation is restricted about that particular linkage, e.g. restriction resulting from the presence of a ring or double bond. Accordingly, all cis/trans and E/Z isomers and rotational isomers are expressly included in the presently disclosed embodiments. The compounds of the presently disclosed embodiments may also be represented in multiple tautomeric forms, in such instances, the presently disclosed embodiments expressly include all tautomeric forms of the compounds described herein, even though only a single tautomeric form may be represented. All such isomeric forms of such compounds are expressly included in the presently disclosed embodiments. Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that the presently disclosed embodiments encompass all possible regioisomers, and mixtures thereof, which can be obtained in pure form by standard separation procedures known to those skilled in the art, and include, but are not limited to, column chromatography, thin-layer chromatography, and high-performance liquid chromatography.

The compounds of the presently disclosed embodiments include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include $C_{1-6}$ alkyl esters of carboxylic acid groups, which, upon administration to a subject, are capable of providing active compounds.

Pharmaceutically acceptable salts of the compounds of the presently disclosed embodiments include those derived from pharmaceutically acceptable inorganic and organic acids and bases. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the presently disclosed embodiments and their pharmaceutically acceptable acid addition salts. Salts derived from appropriate bases include alkali metal (e.g., sodium), alkaline earth metal (e.g., magnesium), ammonium and N-(alkyl)$_4^+$ salts. The presently disclosed embodiments also envision the quaternization of any basic nitrogen-containing groups of the compounds disclosed herein. Water or oil-soluble or dispersible products may be obtained by such quaternization. Salt forms of the compounds of any of the formulae herein can be amino acid salts of carboxyl groups (e.g. L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the presently disclosed embodiments.

In addition to salt forms, the presently disclosed embodiments provide compounds which are in a prodrug form. Prodrugs of the compounds described herein are those compounds that undergo chemical changes under physiological conditions to provide the compounds of the presently disclosed embodiments. Additionally, prodrugs can be converted to the compounds of the presently disclosed embodiments by chemical or biochemical methods in an ex vivo environment. For example, prodrugs can be slowly converted to the compounds of the presently disclosed embodiments when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the presently disclosed embodiments which is administered as an ester (the "prodrug"), but then is metabolically hydrolyzed to the carboxylic acid, the active entity. Additional examples include peptidyl derivatives of a compound of the presently disclosed embodiments.

The presently disclosed embodiments also include various hydrate and solvate forms of the compounds.

The compounds of the presently disclosed embodiments may also contain unnatural proportions of atomic isotopes at one or more of the atoms that constitute such compounds. For example, the compounds may be radiolabeled with radioactive isotopes, for example tritium ($^3$H), iodine-125 ($^{125}$I) or carbon-14 ($^{14}$C). All isotopic variations of the compounds of the presently disclosed embodiments, whether radioactive or not, are intended to be encompassed within the scope of the presently disclosed embodiments.

Pharmaceutical Compositions

The term "pharmaceutically acceptable carrier" refers to a carrier or adjuvant that may be administered to a subject (e.g., a patient), together with a compound of the presently disclosed embodiments, and which does not destroy the pharmacological activity thereof and is nontoxic when administered in doses sufficient to deliver a therapeutic amount of the compound.

Pharmaceutically acceptable carriers, adjuvants and vehicles that may be used in the compositions of the presently disclosed embodiments include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts, or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

The pharmaceutical composition of the present invention can be prepared by blending the compound of the present invention as an active ingredient, a pharmaceutically acceptable carrier and if needed an additive, and formulated into a dosage form. Specific examples of the dosage form include oral preparations such as tablets, coated tablets, pills, powders, granules, capsules, solutions, suspensions and emulsions; and parenteral preparations such as injections, infusions, suppositories, ointments and patches. The blending ratio of the carrier or the additive is appropriately determined based on the range of the blending ratio conventionally adopted in the pharmaceutical field. The carrier or the additive that can be blended is not particularly limited, and examples thereof include water, physiological saline and other aqueous solvents; various carriers such as aqueous bases and oily bases; and various additives such as excipients, binders, pH adjusters, disintegrants, absorption enhancers, lubricants, colorants, corrigents and fragrances.

Examples of the additive that can be blended into tablets, capsules and the like include binders such as gelatin, cornstarch, tragacanth and gum arabic; excipients such as crystalline cellulose; bulking agents such as cornstarch, gelatin and alginic acid; lubricants such as magnesium stearate; sweeteners such as sucrose, lactose and saccharin; and flavors such as peppermint, Gaultheria adenothrix oil and cherry. In the case where the unit dosage form is a capsule, a liquid carrier such as fats and oils can be further blended in addition to the above-mentioned materials. A sterile composition for injection can be prepared according to an ordinary pharmaceutical formulation practice, for example, by dissolving or suspending an active substance in a vehicle such as water for injection and a natural vegetable oil (such as sesame oil and coconut oil). As an aqueous liquid for injection, for example, physiological saline, an isotonic solution containing glucose and an auxiliary substance (for example, D-sorbitol, D-mannitol, sodium chloride, etc.), or the like can be used, optionally together with a suitable solubilizer such as alcohols (for example, ethanol), polyalcohols (for example, propylene glycol, polyethylene glycol) and nonionic surfactants (for example, polysorbate 80™, HCO-50). As an oily liquid, for example, sesame oil, soybean oil or the like can be used, optionally together with a solubilizer such as benzyl benzoate and benzyl alcohol. Further, a buffering agent (for example, a phosphate buffer, a sodium acetate buffer), a soothing agent (for example, benzalkonium chloride, procaine hydrochloride, etc.), a stabilizer (for example, human serum albumin, polyethylene glycol, etc.), a preservative (for example, benzyl alcohol, phenol, etc.), an antioxidant etc. may also be blended.

The pharmaceutical preparation that can be obtained in the above manner is safe and less toxic, and therefore can be administered to, for example, humans and other mammals (rats, mice, rabbits, sheep, pigs, cows, cats, dogs, monkeys, etc.).

Administration

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or administration by injection. The methods herein contemplate administration of an effective amount of compound or compound composition to achieve the desired or stated effect. Typically, the pharmaceutical compositions of the presently disclosed embodiments will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of the presently disclosed embodiments may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The dose may vary depending on patient's state, the cancer type, the condition, the administration method and the like, but in general, the daily oral dose for a human weighing about 60 kg is, for example, about 0.1 to 1000 mg, preferably about 1.0 to 500 mg, and more preferably about 3.0 to 200 mg in terms of the active ingredient. As for the parenteral dose, the amount for one dose may vary depending on patient's state, the cancer type, the condition, the administration method and the like, but for example in the case of injections, it is usually advantageous that the active ingredient is intravenously administered in an amount of, for example, about 0.01 to 100 mg, preferably about 0.01 to 50 mg, and more preferably about 0.01 to 20 mg per kg body weight. The daily total dose may be a single dose or divided into several portions.

In some embodiments, the compounds described herein can be coadministered with one or more other therapeutic agents. In certain embodiments, the additional agents may be administered separately, as part of a multiple dose regimen, from the compounds of the presently disclosed embodiments (e.g., sequentially, e.g., on different overlapping schedules with the administration of one or more compounds of formula (I) (including any subgenera or specific compounds thereof)). In other embodiments, these agents may be part of a single dosage form, mixed together with the compounds of the presently disclosed embodiments in a single composition. In still another embodiment, these agents can be given as a separate dose that is administered at about the same time that one or more compounds of formula (I) (including any subgenera or specific compounds thereof) are administered (e.g., simultaneously with the administration of one or more compounds of formula (I) (including any subgenera or specific compounds thereof)). When the compositions of the presently disclosed embodiments include a combination of a compound of the formulae described herein and one or more additional therapeutic or prophylactic agents, both the compound and the additional agent can be present at dosage levels of between about 1 to 100%, and more preferably between about 5 to 95% of the dosage normally administered in a monotherapy regimen.

According to the present invention, the medicament for cancer treatment can be used in combination with another cancer therapeutic drug. Such another cancer therapeutic drug is not particularly limited, but preferred is a chemotherapeutic drug, an immunotherapeutic drug or a hormone therapy drug, for example. According to the present invention, the medicament for cancer treatment can also be used in combination with radiotherapy.

The chemotherapeutic drug is not particularly limited and examples thereof include:
alkylating agents such as nitrogen mustard, nitrogen mustard N-oxide hydrochloride, chlorambucil, cyclophosphamide, ifosfamide, thiotepa, carboquone, improsulfan tosilate, busulfan, nimustine hydrochloride, mitobronitol, melphalan, dacarbazine, ranimustine, estramustine phosphate sodium, triethylenemelamine, carmustine, lomustine, streptozocin, pipobroman, ethoglucid, carboplatin, cisplatin, miboplatin, nedaplatin, oxaliplatin, altretamine, ambamustine, dibrospidium chloride, fotemustine, prednimustine, pumitepa, Ribomustin, temozolomide, treosulfan, trofosfamide, zinostatin stimalamer, adozelesin, cystemustine and bizelesin; antimetabolites such as mercaptopurine, 6-mercaptopurine riboside, thioinosine, methotrexate, pemetrexed, enocitabine, cytarabine, cytarabine ocfosfate, ancitabine hydrochloride, 5-FU and its derivatives (for example, fluorouracil, tegafur, UFT, doxifluridine, carmofur, galocitabine, emitefur, capecitabine, etc.), aminopterin, nelzarabine, leucovorin calcium, Tabloid, butocin, calcium folinate, calcium levofolinate, cladribine, emitefur, fludarabine, gemcitabine, hydroxycarbamide, pentostatin, piritrexim, idoxuridine, mitoguazone, tiazofurin, ambamustine and bendamustine; anticancer antibiotics such as actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride and idarubicin hydrochloride; and plant-derived anticancer drugs such as etoposide, etoposide phosphate, vinblastine sulfate, vincristine sulfate, vindesine sulfate, teniposide, paclitaxel, docetaxel and vinorelbine.

The immunotherapeutic drug is not particularly limited and examples thereof include picibanil, Krestin, sizofuran, lentinan, ubenimex, interferons, interleukins, macrophage colony-stimulating factor, granulocyte colony-stimulating factor, erythropoietin, lymphotoxins, BCG vaccine, *Corynebacterium parvum*, levamisole, polysaccharide K, procodazole and anti-CTLA4 antibody. The hormone therapy drug is not particularly limited and examples thereof include fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, antiestrogens (for example, tamoxifen citrate, toremifene citrate, etc.), birth-control pills, mepitiostane, testololactone, aminoglutethimide, LH-RH agonists (for example, goserelin acetate, buserelin, leuprorelin, etc.), droloxifene, epitiostanol, ethinylestradiol sulfonate, aromatase inhibitors (for example, fadrozole hydrochloride, anastrozole, letrozole, exemestane, vorozole, formestane, etc.), antiandrogens (for example, flutamide, bicalutamide, nilutamide, etc.), 5.alpha.-reductase inhibitors (for example, finasteride, epristeride, etc.), corticosteroids (for example, dexamethasone, prednisolone, betamethasone, triamcinolone, etc.) and androgen synthesis inhibitors (for example, abiraterone, etc.). The combined use of the medicament for cancer treatment, with another cancer therapeutic drug or radiotherapy, can provide the following effects without any limitation: (1) synergistic effect is obtainable; (2) the dose is reducible; (3) prolonged treatment period is selectable; and (4) persistent therapeutic effect can be expected.

In the case where the medicament for cancer treatment and another cancer therapeutic drug are used in combination, they may be simultaneously administered to a subject, or separately administered thereto at some interval. The dose of the drug in combined use can be determined based on its clinical dose and is appropriately selected depending on the subject, the age and body weight of the subject, the condition, the administration time, the dosage form, the administration method, the combination of drugs, etc.

The compositions of the presently disclosed embodiments may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions may be in the form of a sterile injectable preparation, for example, as a sterile injectable aqueous or oleaginous suspension. This suspension may be formulated according to techniques known in the art using suitable dispersing or wetting agents (for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The compositions of the presently disclosed embodiments may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The compositions of the presently disclosed embodiments may also be administered in the form of suppositories for rectal administration. These compositions can be prepared by mixing a compound of the presently disclosed embodiments with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the compositions of the presently disclosed embodiments is useful when the desired treatment involves areas or organs readily accessible by topical application. For application topically to the skin, the composition should be formulated with a suitable ointment containing the active components suspended or dissolved in a carrier. Carriers for topical administration of the compounds of the presently disclosed embodiments include, but are not limited to, mineral oil, liquid petroleum, white petroleum, propylene glycol, polyoxyethylene polyoxypropylene compound, emulsifying wax and water. Alternatively, the composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The compositions of the presently disclosed embodiments may also be topically applied to the lower intestinal tract by rectal suppository formulation or in a suitable enema formulation.

In some embodiments, topical administration of the compounds and compositions described herein may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Remington's Pharmaceutical Sciences, 21st Edition (2005) published by Mack Publishing Company, which is incorporated herein by reference in its entirety.

Topically-transdermal patches are also included in the presently disclosed embodiments. Also within the presently disclosed embodiments is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing) on the adhesive or device.

The compositions of the presently disclosed embodiments may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formulae herein and an additional agent (e.g., a therapeutic agent) can be administered using any of the routes of administration described herein. In some embodiments, a composition having the compound of the formulae herein and an additional agent (e.g., a therapeutic agent) can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in the presently disclosed embodiments. For example, timed-release formulations based on polymer technologies, sustained-release techniques and encapsulation techniques (e.g., polymeric, liposomal) can also be used for delivery of the compounds and compositions delineated herein.

Compound Synthesis

General Procedure A: Coupling of Heterocyclic Amines and Carboxylic and Sulfonic Acid Chlorides To a reaction vial equipped with a stir bar and Teflon-lined lid were added heterocyclic amine (0.33 mmol), pyridine (0.7 ml), and the acid chloride (0.5 mmol). The vial was flushed with nitrogen, sealed, and heated to 60° C. for 16 h. After cooling to room temperature, the mixture was diluted with water, whereupon a precipitate formed. The precipitate was filtered and washed with water, and dried via aspiration and then vacuum. The products thus obtained were usually >95% by LC/MS, but could be re-crystallized from absolute ethanol if necessary.

General Procedure B: Coupling of Acids and of Heterocyclic Amines with TBTU

To a reaction vial equipped with a stir bar and Teflon-lined lid was added heterocyclic amine (0.28 mmol), acid reactant (0.30 mmol), O-(Benzotriazol-1-yl)-N,N,N',N'-tetramethyluronium tetrafluoroborate (TBTU, 0.6 mmol), 4-(Dimethylamino)pyridine (DMAP, 10 mol %), triethylamine (0.9 mmol), and N,N-dimethylformamide (0.3 ml). The vial was flushed with nitrogen, sealed, and heated to 60° C. for 16 h. After cooling to room temperature, the mixture was diluted with water and the product isolated by filtration.

General Procedure C: Coupling of Heterocyclic Amines and Acids with Propylphosphonic Anhydride (T3P)

To a reaction vial equipped with a stir bar and Teflon-lined lid was added acid (1 equiv), heterocyclic amine (3 equiv), triethylamine (3 equiv), and propylphosphonic anhydride solution (50% w/w in ethyl acetate). The vial was sealed and heated to 50° C. for 16 h. After cooling to room temperature, the mixtures were diluted with water. The product could either be extracted into ethyl acetate or filtered depending on whether precipitation occurred. If extraction is used, the organic layers are dried (sodium sulfate), filtered, and concentrated by vacuum to yield the products, which were purified by re-crystallization from ethanol, or silica gel chromatography, if necessary.

General Procedure D: Coupling of Acids and of Heterocyclic Amines with HATU

To a reaction vial equipped with a stir bar and Teflon-lined lid was added heterocyclic amine (1 equiv), acid reactant (1.1 equiv), 1-[Bis(dimethylamino)methylene]-1H-1,2,3-triazolo[4,5-b]pyridinium 3-oxid hexafluorophosphate (HATU, 1.1 equiv), N,N-diisopropylethylamine (2 equiv), and N,N-dimethylformamide ([1.4M] in limiting reactant). The vial was flushed with nitrogen, sealed, and stirred at room temperature for 2-16 h. The mixture was diluted with water and the product isolated by filtration or extraction with an organic solvent.

EXAMPLES

The present invention will now be illustrated by reference to the following examples which set forth particularly embodiments. However, it should be noted that these embodiments are illustrative and are not to be construed as restricting the invention in any way.

Example 1:
N-(benzo[d]thiazol-2-yl)-3-methylbenzamide

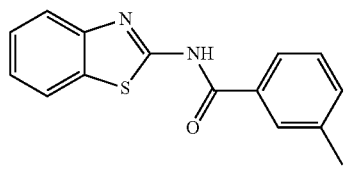 [SMILES: Cc1cccc(C(=O)Nc2nc3ccccc3s2)c1]

The title compound was synthesized according to General Procedure A and isolated as a solid (81 mg, quant.): $^1$H NMR (400 MHz, DMSO-d$_6$) 12.81 (s, 1H), 8.04-7.87 (m, 3H), 7.77 (d, J=8.0 Hz, 1H), 7.49-7.39 (m, 3H), 7.32 (m, 1H), 2.39 (s, 3H); LCMS (ESI) m/z 269.2 [M+1]$^+$.

Example 2: 3-methoxy-N-(6-methoxybenzo[d]thiazol-2-yl)benzamide

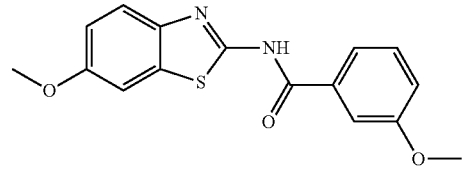

The title compound was synthesized according to General Procedure A and isolated as a solid (39 mg, 44%): $^1$H NMR (400 MHz, DMSO-d$_6$) 12.75 (s, 1H), 7.73-7.58 (m, 4H), 7.46 (t, J=8.1 Hz, 1H), 7.24-7.16 (m, 1H), 7.05 (dd, J=8.8, 2.6 Hz, 1H), 3.84 (s, 3H), 3.81 (s, 3H); LCMS (ESI) m/z 312.8 [M−1]$^-$.

Example 3: N-(6-methoxybenzo[d]thiazol-2-yl)-3-phenylpropanamide

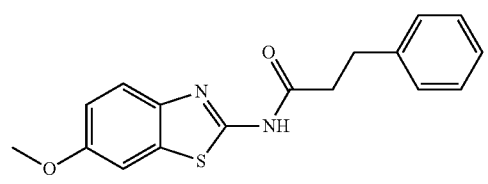 [SMILES: COc1ccc2nc(NC(=O)CCc3ccccc3)sc2c1]

The title compound was synthesized according to General Procedure A and isolated as a solid (21 mg, 24%): $^1$H NMR (400 MHz, DMSO-d6) δ 12.21 (s, 1H), 7.63-7.51 (m, 2H), 7.32-7.12 (m, 5H), 7.00 (dd, J=8.8, 2.6 Hz, 1H), 3.78 (s, 3H), 2.92 (t, J=7.7 Hz, 2H), 2.77 (dd, J=8.6, 6.9 Hz, 2H); LCMS (ESI) m/z 310.8 [M−1]$^-$.

Example 4:
N-(6-methoxybenzo[d]thiazol-2-yl)benzamide

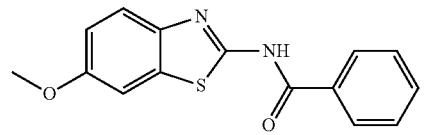 [SMILES: COc1ccc2nc(NC(=O)c3ccccc3)sc2c1]

The title compound was synthesized according to General Procedure A and isolated as a solid (26 mg, 33%): $^1$H NMR (400 MHz, DMSO-d6) δ 12.75 (s, 1H), 8.14-8.07 (m, 2H), 7.70-7.51 (m, 5H), 7.05 (dd, J=8.8, 2.6 Hz, 1H), 3.81 (s, 3H); LCMS (ESI) m/z 282.8 [M−1]$^-$.

Example 5: N-(6-methoxybenzo[d]thiazol-2-yl)-2,3-dihydrobenzo[b][1,4]dioxine-6-sulfonamide

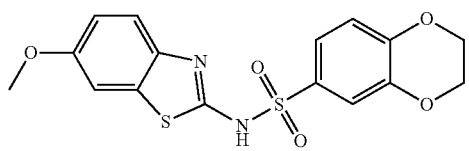 [SMILES: COc1ccc2nc(NS(=O)(=O)c3ccc4c(c3)OCCO4)sc2c1]

The title compound was synthesized according to General Procedure A and isolated as a solid (48 mg, 45%): $^1$H NMR (400 MHz, DMSO-d6) δ 12.98 (s, 1H), 7.44 (d, J=2.7 Hz, 1H), 7.33-7.15 (m, 3H), 7.02-6.92 (m, 2H), 4.31-4.22 (m, 4H), 3.74 (s, 3H); LCMS (ESI) m/z 376.7 [M−1]$^-$.

Example 6: N-(6-methoxybenzo[d]thiazol-2-yl)-3-methylbenzamide

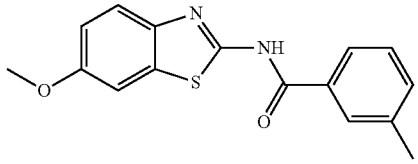

The title compound was synthesized according to General Procedure A and isolated as a solid (34 mg, 41%): $^1$H NMR (400 MHz, DMSO-d6) δ 12.68 (s, 1H), 7.97-7.86 (m, 2H), 7.66 (d, J=8.8 Hz, 1H), 7.60 (d, J=2.5 Hz, 1H), 7.49-7.38 (m, 2H), 7.04 (dd, J=8.9, 2.7 Hz, 1H), 3.81 (s, 3H), 2.39 (s, 3H); LCMS (ESI) m/z 296.8 [M−1]$^-$.

Example 7: 4-methoxy-N-(6-methoxybenzo[d]thiazol-2-yl)benzamide

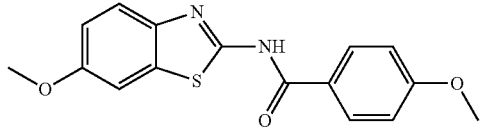

The title compound was synthesized according to General Procedure A and isolated as a solid (38 mg, 43%): $^1$H NMR (400 MHz, DMSO-d6) δ 12.58 (s, 1H), 8.16-8.08 (m, 2H), 7.65 (d, J=8.8 Hz, 1H), 7.58 (d, J=2.5 Hz, 1H), 7.12-7.00 (m, 3H), 3.84 (s, 3H), 3.81 (s, 3H); LCMS (ESI) m/z 312.9 [M−1]$^-$.

Example 8: N-(6-methoxybenzo[d]thiazol-2-yl)-4-(trifluoromethyl)benzenesulfonamide

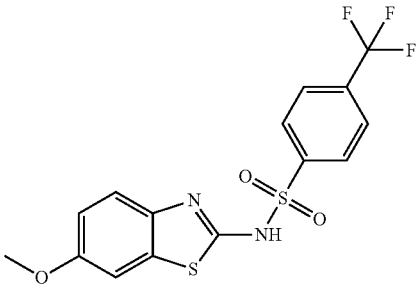 [SMILES: COc1ccc2nc(NS(=O)(=O)c3ccc(C(F)(F)F)cc3)sc2c1]

The title compound was synthesized according to General Procedure A and isolated as a solid (54 mg, 50%): $^1$H NMR (400 MHz, DMSO-d6) δ 13.26 (s, 1H), 8.04 (d, J=8.6 Hz, 2H), 7.93 (d, J=8.3 Hz, 2H), 7.47 (d, J=2.7 Hz, 1H), 7.22 (d, J=8.8 Hz, 1H), 6.99 (dd, J=8.8, 2.6 Hz, 1H), 3.75 (s, 3H); LCMS (ESI) m/z 386.7 [M−1]$^-$.

Example 9: N-(6-methoxybenzo[d]thiazol-2-yl)-2-phenylacetamide

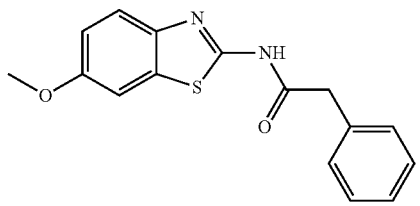 [SMILES: COc1ccc2nc(NC(=O)Cc3ccccc3)sc2c1]

The title compound was synthesized according to General Procedure A and isolated as a solid (7 mg, 8%): $^1$H NMR (400 MHz, DMSO-d6) δ 12.46 (s, 1H), 7.62 (d, J=8.9 Hz, 1H), 7.54 (d, J=2.5 Hz, 1H), 7.37-7.20 (m, 5H), 7.00 (dd, J=8.8, 2.6 Hz, 1H), 3.79 (s, 3H), 3.78 (s, 3H); LCMS (ESI) m/z 296.8 [M−1]$^-$.

Example 10: N-(6-methoxybenzo[d]thiazol-2-yl)benzenesulfonamide

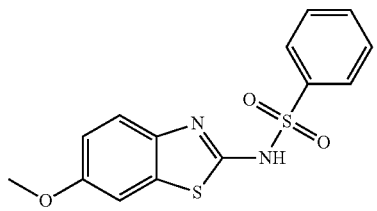 [SMILES: COc1ccc2nc(NS(=O)(=O)c3ccccc3)sc2c1]

The title compound was synthesized according to General Procedure A and isolated as a solid (48 mg, 54%): $^1$H NMR (400 MHz, DMSO-d6) δ 13.06 (s, 1H), 7.86-7.79 (m, 2H), 7.64-7.42 (m, 4H), 7.19 (d, J=8.8 Hz, 1H), 6.97 (dd, J=8.7, 2.6 Hz, 1H), 3.74 (s, 3H); LCMS (ESI) m/z 318.8 [M−1]$^-$.

Example 11: N-(benzo[d]thiazol-2-yl)-4-(trifluoromethyl)benzenesulfonamide

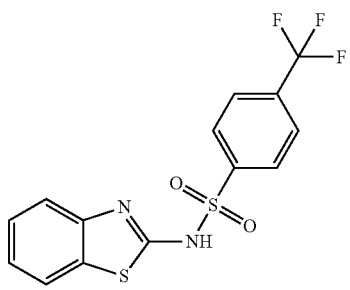 [SMILES: O=S(=O)(Nc1nc2ccccc2s1)c1ccc(C(F)(F)F)cc1]

The title compound was synthesized according to General Procedure A and isolated as a solid (96 mg, 81%): $^1$H NMR (400 MHz, DMSO-d6) δ 8.06 (d, J=8.2 Hz, 2H), 7.93 (d, J=8.2 Hz, 2H), 7.82 (d, J=7.9 Hz, 1H), 7.39 (m, 1H), 7.36-7.21 (m, 2H); LCMS (ESI) m/z 359.0 [M+1]$^+$.

Example 12: 1-(7,7-dimethyl-2-oxobicyclo[2.2.1] heptan-1-yl)-N-(6-methoxybenzo[d]thiazol-2-yl) methanesulfonamide

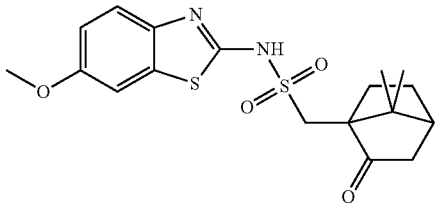 [SMILES: COc1ccc2nc(NS(=O)(=O)CC34CCC(CC3=O)C4(C)C)sc2c1]

The title compound was synthesized according to General Procedure A and isolated as a solid (53 mg, 48%): $^1$H NMR (400 MHz, DMSO-d6) δ 12.78 (s, 1H), 7.43 (d, J=2.6 Hz, 1H), 7.21 (d, J=8.7 Hz, 1H), 6.96 (dd, J=8.8, 2.6 Hz, 1H), 3.75 (s, 3H), 3.38 (d, J=15.1 Hz, 1H), 2.97 (d, J=15.0 Hz, 1H), 2.52-2.37 (m, 2H), 2.28 (ddd, J=18.3, 4.7, 3.0 Hz, 1H), 2.01 (t, J=4.5 Hz, 1H), 1.93-1.82 (m, 2H), 1.53 (ddd, J=13.8, 9.3, 4.6 Hz, 1H), 1.36 (ddd, J=12.8, 9.4, 3.9 Hz, 1H), 1.01 (s, 3H), 0.75 (s, 3H); LCMS (ESI) m/z 392.8 [M−1]−

Example 13: N-(6-methoxybenzo[d]thiazol-2-yl)nicotinamide hydrochloride

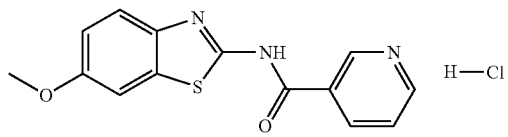

6-methoxybenzo[d]thiazol-2-amine (100 mg, 0.56 mmol) and nicotinoyl chloride hydrochloride (55 mg, 0.62 mmol) were fused under heating with a heat gun until gas evolution ceased. After cooling to room temperature the resulting solid was suspended in ethanol, treated with conc. Hydrochloric acid (2 drops) and filtered to give the title compound as a solid (143 mg, 79%): $^1$H NMR (400 MHz, DMSO-d6) δ 9.30 (d, J=2.3 Hz, 1H), 8.89 (d, J=5.0 Hz, 1H), 8.65 (d, J=8.0 Hz, 1H), 7.79 (dd, J=8.0, 5.1 Hz, 1H), 7.67 (d, J=8.8 Hz, 1H), 7.61 (d, J=2.6 Hz, 1H), 7.07 (dd, J=9.0, 2.7 Hz, 1H), 3.81 (s, 3H); LCMS (ESI) m/z 285.9 [M+1]+

Example 14: 4-benzoyl-N-(6-methoxybenzo[d]thiazol-2-yl)benzamide

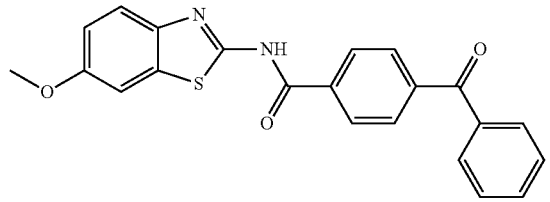

4-benzoyl benzoic acid (500 mg, 2.2 mmol) was suspended in methylene chloride (5 ml) and the resulting mixture was treated with DMF (20 µl) and oxalyl chloride (0.93 ml, 11 mmol). The mixture was stirred at room temperature until gas evolution ceased and a clear solution resulted, about 1 h. The solvent was removed and the resulting solid was fused with 6-methoxybenzo[d]thiazol-2-amine (397 mg, 2.2 mmol) in the manner described in Example 15 to give the title compound (779 mg, 91%) as a solid: $^1$H NMR (400 MHz, Chloroform-d) δ 11.77 (s, 1H), 8.19 (d, J=8.1 Hz, 2H), 7.86 (d, J=8.1 Hz, 2H), 7.76 (d, J=7.6 Hz, 2H), 7.59 (t, J=7.4 Hz, 1H), 7.53 (d, J=8.8 Hz, 1H), 7.47 (t, J=7.6 Hz, 2H), 7.30 (d, J=2.6 Hz, 1H), 6.98 (dd, J=8.9, 2.5 Hz, 1H), 3.85 (s, 3H); LCMS (ESI) m/z 386.1 [M−1]−

Example 15: 4-benzoyl-N-(5-bromo-6-methoxy-benzo[d]thiazol-2-yl)benzamide

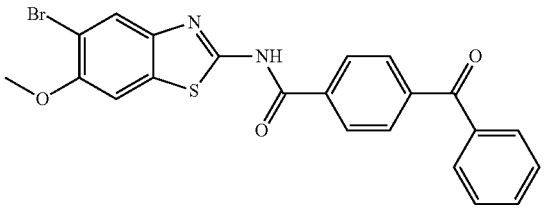 [SMILES: COc1cc2sc(NC(=O)c3ccc(C(=O)c4ccccc4)cc3)nc2cc1Br]

4-benzoyl-N-(6-methoxybenzo[d]thiazol-2-yl)benzamide (50 mg, 0.13 mmol) was suspended in methylene chloride/methanol (10:1, 1.7 ml) and the resulting mixture was treated with bromine (10 µl). After stirring for 16 h at room temperature, the solvent was removed under vacuum and the resulting residue was purified by silica gel chromatography (1% MeOH/CH2Cl2) to give the title compound as a solid: $^1$H NMR (400 MHz, Chloroform-d) δ 10.28 (s, 1H), 8.13-8.06 (m, 2H), 7.97-7.90 (m, 2H), 7.84-7.77 (m, 3H), 7.69-7.60 (m, 1H), 7.59-7.47 (m, 2H), 7.34 (s, 1H), 3.98 (s, 3H); LCMS (ESI) m/z 467.0 [M]+.

Example 16: 2,6-difluoro-3-hydroxy-N-(6-hydroxy-benzo[d]thiazol-2-yl)benzamide

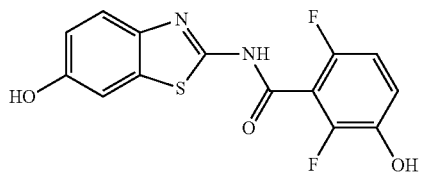 [SMILES: O=C(Nc1nc2ccc(O)cc2s1)c1c(F)ccc(O)c1F]

2,6-difluoro-3-methoxybenzoic acid (100 mg, 0.53 mmol) was treated with oxalyl chloride (135 µl) and DMF (10 µl) in the manner described in Example 16 to give the corresponding acid chloride, which was treated with 6-methoxy-benzo[d]thiazol-2-amine (90 mg, 0.5 mmol) in the manner described in General Procedure A to give 2,6-difluoro-3-methoxy-N-(6-methoxybenzo[d]thiazol-2-yl)benzamide (4.5 mg) as a solid: $^1$H NMR (400 MHz, DMSO-d6) δ 13.07 (s, 1H), 7.68 (d, J=8.9 Hz, 1H), 7.62 (d, J=2.5 Hz, 1H), 7.37 (td, J=9.4, 5.2 Hz, 1H), 7.21 (td, J=9.1, 1.8 Hz, 1H), 7.06 (dd, J=8.8, 2.6 Hz, 1H), 3.87 (s, 3H), 3.81 (s, 3H); LCMS (ESI) m/z 348.8 [M−1]−. This product was then dissolved in methylene chloride (0.2 ml) and cooled to −78° C. under nitrogen and treated with a solution of boron tribromide in methylene chloride (1.0M, 0.15 ml) dropwise. The resulting mixture was allowed to warm to room temperature and stir for 4 h, and then was quenched with water, and the resulting mixture extracted with ethyl acetate several times. The combined organic layer was dried (magnesium sulfate), filtered, and concentrated under vacuum to give the crude product. Purification was achieved by silica gel chromatography (5% MeOH/CH$_2$Cl$_2$) to give the title compound (5 mg): $^1$H NMR (400 MHz, Methanol-d4) δ 7.59 (d, J=8.7 Hz, 1H), 7.26 (d, J=2.4 Hz, 1H), 7.07 (td, J=9.4, 5.4 Hz, 1H), 6.99-6.89 (m, 2H).

Example 17: 4-bromo-N-(6-methoxybenzo[d]thiazol-2-yl)benzamide

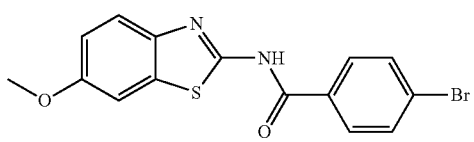 [SMILES: COc1ccc2nc(NC(=O)c3ccc(Br)cc3)sc2c1]

6-methoxybenzo[d]thiazol-2-amine (1 g, 5.6 mmol) and 4-bromobenzoyl chloride (1.2 g, 5.6 mmol) were treated in the manner described for Example 15 to give the title compound (1.4 g, 65%) as a cream-colored crystalline solid (ethanol): $^1$H NMR (400 MHz, Chloroform-d) δ 7.83 (d, J=8.1 Hz, 2H), 7.58 (d, J=6.8 Hz, 2H), 7.33 (s, 1H), 6.95 (s, 2H), 3.88 (s, 3H).

Example 18: N-(6-methoxybenzo[d]thiazol-2-yl)-4-picolinoylbenzamide

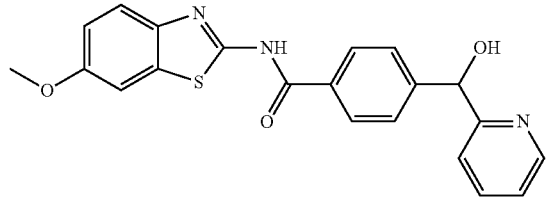

To a solution of 4-bromo-N-(6-methoxybenzo[d]thiazol-2-yl)benzamide (50 mg, 0.13 mmol) in THF (0.5 ml) stirring at −78° C. was added n-butyllithium (2.5M in hexanes, 0.12 ml, 0.3 mmol) and the resulting mixture was stirred at −78° C. for 20 minutes. Pyridine-2-carboxaldehyde (14 μl, 0.14 mmol) was then added to the mixture and stirring was continued for 30 minutes at −78° C., whereupon saturated ammonium chloride (aq) solution was added and the mixture extracted with ethyl acetate several times, and the combined organic layer was dried (sodium sulfate), filtered, and concentrated under vacuum. The resulting residue was purified by silica gel chromatography (20%-100% ethyl acetate/hexanes) to give 4-(hydroxy(pyridin-2-yl)methyl)-N-(6-methoxybenzo[d]thiazol-2-yl)benzamide (2 mg) along with proto-dehalogenated by-product. $^1$H NMR (400 MHz, Methanol-d4) δ 8.46 (dt, J=5.0, 1.1 Hz, 1H), 8.02-7.95 (m, 2H), 7.84 (td, J=7.8, 1.8 Hz, 1H), 7.63 (td, J=8.7, 8.2, 6.0 Hz, 5H), 7.42 (d, J=2.6 Hz, 1H), 7.29 (dd, J=7.5, 5.0 Hz, 1H), 7.02 (dd, J=8.9, 2.5 Hz, 1H), 5.90 (s, 1H), 3.84 (s, 3H); LCMS (ESI) m/z 391.9 [M+1]$^+$.

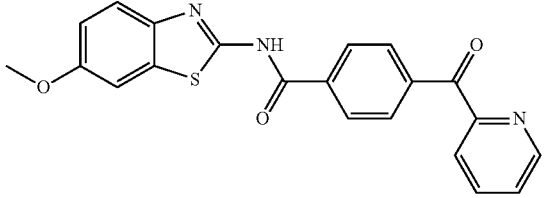

4-(hydroxy(pyridin-2-yl)methyl)-N-(6-methoxybenzo[d]thiazol-2-yl)benzamide (50 mg, 0.13 mmol) was dissolved in methylene chloride and the resulting solution was treated with manganese (IV) oxide (40 mg, excess). The mixture was stirred at room temperature for 72 h, then filtered through celite and the filtrate was concentrated under vacuum. The residue was purified by silica gel chromatography (20% ethyl acetate/hexanes) to give the title compound (2.4 mg, 5%) as a solid: $^1$H NMR (400 MHz, Chloroform-d) δ 10.62 (s, 1H), 8.74 (dt, J=5.0, 1.3 Hz, 1H), 8.18 (d, J=8.4 Hz, 2H), 8.14-8.10 (m, 1H), 8.08 (d, J=8.5 Hz, 2H), 7.94 (td, J=7.7, 1.7 Hz, 1H), 7.54 (ddd, J=7.8, 4.8, 1.2 Hz, 1H), 7.43 (d, J=8.9 Hz, 1H), 7.33 (d, J=2.6 Hz, 1H), 6.98 (dd, J=8.8, 2.6 Hz, 1H), 3.87 (s, 3H); LCMS (ESI) m/z 389.9 [M+1]$^+$.

Example 19: N-(6-methoxybenzo[d]thiazol-2-yl)-4-nicotinoylbenzamide

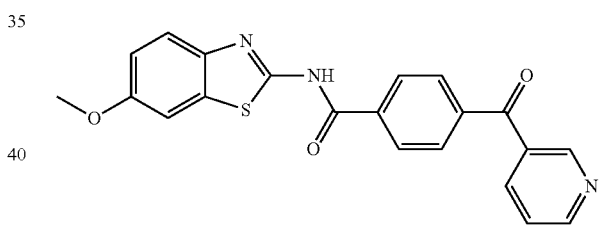

4-bromo-N-(6-methoxybenzo[d]thiazol-2-yl)benzamide (50 mg, 0.13 mmol) and pyridine-3-carboxaldehyde (23 μl, 0.25 mmol) were treated in the same manner described in Example 19, except that methylmagnesium bromide solution (3.0M in ethyl ether, 50 μl, 0.13 mmol) was used for the initial de-protonation of the amide. The crude product thus obtained was not purified but used directly in the next step by dissolving in methylene chloride (1 ml) and treating the resulting solution with manganese (IV) oxide (108 mg, excess). After stirring at room temperature for 72 h, the solution was filtered through celite, and the filtrate was concentrated under vacuum and the resulting solid triturated with ethyl ether to give the title compound (10 mg, 21%) as a solid: $^1$H NMR (400 MHz, DMSO-d6) δ 13.01 (s, 1H), 8.91 (d, J=2.2 Hz, 1H), 8.86 (dd, J=4.8, 1.6 Hz, 1H), 8.28 (d, J=8.1 Hz, 2H), 8.15 (dt, J=7.8, 2.0 Hz, 1H), 7.92 (d, J=8.1 Hz, 2H), 7.68 (d, J=8.8 Hz, 1H), 7.65-7.58 (m, 2H), 7.06 (dd, J=8.8, 2.6 Hz, 1H), 3.82 (s, 3H); LCMS (ESI) m/z 389.9 [M+1]$^+$.

Example 20: 4-isonicotinoyl-N-(6-methoxybenzo[d]thiazol-2-yl)benzamide

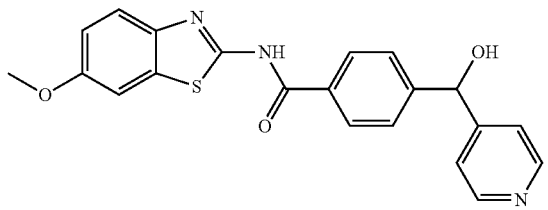 [SMILES: COc1ccc2nc(NC(=O)c3ccc(C(O)c4ccncc4)cc3)sc2c1]

4-bromo-N-(6-methoxybenzo[d]thiazol-2-yl)benzamide (50 mg, 0.13 mmol) and pyridine-4-carboxaldehyde (23 µl, 0.25 mmol) were treated in the manner describe in Example 20 to give 4-(hydroxy(pyridin-4-yl)methyl)-N-(6-methoxybenzo[d]thiazol-2-yl)benzamide (27 mg, 53%) as a solid after silica gel chromatography (10% MeOH/CH$_2$Cl$_2$): $^1$H NMR (400 MHz, Chloroform-d) δ 8.58 (d, J=3.7 Hz, 2H), 7.94 (d, J=8.4 Hz, 2H), 7.52 (dd, J=8.6, 4.8 Hz, 3H), 7.34-7.30 (m, 3H), 6.99 (dd, J=8.9, 2.5 Hz, 1H), 5.88 (s, 1H), 3.89 (s, 3H); LCMS (ESI) m/z 392.1 [M+1]$^+$.

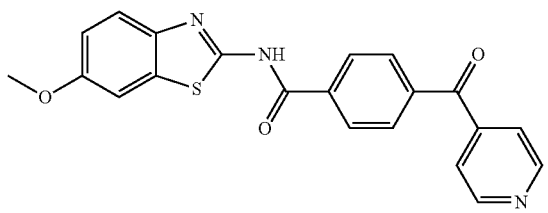 [SMILES: COc1ccc2nc(NC(=O)c3ccc(C(=O)c4ccncc4)cc3)sc2c1]

4-(hydroxy(pyridin-4-yl)methyl)-N-(6-methoxybenzo[d]thiazol-2-yl)benzamide (27 mg, 0.07 mmol) was treated with manganese (IV) oxide (60 mg, excess) in the manner described in Example 20 to give the title compound as a solid: $^1$H NMR (400 MHz, DMSO-d6) δ 13.02 (s, 1H), 8.87-8.80 (m, 2H), 8.28 (d, J=8.2 Hz, 2H), 7.92 (d, J=8.2 Hz, 2H), 7.67-7.63 (m, 2H), 7.61 (d, J=2.6 Hz, 1H), 7.06 (dd, J=8.8, 2.6 Hz, 1H), 3.82 (s, 3H); LCMS (ESI) m/z 392.1 [M+1]$^+$.

Example 21: 3-chloro-N-(4-(4-methoxybenzoyl)phenyl)benzo[b]thiophene-2-carboxamide

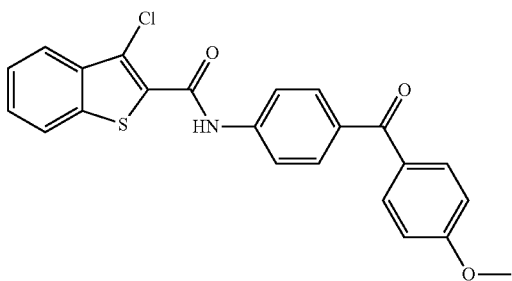 [SMILES: COc1ccc(C(=O)c2ccc(NC(=O)c3sc4ccccc4c3Cl)cc2)cc1]

3-chlorobenzo[b]thiophene-2-carboxylic acid (500 mg, 2.4 mmol) was dissolved in methylene chloride (5 ml) and the resulting solution was treated with DMF (20 g) and oxalyl chloride (1 ml, 11.8 mmol) dropwise. After gas evolution had ceased, the mixture was concentrated under vacuum, and the resulting acid chloride was used directly without further purification and treated with (4-aminophenyl)(4-methoxyphenyl)methanone (485 mg, 2.1 mmol) and pyridine 5 ml) in the manner described in General Procedure A to give the title compound (20 mg) after purification by silica gel chromatography (30% ethyl acetate/hexanes): $^1$H NMR (400 MHz, DMSO-d6) δ 10.90 (s, 1H), 8.21-8.13 (m, 1H), 7.95 (d, J=3.1 Hz, 1H), 7.92-7.85 (m, 2H), 7.79-7.70 (m, 4H), 7.63 (dd, J=6.2, 3.2 Hz, 2H), 7.13-7.04 (m, 2H), 3.85 (s, 3H); LCMS (ESI) m/z 419.7 [M−1]$^-$.

Example 22: 3-chloro-N-(4-(4-hydroxybenzoyl)phenyl)benzo[b]thiophene-2-carboxamide

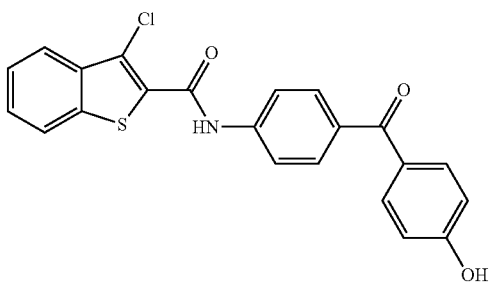 [SMILES: O=C(c1ccc(O)cc1)c1ccc(NC(=O)c2sc3ccccc3c2Cl)cc1]

To a solution of 3-chloro-N-(4-(4-methoxybenzoyl)phenyl)benzo[b]thiophene-2-carboxamide (10 mg, 0.024 mmol) in methylene chloride (0.3 ml) stirring at −78° C. was added a solution of boron tribromide (1.0M in methylene chloride, 0.12 ml, 0.12 mmol), and the mixture was allowed to warm to room temperature over 16 h. The mixture was then quenched with water and extracted with ethyl acetate three times. The combined organic layer was dried (magnesium sulfate), filtered, and concentrated under vacuum. The residue thus obtained was purified by silica gel chromatography (5% MeOH/CH$_2$Cl$_2$) to give the title compound (2 mg, 20%) as a solid: $^1$H NMR (400 MHz, Acetonitrile-d3) δ 9.24 (s, 1H), 8.03 (ddd, J=9.5, 4.7, 3.1 Hz, 2H), 7.88 (d, J=8.6 Hz, 2H), 7.87-7.78 (m, 2H), 7.79-7.69 (m, 2H), 7.63 (dt, J=6.2, 2.4 Hz, 2H), 7.00-6.92 (m, 2H); LCMS (ESI) m/z 405.8 [M−1]$^-$.

Example 23: 3-chloro-N-(3-fluorophenyl)benzo[b]thiophene-2-carboxamide

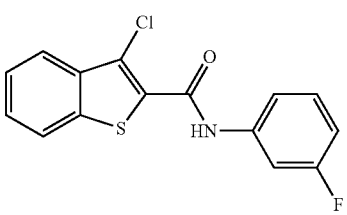 [SMILES: O=C(Nc1cccc(F)c1)c1sc2ccccc2c1Cl]

3-chlorobenzo[b]thiophene-2-carboxylic acid (100 mg, 0.5 mmol), oxalyl chloride (60 µl), DMF (20 µl), and 3-fluoroaniline (0.1 ml, 1 mmol) were treated in the manner describe for Example 21 to give the title compound as a solid: $^1$H NMR (400 MHz, Chloroform-d) δ 8.98 (s, 1H), 7.97-7.83 (m, 2H), 7.67 (dt, J=9.9, 1.8 Hz, 1H), 7.60-7.48 (m, 2H), 7.40-7.28 (m, 2H), 6.95-6.85 (m, 1H); LCMS (ESI) m/z 303.8 [M−1]$^-$.

Example 24: 3-chloro-N-(2-fluoro-4-methylphenyl)benzo[b]thiophene-2-carboxamide

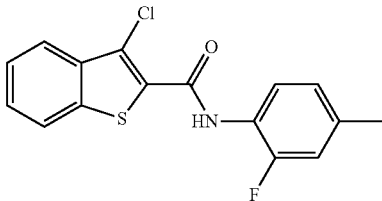 [SMILES: Cc1ccc(NC(=O)c2sc3ccccc3c2Cl)c(F)c1]

3-chlorobenzo[b]thiophene-2-carboxylic acid (100 mg, 0.5 mmol), oxalyl chloride (60 μl), DMF (20 μl), and 2-fluoro-4-methylaniline (0.12 ml, 1 mmol) were treated in the manner describe for Example 21 to give the title compound as a solid: ¹H NMR (400 MHz, Chloroform-d) δ 9.24 (s, 1H), 8.35 (t, J=8.4 Hz, 1H), 7.96-7.90 (m, 1H), 7.90-7.85 (m, 1H), 7.59-7.47 (m, 2H), 7.04-6.95 (m, 2H), 2.36 (s, 3H); LCMS (ESI) m/z 317.9 [M−1]⁻.

Example 25: 3-chloro-N-(2-fluoro-4-nitrophenyl)benzo[b]thiophene-2-carboxamide

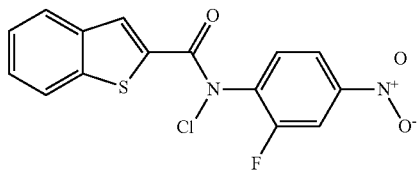

3-chlorobenzo[b]thiophene-2-carboxylic acid (100 mg, 0.5 mmol), oxalyl chloride (60 μl), DMF (20 μl), and 2-fluoro-4-nitroaniline (156 mg, 1 mmol) were treated in the manner describe for Example 21 to give the title compound as a solid: ¹H NMR (400 MHz, Chloroform-d) δ 9.63 (s, 1H), 8.81 (dd, J=9.1, 7.6 Hz, 1H), 8.16 (dt, J=8.8, 1.8 Hz, 1H), 8.10 (dd, J=10.6, 2.6 Hz, 1H), 8.00-7.93 (m, 1H), 7.93-7.87 (m, 1H), 7.63-7.51 (m, 2H); LCMS (ESI) m/z 348.8 [M−1]⁻.

Example 26: 3-chloro-N-(3-fluorophenyl)-N-methylbenzo[b]thiophene-2-carboxamide

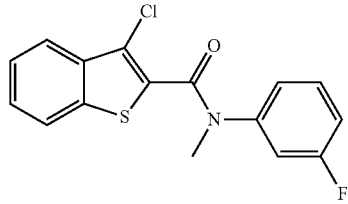 [SMILES: CN(C(=O)c1sc2ccccc2c1Cl)c1cccc(F)c1]

To a solution of 3-chloro-N-(3-fluorophenyl)benzo[b]thiophene-2-carboxamide (20 mg, 0.07 mmol) in DMF (0.15 ml) was added sodium hydride (60% disp. in oil, 3 mg, 0.08 mmol) in one portion. The mixture was cooled to 0° C. after gas evolution ceased, and iodomethane (10 μl) was added dropwise. The ice bath was removed and the mixture allowed to warm to room temperature overnight. The mixture was then quenched with water and extracted with ethyl acetate, and the organic layers were dried (magnesium sulfate), filtered, and concentrated under vacuum. The residue thus obtained was purified by silica gel chromatography (10% ethyl acetate/hexanes) to give the title compound (16 mg, 77%) as a solid: ¹H NMR (400 MHz, Chloroform-d) δ 7.80-7.65 (m, 2H), 7.46-7.34 (m, 2H), 7.19 (td, J=8.3, 6.3 Hz, 1H), 7.02-6.94 (m, 2H), 6.89 (tdd, J=8.4, 2.2, 1.2 Hz, 1H), 3.51 (s, 3H); LCMS (ESI) m/z 319.9 [M+1]⁺.

Example 27: N-(2-carbamoylphenyl)-3-chlorobenzo[b]thiophene-2-carboxamide

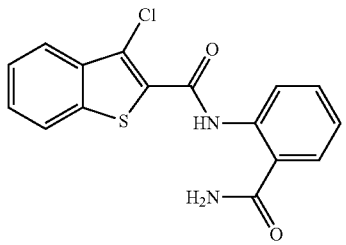 [SMILES: NC(=O)c1ccccc1NC(=O)c1sc2ccccc2c1Cl]

3-chlorobenzo[b]thiophene-2-carboxylic acid (100 mg, 0.5 mmol), oxalyl chloride (60 μl), DMF (20 μl), and 2-aminobenzamide (136 mg, 1 mmol) were treated in the manner describe for Example 21 to give the title compound as a solid: ¹H NMR (400 MHz, Chloroform-d) δ 8.90 (s, 1H), 7.96-7.84 (m, 2H), 7.71-7.62 (m, 2H), 7.59-7.49 (m, 2H), 7.15-7.05 (m, 2H); LCMS (ESI) m/z 328.8 [M−1]⁻.

Example 28: N-(3-(3-chlorobenzo[b]thiophene-2-carboxamido)phenyl)furan-2-carboxamide

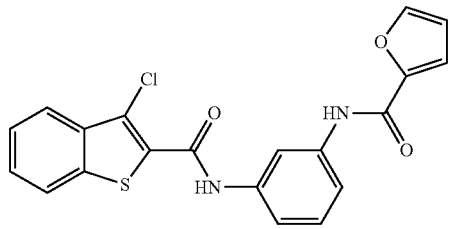 [SMILES: O=C(Nc1cccc(NC(=O)c2sc3ccccc3c2Cl)c1)c1ccco1]

3-chlorobenzo[b]thiophene-2-carboxylic acid (100 mg, 0.5 mmol), oxalyl chloride (60 μl), DMF (20 μl), and N-(3-aminophenyl)furan-2-carboxamide (101 mg, 0.5 mmol) were treated in the manner describe for Example 21 to give the title compound as a solid: ¹H NMR (400 MHz, Chloroform-d) δ 8.99 (s, 1H), 8.15 (s, 1H), 8.12 (t, J=2.0 Hz, 1H), 7.98-7.83 (m, 2H), 7.61-7.45 (m, 6H), 7.39 (t, J=8.1 Hz, 1H), 6.58 (dd, J=3.5, 1.7 Hz, 1H); LCMS (ESI) m/z 394.7 [M−1]⁻.

Example 29: N-(4-(3-chlorobenzo[b]thiophene-2-carboxamido)phenyl)furan-2-carboxamide

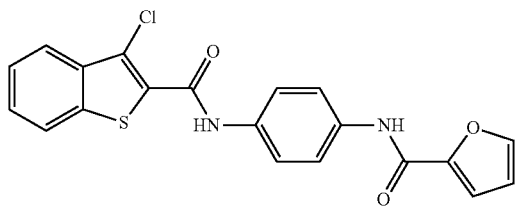 [SMILES: O=C(Nc1ccc(NC(=O)c2sc3ccccc3c2Cl)cc1)c1ccco1]

3-chlorobenzo[b]thiophene-2-carboxylic acid (100 mg, 0.5 mmol), oxalyl chloride (60 μl), DMF (20 μl), and N-(4-aminophenyl)furan-2-carboxamide (101 mg, 0.5 mmol) were treated in the manner describe for Example 21 to give the title compound as a solid: $^1$H NMR (400 MHz, Chloroform-d) δ 8.87 (s, 1H), 8.02 (s, 1H), 7.89-7.77 (m, 2H), 7.64 (s, 4H), 7.46 (d, J=6.5 Hz, 3H), 6.53-6.47 (m, 1H); LCMS (ESI) m/z 394.8 [M−1]$^-$.

Example 30: 3-chloro-N-(2-(pyrrolidin-1-yl)phenyl)benzo[b]thiophene-2-carboxamide

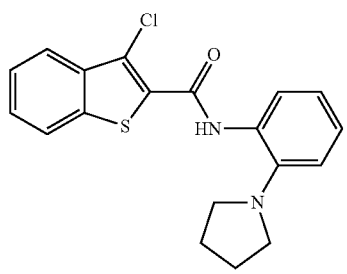 [SMILES: O=C(Nc1ccccc1N1CCCC1)c1sc2ccccc2c1Cl]

3-chlorobenzo[b]thiophene-2-carboxylic acid (100 mg, 0.5 mmol), oxalyl chloride (60 μl), DMF (20 μl), and 2-(pyrrolidin-1-yl)aniline (162 mg, 1.0 mmol) were treated in the manner describe for Example 21 to give the title compound as a solid: $^1$H NMR (400 MHz, Chloroform-d) δ 10.20 (s, 1H), 8.41 (dd, J=7.8, 1.9 Hz, 1H), 7.89-7.75 (m, 2H), 7.49-7.39 (m, 2H), 7.17 (d, J=1.9 Hz, 1H), 7.13-7.01 (m, 2H), 3.07-2.98 (m, 4H), 1.99-1.87 (m, 4H); LCMS (ESI) m/z 354.9 [M−1]$^-$.

Example 31: 4-benzoyl-N-(6-(prop-2-yn-1-yloxy)benzo[d]thiazol-2-yl)benzamide

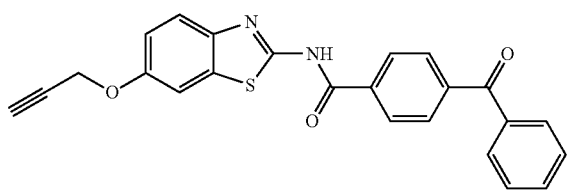 [SMILES: C#CCOc1ccc2nc(NC(=O)c3ccc(C(=O)c4ccccc4)cc3)sc2c1]

6-(prop-2-yn-1-yloxy)benzo[d]thiazol-2-amine (93 mg, 0.46 mmol), 4-benzoylbenzoic acid (113 mg, 0.5 mmol), TBTU (222 mg, 0.69 mmol), triethylamine (192 μl), DMAP (10 mol %), and DMF (1 ml) were treated in the manner described in General Procedure B to give the title compound (138 mg, 73%) as a solid: $^1$H NMR (400 MHz, Chloroform-d) δ 11.23 (s, 1H), 8.09 (d, J=8.3 Hz, 2H), 7.85 (d, J=8.3 Hz, 2H), 7.77-7.72 (m, 2H), 7.66-7.60 (m, 1H), 7.50 (dd, J=8.3, 7.2 Hz, 2H), 7.45 (d, J=2.5 Hz, 1H), 7.31 (d, J=8.9 Hz, 1H), 7.01 (dd, J=8.9, 2.5 Hz, 1H), 4.75 (d, J=2.4 Hz, 2H), 2.54 (t, J=2.4 Hz, 1H); LCMS (ESI) m/z 410.8 [M−1]$^-$.

Example 32: 4-benzoyl-N-(5-methoxythiazolo[5,4-b]pyridin-2-yl)benzamide

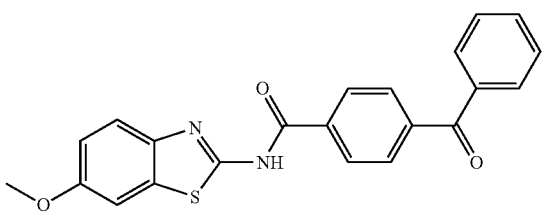 [SMILES: COc1ccc2nc(NC(=O)c3ccc(C(=O)c4ccccc4)cc3)sc2c1]

5-methoxythiazolo[5,4-b]pyridin-2-amine (50 mg, 0.28 mmol), 4-benzoylbenzoic acid (69 mg, 0.3 mmol), TBTU (193 mg, 0.6 mmol), triethylamine (125 μl), DMAP (10 mol %), and DMF (0.3 ml) were treated in the manner described in General Procedure B to give the title compound (58 mg, 53%) as a solid: $^1$H NMR (400 MHz, DMSO-d6) δ 13.07 (s, 1H), 8.26 (d, J=8.2 Hz, 2H), 8.08 (d, J=8.8 Hz, 1H), 7.87 (d, J=8.1 Hz, 2H), 7.77 (d, J=7.6 Hz, 2H), 7.71 (t, J=7.4 Hz, 1H), 7.59 (t, J=7.7 Hz, 2H), 6.94 (d, J=8.7 Hz, 1H), 3.93 (s, 3H); LCMS (ESI) m/z 390.1 [M+1]$^+$.

Example 33: 4-benzoyl-N-(6-(3-bromopropoxy)benzo[d]thiazol-2-yl)benzamide

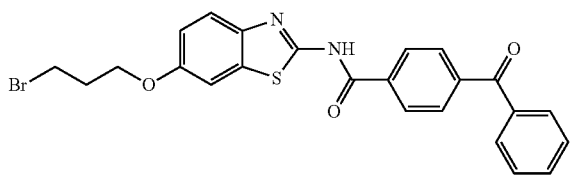 [SMILES: O=C(Nc1nc2ccc(OCCCBr)cc2s1)c1ccc(C(=O)c2ccccc2)cc1]

A solution of 2-aminobenzo[d]thiazol-6-ol (50 mg, 0.3 mmol) in acetone (3 ml) was treated with potassium carbonate (208 mg, 1.5 mmol) and 1,3-dibromopropane (153 μl, 1.5 mmol). The mixture was stirred at room temperature for 16 h, then diluted with water and extracted with ethyl acetate. The organic layer was dried (sodium sulfate), filtered, and concentrated under vacuum to give the crude 6-(3-bromopropoxy)benzo[d]thiazol-2-amine (91 mg), which was not purified but used as is in the next step. This material was treated with 4-benzoylbenzoic acid (69 mg, 0.3 mmol), TBTU (193 mg, 0.6 mmol), triethylamine (125 μl), DMAP (10 mol %), and DMF (0.3 ml) in the manner described in General Procedure B to give the title compound (14 mg, 9%) as a solid: $^1$H NMR (400 MHz, Chloroform-d) δ 11.04 (s, 1H), 8.09 (d, J=8.1 Hz, 2H), 7.87 (d, J=8.1 Hz, 2H), 7.77 (d, J=7.7 Hz, 2H), 7.63 (t, J=7.4 Hz, 1H), 7.50 (t, J=7.7 Hz, 2H), 7.36 (dd, J=5.7, 3.2 Hz, 2H), 6.96 (dd, J=8.8, 2.4 Hz, 1H), 4.17 (t, J=5.8 Hz, 2H), 3.63 (t, J=6.4 Hz, 2H), 2.35 (p, J=6.0 Hz, 2H); LCMS (ESI) m/z 495.0 [M]$^+$.

Example 34: 4-benzoyl-N-(6-(4-bromobutoxy)benzo[d]thiazol-2-yl)benzamide

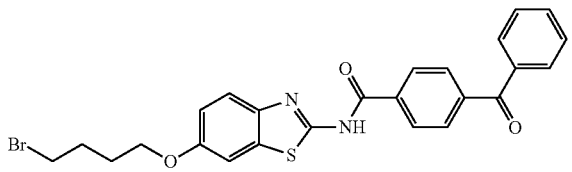 [SMILES: O=C(Nc1nc2ccc(OCCCCBr)cc2s1)c1ccc(C(=O)c2ccccc2)cc1]

Aminobenzo[d]thiazol-6-ol (50 mg, 0.3 mmol), potassium carbonate (208 mg, 1.5 mmol), and 1,4-dibromobutane (180 µl, 1.5 mmol) were treated in the manner described in the previous example to give 6-(4-bromobutoxy)benzo[d]thiazol-2-amine (66 mg) which was used directly without purification. This material was treated with 4-benzoylbenzoic acid (74 mg, 0.33 mmol), TBTU (193 mg, 0.33 mmol), triethylamine (61 µl), DMAP (10 mol %), and DMF (0.3 ml) in the manner described in General Procedure B to give the title compound (15 mg, 13%) as a solid: $^1$H NMR (400 MHz, Chloroform-d) δ 12.34 (s, 1H), 8.12-8.05 (m, 2H), 7.80-7.67 (m, 4H), 7.66-7.56 (m, 1H), 7.47 (t, J=7.8 Hz, 2H), 7.32 (d, J=2.4 Hz, 1H), 7.03 (d, J=8.9 Hz, 1H), 6.83 (dd, J=8.8, 2.5 Hz, 1H), 4.02 (t, J=5.9 Hz, 2H), 3.48 (t, J=6.5 Hz, 2H), 2.12-2.02 (m, 2H), 1.96 (dq, J=9.9, 6.1 Hz, 2H).

Example 35: 4-(4-methoxybenzoyl)-N-(6-(prop-2-yn-1-yloxy)benzo[d]thiazol-2-yl)benzamide

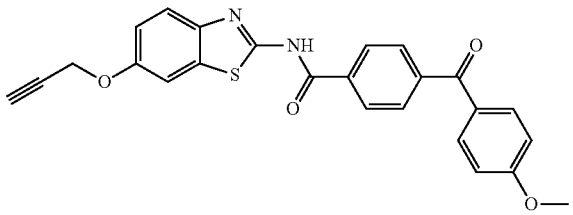 [SMILES: C#CCOc1ccc2nc(NC(=O)c3ccc(C(=O)c4ccc(OC)cc4)cc3)sc2c1]

6-(prop-2-yn-1-yloxy)benzo[d]thiazol-2-amine (4 mg, 0.018 mmol), 4-(4-methoxybenzoyl)benzoic acid (5 mg, 0.02 mmol), TBTU (10 mg, 0.03 mmol), triethylamine (10 µl), DMAP (10 mol %), and DMF (0.2 ml) in the manner described in General Procedure B to give the title compound (2 mg, 25%) as a solid: $^1$H NMR (400 MHz, Chloroform-d) δ 10.49 (s, 1H), 8.11-8.04 (m, 2H), 7.84 (d, J=8.2 Hz, 2H), 7.82-7.75 (m, 2H), 7.50 (d, J=8.9 Hz, 1H), 7.45 (d, J=2.5 Hz, 1H), 7.07 (dd, J=8.9, 2.5 Hz, 1H), 7.02-6.94 (m, 2H), 4.76 (d, J=2.4 Hz, 2H), 3.90 (d, J=4.9 Hz, 3H), 2.55 (t, J=2.4 Hz, 1H); LCMS (ESI) m/z 440.8 [M−1]$^-$.

Example 36: 4-((6-methoxybenzo[d]thiazol-2-yl)carbamoyl)benzoic acid

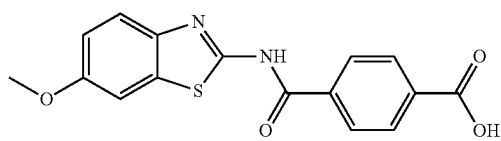 [SMILES: COc1ccc2nc(NC(=O)c3ccc(C(=O)O)cc3)sc2c1]

Mono-methylterephthalate (357 mg, 2 mmol), 6-methoxybenzo[d]thiazol-2-amine (357 mg, 2 mmol), T3P (50% w/w in ethyl acetate, 6 ml), and triethylamine (0.8 ml) were treated according to General Procedure C to give methyl 4-((6-methoxybenzo[d]thiazol-2-yl)carbamoyl)benzoate (416 mg, 61%). The ester (342 mg, 0.6 mmol) was hydrolyzed by dissolving in THF (5 ml) and treating with lithium hydroxide (236 mg, 5.6 mmol) dissolved in water (5 ml). After stirring 16 h at room temperature, the mixture was concentrated under vacuum, and the residue dissolved in water, and the resulting mixture was treated with 2M hydrochloric acid until the pH was 3. The resulting precipitate was filtered and dried under vacuum to give the title compound (180 mg, quant.) as a pale powder: $^1$H NMR (400 MHz, DMSO-d6) δ 12.96 (s, 1H), 8.19 (d, J=8.1 Hz, 2H), 8.10-8.00 (m, 2H), 7.67 (d, J=8.9 Hz, 1H), 7.61 (d, J=2.7 Hz, 1H), 7.06 (dd, J=8.9, 2.6 Hz, 1H), 3.81 (s, 3H).

Example 37: N-(6-methoxybenzo[d]thiazol-2-yl)-4-(4-methylpiperazine-1-carbonyl)benzamide

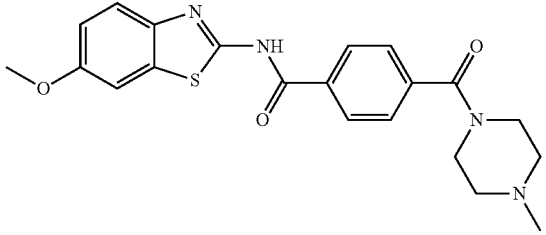

4-((6-methoxybenzo[d]thiazol-2-yl)carbamoyl)benzoic acid (50 mg, 0.15 mmol), 1-methylpiperazine (19 µl, 0.17 mmol), T3P (50% w/w in ethyl acetate, 0.3 ml), and triethylamine (64 µl) were treated in the manner described in General Procedure C to give the title compound (34 mg, 54%) as a tan powder: $^1$H NMR (400 MHz, DMSO-d6) δ 8.22 (d, J=8.1 Hz, 2H), 8.09 (d, J=8.2 Hz, 2H), 7.67 (d, J=8.8 Hz, 1H), 7.60 (d, J=2.6 Hz, 1H), 7.05 (dd, J=8.7, 2.6 Hz, 1H), 3.88 (ad, J=7.5 Hz, 6H).

Example 38: N-(6-methoxybenzo[d]thiazol-2-yl)-4-(piperidine-1-carbonyl)benzamide

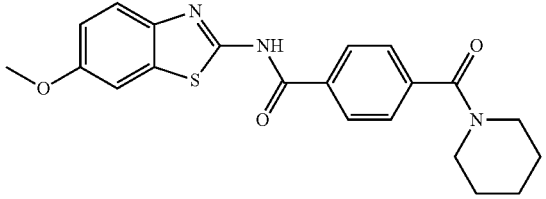 [SMILES: COc1ccc2nc(NC(=O)c3ccc(C(=O)N4CCCCC4)cc3)sc2c1]

4-((6-methoxybenzo[d]thiazol-2-yl)carbamoyl)benzoic acid (50 mg, 0.15 mmol), piperidine (16 µl, 0.17 mmol), T3P (50% w/w in ethyl acetate, 0.3 ml), and triethylamine (64 µl) were treated in the manner described in General Procedure C to give the title compound: $^1$H NMR (400 MHz, DMSO-d6) δ 8.15 (d, J=8.1 Hz, 2H), 7.67 (d, J=8.8 Hz, 1H), 7.60 (d, J=2.6 Hz, 1H), 7.52 (d, J=8.2 Hz, 2H), 7.05 (dd, J=8.9, 2.7 Hz, 1H), 3.81 (s, 3H), 3.59 (s, 2H), 3.23 (s, 2H), 1.60 (s, 2H), 1.46 (s, 2H); LCMS (ESI) m/z 395.9 [M+1]$^+$.

Example 39: N-(6-methoxybenzo[d]thiazol-2-yl)-4-(morpholine-4-carbonyl)benzamide

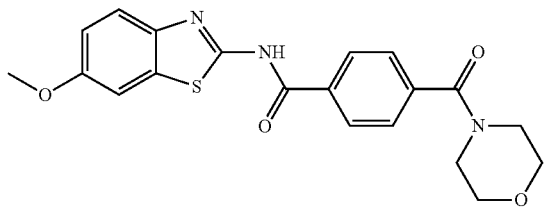 [SMILES: COc1ccc2nc(NC(=O)c3ccc(C(=O)N4CCOCC4)cc3)sc2c1]

4-((6-methoxybenzo[d]thiazol-2-yl)carbamoyl)benzoic acid (50 mg, 0.15 mmol), morpholine (15 μl, 0.17 mmol), T3P (50% w/w in ethyl acetate, 0.3 ml), and triethylamine (64 μl) were treated in the manner described in General Procedure C to give the title compound: $^1$H NMR (400 MHz, DMSO-d6) δ 8.20-8.13 (m, 2H), 7.67 (d, J=8.8 Hz, 1H), 7.61 (d, J=2.6 Hz, 1H), 7.57 (d, J=8.2 Hz, 2H), 7.05 (dd, J=8.8, 2.6 Hz, 1H), 3.81 (s, 3H), 3.64 (s, 4H), 3.55 (s, 2H), 3.33 (s, 2H); LCMS (ESI) m/z 395.8 [M−1]$^-$.

Example 40: N1-benzyl-N4-(6-methoxybenzo[d]thiazol-2-yl)terephthalamide

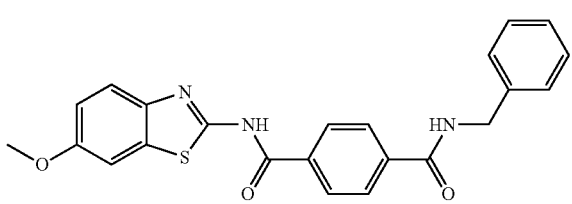 [SMILES: COc1ccc2nc(NC(=O)c3ccc(C(=O)NCc4ccccc4)cc3)sc2c1]

4-((6-methoxybenzo[d]thiazol-2-yl)carbamoyl)benzoic acid (50 mg, 0.15 mmol), benzylamine (18 μl, 0.17 mmol), T3P (50% w/w in ethyl acetate, 0.3 ml), and triethylamine (64 μl) were treated in the manner described in General Procedure C to give the title compound: $^1$H NMR (400 MHz, DMSO-d6) δ 9.25 (t, J=6.0 Hz, 1H), 8.27-8.15 (m, 2H), 8.06-7.99 (m, 2H), 7.71-7.59 (m, 2H), 7.33 (d, J=4.3 Hz, 4H), 7.24 (h, J=4.2 Hz, 1H), 7.05 (dd, J=8.8, 2.6 Hz, 1H), 4.49 (d, J=5.9 Hz, 2H), 3.81 (s, 3H); LCMS (ESI) m/z 415.9 [M−1]$^-$.

Example 41: 4-iodo-N-(6-methoxybenzo[d]thiazol-2-yl)benzamide

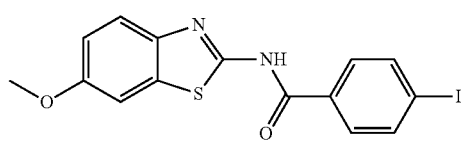 [SMILES: COc1ccc2nc(NC(=O)c3ccc(I)cc3)sc2c1]

6-methoxybenzo[d]thiazol-2-amine (645 mg, 3.6 mmol), 4-iodobenzoic acid (807 mg, 3.3 mmol), T3P (50% w/w in ethyl acetate, 10 ml), and Hunig's base (1.7 ml) were treated in the manner described in General Procedure C to give the title compound (510 mg, 38%) as tan plates (ethanol): $^1$H NMR (400 MHz, Chloroform-d) δ 7.79 (d, J=8.5 Hz, 2H), 7.67 (d, J=8.5 Hz, 2H), 7.32 (d, J=2.6 Hz, 1H), 7.24 (d, J=8.9 Hz, 1H), 6.94 (dd, J=8.9, 2.6 Hz, 1H), 3.89 (s, 2H).

Example 42: N-(6-methoxybenzo[d]thiazol-2-yl)-4-(phenylamino)benzamide

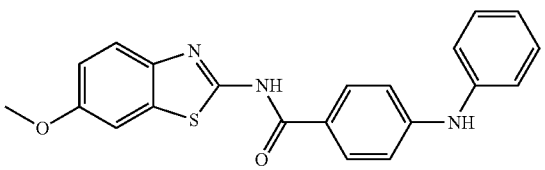 [SMILES: COc1ccc2nc(NC(=O)c3ccc(Nc4ccccc4)cc3)sc2c1]

4-iodo-N-(6-methoxybenzo[d]thiazol-2-yl)benzamide (50 mg, 0.12 mmol), BrettPhos (1 mg, 2 mol %), BrettPhos precatalyst (1 mg, 1 mol %), sodium tert-butoxide (16 mgs, 0.17 mmol), and aniline (15 μl, 0.17 mmol) were charged into a vial, and the vial was flushed with nitrogen. To this vial was added toluene (0.2 ml), and the vial was sealed and heated to 85° C. for 72 h. The mixture was cooled to room temperature, diluted with water, and extracted with ethyl acetate. The combined organic layers were concentrated under vacuum and the residue was purified by silica gel chromatography (20%-50% ethyl acetate/hexanes) to give the title compound (10 mg, 21%) as a solid: $^1$H NMR (400 MHz, Chloroform-d) δ 7.87 (d, J=8.7 Hz, 2H), 7.38-7.30 (m, 5H), 7.13 (d, J=7.8 Hz, 2H), 7.08 (t, J=7.4 Hz, 1H), 6.99-6.91 (m, 4H), 6.09 (s, 1H), 3.86 (s, 3H).

Example 43: 4-chloro-N-(6-methoxybenzo[d]thiazol-2-yl)benzamide

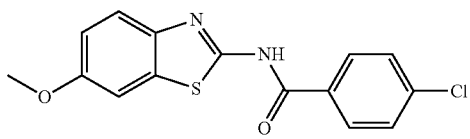 [SMILES: COc1ccc2nc(NC(=O)c3ccc(Cl)cc3)sc2c1]

6-methoxybenzo[d]thiazol-2-amine (1 g, 5.6 mmol), 4-chlorobenzoyl chloride (0.78 ml, 6.1 mmol), and pyridine (10 ml) were treated in the manner described in General Procedure A to give the title compound (1.5 g, 85%) as golden plates (ethanol): $^1$H NMR (400 MHz, DMSO-d6) δ 12.84 (s, 1H), 8.16-8.07 (m, 2H), 7.69-7.55 (m, 4H), 7.04 (dd, J=9.0, 2.6 Hz, 1H), 3.80 (s, 3H); LCMS (ESI) m/z 316.8 [M−1]$^-$.

Example 44: N-(6-methoxybenzo[d]thiazol-2-yl)-4-((4-methoxyphenyl)amino)benzamide

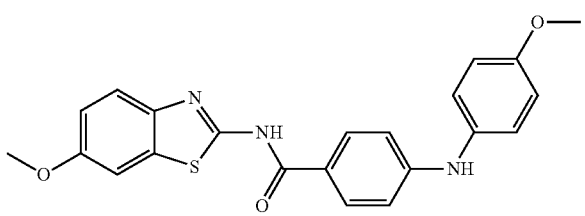

4-chloro-N-(6-methoxybenzo[d]thiazol-2-yl)benzamide (38 mg, 0.12 mmol), p-anisidine (18 mg, 0.14 mmol), Pd2(dba)3 (1.1 mg, 1 mol %), XPhos (1.3 mg, 2 mol %), potassium carbonate (36 mg, 2.62 mmol), and t-BuOH (0.3 ml) were treated in the manner described for Example XX to give the title compound (3.3 mg, 7%) as a solid: $^1$H NMR (400 MHz, Chloroform-d) δ 10.12 (s, 1H), 7.86-7.77 (m, 2H), 7.52 (d, J=8.8 Hz, 1H), 7.31 (d, J=2.6 Hz, 1H), 7.18-7.09 (m, 2H), 7.00 (dd, J=8.9, 2.6 Hz, 1H), 6.95-6.87 (m, 2H), 6.86-6.80 (m, 2H), 5.91 (s, 1H), 3.88 (s, 3H), 3.83 (s, 3H); LCMS (ESI) m/z 406.1 [M+1]$^+$.

Example 45:
4-azido-N-(6-methoxybenzo[d]thiazol-2-yl)benzamide

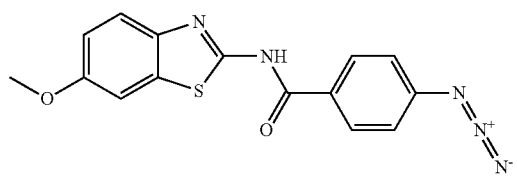 [SMILES: COc1ccc2nc(NC(=O)c3ccc(N=[N+]=[N-])cc3)sc2c1]

6-methoxybenzo[d]thiazol-2-amine (50 mg, 0.3 mmol), 4-azidobenzoic acid (0.5M in TBME, 0.4 mmol), T3P (50% w/w in ethyl acetate, 0.8 ml), and triethylamine (0.4 ml, 2.8 mmol) were treated in the manner described in General Procedure C to give the title compound: $^1$H NMR (400 MHz, DMSO-d6) δ 8.16 (d, J=8.7 Hz, 2H), 7.66 (d, J=8.9 Hz, 1H), 7.60 (d, J=2.5 Hz, 1H), 7.28 (d, J=8.6 Hz, 2H), 7.04 (dd, J=8.8, 2.6 Hz, 1H), 3.81 (s, 3H); LCMS (ESI) m/z 323.8 [M−1]$^-$.

Example 46:
2-azido-N-(6-methoxybenzo[d]thiazol-2-yl)benzamide

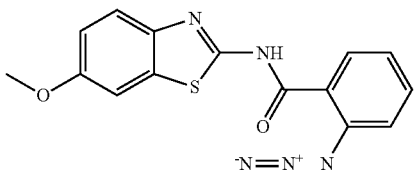

6-methoxybenzo[d]thiazol-2-amine (50 mg, 0.3 mmol), 2-azidobenzoic acid (0.5M in TBME, 0.4 mmol), T3P (50% w/w in ethyl acetate, 0.8 ml), and triethylamine (0.4 ml, 2.8 mmol) were treated in the manner described in General Procedure C to give the title compound: $^1$H NMR (400 MHz, Chloroform-d) δ 11.14 (s, 1H), 8.35 (dd, J=8.0, 1.6 Hz, 1H), 7.71 (d, J=8.9 Hz, 1H), 7.63 (td, J=7.8, 1.7 Hz, 1H), 7.38-7.27 (m, 3H), 7.06 (dd, J=8.9, 2.6 Hz, 1H), 3.88 (s, 3H); LCMS (ESI) m/z 323.8 [M−1]$^-$.

Example 47: 6-(prop-2-yn-1-yl-1,1-deutero-oxy)benzo[d]thiazol-2-amine

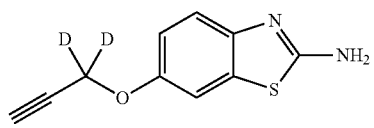 [SMILES: [2H]C([2H])(C#C)Oc1ccc2nc(N)sc2c1]

2-aminobenzo[d]thiazol-6-ol (25 mg, 0.15 mmol) was dissolved in DMF (0.3 ml) and the resulting solution was treated with cesium carbonate (98 mg, 0.3 mmol) and prop-2-yn-1-yl-1,1-deutero-4-methylbenzenesulfonate (35 mg, 0.17 mmol) and the mixture was allowed to stir 16 h at room temperature. The mixture was diluted with water and extracted with ethyl acetate several times, and the combined organic layer was dried (sodium sulfate), filtered, and concentrated under vacuum. The resulting solid was triturated with ether/methanol to give the title compound (25 mgs, 81%) as a solid: $^1$H NMR (400 MHz, Methanol-d4) δ 7.32-7.22 (m, 2H), 6.92 (dd, J=8.8, 2.6 Hz, 1H), 2.91 (s, 1H); LCMS (ESI) m/z 206.9 [M+1]$^+$.

Example 48: 4-benzoyl-N-(6-(prop-2-yn-1,1-deutero-1-yl-oxy)benzo[d]thiazol-2-yl)benzamide

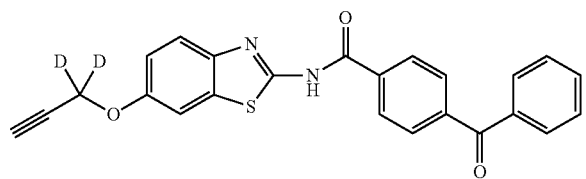 [SMILES: [2H]C([2H])(C#C)Oc1ccc2nc(NC(=O)c3ccc(C(=O)c4ccccc4)cc3)sc2c1]

6-(prop-2-yn-1-yl-1,1-deutero-oxy)benzo[d]thiazol-2-amine (12 mg, 0.056 mmol), 4-benzoylbenzoic acid (14 mg, 0.064 mmol), HATU (24 mg, 0.064 mmol), N,N-diisopropylethylamine (20 μl) and DMF (300 ml) were treated in the manner described in General Procedure D to give the title compound (18 mg, 75%) as a tan powder: $^1$H NMR (400 MHz, Chloroform-d) δ 11.05 (s, 1H), 8.09 (d, J=8.2 Hz, 2H), 7.86 (d, J=8.2 Hz, 2H), 7.79-7.74 (m, 2H), 7.63 (t, J=7.4 Hz, 1H), 7.50 (t, J=7.6 Hz, 2H), 7.45 (d, J=2.5 Hz, 1H), 7.37 (d, J=8.8 Hz, 1H), 7.03 (dd, J=8.9, 2.6 Hz, 1H), 2.54 (s, 1H); LCMS (ESI) m/z 412.9 [M−1]$^-$.

Example 49: 4-benzoyl-N-(6-hydroxybenzo[d]thiazol-2-yl)benzamide

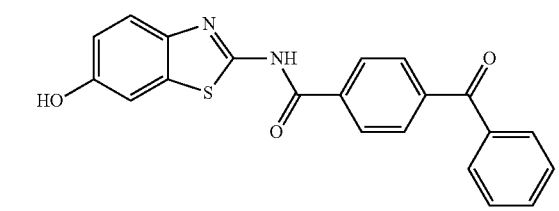 [SMILES: O=C(Nc1nc2ccc(O)cc2s1)c1ccc(C(=O)c2ccccc2)cc1]

2-aminobenzo[d]thiazol-6-ol (100 mg, 0.6 mmol), 4-benzoyl benzoic acid (150 mg, 0.66 mmol), HATU (250 mg, 0.66 mmol), diisopropylethylamine (0.21 ml), and DMF (0.42 ml) were treated in the manner described in General Procedure D to give the title compound (150 mg, 67%) as a solid: $^1$H NMR (400 MHz, DMSO-d6) δ 8.28 (d, J=7.8 Hz, 2H), 7.91 (d, J=8.2 Hz, 2H), 7.78 (d, J=7.5 Hz, 2H), 7.72 (t, J=7.4 Hz, 1H), 7.66 (d, J=2.5 Hz, 1H), 7.59 (t, J=7.6 Hz, 2H), 7.37 (d, J=8.6 Hz, 1H), 7.13 (dd, J=8.7, 2.5 Hz, 1H); LCMS (ESI) m/z 374.9 [M+1]$^+$.

Example 50: N-(5-aminobenzo[d]thiazol-2-yl)benzamide

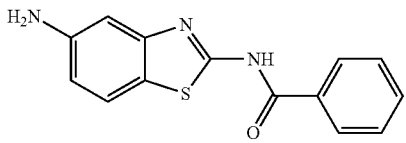 [SMILES: Nc1ccc2sc(NC(=O)c3ccccc3)nc2c1]

A vial was charged with N-(5-nitrobenzo[d]thiazol-2-yl)benzamide (*J. Het. Chem.* 1985, 22(3), 725-8) and palladium on activated carbon (10%), and the mixture was suspended in THF/MeOH/AcOH (8:4:1). The vial was sealed and equipped with a hydrogen balloon. After evacuation and back-filling of the vial, the mixture was stirred at room temperature 4 h, at which time TLC (SiO$_x$, 5% MeOH/CH$_2$Cl$_2$) indicated completion. The mixture was filtered through a pad of celite, and the pad was washed copiously with ethyl acetate. The filtrate was concentrated and the residue purified by silica gel chromatography (5% MeOH/CH$_2$Cl$_2$) to give the title compound as a solid (5 mg, 51%): $^1$H NMR (400 MHz, Chloroform-d) δ 8.08 (dd, J=7.5, 1.6 Hz, 2H), 7.66-7.47 (m, 4H), 6.83 (d, J=2.2 Hz, 1H), 6.73 (dd, J=8.5, 2.2 Hz, 1H); LCMS (ESI) m/z 269.9 [M+1]$^+$.

Example 51: N-(5-aminobenzo[d]thiazol-2-yl)-4-methoxybenzamide

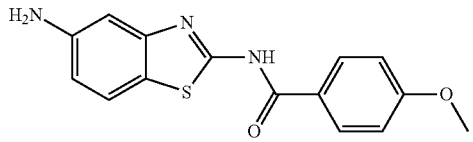 [SMILES: COc1ccc(C(=O)Nc2nc3cc(N)ccc3s2)cc1]

4-methoxy-N-(5-nitrobenzo[d]thiazol-2-yl)benzamide (50 mg, 0.15 mmol) was treated in the manner described for the preceding example, except that ethanol (1 ml) and conc. Hydrochloric acid (20 µl) was used as the solvent, to give the title compound: $^1$H NMR (500 MHz, DMSO-d6) δ 8.12 (d, J=8.7 Hz, 2H), 7.51 (d, J=8.4 Hz, 1H), 7.05 (d, J=8.6 Hz, 2H), 6.89 (d, J=2.1 Hz, 1H), 6.60 (dd, J=8.3, 2.0 Hz, 1H), 3.84 (s, 3H); LCMS (ESI) m/z 300.0 [M+1]$^+$

Example 52: 4-(hydroxy(phenyl)methyl)-N-(6-methoxybenzo[d]thiazol-2-yl)benzamide

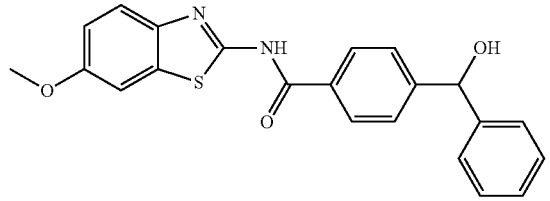 [SMILES: COc1ccc2nc(NC(=O)c3ccc(C(O)c4ccccc4)cc3)sc2c1]

4-benzoyl-N-(6-methoxybenzo[d]thiazol-2-yl)benzamide (20 mg, 0.052 mmol) was suspended in 0.5M ammonia in 1,4-dioxane (0.52 ml) and the mixture was treated with titanium tetraisopropoxide (41 µl, 0.14 mmol). The suspension became a yellow solution within a few minutes. After stirring 4.5 h at room temperature, sodium borohydride (10 mg) was added followed by ethanol (60 ml), whereupon gas evolution was noted. After 1 h TLC (5% MeOH/CH2Cl2) indicated completion. Ammonium hydroxide was added and the mixture was filtered. The filtrate was extracted with ethyl acetate several times and the combined organic layer was dried (sodium sulfate), filtered, and concentrated under vacuum. A white solid was obtained which was found to be the alcohol (17 mg, 84%) resulting from carbonyl reduction, not the desired primary amine, by LC/MS: $^1$H NMR (400 MHz, DMSO-d6) δ 12.65 (s, 1H), 8.09-8.00 (m, 2H), 7.65 (d, J=9.0 Hz, 1H), 7.59 (d, J=2.6 Hz, 1H), 7.54 (d, J=8.2 Hz, 2H), 7.42-7.37 (m, 2H), 7.30 (dd, J=8.4, 6.8 Hz, 2H), 7.23-7.17 (m, 1H), 7.04 (dd, J=8.8, 2.6 Hz, 1H), 6.06 (d, J=4.0 Hz, 1H), 5.78 (d, J=4.0 Hz, 1H), 3.80 (s, 3H); LCMS (ESI) m/z 390.9 [M+1]$^+$.

Example 53: 4-(azido(phenyl)methyl)-N-(6-methoxybenzo[d]thiazol-2-yl)benzamide

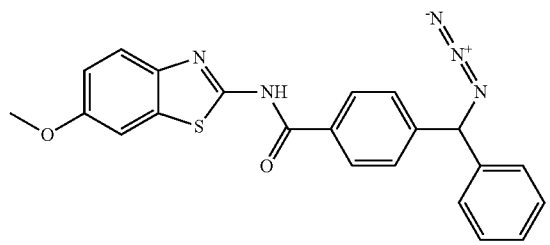

The product of the preceding example (20 mg, 0.05 mmol) was suspended in THF (200 µl), and the resulting mixture was treated with DBU (15 µl) and diphenylphosphoryl azide (22 µl) and heated at 50° C. for 4 h. The mixture cooled to room temperature and concentrated under vacuum, and the resulting residue was purified by silica gel chromatography (20% ethyl acetate/hexanes) to give the title compound (12 mg, 58%) as a solid: $^1$H NMR (500 MHz, DMSO-d6) δ 8.12 (d, J=8.4 Hz, 2H), 7.65 (d, J=8.2 Hz, 3H), 7.61 (d, J=2.5 Hz, 1H), 7.54-7.47 (m, 2H), 7.40 (t, J=7.6 Hz, 2H), 7.32 (dt, J=10.8, 7.4 Hz, 1H), 7.06 (dd, J=8.8, 2.5 Hz, 1H), 6.64 (s, 1H), 3.81 (s, 3H); LCMS (ESI) m/z 413.8 [M−1]$^−$.

Example 54: 4-(amino(phenyl)methyl)-N-(6-methoxybenzo[d]thiazol-2-yl)benzamide

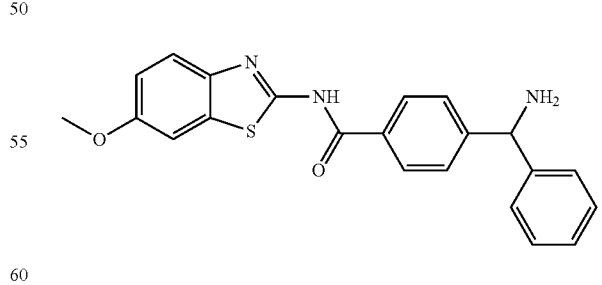

The product of the preceding example (91 mg, 0.22 mmol) was dissolved in THF (1 ml) and methanol (1 ml) and treated with palladium on carbon (10%). The mixture was stirred under a hydrogen atmosphere for 4 h, and the mixture was filtered through celite. The pad was washed copiously with methanol, and the filtrate concentrated under vacuum. The resulting solid was triturated with 40% acetonitrile/ water to give the title compound (58 mg, 68%) as a white solid: $^1$H NMR (400 MHz, Methanol-d4) δ 8.03-7.95 (m, 2H), 7.65 (d, J=8.8 Hz, 1H), 7.56 (d, J=8.3 Hz, 2H), 7.44 (d, J=2.5 Hz, 1H), 7.40-7.36 (m, 2H), 7.35-7.28 (m, 2H), 7.27-7.19 (m, 1H), 7.04 (dd, J=8.9, 2.5 Hz, 1H), 5.24 (s, 1H), 3.86 (s, 3H); LCMS (ESI) m/z 389.9 [M+1]$^+$.

Example 55:
N-(1H-benzo[d]imidazol-2-yl)-4-benzoylbenzamide

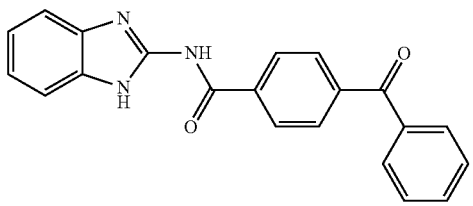 [SMILES: O=C(Nc1nc2ccccc2[nH]1)c1ccc(C(=O)c2ccccc2)cc1]

2-aminobenzimidazole (13 mg, 0.1 mmol), 4-benzoyl benzoic acid (25 mg, 0.11 mmol), HATU (42 mg, 0.11 mmol), diisopropylethylamine (0.34 ml), and DMF (1 ml) were treated in the manner described in General Procedure D to give the title compound (4.5 mg, 15%) as a crystalline solid (ethanol): $^1$H NMR (400 MHz, DMSO-d6) δ 12.45 (s, 2H), 8.32-8.24 (m, 2H), 7.83 (d, J=8.4 Hz, 2H), 7.79-7.74 (m, 2H), 7.73-7.67 (m, 1H), 7.58 (t, J=7.6 Hz, 2H), 7.44 (dd, J=6.0, 3.2 Hz, 2H), 7.16 (dd, J=5.9, 3.2 Hz, 2H); LCMS (ESI) m/z 342.1 [M+1]$^+$.

Example 56: (S)-4-(amino(phenyl)methyl)-N-(6-methoxybenzo[d]thiazol-2-yl)benzamide hydrochloride

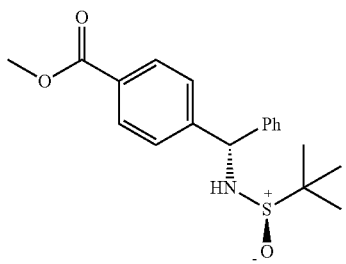

(R,E)-methyl 4-(((tert-butylsulfinyl)imino)methyl)benzoate (200 mg, 0.79 mmol), generated in the manner described by Ellman et al. (*Tetrahedron Lett.* 1999, 55, 8883), was treated with phenylmagnesium bromide (1.7M in ethyl ether) according to the procedure of Ellman et al. (ibid.) to give methyl 4-((S)-((R)-1,1-dimethylethylsulfinamido)(phenyl)methyl)benzoate (218 mg, 83%) as a solid: $^1$H NMR (400 MHz, Chloroform-d) δ 8.01 (d, J=8.3 Hz, 2H), 7.50 (d, J=8.3 Hz, 2H), 7.40-7.26 (m, 7H), 5.70 (d, J=2.2 Hz, 1H), 3.90 (s, 3H), 1.27 (s, 9H); LCMS (ESI) m/z 346.0 [M+1]$^+$.

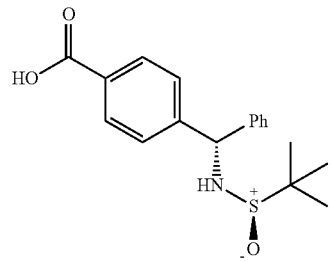

Methyl 4-((S)-((R)-1,1-dimethylethylsulfinamido)(phenyl)methyl)benzoate (100 mg, 0.3 mmol) was dissolved in THF (1 ml) and treated with a solution of lithium hydroxide (29 mg, 1.2 mmol) in water (1 ml). The mixture was stirred at room temperature for 16 h, and then concentrated under vacuum. The residue was dissolved in water (15 ml) and the pH was adjusted to 5 with 0.5M citric acid (aq). A precipitate resulted which was collected by filtration and dried under vacuum to give 4-((S)-((R)-1,1-dimethylethylsulfinamido)(phenyl)methyl)benzoic acid (62 mg, 65%) as a solid: $^1$H NMR (400 MHz, DMSO-d6) δ 12.88 (s, 1H), 7.92-7.82 (m, 2H), 7.48 (d, J=8.3 Hz, 2H), 7.44-7.36 (m, 2H), 7.31 (dd, J=8.3, 6.7 Hz, 2H), 7.28-7.18 (m, 1H), 6.08 (d, J=6.2 Hz, 1H), 5.60 (d, J=6.1 Hz, 1H), 1.12 (s, 9H); LCMS (ESI) m/z 329.9 [M−1]$^−$.

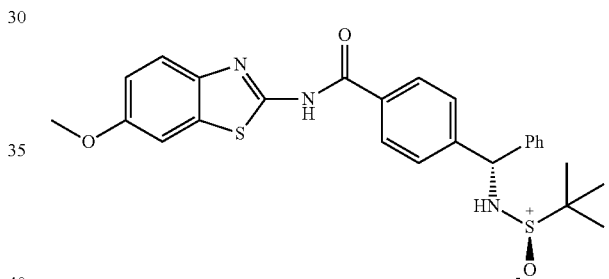

4-((S)-((R)-1,1-dimethylethylsulfinamido)(phenyl)methyl)benzoic acid (10 mg, 0.03 mmol) and 6-methoxybenzo[d]thiazol-2-amine (10 mg, 0.035 mmol) were treated in the manner described in General Procedure B to give 4-((S)-((R)-1,1-dimethylethylsulfinamido)(phenyl)methyl)-N-(6-methoxybenzo[d]thiazol-2-yl)benzamide (9 mg, 61%) as a solid: $^1$H NMR (400 MHz, Methanol-d4) δ 8.05-7.95 (m, 2H), 7.69-7.49 (m, 4H), 7.50-7.22 (m, 7H), 7.03 (dd, J=8.9, 2.6 Hz, 1H), 5.69 (d, J=7.5 Hz, 1H), 3.85 (s, 3H), 1.26 (s, 12H); LCMS (ESI) m/z 491.9 [M−1]$^−$.

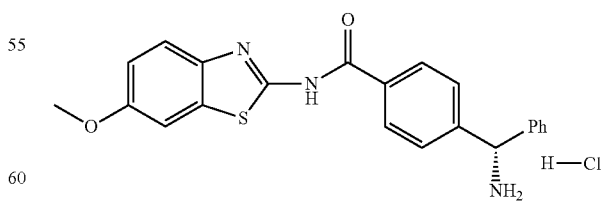

4-((S)-((R)-1,1-dimethylethylsulfinamido)(phenyl)methyl)-N-(6-methoxybenzo[d]thiazol-2-yl)benzamide (9 mg, 0.018 mmol) was dissolved in methanol (0.6 ml) treated with hydrogen chloride (4.0M in 1,4-dioxane, 0.6 ml) in the manner described by Ellman et al. (*Tetrahedron Lett.* 1999, 55, 8883) to give the title compound (6 mg) as a solid: $^1$H NMR (400 MHz, Methanol-d4) δ 8.00 (d, J=8.3 Hz, 2H), 7.64 (d, J=8.9 Hz, 1H), 7.55 (d, J=8.3 Hz, 2H), 7.43 (d, J=2.6 Hz, 1H), 7.38 (d, J=7.3 Hz, 2H), 7.35-7.29 (m, 2H), 7.26-7.20 (m, 1H), 7.03 (dd, J=8.9, 2.5 Hz, 1H), 5.23 (s, 1H), 3.86 (s, 3H); LCMS (ESI) m/z 389.9 [M+1]$^+$.

Example 57: (R)-4-(amino(phenyl)methyl)-N-(6-methoxybenzo[d]thiazol-2-yl)benzamide

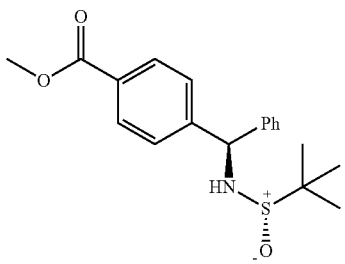

Analogous to the previous example, (S,E)-methyl 4-(((tert-butylsulfinyl)imino)methyl)benzoate (*Tetrahedron Lett.* 1999, 55, 8883; *Tetrahedron* 2008, 64, 6824-6830)(200 mg, 0.79 mmol) was treated with phenylmagnesium bromide (1.7M in ethyl ether, 0.51 ml) to give methyl 4-((R)-((S)-1,1-dimethylethylsulfinamido)(phenyl)methyl)benzoate (230 mg, 88%) as a solid after silica gel chromatography (10% Et$_2$O/CH$_2$Cl$_2$): $^1$H NMR (400 MHz, Chloroform-d) δ 8.01 (d, J=8.3 Hz, 2H), 7.50 (d, J=8.3 Hz, 2H), 7.40-7.26 (m, 5H), 5.70 (d, J=2.2 Hz, 1H), 3.90 (s, 3H), 1.27 (s, 9H).

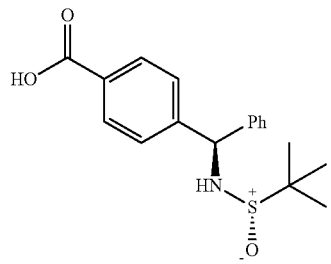

Methyl 4-((R)-((S)-1,1-dimethylethylsulfinamido)(phenyl)methyl)benzoate (230 mg, 0.67 mmol) was treated with lithium hydroxide (80 mg, 3.3 mmol) in the manner described in the previous example to give 4-((R)-((S)-1,1-dimethylethylsulfinamido)(phenyl)methyl)benzoic acid (150 mg, 68%) as a solid: $^1$H NMR (400 MHz, Chloroform-d) δ 8.09-8.01 (m, 2H), 7.57-7.50 (m, 2H), 7.40-7.22 (m, 5H), 5.72 (d, J=2.3 Hz, 1H), 3.92 (d, J=2.4 Hz, 1H), 1.28 (s, 9H); LCMS (ESI) m/z 329.9 [M-1]$^-$.

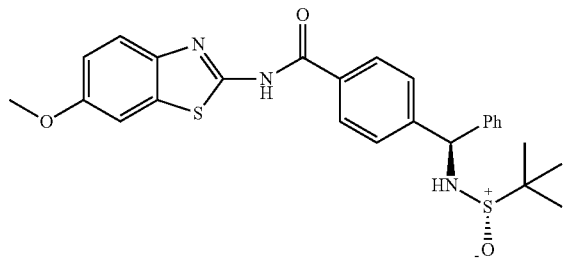

4-((R)-((S)-1,1-dimethylethylsulfinamido)(phenyl)methyl)benzoic acid (60 mg, 0.18 mmol) and 6-methoxybenzo[d]thiazol-2-amine (36 mg, 0.2 mmol) were treated in the manner described in General Procedure B to give 4-((R)-((S)-1,1-dimethylethylsulfinamido)(phenyl)methyl)-N-(6-methoxybenzo[d]thiazol-2-yl)benzamide (78 mg, 88%) as a solid: $^1$H NMR (400 MHz, Chloroform-d) δ 7.97 (d, J=8.2 Hz, 2H), 7.55 (d, J=7.8 Hz, 2H), 7.40-7.27 (m, 5H), 5.71 (d, J=2.3 Hz, 1H), 3.87 (s, 3H), 1.26 (s, 9H); LCMS (ESI) m/z 491.8 [M−1]$^-$.

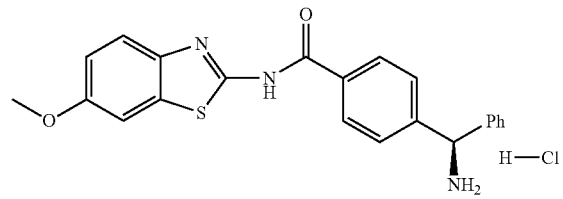

4-((R)-((S)-1,1-dimethylethylsulfinamido)(phenyl)methyl)-N-(6-methoxybenzo[d]thiazol-2-yl)benzamide (78 mg, 0.16 mmol) was dissolved in methanol (0.4 ml) and treated with hydrogen chloride (4.0M in 1,4-dioxane, 0.1 ml) in the manner described by Ellman et al. (*Tetrahedron Lett.* 1999, 55, 8883) to give the title compound (48 mg) as a solid: $^1$H NMR (400 MHz, DMSO-d6) δ 8.03 (d, J=8.2 Hz, 2H), 7.64 (d, J=8.8 Hz, 1H), 7.59-7.54 (m, 3H), 7.41 (d, J=7.6 Hz, 2H), 7.33-7.13 (m, 3H), 7.03 (dd, J=8.9, 2.5 Hz, 1H), 5.17 (s, 1H), 3.80 (s, 3H); LCMS (ESI) m/z 389.9 [M+1]$^+$.

Example 58: 4-benzoyl-N-(6-propoxybenzo[d]thiazol-2-yl)benzamide

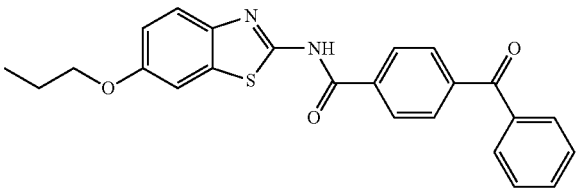 [SMILES: CCCOc1ccc2nc(NC(=O)c3ccc(C(=O)c4ccccc4)cc3)sc2c1]

4-benzoyl-N-(6-(prop-2-yn-1-yloxy)benzo[d]thiazol-2-yl)benzamide (30 mg, 0.07 mmol) and palladium on carbon (20%, Degussa type, 10 mg) were charged into a round-bottom flask, followed by ethyl acetate (1 ml). The flask was equipped with a hydrogen balloon attached to a three-way inlet, and subsequently evacuated and back-filled with hydrogen 4 times. The mixture stirred at room temperature for 1 h, and was then filtered through celite, and the celite pad was washed copiously with ethyl acetate. The filtrate was concentrated under vacuum and the residue triturated with ethyl ether/methanol to give the title compound (15 mg, 52%) as a golden solid: $^1$H NMR (400 MHz, Chloroform-d) δ 10.98 (s, 1H), 8.08 (d, J=8.1 Hz, 2H), 7.86 (d, J=8.1 Hz, 2H), 7.80-7.72 (m, 2H), 7.62 (t, J=7.5 Hz, 1H), 7.49 (t, J=7.6 Hz, 2H), 7.38-7.31 (m, 2H), 6.96 (dd, J=8.9, 2.5 Hz, 1H), 3.97 (t, J=6.5 Hz, 2H), 1.84 (h, J=7.1 Hz, 2H), 1.06 (t, J=7.4 Hz, 3H); LCMS (ESI) m/z 414.9 [M−1]$^−$.

Example 59: N-(4-benzoylphenyl)-6-(prop-2-yn-1-yloxy)benzo[d]thiazole-2-carboxamide

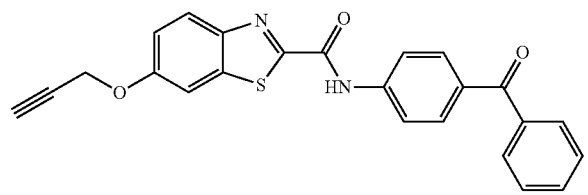 [SMILES: C#CCOc1ccc2nc(C(=O)Nc3ccc(C(=O)c4ccccc4)cc3)sc2c1]

L-Cysteine ethyl ester hydrochloride (1.7 g, 9.2 mmol), 1,4-benzoquinone (1.0 g, 9.25 mmol), and methanol (10 ml) were treated according to a literature procedure (Tetrahedron 2013, 69, 5893-97) to give ethyl 6-hydroxybenzo[d]thiazole-2-carboxylate (9.7 mg) as a solid. Spectroscopic data was consistent with reported values.

Ethyl 6-hydroxybenzo[d]thiazole-2-carboxylate (73 mg, 0.33 mmol) and potassium carbonate (138 mg, 1.0 mmol) were dissolved in DMF (1 ml), and the mixture was then treated with propargyl bromide (80% solution in toluene, 33 ml) and allowed to stir for 16 h at ambient temperature. Water was added to the mixture, and the resulting precipitate filtered, washed with water, and dried by aspiration to give ethyl 6-(prop-2-yn-1-yloxy)benzo[d]thiazole-2-carboxylate (76 mg) as a solid: $^1$H NMR (500 MHz, Chloroform-d) δ 8.15 (dd, J=9.1, 1.0 Hz, 1H), 7.49 (dd, J=2.6, 1.0 Hz, 1H), 7.29-7.21 (m, 1H), 4.81 (dd, J=2.4, 1.0 Hz, 2H), 4.55 (qd, J=7.1, 1.0 Hz, 2H), 2.59 (td, J=2.4, 1.0 Hz, 1H), 1.49 (td, J=7.2, 1.0 Hz, 3H).

Ethyl 6-(prop-2-yn-1-yloxy)benzo[d]thiazole-2-carboxylate was dissolved in 1,4-dioxane (3 ml) and the solution was expunged with nitrogen for 5 min, cooled to 0° C., and treated with 1M sodium hydroxide (also expunged with nitrogen prior to use). The mixture was stirred under nitrogen at 0° C. for 15 minutes, then 1M hydrochloric acid (7.5 ml) was added dropwise, whereupon a white precipitate formed. The precipitate was filtered and briefly dried under aspiration, then under vacuum to give the desired product, which was used directly in the next step.

According to General Procedure D, 6-(prop-2-yn-1-yloxy)benzo[d]thiazole-2-carboxylic acid (46 mg, 0.2 mmol), HATU (110 mg, 0.29 mmol), 4-aminobenzophenone (58 mg, 0.29 mmol) were dissolved in DMF (400 ml) and the resulting mixture was treated with N,N-diisopropylethyl amine (70 ml, 0.4 mmol), and the resulting mixture was stirred at ambient temperature for 16 h. Water was added to the mixture, and the resulting precipitate filtered and washed with water. After drying by aspiration, the solid was recrystallized from methanol/dichloromethane to give the title compound (21 mg) as a crystalline solid: $^1$H NMR (400 MHz, DMSO-d$_6$) δ 11.38 (s, 1H), 8.12 (dd, J=12.2, 8.9 Hz, 3H), 7.87 (d, J=2.6 Hz, 1H), 7.82-7.62 (m, 5H), 7.56 (t, J=7.6 Hz, 2H), 7.30 (dd, J=9.0, 2.6 Hz, 1H), 4.94 (d, J=2.4 Hz, 2H), 3.64 (t, J=2.2 Hz, 1H); LCMS ssg210-150-2

Example 60: N1-(6-hydroxybenzo[d]thiazol-2-yl)-N4-(prop-2-yn-1-yl)terephthalamide

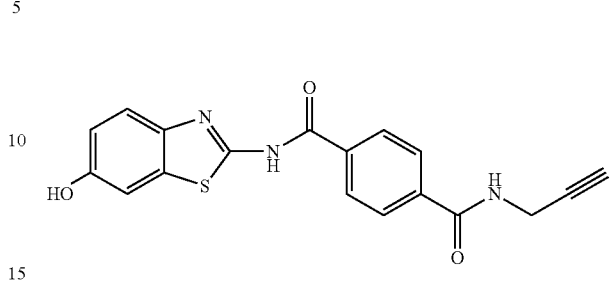

To a vial equipped with a magnetic stir bar was added 2-aminobenzo[d]thiazol-6-ol (500 mg, 3.0 mmol), monomethyl terephthalate (597 mg, 3.3 mmol), HATU (1.38 g, 3.6 mmol), and DMF (6 ml). The resulting solution was treated with N,N-diisopropylethyl amine (1.0 ml, 6.0 mmol), and the mixture was allowed to stir for 16 h at ambient temperature. Water was added to the mixture, and the resulting precipitate was washed with water and dried by aspiration to give methyl 4-((6-hydroxybenzo[d]thiazol-2-yl)carbamoyl)benzoate (907 mg, 92%): LCMS (ESI) m/z 329.2 [M+1]$^+$.

Methyl 4-((6-hydroxybenzo[d]thiazol-2-yl)carbamoyl)benzoate (100 mg, 0.3 mmol) was dissolved in THF (300 μl) and the resulting solution treated with lithium hydroxide (29 mg, 1.22 mmol) in water (300 μl). The mixture was stirred 3 h at ambient temperature, then concentrated in vacuo. The residue was dissolved in water (0.5 ml) and the mixture acidified with 1M hydrochloric acid (aq). The resulting precipitate was filtered, washed with water, and dried in vacuo to give 4-((6-hydroxybenzo[d]thiazol-2-yl)carbamoyl)benzoic acid (61 mg, 65%) as a solid: $^1$H NMR (500 MHz, DMSO-d$_6$) δ 9.62 (s, 1H), 9.10 (s, 1H), 8.19 (d, J=8.0 Hz, 2H), 8.07 (d, J=7.7 Hz, 2H), 7.59 (d, J=8.5 Hz, 1H), 7.35-7.30 (m, 1H), 6.92 (d, J=8.7 Hz, 1H), 6.64 (d, J=8.5 Hz, 1H).

4-((6-hydroxybenzo[d]thiazol-2-yl)carbamoyl)benzoic acid (100 mg, 0.32 mmol), propargylamine (19 mg, 0.35 mmol), and HATU (133 mg, 0.35 mmol) were dissolved in DMF (1 ml) and the resulting mixture was treated with triethylamine (60 ml, 0.4 mmol) and stirred for 16 h at ambient temperature according to General Procedure D. Water and ethyl acetate were added to the mixture and the layers separated, and the aqueous layer was back-extracted twice with ethyl acetate. The combined organic layer was dried (Na$_2$SO$_4$), filtered, and concentrated in vacuo to give the title compound (3.5 mg): $^1$H NMR (400 MHz, DMSO-d$_6$) δ 12.80 (s, 1H), 9.59 (s, 1H), 9.13 (t, J=5.4 Hz, 1H), 8.18 (d, J=8.0 Hz, 2H), 7.98 (d, J=8.1 Hz, 2H), 7.58 (d, J=8.4 Hz, 1H), 7.31 (d, J=2.9 Hz, 1H), 6.95-6.87 (m, 1H), 4.10-4.03 (m, 2H), 3.15 (s, 1H); LCMS ssg220-73-3

Example 61: 4-(4-methoxybenzoyl)-N-(6-(prop-2-yn-1-yloxy)benzo[d]thiazol-2-yl)benzamide

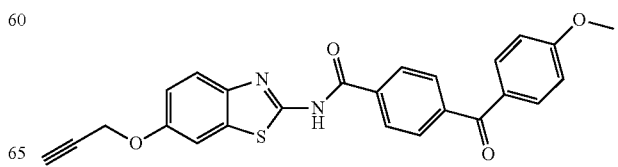

6-(prop-2-yn-1-yloxy)benzo[d]thiazol-2-amine (4 mg, 0.018 mmol), 4-(4-methoxybenzoyl)benzoic acid (synthesized according to Bong et al., *Eur. J. Org. Chem.* 2011, 751-758, 5 mg, 0.020 mmol), TBTU (10 mg, 0.030 mmol), and DMAP (≈10 mol %) were placed in a vial, followed by DMF (200 ml) and triethylamine (10 ml). The mixture was stirred for 1 h at 50° C., then overnight at ambient temperature, and then partitioned between ethyl acetate and water. The layers were separated, and the aqueous layer back-extracted with ethyl acetate twice. The combined organic layer was dried ($Na_2SO_4$), filtered, and concentrated in vacuo to give the crude product, which was purified by silica chromatography (10% ethyl ether/dichloromethane) to give the title compound (1.8 mg): $^1$H NMR (400 MHz, Chloroform-d) δ 10.49 (s, 1H), 8.11-8.04 (m, 2H), 7.88-7.74 (m, 4H), 7.53-7.43 (m, 2H), 7.07 (dd, J=8.9, 2.6 Hz, 1H), 7.02-6.94 (m, 2H), 4.76 (d, J=2.4 Hz, 2H), 3.91 (s, 3H), 2.55 (t, J=2.4 Hz, 1H).

Chromenone General Procedures

General Procedure E: Houben-Hoesch Condensation of Resorcinol with Nitriles

According the method described in *Chem. Het. Comm.* 1997, 33(5), 515, a solution of substituted phenoxyacetonitrile (5.0 mmol) in benzene (4 ml) was cooled to 0° C. and infused with hydrogen chloride gas for 1 h. A solution of freshly calcined zinc chloride (2.5 mmol) and resorcinol (6.0 mmol) in anhydrous ethyl ether (4 ml) was then added to the first solution, and the hydrogen chloride infusion was continued for 3 h while allowing the mixture to warm to ambient temperature. The mixture was allowed to stir 16 h at ambient temperature, and the supernatant liquid was then decanted from the solid precipitate. This solid was treated with water (20 ml) and the resulting mixture boiled for 1 h and then cooled to ambient temperature. The resulting solid was filtered and washed with water until the effluent was neutral as determined by pH paper. The resulting product was dried by aspiration and could be used as is or recrystallized form isopropanol if necessary.

General Procedure F: Cyclization of Aryloxy Ethers

According to the procedure of Garazd et al. (*Chem. Nat. Compd.* 1998, 34(4), 436), the products of General Procedure E (1 mmol) were dissolved in DMF (1.5 ml) and treated with boron trifluoride etherate (2 mmol), then phosphorus pentachloride (1.2 mmol) in portions. The resulting red mixture was stirred at 60° C. under a drying tube for 4 h, then treated with water (20 ml) and the mixture was boiled for 30 min. The mixture was then filtered while hot to remove an oily brown substance, and the filtrate allowed to cool to ambient temperature whereupon a precipitate formed. The precipitate was isolated by filtration and dried in vacuo to give the desired product. Extraction of the filtrate with dichloromethane yielded more product. Alternatively, the crude product can be digested by the addition of 5% hydrochloric acid and ethanol after the water boiling step, and the product thus obtained recrystallized from ethanol.

General Procedure G: Synthesis of Aryl Pyrazole Side-Chains

Ethyl 2-formyl-3-oxopropanoate (EP1364946/2003) (0.69 mmol), arylhydrazine (0.69 mmol), and ethanol (3 ml) were stirred in a sealed vial for 16 h. The solvent was removed in vacuo, and the resulting products dissolved in THF (1.5 ml) and treated with a solution of Red-Al (65% w/w in toluene). The resulting mixtures were stirred at ambient temperature for 2 h, then treated with a solution of Rochelle's Salt (30% aq., 4 ml). The mixtures were then extracted with ethyl acetate twice and the combined organic layer concentrated and passed through a short pad of silica (1:1 ethyl acetate/hexanes), and concentration of the filtrate gave the alcohol products. These products were then dissolved in dichloromethane (1 ml), treated with triethylamine (0.17 ml), cooled to 0° C. under nitrogen, and treated with methanesulfonyl chloride (80 μl), and the resulting mixtures were allowed to warm to ambient temperature over 1.5 h. The chloromethyl products were isolated by dilution with dichloromethane, washing the resulting mixture with water and brine, drying the organic layer ($MgSO_4$), followed by filtration and concentration in vacuo to give the chloromethyl pyrazole products, which were not stable to storage and used directly in the alkylation step.

General Procedure H: Alkylation of Hydroxychromones with Pyrazole Side-Chains

A reaction vial equipped with a stir bar was charged with hydroxychromone product of General Procedure F (0.34 mmol), chloromethyl pyrazole product of General Procedure G (0.34 mmol), cesium carbonate (0.45 mmol), and potassium iodide (10 mol %). The dry components were dissolved in DMF (0.6 ml) and the mixtures heated to 60° C. for 3 h. After cooling to ambient temperature, the reaction mixtures were partitioned between ethyl acetate and water, and the organic layer washed with 1M sodium hydroxide and brine, dried ($MgSO_4$), filtered, and concentrated in vacuo. The resulting crude products were triturated with cold ethanol to give the desired products as solids.

Example 62: 3-(2-chlorophenoxy)-7-((1-phenyl-1H-pyrazol-4-yl)methoxy)-4H-chromen-4-one (52 mg)

$^1$H NMR (400 MHz, DMSO-$d_6$) δ 8.71 (d, J=13.6 Hz, 2H), 7.97 (d, J=8.9 Hz, 1H), 7.90 (s, 1H), 7.87-7.78 (m, 2H), 7.54-7.44 (m, 3H), 7.39 (d, J=2.3 Hz, 1H), 7.35-7.26 (m, 1H), 7.23-7.12 (m, 2H), 7.09-6.94 (m, 2H), 5.23 (s, 2H).

Example 63: 3-(3-chlorophenoxy)-7-((1-phenyl-1H-pyrazol-4-yl)methoxy)-4H-chromen-4-one (34 mg)

$^1$H NMR (400 MHz, DMSO-$d_6$) δ 8.70 (d, J=4.1 Hz, 2H), 7.97 (d, J=8.9 Hz, 1H), 7.90 (s, 1H), 7.88-7.77 (m, 2H), 7.49 (t, J=7.9 Hz, 2H), 7.39 (d, J=2.3 Hz, 1H), 7.31 (dd, J=9.2, 7.4 Hz, 2H), 7.19-6.93 (m, 4H), 5.23 (s, 2H).

Example 64: 3-(3-fluorophenoxy)-7-((1-phenyl-1H-pyrazol-4-yl)methoxy)-4H-chromen-4-one (30 mg)

$^1$H NMR (400 MHz, DMSO-$d_6$) δ 8.70 (d, J=3.0 Hz, 2H), 7.97 (d, J=8.9 Hz, 1H), 7.92-7.76 (m, 3H), 7.58-7.43 (m, 2H), 7.41-7.24 (m, 3H), 7.15 (dd, J=8.9, 2.3 Hz, 1H), 6.96-6.77 (m, 3H), 5.23 (s, 2H).

Example 65: 3-(4-fluorophenoxy)-7-((1-phenyl-1H-pyrazol-4-yl)methoxy)-4H-chromen-4-one (49 mg)

$^1$H NMR (400 MHz, DMSO-$d_6$) δ 8.72-8.64 (m, 2H), 7.96 (d, J=8.9 Hz, 1H), 7.89 (s, 1H), 7.86-7.79 (m, 2H), 7.54-7.43 (m, 2H), 7.41-7.26 (m, 2H), 7.18-6.97 (m, 5H), 5.23 (s, 2H).

Example 66: 3-(4-methoxyphenoxy)-7-((1-phenyl-1H-pyrazol-4-yl)methoxy)-4H-chromen-4-one (32 mg)

$^1$H NMR (400 MHz, DMSO-$d_6$) δ 8.69 (s, 1H), 8.58 (s, 1H), 7.96 (d, J=8.9 Hz, 1H), 7.89 (d, J=0.7 Hz, 1H), 7.87-7.78 (m, 2H), 7.56-7.44 (m, 2H), 7.38-7.26 (m, 2H), 7.13 (dd, J=8.9, 2.3 Hz, 1H), 6.98-6.79 (m, 5H), 5.22 (s, 2H), 3.68 (s, 3H).

Example 67: 3-phenoxy-7-((1-phenyl-1H-pyrazol-4-yl)methoxy)-4H-chromen-4-one (41 mg)

$^1$H NMR (400 MHz, DMSO-d$_6$) δ 8.72-8.64 (m, 2H), 7.97 (d, J=8.9 Hz, 1H), 7.90 (d, J=0.7 Hz, 1H), 7.85-7.78 (m, 2H), 7.56-7.43 (m, 2H), 7.41-7.23 (m, 4H), 7.15 (dd, J=8.9, 2.4 Hz, 1H), 7.06-6.93 (m, 3H), 5.23 (s, 2H).

Example 68: 3-(2-bromophenoxy)-7-((1-phenyl-1H-pyrazol-4-yl)methoxy)-4H-chromen-4-one (53 mg)

$^1$H NMR (400 MHz, DMSO-d$_6$) δ 8.71 (d, J=11.5 Hz, 2H), 7.97 (d, J=8.9 Hz, 1H), 7.90 (s, 1H), 7.86-7.77 (m, 2H), 7.64 (dd, J=7.9, 1.5 Hz, 1H), 7.54-7.42 (m, 2H), 7.39 (d, J=2.3 Hz, 1H), 7.34-7.27 (m, 1H), 7.22 (ddd, J=8.2, 7.4, 1.6 Hz, 1H), 7.16 (dd, J=8.9, 2.4 Hz, 1H), 7.02-6.91 (m, 2H), 5.23 (s, 2H).

Example 69: 7-((1-phenyl-1H-pyrazol-4-yl)methoxy)-4H-chromen-4-one

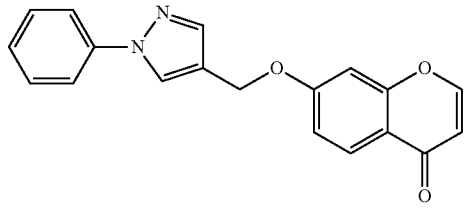 [SMILES: O=c1ccoc2cc(OCc3cnn(-c4ccccc4)c3)ccc12]

7-hydroxy-4H-chromen-4-one (1 g, 6.17 mmol), synthesized according to the method of Yu et al. (*J. Med. Chem.* 2004, 47(16), 4072), 4-(chloromethyl)-1-phenyl-1H-pyrazole (purchased commercially or synthesized according to General Procedure G, 1.3 g, 6.79 mmol), potassium carbonate (1.7 g, 12.3 mmol), and potassium iodide (103 mg, 10 mol %), and DMF (10 ml) were treated in the manner described for Example 88 (vide infra) to give the title compound (1.04 g, 53%) as a purple solid: $^1$H NMR (400 MHz, Chloroform-d) δ 8.14 (d, J=8.9 Hz, 1H), 8.03 (s, 1H), 7.84-7.65 (m, 4H), 7.47 (t, J=7.9 Hz, 2H), 7.36-7.27 (m, 1H), 7.04 (dd, J=8.9, 2.4 Hz, 1H), 6.94 (d, J=2.4 Hz, 1H), 6.29 (d, J=6.0 Hz, 1H), 5.14 (s, 2H).

Example 70: 3-iodo-7-((1-phenyl-1H-pyrazol-4-yl)methoxy)-4H-chromen-4-one

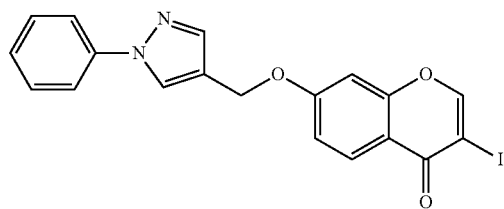 [SMILES: O=c1c(I)coc2cc(OCc3cnn(-c4ccccc4)c3)ccc12]

The product of Example XX (233 mg, 0.73 mmol) was suspended in methanol (1.5 ml) and the mixture was treated with pyrrolidine (300 ml) and heated at reflux for 16 h as described in *Synthesis* 1979, 901. Cooling to ambient temperature and filtering off the resulting precipitate gave the intermediate enamine (240 mg) which was dissolved in chloroform (1.2 ml), cooled to 0° C., and treated with iodine (100 mg). After stirring for 30 min while being allowed to warm to ambient temperature the mixture was diluted with chloroform and washed with sodium thiosulfate (sat. aq.), water, and brine, the organic layer was dried (Na$_2$SO$_4$), filtered, and concentrated in vacuo to give the title compound (230 mg, 88%) as a pale solid: $^1$H NMR (400 MHz, Chloroform-d) δ 8.25-8.14 (m, 2H), 8.03 (dd, J=1.6, 0.8 Hz, 1H), 7.81 (s, 1H), 7.69 (dq, J=7.1, 1.4 Hz, 2H), 7.47 (td, J=8.5, 8.0, 1.6 Hz, 2H), 7.37-7.24 (m, 4H), 7.07 (ddd, J=9.0, 2.5, 1.3 Hz, 1H), 6.94 (dd, J=2.4, 1.3 Hz, 1H), 5.17-5.12 (m, 2H). LCMS (ESI) m/z 444.8 [M]$^+$.

General Procedure I: Suzuki Coupling of Iodochromenone

A reaction vile equipped with a magnetic stir bar was charged with the product of Example XX (40 mg, 0.09 mmol), sodium carbonate (38 mg, 0.36 mmol), [PdCl$_2$(dppf)] (7 mg, 10 mol %), and a boronic acid or pinacolatoboronate ester (0.27 mmol). The vial was evacuated and back-filled with nitrogen, and 1:1 DME/water, previously degassed with nitrogen, was added (300 μl). The vial was heated to 50° C. for 16 h, cooled to ambient temperature, and the reaction mixture was diluted with dichloromethane, filtered through celite, and the filtrate layers separated. The organic layer was dried (Na$_2$SO$_4$), filtered, and concentrated in vacuo to give the crude products, which could be purified either by trituration with methanol or silica gel chromatography (1% methanol/dichloromethane) to give the desired products.

Example 71: 7-((1-phenyl-1H-pyrazol-4-yl)methoxy)-3-(pyridin-3-yl)-4H-chromen-4-one $^1$H NMR (400 MHz, Chloroform-d) δ 8.78 (s, 1H), 8.66 (d, J=4.9 Hz, 1H), 8.21 (d, J=8.9 Hz, 1H), 8.07 (d, J=18.6 Hz, 4H), 7.82 (s, 1H), 7.69 (d, J=8.0 Hz, 3H), 7.51-7.27 (m, 6H), 7.12-7.05 (m, 1H), 6.99 (s, 1H), 5.16 (s, 2H).

Example 72: 7-((1-phenyl-1H-pyrazol-4-yl)methoxy)-3-(pyridin-4-yl)-4H-chromen-4-one $^1$H NMR (400 MHz, Chloroform-d) δ 8.71-8.64 (m, 2H), 8.24 (d, J=8.9 Hz, 1H), 8.05 (d, J=2.4 Hz, 2H), 7.82 (s, 1H), 7.74-7.64 (m, 2H), 7.59-7.52 (m, 2H), 7.52-7.42 (m, 2H), 7.37-7.27 (m, 1H), 7.10 (dd, J=8.9, 2.4 Hz, 1H), 6.99 (d, J=2.4 Hz, 1H), 5.17 (s, 2H).

Example 73: 7-((1-phenyl-1H-pyrazol-4-yl)methoxy)-3-(pyridin-2-yl)-4H-chromen-4-one $^1$H NMR (400 MHz, Chloroform-d) δ 8.79 (s, 1H), 8.64-8.58 (m, 1H), 8.41 (d, J=8.0 Hz, 1H), 8.27 (d, J=8.9 Hz, 1H), 8.05 (s, 1H), 7.83 (s, 1H), 7.76 (td, J=7.7, 1.9 Hz, 1H), 7.70 (d, J=8.0 Hz, 2H), 7.47 (t, J=7.8 Hz, 2H), 7.32 (t, J=7.4 Hz, 1H), 7.29-7.22 (m, 1H), 7.09 (dd, J=8.9, 2.4 Hz, 1H), 7.01 (d, J=2.3 Hz, 1H), 5.16 (s, 2H).

Example 74: 3-(2-fluorophenyl)-7-((1-phenyl-1H-pyrazol-4-yl)methoxy)-4H-chromen-4-one $^1$H NMR (400 MHz, Chloroform-d) δ 8.23 (d, J=8.9 Hz, 1H), 8.05 (s, 1H), 7.98 (d, J=1.2 Hz, 1H), 7.82 (s, 1H), 7.73-7.67 (m, 2H), 7.48 (dtd, J=8.4, 7.3, 1.8 Hz, 4H), 7.41-7.28 (m, 2H), 7.24-7.12 (m, 2H), 7.11-7.03 (m, 1H), 6.98 (d, J=2.4 Hz, 1H), 5.16 (s, 2H).

Example 75: 3-(3-fluorophenyl)-7-((1-phenyl-1H-pyrazol-4-yl)methoxy)-4H-chromen-4-one $^1$H NMR (400 MHz, Chloroform-d) δ 8.24 (d, J=8.9 Hz, 1H), 8.05 (s, 1H), 7.97 (s, 1H), 7.82 (s, 1H), 7.73-7.63 (m, 2H), 7.52-7.43 (m, 2H), 7.43-7.28 (m, 4H), 7.13-7.00 (m, 2H), 6.97 (d, J=2.4 Hz, 1H), 5.16 (s, 2H), 1.30-1.21 (m, 1H), 0.92-0.77 (m, 1H).

Example 76: 3-(4-fluorophenyl)-7-((1-phenyl-1H-pyrazol-4-yl)methoxy)-4H-chromen-4-one $^1$H NMR (400 MHz, Chloroform-d) δ 8.24 (d, J=8.9 Hz, 1H), 8.05 (s, 1H), 7.94 (s, 1H), 7.82 (s, 1H), 7.70 (dd, J=7.9, 1.6 Hz, 2H), 7.58-7.43 (m, 4H), 7.32 (t, J=7.5 Hz, 1H), 7.17-7.03 (m, 3H), 6.97 (d, J=2.3 Hz, 1H), 5.16 (s, 2H), 1.30-1.17 (m, 1H).

Example 77: 3-(3-methoxyphenyl)-7-((1-phenyl-1H-pyrazol-4-yl)methoxy)-4H-chromen-4-one $^1$H NMR (500 MHz, Chloroform-d) δ 8.26 (d, J=8.9 Hz, 1H), 8.06 (d, J=0.9 Hz, 1H), 7.98 (s, 1H), 7.84 (s, 1H), 7.74-7.67 (m, 2H), 7.52-7.44 (m, 2H), 7.40-7.29 (m, 2H), 7.19-7.05 (m, 3H), 7.00-6.92 (m, 2H), 5.17 (s, 2H), 3.86 (s, 3H).

Example 78: 3-(3-hydroxyphenyl)-7-((1-phenyl-1H-pyrazol-4-yl)methoxy)-4H-chromen-4-one $^1$H NMR (400 MHz, DMSO-d$_6$) δ 9.46 (s, 1H), 8.69 (s, 1H), 8.42 (s, 1H), 8.03 (d, J=8.9 Hz, 1H), 7.89 (s, 2H), 7.86-7.79 (m, 3H), 7.49 (q, J=7.8 Hz, 4H), 7.35-7.27 (m, 3H), 7.25-7.10 (m, 3H), 7.03-6.91 (m, 3H), 6.76 (d, J=8.5 Hz, 1H), 5.22 (s, 2H).

Example 79: 3-(cyclohex-1-en-1-yl)-7-((1-phenyl-1H-pyrazol-4-yl)methoxy)-4H-chromen-4-one $^1$H NMR (400 MHz, Chloroform-d) δ 8.16 (d, J=8.9 Hz, 1H), 8.07-8.01 (m, 1H), 7.81 (s, 1H), 7.77-7.65 (m, 3H), 7.52-7.27 (m, 3H), 7.11-6.94 (m, 1H), 6.90 (d, J=2.4 Hz, 1H), 6.02 (tt, J=3.8, 1.7 Hz, 1H), 5.13 (s, 2H), 2.40-2.31 (m, 2H), 2.22-2.13 (m, 2H), 1.81-1.61 (m, 4H).

Example 80: 3-(4-ethoxyphenyl)-7-((1-phenyl-1H-pyrazol-4-yl)methoxy)-4H-chromen-4-one $^1$H NMR (400 MHz, Chloroform-d) δ 8.24 (d, J=8.9 Hz, 1H), 8.05 (d, J=0.8 Hz, 1H), 7.93 (s, 1H), 7.82 (d, J=0.7 Hz, 1H), 7.74-7.66 (m, 2H), 7.53-7.42 (m, 5H), 7.37-7.22 (m, 7H), 7.06 (dd, J=8.9, 2.4 Hz, 1H), 7.00-6.90 (m, 4H), 5.16 (s, 2H), 4.07 (qd, J=7.0, 2.4 Hz, 3H), 1.43 (t, J=7.0 Hz, 5H).

Example 81: 3-(2,4-difluorophenyl)-7-((1-phenyl-1H-pyrazol-4-yl)methoxy)-4H-chromen-4-one $^1$H NMR (500 MHz, Chloroform-d) δ 8.24 (d, J=8.9 Hz, 1H), 8.06 (s, 1H), 7.98 (d, J=1.2 Hz, 1H), 7.84 (s, 1H), 7.74-7.68 (m, 2H), 7.54-7.45 (m, 3H), 7.37-7.30 (m, 1H), 7.12-7.02 (m, 1H), 7.02-6.89 (m, 3H), 5.18 (s, 2H).

Example 82: 3-cyclopropyl-7-((1-phenyl-1H-pyrazol-4-yl)methoxy)-4H-chromen-4-one $^1$H NMR (400 MHz, Chloroform-d) δ 8.17 (d, J=8.9 Hz, 1H), 8.05-8.00 (m, 1H), 7.80 (d, J=0.7 Hz, 1H), 7.73-7.64 (m, 2H), 7.56 (d, J=1.1 Hz, 1H), 7.51-7.41 (m, 2H), 7.36-7.27 (m, 1H), 7.02 (dd, J=8.9, 2.4 Hz, 1H), 6.89 (d, J=2.4 Hz, 1H), 5.13 (s, 2H), 1.87 (dddd, J=8.4, 7.3, 5.9, 4.8 Hz, 1H), 0.95-0.84 (m, 2H), 0.64-0.52 (m, 2H).

Example 83: 3-(naphthalen-2-yl)-7-((1-phenyl-1H-pyrazol-4-yl)methoxy)-4H-chromen-4-one $^1$H NMR (500 MHz, Chloroform-d) δ 8.29 (d, J=8.9 Hz, 1H), 8.11-8.05 (m, 3H), 8.00-7.86 (m, 6H), 7.71 (ddd, J=8.4, 3.6, 1.5 Hz, 3H), 7.54-7.51 (m, 2H), 7.34 (t, J=7.5 Hz, 1H), 7.11 (dd, J=8.9, 2.4 Hz, 1H), 7.01 (d, J=2.4 Hz, 1H), 5.19 (s, 2H).

Example 84: 3-(3,4-difluorophenyl)-7-((1-phenyl-1H-pyrazol-4-yl)methoxy)-4H-chromen-4-one $^1$H NMR (500 MHz, Chloroform-d) δ 8.24 (d, J=8.9 Hz, 1H), 8.06 (s, 1H), 7.97 (s, 1H), 7.84 (s, 1H), 7.74-7.61 (m, 2H), 7.53-7.43 (m, 4H), 7.38-7.31 (m, 1H), 7.23 (dt, J=10.0, 8.2 Hz, 1H), 7.13-7.05 (m, 1H), 6.99 (d, J=2.3 Hz, 1H), 5.18 (s, 2H), 1.57 (s, 1H).

Example 85: 3-(4-methoxy-2-methylphenyl)-7-((1-phenyl-1H-pyrazol-4-yl)methoxy)-4H-chromen-4-one $^1$H NMR (400 MHz, Chloroform-d) δ 8.22 (d, J=8.9 Hz, 1H), 8.05 (d, J=0.8 Hz, 1H), 7.82 (d, J=0.7 Hz, 1H), 7.79 (s, 1H), 7.74-7.64 (m, 2H), 7.52-7.42 (m, 2H), 7.37-7.27 (m, 1H), 7.13-7.02 (m, 2H), 6.97 (d, J=2.3 Hz, 1H), 6.86-6.82 (m, 1H), 6.77 (ddd, J=8.5, 2.7, 0.7 Hz, 1H), 5.16 (s, 2H), 3.82 (s, 3H), 2.23 (s, 3H).

Example 86: 3-(3,5-bis(trifluoromethyl)phenyl)-7-((1-phenyl-1H-pyrazol-4-yl)methoxy)-4H-chromen-4-one $^1$H NMR (500 MHz, Chloroform-d) δ 8.25 (d, J=8.9 Hz, 1H), 8.10-8.05 (m, 4H), 7.91 (d, J=1.8 Hz, 1H), 7.84 (s, 1H), 7.74-7.69 (m, 2H), 7.49 (dd, J=8.6, 7.4 Hz, 2H), 7.38-7.29 (m, 1H), 7.13 (dd, J=8.9, 2.4 Hz, 1H), 7.02 (d, J=2.4 Hz, 1H), 5.19 (s, 2H).

Example 87: 3-(3-hydroxyphenyl)-7-((1-phenyl-1H-pyrazol-4-yl)methoxy)-4H-chromen-4-one $^1$H NMR (400 MHz, DMSO-d$_6$) δ 9.47 (s, 1H), 8.69 (s, 1H), 8.42 (s, 1H), 8.03 (d, J=8.9 Hz, 1H), 7.89 (s, 1H), 7.86-7.78 (m, 2H), 7.54-7.44 (m, 2H), 7.36-7.25 (m, 2H), 7.25-7.08 (m, 2H), 7.04-6.91 (m, 2H), 6.76 (ddd, J=8.1, 2.5, 1.0 Hz, 1H), 5.21 (s, 2H).

Example 88: 7-((1-phenyl-1H-pyrazol-4-yl)methoxy)chroman-4-one

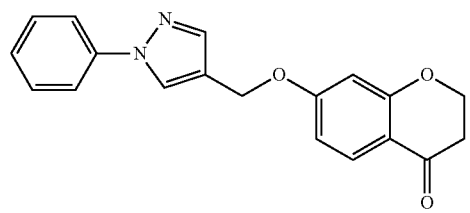 [SMILES: O=C1CCOc2cc(OCc3cnn(-c4ccccc4)c3)ccc21]

7-hydroxychroman-4-one (703 mg, 4.3 mmol), synthesized according to the method of Koch and Biggers (*J. Org. Chem.* 1994, 59, 1216), was placed in a reaction vial, and to the vial was added 4-(chloromethyl)-1-phenyl-1H-pyrazole (purchased commercially or synthesized according to General Procedure G, 900 mg, 4.71 mmol), potassium carbonate (1.8 g, 13 mmol), and potassium iodide (71 mg, 10 mol %), followed by DMF (8 ml). The mixture was heated to 50° C. for 1 h, cooled to ambient temperature, and treated with water (40 ml). The resulting rose-colored precipitate was filtered and dried under aspiration and vacuum, and recrystallized from ethanol to give 970 mg (70%) of desired product as fine needles: $^1$H NMR (400 MHz, Chloroform-d) δ 8.01 (d, J=0.8 Hz, 1H), 7.86 (d, J=8.8 Hz, 1H), 7.78 (d, J=0.7 Hz, 1H), 7.72-7.62 (m, 2H), 7.51-7.41 (m, 2H), 7.39-7.26 (m, 1H), 6.65 (dd, J=8.8, 2.4 Hz, 1H), 6.50 (d, J=2.4 Hz, 1H), 5.07 (s, 2H), 4.53 (t, J=6.3 Hz, 2H), 2.77 (t, J=6.3 Hz, 2H).

General Procedure J: Condensation of Aldehydes with Chromone from Example 88

The product of Example 88 (40 mg, 0.13 mmol), an aldehyde (0.25 mmol), pyrrolidine (0.15 mmol), and methanol (400 μl) were treated in the manner described by Meyers et al. (*J. Med. Chem.* 2010, 53(16), 5979-6002) except that the mixtures were heated at 40° C. for 16 h, to give the corresponding alkene products.

Example 89: (E)-3-(4-fluorobenzylidene)-7-((1-phenyl-1H-pyrazol-4-yl)methoxy)chroman-4-one (35 mg)

$^1$H NMR (400 MHz, Chloroform-d) δ 8.04-7.95 (m, 2H), 7.79 (d, J=6.3 Hz, 2H), 7.72-7.65 (m, 2H), 7.50-7.39 (m, 2H), 7.35-7.23 (m, 4H), 7.18-7.09 (m, 2H), 6.71 (dt, J=9.0, 1.8 Hz, 1H), 6.50 (t, J=1.8 Hz, 1H), 5.34-5.28 (m, 2H), 5.08 (s, 2H).

Example 90: (E)-7-((1-phenyl-1H-pyrazol-4-yl)methoxy)-3-(2-(trifluoromethyl)benzylidene)chroman-4-one (20 mg)

$^1$H NMR (400 MHz, Chloroform-d) δ 8.01 (t, J=4.4 Hz, 3H), 7.81-7.70 (m, 2H), 7.68 (d, J=8.0 Hz, 2H), 7.60 (t, J=7.6 Hz, 1H), 7.48 (dt, J=18.6, 7.8 Hz, 3H), 7.31 (t, J=7.4 Hz, 1H), 7.17 (d, J=7.5 Hz, 1H), 6.72 (dd, J=8.9, 2.3 Hz, 1H), 6.49 (d, J=2.4 Hz, 1H), 5.11-5.02 (m, 4H).

Example 91: (E)-3-(2-fluorobenzylidene)-7-((1-phenyl-1H-pyrazol-4-yl)methoxy)chroman-4-one (32 mg)

$^1$H NMR (400 MHz, Chloroform-d) δ 8.04-7.96 (m, 2H), 7.87-7.76 (m, 2H), 7.72-7.56 (m, 2H), 7.51-7.35 (m, 3H), 7.35-7.28 (m, 1H), 7.25-7.10 (m, 3H), 6.71 (dd, J=8.8, 2.4 Hz, 1H), 6.50 (d, J=2.4 Hz, 1H), 5.18 (t, J=1.7 Hz, 2H), 5.08 (s, 2H).

Example 92: (E)-7-((1-phenyl-1H-pyrazol-4-yl)methoxy)-3-(3-(trifluoromethyl)benzylidene)chroman-4-one (28 mg)

$^1$H NMR (400 MHz, Chloroform-d) δ 8.04-7.92 (m, 2H), 7.87-7.76 (m, 2H), 7.72-7.63 (m, 3H), 7.62-7.51 (m, 2H), 7.46 (t, J=7.7 Hz, 3H), 7.35-7.28 (m, 1H), 6.72 (ddd, J=8.9, 2.4, 1.0 Hz, 1H), 6.55-6.48 (m, 1H), 5.33-5.27 (m, 2H), 5.09 (s, 2H).

Example 93: (E)-7-((1-phenyl-1H-pyrazol-4-yl)methoxy)-3-(4-(trifluoromethyl)benzylidene)chroman-4-one (32 mg)

$^1$H NMR (400 MHz, Chloroform-d) δ 8.04-7.96 (m, 2H), 7.87-7.74 (m, 2H), 7.74-7.65 (m, 4H), 7.51-7.37 (m, 4H), 7.36-7.26 (m, 1H), 6.72 (dd, J=8.9, 2.4 Hz, 1H), 6.51 (d, J=2.4 Hz, 1H), 5.29 (d, J=1.9 Hz, 2H), 5.09 (s, 2H).

Example 94: (E)-3-(4-methylbenzylidene)-7-((1-phenyl-1H-pyrazol-4-yl)methoxy)chroman-4-one (19 mg)

$^1$H NMR (400 MHz, Chloroform-d) δ 8.04-7.93 (m, 2H), 7.88-7.74 (m, 2H), 7.68 (dd, J=8.3, 1.4 Hz, 2H), 7.46 (t, J=7.9 Hz, 2H), 7.37-7.15 (m, 6H), 6.70 (dd, J=8.8, 2.3 Hz, 1H), 6.50 (d, J=2.3 Hz, 1H), 5.35 (d, J=1.9 Hz, 2H), 5.08 (s, 2H), 2.40 (s, 3H).

Example 95: (E)-7-((1-phenyl-1H-pyrazol-4-yl)methoxy)-3-(pyridin-4-ylmethylene)chroman-4-one $^1$H NMR (500 MHz, Chloroform-d) δ 8.93-8.87 (m, 1H), 8.51 (d, J=5.0 Hz, 2H), 8.14 (dd, J=9.0, 1.3 Hz, 1H), 8.04 (s, 1H), 7.81 (s, 1H), 7.76-7.61 (m, 5H), 7.50-7.41 (m, 3H), 7.37-7.25 (m, 2H), 7.23 (d, J=1.6 Hz, 2H), 7.12-7.01 (m, 1H), 6.94-6.90 (m, 1H), 5.13 (s, 2H), 3.78 (s, 2H).

Example 96: (E)-3-((1H-imidazol-5-yl)methylene)-7-((1-phenyl-1H-pyrazol-4-yl)methoxy)chroman-4-one $^1$H NMR (400 MHz, Chloroform-d) δ 8.04-7.92 (m, 2H), 7.78 (d, J=11.6 Hz, 2H), 7.72-7.61 (m, 3H), 7.46 (t, J=7.6 Hz, 2H), 7.38-7.23 (m, 4H), 6.72-6.64 (m, 1H), 6.56-6.50 (m, 1H), 5.83 (s, 2H), 5.08 (s, 2H).

Example 97: (E)-3-((2-methoxypyridin-3-yl)methylene)-7-((1-phenyl-1H-pyrazol-4-yl)methoxy)chroman-4-one $^1$H NMR (400 MHz, Chloroform-d) δ 8.13 (d, J=8.9 Hz, 1H), 8.06-7.99 (m, 2H), 7.82-7.73 (m, 2H), 7.72-7.61 (m, 3H), 7.50-7.40 (m, 2H), 7.35-7.25 (m, 1H), 7.00 (dd, J=8.9, 2.4 Hz, 1H), 6.91-6.78 (m, 2H), 5.11 (s, 2H), 3.96 (s, 3H), 3.71 (s, 2H).

Example 98: (E)-7-((1-phenyl-1H-pyrazol-4-yl)methoxy)-3-(thiazol-2-ylmethylene)chroman-4-one $^1$H NMR (400 MHz, Chloroform-d) δ 8.16 (d, J=8.9 Hz, 1H), 8.04-8.00 (m, 1H), 7.93 (d, J=1.0 Hz, 1H), 7.80 (s, 1H), 7.72-7.66 (m, 4H), 7.50-7.41 (m, 3H), 7.35-7.27 (m, 2H), 7.22 (d, J=3.3 Hz, 1H), 7.03 (dd, J=8.9, 2.4 Hz, 1H), 6.92 (d, J=2.3 Hz, 1H), 5.13 (s, 2H), 4.19 (d, J=1.0 Hz, 2H).

General Procedure K: Isomerization of Alkenes from General Procedure J

The products of General Procedure J were placed in a reaction vial, dissolved in acetonitrile (0.3 ml), and treated with DBU (11 μl). The mixture was heated at 50° C. for 16 h. Upon cooling to ambient temperature, the products usually precipitated and were of sufficient purity, but in some cases had to be purified by silica gel chromatography (methanol/dichloromethane).

Example 99: 3-(4-fluorobenzyl)-7-((1-phenyl-1H-pyrazol-4-yl)methoxy)-4H-chromen-4-one (25 mg)

$^1$H NMR (500 MHz, Chloroform-d) δ 8.15 (d, J=9.0 Hz, 1H), 8.04 (s, 1H), 7.81 (s, 1H), 7.72-7.66 (m, 2H), 7.57 (t, J=1.1 Hz, 1H), 7.51-7.42 (m, 2H), 7.36-7.23 (m, 4H), 7.06-6.95 (m, 3H), 6.90 (d, J=2.4 Hz, 1H), 5.12 (s, 2H), 3.77 (s, 2H).

Example 100: 7-((1-phenyl-1H-pyrazol-4-yl)methoxy)-3-(2-(trifluoromethyl)benzyl)-4H-chromen-4-one (10 mg)

$^1$H NMR (400 MHz, Chloroform-d) δ 8.18 (d, J=8.9 Hz, 4H), 8.03 (s, 4H), 7.80 (s, 4H), 7.72-7.60 (m, 12H), 7.51-7.41 (m, 15H), 7.41-7.27 (m, 11H), 7.04 (dd, J=9.0, 2.4 Hz, 4H), 6.89 (d, J=2.4 Hz, 4H), 5.12 (s, 7H), 4.02 (s, 7H).

Example 101: 3-(2-fluorobenzyl)-7-((1-phenyl-1H-pyrazol-4-yl)methoxy)-4H-chromen-4-one (22 mg)

$^1$H NMR (500 MHz, Chloroform-d) δ 8.16 (d, J=8.9 Hz, 1H), 8.04 (s, 1H), 7.81 (s, 1H), 7.72-7.64 (m, 3H), 7.50-7.37 (m, 3H), 7.32 (t, J=7.5 Hz, 2H), 7.22 (tdd, J=7.6, 5.3, 1.8 Hz, 1H), 7.13-6.99 (m, 3H), 6.90 (d, J=2.4 Hz, 1H), 5.12 (s, 2H), 3.83 (s, 2H), 1.87 (s, 0H).

Example 102: 7-((1-phenyl-1H-pyrazol-4-yl)methoxy)-3-(3-(trifluoromethyl)benzyl)-4H-chromen-4-one (18 mg)

$^1$H NMR (400 MHz, Chloroform-d) δ 8.14 (d, J=8.9 Hz, 1H), 8.02 (d, J=0.9 Hz, 1H), 7.80 (s, 1H), 7.70-7.65 (m, 2H), 7.62 (d, J=1.1 Hz, 1H), 7.56-7.38 (m, 7H), 7.35-7.27 (m, 1H), 7.03 (dd, J=8.9, 2.4 Hz, 1H), 6.90 (d, J=2.3 Hz, 1H), 5.12 (s, 2H), 3.84 (s, 2H).

Example 103: 7-((1-phenyl-1H-pyrazol-4-yl)methoxy)-3-(4-(trifluoromethyl)benzyl)-4H-chromen-4-one (22 mg)

$^1$H NMR (400 MHz, Chloroform-d) δ 8.14 (d, J=8.9 Hz, 1H), 8.02 (s, 1H), 7.80 (s, 1H), 7.72-7.61 (m, 3H), 7.55 (d, J=8.1 Hz, 2H), 7.51-7.39 (m, 4H), 7.36-7.28 (m, 1H), 7.03 (dd, J=8.9, 2.4 Hz, 1H), 6.90 (d, J=2.4 Hz, 1H), 5.13 (s, 2H), 3.84 (s, 2H).

Example 104: 3-(4-methylbenzyl)-7-((1-phenyl-1H-pyrazol-4-yl)methoxy)-4H-chromen-4-one (9 mg)

$^1$H NMR (400 MHz, Chloroform-d) δ 8.15 (d, J=8.9 Hz, 1H), 8.02 (d, J=0.8 Hz, 1H), 7.80 (s, 1H), 7.72-7.62 (m, 2H), 7.52 (d, J=1.1 Hz, 1H), 7.50-7.42 (m, 2H), 7.35-7.28 (m, 1H), 7.19 (d, J=8.0 Hz, 2H), 7.12 (d, J=7.8 Hz, 2H), 7.01 (dd, J=8.9, 2.4 Hz, 1H), 6.88 (d, J=2.3 Hz, 1H), 5.11 (s, 2H), 3.76 (s, 2H), 2.32 (s, 3H).

Example 105: 7-((1-phenyl-1H-pyrazol-4-yl)methoxy)-3-(pyridin-2-ylmethyl)-4H-chromen-4-one (13 mg)

$^1$H NMR (500 MHz, Chloroform-d) δ 8.55-8.49 (m, 1H), 8.13 (d, J=8.9 Hz, 1H), 8.03 (s, 1H), 7.89 (d, J=1.1 Hz, 1H), 7.81 (s, 1H), 7.74-7.66 (m, 2H), 7.62 (td, J=7.7, 1.8 Hz, 1H), 7.50-7.41 (m, 3H), 7.35-7.28 (m, 1H), 7.13 (ddd, J=7.5, 4.9, 1.2 Hz, 1H), 7.01 (dd, J=8.9, 2.4 Hz, 1H), 6.91 (d, J=2.4 Hz, 1H), 5.12 (s, 2H), 3.95 (s, 2H).

Example 106: 3-(4-bromobenzyl)-7-((1-phenyl-1H-pyrazol-4-yl)methoxy)-4H-chromen-4-one (18 mg)

$^1$H NMR (500 MHz, Chloroform-d) δ 8.15 (d, J=8.9 Hz, 4H), 8.04 (s, 4H), 7.81 (s, 4H), 7.72-7.63 (m, 9H), 7.59 (d, J=1.2 Hz, 4H), 7.51-7.37 (m, 18H), 7.37-7.28 (m, 5H), 7.22-7.15 (m, 8H), 7.03 (dd, J=8.9, 2.3 Hz, 4H), 6.90 (d, J=2.3 Hz, 4H), 5.13 (s, 8H), 3.74 (s, 8H).

Example 107: 3-((1H-imidazol-5-yl)methyl)-7-((1-phenyl-1H-pyrazol-4-yl)methoxy)-4H-chromen-4-one $^1$H NMR (400 MHz, Methanol-$d_4$) δ 8.36 (s, 1H), 7.92-7.78 (m, 3H), 7.78-7.67 (m, 2H), 7.63 (t, J=1.9 Hz, 1H), 7.54-7.41 (m, 3H), 7.38-7.28 (m, 1H), 6.74 (dd, J=8.8, 2.4 Hz, 1H), 6.63 (d, J=2.4 Hz, 2H), 5.66 (s, 1H), 5.15 (s, 2H).

Example 108: 7-((1-phenyl-1H-pyrazol-4-yl)methoxy)-3-(thiophen-2-ylmethyl)-4H-chromen-4-one $^1$H NMR (400 MHz, Chloroform-d) δ 8.17 (d, J=8.9 Hz, 1H), 8.03 (s, 1H), 7.80 (s, 1H), 7.72-7.63 (m, 3H), 7.51-7.41 (m, 2H), 7.36-7.26 (m, 1H), 7.16 (dd, J=4.3, 2.2 Hz, 1H), 7.03 (dd, J=8.9, 2.4 Hz, 1H), 6.97-6.92 (m, 2H), 6.90 (d, J=2.4 Hz, 1H), 5.12 (s, 2H), 4.01 (d, J=1.1 Hz, 2H).

Example 109: 7-((1-phenyl-1H-pyrazol-4-yl)methoxy)-3-(thiophen-3-ylmethyl)-4H-chromen-4-one $^1$H NMR (400 MHz, Chloroform-d) δ 8.17 (d, J=8.9 Hz, 1H), 8.03 (d, J=0.9 Hz, 1H), 7.80 (s, 1H), 7.72-7.64 (m, 2H), 7.59-7.54 (m, 1H), 7.51-7.39 (m, 3H), 7.35-7.27 (m, 2H), 7.09 (dq, J=2.9, 0.9 Hz, 1H), 7.06-6.99 (m, 2H), 6.89 (d, J=2.3 Hz, 1H), 5.13 (s, 2H), 3.82 (s, 2H).

Example 110: 3-((6-chloropyridin-3-yl)methyl)-7-((1-phenyl-1H-pyrazol-4-yl)methoxy)-4H-chromen-4-one $^1$H NMR (400 MHz, Chloroform-d) δ 8.55 (dd, J=2.5, 0.8 Hz, 1H), 8.11 (d, J=8.9 Hz, 1H), 8.02 (s, 1H), 7.90 (d, J=1.0 Hz, 1H), 7.80 (s, 1H), 7.76-7.64 (m, 3H), 7.51-7.41 (m, 2H), 7.39-7.27 (m, 2H), 7.01 (dd, J=8.9, 2.4 Hz, 1H), 6.91 (d, J=2.3 Hz, 1H), 5.12 (s, 2H), 3.89 (s, 2H).

Example 111: 7-((1-phenyl-1H-pyrazol-4-yl)methoxy)-3-(pyrazin-2-ylmethyl)-4H-chromen-4-one $^1$H NMR (400 MHz, Chloroform-d) δ 8.74 (d, J=1.5 Hz, 1H), 8.49-8.39 (m, 2H), 8.11 (d, J=8.9 Hz, 1H), 8.03 (d, J=0.8 Hz, 1H), 7.93 (d, J=1.0 Hz, 1H), 7.80 (s, 1H), 7.72-7.64 (m, 2H), 7.51-7.41 (m, 2H), 7.36-7.27 (m, 1H), 7.02 (dd, J=8.9, 2.4 Hz, 1H), 6.92 (d, J=2.3 Hz, 1H), 5.13 (s, 2H), 3.96 (s, 2H).

Example 112: 7-((1-phenyl-1H-pyrazol-4-yl)methoxy)-3-(3-(prop-2-yn-1-yloxy)phenyl)-4H-chromen-4-one

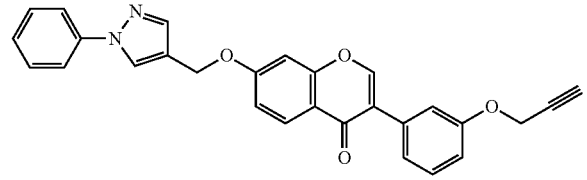 [SMILES: C#CCOc1cccc(-c2coc3cc(OCc4cnn(-c5ccccc5)c4)ccc3c2=O)c1]

The product of Example 87 (37 mg, 0.09 mmol) was placed in a vial with potassium carbonate (50 mg) and DMF (1 ml). The mixture was treated with propargyl bromide (80% in toluene, 50 μl) and heated at 50° C. for 2 h. After cooling to ambient temperature, the mixture was treated with water and the resulting precipitate was filtered and dried by aspiration to give the title compound (8.8 mg) as a tan solid: $^1$H NMR (400 MHz, Chloroform-d) δ 8.24 (d, J=8.9 Hz, 1H), 8.05 (s, 1H), 7.97 (s, 1H), 7.82 (s, 1H), 7.73-7.65 (m, 2H), 7.52-7.42 (m, 2H), 7.41-7.27 (m, 2H), 7.24-7.15 (m, 2H), 7.07 (dd, J=8.9, 2.4 Hz, 1H), 7.01 (ddd, J=8.3, 2.6, 1.0 Hz, 1H), 6.97 (d, J=2.3 Hz, 1H), 5.16 (s, 2H), 4.74 (d, J=2.4 Hz, 2H), 2.53 (t, J=2.4 Hz, 1H); LCMS (ESI) m/z 449.2 [M+1]$^+$.

Example 113: 7-((1-phenyl-1H-pyrazol-4-yl)methoxy)-3-(3-(prop-2-yn-1-yloxy)benzyl)-4H-chromen-4-one 3-(3-hydroxybenzyl)-7-((1-phenyl-1H-pyrazol-4-yl)methoxy)-4H-chromen-4-one (23 mg), synthesized as described in General Procedures J and K, was treated with potassium carbonate (15 mg), DMF (0.3 ml), and propargyl bromide (20 μl) as described in Example 112 to give the title compound (4.8 mg) as a solid after silica chromatography (20% ethyl acetate/hexanes): $^1$H NMR (500 MHz, Chloroform-d) δ 8.17 (d, J=8.9 Hz, 1H), 8.04 (s, 1H), 7.82 (s, 1H), 7.72-7.66 (m, 2H), 7.56 (t, J=1.0 Hz, 1H), 7.51-7.43 (m, 2H), 7.36-7.29 (m, 1H), 7.25 (d, J=7.9 Hz, 1H), 7.03 (dd, J=8.9, 2.4 Hz, 1H), 6.97-6.93 (m, 1H), 6.91 (dd, J=8.2, 2.3 Hz, 2H), 6.88-6.84 (m, 1H), 5.13 (s, 2H), 4.69 (d, J=2.4 Hz, 2H), 3.79 (s, 2H), 2.51 (t, J=2.4 Hz, 1H); LCMS (ESI) m/z 463.2 [M+1]$^+$.

Example 114: N1-(4-hydroxyphenethyl)-N2-(4-(4-(prop-2-yn-1-yloxy)benzoyl)phenyl)oxalamide

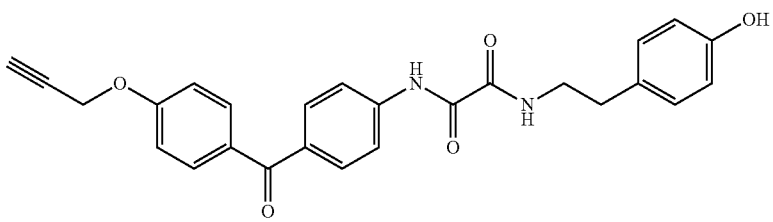 [SMILES: C#CCOc1ccc(C(=O)c2ccc(NC(=O)C(=O)NCCc3ccc(O)cc3)cc2)cc1]

¹H NMR (400 MHz, DMSO-d₆) δ 10.94 (s, 1H), 9.18 (s, 1H), 9.04 (t, J=6.1 Hz, 1H), 8.02-7.95 (m, 2H), 7.77-7.67 (m, 4H), 7.16-7.06 (m, 2H), 7.06-6.96 (m, 2H), 6.70-6.63 (m, 2H), 4.91 (d, J=2.4 Hz, 2H), 3.67-3.61 (m, 1H), 3.37 (q, J=6.9 Hz, 2H), 2.74-2.67 (m, 2H); LCMS (ESI) m/z 441.1 [M−1]⁻.

Oxalamides

General Procedure I

Procedure modified from WO/2005/30140 (2005)

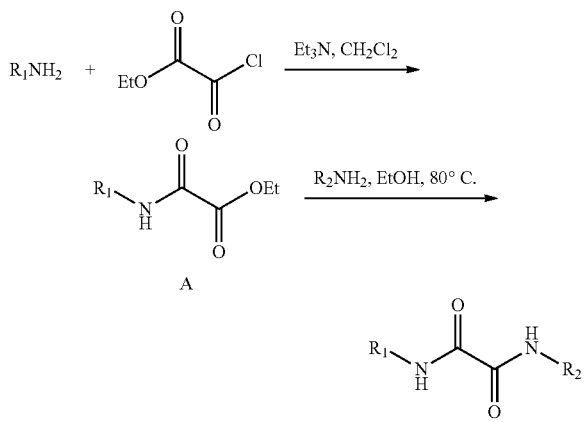

Step 1

To a solution of aniline or amine derivatives (1 eq) and Et₃N (2 eq) dissolved in anhydrous CH₂Cl₂ (0.1 M), a solution of ethyl chlorooxoacetate (1 eq) in anhydrous CH₂Cl₂ (0.86 M) was added dropwise, slowly. The reaction stirred at least 3 hours at rt, typically overnight. Then, the solution was washed with sat. NaHCO₃. The organic layer was dried over Na₂SO₄ and concentrated to yield intermediate A, which was used immediately in Step 2.

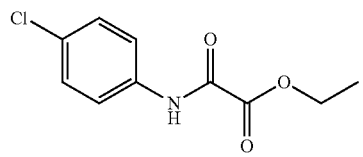

White solid, 595.1 mg, 86% yield. ¹H NMR (400 MHz, DMSO-d₆) δ 10.90 (s, 1H), 7.79-7.73 (m, 2H), 7.43-7.38 (m, 2H), 4.29 (q, J=7.1 Hz, 2H), 1.29 (t, J=7.1 Hz, 3H). ESI-MS (m/z): 227.9 [M]⁺.

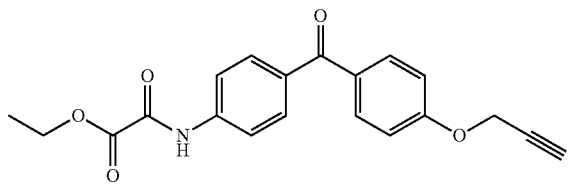 [SMILES: C#CCOc1ccc(C(=O)c2ccc(NC(=O)C(=O)OCC)cc2)cc1]

Cream-colored solid, 26.9 mg, 42% yield. ESI-MS (m/z): 351.9 [M]⁺.

Step 2

The second amine (R₂) (5-10 eq) was added to a solution of crude intermediate A in ethanol (EtOH) (0.1 M) at 80° C. and heated at 80° C. for 3 h. Usually, a precipitate formed immediately. After cooling to rt, the precipitate was filtered and washed with EtOH before drying under vacuum to give the final product. If the product was an oil or sometimes a solid, a precipitate did not form, so after cooling, the reaction mixture was diluted with water and extracted into EtOAc (3×). The organic layer was washed with brine, dried over Na₂SO₄, and then concentrated to give the final product. The final product was not purified unless otherwise noted.

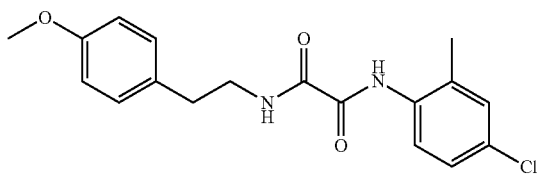 [SMILES: COc1ccc(CCNC(=O)C(=O)Nc2ccc(Cl)cc2C)cc1]

SW206926-1-A,

White solid, 54.7 mg, 78% yield. ¹H NMR (500 MHz, DMSO-d₆) δ 10.13 (s, 1H), 9.02 (t, J=6.0 Hz, 1H), 7.46 (d, J=8.5 Hz, 1H), 7.36 (d, J=2.4 Hz, 1H), 7.27 (dd, J=8.5, 2.6 Hz, 1H), 7.12-7.14 (m, 2H), 6.87-6.83 (m, 2H), 3.71 (s, 3H), 3.40-3.35 (m, 2H), 2.75 (t, J=7.5 Hz, 2H), 2.19 (s, 3H). ¹³C NMR (400 MHz, DMSO-d₆) δ 160.0, 159.0, 158.2, 135.1, 134.6, 131.3, 130.4, 130.4, 130.0, 126.7, 126.5, 114.2, 55.4, 41.3, 34.1, 17.8. ESI-MS (m/z): 346.9 [M]⁺.

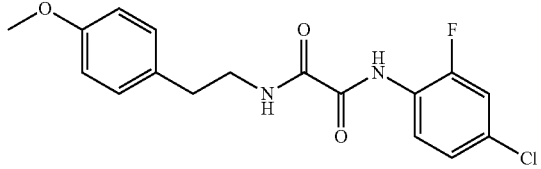

SW206951-1-A,

White solid, 65.5 mg, 62% yield. ¹H NMR (500 MHz, DMSO-d₆) δ 10.21 (s, 1H), 9.08 (t, J=6.0 Hz, 1H), 7.68 (t, J=8.6 Hz, 1H), 7.56 (dd, J=10.3, 2.4 Hz, 1H), 7.32 (ddd, J=8.3, 2.3, 1.0 Hz, 1H), 7.16-7.10 (m, 2H), 6.88-6.82 (m, 2H), 3.71 (s, 3H), 3.41-3.35 (m, 2H), 2.75 (t, J=7.5 Hz, 2H).). ¹³C NMR (400 MHz, DMSO-d₆) δ 159.6, 159.1, 158.2, 155.3 (J=251.9 Hz), 131.3, 130.7 (J=10.1 Hz), 130.0, 127.0 (J=2.2 Hz), 125.1 (J=3.7 Hz), 124.2 (J=12.0 Hz), 117.0 (J=23.4 Hz), 114.2, 55.4, 41.3, 34.1. ESI-MS (m/z): 351.9 [M+H]⁺.

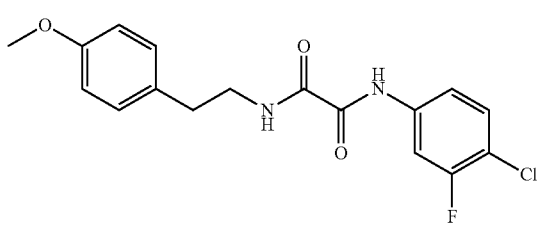 [SMILES: COc1ccc(CCNC(=O)C(=O)Nc2ccc(Cl)c(F)c2)cc1]

SW206952-1-A

White solid, 86.0 mg, 82% yield. ¹H NMR (400 MHz, DMSO-d₆) δ 10.96 (s, 1H), 9.04 (t, J=6.0 Hz, 1H), 7.92 (dd, J=11.9, 2.4 Hz, 1H), 7.70 (ddd, J=8.9, 2.4, 1.0 Hz, 1H), 7.55 (t, J=8.7 Hz, 1H), 7.14-7.09 (m, 2H), 6.85-6.81 (m, 2H), 3.69 (s, 3H), 3.41-3.34 (m, 2H), 2.74 (t, J=7.4 Hz, 2H). ¹³C NMR (400 MHz, DMSO-d₆) δ 159.7, 159.4, 158.2, 157.2

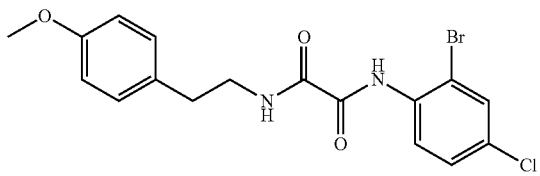 [SMILES: COc1ccc(CCNC(=O)C(=O)Nc2ccc(Cl)cc2Br)cc1]

SW206953-1-A

White solid, mg, yield. $^1$H NMR (500 MHz, DMSO-d$_6$) δ 10.16 (s, 1H), 9.18 (t, J=6.0 Hz, 1H), 7.95 (d, J=8.8 Hz, 1H), 7.87 (d, J=2.4 Hz, 1H), 7.53 (dd, J=8.7, 2.4 Hz, 1H), 7.15-7.11 (m, 2H), 6.87-6.83 (m, 2H), 3.71 (s, 3H), 3.41-3.35 (m, 2H), 2.76 (t, J=7.5 Hz, 2H). $^{13}$C NMR (400 MHz, DMSO-d$_6$) δ 159.6, 158.6, 158.2, 134.6, 132.4, 131.2, 130.6, 130.0, 129.0, 125.2, 117.5, 114.2, 55.4, 41.5, 34.0. ESI-MS (m/z): 410.8 [M−H]$^+$.

(J=244.1 Hz), 138.7 (J=10.1 Hz) 131.3, 131.0, 130.0, 117.8 (J=3.3 Hz), 114.8 (J=17.8 Hz), 114.2, 108.9 (J=26.0 Hz), 55.4, 41.3, 34.1. ESI-MS (m/z): 350.9 [M]$^+$.

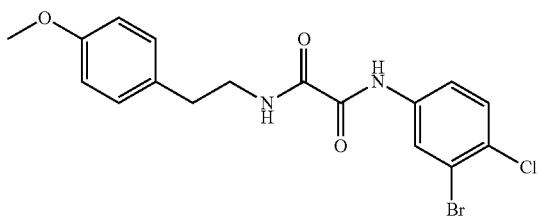 [SMILES: COc1ccc(CCNC(=O)C(=O)Nc2ccc(Cl)c(Br)c2)cc1]

SW206954-1-A

White solid, 87 mg, 70% yield. $^1$H NMR (400 MHz, DMSO-d$_6$) δ 10.91 (s, 1H), 9.01 (t, J=6.0 Hz, 1H), 8.28 (d, J=2.4 Hz, 1H), 7.85 (dd, J=8.9, 2.5 Hz, 1H), 7.59 (d, J=8.8 Hz, 1H), 7.14-7.09 (m, 2H), 6.86-6.81 (m, 2H), 3.69 (s, 3H), 3.41-3.34 (m, 2H), 2.74 (t, J=7.3 Hz, 2H). $^{13}$C NMR (400 MHz, DMSO-d$_6$) δ 159.8, 159.4, 158.2, 138.2, 131.3, 130.9, 130.0, 128.5, 125.2, 121.6, 121.4, 114.2, 55.4, 41.3, 34.1. ESI-MS (m/z): 410.8 [M−H]$^+$.

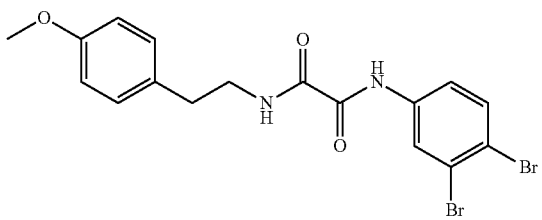 [SMILES: COc1ccc(CCNC(=O)C(=O)Nc2ccc(Br)c(Br)c2)cc1]

SW206955-1-A

Brown solid, 108.7 mg 79% yield. $^1$H NMR (400 MHz, DMSO-d$_6$) δ 10.90 (s, 1H), 9.01 (t, J=6.1 Hz, 1H), 8.27 (dd, J=2.4, 0.9 Hz, 1H), 7.77 (ddd, J=8.8, 2.4, 1.0 Hz, 1H), 7.71 (dd, J=8.8, 1.0 Hz, 1H), 7.15-7.09 (m, 2H), 6.86-6.80 (m, 2H), 3.71-3.68 (s, 3H), 3.41-3.34 (m, 2H), 2.74 (t, J=7.4 Hz, 2H).). $^{13}$C NMR (400 MHz, DMSO-d$_6$) δ 159.7, 159.4, 158.2, 138.8, 134.2, 131.3, 130.0, 125.2, 124.1, 121.5, 118.8, 114.2, 55.4, 41.3, 34.1. ESI-MS (m/z): 454.7 [M−2H]$^+$.

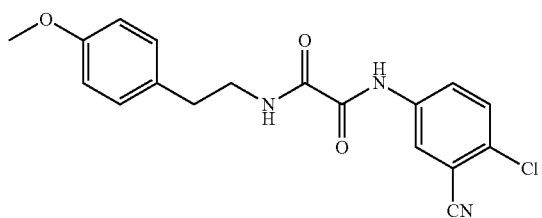 [SMILES: COc1ccc(CCNC(=O)C(=O)Nc2ccc(Cl)c(C#N)c2)cc1]

SW206959-1-A

White solid, 34.1 mg, 66% yield. $^1$H NMR (400 MHz, DMSO-d$_6$) δ 11.09 (s, 1H), 9.06 (t, J=6.0 Hz, 1H), 8.33 (d, J=2.5 Hz, 1H), 8.14 (dd, J=9.0, 2.6 Hz, 1H), 7.73 (d, J=9.0 Hz, 1H), 7.15-7.08 (m, 2H), 6.86-6.82 (m, 2H), 3.69 (s, 3H), 3.41-3.34 (m, 2H), 2.74 (t, J=7.3 Hz, 2H). $^{13}$C NMR (400 MHz, DMSO-d$_6$) δ 159.6, 159.6, 158.2, 137.9, 131.3, 131.0, 130.5, 130.0, 126.9, 125.6, 116.3, 114.2, 112.4, 55.4, 41.3, 34.1. ESI-MS (m/z): 358.1 [M+1]$^+$.

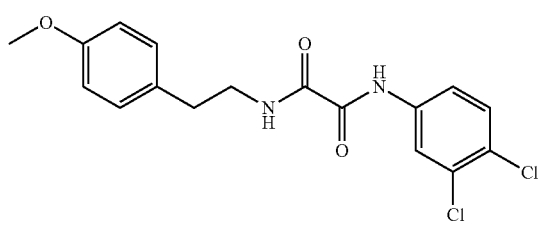 [SMILES: COc1ccc(CCNC(=O)C(=O)Nc2ccc(Cl)c(Cl)c2)cc1]

SW206960-1-A

White solid, 93.3 mg, 69% yield. $^1$H NMR (500 MHz, DMSO-d$_6$) δ 10.96 (s, 1H), 9.05 (t, J=6.0 Hz, 1H), 8.15 (d, J=2.4 Hz, 1H), 7.83 (dd, J=8.9, 2.5 Hz, 1H), 7.62 (d, J=8.8 Hz, 1H), 7.14-7.11 (m, 2H), 6.86-6.83 (m, 2H), 3.71 (s, 3H), 3.42-3.36 (m, 2H), 2.75 (t, J=7.4 Hz, 2H). $^{13}$C NMR (400 MHz, DMSO-d$_6$) δ 159.7, 159.4, 158.2, 138.3, 131.4, 131.3, 131.1, 130.0, 126.5, 122.1, 120.9, 114.2, 55.4, 41.3, 34.1. ESI-MS (m/z): 368.8 [M+H]$^+$.

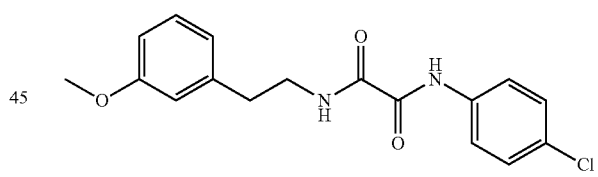

SW206964-1-A

White solid, 77.1 mg, 76% yield. $^1$H NMR (400 MHz, DMSO-d$_6$) δ 10.77 (s, 1H), 9.02 (t, J=6.0 Hz, 1H), 7.86-7.81 (m, 2H), 7.42-7.37 (m, 2H), 7.18 (t, J=8.0 Hz, 1H), 6.79-6.73 (m, 3H), 3.71 (s, 3H), 3.46-3.38 (m, 2H), 2.79 (t, J=7.3 Hz, 2H). $^{13}$C NMR (400 MHz, DMSO-d$_6$) δ 160.1, 159.7, 159.1, 141.1, 137.1, 129.8, 129.1, 128.6, 122.4, 121.3, 114.6, 112.1, 55.3, 40.9, 35.0. ESI-MS (m/z): 333.9 [M+H]$^+$.

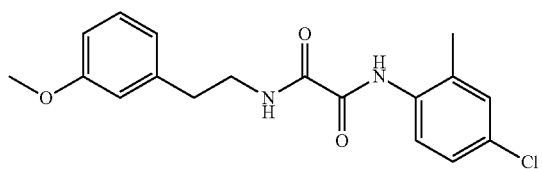 [SMILES: COc1cccc(CCNC(=O)C(=O)Nc2ccc(Cl)cc2C)c1]

SW206965-1-A

White solid, 65.4 mg, 63% yield. $^1$H NMR (400 MHz, DMSO-d$_6$) δ 10.12 (s, 1H), 9.01 (t, J=6.0 Hz, 1H), 7.45 (d, J=8.6 Hz, 1H), 7.34 (d, J=2.4 Hz, 1H), 7.26 (dd, J=8.6, 2.5 Hz, 1H), 7.21-7.16 (m, 1H), 6.80-6.73 (m, 3H), 3.71 (s, 3H), 3.45-3.37 (m, 2H), 2.79 (t, J=7.4 Hz, 2H), 2.18 (s, 3H).). $^{13}$C NMR (400 MHz, DMSO-d$_6$) δ 160.1, 159.7, 159.0, 141.1, 135.1, 134.6, 130.4, 129.8, 126.7, 126.5, 121.3, 114.6, 112.1, 55.3, 40.9, 35.0, 17.8. ESI-MS (m/z): 346.9 [M]$^+$.

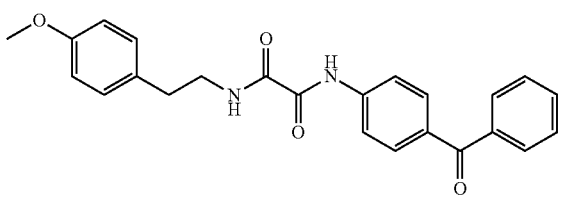 [SMILES: COc1ccc(CCNC(=O)C(=O)Nc2ccc(C(=O)c3ccccc3)cc2)cc1]

SW206966-1-A

White solid, 42.1 mg, 69% yield. $^1$H NMR (500 MHz, DMSO-d$_6$) δ 10.99 (s, 1H), 9.08 (t, J=6.2 Hz, 1H), 8.01 (d, J=8.4 Hz, 2H), 7.73 (dd, J=18.3, 7.9 Hz, 4H), 7.67 (t, J=7.4 Hz, 1H), 7.55 (t, J=7.5 Hz, 2H), 7.14 (d, J=8.2 Hz, 2H), 6.85 (d, J=8.0 Hz, 2H), 3.71 (s, 3H), 3.45-3.37 (m, 2H), 2.77 (t, J=7.3 Hz, 2H). $^{13}$C NMR (400 MHz, DMSO-d$_6$) δ 195.1, 159.9, 159.5, 158.2, 142.1, 137.7, 133.0, 132.9, 131.3, 131.3, 130.0, 129.9, 129.0, 120.2, 114.2, 55.4, 41.3, 34.1. ESI-MS (m/z): 402.9 [M]$^+$.

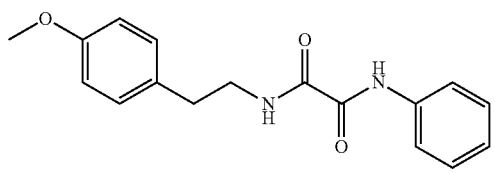 [SMILES: COc1ccc(CCNC(=O)C(=O)Nc2ccccc2)cc1]

SW206967-1-A

White solid, 18.0 mg, 31% yield. $^1$H NMR (500 MHz, DMSO-d$_6$) δ 10.60 (s, 1H), 9.00 (t, J=6.0 Hz, 1H), 7.83-7.78 (m, 2H), 7.34 (t, J=7.9 Hz, 2H), 7.13 (dd, J=8.2, 2.4 Hz, 3H), 6.85 (dd, J=9.0, 2.3 Hz, 2H), 3.71 (s, 3H), 3.43-3.36 (m, 2H), 2.76 (t, J=7.4 Hz, 2H). $^{13}$C NMR (400 MHz, DMSO-d$_6$) δ 160.2, 159.0, 158.1, 138.1, 131.3, 130.0, 129.1, 124.9, 120.8, 114.2, 55.4, 41.2, 34.1. ESI-MS (m/z): 299.0 [M–H]$^+$.

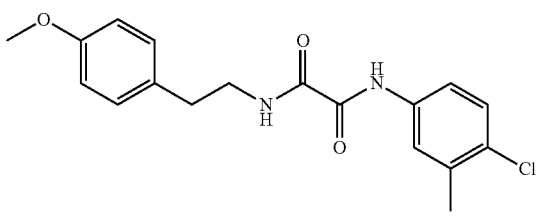 [SMILES: COc1ccc(CCNC(=O)C(=O)Nc2ccc(Cl)c(C)c2)cc1]

SW206974-1-A

White solid, 41.8 mg, 80% yield. $^1$H NMR (400 MHz, DMSO-d$_6$) δ 10.65 (s, 1H), 8.95 (t, J=6.0 Hz, 1H), 7.79 (d, J=2.4 Hz, 1H), 7.66 (dd, J=8.7, 2.6 Hz, 1H), 7.36 (d, J=8.7 Hz, 1H), 7.14-7.09 (m, 2H), 6.86-6.81 (m, 2H), 3.69 (s, 3H), 3.41-3.34 (m, 2H), 2.74 (t, J=7.4 Hz, 2H), 2.28 (s, 3H). $^{13}$C NMR (400 MHz, DMSO-d$_6$) δ 160.1, 159.1, 158.2, 137.0, 136.0, 131.3, 130.0, 129.4, 128.9, 123.2, 120.0, 114.2, 55.4, 41.3, 34.1, 20.4. ESI-MS (m/z): 346.9 [M]$^+$.

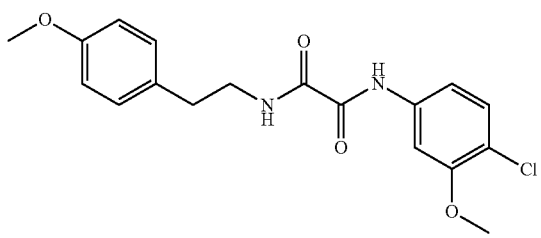 [SMILES: COc1ccc(CCNC(=O)C(=O)Nc2ccc(Cl)c(OC)c2)cc1]

SW206973-1-A

White solid, 38.8 mg, 71% yield. $^1$H NMR (400 MHz, DMSO-d$_6$) δ 10.70 (s, 1H), 8.99 (t, J=6.0 Hz, 1H), 7.71 (d, J=2.3 Hz, 1H), 7.49 (dd, J=8.7, 2.3 Hz, 1H), 7.36 (d, J=8.6 Hz, 1H), 7.14-7.10 (m, 2H), 6.86-6.81 (m, 2H), 3.80 (s, 3H), 3.70 (s, 3H), 3.42-3.34 (m, 2H), 2.74 (t, J=7.4 Hz, 2H). $^{13}$C NMR (400 MHz, DMSO-d$_6$) δ 160.0, 159.1, 158.2, 154.8, 138.3, 131.3, 130.1, 130.0, 116.6, 114.2, 113.3, 105.6, 56.3, 55.4, 41.3, 34.1. ESI-MS (m/z): 362.9 [M]$^+$.

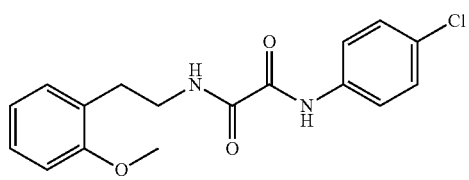 [SMILES: COc1ccccc1CCNC(=O)C(=O)Nc1ccc(Cl)cc1]

SW207004-1-A

White solid, 37.9 mg, 72% yield. $^1$H NMR (500 MHz, DMSO-d$_6$) δ 10.79 (s, 1H), 8.98 (t, J=6.0 Hz, 1H), 7.86-7.83 (m, 2H), 7.42-7.38 (m, 2H), 7.19 (ddd, J=7.9, 7.9, 1.6 Hz, 1H), 7.12 (dd, J=7.4, 1.7 Hz, 1H), 6.95 (dd, J=8.3, 1.0 Hz, 1H), 6.86 (ddd, J=7.4, 7.5, 1H), 3.78 (s, 3H), 3.43-3.37 (m, 2H), 2.80 (t, J=7.2 Hz, 2H). $^{13}$C NMR (400 MHz, DMSO-d$_6$) δ 160.1, 159.1, 157.7, 137.1, 130.4, 129.1, 128.2, 127.3, 122.3, 120.7, 111.1, 55.7, 29.7. $^{13}$C NMR (400 MHz, CDCl$_3$) δ 157.4, 135.0, 130.6, 129.2, 128.3, 126.7, 120.9, 120.8, 110.4, 55.3, 40.8, 29.8. ESI-MS (m/z): 332.9 [M]$^+$.

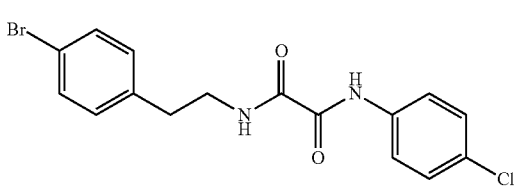

SW207005-1-A

White solid, 42.2 mg, 74% yield. $^1$H NMR (500 MHz, DMSO-d$_6$) δ 10.78 (s, 1H), 9.07 (t, J=6.1 Hz, 1H), 7.87-7.82 (m, 2H), 7.49-7.45 (m, 2H), 7.43-7.38 (m, 2H), 7.21-7.16 (m, 2H), 3.46-3.39 (m, 2H), 2.80 (t, J=7.2 Hz, 2H). $^{13}$C NMR (400 MHz, DMSO-d$_6$) 160.1, 159.0, 139.0, 137.0, 131.6, 131.4, 129.1, 128.6, 122.4, 119.7, 40.7, 34.3.

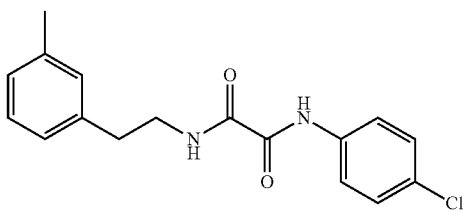 [SMILES: Cc1cccc(CCNC(=O)C(=O)Nc2ccc(Cl)cc2)c1]

SW207006-1-A

White solid, 31.6 mg, 67% yield. $^1$H NMR (500 MHz, DMSO-d$_6$) δ 10.80 (s, 1H), 9.06 (t, J=6.0 Hz, 1H), 7.87-7.83 (m, 2H), 7.43-7.38 (m, 2H), 7.17 (t, J=7.5 Hz, 1H), 7.03 (s, 1H), 7.02-6.98 (m, 2H), 3.44-3.38 (m, 2H), 2.78 (t, J=7.4 Hz, 2H), 2.27 (s, 3H). $^{13}$C NMR (400 MHz, DMSO-d$_6$) δ 160.1, 159.1, 139.4, 137.8, 137.1, 129.7, 129.1, 128.7, 128.6, 127.3, 126.1, 122.4, 41.0, 34.9, 21.5. ESI-MS (m/z): 316.9 [M]$^+$.

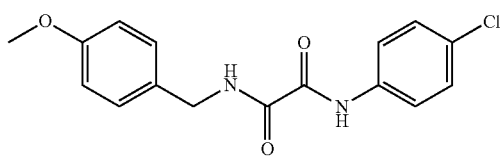 [SMILES: COc1ccc(CNC(=O)C(=O)Nc2ccc(Cl)cc2)cc1]

SW027902-2-A

White solid, 32.3 mg, 68% yield. $^1$H NMR (500 MHz, DMSO-d$_6$) 10.83 (s, 1H), 9.50 (t, J=6.4 Hz, 1H), 7.87-7.83 (m, 2H), 7.43-7.39 (m, 2H), 7.25-7.21 (m, 2H), 6.90-6.85 (m, 2H), 4.30 (d, J=6.4 Hz, 2H), 3.72 (s, 3H). $^{13}$C NMR (400 MHz, DMSO-d$_6$) δ 160.2, 159.2, 158.7, 137.1, 131.0, 129.3, 129.1, 128.6, 122.4, 114.1, 55.5, 42.5.

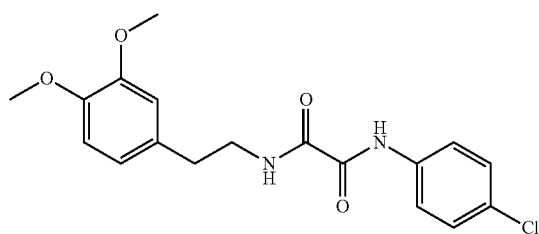 [SMILES: COc1ccc(CCNC(=O)C(=O)Nc2ccc(Cl)cc2)cc1OC]

SW207007-1-A

White solid, 38.0 mg, 67% yield. $^1$H NMR (500 MHz, DMSO-d$_6$) δ 10.79 (s, 1H), 9.01 (t, J=6.0 Hz, 1H), 7.87-7.83 (m, 2H), 7.43-7.39 (m, 2H), 6.85 (d, J=8.2 Hz, 1H), 6.81 (d, J=2.0 Hz, 1H), 6.71 (dd, J=8.1, 2.0 Hz, 1H), 3.72 (s, 3H), 3.70 (s, 3H), 3.44-3.38 (m, 2H), 2.75 (t, J=7.2 Hz, 2H). $^{13}$C NMR (400 MHz, DMSO-d$_6$) δ 160.1, 159.2, 149.0, 147.7, 137.1, 131.9, 129.1, 128.6, 122.4, 120.9, 112.9, 112.2, 55.9, 55.8, 41.1, 34.5. ESI-MS (m/z): 362.9 [M]$^+$.

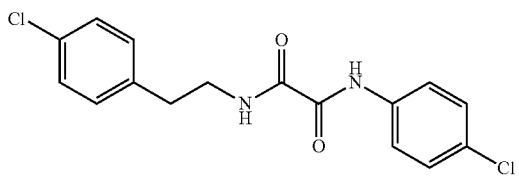 [SMILES: O=C(NCCc1ccc(Cl)cc1)C(=O)Nc1ccc(Cl)cc1]

SW207008-1-A

White solid, 36.7 mg, 72% yield. $^1$H NMR (500 MHz, DMSO-d$_6$) δ 10.78 (s, 1H), 9.07 (t, J=6.1 Hz, 1H), 7.86-7.83 (m, 2H), 7.42-7.38 (m, 2H), 7.36-7.32 (m, 2H), 7.26-7.22 (m, 2H), 3.45-3.39 (m, 2H), 2.82 (t, J=7.2 Hz, 2H). $^{13}$C NMR (400 MHz, DMSO-d$_6$) δ 160.1, 159.1, 138.6, 137.1, 131.3, 131.0, 129.1, 128.7, 128.6, 122.4, 40.8, 34.2. ESI-MS (m/z): 336.9 [M−H]$^+$.

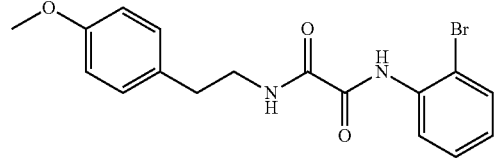 [SMILES: COc1ccc(CCNC(=O)C(=O)Nc2ccccc2Br)cc1]

SW207009-1-A

White solid, 34.4 mg, 30% yield after flash chromatography (silica gel, 0→30% EtOAc in hexanes). $^1$H NMR (500 MHz, DMSO-d$_6$) δ 10.12 (s, 1H), 9.17 (t, J=6.0 Hz, 1H), 7.97 (dd, J=8.1, 1.6 Hz, 1H), 7.71 (dd, J=8.1, 1.4 Hz, 1H), 7.44 (td, J=7.8, 1.4 Hz, 1H), 7.18 (td, J=7.8, 1.6 Hz, 1H), 7.15-7.11 (m, 2H), 6.87-6.83 (m, 2H), 3.71 (s, 3H), 3.42-3.35 (m, 2H), 2.76 (t, J=7.5 Hz, 2H). $^{13}$C NMR (400 MHz, DMSO-d$_6$) δ 159.7, 158.4, 158.2, 135.2, 133.2, 131.3, 130.0, 129.0, 127.6, 124.0, 116.5, 114.2, 55.4, 41.5, 34.1. ESI-MS (m/z): 376.9 [M−H]$^+$.

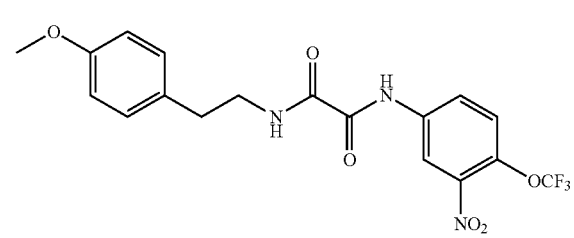 [SMILES: COc1ccc(CCNC(=O)C(=O)Nc2ccc(OC(F)(F)F)c([N+](=O)[O-])c2)cc1]

SW207010-1-A

Orange solid, 13.7 mg, 21% yield after flash chromatography (silica gel, 0→30% EtOAc in hexanes). $^1$H NMR (500 MHz, DMSO-d$_6$) δ 11.30 (s, 1H), 9.12 (t, J=6.0 Hz, 1H), 8.72 (d, J=2.7 Hz, 1H), 8.25 (dd, J=9.1, 2.7 Hz, 1H), 7.77 (dd, J=9.0, 1.4 Hz, 1H), 7.15-7.11 (m, 2H), 6.87-6.83 (m, 2H), 3.71 (s, 3H), 3.43-3.37 (m, 2H), 2.76 (t, J=7.4 Hz, 2H). $^{13}$C NMR (400 MHz, DMSO-d$_6$) δ 159.7, 159.5, 158.2, 142.4, 138.2, 135.9, 131.3, 130.0, 126.8, 125.0, 120.3 (J=259.4 Hz), 117.6, 114.2, 55.4, 41.3, 34.1. ESI-MS (m/z): 427.9 [M]$^+$.

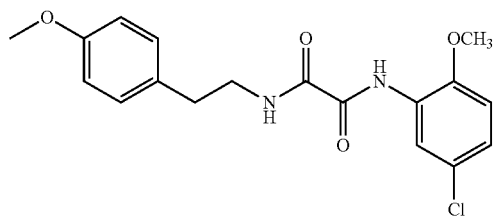 [SMILES: COc1ccc(CCNC(=O)C(=O)Nc2cc(Cl)ccc2OC)cc1]

SW207011-1-A

White solid, 27.0 mg, 50% yield after flash chromatography (silica gel, 0→30% EtOAc in hexanes). $^1$H NMR (500 MHz, DMSO-d$_6$) δ 9.78 (s, 1H), 9.20 (t, J=6.0 Hz, 1H), 8.19 (d, J=2.5 Hz, 1H), 7.22 (dd, J=8.8, 2.6 Hz, 1H), 7.16-7.10

(m, 3H), 6.87-6.83 (m, 2H), 3.89 (s, 3H), 3.71 (s, 3H), 3.41-3.35 (m, 2H), 2.75 (t, J=7.4 Hz, 2H). $^{13}$C NMR (400 MHz, DMSO-d$_6$) δ 159.6, 158.2, 158.0, 148.1, 131.2, 130.0, 127.3, 125.0, 124.6, 119.1, 114.2, 113.1, 56.9, 55.4, 41.5, 34.0. ESI-MS (m/z): 362.9 [M]$^+$.

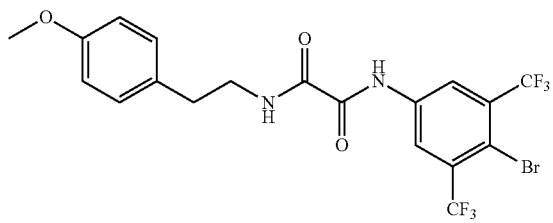 [SMILES: COc1ccc(CCNC(=O)C(=O)Nc2cc(C(F)(F)F)c(Br)c(C(F)(F)F)c2)cc1]

SW207012-1-A

White solid, 20.8 mg, 26% yield after flash chromatography (silica gel, 0→30% EtOAc in hexanes). $^1$H NMR (500 MHz, DMSO-d$_6$) δ 11.40 (s, 1H), 9.13 (t, J=6.0 Hz, 1H), 8.70 (s, 2H), 7.15-7.11 (m, 2H), 6.86-6.83 (m, 2H), 3.70 (s, 3H), 3.43-3.37 (m, 2H), 2.76 (t, J=7.3 Hz, 2H). $^{13}$C NMR (400 MHz, DMSO-d$_6$) δ 159.9, 159.3, 158.2, 138.7, 132.0, 131.8 (J=91.7 Hz), 131.7, 131.3, 130.0, 124.2, 123.1 (J=6.2 Hz), 121.5, 114.2, 111.6, 55.4, 41.3, 34.1.

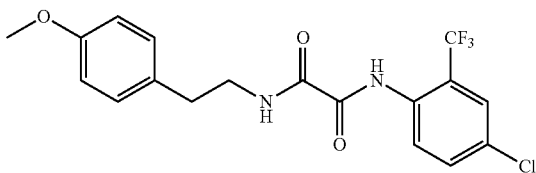

SW207013-1-A

White solid, 8.6 mg, 7% yield after flash chromatography (silica gel, 0→20% EtOAc in hexanes). $^1$H NMR (500 MHz, DMSO-d$_6$) δ 10.27 (s, 1H), 9.14 (t, J=6.2 Hz, 1H), 7.87 (s, 1H), 7.83 (d, J=1.4 Hz, 2H), 7.15-7.11 (m, 2H), 6.87-6.83 (m, 2H), 3.71 (s, 3H), 3.40-3.35 (m, 2H), 2.75 (t, J=7.5 Hz, 2H). $^{13}$C NMR (400 MHz, CDCl$_3$) δ 158.2, 157.7, 156.9, 132.0, 131.7 (J=1.7 Hz), 129.8, 129.0, 128.8, 125.8, 125.7 (J=5.4 Hz), 120.7 (J=273.6 Hz), 120.67 (J=62.3 Hz), 113.4, 54.4, 40.6, 33.6. ESI-MS (m/z): 400.9 [M]$^+$.

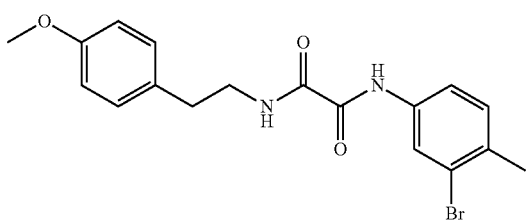

SW207014-1-A

White solid, 7.2 mg, 12% yield after flash chromatography (silica gel, 0→40% EtOAc in hexanes). $^1$H NMR (500 MHz, DMSO-d$_6$) δ 10.74 (s, 1H), 9.00 (t, J=6.0 Hz, 1H), 8.12 (d, J=2.1 Hz, 1H), 7.71 (dd, J=8.3, 2.2 Hz, 1H), 7.31 (d, J=8.4 Hz, 1H), 7.15-7.11 (m, 2H), 6.86-6.83 (m, 2H), 3.71 (s, 3H), 3.41-3.35 (m, 2H), 2.75 (t, J=7.4 Hz, 2H), 2.29 (s, 3H). $^{13}$C NMR (400 MHz, CDCl$_3$) δ 159.5, 158.5, 157.3, 135.1, 134.9, 131.0, 129.9, 129.6, 125.0, 123.3, 118.5, 114.2, 55.3, 41.3, 34.5, 22.4. ESI-MS (m/z): 390.9 [M−H]$^+$.

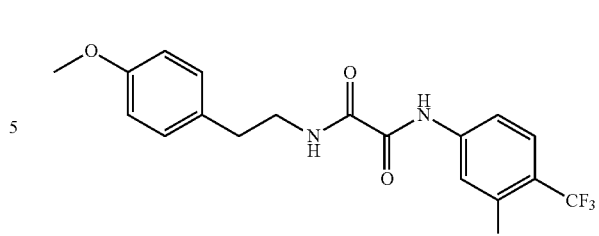

SW207015-1-A

White solid, mg, % yield after triturating in CH$_2$Cl$_2$. $^1$H NMR (400 MHz, DMSO-d$_6$) δ 11.11 (s, 1H), 9.07 (t, J=6.1 Hz, 1H), 8.37 (s, 1H), 8.03 (d, J=8.7 Hz, 1H), 7.82 (d, J=8.7 Hz, 1H), 7.15-7.09 (m, 2H), 6.87-6.80 (m, 2H), 3.70 (s, J=1.3 Hz, 3H), 3.43-3.34 (m, 2H), 2.75 (t, J=7.4 Hz, 2H). $^{13}$C NMR (400 MHz, DMSO-d$_6$) δ 159.8, 159.5, 158.2, 142.7, 131.3, 130.0, 129.2 (J=5.6 Hz), 126.0, 124.1 ($^2$J=30.9 Hz), 123.5 ($^1$J=272.4 Hz), 119.5 (J=1.8 Hz), 119.3, 114.2, 55.4, 41.3, 34.1. ESI-MS (m/z): 343.0 [M+H]$^+$. ESI-MS (m/z): 444.8 [M−1]$^+$.

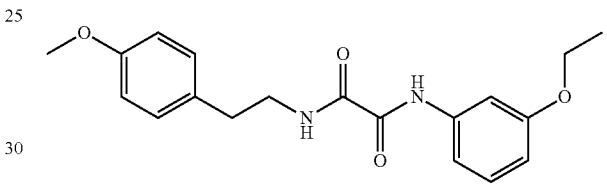

SW207016-1-A

White solid, 40.5 mg, 83% yield. $^1$H NMR (400 MHz, DMSO-d$_6$) δ 10.52 (s, 1H), 8.96 (t, J=6.0 Hz, 1H), 7.44 (dd, J=2.2, 2.2 Hz, 1H), 7.39 (ddd, J=8.1, 2.0, 0.9 Hz, 1H), 7.21 (dd, J=8.2, 8.2 Hz, 1H), 7.14-7.10 (m, 2H), 6.86-6.81 (m, 2H), 6.67 (ddd, J=8.3, 2.5, 0.9 Hz, 1H), 3.97 (q, J=6.9 Hz, 2H), 3.70 (s, 3H), 3.41-3.34 (m, 2H), 2.74 (t, J=7.3 Hz, 2H), 1.30 (t, J=6.9 Hz, 3H). $^{13}$C NMR (400 MHz, DMSO-d$_6$) δ 160.2, 159.1, 159.0, 158.2, 139.2, 131.4, 130.0, 129.9, 114.2, 112.9, 110.8, 107.0, 63.4, 55.4, 41.2, 34.1, 15.1. ESI-MS (m/z): 343.0 [M+H]$^+$.

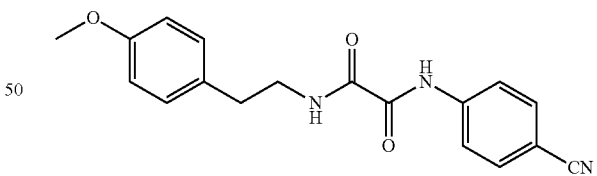

SW207017-1-A

White solid, 14.6 mg, 30% isolated yield after triturating with CH$_2$Cl$_2$, filtering, and drying under vacuum. $^1$H NMR (400 MHz, DMSO-d$_6$) δ 11.04 (s, 1H), 9.07 (t, J=6.0 Hz, 1H), 8.01 (d, J=8.5 Hz, 2H), 7.81 (d, J=8.4 Hz, 2H), 7.12 (d, J=8.2 Hz, 2H), 6.83 (d, J=8.2 Hz, 2H), 3.69 (s, 3H), 3.43-3.34 (m, 2H), 2.75 (t, J=7.4 Hz, 2H). $^{13}$C NMR (400 MHz, DMSO-d$_6$) δ 159.7, 159.7, 158.2, 142.4, 133.6, 131.3, 130.0, 120.9, 119.3, 114.2, 106.8, 55.4, 41.3, 34.1. ESI-MS (m/z): 323.9 [M]$^+$.

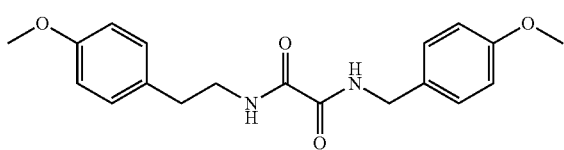

SW207018-1-A

White solid, 52.7 mg, 99% yield. $^1$H NMR (400 MHz, DMSO-d$_6$) δ 9.16 (t, J=6.5 Hz, 1H), 8.72 (t, J=6.1 Hz, 1H), 7.19-7.14 (m, 2H), 7.11-7.06 (m, 2H), 6.87-6.80 (m, 4H), 4.21 (d, J=6.5 Hz, 2H), 3.70 (s, 3H), 3.69 (s, 3H), 3.35-3.27 (m, 2H), 2.69 (t, J=7.4 Hz, 2H). $^{13}$C NMR (400 MHz, DMSO-d$_6$) δ 160.4, 160.3, 158.7, 158.1, 131.4, 131.2, 130.0, 129.2, 114.2, 114.1, 55.5, 55.4, 42.2, 41.0, 34.2. ESI-MS (m/z): 364.9 [M+Na]$^+$.

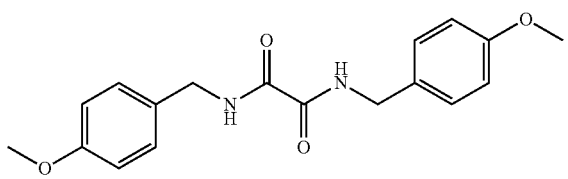

SW207019-1-A

White solid, 41.0 mg, 81% yield. $^1$H NMR (400 MHz, DMSO-d$_6$) δ 9.20 (t, J=6.5 Hz, 2H), 7.20-7.15 (m, 4H), 6.87-6.82 (m, 4H), 4.22 (d, J=6.5 Hz, 4H), 3.70 (s, 6H). $^{13}$C NMR (400 MHz, DMSO-d$_6$) δ 160.4, 158.7, 131.2, 129.2, 114.1, 55.5, 42.3. $^{13}$C NMR (400 MHz, DMSO-d$_6$) δ ESI-MS (m/z): 350.9 [M+Na]$^+$.

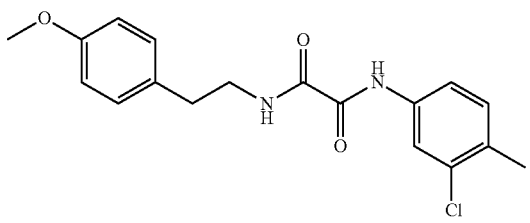

SW207020-1-A

White solid, 50.5 mg, 87% yield. $^1$H NMR (400 MHz, DMSO-d$_6$) δ 10.71 (s, 1H), 8.97 (t, J=6.1 Hz, 1H), 7.93 (d, J=2.0 Hz, 1H), 7.66 (dt, J=8.4, 1.7 Hz, 1H), 7.29 (d, J=8.4 Hz, 1H), 7.14-7.09 (m, 2H), 6.86-6.80 (m, 2H), 3.39-3.33 (m, 2H), 3.69 (s, 3H), 2.74 (t, J=7.4 Hz, 2H), 2.26 (s, 3H). $^{13}$C NMR (400 MHz, DMSO-d$_6$) δ 160.0, 159.1, 158.2, 137.3, 133.4, 131.7, 131.6, 131.3, 130.0, 120.7, 119.4, 114.2, 55.4, 41.3, 34.1, 19.5. ESI-MS (m/z): 347.9 [M+H]$^+$.

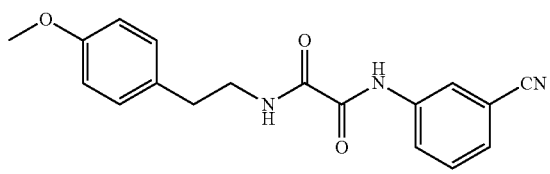 [SMILES: COc1ccc(CCNC(=O)C(=O)Nc2cccc(C#N)c2)cc1]

SW207021-1-A

White solid, 4.4 mg, 5% yield after flash chromatography (silica gel, 0→40% EtOAc in hexanes). $^1$H NMR (400 MHz, DMSO-d$_6$) δ 10.97 (s, 1H), 9.05 (t, J=6.0 Hz, 1H), 8.22 (dd, J=1.8, 1.8 Hz, 1H), 8.12 (dt, J=7.6, 2.0 Hz, 1H), 7.61-7.53 (m, 2H), 7.15-7.05 (m, 2H), 6.86-6.80 (m, 2H), 3.69 (s, 3H), 3.42-3.35 (m, 2H), 2.75 (t, J=7.3 Hz, 2H). ESI-MS (m/z): 323.9 [M]$^+$.

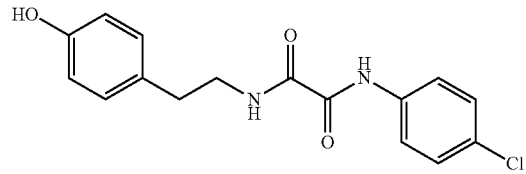 [SMILES: O=C(NCCc1ccc(O)cc1)C(=O)Nc1ccc(Cl)cc1]

SW208023-1-A

White solid, 35.2 mg, 68% yield. $^1$H NMR (500 MHz, DMSO-d$_6$) δ 10.79 (s, 1H), 9.20 (s, 1H), 9.01 (t, J=6.1 Hz, 1H), 7.88-7.82 (m, 2H), 7.44-7.37 (m, 2H), 7.00 (d, J=8.2 Hz, 2H), 6.70-6.65 (m, 2H), 3.39-3.35 (m, 2H), 2.69 (t, J=7.5 Hz, 2H). $^{13}$C NMR (400 MHz, DMSO-d$_6$) δ 160.0, 159.2, 156.1, 137.1, 129.9, 129.5, 129.1, 128.6, 122.4, 115.6, 41.4, 34.2.

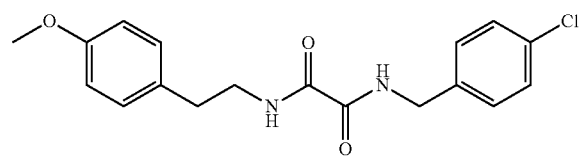 [SMILES: COc1ccc(CCNC(=O)C(=O)NCc2ccc(Cl)cc2)cc1]

SW208025-1-A

White solid, 12 mg, 23% yield. $^1$H NMR (500 MHz, DMSO-d$_6$) δ 9.33 (t, J=6.6 Hz, 1H), 8.78 (t, J=6.1 Hz, 1H), 7.39-7.35 (m, 2H), 7.30-7.24 (m, 2H), 7.12-7.08 (m, 2H), 6.85-6.81 (m, 2H), 4.28 (d, J=6.5 Hz, 2H), 3.70 (s, 3H), 3.33-3.29 (m, 2H), 2.70 (t, J=7.4 Hz, 2H). $^{13}$C NMR (400 MHz, DMSO-d$_6$) δ160.6, 160.2, 158.1, 138.2, 131.9, 131.4, 130.0, 129.7, 128.7, 114.2, 55.4, 42.2, 41.0, 34.2. ESI-MS (m/z): 346.9 [M]$^+$.

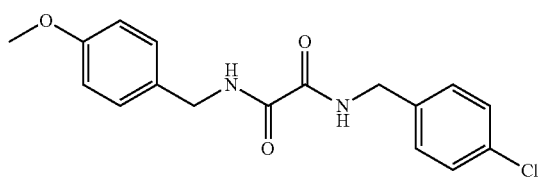 [SMILES: COc1ccc(CNC(=O)C(=O)NCc2ccc(Cl)cc2)cc1]

SW208026-1-A

White solid, 31.4 mg, 64% yield. $^1$H NMR (500 MHz, DMSO-d$_6$) δ 9.37 (t, J=6.5 Hz, 1H), 9.26 (t, J=6.5 Hz, 1H), 7.38-7.35 (m, 2H), 7.29-7.25 (m, 2H), 7.21-7.17 (m, 2H), 6.88-6.84 (m, 2H), 4.29 (d, J=6.5 Hz, 2H), 4.24 (d, J=6.5 Hz, 2H), 3.71 (s, 3H). $^{13}$C NMR (400 MHz, DMSO-d$_6$) δ 160.7, 160.3, 158.7, 138.2, 131.9, 131.2, 129.7, 129.3, 128.7, 114.1, 55.5, 42.3, 42.2. ESI-MS (m/z): 354.9 [M+Na]$^+$.

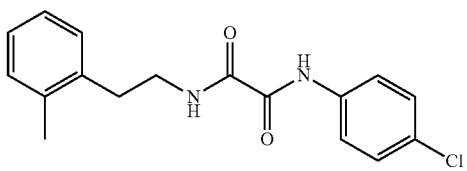 [SMILES: Cc1ccccc1CCNC(=O)C(=O)Nc1ccc(Cl)cc1]

SW208027-1-A

White solid, 7.5 mg, 20% yield. In step 2, Et$_3$N (2 eq) was added, because the synthesized amine was a salt (sew-189-116-ML). $^1$H NMR (500 MHz, DMSO-d$_6$) δ 10.83 (s, 1H), 9.15 (t, J=6.2 Hz, 1H), 7.88-7.83 (m, 2H), 7.43-7.39 (m, 2H), 7.17-7.07 (m, 4H), 3.39-3.35 (m, 2H), 2.81 (t, J=7.6 Hz, 2H), 2.31 (s, 3H). $^{13}$C NMR (400 MHz, DMSO-d$_6$) δ 160.1, 159.1, 137.5, 137.1, 136.4, 130.5, 129.5, 129.1, 128.6, 126.8, 126.4, 122.4, 32.8, 19.3. $^{13}$C NMR (400 MHz, DMSO-d$_6$) δ 165.5, 158.1, 136.3, 133.8, 131.7, 130.0, 129.5, 128.8, 114.2, 55.4, 41.6, 34.6. ESI-MS (m/z): 316.9 [M]$^+$.

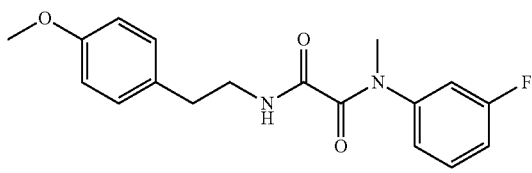 [SMILES: COc1ccc(CCNC(=O)C(=O)N(C)c2cccc(F)c2)cc1]

SW208028-1-A

Yellow oil, 2 mg, 2% yield after flash chromatography (silica gel, EtOAc:hexanes, 1:3). $^1$H NMR (500 MHz, DMSO-d$_6$) δ 8.70 (t, J=6.1 Hz, 1H), 7.36 (dd, J=2.4, 0.96 Hz, 1H), 7.26-7.04 (m, 3H), 7.04-6.99 (m, 2H) 6.89-6.74 (m, 2H), 3.71 (s, 3H), 3.22 (s, 3H), 3.14-3.06 (m, 2H), 2.44 (t, J=7.6 Hz, 2H). $^{13}$C NMR (400 MHz, DMSO-d$_6$) δ 165.0, 163.6 (d, $^1$J=244.8 Hz), 163.3, 158.2, 144.4 (d, $^3$J=10.1 Hz), 131.4, 131.2, 131.0 (d, $^3$J=9.01 Hz), 130.0, 130.0, 129.9, 122.5, 114.6 (d, $^2$J=20.3 Hz), 114.2, 113.7 (d, $^2$J=23.7 Hz), 55.4, 36.2, 34.0. ESI-MS (m/z): 331.1 [M+H]$^+$.

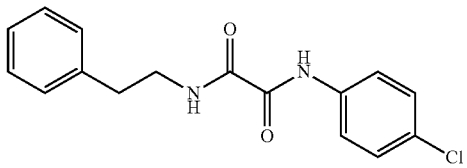 [SMILES: O=C(NCCc1ccccc1)C(=O)Nc1ccc(Cl)cc1]

SW113361-2-A

White solid, 32.6 mg, 77% yield. In step 2, Et$_3$N (2 eq) was added, because the synthesized amine was a salt (sew-189-110-ML). $^1$H NMR (400 MHz, DMSO-d$_6$) δ 10.77 (s, 1H), 9.03 (t, J=6.0 Hz, 1H), 7.86-7.81 (m, 2H), 7.42-7.36 (m, 2H), 7.31-7.25 (m, 2H), 7.23-7.16 (m, 3H), 3.46-3.38 (m, 2H), 2.82 (t, J=7.4 Hz, 2H). $^{13}$C NMR (400 MHz, DMSO-d$_6$) δ 160.1, 159.1, 139.5, 137.1, 129.0, 128.8, 128.6, 126.6, 122.4, 41.0, 35.0. ESI-MS (m/z): 304.9 [M+2H]$^+$.

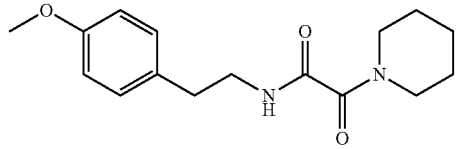 [SMILES: COc1ccc(CCNC(=O)C(=O)N2CCCCC2)cc1]

SW208030-1-A

Yellow oil, 180.3 mg, % yield. $^1$H NMR (500 MHz, DMSO-d$_6$) δ 8.64 (t, J=5.7 Hz, 1H), 7.14-7.10 (m, 2H), 6.86-6.81 (m, 2H), 3.70 (s, 3H), 3.38 (t, J=5.6 Hz, 2H), 3.34-3.29 (m, 2H), 3.13 (t, J=5.5 Hz, 2H), 2.67 (t, J=7.1 Hz, 2H), 1.59-1.52 (m, 2H), 1.47-1.35 (m, 4H). $^{13}$C NMR (400 MHz, DMSO-d$_6$) δ 160.1, 159.1, 138.6, 137.1, 131.3, 131.0, 129.1, 128.7, 128.6, 122.4, 40.8, 34.2. ESI-MS (m/z): 291.0 [M+H]$^+$.

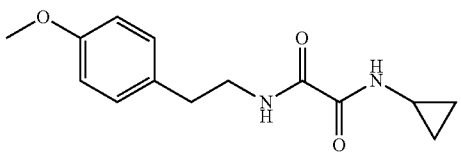 [SMILES: COc1ccc(CCNC(=O)C(=O)NC2CC2)cc1]

SW208031-1-A)

White solid, 142.6, % yield. $^1$H NMR (400 MHz, DMSO-d$_6$) δ 8.74-8.69 (m, 2H), 7.11-7.06 (m, 2H), 6.85-6.80 (m, 2H), 3.69 (s, 3H), 3.33-3.26 (m, 2H), 2.77-2.71 (m, 1H), 2.69 (t, J=7.4 Hz, 2H), 0.60 (m, 4H). $^{13}$C NMR (400 MHz, DMSO-d$_6$) δ 161.7, 160.2, 158.1, 131.4, 130.0, 114.2, 55.4, 40.9, 34.2, 23.2, 5.8. ESI-MS (m/z): 263.0 [M+H]$^+$.

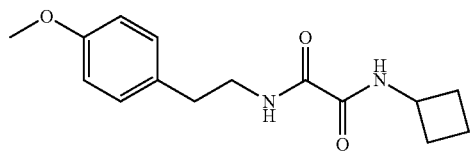 [SMILES: COc1ccc(CCNC(=O)C(=O)NC2CCC2)cc1]

SW208032-1-A

White solid, 169.6 mg, % yield. $^1$H NMR (500 MHz, DMSO-d$_6$) δ 8.95 (d, J=8.5 Hz, 1H), 8.71 (t, J=6.1 Hz, 1H), 7.12-7.07 (m, 2H), 6.85-6.81 (m, 2H), 4.22 (m, 1H) 3.70 (s, 3H), 3.34-3.28 (m, 2H), 2.70 (t, J=7.4 Hz, 2H), 2.13-2.05 (m, 4H), 1.64-1.55 (m, 2H). $^{13}$C NMR (400 MHz, DMSO-d$_6$) δ 160.3, 159.3, 158.1, 131.4, 130.0, 114.2, 55.4, 44.5, 41.0, 34.2, 30.0, 15.1. ESI-MS (m/z): 277.0 [M+H]$^+$.

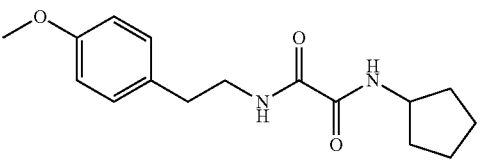 [SMILES: COc1ccc(CCNC(=O)C(=O)NC2CCCC2)cc1]

SW208033-1-A

White solid, 187.3 mg, % yield. $^1$H NMR (400 MHz, DMSO-d$_6$) δ 8.69 (t, J=6.1 Hz, 1H), 8.53 (d, J=8.1 Hz, 1H), 7.12-7.07 (m, 2H), 6.85-6.80 (m, 2H), 4.06-3.95 (m, 1H), 3.69 (s, 3H), 3.34-3.27 (m, 2H), 2.69 (t, J=7.4 Hz, 2H), 1.83-1.70 (m, 2H), 1.69-1.56 (m, 2H), 1.56-1.40 (m, 4H).

$^{13}$C NMR (400 MHz, DMSO-d$_6$) δ 160.4, 160.0, 158.1, 131.4, 130.0, 114.2, 55.4, 51.0, 41.0, 34.2, 32.1, 23.9. ESI-MS (m/z): 291.0 [M+H]$^+$.

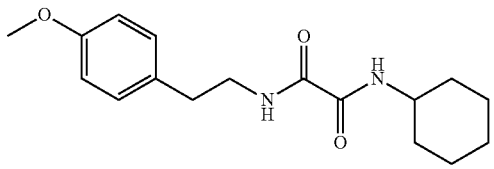 [SMILES: COc1ccc(CCNC(=O)C(=O)NC2CCCCC2)cc1]

SW208034-1-A
White solid, 224.7 mg, % yield. $^1$H NMR (400 MHz, DMSO-d$_6$) δ 8.69 (t, J=6.3 Hz, 1H), 8.43 (d, J=8.7 Hz, 1H), 7.09 (d, J=8.1 Hz, 2H), 6.83 (d, J=8.0 Hz, 2H), 3.69 (s, 3H), 3.61-3.45 (m, 1H), 2.69 (t, J=7.6 Hz, 2H), 1.74-1.60 (m, 4H), 1.59-1.48 (m, 1H), 1.42-1.14 (m, 4H), 1.14-0.95 (m, 1H). ESI-MS (m/z): 305.0 [M+H]$^+$.

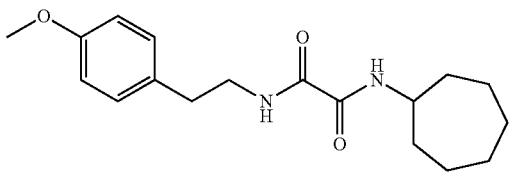 [SMILES: COc1ccc(CCNC(=O)C(=O)NC2CCCCCC2)cc1]

SW208035-1-A
White solid, 238.8 mg, % yield. $^1$H NMR (500 MHz, DMSO-d$_6$) δ 8.71 (apps, 1H), 8.49 (d, J=8.8 Hz, 1H), 7.10 (d, J=8.0 Hz, 2H), 6.84 (d, J=8.0 Hz, 2H), 3.79-3.59 (m, 4H), 3.32-3.25 (m, 2H), 2.70 (t, J=7.1 Hz, 2H), 1.79-1.25 (m, 12H). ESI-MS (m/z): 319.0 [M+H]$^+$.

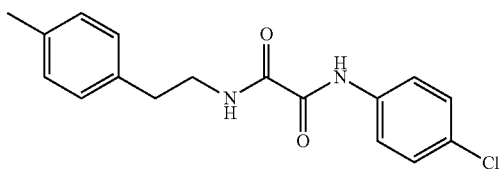 [SMILES: Cc1ccc(CCNC(=O)C(=O)Nc2ccc(Cl)cc2)cc1]

SW208036-1-A
White solid, 27.4 mg, 53% yield. In step 2, Et$_3$N (2.5 eq) were added, because the synthesized amine was a salt (sew-189-158) and 3 eq of amine were used. $^1$H NMR (500 MHz, DMSO-d$_6$) δ 10.79 (s, 1H), 9.04 (t, J=6.0 Hz, 1H), 7.88-7.82 (m, 2H), 7.43-7.38 (m, 2H), 7.09 (m, 4H), 3.43-3.37 (m, 2H), 2.77 (t, J=7.4 Hz, 2H), 2.25 (s, 3H). $^{13}$C NMR (400 MHz, DMSO-d$_6$) δ 160.0, 159.1, 137.1, 136.4, 135.5, 129.4, 129.1, 128.9, 128.6, 122.4, 41.1, 34.6, 21.1. ESI-MS (m/z): 316.9 [M]$^+$.

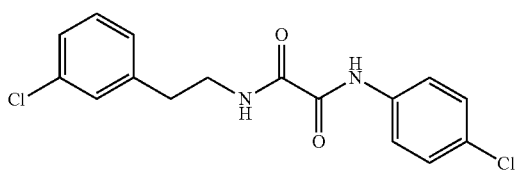 [SMILES: O=C(NCCc1cccc(Cl)c1)C(=O)Nc1ccc(Cl)cc1]

SW208037-1-A
White solid, 22.6 mg, 40% yield. In step 2, Et$_3$N (2.5 eq) was added, because the synthesized amine was a salt (sew-189-163), and 3 eq of amine were used. $^1$H NMR (500 MHz, DMSO-d$_6$) δ 10.79 (s, 1H), 9.09 (t, J=6.1 Hz, 1H), 7.89-7.82 (m, 2H), 7.43-7.38 (m, 2H), 7.38-7.16 (m, 4H), 3.48-3.41 (m, 2H), 2.84 (t, J=7.2 Hz, 2H). $^{13}$C NMR (400 MHz, DMSO-d$_6$) δ 160.1, 159.1, 142.2, 137.1, 133.4, 130.6, 129.1, 129.0, 128.6, 127.9, 126.6, 122.4, 40.2, 34.4. ESI-MS (m/z): 338.9 [M+H]$^+$.

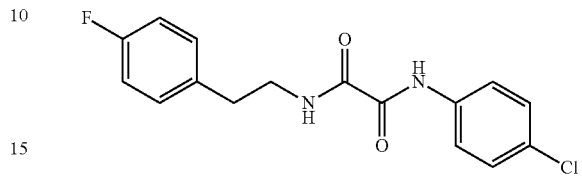

SW208039-1-A
White solid, 8.6 mg, 20% yield. In step 2, Et$_3$N (3 eq) was added, because the synthesized amine was a salt (sew-189-175), and 3 eq of amine were used. $^1$H NMR (500 MHz, DMSO-d6) δ 10.78 (s, 1H), 9.06 (t, J=6.0 Hz, 1H), 7.87-7.82 (m, 2H), 7.42-7.38 (m, 2H), 7.27-7.22 (m, 2H), 7.13-7.08 (m, 2H), 3.45-3.39 (m, 2H), 2.81 (t, J=7.3 Hz, 2H). $^{13}$C NMR (400 MHz, DMSO-d$_6$) δ 160.1, 159.1, 137.1, 135.7, 130.9 (d, $^3$J=7.83 Hz), 129.1, 128.6, 122.4, 115.6 (d, $^2$J=21.2 Hz), 41.0, 34.1. ESI-MS (m/z): 320.9 [M]$^+$.

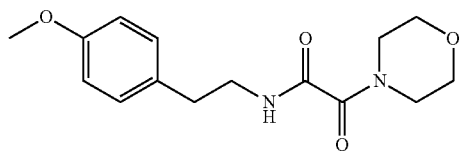 [SMILES: COc1ccc(CCNC(=O)C(=O)N2CCOCC2)cc1]

SW208044-1-A
Yellow solid, 271.6 mg, % yield after flash chromatography, (silica gel, 0→100% EtOAc in hexanes). $^1$H NMR (500 MHz, DMSO-d6) δ 8.73 (t, J=5.8 Hz, 1H), 7.15-7.09 (m, 2H), 6.86-6.81 (m, 2H), 3.55 (dd, J=5.6, 4.2 Hz, 2H), 3.46 (dd, J=5.5, 4.1 Hz, 2H), 3.43 (dd, J=5.6, 4.1 Hz, 2H), 3.37-3.31 (m, 3H), 3.23 (t, J=4.8 Hz, 2H), 3.72-3.70 (m, 3H), 2.68 (t, J=7.1 Hz, 2H). $^{13}$C NMR (400 MHz, DMSO-d6) δ 163.7, 163.5, 158.2, 131.3, 130.1, 114.1, 66.6, 66.2, 55.4, 55.4, 46.3, 41.6, 34.1. ESI-MS (m/z): 293.0 [M+H]$^+$.

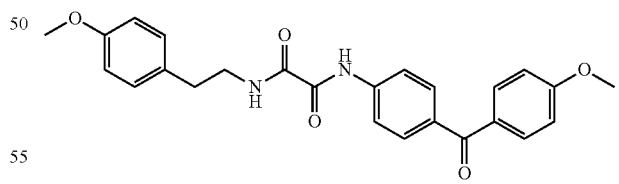

SW208009-1-A
White solid, 7 mg, 5% isolated yield after triturating in CH$_2$Cl$_2$ to remove impurities. $^1$H NMR (400 MHz, DMSO-d6) δ 10.93 (s, 1H), 9.04 (t, J=6.0 Hz, 1H), 8.01-7.95 (m, 2H), 7.75-7.67 (m, 4H), 7.16-7.10 (m, 2H), 7.10-7.05 (m, 2H), 6.87-6.80 (m, 2H), 3.84 (s, 3H), 3.70 (s, 3H), 3.43-3.35 (m, 2H), 2.76 (t, J=7.4 Hz, 2H). $^{13}$C NMR (400 MHz, DMSO-d$_6$) δ 193.8, 163.2, 160.0, 159.5, 158.2, 141.6, 133.8, 132.5, 131.3, 130.9, 130.1, 130.0, 120.2, 114.3, 114.2, 56.0, 55.4, 41.3, 34.1. ESI-MS (m/z): 432.9 [M]$^+$.

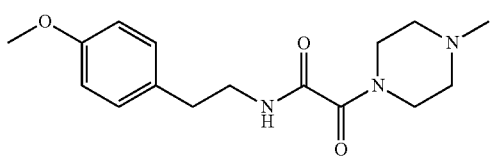

SW208048-1-A

Yellow oil, 349.6 mg, % yield after flash chromatography (silica gel, 0→100% EtOAc in hexanes, then 100% EtOH). $^1$H NMR (500 MHz, DMSO-$d_6$) δ 8.69 (t, J=5.8 Hz, 1H), 7.14-7.08 (m, 4H), 6.85-6.81 (m, 4H), 3.70 (d, J=1.2 Hz, 6H), 3.44-3.39 (m, 2H), 3.36-3.34 (m, 3H), 3.18 (dd, J=6.0, 4.0 Hz, 3H), 2.69 (dt, J=, 4H), 2.56 (t, J=7.3 Hz, 2H), 2.25 (t, J=5.2 Hz, 2H), 2.18 (t, J=5.0 Hz, 2H), 2.16 (s, 3H). $^{13}$C NMR (400 MHz, DMSO-$d_6$) δ 163.8, 163.7, 158.1, 157.9, 132.5, 131.3, 130.1, 130.0, 114.1, 55.4, 55.4, 54.3, 46.0, 45.7, 44.1, 34.2. ESI-MS (m/z): 306.0 [M+H]$^+$.

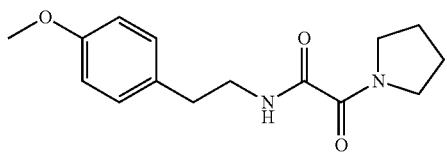 [SMILES: COc1ccc(CCNC(=O)C(=O)N2CCCC2)cc1]

SW208049-1-A

Cream-colored solid, 161.5 mg, % yield after flash chromatography (silica gel, 0→100% EtOAc in hexanes). $^1$H NMR (400 MHz, DMSO-$d_6$) δ 8.59 (t, J=5.9 Hz, 1H), 7.13-7.08 (m, 2H), 6.85-6.80 (m, 2H), 3.70-3.68 (s, 3H), 3.53-3.48 (m, 2H), 3.34-3.26 (m, 4H), 2.67 (t, J=7.4 Hz, 2H), 1.84-1.70 (m, 4H). $^{13}$C NMR (400 MHz, DMSO-$d_6$) δ162.6, 161.3, 158.1, 131.4, 130.0, 114.1, 55.4, 47.8, 46.6, 40.5, 34.2, 26.3, 23.7. ESI-MS (m/z): 277.0 [M+H]$^+$.

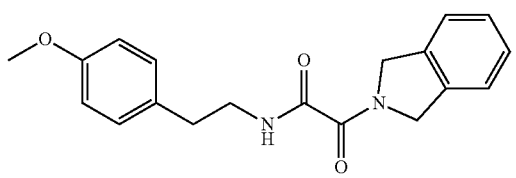 [SMILES: COc1ccc(CCNC(=O)C(=O)N2Cc3ccccc3C2)cc1]

SW208058-1-A

Cream-colored solid, 140.0 mg, % yield. $^1$H NMR (400 MHz, DMSO-$d_6$) δ 8.75 (t, J=6.0 Hz, 1H), 7.38-7.32 (m, 1H), 7.32-7.25 (m, 3H), 7.16-7.10 (m, 2H), 6.87-6.81 (m, 2H), 4.92 (s, 2H), 4.71 (s, 2H), 3.69 (s, 3H), 3.40-3.34 (m, 2H), 2.72 (t, J=7.3 Hz, 2H). $^{13}$C NMR (400 MHz, DMSO-$d_6$) δ 161.9, 161.3, 158.2, 137.5, 135.3, 131.4, 130.0, 127.9, 127.9, 123.3, 123.2, 114.2, 55.4, 53.7, 53.0, 40.4, 34.2. ESI-MS (m/z): 325.0 [M+H]$^+$.

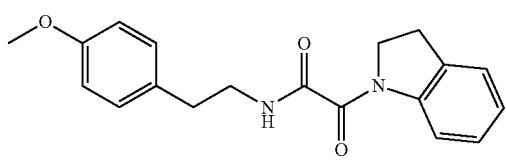 [SMILES: COc1ccc(CCNC(=O)C(=O)N2CCc3ccccc32)cc1]

SW208059-1-A

White solid, 157.6 mg, % yield. $^1$H NMR (400 MHz, DMSO-$d_6$) δ 8.84 (t, J=5.9 Hz, 1H), 8.02 (d, J=8.0 Hz, 1H), 7.23-7.17 (m, 1H), 7.17-7.12 (m, 2H), 7.11-7.03 (m, 2H), 6.88-6.82 (m, 2H), 4.03 (t, J=8.2 Hz, 2H), 3.71 (s, 3H), 3.41-3.34 (m, 2H), 3.07 (t, J=8.4 Hz, 2H), 2.72 (t, J=7.1 Hz, 2H). $^{13}$C NMR (400 MHz, DMSO-$d_6$) δ 162.7, 161.8, 158.2, 142.4, 133.1, 131.3, 130.2, 127.5, 125.5, 125.0, 117.1, 114.2, 55.4, 48.8, 40.5, 34.2, 28.2. ESI-MS (m/z): 325.0 [M+H]$^+$.

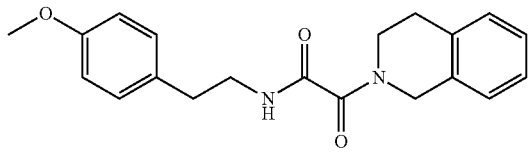 [SMILES: COc1ccc(CCNC(=O)C(=O)N2CCc3ccccc3C2)cc1]

SW208060-1-A

Yellow oil, 103.6 mg, 95% yield after flash chromatography (silica gel, 0→100% EtOAc in hexanes). $^1$H NMR (500 MHz, DMSO-$d_6$) δ 8.79-8.71 (m, 1H), 7.22-7.11 (m, 6H), 6.90-6.81 (m, 2H), 4.60 (s, 1H), 4.47 (s, 1H), 3.72 (s, 3H), 3.67 (t, J=6.1 Hz, 1H), 3.48 (t, J=5.9 Hz, 1H), 3.41-3.36 (m, 2H), 2.79 (t, J=6.1 Hz, 1H), 2.75 (t, J=5.9 Hz, 1H), 2.71 (t, J=7.2 Hz, 2H). ESI-MS (m/z): 339.0 [M+H]$^+$.

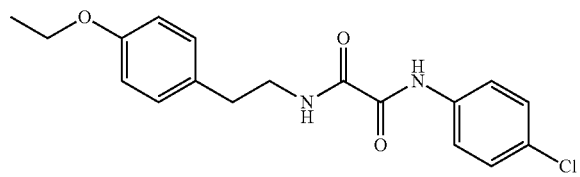 [SMILES: CCOc1ccc(CCNC(=O)C(=O)Nc2ccc(Cl)cc2)cc1]

SW208061-1-A

White solid, 43.1 mg, 77% yield. $^1$H NMR (500 MHz, DMSO-$d_6$) δ 10.79 (s, 1H), 9.02 (s, 1H), 7.85 (d, J=8.7 Hz, 2H), 7.40 (d, J=8.4 Hz, 2H), 7.11 (d, J=7.9 Hz, 2H), 6.83 (s, 2H), 4.03-3.89 (m, 2H), 2.74 (s, 3H), 1.29 (s, 4H). ESI-MS (m/z): 346.9 [M]$^+$.

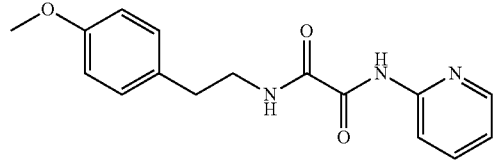 [SMILES: COc1ccc(CCNC(=O)C(=O)Nc2ccccn2)cc1]

SW208122-1-A

Yellow solid, 10.5 mg, 11% yield after flash chromatography (silica gel, 0→100% EtOAc in hexanes). $^1$H NMR (500 MHz, DMSO-$d_6$) δ 9.18 (t, J=6.0 Hz, 1H), 8.39 (ddd, J=4.9, 1.9, 0.9 Hz, 1H), 8.06-8.02 (m, 1H), 7.89 (ddd, J=8.3, 7.4, 1.9 Hz, 1H), 7.22 (ddd, J=7.4, 4.9, 1.0 Hz, 1H), 7.15-7.11 (m, 2H), 6.87-6.83 (m, 3H), 3.71 (s, 3H), 3.42-3.36 (m, 2H), 2.76 (t, J=7.5 Hz, 2H). $^{13}$C NMR (400 MHz, DMSO-$d_6$) δ 159.6, 158.7, 158.2, 150.3, 149.0, 139.1, 131.3, 130.0, 121.3, 114.2, 114.1, 55.4, 41.5, 34.1. ESI-MS (m/z): 300.0 [M+H]$^+$.

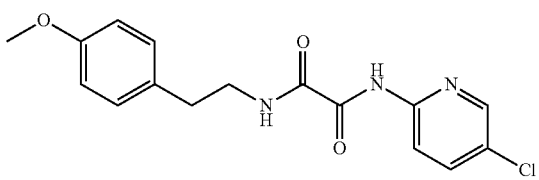 [SMILES: COc1ccc(CCNC(=O)C(=O)Nc2ccc(Cl)cn2)cc1]

SW208123-1-A

Orange solid, 9.1 mg, 9% yield after flash chromatography (silica gel, 0→100% EtOAc in hexanes). $^1$H NMR (500 MHz, DMSO-d$_6$) δ 9.18 (t, J=6.0 Hz, 1H), 8.45 (dd, J=2.6, 0.8 Hz, 1H), 8.06 (dd, J=8.9, 0.8 Hz, 1H), 8.01 (dd, J=8.9, 2.6 Hz, 1H), 7.15-7.11 (m, 2H), 6.87-6.83 (m, 2H), 3.71 (s, 3H), 3.41-3.35 (m, 2H), 2.75 (t, J=7.5 Hz, 2H). $^{13}$C NMR (400 MHz, DMSO-d$_6$) δ 159.5, 159.0, 158.2, 149.1, 147.3, 138.8, 131.2, 130.0, 127.1, 115.5, 114.2, 55.4, 41.4, 34.1. ESI-MS (m/z): 333.9 [M]$^+$.

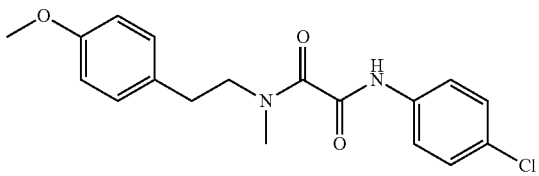 [SMILES: COc1ccc(CCN(C)C(=O)C(=O)Nc2ccc(Cl)cc2)cc1]

SW208153-1-A

Cream-colored solid, 4.4 mg, 11% yield after flash chromatography (silica gel, 0→100% EtOAc in hexanes). $^1$H NMR (400 MHz, DMSO-d$_6$) δ 7.70-7.67 (m, 1H), 7.67-7.63 (m, 2H), 7.41-7.37 (m, 3H), 7.19-7.15 (m, 1H), 7.06-7.01 (m, 2H), 6.88-6.84 (m, 2H), 6.79-6.74 (m, 2H), 5.74 (s, 4H), 3.71 (s, 2H), 3.64 (s, 3H), 3.59-3.53 (m, 2H), 3.53-3.46 (m, 2H), 2.97 (s, 2H), 2.91 (s, 3H), 2.85-2.77 (m, 3H), 2.77-2.70 (m, 2H). ESI-MS (m/z): 346.9 [M]$^+$.

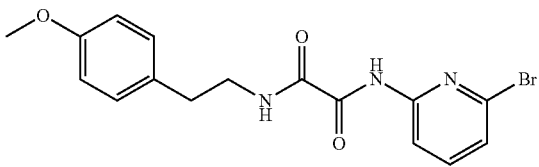 [SMILES: COc1ccc(CCNC(=O)C(=O)Nc2cccc(Br)n2)cc1]

SW208126-1-A

White solid, 37.2 mg, 33% yield after flash chromatography (silica gel, 0→100% EtOAc in hexanes). $^1$H NMR (400 MHz, DMSO-d$_6$) δ 10.21 (s, 1H), 9.13 (t, J=6.0 Hz, 1H), 8.01 (dd, J=8.2, 0.8 Hz, 1H), 7.81 (t, J=7.9 Hz, 1H), 7.45 (dd, J=7.7, 0.7 Hz, 1H), 7.15-7.09 (m, 2H), 6.86-6.81 (m, 2H), 3.69 (s, 3H), 3.41-3.33 (m, 2H), 2.74 (t, J=7.4 Hz, 2H). $^{13}$C NMR (400 MHz, DMSO-d$_6$) δ 159.4, 159.1, 158.2, 150.7, 142.1, 139.6, 131.2, 130.0, 125.0, 114.2, 113.5, 55.4, 41.5, 34.1. ESI-MS (m/z): 379.8 [M+H]$^+$.

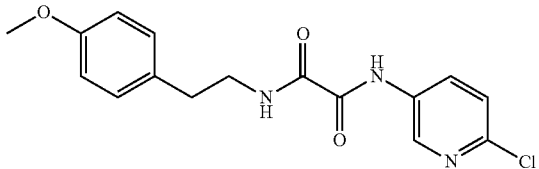 [SMILES: COc1ccc(CCNC(=O)C(=O)Nc2ccc(Cl)nc2)cc1]

SW208127-1-A

White solid, 103.4 mg, 96% yield. $^1$H NMR (400 MHz, DMSO-d$_6$) δ 11.03 (s, 1H), 9.05 (t, J=6.0 Hz, 1H), 8.83 (dd, J=2.7, 0.7 Hz, 1H), 8.24 (dd, J=8.7, 2.8 Hz, 1H), 7.51 (dd, J=8.7, 0.7 Hz, 1H), 7.15-7.10 (m, 2H), 6.86-6.82 (m, 2H), 3.69 (s, 3H), 3.42-3.35 (m, 2H), 2.75 (t, J=7.4 Hz, 2H). $^{13}$C NMR (400 MHz, DMSO-d$_6$) δ 160.2, 159.6, 158.1, 145.3, 142.3, 134.5, 131.4, 131.3, 130.0, 124.6, 114.2, 55.4, 41.3, 34.1. ESI-MS (m/z): 333.9 [M]$^+$.

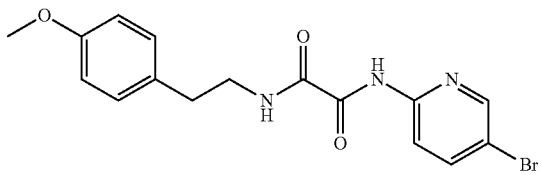 [SMILES: COc1ccc(CCNC(=O)C(=O)Nc2ccc(Br)cn2)cc1]

SW208128-1-A

White solid, 13.1 mg, 12% yield after flash chromatography (silica gel, 0→100% EtOAc in hexanes). $^1$H NMR (500 MHz, DMSO-d$_6$) δ 10.22 (s, 1H), 9.19 (t, J=6.0 Hz, 1H), 8.52 (dd, J=2.5, 0.7 Hz, 1H), 8.12 (dd, J=8.8, 2.5 Hz, 1H), 8.00 (d, J=8.7 Hz, 1H), 7.15-7.11 (m, 2H), 6.87-6.83 (m, 2H), 3.70 (s, 3H), 3.41-3.35 (m, 2H), 2.75 (t, J=7.5 Hz, 2H). $^{13}$C NMR (400 MHz, DMSO-d$_6$) δ 159.5, 159.0, 158.2, 149.5, 149.4, 141.5, 131.2, 130.0, 116.0, 115.6, 114.2, 55.4, 41.5, 34.0. ESI-MS (m/z): 377.8 [M–H]$^+$.

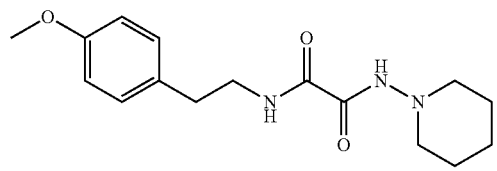 [SMILES: COc1ccc(CCNC(=O)C(=O)NN2CCCCC2)cc1]

SW208129-1-A

White solid, 175.0 mg, % yield. $^1$H NMR (400 MHz, DMSO-d$_6$) δ 9.57 (s, 1H), 8.70 (t, J=6.1 Hz, 1H), 7.09 (d, J=8.1 Hz, 2H), 6.82 (d, J=8.1 Hz, 2H), 3.69 (s, 3H), 3.30-3.25 (m, 2H), 2.75-2.61 (m, 6H), 1.59-1.47 (m, 4H), 1.36-1.35 (m, 2H). $^{13}$C NMR (400 MHz, DMSO-d$_6$) δ 160.5, 158.1, 157.3, 131.4, 130.0, 114.2, 55.4, 55.4, 40.9, 34.2, 25.6, 23.4. ESI-MS (m/z): 306.0 [M+H]$^+$.

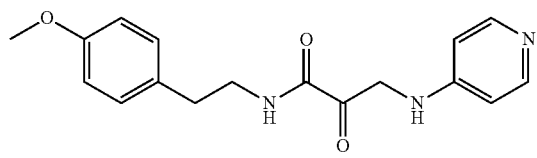 [SMILES: COc1ccc(CCNC(=O)C(=O)CNc2ccncc2)cc1]

SW208130-1-A

White solid, 85.6 mg, 92% yield. $^1$H NMR (400 MHz, DMSO-d$_6$) δ 9.37 (t, J=6.5 Hz, 1H), 8.78 (t, J=6.1 Hz, 1H), 8.47 (d, J=5.3 Hz, 2H), 7.20 (d, J=5.5 Hz, 2H), 7.10 (d, J=8.2 Hz, 2H), 6.83 (d, J=8.3 Hz, 2H), 4.32 (d, J=6.7 Hz, 2H), 3.69 (s, 3H), 3.34-3.29 (m, 2H), 2.71 (t, J=7.4 Hz, 2H). $^{13}$C NMR (400 MHz, DMSO-d$_6$) δ 160.9, 160.0, 158.1, 150.0, 148.0, 131.3, 130.0, 122.6, 114.2, 55.4, 41.9, 41.0, 34.2. ESI-MS (m/z): 314.0 [M+H]$^+$.

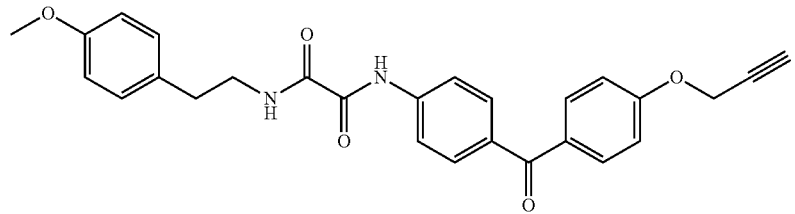

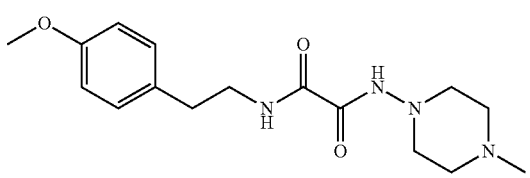

SW208131-1-A

White solid, 11.7 mg, 11% yield. $^1$H NMR (400 MHz, DMSO-d$_6$) δ 9.68 (s, 1H), 8.74-8.66 (m, 1H), 7.11-7.05 (m, 2H), 6.85-6.80 (m, 2H), 3.69 (s, 3H), 3.31-3.24 (m, 3H), 2.75 (t, J=4.9 Hz, 3H), 2.68 (t, J=7.5 Hz, 3H), 2.34 (s, 3H), 2.13 (s, 3H). $^{13}$C NMR (400 MHz, DMSO-d$_6$) δ 160.4, 158.1, 157.5, 131.4, 130.0, 114.2, 55.4, 54.6, 53.8, 45.9, 40.9, 34.1. ESI-MS (m/z): 321.0 [M+H]$^+$.

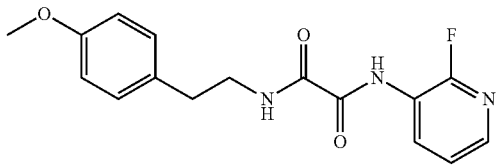

SW208133-1-A

White solid, 213.3 mg, % yield. $^1$H NMR (400 MHz, DMSO-d$_6$) δ 10.26 (s, 1H), 9.08 (t, J=6.0 Hz, 1H), 8.15 (ddd, J=9.7, 7.7, 1.8 Hz, 1H), 8.06 (dt, J=4.9, 1.5 Hz, 1H), 7.38 (ddd, J=7.8, 4.9, 1.2 Hz, 1H), 7.15-7.10 (m, 2H), 6.87-6.81 (m, 2H), 3.70 (s, 3H), 3.42-3.35 (m, 2H), 2.75 (t, J=7.4 Hz, 2H). $^{13}$C NMR (400 MHz, DMSO-d$_6$) δ 159.4, 159.4, 158.2, 156.2 (d, $J_{C-F}$=237.6 Hz), 144.1 (d, $J_{C-F}$=14.3 Hz), 136.1 (d, $J_{C-F}$=3.2 Hz), 131.3, 130.0, 122.7 (d, $J_{C-F}$=4.2 Hz), 120.4 (d, $J_{C-F}$=27.5 Hz), 114.2, 55.4, 41.3, 34.1. ESI-MS (m/z): 318.0 [M+H]$^+$.

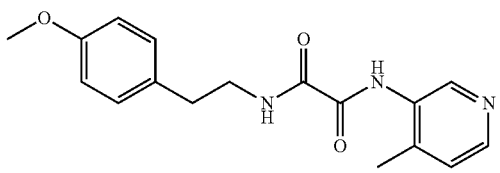 [SMILES: COc1ccc(CCNC(=O)C(=O)Nc2cnccc2C)cc1]

SW208134-1-A

Pink solid, 68.3 mg, 73% yield. $^1$H NMR (400 MHz, DMSO-d$_6$) δ 10.23 (s, 1H), 8.99 (t, J=6.1 Hz, 1H), 8.46 (s, 1H), 8.29 (d, J=4.9 Hz, 1H), 7.30-7.27 (m, 1H), 7.15-7.10 (m, 2H), 6.87-6.82 (m, 2H), 3.70 (s, 3H), 3.42-3.35 (m, 2H), 2.75 (t, J=7.5 Hz, 2H), 2.19 (s, 3H). $^{13}$C NMR (400 MHz, DMSO-d$_6$) δ 159.9, 159.6, 158.2, 147.4, 147.0, 142.6, 132.8, 131.3, 130.0, 125.8, 114.2, 55.4, 41.3, 34.1, 17.6. ESI-MS (m/z): 314.0 [M+H]$^+$.

SW208108-1-A

Cream-colored solid, 385.7 mg, 32% yield. $^1$H NMR (400 MHz, DMSO-d$_6$) δ 9.05 (t, J=6.1 Hz, 1H), 8.02-7.96 (m, 2H), 7.78-7.67 (m, 4H), 7.16-7.10 (m, 4H), 6.88-6.81 (m, 2H), 4.91 (d, J=2.4 Hz, 2H), 3.70 (s, 3H), 3.64 (t, J=2.4 Hz, 1H), 3.44-3.36 (m, 2H), 2.76 (t, J=7.4 Hz, 2H). $^{13}$C NMR (400 MHz, DMSO-d$_6$) δ 193.8, 161.1, 159.9, 159.4, 158.2, 141.6, 133.6, 132.3, 131.3, 130.9, 130.7, 130.0, 130.0, 120.1, 115.1, 114.2, 79.2, 56.1, 55.4, 41.2, 34.1. ESI-MS (m/z): 456.9 [M]$^+$.

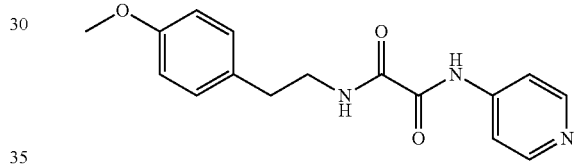

SW208135-1-A

White solid, 44.6 mg, 49% yield. $^1$H NMR (400 MHz, DMSO-d$_6$) δ 9.08 (t, J=6.1 Hz, 1H), 8.49-8.45 (m, 2H), 7.82-7.79 (m, 2H), 7.14-7.10 (m, 2H), 6.86-6.82 (m, 2H), 3.69 (s, 3H), 3.43-3.35 (m, 2H), 2.75 (t, J=7.4 Hz, 2H). $^{13}$C NMR (400 MHz, DMSO-d$_6$) δ 160.1, 159.2, 158.2, 150.8, 144.9, 131.3, 130.0, 114.7, 114.2, 55.4, 41.3, 34.1. ESI-MS (m/z): 300.0 [M+H]$^+$.

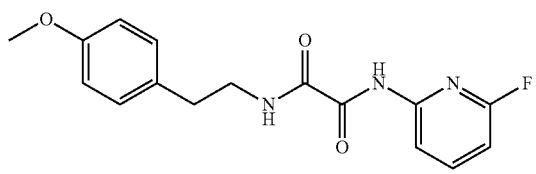 [SMILES: COc1ccc(CCNC(=O)C(=O)Nc2cccc(F)n2)cc1]

SW208136-1-A

White solid, 35.2 mg, 37% yield. $^1$H NMR (400 MHz, DMSO-d$_6$) δ 9.14 (t, J=6.0 Hz, 1H), 8.04 (dd, J=8.2, 8.2 Hz, 1H), 7.92 (dd, J=8.0, 2.0 Hz, 1H), 7.14-7.10 (m, 2H), 6.97 (dd, J=8.0, 2.4 Hz, 1H), 6.86-6.82 (m, 2H), 3.69 (s, 3H), 3.41-3.33 (m, 2H), 2.74 (t, J=7.5 Hz, 2H). $^{13}$C NMR (400 MHz, DMSO-d$_6$) δ 161.9 (d, $^1J_{CF}$=238.2 Hz), 159.4, 159.2, 158.2, 148.8 (d, $^3J_{CF}$=15.2 Hz), 144.7 (d, $^3J_{CF}$=7.8 Hz), 131.2, 130.0, 114.2, 111.6 (d, $^4J_{CF}$=4.1 Hz), 105.8 ($^2J_{CF}$=35.9 Hz), 55.4, 41.4, 34.0. ESI-MS (m/z): 318.0 [M+H]$^+$.

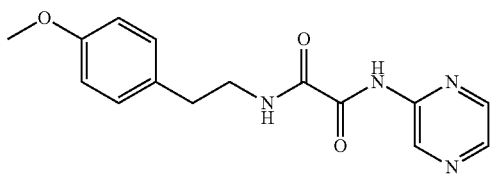 [SMILES: COc1ccc(CCNC(=O)C(=O)Nc2cnccn2)cc1]

SW208137-1-A

White solid, 26.0 mg, 29% yield after flash chromatography (silica gel, 0→100% EtOAc in hexanes). $^1$H NMR (500 MHz, DMSO-$d_6$) δ 10.56 (s, 1H), 9.23 (d, J=1.4 Hz, 1H), 9.21 (t, J=6.0 Hz, 1H), 8.49 (dd, J=2.6, 1.5 Hz, 1H), 8.47 (d, J=2.6 Hz, 1H), 7.16-7.12 (m, 2H), 6.87-6.84 (m, 2H), 3.71 (s, 3H), 3.42-3.36 (m, 2H), 2.76 (t, J=7.4 Hz, 2H). $^{13}$C NMR (400 MHz, DMSO-$d_6$) δ 160.2, 159.3, 158.2, 147.5, 143.5, 141.5, 137.4, 131.3, 130.0, 114.2, 55.4, 41.4, 34.1. ESI-MS (m/z): 301.0 [M+H]$^+$.

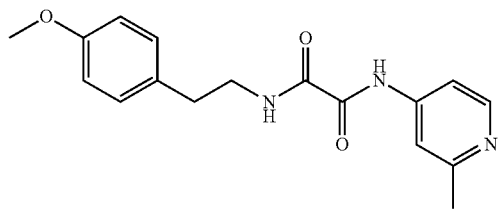 [SMILES: COc1ccc(CCNC(=O)C(=O)Nc2ccnc(C)c2)cc1]

SW208138-1-A

White solid, 22.3 mg, 24% yield after flash chromatography (silica gel, 0→100% EtOAc in hexanes). $^1$H NMR (400 MHz, DMSO-$d_6$) δ 10.86 (s, 1H), 9.03 (t, J=6.0 Hz, 1H), 8.32 (d, J=5.6 Hz, 1H), 7.67 (d, J=2.0 Hz, 1H), 7.61 (dd, J=5.8, 1.8 Hz, 1H), 7.14-7.09 (m, 2H), 6.86-6.82 (m, 2H), 3.69 (s, 3H), 3.42-3.34 (m, 2H), 2.74 (t, J=7.4 Hz, 2H), 2.40 (s, 3H). $^{13}$C NMR (400 MHz, DMSO-$d_6$) δ 160.0, 159.6, 159.1, 158.2, 150.1, 145.1, 131.3, 130.0, 114.2, 113.6, 112.1, 55.4, 41.3, 34.1, 24.8. ESI-MS (m/z): 314.0 [M+H]$^+$.

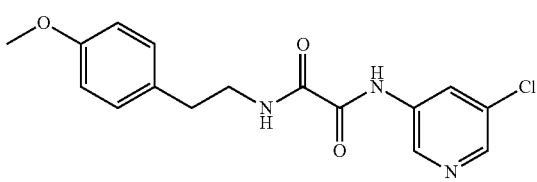 [SMILES: COc1ccc(CCNC(=O)C(=O)Nc2cncc(Cl)c2)cc1]

SW208139-1-A

Cream-colored solid, 93.2 mg, 89% yield. $^1$H NMR (400 MHz, DMSO-$d_6$) δ 9.07 (t, J=6.1 Hz, 1H), 8.96 (d, J=2.1 Hz, 1H), 8.68 (appt, J=6.1 Hz, 1H), 8.38 (d, J=2.2 Hz, 1H), 8.34 (t, J=2.2 Hz, 1H), 7.15-7.10 (m, 2H), 6.86-6.82 (m, 2H), 3.69 (s, 3H), 3.43-3.35 (m, 2H), 2.75 (t, J=7.4 Hz, 2H). $^{13}$C NMR (400 MHz, DMSO-$d_6$) δ 160.2, 159.5, 158.2, 143.9, 140.7, 135.8, 132.5, 131.3, 130.0, 127.0, 114.2, 55.4, 41.3, 34.1. ESI-MS (m/z): 333.9 [M]$^+$.

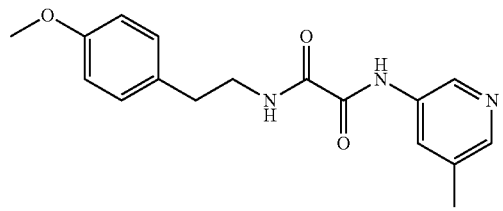 [SMILES: COc1ccc(CCNC(=O)C(=O)Nc2cncc(C)c2)cc1]

SW208140-1-A

Cream-colored solid, 79.8 mg, 87% yield. $^1$H NMR (400 MHz, DMSO-$d_6$) δ 9.00 (t, J=6.0 Hz, 1H), 8.77 (d, J=2.3 Hz, 1H), 8.68 (t, J=6.1 Hz, 1H), 8.18-8.16 (m, 1H), 8.02-7.99 (m, 1H), 7.15-7.10 (m, 2H), 6.86-6.83 (m, 2H), 3.69 (s, 3H), 3.43-3.35 (m, 2H), 2.79-2.72 (m, 2H), 2.27 (s, J=0.9 Hz, 3H). $^{13}$C NMR (400 MHz, DMSO-$d_6$) δ 160.2, 159.5, 158.2, 146.1, 139.9, 134.4, 133.2, 131.3, 130.0, 128.1, 114.2, 55.4, 41.3, 34.1, 18.4. ESI-MS (m/z): 314.0 [M+H]$^+$.

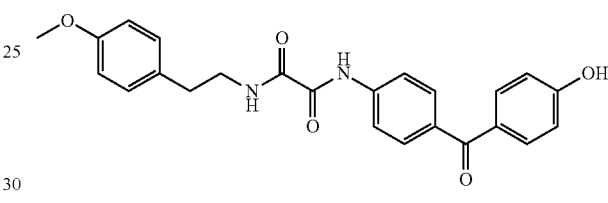

SW208141-1-A

Cream-colored solid, 19.8 mg, 20% yield after flash chromatography (silica gel, 0→100% EtOAc in hexanes). $^1$H NMR (500 MHz, DMSO-$d_6$) δ 10.95 (s, 1H), 9.09 (t, J=6.0 Hz, 1H), 8.00-7.96 (m, 2H), 7.70-7.66 (m, 2H), 7.67-7.63 (m, 2H), 7.16-7.12 (m, 2H), 6.90-6.87 (m, 2H), 3.71 (s, 3H), 3.44-3.37 (m, 2H), 2.77 (t, J=7.4 Hz, 2H). $^{13}$C NMR (400 MHz, DMSO-$d_6$) δ 193.7, 162.2, 160.2, 160.0, 159.4, 158.2, 158.1, 141.3, 134.1, 132.8, 131.3, 130.7, 130.0, 120.1, 115.6, 114.2, 55.4, 34.1. ESI-MS (m/z): 418.9 [M]$^+$.

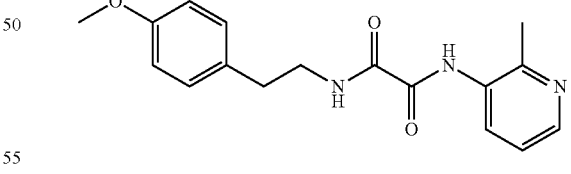

SW208143-1-A

White solid, 21.8 mg, 57% yield. $^1$H NMR (400 MHz, DMSO-$d_6$) δ 10.3 (s, 1H), 9.00 (t, J=6.0 Hz, 1H), 8.31 (dd, J=4.8, 1.6 Hz, 1H), 7.76 (dd, J=8.0, 1.6 Hz, 1H), 7.25 (ddd, J=8.1, 4.8, 0.7 Hz, 1H), 7.16-7.10 (m, 2H), 6.87-6.82 (m, 2H), 3.70 (s, 3H), 3.42-3.34 (m, 2H), 2.75 (t, J=7.5 Hz, 2H), 2.38 (s, 3H). $^{13}$C NMR (400 MHz, DMSO-$d_6$) δ 159.9, 159.3, 158.2, 153.3, 146.8, 133.0, 131.8, 131.3, 130.0, 121.9, 114.2, 55.4, 41.3, 34.1, 21.3. ESI-MS (m/z): 314.0 [M+H]$^+$.

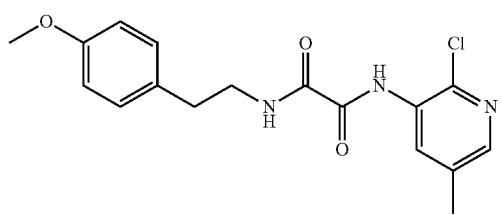 [SMILES: COc1ccc(CCNC(=O)C(=O)Nc2cc(C)cnc2Cl)cc1]

SW208144-1-A

White solid, 56.3 mg, 48% yield. $^1$H NMR (400 MHz, DMSO-d$_6$) δ 10.15 (s, 1H), 9.13 (t, J=6.1 Hz, 1H), 8.14-8.07 (m, 2H), 7.17-7.05 (m, 2H), 6.88-6.79 (m, 2H), 3.70 (s, 3H), 3.42-3.35 (m, 2H), 2.75 (t, J=7.4 Hz, 2H), 2.30 (s, 3H). $^{13}$C NMR (400 MHz, DMSO-d$_6$) δ 159.4, 159.0, 158.2, 146.6, 141.0, 134.1, 133.3, 131.2, 130.6, 130.0, 114.2, 55.4, 41.5, 34.0, 17.6. ESI-MS (m/z): 347.9 [M]$^+$.

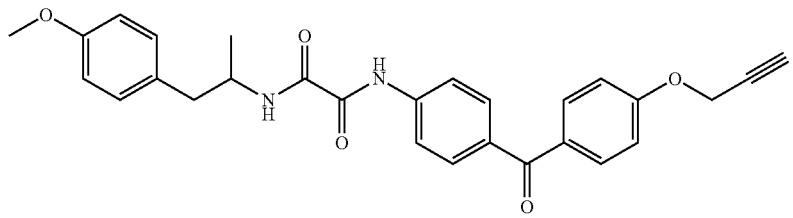 [SMILES: C#CCOc1ccc(C(=O)c2ccc(NC(=O)C(=O)NC(C)Cc3ccc(OC)cc3)cc2)cc1]

SW208217-1-A

White solid, 8.8 mg, 25% yield. $^1$H NMR (400 MHz, DMSO-d$_6$) δ 10.48 (s, 1H), 8.90 (d, J=8.9 Hz, 1H), 8.01-7.89 (m, 3H), 7.77-7.62 (m, 5H), 7.15-7.09 (m, 3H), 6.84-6.78 (m, 1H), 4.92-4.89 (m, 2H), 4.09-3.99 (m, 1H), 3.68 (s, 3H), 3.65-3.62 (m, 1H), 2.82 (dd, J=13.5, 8.2 Hz, 1H), 2.67 (dd, J=13.5, 6.0 Hz, 1H), 1.14 (d, J=6.6 Hz, 3H). $^{13}$C NMR (400 MHz, DMSO-d$_6$) δ 193.8, 161.1, 160.9, 159.8, 159.5, 159.2, 132.3, 132.2, 131.3, 131.1, 130.9, 130.4, 120.1, 115.1, 114.0, 79.2, 79.2, 56.2, 55.4, 47.7, 20.4. ESI-MS (m/z): 471.0 [M+H]$^+$.

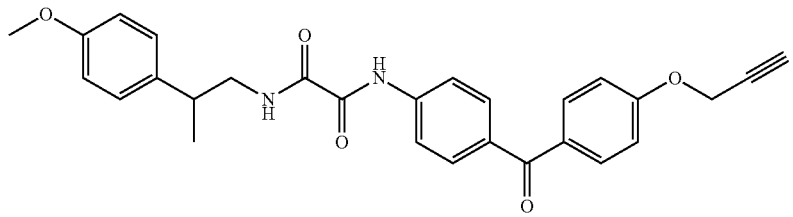 [SMILES: C#CCOc1ccc(C(=O)c2ccc(NC(=O)C(=O)NCC(C)c3ccc(OC)cc3)cc2)cc1]

SW208219-1-A

White solid, 7.9 mg, 14% yield. $^1$H NMR (400 MHz, DMSO-d$_6$) δ 10.93 (s, 1H), 8.93 (t, J=6.1 Hz, 1H), 8.00-7.95 (m, 2H), 7.75-7.67 (m, 4H), 7.18-7.09 (m, 4H), 6.88-6.82 (m, 2H), 4.91 (d, J=2.4 Hz, 2H), 3.70 (s, 3H), 3.63 (t, J=2.3 Hz, 1H), 3.30-3.24 (m, 2H), 3.06-2.96 (m, 1H), 1.16 (d, J=6.9 Hz, 3H). $^3$C NMR (400 MHz, DMSO-d$_6$) δ 193.8, 161.1, 159.9, 159.5, 158.2, 141.7, 136.6, 133.6, 132.3, 130.9, 130.7, 128.4, 120.1, 115.1, 114.2, 79.23, 79.17, 56.1, 55.4, 46.6, 38.3, 19.9. ESI-MS (m/z): 471.0 [M+H]$^+$. ESI-MS (m/z): 471.0 [M+H]$^+$.

Synthesis of Amines Via Nitromethane

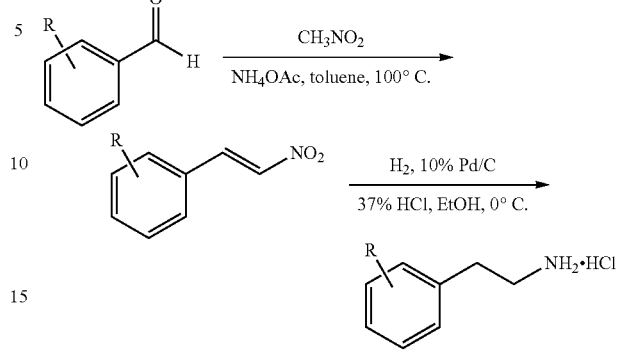

Step 1:

Nitromethane (79.8 eq) was added to a solution of benzaldehyde derivatives (1 eq) and ammonium acetate (NH$_4$OH) (0.6 eq) in toluene (0.1 M) and then heated to 100° C. overnight. After cooling to rt, water was added and the yellow reaction mixture was extracted three times with EtOAc. The combined organic extracts were washed with brine, dried over Na$_2$SO$_4$, and concentrated to give the crude nitro product, which was used without further purification, unless otherwise noted.

Step 2:

10% Pd/C (1.6 eq) was added to a solution of nitro compound (1 eq) from step 1 in EtOH (0.067 M) and 37% HCl (6.25 M) under nitrogen in an ice bath at 0° C. The nitrogen was purged and replaced with a H$_2$ balloon. When the reaction was finished (6+ hours), the reaction was filtered through celite to remove Pd/C. The celite was washed with EtOH, and the filtrate was concentrated. Then CH$_3$CN was added and a white precipitate formed. The precipitate was collected through filtration and dried to yield the final product as the amine salt.

Nitromethane Intermediates:

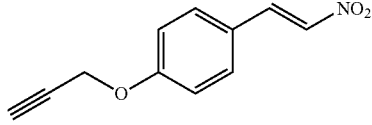

Orange solid, 580.3 mg, 63% yield (after flash chromatography (silica gel, 0→30% EtOAc in hexanes). Synthesized from propargyl bromide with sew-189-098). $^1$H NMR (500 MHz, CDCl$_3$) δ 7.99 (d, J=13.6 Hz, 1H), 7.57-7.51 (m, 3H), 7.08-7.03 (m, 2H), 4.77 (d, J=2.4 Hz, 2H), 2.58 (t, J=2.4 Hz, 1H).

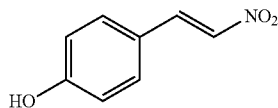 [SMILES: O=[N+]([O-])/C=C/c1ccc(O)cc1]

Orange solid, 767.5 mg, 92% yield. $^1$H NMR (500 MHz, Methanol-d$_4$) δ 8.01 (d, J=13.5 Hz, 1H), 7.78 (d, J=13.5 Hz, 1H), 7.59-7.55 (m, 2H), 6.88-6.83 (m, 2H).

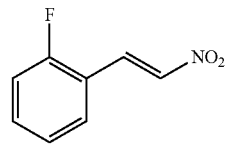 [SMILES: O=[N+]([O-])/C=C/c1ccccc1F]

Orange solid, 293.5 mg, 99% yield. $^1$H NMR (400 MHz, DMSO-d$_6$) δ 8.22 (d, J=13.7 Hz, 1H), 8.12 (d, J=13.7 Hz, 1H), 7.87-7.82 (m, 2H), 7.50-7.46 (m, 3H).

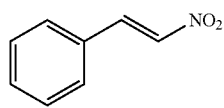

Cream-colored solid, 236.7 mg, % yield. $^1$H NMR (500 MHz, CDCl$_3$) δ 8.07 (d, J=13.8 Hz, 1H), 7.75 (d, J=13.8 Hz, 1H), 7.56-7.47 (m, 2H), 7.27-7.17 (m, 2H).

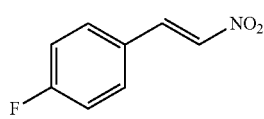 [SMILES: O=[N+]([O-])/C=C/c1ccc(F)cc1]

Orange solid, 300.4 mg, % yield. $^1$H NMR (400 MHz, DMSO-d$_6$) δ 8.25 (d, J=7.1 Hz, 1H), 8.03 (d, J=7.8, 1H), 7.62 (dd, J=8.2, 8.2 Hz, 1H), 7.55 (ddd, J=8.0, 7.5, 1.4 Hz, 1H), 7.48-7.29 (m, 2H).

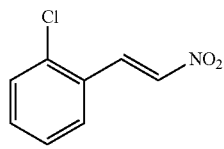

Yellow solid, 196.9 mg, 96% yield. $^1$H NMR (500 MHz, CDCl$_3$) δ 8.00 (d, J=13.7 Hz, 1H), 7.61-7.55 (m, 3H), 7.20-7.13 (m, 2H). ESI-MS (m/z): 168.0 [M+H]$^+$.

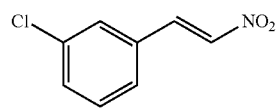 [SMILES: O=[N+]([O-])/C=C/c1cccc(Cl)c1]

Orange oil, 267.8 mg, % yield. $^1$H NMR (400 MHz, DMSO-d$_6$) δ 8.23 (d, J=13.5 Hz, 1H), 8.08 (d, J=13.5 Hz, 1H), 7.82 (dd, J=7.9, 1.3 Hz, 1H), 7.41 (ddd, J=7.6, 7.5, 1.3 Hz, 1H), 7.34-7.30 (m, 1H), 7.27 (ddd, J=7.6, 7.6, 1.4 Hz, 1H), 2.44 (s, 3H).

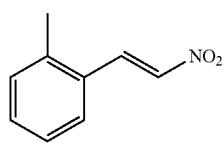

Green solid, 194.7 mg, 85% yield after flash chromatography (silica gel, 0→30% EtOAc in hexanes). ESI-MS (m/z): 183.9 [M]$^+$.

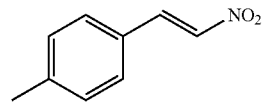

Green solid, 221.9 mg, % yield after flash chromatography (silica gel, 0→24% EtOAc in hexanes). ESI-MS (m/z): 164.0 [M+H]$^+$.

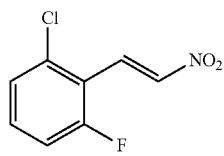

Orange solid, 198.7 mg, 80% yield. $^1$H NMR (400 MHz, DMSO-d$_6$) δ 8.12 (d, J=13.8 Hz, 1H), 7.95 (dd, J=13.8, 1.2 Hz, 1H), 7.64-7.57 (m, 1H), 7.55-7.51 (m, 1H), 7.47-7.40 (m, 1H).

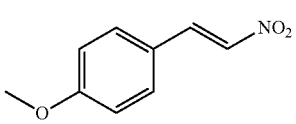

Yellow solid, 176.7 mg, 80% yield after flash chromatography (silica gel, 0→20% EtOAc in hexanes). $^1$H NMR (500 MHz, CDCl$_3$) δ 8.00 (d, J=13.6 Hz, 1H), 7.55-7.50 (m, 3H), 6.99-6.94 (m, 2H), 3.88 (s, 3H). ESI-MS (m/z): 180.0 [M+H]$^+$.

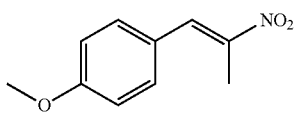

Yellow solid, 312.1 mg, % yield after flash chromatography (silica gel, 0→30% EtOAc in hexanes). Used nitroethane instead of nitromethane. $^1$H NMR (500 MHz, CDCl$_3$) δ 8.09 (s, 1H), 7.46-7.53 (m, 2H), 7.01-6.97 (m, 2H), 3.88 (s, 3H), 2.49 (d, J=1.0 Hz, 3H). ESI-MS (m/z): 194.0 [M+H]$^+$.

Reduction of Nitro Group

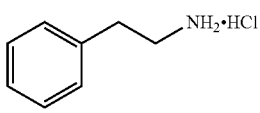

White solid, 120.6 mg, (80 mg recovered from ML), 51% yield. $^1$H NMR (500 MHz, DMSO-d$_6$) δ 8.10 (s, 2H), 7.35-7.30 (m, 2H), 7.25 (d, J=7.3 Hz, 3H), 3.04-2.98 (m, 1H), 2.91-2.86 (m, 1H).

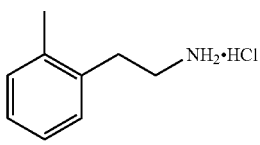

white solid, 116.6 mg, (80 mg recovered from ML), 52% yield.

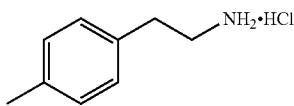

White solid, 135.3, 73% yield. $^1$H NMR (400 MHz, DMSO-d6) δ 8.20 (s, 2H), 7.11 (s, 4H), 2.87-2.80 (m, 2H), 12.25 (s, 3H).

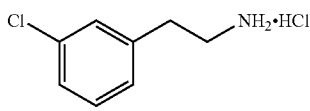

White solid, 74.6 mg, 45% yield.

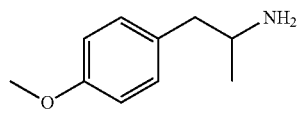

White solid, 88.0 mg, 32% yield. Reaction stirred overnight at rt. $^1$H NMR (400 MHz, DMSO-d$_6$) δ 7.93 (s, 2H), 7.16-7.11 (m, 2H), 6.91-6.85 (m, 2H), 3.72 (s, 3H), 2.90 (dd, J=13.4, 5.4 Hz, 1H), 2.58 (dd, J=13.5, 8.9 Hz, 1H), 1.07 (d, J=6.5 Hz, 3H).

Reduction of Alkyl Nitro

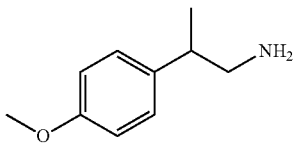

10% Pd/C (1.8 eq) was added to a solution of the alkyl nitro derivative (derived from aryl Grignard addition to the corresponding vinyl nitro compound in the presence of CeCl3) (1 eq) in EtOAc (0.1 M). The reaction solution was N2 purged before adding H2 at 50 psi. The reaction mixture stirred for 1 h 15 min, then filtered through celite, and the filtrate was concentrated and dried to yield the desired product as a cream-colored solid in 48% yield (42.5 mg) (GCMS-m=165) and HNMR (sew-192-189-1)

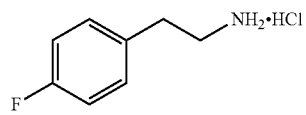

White solid, 55.7 mg, 35% yield. $^1$H NMR

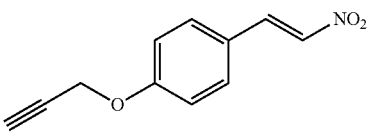

Orange solid, 580.3 mg, 63% yield (after flash chromatography (silica gel, 0→30% EtOAc in hexanes). Synthesized from propargyl bromide with sew-189-098). $^1$H NMR (500 MHz, CDCl$_3$) δ 7.99 (d, J=13.6 Hz, 1H), 7.57-7.51 (m, 3H), 7.08-7.03 (m, 2H), 4.77 (d, J=2.4 Hz, 2H), 2.58 (t, J=2.4 Hz, 1H).

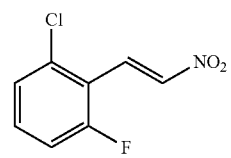

Orange solid, 198.7 mg, 80% yield. $^1$H NMR (400 MHz, DMSO-d$_6$) δ 8.12 (d, J=13.8 Hz, 1H), 7.95 (dd, J=13.8, 1.2 Hz, 1H), 7.64-7.57 (m, 1H), 7.55-7.51 (m, 1H), 7.47-7.40 (m, 1H).

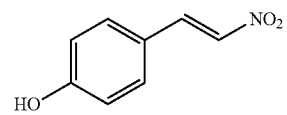 [SMILES: O=[N+]([O-])/C=C/c1ccc(O)cc1]

Orange solid, 767.5 mg, 92% yield. $^1$H NMR (500 MHz, Methanol-d$_4$) δ 8.01 (d, J=13.5 Hz, 1H), 7.78 (d, J=13.5 Hz, 1H), 7.59-7.55 (m, 2H), 6.88-6.83 (m, 2H).

Procedure from Tetrahedron Letters, 35, 1994, 8651-8654

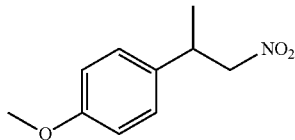

CeCl3.7H2O was dried by heating cerium(III) chloride heptahydride to 140° C. under vacuum with stirring overnight. Then a slurry of CeCl3 (2 eq) in anhydrous THF (0.125 M) was cooled to −78° C. under nitrogen for 20 minutes before CH3MgBr (3.0 M in ether, 2 eq) was added. The reaction mixture stirred at −78° C. under nitrogen for 1½ hours before warming to −40° C. Then the nitro anisole analog (sew-192-153-2) (1 eq) in anhydrous THF (0.4 M) was added slowly to the reaction mixture. The reaction was finished in 10 minutes. Acetic acid (10 eq) was added to quench the reaction. The solution stirred under nitrogen for 5 minutes and the solution turned yellow. The reaction mixture was diluted with water and extracted into hexanes. The organic extracts were dried with Na2SO4 and concentrated before azeotroping with toluene to remove the acetic acid and drying under vacuum to give the product as a yellow solid in 82% yield (158.5 mg). $^1$H NMR (400 MHz, CDCl$_3$) δ 7.17-7.12 (m, 2H), 6.89-6.84 (m, 2H), 4.48 (qd, J=11.9, 7.8 Hz, 2H), 3.79 (s, 3H), 3.62-3.56 (m, 1H), 1.35 (d, J=7.0 Hz, 3H). (no ionization in mass) (sew-192-177-2) (used 177-2 also 192-159-1)

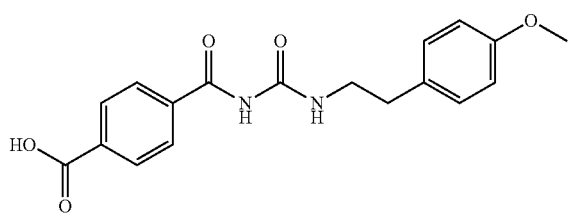 [SMILES: COc1ccc(CCNC(=O)NC(=O)c2ccc(C(=O)O)cc2)cc1]

SW208395-1-A White Solid, 561.0 mg, 82% Yield.

$^1$H NMR (500 MHz, DMSO-d$_6$) δ 10.84 (s, 1H), 8.63 (t, J=5.7 Hz, 1H), 8.03-7.98 (m, 4H), 7.19-7.14 (m, 2H), 6.90-6.84 (m, 2H), 3.71 (s, 3H), 3.46-3.41 (m, 2H), 2.75 (t, J=7.2 Hz, 2H). $^{13}$C NMR (400 MHz, DMSO-d$_6$) δ 168.1, 167.2, 158.2, 153.7, 136.5, 131.4, 130.1, 129.8, 129.6, 128.7, 114.3, 55.4, 41.3, 34.8. ESI-MS (m/z): 342.9 [M]$^+$.

Procedure for SW207038-1-A

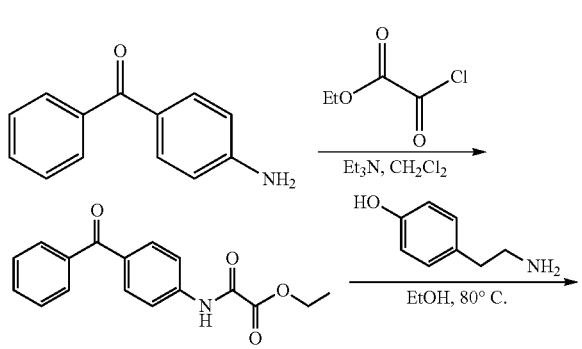

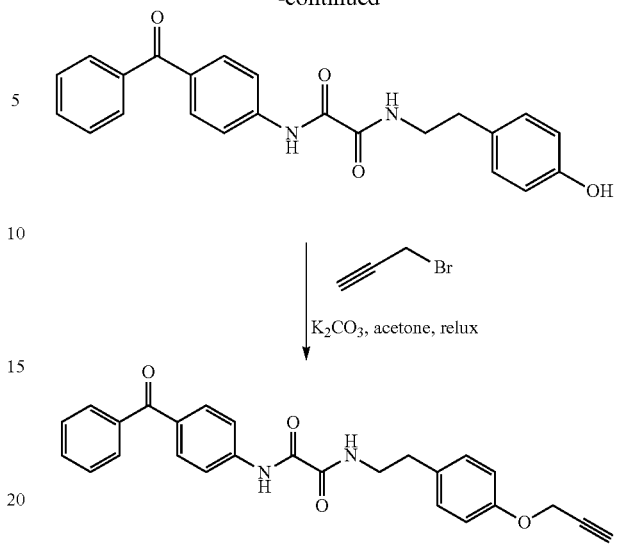

Step 1 and Step 2 same as general procedures described above.

Step 1 product: ethyl ester: orange solid, % yield $^1$H NMR (400 MHz, Acetonitrile-d$_3$) δ 9.61 (s, 1H), 7.89-7.81 (m, 4H), 7.80-7.75 (m, 2H), 7.69-7.64 (m, 1H), 7.56 (ddt, J=7.5, 5.7, 1.7 Hz, 2H), 4.38 (q, J=7.1 Hz, 2H), 3.06 (q, J=7.3 Hz, 2H), 1.39 (t, J=7.1 Hz, 3H), 1.23 (t, J=7.3 Hz, 2H). ESI-MS (m/z): 298.0 [M+H]$^+$.

Step 2 product: oxalamide phenol: orange solid, 37.5 mg, 48% yield. $^1$H NMR (400 MHz, CDCl$_3$) δ 9.42 (s, 1H), 7.86 (d, J=8.4 Hz, 2H), 7.76 (dd, J=12.3, 8.0 Hz, 4H), 7.53 (dt, J=35.7, 7.5 Hz, 5H), 7.09 (d, J=8.1 Hz, 2H), 6.80 (d, J=8.2 Hz, 2H), 4.89 (s, 1H), 3.72 (d, J=7.9 Hz, 2H), 3.61 (q, J=6.8 Hz, 2H), 2.84 (t, J=7.1 Hz, 2H), 1.24 (t, J=7.0 Hz, 3H). ESI-MS (m/z): 388.9 [M]$^+$.

Step 3 Procedure:

A solution of alcohol (1 eq) and potassium carbonate (K$_2$CO$_3$) (1.4 eq) in acetone (0.2 M) refluxed for 30 minutes before adding propargyl bromide (80 wt % in toluene, 2 eq). When TLC showed no more starting material (7-18 hours) the reaction mixture was cooled to rt and then concentrated. Water was added to the residue and extracted into EtOAc (3×). The organic extracts were washed with brine, dried with Na$_2$SO$_4$, and concentrated. The crude material was purified by flash chromatography (silica gel, 0→33% EtOAc in hexanes) to give final product.

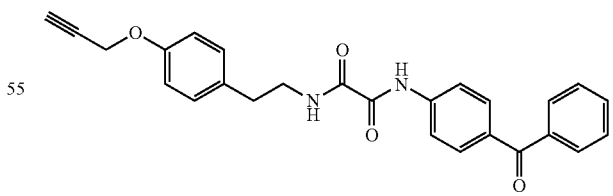

SW207038-1-A

Cream solid, 13.9 mg, 33% yield after flash chromatography (silica gel, 0→33% EtOAc in hexanes). $^1$H NMR (500 MHz, DMSO-d$_6$) δ 11.00 (s, 1H), 9.11 (t, J=6.0 Hz, 1H), 8.03-7.99 (m, 2H), 7.78-7.74 (m, 2H), 7.73-7.70 (m, 2H), 7.69-7.64 (m, 1H), 7.58-7.54 (m, 2H), 7.18-7.14 (m, 2H), 6.93-6.88 (m, 2H), 4.75 (d, J=2.4 Hz, 2H), 3.55 (t, J=2.4 Hz, 1H), 3.44-3.38 (m, 2H), 2.78 (t, J=7.4 Hz, 2H). $^{13}$C NMR (400 MHz, DMSO-$d_6$) δ 195.1, 160.0, 159.5, 156.1, 142.1, 137.7, 133.0, 132.9, 132.2, 131.2, 130.0, 130.0, 129.0, 120.2, 115.2, 79.9, 78.6, 55.8, 41.3, 34.1. ESI-MS (m/z): 427.9 [M+H]$^+$.

SW207038-2-A

White solid, 45.6 mg, 50% yield after flash chromatography (silica gel, 0→50% EtOAc in hexanes). $^1$H NMR (500 le;5qMHz, DMSO-$d_6$) δ 11.00 (s, 1H), 9.11 (t, J=6.0 Hz, 1H), 8.03-7.99 (m, 2H), 7.78-7.74 (m, 2H), 7.73-7.69 (m, 2H), 7.69-7.64 (m, 1H), 7.58-7.54 (m, 2H), 7.18-7.13 (m, 2H), 6.93-6.88 (m, 2H), 4.75 (d, J=2.3 Hz, 2H), 3.55 (t, J=2.4 Hz, 1H), 3.44-3.38 (m, 2H), 2.78 (t, J=7.4 Hz, 2H). ESI-MS (m/z): 426.9 [M]$^+$.

Procedure for SW208117

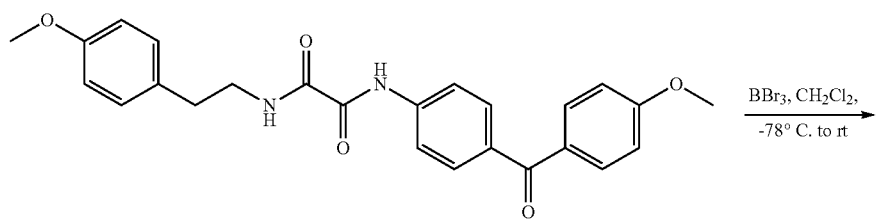

SW208009

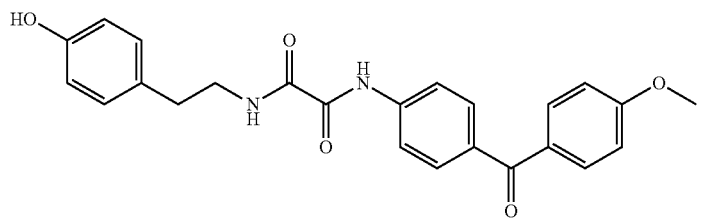

SW208117-1-A:

A solution of SW208009 (1 eq) in $CH_2Cl_2$ (0.2 M) was cooled to −78° C. for 20 minutes before adding BBr$_3$/ $CH_2Cl_2$ (1.0 M, 2 eq) dropwise and warmed to rt after an hour. The solution stirred overnight at rt. After 20 hours, the solution was cooled to 0° C., and BBr$_3$ (1.0 M, 8 eq) was added, and the reaction mixture stirred for 4 more hours at rt before it was complete by TLC. The reaction mixture was poured into ice water and a precipitate formed. The precipitate was collected by filtration and purified by flash chromatography (silica gel, 0→100% EtOAc in hexanes) to give the final product as a yellow solid in 13% yield (11.4 mg). ¹H NMR (400 MHz, DMSO-d₆) δ 10.93 (s, 1H), 9.17 (s, 1H), 9.02 (t, J=6.0 Hz, 1H), 8.00-7.96 (m, 2H), 7.75-7.71 (m, 2H), 7.71-7.67 (m, 2H), 7.10-7.04 (m, 2H), 7.02-6.97 (m, 2H), 6.68-6.63 (m, 2H), 3.84 (s, 3H), 3.40-3.33 (m, 2H), 2.70 (t, J=7.5 Hz, 2H). ¹³C NMR (400 MHz, DMSO-d₆) δ 193.8, 163.2, 159.9, 159.5, 156.1, 141.6, 133.8, 132.5, 130.9, 130.1, 129.9, 129.5, 120.2, 115.6, 114.3, 56.0, 41.4, 34.2. ESI-MS (m/z): 418.0 [M]⁺.

Representative Synthesis of N-Acyl Ureas Derived from Anilines. reaction mixture stirred for 20 minutes at rt. The reaction mixture was extracted into CH₂Cl₂ and the organic layer was dried with Na₂SO₄ and concentrated to give the amide as a white solid in 35% yield over 2 steps, 33.4 mg. ¹H NMR (500 MHz, DMSO-d₆) δ 7.27 (s, 1H), 7.12-7.08 (m, 2H), 6.84-6.79 (m, 2H), 6.78-6.73 (m, 1H), 3.70 (s, 3H), 2.71 (t, J=7.7 Hz, 2H), 2.29 (t, J=7.8 Hz, 2H). ESI-MS (m/z): 180.0 [M+H]⁺.

Step 3-4 Procedure from J. Med. Chem. 2007, 50, 24, 6080-6094.

Step 2

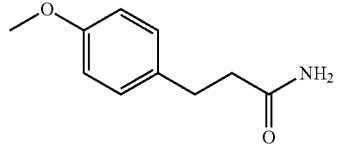

Ammonium hydroxide (0.13 M) was added to a solution of acid chloride (1 eq) in CH₂Cl₂ (0.2 M) at 0° C. The Step 3:

Oxalyl chloride (1.5 eq) was added to a solution of amide (1 eq) in CH₂Cl₂ (0.025 M) and heated at 50° C. for 3 hours. Then, the reaction mixture was concentrated and N₂ purged for 15 minutes to remove excess oxalyl chloride. The isocyanate intermediate was used immediately in the next step.

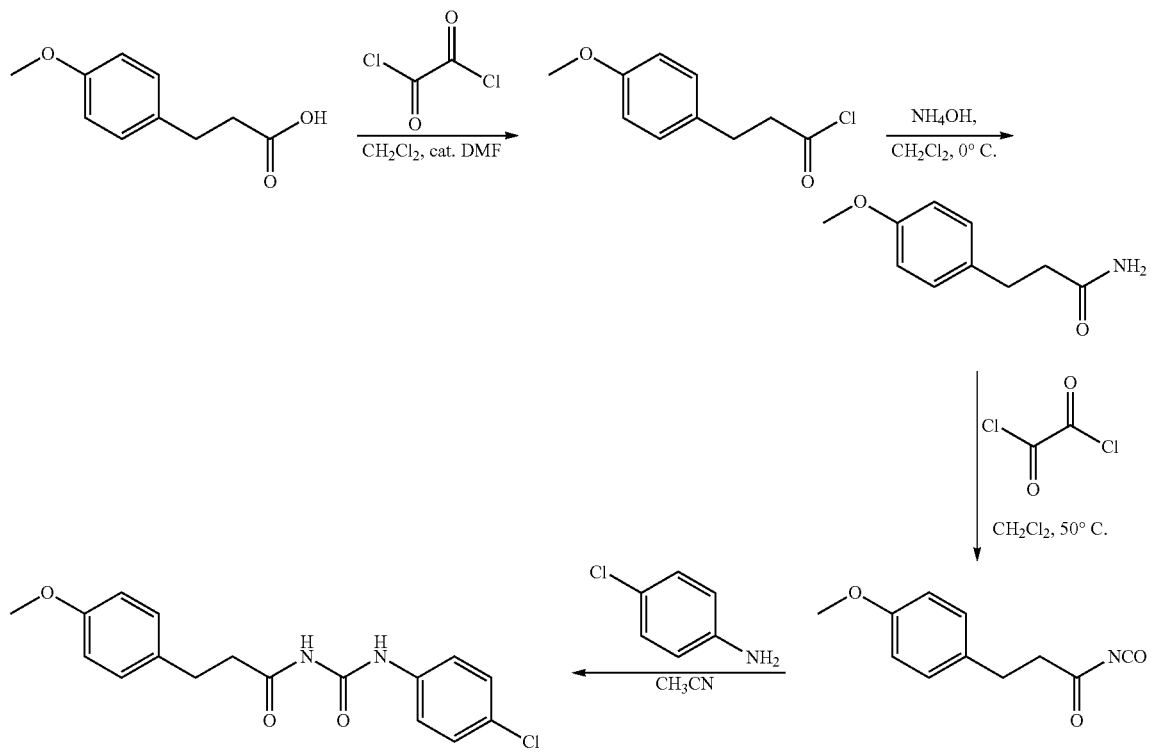

Step 1

Oxalyl chloride (5 eq) was added to a solution of 4-methoxyphenyl)propionic acid (1 eq) in CH₂Cl₂ (0.1 M), and then a catalytic amount of DMF was added to the reaction mixture to initiate the reaction and bubbling occurred. The reaction was complete in 2 hours, and the solution was dried with N₂ for one hour to give the acid chloride, which was used immediately in the next step.

Step 4:

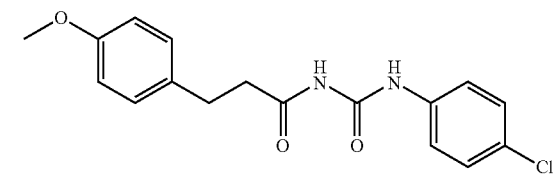 [SMILES: COc1ccc(CCC(=O)NC(=O)Nc2ccc(Cl)cc2)cc1]

4-chloroaniline (1 eq) was added to a solution of the isocyanate intermediate (1 eq) in acetonitrile (0.1 M) and a white precipitate formed immediately. The reaction mixture stirred for 4 hours. Then, the white precipitate was collected by filtration, rinsed with acetonitrile, and purified by flash chromatography (silica gel, 0→100% EtOAc in hexanes) to give the final product as a white solid in 36% yield (18.7 mg). $^1$H NMR (500 MHz, DMSO-$d_6$) δ 10.77 (s, 1H), 10.59 (s, 1H), 7.59-7.54 (m, 2H), 7.39-7.34 (m, 2H), 7.16-7.12 (m, 2H), 6.87-6.82 (m, 2H), 3.70 (s, 3H), 2.81 (t, J=7.6 Hz, 2H), 2.65 (t, J=7.5 Hz, 2H). $^{13}$C NMR (400 MHz, DMSO-$d_6$) δ 175.5, 158.1, 151.3, 137.0, 132.7, 129.6, 129.2, 127.7, 121.8, 114.2, 55.4, 38.1, 29.6. ESI-MS (m/z): 332.9 [M]$^+$.

General Procedure to Make Isocyanate and N-Acyl Ureas Derived from (Hetero)Aryl Carboxylic Amides.

Procedure from J. Med. Chem. 2007, 50, 24, 6080-6094.

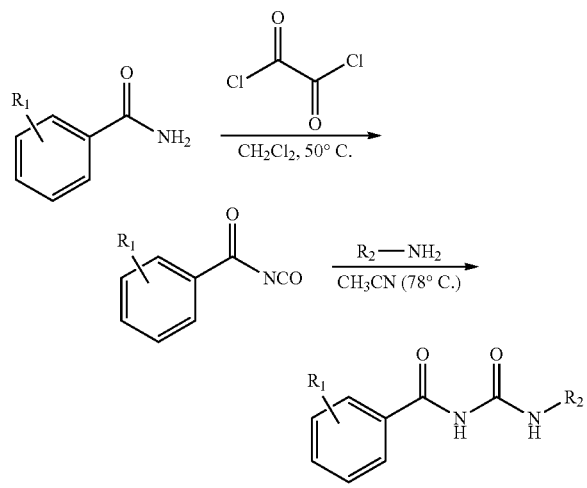

Step 1:

Oxalyl chloride (2 eq) was added to a solution of benzamide derivatives (1 eq) in CH$_2$Cl$_2$ (0.1 M) and heated at 50° C. for 5-9 hours, unless otherwise noted. Then, the reaction mixture was concentrated and N$_2$ purged for 10 minutes to remove excess oxalyl chloride. The isocyanate intermediate was used immediately in the next step.

Step 2:

Amine (1.2 eq) was added to a solution of isocyanate intermediate (1 eq) in acetonitrile (0.1 M) and usually a white precipitate formed immediately. The reaction mixture stirred overnight at rt. (If the amine was tyramine, the solution was heated at 78° C. for 3-5 hours.) Then, the reaction mixture was concentrated. Water and EtOAc were added to the residue. If the precipitate didn't dissolve, the white precipitate was collected by filtration and dried under vacuum to give the final product. If the precipitate did dissolve, the solution was extracted into EtOAc (3×) and the organic layer was washed with brine, dried with Na$_2$SO$_4$, and concentrated to give the final product. The final product was not purified unless otherwise noted.

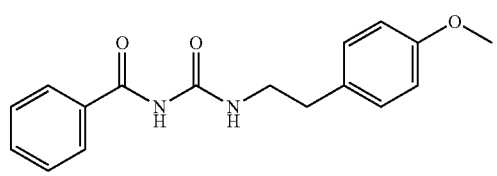 [SMILES: COc1ccc(CCNC(=O)NC(=O)c2ccccc2)cc1]

SW208142-1-A

White solid, 8.6 mg, 11% yield after flash chromatography (silica gel, 0→100% EtOAc in hexanes). 1.5 eq of oxalyl chloride and 0.025 M CH$_2$Cl$_2$ were used in the first step. $^1$H NMR (400 MHz, DMSO-$d_6$) δ 10.66 (s, 1H), 8.67 (t, J=5.7 Hz, 1H), 7.94-7.90 (m, 2H), 7.63-7.56 (m, 1H), 7.51-7.44 (m, 2H), 7.18-7.13 (m, 2H), 6.88-6.83 (m, 2H), 3.70 (s, 3H), 3.46-3.38 (m, 2H), 2.74 (t, J=7.2 Hz, 2H). $^{13}$C NMR (400 MHz, DMSO-$d_6$) δ 168.6, 158.2, 153.9, 133.2, 133.0, 131.5, 130.1, 128.9, 128.6, 114.3, 55.4, 41.3, 34.8. ESI-MS (m/z): 299.0 [M+H]$^+$.

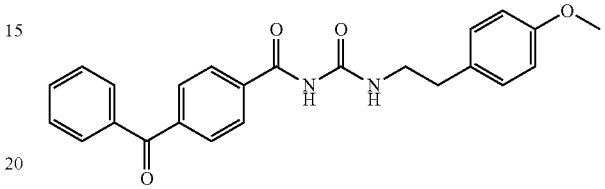

SW208222-1-A

White solid, 17.7 mg, 18% yield. $^1$H NMR (400 MHz, DMSO-$d_6$) δ 10.83 (s, 1H), 8.62 (t, J=5.7 Hz, 1H), 8.09-8.04 (m, 2H), 7.81-7.76 (m, 2H), 7.76-7.72 (m, 2H), 7.72-7.67 (m, 1H), 7.57 (appt, J=7.6 Hz, 2H), 7.19-7.13 (m, 2H), 6.88-6.83 (m, 2H), 3.71 (s, 3H), 3.48-3.40 (m, 2H), 2.75 (t, J=7.2 Hz, 2H). $^{13}$C NMR (400 MHz, DMSO-$d_6$) δ 195.7, 168.0, 160.2, 158.2, 158.1, 153.7, 140.8, 136.9, 136.3, 133.6, 131.4, 130.2, 130.1, 129.8, 129.2, 128.8, 114.3, 55.4, 41.0, 34.1. ESI-MS (m/z): 403.0 [M+H]$^+$.

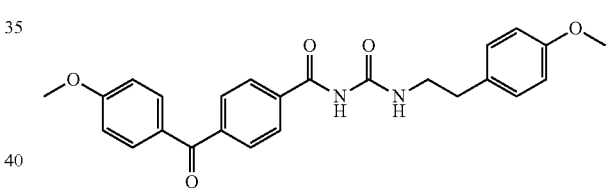

SW208220-1-A

White solid, 57.6 mg, 53% yield. Used 1.5 eq oxalyl chloride. $^1$H NMR (400 MHz, DMSO-$d_6$) δ 10.67 (s, 1H), 8.68 (t, J=6.0 Hz, 1H), 8.09-8.02 (m, 2H), 7.78-7.70 (m, 4H), 7.19-7.13 (m, 2H), 7.12-7.05 (m, 2H), 6.89-6.84 (m, 2H), 3.85 (s, 3H), 3.71 (s, 3H), 3.48-3.39 (m, 2H), 2.76 (t, J=7.2 Hz, 2H). $^{13}$C NMR (400 MHz, DMSO-$d_6$) δ 194.3, 168.0, 163.8, 160.2, 158.2, 158.1, 153.7, 141.7, 135.8, 132.8, 131.4, 131.4, 130.1, 130.0, 129.5, 129.3, 128.7, 114.5, 114.3, 114.2, 56.1, 55.4, 43.4, 41.0, 34.8, 34.1. ESI-MS (m/z): 432.9 [M+H]$^+$.

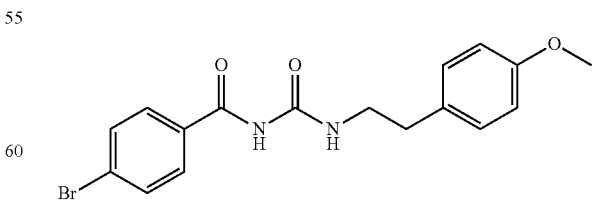

SW208388-1-A

White solid, 279.4 mg, 70% yield. Used 1.5 eq oxalyl chloride. $^1$H NMR (500 MHz, DMSO-$d_6$) δ 10.75 (s, 1H), 8.62 (t, J=5.7 Hz, 1H), 7.88-7.83 (m, 2H), 7.73-7.68 (m, 2H), 7.18-7.13 (m, 2H), 6.88-6.83 (m, 2H), 3.71 (s, 3H), 3.46-3.39 (m, 2H), 2.74 (t, J=7.2 Hz, 2H). $^{13}$C NMR (400 MHz, DMSO-d$_6$) δ 167.8, 158.2, 153.8, 132.2, 131.9, 131.4, 130.7, 130.0, 127.1, 114.3, 55.4, 41.3, 34.8. ESI-MS (m/z): 377.0 [M]$^+$.

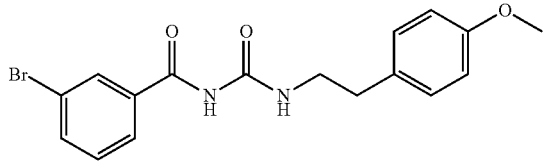

SW208388-1-A

White solid, 144.2 mg, 40% yield. Used 1.5 eq oxalyl chloride. $^1$H NMR (400 MHz, DMSO-d$_6$) δ 10.76 (s, 1H), 8.56 (t, J=5.7 Hz, 1H), 8.10 (appt, J=1.8 Hz, 1H), 7.90 (ddd, J=7.8, 1.8, 1.0 Hz, 1H), 7.79 (ddd, J=8.0, 2.0, 1.0 Hz, 1H), 7.44 (appt, J=7.9 Hz, 1H), 7.18-7.12 (m, 2H), 6.88-6.82 (m, 2H), 3.70 (s, 3H), 3.45-3.38 (m, 2H), 2.74 (t, J=7.2 Hz, 2H). $^{13}$C NMR (400 MHz, DMSO-d$_6$) δ 167.2, 158.2, 153.6, 135.8, 135.2, 131.4, 131.2, 131.1, 130.1, 127.9, 122.1, 114.3, 55.4, 41.3, 34.8. ESI-MS (m/z): 377.0 [M]$^+$.

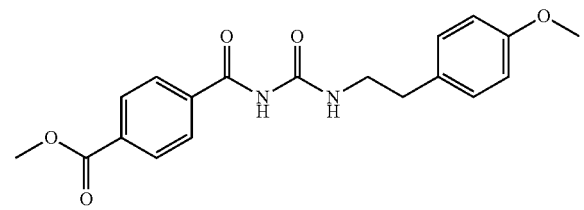

SW208390-1-A

White solid, 707.8 mg, 35% yield. Used 1.5 eq oxalyl chloride. $^1$H NMR (400 MHz, DMSO-d$_6$) δ 10.81 (s, 1H), 8.58 (t, J=5.6 Hz, 1H), 8.02 (s, 4H), 7.15 (d, J=8.5 Hz, 2H), 6.88-6.82 (m, 2H), 3.87 (s, 3H), 3.70 (s, 3H), 3.47-3.39 (m, 2H), 2.74 (t, J=7.2 Hz, 2H). $^{13}$C NMR (400 MHz, DMSO-d$_6$) δ 168.0, 166.0, 158.2, 153.7, 137.2, 133.3, 131.4, 130.1, 129.5, 129.0, 114.3, 55.4, 52.9, 41.3, 34.8. ESI-MS (m/z): 357.1 [M+H]$^+$.

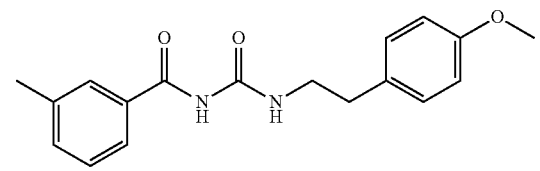

SW208399-1-A

White solid, 19.7 mg, 30% yield, after flash chromatography (silica gel, 0→100% EtOAc in hexanes). Used 5 eq oxalyl chloride and stirred over weekend at rt for 2$^{nd}$ step. $^1$H NMR (500 MHz, DMSO-d$_6$) δ 10.60 (s, 1H), 8.68 (t, J=5.7, 1H), 7.78-7.76 (m, 1H), 7.75-7.70 (m, 1H), 7.43-7.40 (m, 1H), 7.39-7.35 (m, 1H), 7.19-7.14 (m, 2H), 6.89-6.85 (m, 2H), 3.72 (s, J=4.8 Hz, 3H), 3.46-3.39 (m, 2H), 2.75 (t, J=7.2 Hz, 2H), 2.35 (s, 3H). $^{13}$C NMR (400 MHz, DMSO-d$_6$) δ 168.7, 158.2, 153.9, 138.3, 133.7, 132.9, 131.5, 130.1, 129.1, 128.8, 125.7, 114.3, 55.4, 41.3, 34.8, 21.3. ESI-MS (m/z): 313.1 [M+H]$^+$.

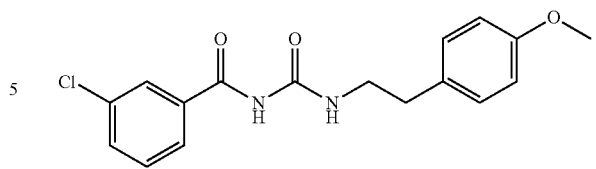

SW208400-1-A

White solid, 11.6 mg, 17% yield, after flash chromatography (silica gel, 0→60% EtOAc in hexanes). Used 5 eq oxalyl chloride and stirred over weekend at rt for 2$^{nd}$ step. $^1$H NMR (400 MHz, DMSO-d$_6$) δ 10.6 (s, 1H), 8.57 (t, J=5.7 Hz, 1H), 7.97 (appt, J=1.9 Hz, 1H), 7.87 (dt, J=7.9, 1.3 Hz, 1H), 7.66 (ddd, J=8.0, 2.1, 1.0 Hz, 1H), 7.51 (appt, J=7.9 Hz, 1H), 7.18-7.13 (m, 2H), 6.88-6.82 (m, 2H), 3.70 (s, 3H), 3.47-3.38 (m, 2H), 2.74 (t, J=7.2 Hz, 2H). $^{13}$C NMR (400 MHz, DMSO-d$_6$) δ 167.3, 158.2, 153.6, 135.1, 133.7, 132.9, 131.4, 130.9, 130.1, 128.4, 127.3, 114.3, 55.4, 41.3, 34.8. ESI-MS (m/z): 332.9 [M]$^+$.

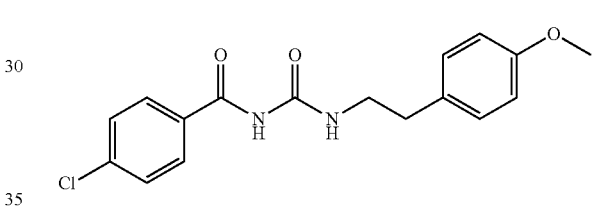

SW208401-1-A

White solid, 234.4 mg, 82% yield. Used 5 eq oxalyl chloride and stirred over weekend at rt for 2$^{nd}$ step. $^1$H NMR (400 MHz, DMSO-d$_6$) δ 10.72 (s, 1H), 8.64 (t, J=5.7 Hz, 1H), 7.96-7.91 (m, 2H), 7.56-7.50 (m, 2H), 7.18-7.11 (m, 2H), 6.88-6.81 (m, 2H), 3.70 (s, 3H), 3.45-3.38 (m, 2H), 2.73 (t, J=7.2 Hz, 2H). $^{13}$C NMR (400 MHz, DMSO-d$_6$) δ 167.8, 158.2, 154.3, 137.9, 132.2, 131.5, 130.5, 130.0, 128.9, 114.3, 55.4, 41.3, 34.8. ESI-MS (m/z): 332.9 [M]$^+$.

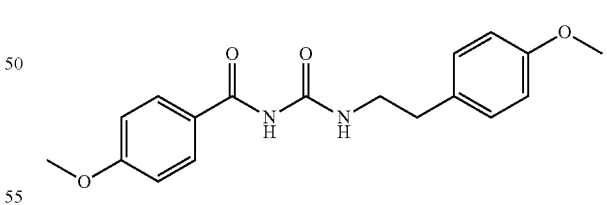

SW208402-1-A

White solid, 63.9 mg, 29% yield. Used 5 eq oxalyl chloride and stirred over weekend at rt for 2$^{nd}$ step. $^1$H NMR (400 MHz, DMSO-d$_6$) δ 10.5 (s, 1H), 8.72 (t, J=5.6 Hz, 1H), 7.97-7.92 (m, 2H), 7.17-7.12 (m, 2H), 7.11-7.06 (m, 2H), 6.87-6.84 (m, 2H), 3.81 (s, 3H), 3.70 (s, J=3.3 Hz, 3H), 3.46-3.38 (m, 2H), 2.73 (t, J=7.2 Hz, 2H). $^{13}$C NMR (400 MHz, DMSO-d$_6$) δ 167.9, 163.2, 158.2, 154.1, 131.5, 130.7, 130.0, 124.9, 114.3, 114.2, 56.1, 55.4, 41.3, 34.9. ESI-MS (m/z): 329.1 [M+H]$^+$.

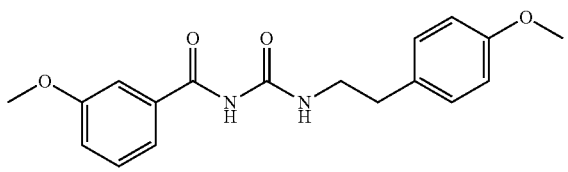

SW208403-1-A

White solid, 124.1 mg, 39% yield after flash chromatography (silica gel, 0→100% EtOAc in hexanes). Used 5 eq oxalyl chloride and stirred over weekend at rt for $2^{nd}$ step. $^1$H NMR (500 MHz, DMSO-$d_6$) δ 10.69 (s, 1H), 8.68 (t, J=5.6 Hz, 1H), 7.53-7.48 (m, 2H), 7.40 (appt, J=7.9 Hz, 1H), 7.18-7.14 (m, 3H), 6.88-6.84 (m, 2H), 3.81 (s, 3H), 3.71 (s, 3H), 3.46-3.40 (m, 2H), 2.75 (t, J=7.2 Hz, 2H). $^{13}$C NMR (400 MHz, DMSO-$d_6$) δ 168.3, 159.5, 158.2, 153.9, 134.3, 131.4, 130.1, 120.9, 119.5, 114.3, 113.2, 55.8, 55.4, 41.3, 34.8. ESI-MS (m/z): 329.0 [M+H]$^+$.

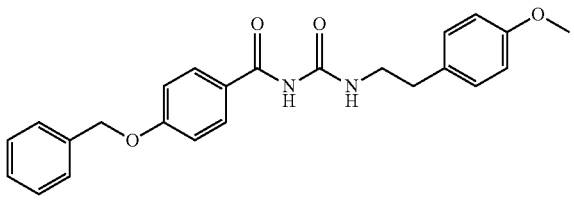 [SMILES: COc1ccc(CCNC(=O)NC(=O)c2ccc(OCc3ccccc3)cc2)cc1]

SW208457-1-A

White solid, 35.3 mg, 36% yield. The isocyanate intermediate was heated to 40° C. to dissolve in CH$_3$CN before adding amine. $^1$H NMR (400 MHz, DMSO-$d_6$) δ 10.48 (s, 1H), 8.71 (t, J=5.7 Hz, 1H), 7.97-7.90 (m, 2H), 7.46-7.42 (m, 2H), 7.41-7.35 (m, 2H), 7.35-7.30 (m, 1H), 7.18-7.12 (m, 2H), 7.11-7.05 (m, 2H), 6.87-6.82 (m, 2H), 5.18 (s, 2H), 3.70 (s, 3H), 3.46-3.38 (m, 2H), 2.73 (t, J=7.2 Hz, 2H). $^{13}$C NMR (400 MHz, DMSO-$d_6$) δ 167.8, 162.3, 158.2, 154.1, 137.1, 131.5, 130.7, 130.0, 128.9, 128.5, 128.2, 125.1, 115.0, 114.3, 69.9, 55.4, 41.3, 34.9. ESI-MS (m/z): 405.1 [M+H]$^+$.

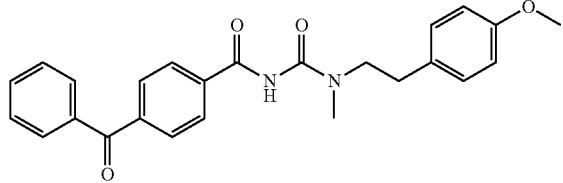

SW208461-1-A 1.7 mg, 3% yield. The isocyanate intermediate was heated to 50° C. to dissolve in CH$_3$CN before adding amine. $^1$H NMR (400 MHz, DMSO-$d_6$) δ 10.27 (s, 1H), 7.91 (s, 2H), 7.81-7.73 (m, 4H), 7.73-7.67 (m, 1H), 7.61-7.55 (m, 2H), 7.19-7.10 (m, 2H), 6.88-6.80 (m, 2H), 3.69 (s, 3H), 3.48 (t, J=7.8 Hz, 2H), 2.91 (s, 3H), 2.81-2.75 (t, J=7.7 Hz, 2H). ESI-MS (m/z): 417.1 [M+H]$^+$.

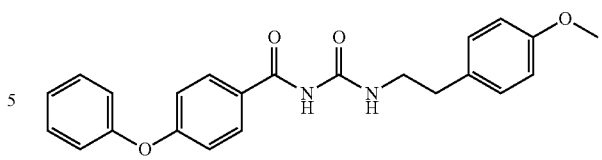

SW208456-1-A

White solid, 23.8 mg, 24% yield. The isocyanate intermediate was heated to 50° C. to dissolve in CH3CN before adding amine. $^1$H NMR (400 MHz, DMSO-$d_6$) δ 10.56 (s, 1H), 8.68 (t, J=5.7 Hz, 1H), 8.00-7.95 (m, 2H), 7.48-7.41 (m, 2H), 7.26-7.20 (m, 1H), 7.18-7.13 (m, 2H), 7.12-7.08 (m, 2H), 7.02-6.97 (m, 2H), 6.88-6.82 (m, 2H), 3.70 (s, 3H), 3.46-3.37 (m, 2H), 2.74 (t, J=7.2 Hz, 2H). $^{13}$C NMR (400 MHz, DMSO-$d_6$) δ 167.7, 161.4, 158.2, 155.4, 154.0, 131.5, 131.0, 130.8, 130.1, 127.2, 125.2, 120.5, 117.4, 114.3, 55.4, 41.3, 34.8. ESI-MS (m/z): 391.0 [M+H]$^+$.

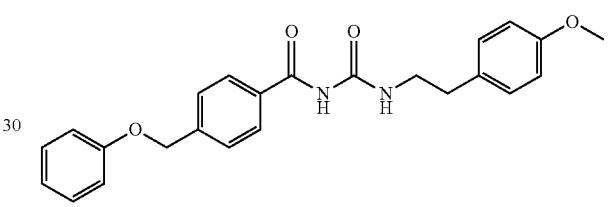

SW208458-1-A

White solid, 26.5 mg, 36% yield. $^1$H NMR (400 MHz, DMSO-$d_6$) δ 10.63 (s, 1H), 8.67 (t, J=5.7 Hz, 1H), 7.56-7.50 (m, 2H), 7.31-7.25 (m, 2H), 7.18-7.12 (m, 2H), 7.02-6.97 (m, 2H), 6.96-6.91 (m, 1H), 6.88-6.82 (m, 2H), 5.17 (s, 2H), 3.70 (s, 3H), 3.46-3.38 (m, 2H), 2.74 (t, J=7.2 Hz, 2H). ESI-MS (m/z): 405.1 [M+H]$^+$.

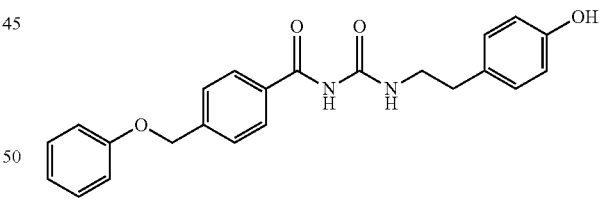

SW208522-1-A

White solid, 18.6 mg, 22% yield. $^1$H NMR (400 MHz, DMSO-$d_6$) δ 10.65 (s, 1H), 9.19 (s, 1H), 8.65 (t, J=5.7 Hz, 1H), 7.97-7.91 (m, 2H), 7.56-7.51 (m, 2H), 7.31-7.25 (m, 2H), 7.05-6.97 (m, 4H), 6.96-6.90 (m, 1H), 6.69-6.65 (m, 2H), 5.17 (s, 2H), 3.43-3.36 (m, 2H), 2.68 (t, J=7.2 Hz, 2H). $^{13}$C NMR (400 MHz, DMSO-$d_6$) δ 168.3, 158.5, 156.1, 133.9, 142.5, 132.3, 130.0, 130.0, 129.6, 128.8, 127.7, 121.3, 115.6, 115.2, 68.8, 41.4, 34.9. ESI-MS (m/z): 391.1 [M+H]$^+$. (heated overnight at 50° C.) and for $2^{nd}$ step, dissolved tyramine (2 eq) in 1 ml CH3CN by heating and added to solution of isocyanate intermediate dissolved in CH3CN at 80° C. Stirred at 80° C. for 4 hours.

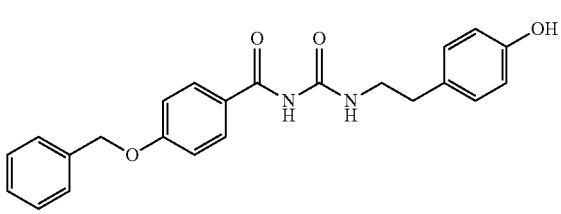 [SMILES: O=C(NCCc1ccc(O)cc1)NC(=O)c1ccc(OCc2ccccc2)cc1]

SW208524-1-A

White solid, 12.3 mg, 14% yield after flash chromatography (silica gel, 0→100% EtOAc in hexanes). $^1$H NMR (400 MHz, DMSO-d$_6$) δ 10.47 (s, 1H), 9.18 (s, 1H), 8.70 (t, J=5.6 Hz, 1H), 7.97-7.90 (m, 2H), 7.47-7.41 (m, 2H), 7.41-7.35 (m, 2H), 7.35-7.28 (m, 1H), 7.11-7.04 (m, 2H), 7.05-6.98 (m, 2H), 6.70-6.64 (m, 2H), 5.17 (s, 2H), 3.42-3.35 (m, 2H), 2.68 (t, J=7.2 Hz, 2H). $^{13}$C NMR (400 MHz, DMSO-d$_6$) δ 167.8, 162.3, 156.1, 154.1, 136.9, 130.7, 130.0, 129.6, 128.9, 128.5, 128.2, 125.1, 115.6, 115.0, 69.9, 41.3, 34.9. ESI-MS (m/z): 391.1 [M+H]$^+$. (heated overnight at 50° C.) and for $2^{nd}$ step, dissolved tyramine (2 eq) in 1 ml CH$_3$CN by heating and added to solution of isocyanate intermediate dissolved in CH$_3$CN at 80° C. Stirred at 80° C. for 4 hours.

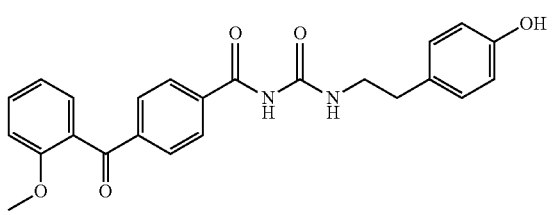 [SMILES: COc1ccccc1C(=O)c1ccc(C(=O)NC(=O)NCCc2ccc(O)cc2)cc1]

SW208579-1-A

White solid, 15.6 mg, 20% yield after flash chromatography (silica gel, 0→100% EtOAc in hexanes). $^1$H NMR (400 MHz, DMSO-d$_6$) δ 10.85 (s, 1H), 9.18 (s, 1H), 8.72 (t, J=5.6 Hz, 1H), 7.94 (d, J=8.0 Hz, 2H), 7.79 (d, J=8.0 Hz, 2H), 7.51-7.43 (m, 1H), 7.29-7.23 (m, 3H), 7.05-6.99 (m, 2H), 6.71-6.63 (m, 2H), 3.81 (s, 3H), 3.46-3.37 (m, 2H), 2.72 (t, J=7.5 Hz, 2H). $^{13}$C NMR (400 MHz, CDCl$_3$) δ 195.8, 166.8, 159.7, 155.1, 140.3, 138.0, 137.8, 130.1, 130.0, 129.4, 127.6, 126.8, 122.9, 119.4, 115.6, 114.3, 55.5, 41.5, 34.6. ESI-MS (m/z): 420.1 [M−H]$^-$. For the first step, the solution was heated for 5 hours, and for the second step, tyramine (2 eq) was dissolved in CH$_3$CN (1 ml) by heating and was then added to the solution of the isocyanate intermediate also dissolved in CH$_3$CN. This mixture stirred at 80° C. overnight.

SW208580-1-A

Cream-colored solid, 5.3 mg, 42% yield after flash chromatography (silica gel, 0→100% EtOAc in hexanes). $^1$H NMR (400 MHz, DMSO-d$_6$) δ 9.16 (s, 1H), 8.69 (t, J=5.8 Hz, 1H), 7.91-7.86 (m, 2H), 7.74-7.69 (m, 2H), 7.56 (ddd, J=8.4, 7.4, 1.8 Hz, 1H), 7.34 (dd, J=7.5, 1.8 Hz, 1H), 7.19 (d, J=8.3 Hz, 1H), 7.09 (td, J=7.4, 0.9 Hz, 1H), 7.03-6.99 (m, 2H), 6.69-6.62 (m, 2H), 3.65 (s, 3H), 3.43-3.37 (m, 2H), 2.71 (t, J=7.5 Hz, 2H). $^{13}$C NMR (400 MHz, CDCl$_3$) δ 195.8, 166.8, 157.5, 154.7, 140.3, 138.1, 132.5, 130.3, 129.9, 129.9, 129.9, 128.1, 126.7, 120.7, 115.6, 111.5, 55.5, 41.4, 34.7. ESI-MS (m/z): 420.0 [M−H]$^-$. For the first step, the solution was heated for 5 hours, and for the second step, tyramine (2 eq) was dissolved in CH$_3$CN (1 ml) by heating and was then added to the solution of the isocyanate intermediate also dissolved in CH$_3$CN. This mixture stirred at 80° C. overnight.

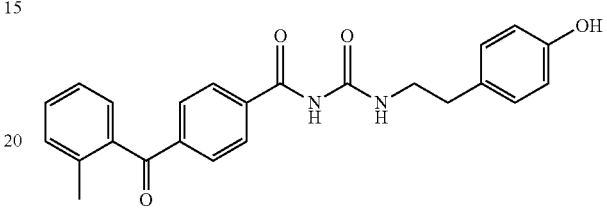

SW208581-1-A

Yellow oil, 33.4 mg, 43% yield after flash chromatography (silica gel, 0→100% EtOAc in hexanes). $^1$H NMR (400 MHz, CDCl$_3$) δ 7.84-7.78 (m, 2H), 7.77-7.71 (m, 2H), 7.45-7.38 (m, 1H), 7.35-7.26 (m, 3H), 7.13-7.05 (m, 2H), 6.84-6.77 (m, 2H), 6.22 (t, J=5.9 Hz, 1H), 3.73-3.66 (m, 2H), 2.87 (t, J=6.9 Hz, 2H), 2.33 (s, 3H). $^{13}$C NMR (400 MHz, CDCl$_3$) δ 197.9, 166.7, 154.8, 140.1, 138.4, 137.9, 137.1, 131.2, 130.7, 130.5, 130.3, 130.3, 129.9, 128.8, 127.0, 125.3, 115.7, 41.4, 34.6, 20.1. ESI-MS (m/z): 404.0 [M−H]$^-$. For the first step, the solution was heated for 5 hours, and for the second step, tyramine (2 eq) was dissolved in CH$_3$CN (1 ml) by heating and was then added to the solution of the isocyanate intermediate also dissolved in CH$_3$CN. This mixture stirred at 80° C. overnight.

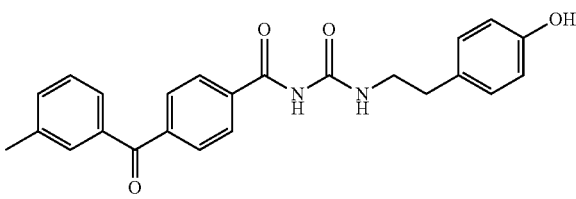 [SMILES: Cc1cccc(C(=O)c2ccc(C(=O)NC(=O)NCCc3ccc(O)cc3)cc2)c1]

SW208582-1-A

White solid, 22.5 mg, % yield after flash chromatography (silica gel, 0→100% EtOAc in hexanes). $^1$H NMR (400 MHz, DMSO-d$_6$) δ 9.17 (s, 1H), 8.72 (t, J=5.6 Hz, 1H), 7.97-7.91 (m, 2H), 7.79-7.73 (m, 2H), 7.58-7.40 (m, 5H), 7.04-6.97 (m, 2H), 6.69-6.63 (m, 2H), 3.46-3.39 (m, 2H), 2.72 (t, J=7.5 Hz, 2H), 2.37 (s, 3H). $^{13}$C NMR (400 MHz, CDCl$_3$) δ 196.0, 165.8, 156.1, 139.6, 138.6, 138.4, 137.2, 134.1, 130.4, 130.0, 129.9, 129.9, 129.0, 127.7, 127.5, 115.6, 41.8, 34.7, 21.3. ESI-MS (m/z): 404.0 [M−H]$^-$. For the first step, the solution was heated for 5 hours, and for the second step, tyramine (2 eq) was dissolved in CH$_3$CN (1 ml) by heating and was then added to the solution of the isocyanate intermediate also dissolved in CH$_3$CN. This mixture stirred at 80° C. overnight.

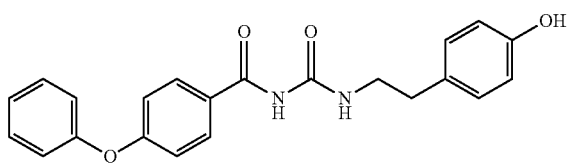 [SMILES: O=C(NCCc1ccc(O)cc1)NC(=O)c1ccc(Oc2ccccc2)cc1]

SW208523-2-A:

White solid, mg, % yield yield after triturating in CH$_2$Cl$_2$. $^1$H NMR (400 MHz, DMSO-d$_6$) δ 10.58 (s, 1H), 9.18 (s, 1H), 8.66 (t, J=5.7 Hz, 1H), 8.00-7.95 (m, 2H), 7.48-7.41 (m, 2H), 7.26-7.20 (m, 1H), 7.13-7.08 (m, 2H), 7.04-6.96 (m, 4H), 6.69-6.64 (m, 2H), 3.43-3.35 (m, 2H), 2.68 (t, J=7.2 Hz, 2H). $^{13}$C NMR (400 MHz, DMSO-d$_6$) δ 167.7, 161.4, 156.1, 155.4, 154.0, 131.0, 130.8, 130.0, 129.6, 127.2, 125.2, 120.5, 117.4, 115.6, 41.4, 34.9. ESI-MS (m/z): 377.1 [M+H]$^+$. For the first step, the solution was heated for 5 hours, and for the second step, tyramine (2 eq) was dissolved in CH$_3$CN (1 ml) by heating and was then added to the solution of the isocyanate intermediate also dissolved in CH$_3$CN. This mixture stirred at 80° C. overnight.

Methylation

Methyl iodide (5 eq) was added to a solution of SW208222-1-A (1 eq) and base (2-3 eq) in DMF (0.2 M). When the reaction was complete by TLC (3 h), EtOAc was added and the organic layer was washed with water and brine, dried with Na2SO4, and concentrated to give the product. The product wasn't purified unless otherwise noted.

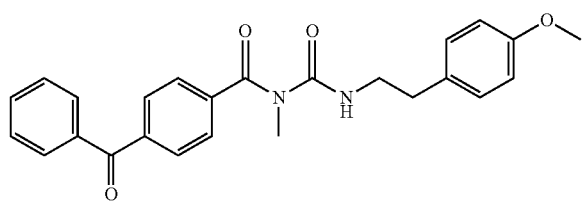

SW208566-1-A

White solid, 23.3 mg, 73% yield. The base used was K$_2$CO$_3$ (3 eq). $^1$H NMR (400 MHz, DMSO-d$_6$) δ 8.52 (t, J=5.6 Hz, 1H), 7.77-7.65 (m, 5H), 7.62-7.51 (m, 4H), 7.12-7.06 (m, 2H), 6.85-6.79 (m, 2H), 3.68 (s, 3H), 3.27 (dt, J=7.9, 6.0 Hz, 2H), 3.10 (s, 3H), 2.59 (t, J=7.3 Hz, 2H). $^{13}$C NMR (400 MHz, DMSO-d$_6$) δ 195.7, 171.6, 158.2, 155.7, 140.3, 138.8, 137.0, 133.5, 131.3, 130.1, 130.0, 129.9, 129.1, 127.4, 114.2, 55.4, 42.3, 34.3, 34.1. ESI-MS (m/z): 417.1 [M+H]$^+$.

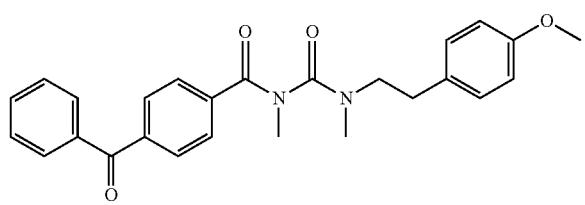 [SMILES: COc1ccc(CCN(C)C(=O)N(C)C(=O)c2ccc(C(=O)c3ccccc3)cc2)cc1]

SW208567-1-A

Colorless oil, 11.0 mg, % yield. The base used was NaH (60% dispersion in mineral oil, 2 eq). $^1$H NMR (400 MHz, CDCl$_3$) δ 7.83-7.76 (m, 3H), 7.76-7.74 (m, 1H), 7.69 (s, 2H), 7.63-7.57 (m, 1H), 7.53-7.43 (m, 2H), 7.06-7.00 (m, 2H), 6.88-6.79 (m, 2H), 3.77 (s, 3H), 3.43-3.28 (m, 2H), 3.20 (s, 3H), 2.77 (s, 3H), 2.65 (t, J=7.3 Hz, 2H). $^{13}$C NMR (400 MHz, CDCl$_3$) δ 195.8, 158.4, 157.8, 139.7, 138.7, 136.9, 132.9, 130.0, 130.0, 129.8, 129.7, 128.4, 128.4, 127.4, 114.1, 55.3, 51.1, 33.2, 32.9, 29.7. ESI-MS (m/z): 431.1 [M+H]$^+$.

Boronic Acid Procedure

A solution of aryl bromide, boronic acid, (dppf)PdCl2, cesium fluoride, isopropanol, and Et3N was heated to 100 C for 5 hours. Then, water was added to the reaction solution and it was extracted into EtOAc. The organic layer was washed with brine, dried with Na2SO4, concentrated before purification by flash chromatography (silica gel, 0→100% EtOAc in hexanes) to give product.

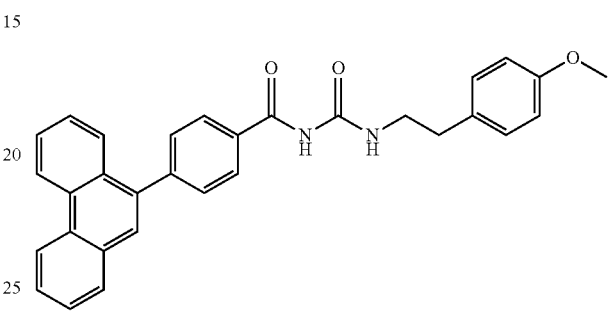

SW208391-1-A

Cream-colored solid, 7.7 mg, 10% yield after triturating in CH$_2$Cl$_2$. $^1$H NMR (400 MHz, DMSO-d$_6$) δ 10.79 (s, 1H), 8.94 (d, J=8.4 Hz, 1H), 8.88 (d, J=8.2 Hz, 1H), 8.74 (t, J=5.6 Hz, 1H), 8.13 (d, J=8.1 Hz, 2H), 8.04 (d, J=7.7 Hz, 1H), 7.81 (s, 1H), 7.80-7.69 (m, 3H), 7.66 (d, J=8.2 Hz, 3H), 7.62 (appt, J=7.5 Hz, 1H), 7.18 (d, J=8.0 Hz, 2H), 6.87 (d, J=8.1 Hz, 2H), 3.72 (s, 3H), 3.50-3.41 (m, 2H), 2.78 (t, J=7.3 Hz, 2H). $^{13}$C NMR (400 MHz, DMSO-d$_6$) δ 168.3, 158.2, 154.0, 144.8, 137.3, 132.1, 131.5, 131.3, 130.6, 130.4, 130.2, 130.1, 130.0, 129.3, 128.9, 128.0, 127.8, 127.7, 127.5, 127.4, 126.4, 124.0, 123.3, 114.3, 55.4, 41.4, 34.8. ESI-MS (m/z): 475.2 [M+H]$^+$.

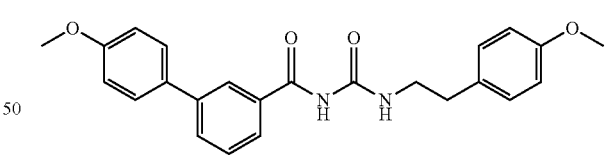

SW208386-1-A

Cream-colored solid, 31.4 mg, 52% yield. $^1$H NMR (500 MHz, DMSO-d$_6$) δ 10.86 (s, 1H), 8.72 (t, J=5.7 Hz, 1H), 8.21-8.19 (m, 1H), 7.88-7.81 (m, 2H), 7.73 (appt, J=8.5 Hz, 2H), 7.55 (appt, J=7.7 Hz, 1H), 7.17 (d, J=8.3 Hz, 2H), 7.05 (d, J=8.5 Hz, 2H), 6.89-6.85 (m, 2H), 3.80 (s, 3H), 3.71 (s, 3H), 3.48-3.42 (m, 2H), 2.76 (t, J=7.2 Hz, 2H). $^{13}$C NMR (400 MHz, DMSO-d$_6$) δ 168.6, 159.7, 158.2, 154.0, 140.4, 136.3, 133.6, 131.9, 131.5, 130.1, 129.6, 128.5, 126.0, 114.8, 114.3, 113.4, 55.7, 55.4, 41.3, 34.8. ESI-MS (m/z): 405.0 [M+H]$^+$.

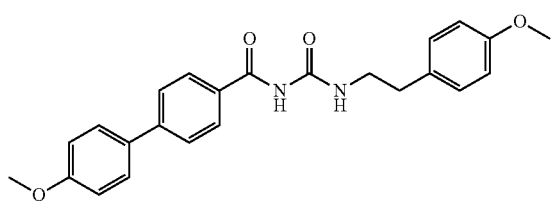

SW208387-1-A

White solid, 31.8 mg, 53% yield. ¹H NMR (400 MHz, DMSO-$d_6$) δ 10.65 (s, 1H), 8.71 (t, J=5.7 Hz, 1H), 8.02-7.97 (m, 2H), 7.76-7.72 (m, 2H), 7.72-7.67 (m, 2H), 7.19-7.13 (m, 2H), 7.07-7.01 (m, 2H), 6.88-6.82 (m, 2H), 3.79 (s, 3H), 3.71 (s, 3H), 3.47-3.39 (m, 2H), 2.75 (t, J=7.2 Hz, 2H). ¹³C NMR (400 MHz, DMSO-$d_6$) δ 168.2, 160.1, 158.2, 154.0, 144.3, 131.5, 131.4, 130.9, 129.3, 128.6, 126.4, 115.0, 114.3, 55.9, 55.4, 41.3, 34.8. ESI-MS (m/z): 405.0 [M+H]⁺.

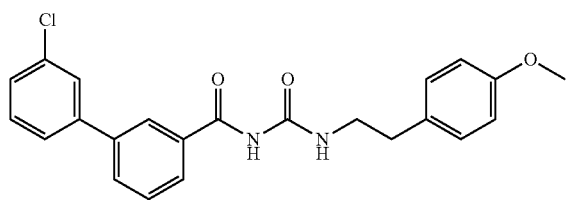 [SMILES: COc1ccc(CCNC(=O)NC(=O)c2cccc(-c3cccc(Cl)c3)c2)cc1]

SW208392-1-A

White solid, 58.8 mg, 98% yield. ¹H NMR (400 MHz, DMSO-$d_6$) δ 10.86 (s, 1H), 8.70 (t, J=5.7 Hz, 1H), 8.24 (d, J=6.8 Hz, 3H), 7.96-7.88 (m, 3H), 7.78-7.68 (m, 3H), 7.59 (td, J=7.8, 1.6 Hz, 1H), 7.51 (td, J=7.8, 2.3 Hz, 1H), 7.47-7.41 (m, 2H), 7.35 (t, J=7.6 Hz, 1H), 7.20-7.13 (m, 2H), 6.88-6.82 (m, 2H), 3.70 (s, 3H), 3.49-3.41 (m, 2H), 2.76 (t, J=7.2 Hz, 2H). ¹³C NMR (400 MHz, DMSO-$d_6$) δ 168.4, 158.2, 154.0, 141.8, 139.1, 134.3, 134.0, 133.7, 133.1, 132.0, 130.3, 130.1, 129.9, 129.8, 128.5, 128.2, 127.2, 126.7, 126.1, 114.3, 55.4, 41.3, 34.8. ESI-MS (m/z): 408.9 [M]⁺.

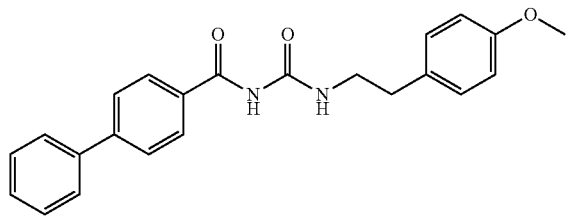 [SMILES: COc1ccc(CCNC(=O)NC(=O)c2ccc(-c3ccccc3)cc2)cc1]

SW208393-1-A

White solid, 20.3 mg, 36% yield. ¹H NMR (500 MHz, DMSO-$d_6$) δ 10.73 (s, 1H), 8.72 (t, J=5.7 Hz, 1H), 8.06-8.02 (m, 2H), 7.82-7.78 (m, 2H), 7.76-7.72 (m, 2H), 7.53-7.48 (m, J=7.6 Hz, 2H), 7.44-7.38 (m, 1H), 7.19-7.16 (m, 2H), 6.89-6.85 (m, 2H), 3.72 (s, 3H), 3.48-3.42 (m, 2H), 2.79-2.74 (t, J=7.2 Hz, 2H). ¹³C NMR (400 MHz, DMSO-$d_6$) δ 168.2, 158.2, 154.0, 144.6, 139.2, 131.7, 131.5, 130.1, 129.5, 129.3, 128.8, 127.4, 127.1, 114.3, 55.4, 41.3, 34.8. ESI-MS (m/z): 375.1 [M+H]⁺.

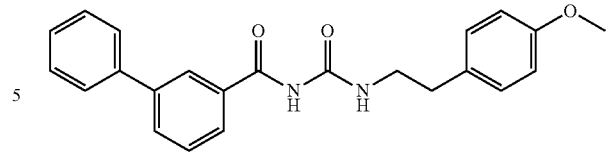

SW208394-1-A

White solid, 3.0 mg, 5% yield. ¹H NMR (500 MHz, DMSO-$d_6$) δ 10.89 (s, 1H), 8.72 (t, J=5.7 Hz, 1H), 8.25 (appt, J=1.8 Hz, 1H), 7.95-7.88 (m, 2H), 7.81-7.78 (m, 2H), 7.59 (appt, J=7.7 Hz, 1H), 7.52-7.47 (m, 2H), 7.43-7.38 (m, 1H), 7.20-7.15 (m, 2H), 6.89-6.84 (m, 2H), 3.72 (s, 3H), 3.48-3.42 (m, 2H), 2.77 (t, J=7.2 Hz, 2H). ¹³C NMR (400 MHz, DMSO-$d_6$) δ 168.5, 158.2, 154.0, 140.7, 139.6, 133.7, 131.5, 131.3, 130.1, 129.7, 129.4, 128.4, 127.8, 127.4, 126.6, 114.3, 55.4, 41.3, 34.8. ESI-MS (m/z): 375.1 [M+H]⁺.

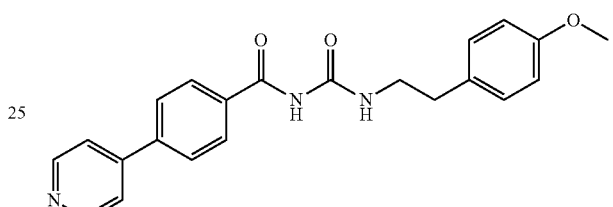

SW208404-1-A 7.3 mg, 13% yield. ¹H NMR (500 MHz, CDCl₃) δ 8.70 (t, J=5.9 Hz, 1H), 8.60 (s, 1H), 8.18-8.14 (m, 1H), 7.89-7.85 (m, 1H), 7.73-7.69 (m, 1H), 7.63-7.58 (m, 1H), 7.53-7.48 (m, 3H), 7.20-7.16 (m, 1H), 7.15-7.10 (m, 2H), 6.90-6.84 (m, 2H), 3.81 (s, 3H), 3.59 (m, 1H), 2.87 (t, J=7.3 Hz, 2H). ¹³C NMR (400 MHz, CDCl₃) δ 167.7, 165.6, 159.7, 158.4, 133.1, 130.8, 130.3, 130.1, 129.7, 128.9, 127.4, 126.9, 114.0, 55.3, 41.6, 35.0. ESI-MS (m/z): [M+H]⁺.

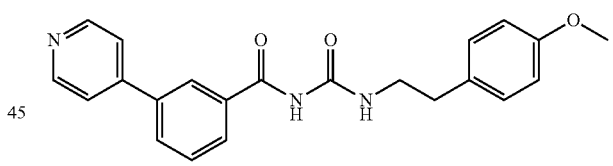

SW208396-1-A

White solid, 10.1 mg, 19% yield. ¹H NMR (500 MHz, DMSO-$d_6$) δ 10.92 (s, 1H), 8.70 (t, J=5.7 Hz, 1H), 8.69-8.66 (m, 2H), 8.40-8.37 (m, 1H), 8.07-8.03 (m, 1H), 8.01-7.98 (m, 1H), 7.86-7.82 (m, 2H), 7.66 (appt, J=7.8 Hz, 1H), 7.20-7.15 (m, 2H), 6.89-6.84 (m, 2H), 3.71 (s, 3H), 3.48-3.43 (m, 2H), 2.77 (t, J=7.2 Hz, 2H). ¹³C NMR (400 MHz, DMSO-$d_6$) δ 168.2, 158.2, 153.9, 150.7, 146.5, 137.8, 133.9, 131.4, 130.1, 130.0, 129.5, 126.8, 121.9, 114.3, 55.4, 41.3, 34.8. ESI-MS (m/z): 376.0 [M+H]⁺.

General Procedure for EDI Couplings

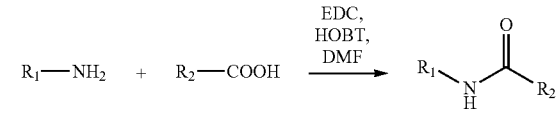

Where EDC=1-(3-dimethylaminopropyl)-3-ethylcarbodiimide HCl
HOBT=1-hydroxybenzotriazole hydrate The carboxylic acid (1 eq), EDC (1.05 eq), and HOBT (1.05 eq) were dissolved in DMF (0.1M) and stirred for 20 minutes before adding the amine (1 eq). The reaction mixture stirred overnight. Water was added to the reaction mixture to precipitate out the desired material, and the precipitate was collected by filtration, washed with water, and dried under vacuum to give the final product. If a precipitate did not form, EtOAc was added and was washed with 1M NaOH (3×), water (3×), 1M HCl (3×), water (3×), and brine. Then the organic layer was dried with $Na_2SO_4$ and concentrated to give final product. Final product was not purified unless otherwise noted.

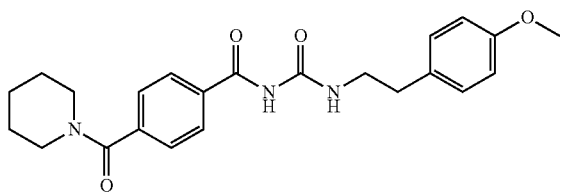 [SMILES: COc1ccc(CCNC(=O)NC(=O)c2ccc(C(=O)N3CCCCC3)cc2)cc1]

SW208397-1-A

White solid, 15.7 mg, 38% yield. $^1$H NMR (400 MHz, DMSO-$d_6$) δ 10.73 (s, 1H), 8.64 (t, J=5.7 Hz, 1H), 7.98-7.93 (m, 2H), 7.47-7.41 (m, 2H), 7.18-7.12 (m, 2H), 6.88-6.82 (m, 2H), 3.70 (s, 3H), 3.52 (s, 2H), 3.46-3.39 (m, 2H), 3.20 (s, 2H), 2.74 (t, J=7.2 Hz, 2H), 1.65-1.37 (m, 6H). $^{13}$C NMR (400 MHz, DMSO-$d_6$) δ 168.3, 168.1, 158.2, 153.9, 140.9, 133.5, 131.4, 130.1, 128.8, 127.0, 114.3, 55.4, 41.3, 34.8, 24.5, 24.4. ESI-MS (m/z): 410.0 [M+H]$^+$.

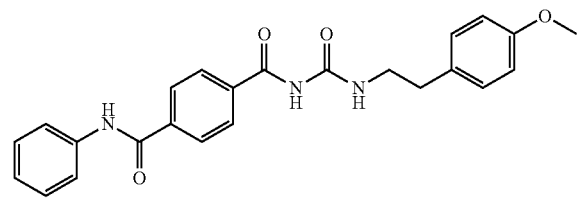 [SMILES: COc1ccc(CCNC(=O)NC(=O)c2ccc(C(=O)Nc3ccccc3)cc2)cc1]

SW208398-1-A

White solid, 0.7 mg, 2% yield after flash chromatography (silica gel, 0→100% EtOAc in hexanes). $^1$H NMR (500 MHz, DMSO-$d_6$) δ 10.8 (s, 1H), 10.39 (s, 1H), 8.75 (s, 1H), 8.10-8.05 (m, 2H), 8.01 (d, J=8.3 Hz, 2H), 7.81-7.76 (m, 2H), 7.39-7.33 (m, 2H), 7.20-7.15 (m, 2H), 7.14-7.09 (m, 1H), 6.89-6.84 (m, 2H), 3.72 (s, 3H), 3.47-3.40 (m, 2H), 2.75 (t, J=7.2 Hz, 2H). ESI-MS (m/z): 418.0 [M+H]$^+$.

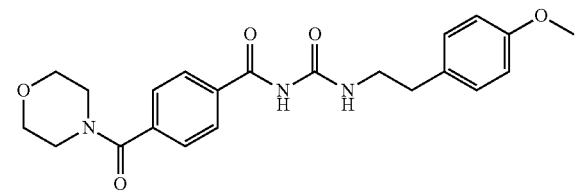 [SMILES: COc1ccc(CCNC(=O)NC(=O)c2ccc(C(=O)N3CCOCC3)cc2)cc1]

SW208408-1-A

White solid, 3.8 mg, 12% yield. $^1$H NMR (400 MHz, CDCl$_3$) δ 8.84 (s, 1H), 8.65 (t, J=5.6 Hz, 1H), 7.97-7.92 (m, 2H), 7.55-7.49 (m, 2H), 7.19-7.13 (m, 2H), 6.90-6.83 (m, 2H), 3.84-3.62 (m, 8H), 3.62-3.54 (m, 3H), 3.38 (s, 2H), 2.86 (t, J=7.2 Hz, 2H). ESI-MS (m/z): 412.1 [M+H]$^+$.

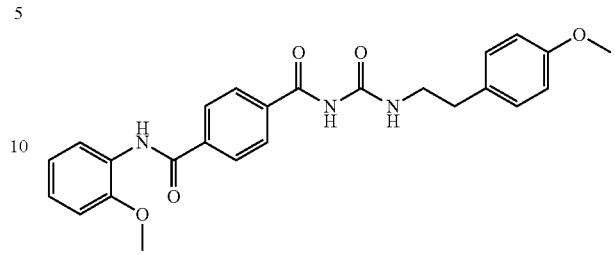

SW208409-1-A

White solid, 18.6 mg, 16% yield. $^1$H NMR (400 MHz, DMSO-$d_6$) δ 10.82 (s, 1H), 9.63 (s, 1H), 8.64 (t, J=5.7 Hz, 1H), 8.06-8.00 (m, 4H), 7.71 (dd, J=7.9, 1.6 Hz, 1H), 7.22-7.18 (m, 1H), 7.18-7.14 (m, 2H), 7.12-7.07 (m, 1H), 7.00-6.93 (m, 1H), 6.89-6.84 (m, 2H), 3.82 (s, 3H), 3.71 (s, 3H), 3.49-3.40 (m, 2H), 2.76 (t, J=7.2 Hz, 2H). $^{13}$C NMR (400 MHz, DMSO-$d_6$) δ 168.0, 164.6, 158.2, 153.8, 152.3, 138.4, 135.5, 131.4, 130.1, 128.7, 128.0, 126.9, 126.6, 125.3, 120.6, 114.3, 111.9, 56.2, 55.4, 41.3, 34.8. ESI-MS (m/z): 448.0 [M+H]$^+$.

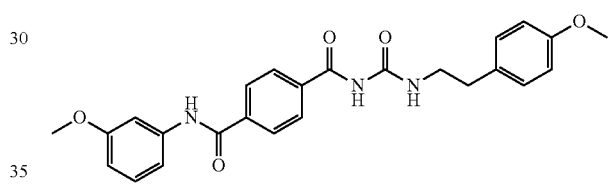

SW208410-1-A

White solid, 10.1 mg, 29% yield. $^1$H NMR (400 MHz, DMSO-$d_6$) δ 10.83 (s, 1H), 10.35 (s, 1H), 8.64 (t, J=5.7 Hz, 1H), 8.07-7.98 (m, 4H), 7.46 (t, J=2.2 Hz, 1H), 7.39-7.34 (m, 1H), 7.28-7.22 (m, 1H), 7.19-7.14 (m, 2H), 6.88-6.83 (m, 2H), 6.69 (ddd, J=8.3, 2.5, 0.9 Hz, 1H), 3.74 (s, 3H), 3.71 (s, 3H), 3.47-3.41 (m, 2H), 2.76 (t, J=7.1 Hz, 2H). $^{13}$C NMR (400 MHz, DMSO-$d_6$) δ 168.0, 165.1, 159.9, 158.2, 153.8, 140.5, 138.8, 135.5, 131.4, 130.1, 129.9, 128.6, 128.2, 114.3, 113.0, 109.9, 106.5, 55.47, 55.41, 41.3, 34.8. ESI-MS (m/z): 448.0 [M+H]$^+$.

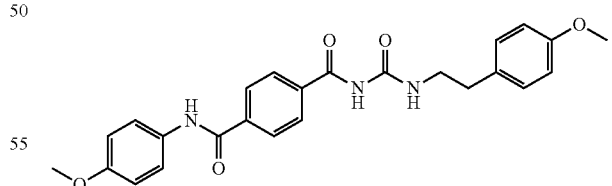

SW208411-1-A

White solid, 16.8 mg, 43% yield. $^1$H NMR (400 MHz, DMSO-$d_6$) δ 10.81 (s, 1H), 10.27 (s, 1H), 8.64 (t, J=5.7 Hz, 1H), 8.10-7.98 (m, 4H), 7.72-7.63 (m, 2H), 7.20-7.12 (m, 2H), 6.95-6.89 (m, 2H), 6.89-6.82 (m, 2H), 3.73 (s, 3H), 3.71 (s, 3H), 3.48-3.40 (m, 2H), 2.75 (t, J=7.1 Hz, 2H$^{13}$). $^{13}$C NMR (400 MHz, DMSO-$d_6$) δ 168.0, 164.5, 158.2, 156.1, 153.8, 138.9, 135.3, 132.4, 131.4, 130.1, 128.6, 128.1, 122.5, 114.3, 114.2, 55.6, 55.4, 41.3, 34.8.

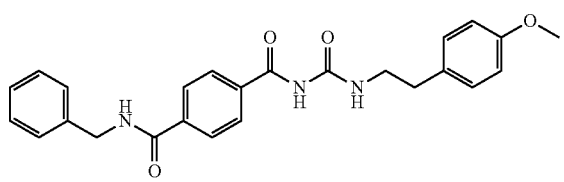 [SMILES: COc1ccc(CCNC(=O)NC(=O)c2ccc(C(=O)NCc3ccccc3)cc2)cc1]

SW208412-1-A

White solid, 15.0 mg, 40% yield. $^1$H NMR (400 MHz, DMSO-d$_6$) δ 10.76 (s, 1H), 9.25 (t, J=6.0 Hz, 1H), 8.63 (t, J=5.7 Hz, 1H), 8.03-7.94 (m, 4H), 7.31 (d, J=4.4 Hz, 4H), 7.26-7.20 (m, 1H), 7.19-7.13 (m, 2H), 6.88-6.82 (m, 2H), 4.47 (d, J=5.9 Hz, 2H), 3.70 (s, 3H), 3.47-3.39 (m, 2H), 2.74 (t, J=7.2 Hz, 2H). $^{13}$C NMR (400 MHz, DMSO-d$_6$) δ 168.0, 165.7, 158.2, 153.8, 139.9, 138.2, 135.3, 131.4, 130.1, 128.7, 128.6, 127.8, 127.7, 127.2, 114.3, 55.4, 43.2, 41.3, 34.8. ESI-MS (m/z): 432.0 [M+H]$^+$.

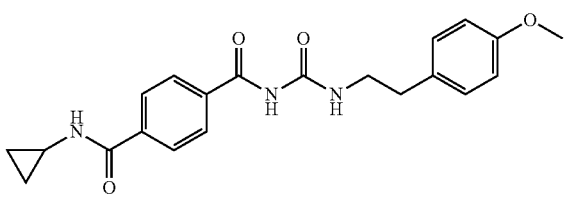 [SMILES: COc1ccc(CCNC(=O)NC(=O)c2ccc(C(=O)NC3CC3)cc2)cc1]

SW208452-1-A

White solid, 1.9 mg, 9% yield. $^1$H NMR (400 MHz, DMSO-d$_6$) δ 10.77 (s, 1H), 8.63 (t, J=5.7 Hz, 1H), 8.58 (d, J=4.3 Hz, 1H), 8.00-7.95 (m, 2H), 7.90-7.85 (m, 2H), 7.19-7.12 (m, 2H), 6.88-6.81 (m, 2H), 3.70 (s, 3H), 3.47-3.39 (m, 2H), 2.88-2.81 (m, 1H), 2.74 (t, J=7.2 Hz, 2H), 0.72-0.65 (m, 2H), 0.59-0.54 (m, 2H). $^{13}$C NMR (400 MHz, DMSO-d$_6$) δ 168.0, 167.0, 158.2, 153.8, 138.3, 135.1, 131.4, 130.1, 128.5, 127.6, 114.3, 55.4, 41.3, 34.8, 22.6, 6.2. ESI-MS (m/z): 382.1 [M+H]$^+$.

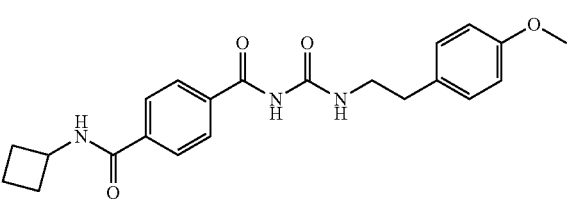 [SMILES: COc1ccc(CCNC(=O)NC(=O)c2ccc(C(=O)NC3CCC3)cc2)cc1]

SW208453-1-A

White solid, 7.2 mg, 33% yield. $^1$H NMR (400 MHz, DMSO-d$_6$) δ 10.75 (s, 1H), 8.76 (d, J=7.5 Hz, 1H), 8.62 (t, J=5.7 Hz, 1H), 8.00-7.96 (m, 2H), 7.93-7.88 (m, 2H), 7.18-7.13 (m, 2H), 6.88-6.83 (m, 2H), 4.46-4.34 (m, 1H), 3.71 (s, 3H), 3.47-3.39 (m, 2H), 2.74 (t, J=7.2 Hz, 2H), 2.26-2.15 (m, 2H), 2.12-1.99 (m, 2H), 1.71-1.59 (m, 2H). $^{13}$C NMR (400 MHz, DMSO-d$_6$) δ 168.0, 164.7, 158.2, 153.8, 138.4, 135.1, 131.4, 130.1, 128.5, 127.7, 114.3, 55.4, 45.1, 41.3, 34.8, 30.4, 15.2. ESI-MS (m/z): 396.1 [M+H]$^+$.

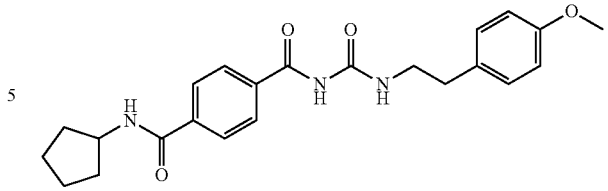

SW208454-1-A

White solid, 4.1 mg, 17% yield. $^1$H NMR (400 MHz, DMSO-d$_6$) δ 10.74 (s, 1H), 8.63 (t, J=5.7 Hz, 1H), 8.43 (d, J=7.2 Hz, 1H), 8.00-7.96 (m, 2H), 7.92-7.87 (m, 2H), 7.18-7.13 (m, 2H), 6.88-6.83 (m, 2H), 4.26-4.16 (m, 1H), 3.71 (s, 3H), 3.47-3.39 (m, 2H), 2.74 (t, J=7.1 Hz, 2H), 1.93-1.81 (m, 2H), 1.74-1.63 (m, 2H), 1.58-1.45 (m, 4H). $^{13}$C NMR (400 MHz, DMSO-d$_6$) δ 168.1, 165.4, 158.2, 153.8, 139.5, 138.7, 131.4, 130.1, 128.5, 127.8, 114.3, 55.4, 51.5, 41.3, 34.8, 32.5, 24.1. ESI-MS (m/z): 401.1 [M+H]$^+$.

General Procedure for HATU Couplings

HATU=1-[Bis(dimethylamino)methylene]-1H-1,2,3-triazolo[4,5-b]pyridinium 3-oxid hexafluorophosphate DIEA=N,N-Diisopropylethylamine A solution of carboxylic acid (1 eq), HATU (1 eq), and DIEA (2 eq) in DMF (0.1 M) was stirred for 20 minutes before the amine (1.5 eq) was added. When the reaction was complete (4 hours), added water and extracted the reaction mixture into EtOAc. The organic extracts were washed with brine, dried with Na2SO4, and concentrated to give the product, that was used without further purification, unless otherwise noted.

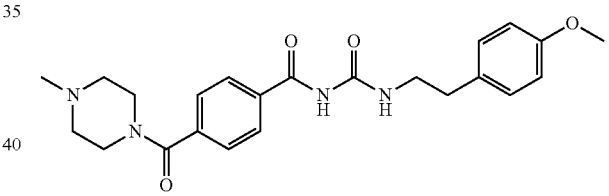

SW208414-1-A

Yellow solid, 3.5 mg, 10% yield. $^1$H NMR (400 MHz, DMSO-d$_6$) δ 10.74 (s, 1H), 8.63 (t, J=5.7 Hz, 1H), 7.99-7.93 (m, 2H), 7.48-7.43 (m, 2H), 7.19-7.12 (m, 2H), 6.88-6.82 (m, 2H), 3.71 (s, 3H), 3.60 (s, 2H), 3.46-3.39 (m, 2H), 3.25 (s, 2H), 2.74 (t, J=7.2 Hz, 2H), 2.35 (s, 2H), 2.24 (s, 2H), 2.18 (s, 3H). ESI-MS (m/z): 425.2 [M+H]$^+$.

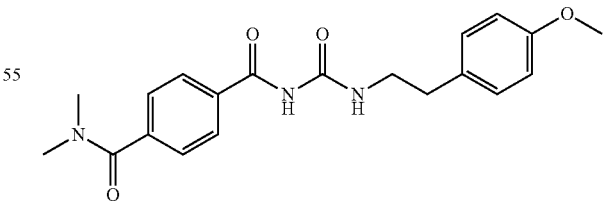

SW208455-1-A

Orange solid, 1.1 mg, 3% yield. $^1$H NMR (400 MHz, DMSO-d$_6$) δ 10.74 (s, 1H), 8.63 (t, J=5.6 Hz, 1H), 7.98-7.93 (m, 2H), 7.48 (dd, J=8.3, 1.5 Hz, 2H), 7.19-7.12 (m, 2H), 6.88-6.82 (m, 2H), 3.71 (s, 3H), 3.47-3.39 (m, 2H), 2.98 (s, 3H), 2.86 (s, 3H), 2.75 (t, J=7.2 Hz, 2H). $^{13}$C NMR (400

MHz, DMSO-d$_6$) δ 169.6, 168.1, 158.2, 153.8, 140.9, 133.5, 131.4, 130.1, 128.7, 127.3, 114.3, 55.4, 41.3, 34.8. ESI-MS (m/z): 370.1 [M+H]$^+$.

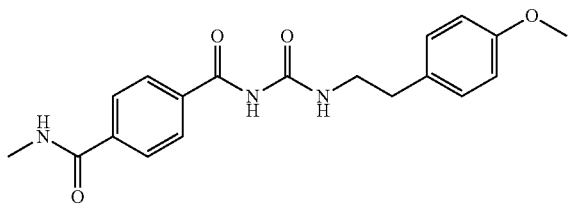

SW208413-1-A, 2.7 mg, 9% yield. $^1$H NMR (400 MHz, DMSO-d$_6$) δ 10.76 (s, 1H), 8.69-8.64 (m, 1H), 8.62 (t, J=5.7 Hz, 1H), 8.00-7.96 (m, 2H), 7.93-7.88 (m, 2H), 7.18-7.13 (m, 2H), 6.88-6.82 (m, 2H), 3.70 (s, 3H), 3.46-3.38 (m, 2H), 2.79-2.70 (m, 5H). $^{13}$C NMR (400 MHz, DMSO-d$_6$) δ 168.0, 166.1, 158.2, 153.8, 138.4, 135.1, 131.4, 130.1, 128.6, 127.6, 114.3, 55.4, 41.3, 34.8, 26.8. ESI-MS (m/z): 370.1 [M+H]$^+$.

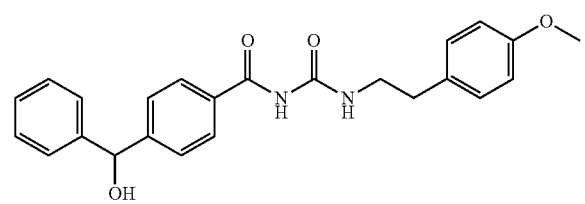 [SMILES: COc1ccc(CCNC(=O)NC(=O)c2ccc(C(O)c3ccccc3)cc2)cc1]

SW208460-1-A

Ti(iPrO)4 (2 eq) was added dropwise over 5 minutes to a cloudy solution of SW208222-1-A (1 eq) in 1,4-dioxane (1 M) under N2. Then, NaBH4 (1.5 eq) was added, and lastly, MeOH (0.64M) was added and the reaction solution bubbled and turned clear. The reaction mixture stirred at rt for 2 hours until reaction was complete by TLC. NH4OH was added and then water was added. The reaction mixture was extracted into EtOAc and the organic extracts were washed with brine, dried with Na2SO4, concentrated, and dried under vacuum to give the alcohol product as a white solid in 35% yield (73.3 mg). $^1$H NMR (400 MHz, DMSO-d$_6$) δ 10.58 (s, 1H), 8.66 (t, J=5.7 Hz, 1H), 7.89-7.84 (m, 2H), 7.50-7.44 (m, 2H), 7.39-7.34 (m, 2H), 7.32-7.25 (m, 2H), 7.22-7.16 (m, 1H), 7.16-7.11 (m, 2H), 6.87-6.81 (m, 2H), 6.04 (d, J=4.0 Hz, 1H), 5.75 (d, J=3.9 Hz, 1H), 3.70 (s, 3H), 3.45-3.37 (m, 2H), 2.73 (t, J=7.2 Hz, 2H). $^{13}$C NMR (400 MHz, DMSO-d$_6$) δ 168.4, 158.2, 153.9, 151.0, 145.5, 131.4, 131.4, 130.0, 128.7, 128.5, 127.4, 126.7, 126.5, 114.2, 74.2, 55.4, 41.3, 34.8. ESI-MS (m/z): 405.1 [M+H]$^+$.

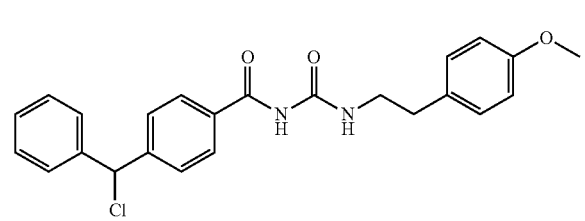 [SMILES: COc1ccc(CCNC(=O)NC(=O)c2ccc(C(Cl)c3ccccc3)cc2)cc1]

SW208563 Thionyl chloride (5 eq) was added to a solution of SW208460 in CH2Cl2. After 1½ hours, another 5 eq of thionyl chloride were added. When the reaction was complete by TLC (3 more hours), the reaction mixture was concentrated and dried under vacuum to give the desired product in 40.7 mg, 83% yield. $^1$H NMR (400 MHz, DMSO-d$_6$) δ 10.67 (s, 1H), 8.63 (t, J=5.7 Hz, 1H), 7.95-7.89 (m, 2H), 7.61-7.54 (m, 2H), 7.49-7.42 (m, 2H), 7.42-7.34 (m, 2H), 7.34-7.27 (m, 1H), 7.17-7.11 (m, 2H), 6.87-6.81 (m, 2H), 6.58 (s, 1H), 3.70 (s, 3H), 3.45-3.38 (m, 2H), 2.73 (t, J=7.2 Hz, 2H). ESI-MS (m/z): 422.9 [M]$^+$. (sew-197-153-1)

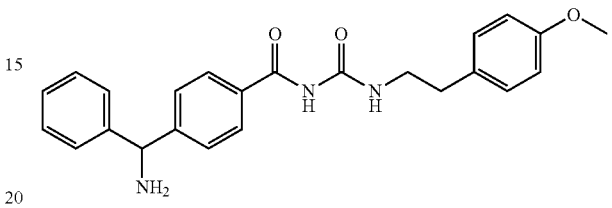

SW208564-1-A Sodium azide (2 eq) was added to a solution of SW208563 (1 eq) in DMF (0.1 M) and stirred overnight at rt. Then, water was added to the reaction and a precipitate formed. The precipitate was collected by filtration, rinsed with water, and dried under vacuum to give the desired product in 74% yield (30.6 mg). ESI-MS (m/z): 430.1 [M+H]$^+$. 10% Pd/C (1.8 eq) was added to a solution of the azide described above (1 eq) in MeOH (0.1M) and after N2 purging, the solution stirred under H2 at 50 psi for 2½ hours. Then, the solution was filtered through celite to remove Pd/C and the filtrate was concentrated. The residue was purified by flash chromatography (silica gel, 0→20% MeOH in CH2Cl2) to give the desired product as a white solid in 37% yield (10.7 mg). $^1$H NMR (400 MHz, DMSO-d$_6$) δ 10.56 (s, 1H), 8.67 (t, J=5.7 Hz, 1H), 7.87-7.82 (m, 2H), 7.52-7.47 (m, 2H), 7.40-7.35 (m, 2H), 7.29-7.23 (m, 2H), 7.19-7.11 (m, 3H), 6.87-6.81 (m, 2H), 5.12 (s, 1H), 3.70 (s, 3H), 3.45-3.37 (m, 2H), 2.73 (t, J=7.2 Hz, 2H). $^{13}$C NMR (400 MHz, DMSO-d$_6$) δ 168.4, 158.2, 154.0, 152.4, 146.7, 131.4, 131.0, 130.0, 128.7, 128.5, 127.2, 127.2, 127.0, 114.2, 59.4, 55.4, 41.3, 34.8. ESI-MS (m/z): 402.0 [M−H]$^+$.

General Procedure for Demethylation of Aryl Methyl Ethers.

A solution of aryl methyl ester or secondary amine (1 eq) in CH$_2$Cl$_2$ (0.2 M) was cooled to −78° C. for 20 minutes before adding BBr$_3$/CH$_2$Cl$_2$ (1.0 M, 10 eq) dropwise at −78° C. for 4-5 hours before warming to rt. The reaction mixture was poured into ice water and extracted into EtOAc. The organic extracts were washed with brine, dried with Na$_2$SO$_4$, and concentrated to give the product. The product was not purified unless otherwise noted.

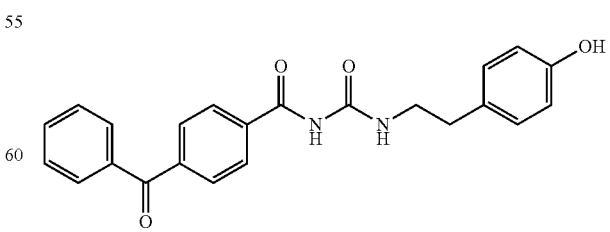

SW208459-1-A:

White solid, 7.3 mg, 26% yield after flash chromatography (silica gel, 0→100% EtOAc in hexanes). 5 hour reaction time. ¹H NMR (400 MHz, DMSO-d₆) δ 10.86 (s, 1H), 9.18 (s, 1H), 8.60 (t, J=5.7 Hz, 1H), 8.09-8.04 (m, 2H), 7.81-7.76 (m, 2H), 7.76-7.66 (m, 3H), 7.61-7.53 (m, 2H), 7.06-7.00 (m, 2H), 6.71-6.65 (m, 2H), 3.46-3.37 (m, 2H), 2.70 (t, J=7.2 Hz, 2H). ¹³C NMR (400 MHz, DMSO-d₆) δ 195.7, 168.0, 156.1, 153.7, 140.8, 136.8, 136.3, 133.6, 130.2, 130.0, 129.8, 129.6, 129.2, 128.8, 115.6, 41.4, 34.8. ESI-MS (m/z): 389.1 [M+H]⁺.

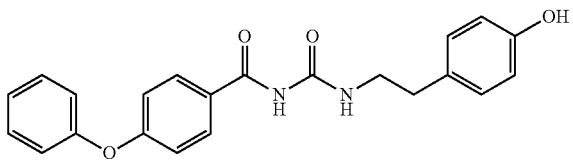 [SMILES: O=C(NCCc1ccc(O)cc1)NC(=O)c1ccc(Oc2ccccc2)cc1]

SW208523-1-A:

White solid, 8.4 mg, 95% yield. 4 hour ¹H NMR (400 MHz, DMSO-d₆) δ 10.58 (s, 1H), 9.18 (d, J=1.2 Hz, 1H), 8.66 (t, J=5.6 Hz, 1H), 8.00-7.94 (m, 2H), 7.45 (td, J=8.4, 8.0, 1.3 Hz, 2H), 7.23 (td, J=7.3, 1.3 Hz, 1H), 7.13-7.08 (m, 2H), 7.04-7.00 (m, 4H), 6.70-6.64 (m, 2H), 3.42-3.35 (m, 2H), 2.68 (t, J=7.3 Hz, 2H). ¹³C NMR (400 MHz, DMSO-d₆) δ 167.7, 161.4, 156.1, 155.4, 154.0, 131.0, 130.8, 130.0, 129.6, 127.2, 125.2, 120.5, 117.4, 115.6, 41.4, 34.9. ESI-MS (m/z): 377.1 [M+H]⁺.

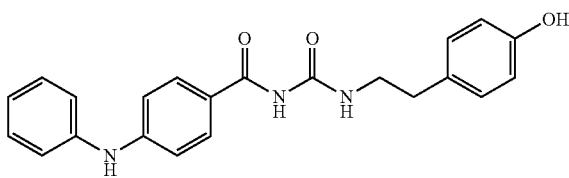 [SMILES: O=C(NCCc1ccc(O)cc1)NC(=O)c1ccc(Nc2ccccc2)cc1]

SW208566-1-A

Yellow solid, 2.0 mg, 57% yield. 4 hour ¹H NMR (400 MHz, DMSO-d₆) δ 10.28 (s, 1H), 9.18 (s, 1H), 8.78-8.73 (m, 2H), 7.87-7.82 (m, 2H), 7.34-7.27 (m, 2H), 7.18-7.13 (m, 2H), 7.06-6.93 (m, 5H), 6.69-6.64 (m, 2H), 3.42-3.34 (m, 2H), 2.67 (t, J=7.3 Hz, 2H). ESI-MS (m/z): 376.1 [M+H]⁺.

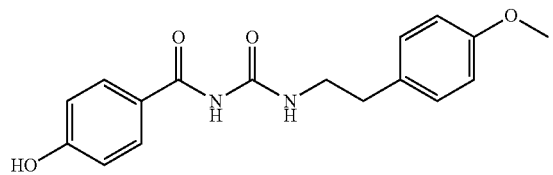 [SMILES: COc1ccc(CCNC(=O)NC(=O)c2ccc(O)cc2)cc1]

SW208565-1-A

10% Pd/C (1.8 eq) was added so a solution of SW208458 (1 eq) in anhydrous MeOH (0.1 M). After N₂ purging, H₂ was added at 50 psi and the solution stirred for 1½ hours. Then, the reaction mixture was filtered through celite to remove the Pd/C and the filtrate was concentrated and dried under vacuum to give the product as a white solid in 94% yield (153.4 mg). ¹H NMR (400 MHz, DMSO-d₆) δ 10.36 (s, 1H), 10.28 (s, 1H), 8.73 (t, J=5.8 Hz, 1H), 7.84 (d, J=8.4 Hz, 2H), 7.14 (d, J=8.3 Hz, 2H), 6.88-6.76 (m, 4H), 3.70 (s, 3H), 3.41 (m, 2H), 3.15 (d, J=4.3 Hz, 1H), 2.73 (t, J=7.2 Hz, 2H). ¹³C NMR (400 MHz, DMSO-d₆) δ 168.0, 162.1, 158.1, 154.2, 131.5, 130.9, 130.0, 123.3, 115.5, 114.2, 55.4, 41.2, 34.9. ESI-MS (m/z): 315.1 [M+H]⁺.

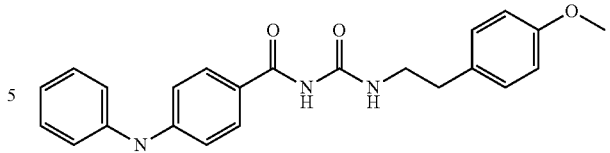

SW208561-1-A

Following a procedure from Tetrahedron Letters 38, 1997, 6359-6362 the aryl bromide (1 eq), Pd2(dba)3 (0.05 eq), BINAP (0.08 eq), Cs2CO3 (1.4 eq) were purged under n2 for 20 min before adding toluene (0.5 M) and aniline (1.2 eq). The reaction solution stirred at 100 C overnight. The reaction mixture was cooled and then EtOAc was added and washed with 1M HCl, brine, and dried with Na2SO4, and concentrated. The residue was purified by flash chromatography (silica gel, 0→100% EtOAc in hexanes) to give the product as a cream-colored solid, 3.2 mg in 15% yield. ¹H NMR (400 MHz, DMSO-d₆) δ 10.29 (s, 1H), 8.80-8.72 (m, 2H), 7.88-7.81 (m, 2H), 7.34-7.27 (m, 2H), 7.18-7.11 (m, 4H), 7.03-6.93 (m, 3H), 6.87-6.81 (m, 2H), 3.70 (s, 3H), 3.45-3.37 (m, 2H), 2.73 (t, J=7.2 Hz, 2H). ¹³C NMR (400 MHz, DMSO-d₆) δ 167.7, 158.1, 154.3, 148.7, 141.7, 131.5, 130.5, 130.1, 129.8, 122.4, 122.0, 119.8, 114.2, 114.2, 55.4, 41.2, 34.9. ESI-MS (m/z): 390.2 [M+H]⁺.

General Procedure for 1-Carbonyl Ureas:

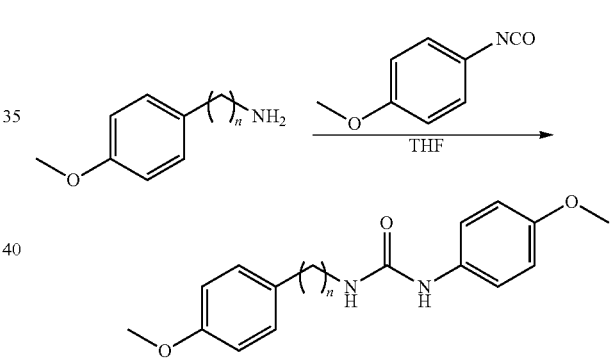

4-methoxyphenyl isocyanate (1 eq) was added to a solution of amine (1.4 eq) in THF (0.1 M). If a precipitate formed immediately, the reaction was complete in 2 hours and the precipitate was collected by filtration, rinsed with THF, and dried under vacuum to yield final product.

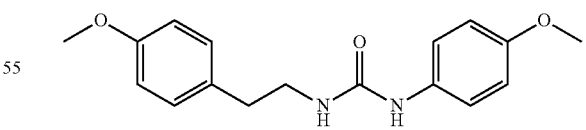

SW208024-1-A

White solid, 163.2 mg, % yield. ¹H NMR (500 MHz, DMSO-d₆) δ 8.26 (s, 1H), 7.28-7.24 (m, 2H), 7.16-7.12 (m, 2H), 6.88-6.84 (m, 2H), 6.81-6.77 (m, 2H), 5.95 (t, J=5.7 Hz, 1H), 3.71 (s, 3H), 3.68 (s, 3H), 3.29-3.23 (m, 2H), 2.65 (t, J=7.2 Hz, 2H). ESI-MS (m/z): 301.0 [M+1]⁺. ¹³C NMR (400 MHz, DMSO-d₆) δ 158.1, 155.8, 154.3, 134.1, 131.9, 130.1, 119.7, 114.3, 114.2, 55.6, 55.4, 41.3, 35.5.

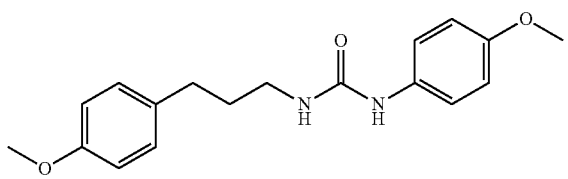

SW208029-1-A

White solid, 29.1 mg, 31% yield after flash chromatography (silica gel, 0→60% EtOAc in hexanes). A precipitate did not form when 4-methoxphenyl isocyanate reacted with the 3-carbon synthesized amine, so $Et_3N$ (2 eq) was added to the reaction mixture, which stirred overnight. A precipitate formed and was filtered and washed with THF, before drying under vacuum, giving a side product (SW11378-2-1). The ML contained crude SW208029-1-A, so the ML was concentrated, and the residue was purified by flash chromatography (silica gel, 0→60% EtOAc in hexanes) to give the final product. $^1$H NMR (500 MHz, DMSO-$d_6$) δ 8.19 (s, 1H), 7.29-7.24 (m, 2H), 7.13-7.09 (m, 2H), 6.85-6.82 (m, 2H), 6.81-6.77 (m, 2H), 6.06 (t, J=5.7 Hz, 1H), 3.71 (s, 3H), 3.68 (s, 3H), 3.07-3.01 (m, 2H), 2.53 (t, J=7.5 Hz, 2H), 1.70-1.63 (m, 2H). $^{13}$C NMR (400 MHz, DMSO-$d_6$) δ 157.8, 155.9, 154.3, 134.2, 134.0, 192.6, 119.8, 114.3, 144.2, 55.6, 55.4, 39.1, 32.3, 32.0. ESI-MS (m/z): 315.0 [M+H]$^+$.

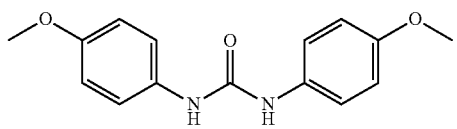

SW113878-2-A

White solid, 34.7 mg, 55% yield. A precipitate did not form when 4-methoxphenyl isocyanate reacted with the 3-carbon synthesized amine, so $Et_3N$ (2 eq) was added to the reaction mixture, which stirred overnight. A precipitate formed and was filtered and washed with THF, before drying under vacuum, giving the final product. $^1$H NMR (400 MHz, DMSO-$d_6$) δ 8.35 (s, 2H), 7.35-7.28 (m, 4H), 6.86-6.80 (m, 4H), 3.69 (s, 6H). $^{13}$C NMR (400 MHz, DMSO-$d_6$) δ 154.8, 153.4, 133.4, 120.3, 114.4, 55.6. ESI-MS (m/z): 273.0 [M+H]$^+$.

Procedure for SW208062-1-A:

Procedure from J Label Compd Radiopharm 2006, 49, 1037-1050.

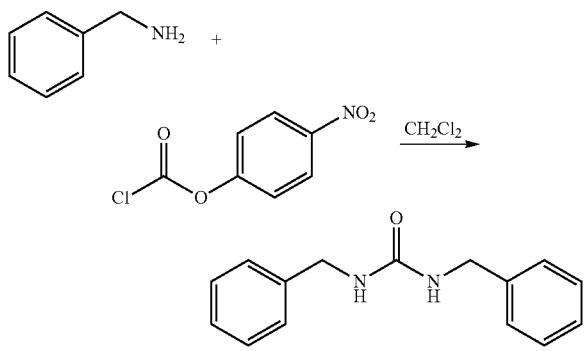

A solution of 4-nitrophenyl chloroformate (1 eq) in $CH_2Cl_2$ (2 M) was cooled to 0° C. before a solution of benzylamine (1 eq) and diisopropylamine (1 eq) in $CH_2Cl_2$ (2 M) was added dropwise. The yellow reaction mixture was warmed to room temperature and stirred overnight. The reaction mixture was washed with 1 M HCl, and the organic layer was washed with brine, dried with $Na_2SO_4$, and concentrated to give crude product. The crude residue was purified by flash chromatography (silica gel, 0→40% EtOAc in hexanes) to give the final product as a white solid in 19% yield (21.6 mg). $^1$H NMR (400 MHz, DMSO-$d_6$) δ 7.33-7.26 (m, 4H), 7.26-7.17 (m, 6H), 6.42 (t, J=6.1 Hz, 2H), 4.21 (d, J=6.0 Hz, 4H). $^{13}$C NMR (400 MHz, DMSO-$d_6$) δ 158.5, 141.3, 128.6, 127.4, 127.0, 43.4. ESI-MS (m/z): 241.0 [M+H]$^+$.

General Procedure for 1-Carbonyl Ureas:

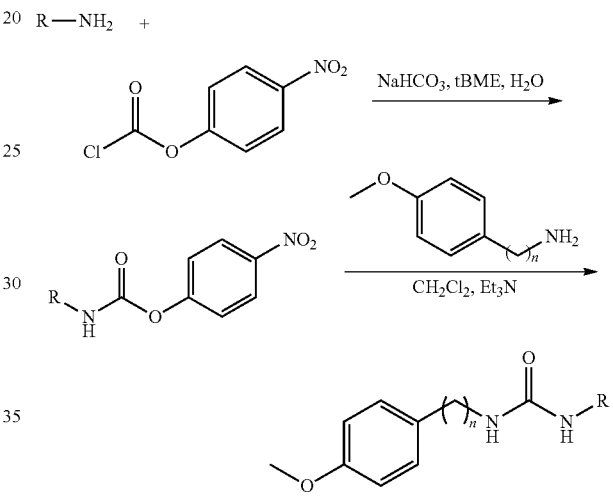

Step 1:

Procedure from Angewandte Chemie 116, 10, 2004, 1290-1292.

4-nitrophenyl chloroformate (1.1 eq) was added to a solution of amine (1 eq), sat. $NaHCO_3$ (1.3 eq), t-butyl methyl ether (0.71 M), and water (0.35 M). The aqueous layer was yellow and the organic layer contained a white solid. The reaction was complete after 2 hours. The reaction mixture was either filtered to collect white precipitate, which was the desired product, or rinsed with 1 M HCl (3x), and the organic layer was washed with brine, dried with $Na_2SO_4$, and concentrated to yield the desired product in 60-90% yield. A higher yield was achieved when the product was collected by filtration.

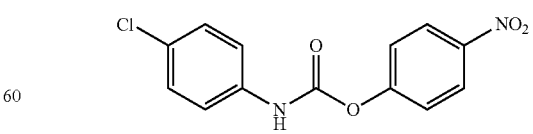

Cream-colored solid, 213.2 mg, 82% yield. $^1$H NMR (500 MHz, CDCl$_3$) δ 8.33-8.29 (m, 2H), 7.45-7.38 (m, 4H), 7.37-7.33 (m, 2H), 7.02 (s, 1H). ESI-MS (m/z): 293.8 [M+H]$^+$.

313

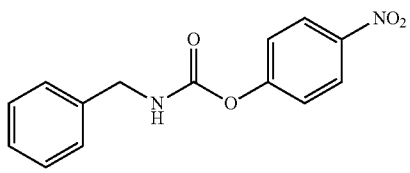 [SMILES: O=C(NCc1ccccc1)Oc1ccc([N+](=O)[O-])cc1]

Cream-colored solid, 201.0 mg, 96% yield. $^1$H NMR (500 MHz, CDCl$_3$) δ 8.30-8.23 (m, 2H), 7.45-7.28 (m, 7H), 5.45 (s, 1H), 4.49 (d, J=5.9 Hz, 2H). ESI-MS (m/z): 272.9 [M]$^+$.

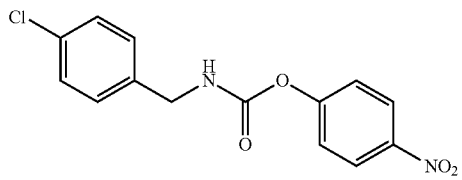 [SMILES: O=C(NCc1ccc(Cl)cc1)Oc1ccc([N+](=O)[O-])cc1]

Cream-colored solid, 157.5 mg, 67% yield. $^1$H NMR (500 MHz, CDCl$_3$) δ 8.29-8.24 (m, 2H), 7.40-7.33 (m, 4H), 7.32-7.28 (m, 2H), 5.46 (t, J=6.3 Hz, 1H), 4.46 (d, J=6.1 Hz, 2H). ESI-MS (m/z): 306.9 [M]$^+$.

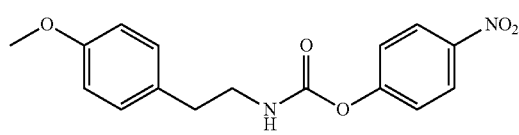 [SMILES: COc1ccc(CCNC(=O)Oc2ccc([N+](=O)[O-])cc2)cc1]

White solid, 89.7 mg, 58% yield. $^1$H NMR (400 MHz, CDCl$_3$) δ 8.24-8.19 (m, 2H), 7.30-7.25 (m, 2H), 7.16-7.11 (m, 2H), 7.09-7.04 (m, 2H), 6.89-6.85 (m, 2H), 6.84-6.79 (m, 2H), 3.78 (d, J=9.3 Hz, 7H), 3.51 (td, J=6.9, 5.9 Hz, 2H), 3.35 (td, J=6.8, 5.7 Hz, 2H), 2.83 (t, J=6.9 Hz, 2H), 2.70 (t, J=6.9 Hz, 2H). ESI-MS (m/z): 316.9 [M]$^+$.

Step 2

When Et$_3$N (1 eq) was added to a solution of intermediate (1 eq) in CH$_2$Cl$_2$ (0.125 M), the reaction mixture turned yellow. Then, 4-methoxyphenethylamine (1 eq) was added to the solution. The reaction was complete after one hour when a precipitate had formed. 3M NaOH was added to the reaction mixture. Then the precipitate was collected by filtration and rinsed with water to remove the yellow color, to give the final product, which was used without purification.

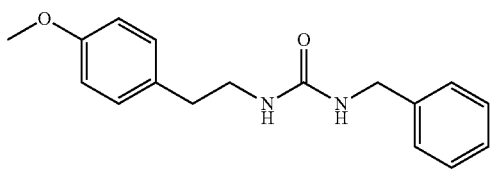 [SMILES: COc1ccc(CCNC(=O)NCc2ccccc2)cc1]

SW208043-2-A

White solid, 73.6 mg, 85% yield. $^1$H NMR (400 MHz, DMSO-d6) δ 7.32-7.25 (m, 2H), 7.23-7.17 (m, 3H), 7.12-7.06 (m, 2H), 6.86-6.80 (m, 2H), 6.34 (t, J=6.1 Hz, 1H), 5.88 (t, J=5.8 Hz, 1H), 4.17 (d, J=6.0 Hz, 2H), 3.70 (s, 3H), 3.23-3.15 (m, 2H), 2.60 (t, J=7.2 Hz, 2H). $^{13}$C NMR (101 MHz, DMSO-d6) δ 158.4, 158.0, 141.4, 132.0, 130.1, 128.6, 127.4, 126.9, 114.2, 55.4, 43.4, 41.7, 35.7. ESI-MS (m/z): 285.0 [M+H]$^+$.

314

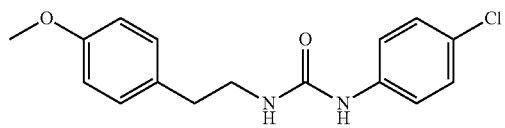 [SMILES: COc1ccc(CCNC(=O)Nc2ccc(Cl)cc2)cc1]

SW208045-1-A

White solid, 55.7 mg, 61% yield. $^1$H NMR (500 MHz, DMSO-d$_6$) δ 8.62 (s, 1H), 7.42-7.37 (m, 2H), 7.26-7.22 (m, 2H), 7.16-7.12 (m, 2H), 6.88-6.84 (m, 2H), 6.11 (t, J=5.7 Hz, 1H), 3.71 (s, 3H), 3.30-3.24 (m, 2H), 2.66 (t, J=7.2 Hz, 2H). $^{13}$C NMR (400 MHz, DMSO-d6) δ 158.1, 155.4, 140.0, 131.7, 130.1, 128.9, 124.8, 119.5, 114.2, 55.4, 41.3, 35.3. ESI-MS (m/z): 304.9 [M]$^+$.

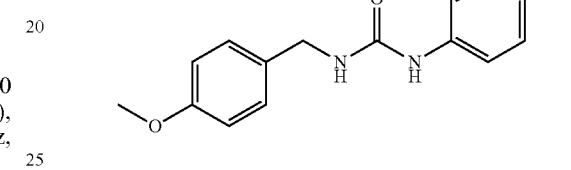

SW208046-1-A

White solid, 59.8 mg, 68% yield. $^1$H NMR (500 MHz, DMSO-d6) δ 8.66 (s, 1H), 7.43-7.40 (m, 2H), 7.27-7.23 (m, 2H), 7.23-7.19 (m, 2H), 6.90-6.86 (m, 2H), 6.57 (t, J=5.9 Hz, 1H), 4.20 (d, J=5.8 Hz, 2H), 3.72 (s, 3H). $^{13}$C NMR (400 MHz, DMSO-d6) δ 158.6, 155.4, 139.9, 132.5, 129.0, 128.9, 124.9, 119.6, 114.1, 55.5, 42.7. ESI-MS (m/z): 290.9 [M]$^+$.

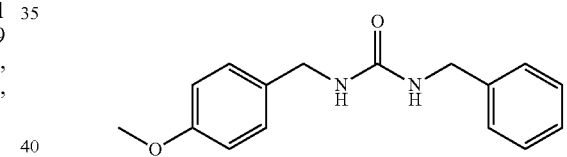

SW208047-1-A

White solid, 39.9 mg, 47% yield. $^1$H NMR (500 MHz, DMSO-d$_6$) δ 7.32-7.28 (m, 2H), 7.25-7.19 (m, 3H), 7.18-7.15 (m, 2H), 6.88-6.84 (m, 2H), 6.38 (t, J=6.1 Hz, 1H), 6.34 (t, J=6.0 Hz, 1H), 4.21 (d, J=5.9 Hz, 2H), 4.14 (d, J=6.0 Hz, 2H), 3.72 (s, 3H). $^{13}$C NMR (400 MHz, DMSO-d$_6$) δ 158.5, 158.5, 141.4, 133.2, 128.8, 218.6, 127.4, 127.0, 114.7, 55.5, 43.4, 42.9. ESI-MS (m/z): 271.0 [M+H]$^+$.

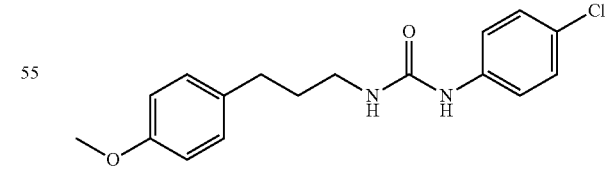

SW208119-1-A

White solid, 27.6 mg, 66% yield after flash chromatography (silica gel, 0→100% EtOAc in hexanes). $^1$H NMR (400 MHz, DMSO-d$_6$) δ 8.54 (s, 1H), 7.42-7.37 (m, 2H), 7.26-7.20 (m, 2H), 7.13-7.07 (m, 2H), 6.85-6.79 (m, 2H), 6.20 (t, J=5.7 Hz, 1H), 3.69 (s, 3H), 3.09-3.01 (m, 2H), 2.52 (t, J=7.5 Hz, 2H), 1.72-1.61 (m, 2H). $^{13}$C NMR (400 MHz, DMSO-$d_6$) δ 157.8, 155.5, 140.0, 133.9, 129.6, 128.9, 124.8, 119.5, 114.2, 55.4, 39.1, 32.2, 32.0. ESI-MS (m/z): 318.9 [M]+.

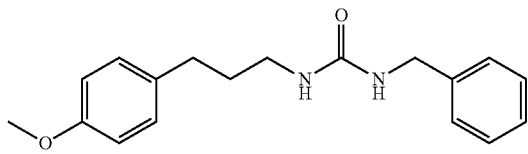 [SMILES: COc1ccc(CCCNC(=O)NCc2ccccc2)cc1]

SW208120-1-A

White solid, 13.1 mg, 40% yield after flash chromatography (silica gel, 0→100% EtOAc in hexanes). $^1$H NMR (500 MHz, DMSO-$d_6$) δ 7.32-7.27 (m, 2H), 7.25-7.18 (m, 3H), 7.11-7.07 (m, 2H), 6.85-6.81 (m, 2H), 6.29 (t, J=6.1 Hz, 1H), 5.98 (t, J=5.7 Hz, 1H), 4.19 (d, J=6.0 Hz, 2H), 3.70 (s, 3H), 3.01-2.96 (m, 2H), 2.51-2.47 (m, 2H), 1.66-1.58 (m, 2H). $^{13}$C NMR (400 MHz, DMSO-$d_6$) δ 158.5, 157.8, 141.5, 134.1, 129.6, 128.6, 127.4, 126.9, 114.1, 55.4, 43.3, 32.5, 32.0. ESI-MS (m/z): 299.0 [M+H]+.

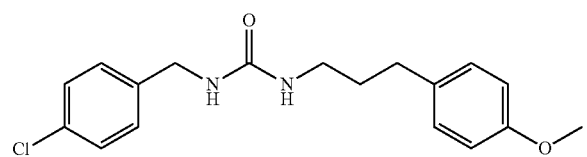 [SMILES: COc1ccc(CCCNC(=O)NCc2ccc(Cl)cc2)cc1]

SW208121-1-A

White solid, 22.2 mg, 95% yield after flash chromatography (silica gel, 0→100% EtOAc in hexanes). $^1$H NMR (500 MHz, DMSO-$d_6$) δ 7.38-7.34 (m, 2H), 7.27-7.23 (m, 2H), 7.11-7.06 (m, 2H), 6.85-6.80 (m, 2H), 6.35 (t, J=6.1 Hz, 1H), 6.02 (t, J=5.7 Hz, 1H), 4.17 (d, J=6.0 Hz, 2H), 3.70 (s, 3H), 3.01-2.95 (m, 2H), 2.47 (t, J=7.7 Hz, 2H), 1.65-1.58 (m, 2H). $^{13}$C NMR (400 MHz, DMSO-$d_6$) δ 158.5, 157.8, 140.7, 134.1, 131.4, 129.6, 129.3, 128.5, 114.1, 55.4, 42.7, 32.5, 32.0. ESI-MS (m/z): 333.0 [M+H]+.

General Procedure for:

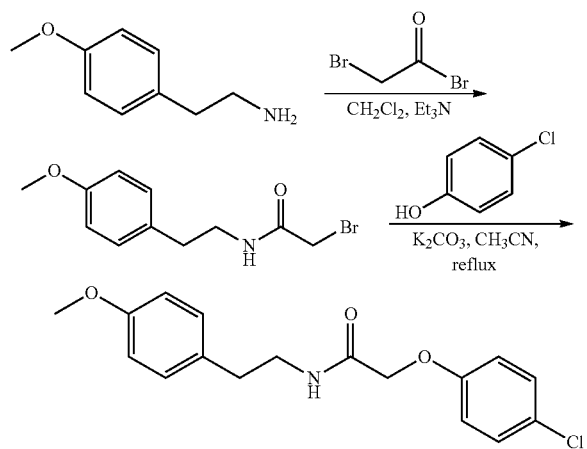

Step 1

Procedure from Journal of Molecular Structure, 935, 2009, 47-52

A solution of amine (1 eq), CH$_2$Cl$_2$ (0.5 M), and Et$_3$N (1 eq) stirred for 30 minutes at 0° C. before adding bromoacetyl bromide (1.2 eq) dropwise over 20 minutes to form a cloudy yellow solution. It warmed up to room temperature and stirred overnight. Then, the reaction was filtered to remove the HBr salts, and the filtrate was washed with water. The organic layer was dried with Na$_2$SO$_4$, concentrated, and dried to yield the crude intermediate, which was used without further purification.

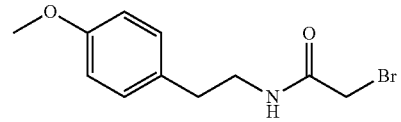

Brown solid, 1.2053 g, 88% yield. $^1$H NMR (500 MHz, CDCl$_3$) δ 7.16-7.11 (m, 2H), 6.90-6.85 (m, 2H), 3.87 (s, 2H), 3.81 (s, 3H), 3.56-3.49 (m, 2H), 2.79 (t, J=7.0 Hz, 2H). ESI-MS (m/z): 273.9 [M+H]+.

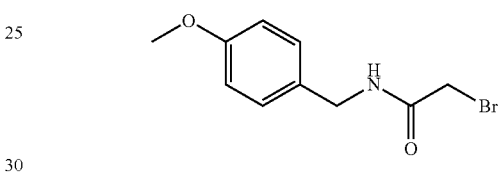

Brown solid, 1.2219 g, 95% yield. $^1$H NMR (500 MHz, Chloroform-d) δ 7.25-7.21 (m, 2H), 6.92-6.87 (m, 2H), 4.42 (d, J=5.7 Hz, 2H), 3.93 (s, 3H), 3.82 (s, 2H). ESI-MS (m/z): 259.9 [M+H]+.

Step 2:

4-chlorophenol or 4-chloroaniline (1 eq) was added to the crude intermediate (1 eq) from step 1 and potassium carbonate (1 eq) in acetonitrile (0.5 M) and refluxed for 6½-12 hours. After cooling to rt, the reaction mixture was filtered to remove salts, and the filtrate was concentrated. Water and diethyl ether (1:1 v/v, 4 ml) were added to the residue with stirring and a precipitate formed. The precipitate was collected by filtration, rinsed with diethyl ether, and dried to give the final product.

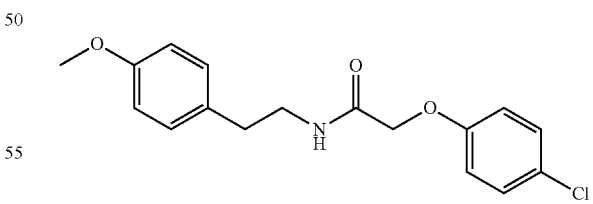

SW208038-1-A

Cream solid, 83.1 mg, 17% yield. $^1$H NMR (500 MHz, DMSO-$d_6$) δ 8.14 (t, J=5.8 Hz, 1H), 7.35-7.31 (m, 2H), 7.11-7.06 (m, 2H), 6.95-6.91 (m, 2H), 6.84-6.81 (m, 2H), 4.45 (s, 2H), 3.71 (s, 3H), 3.33-3.26 (m, 2H), 2.66 (t, J=7.4 Hz, 2H). $^{13}$C NMR (400 MHz, DMSO-$d_6$) δ 167.6, 158.1, 157.0, 131.5, 130.0, 129.7, 125.3, 116.9, 114.2, 67.6, 55.4, 55.4, 34.6. ESI-MS (m/z): 319.9 [M]+.

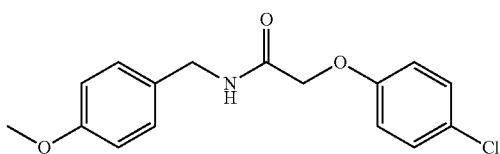 [SMILES: COc1ccc(CNC(=O)COc2ccc(Cl)cc2)cc1]

SW208040-1-A

White solid, 153.5 mg, 34% yield after flash chromatography (silica gel, 0→100% EtOAc in hexanes). $^1$H NMR (500 MHz, DMSO-d6) δ 8.60 (t, J=6.2 Hz, 1H), 7.36-7.32 (m, 2H), 7.18-7.14 (m, 2H), 7.00-6.96 (m, 2H), 6.88-6.84 (m, 2H), 4.53 (s, 2H), 4.26 (d, J=6.1 Hz, 2H), 3.71 (s, 3H). $^{13}$C NMR (400 MHz, DMSO-d6) δ 167.7, 158.6, 157.0, 131.6, 129.7, 129.1, 125.3, 117.0, 114.1, 67.6, 55.5, 41.7. ESI-MS (m/z): 305.9 [M]$^+$.

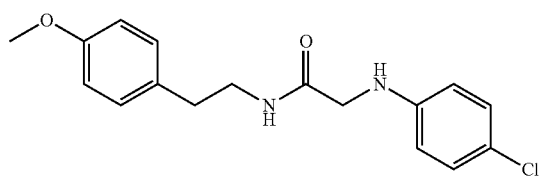 [SMILES: COc1ccc(CCNC(=O)CNc2ccc(Cl)cc2)cc1]

SW208041-1-A

Orange solid, 244.7 mg, 50% yield after flash chromatography (silica gel, 0→100% EtOAc in hexanes). $^1$H NMR (500 MHz, DMSO-d6) δ 7.89 (t, J=5.8 Hz, 1H), 7.12-7.07 (m, 2H), 7.07-7.02 (m, 2H), 6.82-6.78 (m, 2H), 6.51-6.45 (m, 2H), 6.16 (t, J=6.0 Hz, 1H), 3.70 (s, 3H), 3.57 (d, J=5.8 Hz, 2H), 3.28-3.21 (m, 2H), 2.61 (t, J=7.3 Hz, 2H). $^{13}$C NMR (400 MHz, DMSO-d6) δ 170.1, 158.1, 147.7, 131.6, 130.0, 128.9, 120.0, 114.1, 114.1, 55.4, 47.2, 40.7, 34.7. ESI-MS (m/z): 318.9 [M]$^+$.

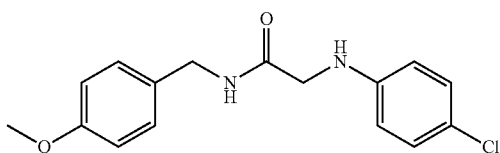 [SMILES: COc1ccc(CNC(=O)CNc2ccc(Cl)cc2)cc1]

SW208042-1-A

Yellow oil, 120.5 mg, 38% yield. $^1$H NMR (500 MHz, DMSO-d6) δ 8.36 (t, J=6.0 Hz, 1H), 7.15-7.11 (m, 2H), 7.11-7.08 (m, 2H), 6.86-6.82 (m, 2H), 6.55-6.51 (m, 2H), 6.18 (s, 1H), 4.20 (d, J=6.0 Hz, 2H), 3.71 (s, 3H), 3.65 (d, J=3.8 Hz, 2H). $^{13}$C NMR (400 MHz, DMSO-d6) δ 170.2, 158.6, 147.8, 131.8, 129.0, 128.9, 120.0, 114.1, 114.0, 55.5, 47.2, 41.9. ESI-MS (m/z): 304.9 [M]$^+$.

General Procedure for:

Procedure from: Chemistry—A European Journal, 2008, 14, 25, 7524-7556.

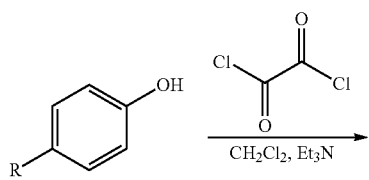

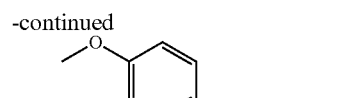

Oxalyl chloride (1 eq) was added dropwise to a solution of phenol derivative (1 eq) in CH$_2$Cl$_2$ (1.1 M). The reaction mixture was cooled to 0° C. Then Et$_3$N (1 eq) was added dropwise over 30 minutes. The reaction turned an orange-brown color and a precipitate formed as the reaction warmed to rt over 45 minutes. When the reaction mixture showed no phenol by TLC, the reaction mixture was cooled to 0° C. and 4-methoxyphenethylamine was added. A solid formed and the reaction was complete within an hour. The reaction mixture was washed with NaHCO$_3$ and the solid disappeared. The organic layer was dried with Na$_2$SO$_4$ and concentrated. The residue was purified by flash chromatography (silica gel, 0→100% EtOAc in hexanes) to give the final product.

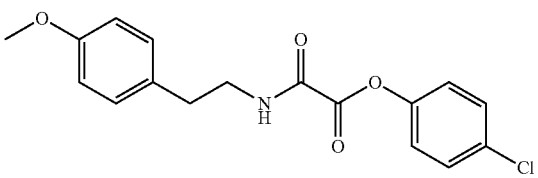 [SMILES: COc1ccc(CCNC(=O)C(=O)Oc2ccc(Cl)cc2)cc1]

SW208147-1-A

Cream-colored solid, 9.9 mg, 8% yield. $^1$H NMR (500 MHz, DMSO-d$_6$) δ 9.25 (t, J=5.9 Hz, 1H), 7.50-7.44 (m, 2H), 7.34-7.30 (m, 1H), 7.26-7.22 (m, 2H), 7.17-7.13 (m, 2H), 6.89-6.84 (m, 2H), 3.72 (s, 3H), 3.41-3.35 (m, 2H), 2.76 (t, J=7.5 Hz, 2H). $^{13}$C NMR (400 MHz, DMSO-d$_6$) δ 159.6, 158.2, 156.7, 150.5, 131.2, 130.2, 130.0, 126.9, 121.9, 114.3, 55.4, 41.5, 34.0. ESI-MS (m/z): 301.0 [M+2H]$^+$.

SW208148-1-A

Orange solid, 46.9 mg, 14% yield. $^1$H NMR (400 MHz, DMSO-d$_6$) δ 9.22 (t, J=6.0 Hz, 1H), 7.55-7.48 (m, 2H), 7.32-7.26 (m, 2H), 7.17-7.11 (m, 2H), 6.88-6.82 (m, 2H), 3.70 (s, 3H), 3.40-3.33 (m, 2H), 2.74 (t, J=7.5 Hz, 2H). $^{13}$C NMR (400 MHz, DMSO-d$_6$) δ 159.3, 158.2, 156.4, 149.3, 131.2, 131.1, 130.1, 130.0, 123.9, 114.3, 55.4, 41.5, 34.0. ESI-MS (m/z): 333.9 [M]$^+$.

General Procedure for EDC Couplings

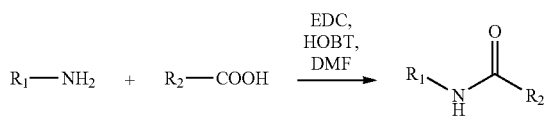

Where EDC=1-(3-dimethylaminopropyl)-3-ethylcarbodiimide HCl
HOBT=1-hydroxybenzotriazole hydrate The carboxylic acid (1 eq), EDC (1.05 eq), and HOBT (1.05 eq) were dissolved in DMF (0.1M) and stirred for 20 minutes before adding the amine (1 eq). The reaction mixture stirred overnight. Water was added to the reaction mixture to precipitate out the desired material, and the precipitate was collected by filtration, washed with water, and dried under vacuum to give the final product. If a precipitate did not form, EtOAc was added and was washed with 1M NaOH (3×), water (3×), 1M HCl, water (3×), and brine. Then the organic layer was dried with $Na_2SO_4$ and concentrated to give final product. Final product was not purified unless otherwise noted.

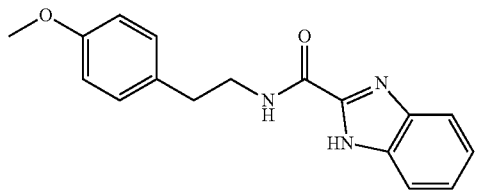 [SMILES: COc1ccc(CCNC(=O)c2nc3ccccc3[nH]2)cc1]

SW208050-1-A

White solid, 132.7 mg, 65% yield. $^1$H NMR (400 MHz, DMSO-$d_6$) δ 13.19 (s, 1H), 8.93 (t, J=6.0 Hz, 1H), 7.74-7.65 (m, 1H), 7.54-7.46 (m, 1H), 7.33-7.20 (m, 2H), 7.17-7.12 (m, 2H), 6.86-6.80 (m, 2H), 3.69 (s, 3H), 3.54-3.46 (m, 2H), 2.80 (t, J=7.4 Hz, 2H). $^{13}$C NMR (400 MHz, DMSO-$d_6$) δ 159.0, 158.1, 146.1, 142.9, 134.9, 131.6, 130.0, 124.4, 122.9, 120.3, 114.2, 113.0, 55.4, 40.9, 34.5. ESI-MS (m/z): 296.0 $[M+H]^+$.

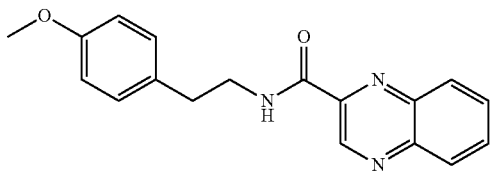 [SMILES: COc1ccc(CCNC(=O)c2cnc3ccccc3n2)cc1]

SW208051-1-A

Peach-colored solid, 144.1 mg, 68% yield. $^1$H NMR (400 MHz, DMSO-$d_6$) δ 9.45 (s, 1H), 9.08 (t, J=6.0 Hz, 1H), 8.20-8.14 (m, 2H), 8.00-7.94 (m, 2H), 7.19-7.14 (m, 2H), 6.87-6.82 (m, 2H), 3.70 (s, 3H), 3.58-3.50 (m, 2H), 2.84 (t, J=7.5 Hz, 2H). $^{13}$C NMR (400 MHz, DMSO-$d_6$) δ 163.4, 158.2, 144.8, 144.1, 143.4, 140.2, 132.3, 131.7, 131.6, 130.0, 129.8, 129.6, 114.3, 55.4, 41.3, 34.7. ESI-MS (m/z): 308.0 $[M+H]^+$.

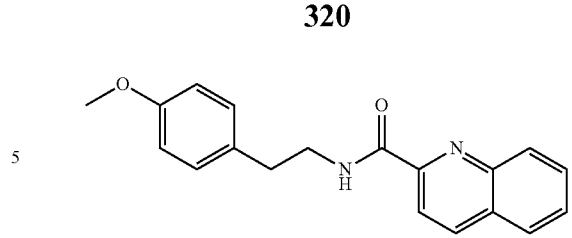

SW208052-1-A

White solid, 139.7 mg, 66% yield. $^1$H NMR (400 MHz, DMSO-$d_6$) δ 8.94 (t, J=6.1 Hz, 1H), 8.54 (d, J=8.6 Hz, 1H), 8.14 (d, J=8.5 Hz, 1H), 8.12-8.04 (m, 2H), 7.85 (ddd, J=8.5, 6.8, 1.5 Hz, 1H), 7.70 (ddd, J=8.1, 6.8, 1.2 Hz, 1H), 7.20-7.15 (m, 2H), 6.88-6.82 (m, 2H), 3.70 (s, 3H), 3.58-3.51 (m, 2H), 2.83 (t, J=7.5 Hz, 2H). $^{13}$C NMR (400 MHz, DMSO-$d_6$) δ 164.3, 158.1, 150.6, 146.4, 138.3, 131.7, 131.0, 130.0, 129.6, 129.2, 128.5, 128.5, 119.0, 114.3, 55.4, 41.3, 34.8. ESI-MS (m/z): 307.0 $[M+H]^+$.

SW208053-1-A

Yellow solid, 136.8 mg, 60% yield. $^1$H NMR (400 MHz, DMSO-$d_6$) δ 8.89 (t, J=6.1 Hz, 1H), 8.17 (appd, J=8.6 Hz, 1H), 8.02 (appd, J=8.6 Hz, 1H), 7.85-7.79 (m, 1H), 7.67-7.61 (m, 1H), 7.59 (s, 1H), 7.20-7.14 (m, 2H), 6.88-6.82 (m, 2H), 4.11 (s, 3H), 3.70 (s, 3H), 3.58-3.50 (m, 2H), 2.83 (t, J=7.5 Hz, 2H). $^{13}$C NMR (400 MHz, DMSO-$d_6$) δ 164.3, 163.4, 158.1, 152.2, 147.5, 131.6, 131.1, 130.0, 129.4, 127.6, 122.0, 121.7, 114.3, 98.4, 56.8, 55.4, 41.3, 34.8. ESI-MS (m/z): 338.0 $[M+2H]^+$.

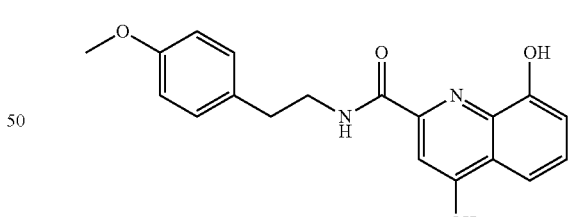

SW208054-1-A

Peach-colored solid, 192.0 mg, 83% yield. $^1$H NMR (400 MHz, DMSO-$d_6$) δ 11.72 (s, 1H), 9.83 (s, 1H), 9.65 (t, J=6.0 Hz, 1H), 7.54 (appd, J=8.6 Hz, 1H), 7.51 (s, 1H), 7.40 (appt, J=8.0 Hz, 1H), 7.20-7.14 (m, 2H), 7.11-7.06 (m, 1H), 6.87-6.81 (m, 2H), 3.69 (s, 3H), 3.55-3.46 (m, 2H), 2.83 (t, J=7.7 Hz, 2H). $^{13}$C NMR (400 MHz, DMSO-$d_6$) δ 164.3, 162.9, 158.2, 153.8, 149.3, 138.6, 131.7, 130.0, 127.7, 122.3, 114.3, 112.2, 111.8, 102.3, 55.4, 41.3, 35.0. ESI-MS (m/z): 388.9 $[M]^+$.

321

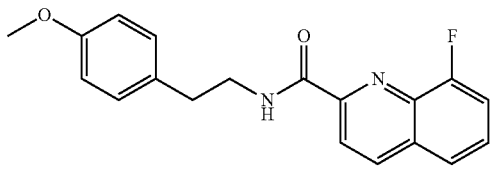 [SMILES: COc1ccc(CCNC(=O)c2ccc3cccc(F)c3n2)cc1]

SW208055-1-A

Cream-colored solid, 193.8 mg, 87% yield. $^1$H NMR (400 MHz, DMSO-d$_6$) δ 8.80 (t, J=6.1 Hz, 1H), 8.62 (dd, J=8.6, 1.6 Hz, 1H), 8.21 (d, J=8.6 Hz, 1H), 7.92-7.87 (m, 1H), 7.71-7.65 (m, 2H), 7.20-7.15 (m, 2H), 6.88-6.83 (m, 2H), 3.70 (s, 3H), 3.59-3.51 (m, 2H), 2.83 (t, J=7.5 Hz, 2H). $^{13}$C NMR (400 MHz, DMSO-d$_6$) δ 163.9, 157.6 (J$_{C-F}$=256.7 Hz), 158.2, 150.8 (J$_{C-F}$=1.4 Hz), 138.4 (J$_{C-F}$=2.84 Hz), 136.5 (J$_{C-F}$=12.1 Hz), 131.6, 130.8 (J$_{C-F}$=1.81 Hz), 130.1, 128.7 (J$_{C-F}$=1.88 Hz), 124.5 (J$_{C-F}$=4.69 Hz), 120.1, 115.0 (J$_{C-F}$=18.2 Hz), 114.3, 55.4, 41.3, 34.8. ESI-MS (m/z): 324.9 [M]$^+$.

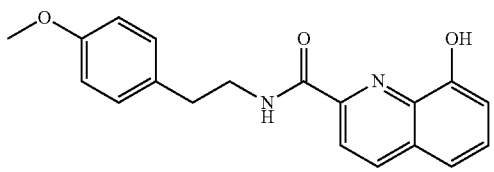 [SMILES: COc1ccc(CCNC(=O)c2ccc3cccc(O)c3n2)cc1]

SW208056-1-A

Red oil, 108.5 mg, 49% yield. $^1$H NMR (500 MHz, DMSO-d$_6$) δ 10.12 (s, 1H), 9.73 (t, J=6.0 Hz, 1H), 8.49 (d, J=8.5 Hz, 1H), 8.13 (d, J=8.5 Hz, 1H), 7.55 (appt, J=7.9 Hz, 1H), 7.47 (appd, J=8.2 Hz, 1H), 7.21-7.15 (m, 3H), 6.88-6.84 (m, 2H), 3.70 (s, 3H), 3.59-3.53 (m, 2H), 2.86 (t, J=7.6 Hz, 2H). $^{13}$C NMR (400 MHz, DMSO-d$_6$) δ 164.0, 158.2, 154.0, 147.9, 138.2, 136.8, 131.7, 130.0, 129.9, 129.8, 119.2, 118.0, 114.3, 112.0, 55.4, 41.3, 35.0. ESI-MS (m/z): 323.0 [M+H]$^+$.

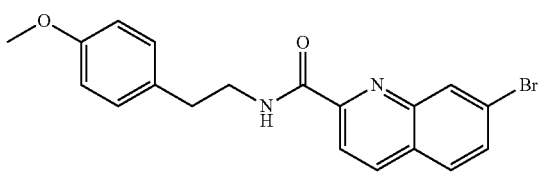 [SMILES: COc1ccc(CCNC(=O)c2ccc3ccc(Br)cc3n2)cc1]

SW208057-1-A

Cream-colored solid, 109.2 mg, 79% yield. $^1$H NMR (500 MHz, DMSO-d$_6$) δ 8.97 (t, J=6.1 Hz, 1H), 8.60 (d, J=8.5 Hz, 1H), 8.28 (d, J=1.9 Hz, 1H), 8.17 (d, J=8.5 Hz, 1H), 8.07 (d, J=8.7 Hz, 1H), 7.87 (dd, J=8.7, 2.0 Hz, 1H), 7.21-7.16 (m, 2H), 6.88-6.84 (m, 2H), 3.71 (s, 3H), 3.58-3.51 (m, 2H), 2.84 (t, J=7.6 Hz, 2H). $^{13}$C NMR (400 MHz, DMSO-d$_6$) δ 163.9, 158.2, 151.6, 147.0, 138.6, 131.6, 131.6, 131.4, 130.6, 130.0, 128.0, 124.1, 119.6, 114.3, 55.4, 41.3, 34.7. ESI-MS (m/z): 386.8 [M+H]$^+$.

322

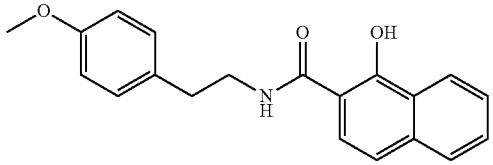 [SMILES: COc1ccc(CCNC(=O)c2ccc3ccccc3c2O)cc1]

SW208124-1-A

Brown solid, 57.4 mg, 56% yield. $^1$H NMR (400 MHz, DMSO-d$_6$) δ 9.04 (t, J=5.7 Hz, 1H), 8.26-8.22 (m, 1H), 7.87-7.81 (m, 2H), 7.61 (ddd, J=8.2, 6.8, 1.3 Hz, 1H), 7.53 (ddd, J=8.2, 6.9, 1.3 Hz, 1H), 7.38-7.33 (m, 1H), 7.20-7.14 (m, 2H), 6.88-6.82 (m, 2H), 3.69 (s, 3H), 3.56-3.48 (m, 2H), 2.83 (t, J=7.5 Hz, 2H). $^{13}$C NMR (400 MHz, DMSO-d$_6$) δ 170.8, 160.1, 158.2, 136.2, 131.5, 130.1, 129.2, 127.9, 126.2, 125.2, 123.4, 123.0, 118.0, 114.3, 107.5, 55.4, 41.4, 34.4. ESI-MS (m/z): 322.0 [M+H]$^+$.

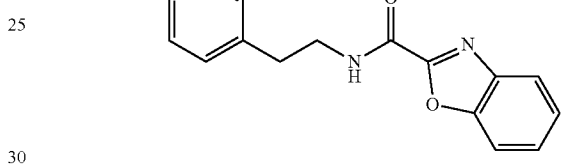

SW208125-1-A

Cream-colored solid, 6.3 mg, 7% yield, after flash chromatography (silica gel, 0→100% EtOAc in hexanes). $^1$H NMR (400 MHz, DMSO-d$_6$) δ 9.31 (t, J=5.9 Hz, 1H), 7.89-7.86 (m, 1H), 7.86-7.83 (m, 1H), 7.55 (ddd, J=8.3, 7.4, 1.4 Hz, 1H), 7.48 (ddd, J=7.7, 7.5, 1.2 Hz, 1H), 7.17-7.12 (m, 2H), 6.86-6.81 (m, 2H), 3.69 (s, 3H), 3.51-3.44 (m, 2H), 2.80 (t, J=7.4 Hz, 2H). $^{13}$C NMR (400 MHz, DMSO-d$_6$) δ 158.2, 156.2, 155.4, 150.6, 140.3, 131.3, 130.1, 127.8, 126.1, 121.4, 114.2, 112.3, 55.4, 41.4, 34.2. ESI-MS (m/z): 297.0 [M+H]$^+$.

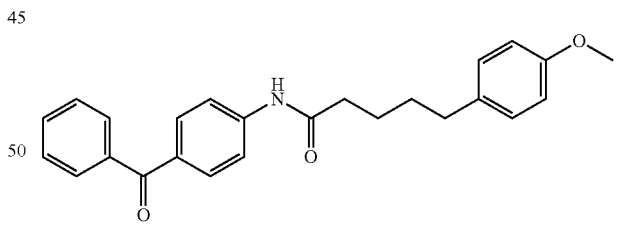

SW208480-1-A

Cream-colored solid, 17.4 mg, 15% yield, after flash chromatography (silica gel, 0→30% EtOAc in hexanes). $^1$H NMR (400 MHz, CDCl$_3$) δ 7.83-7.74 (m, 2H), 7.74-7.69 (m, 6H), 7.66-7.61 (m, 1H), 7.60-7.42 (m, 7H), 7.11-7.06 (m, 1H), 6.85-6.79 (m, 1H), 6.70-6.64 (m, 3H), 4.23-4.06 (m, 4H), 3.78 (s, 2H), 2.60 (t, J=7.4 Hz, 1H), 2.43-2.35 (m, 1H), 1.83-1.63 (m, 3H), 1.30-1.21 (m, 2H). $^{13}$C NMR (400 MHz, CDCl$_3$) δ 195.7, 195.4, 157.7, 150.9, 142.0, 138.8, 137.8, 134.1, 133.0, 132.2, 131.6, 131.4, 129.9, 129.5, 129.3, 129.3, 128.1, 127.4, 118.7, 113.8, 113.6, 55.3, 37.7, 34.7, 31.2, 25.0. ESI-MS (m/z): [M+H]$^+$.

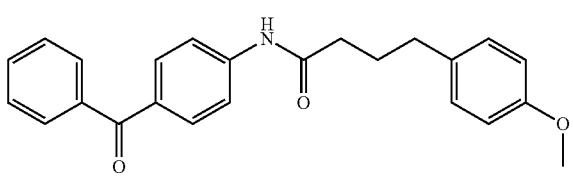 [SMILES: COc1ccc(CCCC(=O)Nc2ccc(C(=O)c3ccccc3)cc2)cc1]

SW208470-1-A

Cream-colored solid, 39.7 mg, 35% yield, after flash chromatography (silica gel, 0→30% EtOAc in hexanes). $^1$H NMR (400 MHz, CDCl$_3$) δ 7.83-7.74 (m, 4H), 7.65-7.55 (m, 3H), 7.50-7.44 (m, 2H), 7.40 (s, 1H), 7.14-7.07 (m, 2H), 6.86-6.80 (m, 2H), 3.78 (s, 3H), 2.66 (t, J=7.4 Hz, 2H), 2.37 (t, J=7.3 Hz, 2H), 2.05 (m, 2H). $^{13}$C NMR (400 MHz, CDCl$_3$) δ 195.6, 171.3, 158.0, 141.8, 137.8, 133.1, 132.9, 132.2, 131.6, 129.9, 129.4, 128.3, 118.7, 113.9, 55.3, 36.8, 34.1, 26.9. ESI-MS (m/z): 374.1 [M+H]$^+$.

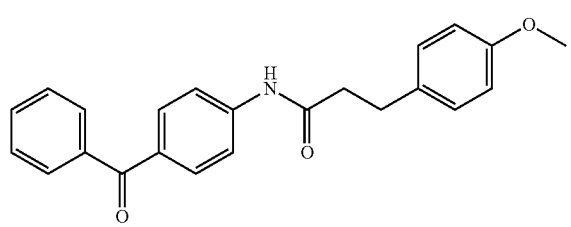 [SMILES: COc1ccc(CCC(=O)Nc2ccc(C(=O)c3ccccc3)cc2)cc1]

SW208466-1-A

Orange solid, 43.8 mg, 41% yield. $^1$H NMR (400 MHz, DMSO-d$_6$) δ 10.27 (s, 1H), 7.77-7.66 (m, 6H), 7.66-7.60 (m, 1H), 7.58-7.50 (m, 2H), 7.18-7.12 (m, 2H), 6.85-6.80 (m, 2H), 3.69 (s, 3H), 2.85 (t, J=7.5 Hz, 2H), 2.64 (t, J=7.5 Hz, 2H). $^{13}$C NMR (400 MHz, DMSO-d$_6$) δ 195.0, 171.6, 158.0, 143.8, 138.0, 133.3, 132.7, 131.6, 131.6, 129.8, 129.7, 128.9, 118.7, 114.2, 55.4, 38.8, 30.3. ESI-MS (m/z): 360.1 [M+H]$^+$.

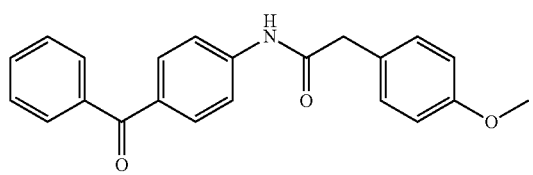 [SMILES: COc1ccc(CC(=O)Nc2ccc(C(=O)c3ccccc3)cc2)cc1]

SW208583-1-A

White solid, 7.8 mg, 7% yield. $^1$H NMR (400 MHz, DMSO-d$_6$) δ 10.49 (s, 1H), 7.77-7.72 (m, 3H), 7.71-7.66 (m, 2H), 7.66-7.60 (m, 2H) 7.56-7.49 (m, 2H), 7.27-7.22 (m, 2H), 6.91-6.86 (m, 2H), 3.71 (s, 3H), 3.60 (s, 2H). $^{13}$C NMR (400 MHz, DMSO-d$_6$) δ 195.0, 170.6, 158.5, 143.9, 138.0, 132.7, 131.6, 130.6, 129.8, 129.4, 128.9, 127.9, 118.8, 114.2, 55.5, 42.9. ESI-MS (m/z): 346.1 [M+H]$^+$.

Procedure for SW208063-1-A

Procedure for steps 1-2 from J. Org. Chem. 2007, 72, 6270-6272

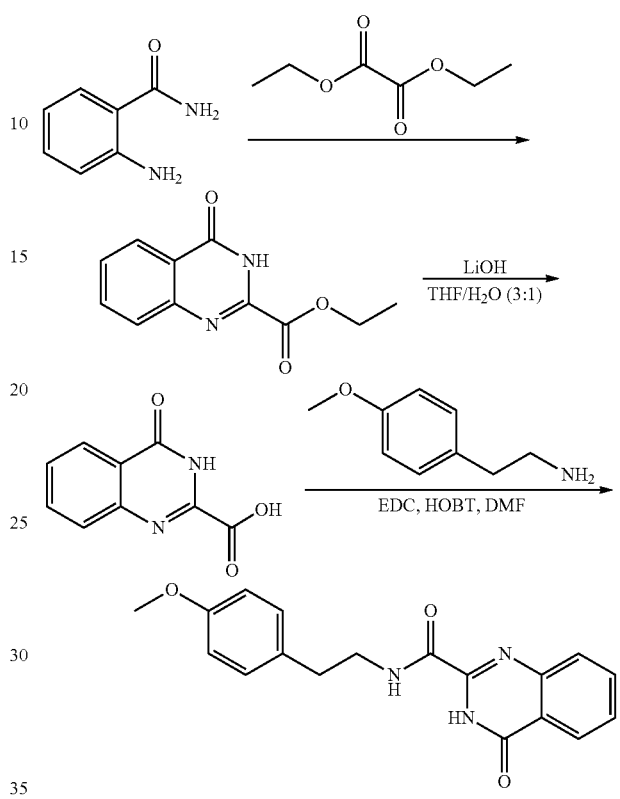

Step 1:

Anthranilamide (1 eq) and diethyl oxalate (3 eq) refluxed at 185° C. for 6 hours. Then, the reaction was cooled to rt and a precipitate formed upon cooling. The precipitate was collected by filtration, rinsed with diethyl ether, and dried under vacuum to yield the desired intermediate, which was used without purification. Cream-colored solid, 170.0 mg, 76% yield. $^1$H NMR (400 MHz, DMSO-d$_6$) δ 12.62 (s, 1H), 8.16 (dd, J=8.0, 1.5 Hz, 1H), 7.88 (ddd, J=8.5, 7.0, 1.5 Hz, 1H), 7.84-7.80 (m, 1H), 7.63 (ddd, J=8.1, 7.1, 1.3 Hz, 1H), 4.37 (q, J=7.1 Hz, 2H), 1.34 (t, J=7.1 Hz, 3H). ESI-MS (m/z): 219.0 [M+H]$^+$.

Step 2:

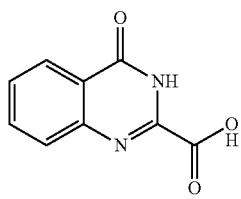 [SMILES: O=C(O)c1nc2ccccc2c(=O)[nH]1]

Lithium hydroxide (3 eq) was added to a solution of the step 1 intermediate (1 eq) in 3:1 THF/H$_2$O (2 M). A white precipitate formed and the reaction was finished in 2 hours. 1M HCl was added until the reaction mixture became acidic. Then, the precipitate was collected by filtration, rinsed with water, and dried under vacuum to give the desired intermediate, which was used without purification. White solid, 41.5 mg, 6-46% yield. ESI-MS (m/z): 190.9 [M]$^+$.

Step 3: Amide Coupling with HOBT
Where EDC=1-Ethyl-3-(3-dimethylaminopropyl)carbodiimide
HOBT=1-hydroxybenzotriazole hydrate The carboxylic acid (1 eq), EDC (1.05 eq), and HOBT (1.05 eq) were dissolved in DMF (0.1M) and stirred for 20 minutes before adding the amine (1 eq), and a precipitate immediately formed. The reaction mixture stirred overnight. Water was added to the reaction mixture, and the precipitate disappeared. EtOAc was added to the reaction mixture and EtOAc layer was washed with 1M NaOH (3×), water (3×), 1M HCl, water (3×), and brine. Then the organic layer was dried with $Na_2SO_4$ and concentrated. The residue was triturated in $CH_2Cl_2$ to give the final product as a white solid in 9% isolated yield (6.4 mg). $^1$H NMR (400 MHz, DMSO-$d_6$) δ 8.74 (t, J=6.2 Hz, 1H), 7.94 (dd, J=8.1, 1.5 Hz, 1H), 7.56-7.52 (m, 1H), 7.48 (ddd, J=8.3, 6.7, 1.6 Hz, 1H), 7.19 (ddd, J=8.1, 6.8, 1.4 Hz, 1H), 7.17-7.13 (m, 2H), 6.87-6.83 (m, 2H), 3.70 (s, 3H), 3.48-3.41 (m, 2H), 2.76 (t, J=7.4 Hz, 2H). ESI-MS (m/z): 324.0 [M+H]$^+$.

Procedure for

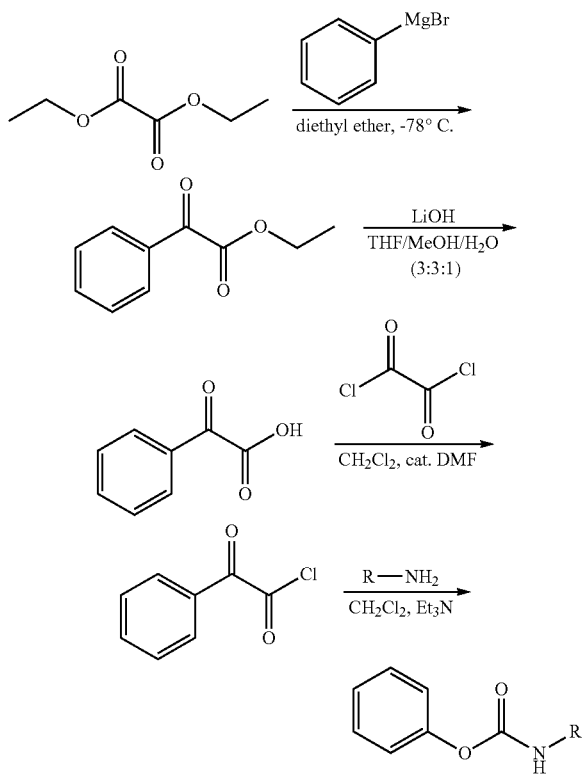

Step 1:
Diethyl oxalate (1 eq) in anhydrous diethyl ether (0.3 M) was cooled to −78° C. under nitrogen for 30 minutes before adding phenyl magnesium bromide (1.0 M in THF, 1.2 eq). The reaction mixture was warmed to 0° C. for 2 hours and a precipitate formed. The reaction mixture was quenched with sat. NH$_4$Cl and then extracted with diethyl ether. The organic layer was dried with Na$_2$SO4, concentrated, and dried under vacuum to give the product as a yellow oil in % yield (1.149 g), which was used without further purification. $^1$H NMR (400 MHz, CDCl$_3$) δ 8.03-7.98 (m, 2H), 7.68-7.63 (m, 1H), 7.54-7.47 (m, 2H), 4.45 (q, J=7.1 Hz, 2H), 1.42 (t, J=7.2 Hz, 3H).

Step 2

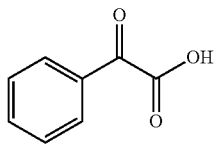 [SMILES: O=C(O)C(=O)c1ccccc1]

Lithium hydroxide (3 eq) was added to a solution of ester (1 eq) in 3:3:1 THF/MeOH/H$_2$O (2 M). A white precipitate formed and the reaction was finished in 2 hours. 1M HCl was added until the reaction mixture became acidic. Then, the reaction mixture was extracted into EtOAc. The organic layer was washed with water and brine, dried with Na$_2$SO$_4$, and concentrated. The residue was purified by flash chromatography (silica gel, 0→30% EtOAc in hexanes) to give the carboxylic acid. ESI-MS (m/z): [M+H]$^+$.

Step 3
Oxalyl chloride (5 eq) was added to a solution of carboxylic acid (1 eq) in CH$_2$Cl$_2$ (0.1 M), and then a catalytic amount of DMF was added to the reaction mixture to initiate the reaction and bubbling occurred. The reaction was complete in 1 hour, and the solution was dried with N$_2$ for one hour to give the acid chloride as a yellow oil, which was used immediately in the next step.

Step 4
Amine (1 eq) was added to a solution of acid chloride (1 eq) and Et$_3$N (2 eq) in CH$_2$Cl$_2$ (0.1 M) and a white precipitate formed. The reaction mixture stirred overnight at rt. The reaction mixture was washed with NaHCO$_3$. The organic layer was dried with Na$_2$SO$_4$ and concentrated. The residue was purified by flash chromatography (silica gel, 0→30% EtOAc in hexanes) to give the amide.

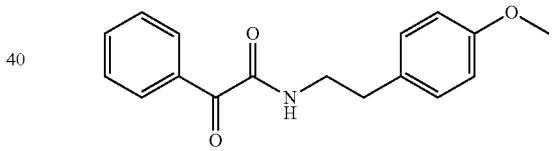

SW208145-1-A
mg, yield. $^1$H NMR (400 MHz, DMSO-$d_6$) δ 8.93 (t, J=5.7 Hz, 1H), 7.81-7.76 (m, 2H), 7.72-7.66 (m, 1H), 7.53-7.48 (m, 2H), 7.18-7.13 (m, 2H), 6.88-6.83 (m, 2H), 3.72 (s, 3H), 3.49-3.42 (m, 2H), 2.75 (t, J=7.2 Hz, 2H). $^{13}$C NMR (400 MHz, DMSO-$d_6$) δ 191.0, 165.4, 158.2, 135.0, 133.2, 131.3, 130.2, 130.1, 129.3, 114.2, 55.4, 34.3, 40.3. ESI-MS (m/z): 284.0 [M+H]$^+$.

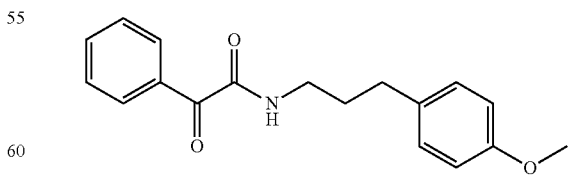

SW208152-1-A
Yellow oil, 48.8 mg, 65% yield overall. $^1$H NMR (500 MHz, DMSO-$d_6$) δ 8.98 (t, J=5.7 Hz, 1H), 7.98-7.94 (m, 2H), 7.75-7.70 (m, 1H), 7.61-7.55 (m, 2H), 7.16-7.11 (m, 2H), 6.87-6.82 (m, 2H), 3.71 (s, 3H), 3.26-3.21 (m, 2H), 2.56 (t, J=7.5 Hz, 2H), 1.81-1.74 (m, 2H). $^{13}$C NMR (400 MHz, DMSO-d$_6$) δ 191.0, 165.5, 157.9, 135.0, 133.7, 133.4, 130.2, 129.9, 129.4, 114.2, 55.4, 38.4, 32.0, 31.4. ESI-MS (m/z): 298.0 [M+H]$^+$.

General Procedure for Amidation Via Acid Chlorides.

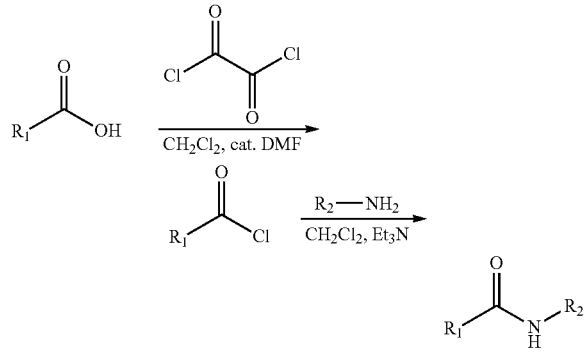

Step 1:

Oxalyl chloride (5 eq) was added to a solution of carboxylic acid (1 eq) in CH$_2$Cl$_2$ (0.1 M), and then a catalytic amount of DMF was added to the reaction mixture to initiate the reaction and bubbling occurred. The reaction was complete in 1 hour, and the solution was dried with N$_2$ for at least one hour to give the acid chloride, which was used immediately in the next step.

Step 2:

Amine (1 eq) was added to a solution of acid chloride (1 eq) and Et$_3$N (2 eq) in CH$_2$Cl$_2$ (0.1 M) and a white precipitate formed. The reaction mixture stirred overnight at rt. The reaction mixture was washed with NaHCO$_3$. The organic layer was dried with Na$_2$SO$_4$ and concentrated to give the product. The final product was not purified unless otherwise noted.

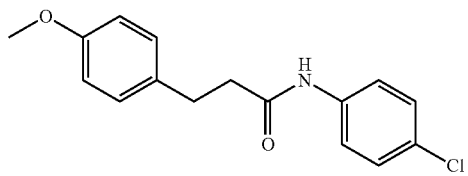 [SMILES: COc1ccc(CCC(=O)Nc2ccc(Cl)cc2)cc1]

SW208146-1-A

White solid, 12.9 mg, 23% yield after flash chromatography (silica gel, 0→30% EtOAc in hexanes). $^1$H NMR (400 MHz, DMSO-d$_6$) δ 10.00 (s, 1H), 7.62-7.55 (m, 2H), 7.35-7.29 (m, 2H), 7.16-7.10 (m, 2H), 6.85-6.79 (m, 2H), 3.69 (s, 3H), 2.82 (t, J=7.5 Hz, 2H), 2.56 (t, J=7.5 Hz, 2H). $^{13}$C NMR (400 MHz, DMSO-d$_6$) δ 171.0, 158.0, 138.6, 133.4, 129.6, 129.0, 126.9, 121.0, 114.2, 55.4, 38.7, 30.2. ESI-MS (m/z): 290.0 [M+H]$^+$.

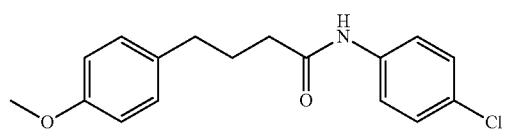 [SMILES: COc1ccc(CCCC(=O)Nc2ccc(Cl)cc2)cc1]

SW208151-1-A

White solid, 125.9 mg, 83% yield. $^1$H NMR (500 MHz, DMSO-d$_6$) δ 10.01 (s, 1H), 7.63-7.59 (m, 2H), 7.35-7.30 (m, 2H), 7.14-7.09 (m, 2H), 6.86-6.81 (m, 2H), 3.70 (s, 3H), 2.54 (t, J=7.6 Hz, 2H), 2.29 (t, J=7.5 Hz, 2H), 1.88-1.79 (m, 2H). $^{13}$C NMR (400 MHz, DMSO-d$_6$) δ 171.6, 157.9, 138.7, 133.9, 129.7, 129.0, 126.9, 121.0, 114.2, 55.4, 36.1, 34.1, 27.3. ESI-MS (m/z): 304.0 [M]$^+$.

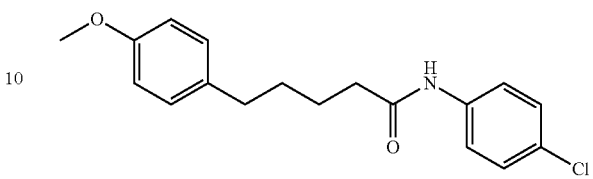

SW208189-1-A

Cream-colored solid, 1.9 mg, 1% yield after flash chromatography (silica gel, 0→100% EtOAc in hexanes). $^1$H NMR (500 MHz, DMSO-d$_6$) δ 10.02 (s, 1H), 7.62-7.58 (m, 2H), 7.35-7.30 (m, 2H), 7.11-7.07 (m, 2H), 6.84-6.80 (m, 2H), 3.70 (s, 3H), 2.53 (t, J=7.2 Hz, 2H), 2.31 (t, J=6.9 Hz, 2H), 1.59-1.51 (m, 4H). $^{13}$C NMR (400 MHz, DMSO-d$_6$) δ 171.8, 157.8, 138.7, 134.3, 129.6, 129.0, 126.9, 120.9, 114.1, 55.4, 36.7, 34.4, 31.3, 25.1. ESI-MS (m/z): 318.0 [M+H]$^+$.

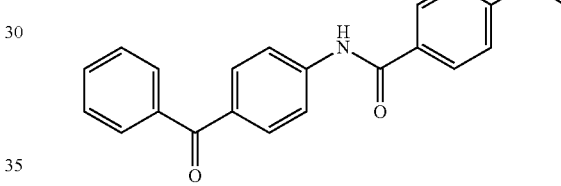

SW208465-1-A

White solid, 6.3 mg, 6% yield, after flash chromatography (silica gel, 0→100% EtOAc in hexanes). $^1$H NMR (400 MHz, DMSO-d$_6$) δ 10.43 (s, 1H), 8.01-7.94 (m, 4H), 7.80-7.73 (m, 2H), 7.74-7.68 (m, 2H), 7.68-7.62 (m, 1H), 7.59-7.52 (m, 2H), 7.10-7.04 (m, 2H), 3.83 (s, 3H). $^{13}$C NMR (400 MHz, DMSO-d$_6$) δ 195.1, 165.8, 162.6, 144.1, 138.0, 132.7, 131.9, 131.4, 130.3, 129.8, 129.0, 127.0, 119.8, 114.1, 55.9. ESI-MS (m/z): 332.0 [M+H]$^+$. Used p-anisoyl chloride so started from 2$^{nd}$ step

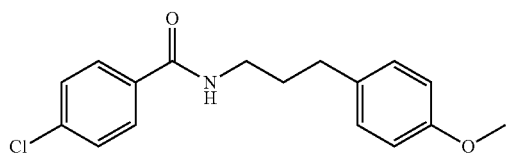 [SMILES: COc1ccc(CCCNC(=O)c2ccc(Cl)cc2)cc1]

SW208462-1-A

White solid, 51.2 mg, 54% yield, after flash chromatography (silica gel, 0→100% EtOAc in hexanes). $^1$H NMR (400 MHz, DMSO-d$_6$) δ 8.52 (t, J=5.6 Hz, 1H), 7.87-7.81 (m, 2H), 7.54-7.47 (m, 2H), 7.15-7.07 (m, 2H), 6.86-6.78 (m, 2H), 3.69 (s, 3H), 3.27-3.20 (m, 2H), 2.54 (t, J=7.6 Hz, 2H), 1.81-1.72 (m, 2H). $^{13}$C NMR (400 MHz, DMSO-d$_6$) δ 165.5, 157.8, 136.3, 134.0, 133.8, 129.7, 129.5, 128.8, 114.1, 55.4, 39.3, 32.2, 31.5. ESI-MS (m/z): 304.1 [M+H]$^+$. Used 4-chlorobenzoyl chloride so started from 2$^{nd}$ step.

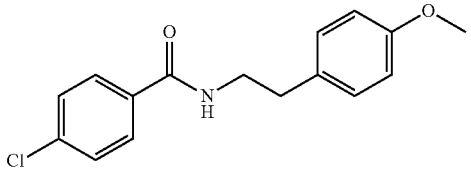 [SMILES: COc1ccc(CCNC(=O)c2ccc(Cl)cc2)cc1]

SW208463-1-A

White solid, 18.6 mg, 21% yield, after flash chromatography (silica gel, 0→100% EtOAc in hexanes). $^1$H NMR (400 MHz, DMSO-$d_6$) δ 8.60 (t, J=5.6 Hz, 1H), 7.85-7.79 (m, 2H), 7.55-7.48 (m, 2H), 7.16-7.09 (m, 2H), 6.86-6.80 (m, 2H), 3.69 (s, 3H), 3.45-3.38 (m, 2H), 2.75 (t, J=7.5 Hz, 2H). ESI-MS (m/z): 290.1 [M+H]$^+$. Used 4-chlorobenzoyl chloride so started from $2^{nd}$ step.

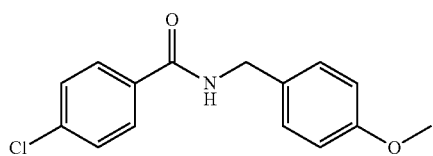 [SMILES: COc1ccc(CNC(=O)c2ccc(Cl)cc2)cc1]

SW208464-1-A

White solid, 30.7 mg, 35% yield, after flash chromatography (silica gel, 0→100% EtOAc in hexanes). $^1$H NMR (400 MHz, DMSO-$d_6$) δ 9.03 (t, J=5.9 Hz, 1H), 7.90-7.84 (m, 2H), 7.55-7.49 (m, 2H), 7.25-7.19 (m, 2H), 6.89-6.84 (m, 2H), 4.38 (d, J=5.9 Hz, 2H), 3.70 (s, 3H). $^{13}$C NMR (400 MHz, DMSO-$d_6$) δ 165.4, 158.6, 136.4, 133.6, 131.9, 129.6, 129.1, 128.8, 114.1, 55.5, 42.6. ESI-MS (m/z): 275.9 [M]$^+$. Used 4-chlorobenzoyl chloride so started from $2^{nd}$ step.

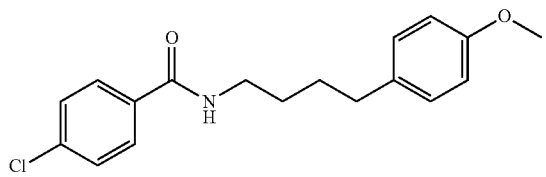 [SMILES: COc1ccc(CCCCNC(=O)c2ccc(Cl)cc2)cc1]

SW208585-1-A 4-chlorobenzoyl chloride (1 eq) was added to a solution of 4-(4-methyoxy)-aminopropane (1 eq) and Et$_3$N (2 eq) in CH$_2$Cl$_2$ (0.1M). After 5 hours, the reaction was washed with NaHCO$_3$ and the organic extracts were dried with Na$_2$SO$_4$ and concentrated. The residue was purified by flash chromatography (silica gel, 0→100% EtOAc in hexanes) to give the product as a white solid in 14% yield (16.7 mg). $^1$H NMR (400 MHz, DMSO-$d_6$) δ 8.51 (t, J=5.7 Hz, 1H), 7.85-7.79 (m, 2H), 7.52-7.46 (m, 2H), 7.11-7.05 (m, 2H), 6.83-6.77 (m, 2H), 3.69 (s, 3H), 3.27-3.29 (m, 2H), 2.51 (t, J=6.9 Hz, 2H), 1.60-1.41 (m, 4H), peaks at δ 7.94-7.90 (m, 2H), 7.57-7.53 (m, 2H) are 4-chlorobenzoyl chloride. $^{13}$C NMR (400 MHz, DMSO-$d_6$) δ 165.4, 157.8, 136.2, 134.4, 133.8, 131.6, 129.5, 128.8, 114.1, 55.4, 34.3, 29.2, 29.1, δ 129.6 and 129.2 are from 4-chlorobenzoyl chloride. ESI-MS (m/z): 318.1 [M+H]$^+$.

REFERENCES

1. Sawyers, C. L. Making progress through molecular attacks on cancer. *Cold Spring Harbor symposia on quantitative biology* 70, 479-482, doi:10.1101/sqb.2005.70.034 (2005).
2. Kwak, E. L. et al. Anaplastic lymphoma kinase inhibition in non-small-cell lung cancer. *The New England journal of medicine* 363, 1693-1703, doi:10.1056/NEJMoa1006448 (2010).
3. Lynch, T. J. et al. Activating mutations in the epidermal growth factor receptor underlying responsiveness of non-small-cell lung cancer to gefitinib. *The New England journal of medicine* 350, 2129-2139, doi:10.1056/NEJMoa040938 (2004).
4. Govindan, R. et al. Genomic landscape of non-small cell lung cancer in smokers and never-smokers. *Cell* 150, 1121-1134, doi:10.1016/j.cell.2012.08.024 (2012).
5. Imielinski, M. et al. Mapping the hallmarks of lung adenocarcinoma with massively parallel sequencing. *Cell* 150, 1107-1120, doi:10.1016/j.cell.2012.08.029 (2012).
6. Weir, B. A. et al. Characterizing the cancer genome in lung adenocarcinoma. *Nature* 450, 893-898, doi:10.1038/nature06358 (2007).
7. Barretina, J. et al. The Cancer Cell Line Encyclopedia enables predictive modelling of anticancer drug sensitivity. *Nature* 483, 603-607, doi:10.1038/nature11003 (2012).
8. Garnett, M. J. et al. Systematic identification of genomic markers of drug sensitivity in cancer cells. *Nature* 483, 570-575, doi:10.1038/nature11005 (2012).
9. D'Angelo, N. D. et al. Discovery and optimization of a series of benzothiazole phosphoinositide 3-kinase (PI3K)/mammalian target of rapamycin (mTOR) dual inhibitors. *Journal of medicinal chemistry* 54, 1789-1811, doi: 10.1021/jm1014605 (2011).

The invention claimed is:

1. A method for selectively treating cancer or killing a cancer cell, comprising administering a prodrug of formula (IV), or a pharmaceutically acceptable salt thereof, to a patient in need thereof, wherein said prodrug is activated by a cytochrome P450 enzyme, and the activated drug inhibits SCD1:

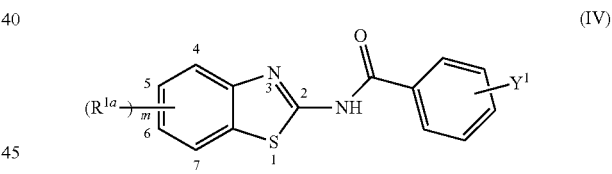

(IV)

wherein:

$R^{1a}$ is attached to any one or more of C4, C5, C6 and C7 position, and at each occurrence is selected from: hydrogen; halo; hydroxyl; $C_{1-6}$ alkoxyl optionally substituted with 1 or more hydroxyl, cyano and/or halo; $C_{1-6}$ carbonyl; $C_{1-6}$ alkoxycarbonyl; cyano; nitro; amine; —(O(CH$_2$)$_{1-3}$)$_n$—CCH wherein n is an integer selected from 1-5; and $R^A$;

m is an integer selected from 0-4; and $Y^1$ is selected from: azide; —C(O)R$^a$, —CH(OH)R$^a$, —CH(NH$_2$)R$^a$, —NHR$^a$, —C(O)NH(CH$_2$)$_{0-6}$R$^a$ and —C(O)N(R$^b$)(R$^c$), each optionally substituted with 1 or more R$^A$;

wherein R$^A$ is selected from $C_{1-6}$ (e.g., $C_{1-3}$) alkyl, $C_{2-6}$ (e.g., $C_{2-3}$) alkenyl and $C_{2-6}$ (e.g., $C_{2-3}$) alkynyl, each optionally substituted with 1 or more halo, hydroxyl, $C_{1-6}$ (e.g., $C_{1-3}$) alkoxyl, $C_{1-6}$ (e.g., $C_{1-3}$) carbonyl, $C_{1-6}$ (e.g., $C_{1-3}$) alkoxycarbonyl, cyano, nitro, and/or amine;

wherein R$^a$ is, at each occurrence, independently selected from $C_{3-12}$ cycloalkyl, $C_{2-6}$ heterocyclyl, $C_{6-12}$ aryl and $C_{4-12}$ heteroaryl, each optionally substituted with 1 or more halo, hydroxyl, $C_{1-6}$ alkyl, $C_{1-6}$ (e.g., $C_{1-3}$) alkoxyl, $C_{1-6}$ (e.g., $C_{1-3}$) alkoxycarbonyl, cyano, nitro and/or amine;

wherein $R^b$ and $R^c$ are each independently selected from $R^a$ and $R^A$; or $R^b$ and $R^c$ together with the nitrogen they are attached to form a $C_{2-6}$ heterocyclyl or $C_{4-12}$ heteroaryl ring.

2. The method of claim 1, wherein said cytochrome P450 enzyme is CYP4F11.

3. The method of claim 2, wherein said CYP4F11 is overexpressed in the cancer cell in the patient.

4. The method of claim 1, wherein said cancer is non-small cell lung cancer.

5. The method of claim 1, wherein $Y^1$ is at the para position.

6. The method of claim 1, wherein $R^{1a}$ is methoxy, m is 1, and $Y^1$ is —CH(NH$_2$)Ph.

* * * * *